(12) United States Patent
Koepke et al.

(10) Patent No.: US 9,957,531 B1
(45) Date of Patent: May 1, 2018

(54) GENETICALLY ENGINEERED BACTERIUM FOR THE PRODUCTION OF 3-HYDROXYBUTYRATE

(71) Applicant: LanzaTech New Zealand Limited, Skokie, IL (US)

(72) Inventors: Michael Koepke, Skokie, IL (US); Rasmus Overgaard Jensen, Skokie, IL (US); James Bruce Yarnton Haycock Behrendorff, Copenhagen (DK); Ryan Edward Hill, Stockholm (SE); Darmawi Juminaga, Skokie, IL (US); Alexander Paul Mueller, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days. days.

(21) Appl. No.: 15/658,668

(22) Filed: Jul. 25, 2017

Related U.S. Application Data

(63) Continuation of application No. 15/293,191, filed on Oct. 13, 2016, now Pat. No. 9,738,875.

(60) Provisional application No. 62/240,850, filed on Oct. 13, 2015.

(51) Int. Cl.
| | | |
|---|---|---|
| *C12N 1/20* | (2006.01) |
| *C12P 7/42* | (2006.01) |
| *C12N 9/10* | (2006.01) |
| *C12N 9/02* | (2006.01) |
| *C12N 9/04* | (2006.01) |
| *C12N 9/12* | (2006.01) |
| *C12N 9/16* | (2006.01) |
| *C12P 7/24* | (2006.01) |
| *C12P 7/18* | (2006.01) |

(52) U.S. Cl.
CPC .............. *C12P 7/42* (2013.01); *C12N 9/0006* (2013.01); *C12N 9/0008* (2013.01); *C12N 9/1029* (2013.01); *C12N 9/1217* (2013.01); *C12N 9/16* (2013.01); *C12P 7/18* (2013.01); *C12P 7/24* (2013.01); *C12Y 101/01001* (2013.01); *C12Y 101/01002* (2013.01); *C12Y 102/07005* (2013.01); *C12Y 203/01008* (2013.01); *C12Y 203/01009* (2013.01); *C12Y 207/02001* (2013.01); *C12Y 301/0202* (2013.01)

(58) Field of Classification Search
CPC ............................ C12N 9/1217; C12N 9/0008
USPC ........................................ 435/252.3
See application file for complete search history.

(56) References Cited

U.S. PATENT DOCUMENTS

| 5,593,886 | A | 1/1997 | Gaddy |
| 6,368,819 | B1 | 4/2002 | Gaddy et al. |
| 7,262,037 | B2 | 8/2007 | Chen et al. |
| 9,096,860 | B2 * | 8/2015 | Park ..................... C12N 15/77 |
| 9,297,026 | B2 | 3/2016 | Koepke et al. |
| 2011/0151530 | A1 | 6/2011 | Soucaille et al. |
| 2011/0165644 | A1 | 7/2011 | Marliere |
| 2011/0201089 | A1 | 8/2011 | Burgard et al. |
| 2012/0252083 | A1 | 10/2012 | Koepke et al. |

FOREIGN PATENT DOCUMENTS

| EP | 2295593 A1 | 3/2011 |
| WO | 2007117157 A1 | 10/2007 |
| WO | 2008028055 A2 | 3/2008 |
| WO | 2008115080 A1 | 9/2008 |
| WO | 2009064200 A1 | 5/2009 |
| WO | 2009151342 A1 | 12/2009 |
| WO | 2010001078 A2 | 1/2010 |
| WO | 2011076691 A1 | 6/2011 |
| WO | 2011112103 A1 | 9/2011 |
| WO | 2012024522 A2 | 2/2012 |
| WO | 2012026833 A1 | 3/2012 |
| WO | 2012053905 A1 | 4/2012 |
| WO | 2012115527 A2 | 8/2012 |
| WO | 2013036147 A2 | 3/2013 |
| WO | 2013180581 A1 | 12/2013 |
| WO | 2013180584 A1 | 12/2013 |
| WO | 2013185123 A1 | 12/2013 |
| WO | 2013191567 A1 | 12/2013 |
| WO | 2014036152 A1 | 3/2014 |
| WO | 2015085015 A1 | 6/2015 |
| WO | 2015101493 A1 | 7/2015 |
| WO | 2016034691 A1 | 10/2016 |

OTHER PUBLICATIONS

Abrini, Arch Microbiol, 161: 345-351, 1994.
Barker, PNAS USA, 31: 373-381, 1945.
Cheong, Nature Biotechnol, 34: 556-561, 2016.
Cho, Biotechnol Adv, 33: 1455-1466, 2015.
Clomburg, Appl Microbiol Biotechnol, 86: 419-434, 2010.
Drake, Acetogenic Prokaryotes, In: The Prokaryotes, 3rd edition, pp. 354-420, New York, NY, Springer, 2006.
Heap, J Microbiol Meth, 78: 79-85, 2009.
Huang, Nature, 537: 320-327, 2016.
Hungate, Meth Microbiol, 3B: 117-132, 1969.
Jones, Microbiol Rev, 50: 484-524, 1986.
Kataoka, J Biosci Bioeng, 115: 475-480, 2013.
Khoury, Trends Biotechnol, 32: 99-109, 2014.
Köpke, Appl Environ Microbiol, 80: 3394-3403, 2014.
Köpke, Curr Opin Biotechnol, 22: 320-325, 2011.
Köpke, PNAS USA, 107: 13087-13092, 2010.
Liu, Appl Microbiol Biotechnol, 53: 545-552, 2000.
Bevers, J Bacterial, 187: 7056-7061, 2005.
Makshina, Chem Soc Rev, 43: 7917-7953, 2014.
Marcellin, Green Chem, 18: 3020-3028, 2016.
Matsumoto, Appl Microbiol Biotechnol, 97: 205-210, 2013.

(Continued)

*Primary Examiner* — Tekchand Saidha
(74) *Attorney, Agent, or Firm* — Andrea Schoen

(57) ABSTRACT

The invention relates to a genetically engineered bacterium having an enzyme that converts acetyl-CoA to acetoacetyl-CoA, an enzyme that converts acetoacetyl-CoA to 3-hydroxybutyryl-CoA, and an enzyme that converts 3-hydroxybutyryl-CoA to 3-hydroxybutyrate. The bacterium may also have enzymes to produce other downstream products, such as 3-hydroxybutyryaldehyde, and 1,3-butanediol. Typically, the bacterium is capable of producing these products from a gaseous substrate, such as syngas or an industrial waste gas.

20 Claims, 43 Drawing Sheets

(56) References Cited

OTHER PUBLICATIONS

May, Metabol Eng, 15: 218-225, 2013.
Mock, J Bacteriol, 197: 2965-2980, 2015.
Nagarajan, Microb Cell Factories, 12: 118, 2013.
Packer, Nature Rev Genetics, 16: 379-394, 2015.
Peralta-Yahya, Biotechnol J, 5: 147-162, 2010.
Perez, Biotechnol Bioeng, 110:1066-1077, 2012.
Privett PNAS USA, 109: 3790-3795, 2012.
Quan, PloS One, 4:e6441, 2009.
Ragsdale, Biochim Biophys Acta, 1784: 1873-1898, 2008.
Schiel-Bengelsdorf, FEBS Lett, 586: 2191-2198, 2012.
Schuchmann, Nat Rev Microbiol, 12: 809-821, 2014.
Seedorf, PNAS USA, 105: 2128-2133, 2008.
Takanashi, J Biosci Bioeng, 101: 501-507, 2006.
Tanner, Int J Syst Bacteriol, 43: 232-236, 1993.
Thauer, Bacteriol Rev, 41: 100-180, 1977.
Thompson, Appl Environ Microbiol, 56: 607-613, 1990.
Tseng, Appl Environ Microbiol, 75: 3137-3145, 2009.
van Leeuwen, Appl Microbiol Biotechnol, 93: 1377-1387, 2012.
Williams, J Gen Microbiol, 1136: 819-826, 1990.
Wolfe, Adv Microb Physiol, 6: 107-146, 1971.
Yaneva, J Biol Chem, 287: 15502-15511, 2012.
Yu, Biotechnol Bioeng, 111: 2580-2586, 2014.

\* cited by examiner

GENETICALLY ENGINEERED BACTERIUM FOR THE PRODUCTION OF 3-HYDROXYBUTYRATE

CROSS REFERENCE TO RELATED APPLICATIONS

This application is a continuation of U.S. patent application Ser. No. 15/293,191 filed Oct. 13, 2016, which claims the benefit of U.S. Provisional Patent Application No. 62/240,850 filed Oct. 13, 2015, the entireties of which are incorporated herein by reference.

BACKGROUND OF THE INVENTION

With recent advances in fermentation and metabolic engineering, fermentation routes to various products have been identified and developed (Clomburg, *Appl Microbiol Biotechnol*, 86: 419-434, 2010; Peralta-Yahya, *Biotechnol J*, 5: 147-162, 2010; Cho, *Biotechnol Adv*, pii: S0734-9750(14) 00181-5, 2014. However, all of these fermentation routes are energy (ATP)-consuming or, at best, energy (ATP)-neutral, which restricts product yield in energy-limited systems and uncouples product production from microorganism growth. The present invention provides energy (ATP)-generating pathways that overcome these limitations by providing novel fermentation routes and pathways to a variety of products, including acids, alkenes, aldehydes, alcohols, and diols. These pathways are directly coupled to microorganism growth and offer high product yields.

In particular, the invention relates to fermentation pathways involving Ptb-Buk. Phosphate butyryltransferase (Ptb) (EC 2.3.1.19) natively catalyzes the reaction of butanoyl-CoA and phosphate to form CoA and butanoyl phosphate. Butyrate kinase (Buk) (EC 2.7.2.7) natively catalyzes the reaction of butanoyl phosphate and ADP to form butyrate (butanoate) and ATP. Accordingly, these enzymes together (Ptb-Buk) natively catalyze the conversion of butanoyl-CoA to butyrate and generate one ATP via substrate level phosphorylation (SLP).

The inventors have discovered that Ptb is promiscuous and is capable of accepting a variety of acyl-CoAs and enoyl-CoAs as substrates, such that Ptb-Buk may be used to convert a number of acyl-CoAs and enoyl-CoAs to their corresponding acids or alkenates, respectively, while simultaneously generating ATP via substrate level phosphorylation.

Furthermore, in combination with an aldehyde ferredoxin oxidoreductase (AOR) and an alcohol dehydrogenase, acids formed via the Ptb-Buk system can be further converted to their respective aldehydes, alcohols, or diols. AOR (EC 1.2.7.5) catalyzes the reaction of an acid and reduced ferredoxin (which can, for example, be generated from oxidation of CO or hydrogen) to form an aldehyde and oxidized ferredoxin. Alcohol dehydrogenase (EC 1.1.1.1 and EC 1.1.1.2) can convert an aldehyde and NAD(P)H to an alcohol and NAD(P).

Introduction of Ptb-Buk and/or AOR into a heterologous species, therefore, provides a novel, alternate route to the formation of native and non-native products, such as as acids, alkenes, ketones, aldehydes, alcohols, and diols at high yields, thus overcoming limitations of the current state of the art.

SUMMARY OF THE INVENTION

The invention provides a genetically engineered bacterium comprising exogenous phosphate butyryltransferase (Ptb) and exogenous butyrate kinase (Buk) (Ptb-Buk). Generally, the Ptb-Buk acts on a non-native substrate, e.g., a substrate other than butanoyl-CoA and/or butanoyl phosphate, and produces a non-native product, e.g., a product other than butanoyl phosphate or butyrate. In certain embodiments, the Ptb-Buk converts acetoacetyl-CoA to acetoacetate, 3-hydroxyisovaleryl-CoA to 3-hydroxyisovalerate, 3-hydroxybutyryl-CoA to 3-hydroxybutyrate, or 2-hydroxyisobutyryl-CoA to 2-hydroxyisobutyrate.

The bacterium may produce one or more of an acid, an alkene, a ketone, an aldehyde, an alcohol, or a diol. More specifically, the bacterium may produce one or more of acetone or a precursor thereof, isopropanol or a precursor thereof, isobutylene or a precursor thereof, 3-hydroxybutyrate or a precursor thereof, 1,3-butanediol or a precursor thereof, 2-hydroxyisobutyrate or a precursor thereof, adipic acid or a precursor thereof, 1,3-hexanediol or a precursor thereof, 3-methyl-2-butanol or a precursor thereof, 2-buten-1-ol or a precursor thereof, isovalerate or a precursor thereof, or isoamyl alcohol or a precursor thereof. The bacterium does not typically produce butanol.

The bacterium may further comprise a disruptive mutation in a phosphotransacetylase (Pta) and an acetate kinase (Ack). The bacterium may further comprise a disruptive mutation in a thioesterase. In another embodiment, the invention provides a genetically engineered bacterium comprising exogenous Ptb-Buk and exogenous or endogenous aldehyde:ferredoxin oxidoreductase.

The invention further provides a method of producing a product comprising culturing the bacterium of any of the aforementioned embodiments in the presence of a substrate. The product may be, for example, acetone or a precursor thereof, isopropanol or a precursor thereof, isobutylene or a precursor thereof, 3-hydroxybutyrate or a precursor thereof, 1,3-butanediol or a precursor thereof, 2-hydroxyisobutyrate or a precursor thereof, adipic acid or a precursor thereof, 1,3-hexanediol or a precursor thereof, 3-methyl-2-butanol or a precursor thereof, 2-buten-1-ol or a precursor thereof, isovalerate or a precursor thereof, or isoamyl alcohol or a precursor thereof. Typically, the substrate is a gaseous substrate comprising, for example, one or more of CO, $CO_2$, and $H_2$. In one embodiment, the gaseous substrate is syngas. In another embodiment, the gaseous substrate is an industrial waste gas.

BRIEF DESCRIPTION OF THE DRAWINGS

FIG. 13A: pACYC-ptb-buk, pCOLA-thlA-adc, pCDF-phaB. FIG. 13B: pACYC-ptb-buk, pCOLA-thlA-adc, pCDF-phaB-bdh1. FIG. 13C: pCOLA-thlA-adc, pCDF-phaB-bdh1. FIG. 13D: pCOLA-thlA-adc. FIG. 13E: pCDF-phaB-bdh1. FIG. 13F: pCDF-phaB.

FIG. 29A: 1 mM 2-HIB standard. FIG. 29B: 1 mM 2-HB standard.

FIG. 29C: 0.5 mM 2-HB and 2-HIB standard. FIG. 29D: duplicate of *C. autoethanogenum* sample showing 2-HIB and 2-HB production from gas.

DETAILED DESCRIPTION OF THE INVENTION

Figure 1:
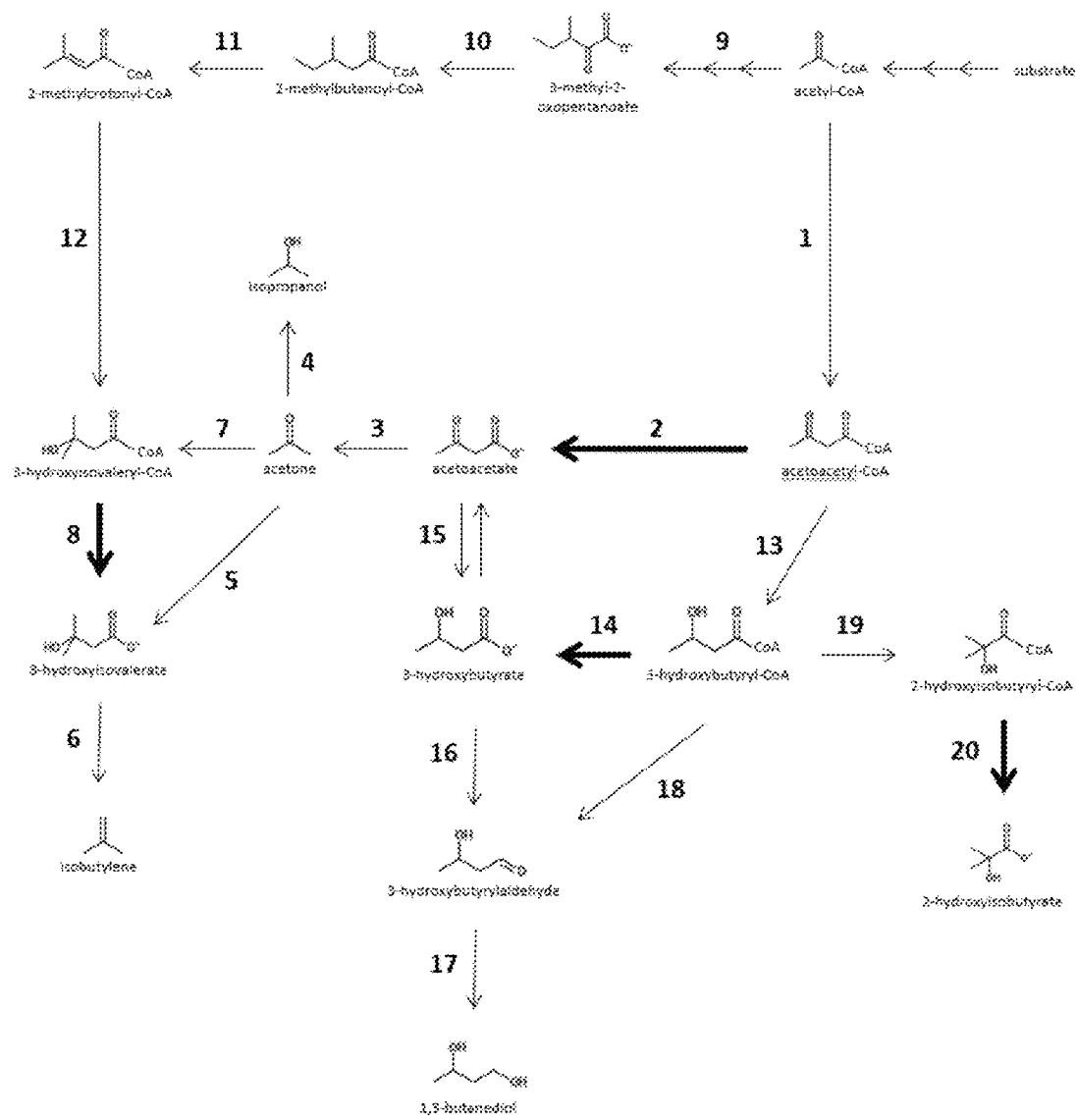
FIG. 1 is a diagram of metabolic pathways for the production of various products, including acetone, isopropanol, isobutylene, 3-hydroxybutyrate, 1,3-butanediol, and 2-hydroxyisobutyrate from acetyl-CoA. Acetyl-CoA may be generated from any suitable substrate, such as a carbohydrate (e.g., sugar) substrate or a gaseous substrate. In the present invention, acetyl-CoA is often generated from a gaseous substrate. Bold arrows indicate steps that may be catalyzed by Ptb-Buk.

Metabolic Pathways of FIGS. 1 and 34-36

FIGS. 1 and 34-36 are diagrams of metabolic pathways for the production of various acid, alkene, ketone, aldehyde, alcohol, and diol products, including acetone, isopropanol, isobutylene, 3-hydroxybutyrate (R- and S-isomers), 1,3-butanediol, 2-hydroxyisobutyrate, adipic acid, 1,3-hexanediol, 2-methyl-2-butanol, 2-buten-1-ol, isovalerate, and isoamyl alcohol from a substrate. Bold arrows indicate steps that may be catalyzed by Ptb-Buk. Exemplary enzymes are provided for each of the steps and enzymatic pathways detailed in FIGS. 1 and 34-36. However, additional suitable enzymes may be known to a person of ordinary skill in the art.

Step 1 shows the conversion of acetyl-CoA to acetoacetyl-CoA. This step may be catalyzed by thiolase (i.e., acetyl-CoA acetyltransferase) (EC 2.3.1.9). The thiolase may be, for example, ThlA from *Clostridium acetobutylicum* (WP_010966157.1) (SEQ ID NO: 1), PhaA from *Cupriavidus necator* (WP_013956452.1) (SEQ ID NO: 2), BktB from *Cupriavidus necator* (WP_011615089.1) (SEQ ID NO: 3), or AtoB from *Escherichia coli* (NP_416728.1) (SEQ ID NO: 4). *Clostridium autoethanogenum, Clostridium ljungdahlii*, and *Clostridium ragsdalei* do not have known native activity for this step. *Escherichia coli* has native activity for this step.

Step 2 shows the conversion of acetoacetyl-CoA to acetoacetate. This step may be catalyzed by CoA-transferase (i.e., acetyl-CoA:acetoacetyl-CoA transferase) (EC 2.8.3.9). The CoA-transferase may be, for example, CtfAB, a heterodimer comprising subunits CtfA and CtfB, from *Clostridium beijerinckii* (CtfA, WP_012059996.1) (SEQ ID NO: 5) (CtfB, WP_012059997.1) (SEQ ID NO: 6). This step may also be catalyzed by thioesterase (EC 3.1.2.20). The thioesterase may be, for example, TesB from *Escherichia coli* (NP_414986.1) (SEQ ID NO: 7). This step may also be catalyzed by a putative thioesterase, e.g., from *Clostridium autoethanogenum* or *Clostridium ljungdahlii*. In particular, three putative thioesterases have been identified in *Clostridium autoethanogenum*: (1) "thioesterase 1" (AGY74947.1; annotated as palmitoyl-CoA hydrolase; SEQ ID NO: 8), (2) "thioesterase 2" (AGY75747.1; annotated as 4-hydroxybenzoyl-CoA thioesterase; SEQ ID NO: 9), and (3) "thioesterase 3" (AGY75999.1; annotated as putative thioesterase; SEQ ID NO: 10). Three putative thioesterases have also been identified in *Clostridium ljungdahlii*: (1) "thioesterase 1" (ADK15695.1; annotated as predicted acyl-CoA thioesterase 1; SEQ ID NO: 11), (2) "thioesterase 2" (ADK16655.1; annotated as predicted thioesterase; SEQ ID NO: 12), and (3) "thioesterase 3" (ADK16959.1; annotated as predicted thioesterase; SEQ ID NO: 13). This step may also be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum, Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 3 shows the conversion of acetoacetate to acetone. This step may be catalyzed by an acetoacetate decarboxylase (EC 4.1.1.4). The acetoacetate decarboxylase may be, for example, Adc from *Clostridium beijerinckii* (WP_012059998.1) (SEQ ID NO: 14). This step may also be catalyzed by an alpha-ketoisovalerate decarboxylase (EC 4.1.1.74). The alpha-ketoisovalerate decarboxylase may be, for example, KivD from *Lactococcus lactis* (SEQ ID NO: 15). *Clostridium autoethanogenum, Clostridium ljungdahlii*, and *Clostridium ragsdalei* do not have known native activity for this step. Additionally, *Escherichia coli* does not have known native activity for this step. Rarely, conversion of acetoacetate to acetone may occur spontaneously. However, spontaneous conversion is highly inefficient and unlikely to result in the production of downstream products at desirable levels.

Step 4 shows the conversion of acetone to isopropanol. This step may be catalyzed by a primary:secondary alcohol dehydrogenase (EC 1.1.1.2). The primary:secondary alcohol dehydrogenase may be, for example, SecAdh from *Clostridium autoethanogenum* (AGY74782.1) (SEQ ID NO: 16), SecAdh from *Clostridium ljungdahlii* (ADK15544.1) (SEQ ID NO: 17), SecAdh from *Clostridium ragsdalei* (WP_013239134.1) (SEQ ID NO: 18), or SecAdh from *Clostridium beijerinckii* (WP_026889046.1) (SEQ ID NO: 19). This step may also be catalyzed by a primary: secondary alcohol dehydrogenase (EC 1.1.1.80), such as SecAdh from *Thermoanaerobacter brokii* (3FSR_A) (SEQ ID NO: 20). *Clostridium autoethanogenum*, *Clostridium ljungdahlii*, and *Clostridium ragsdalei* have native activity for this step (Köpke, *Appl Environ Microbiol*, 80: 3394-3403, 2014). However, *Escherichia coli* does not have known native activity for this step. Knocking down or knocking out this enzyme in *Clostridium autoethanogenum*, *Clostridium ljungdahlii*, or *Clostridium ragsdalei* results in the production and accumulation of acetone rather than isopropanol (WO 2015/085015).

Step 5 shows the conversion of acetone to 3-hydroxyisovalerate. This step may be catalyzed by a hydroxyisovalerate synthase, such as hydroxymethylglutaryl-CoA synthase (HMG-CoA synthase) (EC 2.3.3.10) from *Mus musculus* (SEQ ID NO: 21) (US 2012/0110001). The hydroxymethylglutaryl-CoA synthase may be engineered to improve activity. *Clostridium autoethanogenum*, *Clostridium ljungdahlii*, and *Clostridium ragsdalei* do not have known native activity for this step. *Escherichia coli* does not have known native activity for this step.

Step 6 shows the conversion of 3-hydroxyisovalerate to isobutylene (isobutene). This step may be catalyzed by a hydroxyisovalerate phosphorylase/decarboxylase. This step may also be catalyzed by mevalonate diphosphate decarboxylase (hydroxyisovalerate decarboxylase) (EC 4.1.1.33). The mevalonate diphosphate decarboxylase may be, for example, Mdd from *Saccharomyces cerevisiae* (CAA96324.1) (SEQ ID NO: 22) or Mdd from *Picrophilus torridus* (WP_011178157.1) (SEQ ID NO: 23) (US 2011/0165644; van Leeuwen, *Appl Microbiol Biotechnol*, 93: 1377-1387, 2012). *Clostridium autoethanogenum*, *Clostridium ljungdahlii*, and *Clostridium ragsdalei* do not have known native activity for this step. *Escherichia coli* does not have known native activity for this step Step 7 shows the conversion of acetone to 3-hydroxyisovaleryl-CoA. This step may be catalyzed by a 3-hydroxyisovaleryl-CoA synthase. *Clostridium autoethanogenum*, *Clostridium ljungdahlii*, and *Clostridium ragsdalei* do not have known native activity for this step. *Escherichia coli* does not have known native activity for this step Step 8 shows the conversion of 3-hydroxyisovaleryl-CoA to 3-hydroxyisovalerate. This step may be catalyzed by CoA-transferase (i.e., acetyl-CoA:acetoacetyl-CoA transferase) (EC 2.8.3.9). The CoA-transferase may be, for example, CtfAB, a heterodimer comprising subunits CtfA and CtfB, from *Clostridium beijerinckii* (CtfA, WP_012059996.1) (SEQ ID NO: 5) (CtfB, WP_012059997.1) (SEQ ID NO: 6). This step may also be catalyzed by thioesterase (EC 3.1.2.20). The thioesterase may be, for example, TesB from *Escherichia coli* (NP_414986.1) (SEQ ID NO: 7). This step may also be catalyzed by a putative thioesterase, e.g., from *Clostridium autoethanogenum* or *Clostridium ljungdahlii*. In particular, three putative thioesterases have been identified in *Clostridium autoethanogenum*: (1) "thioesterase 1" (AGY74947.1; annotated as palmitoyl-CoA hydrolase; SEQ ID NO: 8), (2) "thioesterase 2" (AGY75747.1; annotated as 4-hydroxybenzoyl-CoA thioesterase; SEQ ID NO: 9), and (3) "thioesterase 3" (AGY75999.1; annotated as putative thioesterase; SEQ ID NO: 10). Three putative thioesterases have also been identified in *Clostridium ljungdahlii*: (1) "thioesterase 1" (ADK15695.1; annotated as predicted acyl-CoA thioesterase 1; SEQ ID NO: 11), (2) "thioesterase 2" (ADK16655.1; annotated as predicted thioesterase; SEQ ID NO: 12), and (3) "thioesterase 3" (ADK16959.1; annotated as predicted thioesterase; SEQ ID NO: 13). This step may also be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum*, *Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 9 shows the conversion of acetyl-CoA to 3-methyl-2-oxopentanoate. This step encompasses a number of enzymatic reactions involved in the isoleucine biosynthesis pathway, which is natively present in many bacteria, including *Clostridium autoethanogenum*, *Clostridium ljungdahlii*, and *Clostridium ragsdalei* (and *Escherichia coli*). Enzymes involved in the conversion of acetyl-CoA to 3-methyl-2-oxopentanoate may include citramalate synthase (EC 2.3.1.182), 3-isopropylmalate dehydratase (EC 4.2.1.35), 3-isopropylmalate dehydrogenase (EC 1.1.1.85), acetolactate synthase (EC 2.2.1.6), ketol-acid reductoisomerase (EC 1.1.1.86), and/or dihydroxyacid dehydratase (EC 4.2.1.9). The citramalate synthase may be, for example, CimA from *Clostridium autoethanogenum* (AGY76958.1) (SEQ ID NO: 24) or CimA from *Methanocaldococcus jannaschii* (NP_248395.1) (SEQ ID NO: 25). The 3-isopropylmalate dehydratase may be, for example, LeuCD from *Clostridium autoethanogenum* (WP_023162955.1, LeuC; AGY77204.1, LeuD) (SEQ ID NOs: 26 and 27, respectively) or LeuCD from *Escherichia coli* (NP_414614.1, LeuC; NP_414613.1, LeuD) (SEQ ID NOs: 28 and 29, respectively). The 3-isopropylmalate dehydrogenase may be, for example, LeuB from *Clostridium autoethanogenum* (WP_023162957.1) (SEQ ID NO: 30) or LeuB from *Escherichia coli* (NP_414615.4) (SEQ ID NO: 31). The acetolactate synthase may be, for example, IlvBN from *Clostridium autoethanogenum* (AGY74359.1, IlvB; AGY74635.1, IlvB; AGY74360.1, IlvN) (SEQ ID NOs: 32, 33, and 34, respectively) or IlvBN from *Escherichia coli* (NP_418127.1, IlvB; NP_418126.1, IlvN) (SEQ ID NOs: 35 and 36, respectively). The ketol-acid reductoisomerase may be, for example, IlvC from *Clostridium autoethanogenum* (WP_013238693.1) (SEQ ID NO: 37) or IlvC from *Escherichia coli* (NP_418222.1) (SEQ ID NO: 38). The dihydroxyacid dehydratase may be, for example, IlvD from *Clostridium autoethanogenum* (WP_013238694.1) (SEQ ID NO: 39) or IlvD from *Escherichia coli* (YP_026248.1) (SEQ ID NO: 40). *Clostridium autoethanogenum*, *Clostridium ljungdahlii*, and *Clostridium ragsdalei* have native activity for this step.

Step 10 shows the conversion of 3-methyl-2-oxopentoate to 2-methylbutanoyl-CoA. This step may be catalyzed by ketoisovalerate oxidoreductase (EC 1.2.7.7). The ketoisovalerate oxidoreductase may be, for example, the VorABCD from *Methanothermobacter thermautotrophicus* (WP_010876344.1, VorA; WP_010876343.1, VorB; WP_010876342.1, VorC; WP_010876341.1, VorD) (SEQ ID NOs: 41-44, respectively) or VorABCD from *Pyococcus furiosus* (WP_011012106.1, VorA; WP_011012105.1, VorB; WP_011012108.1, VorC; WP_011012107.1, VorD) (SEQ ID NOs: 45-48, respectively). VorABCD is a 4-subunit enzyme. *Clostridium autoethanogenum, Clostridium ljungdahlii,* and *Clostridium ragsdalei* do not have known native activity for this step. *Escherichia coli* does not have known native activity for this step.

Step 11 shows the conversion of 2-methylbutanoyl-CoA to 2-methylcrotonyl-CoA. This step may be catalyzed by 2-methylbutanoyl-CoA dehydrogenase (EC 1.3.99.12). The 2-methylbutanoyl-CoA dehydrogenase may be, for example, AcdH from *Streptomyces avermitilis* (AAD44196.1 or BAB69160.1) (SEQ ID NO: 49) or AcdH from *Streptomyces coelicolor* (AAD44195.1) (SEQ ID NO: 50). *Clostridium autoethanogenum, Clostridium ljungdahlii,* and *Clostridium ragsdalei* do not have known native activity for this step. *Escherichia coli* does not have known native activity for this step.

Step 12 shows the conversion of 2-methylcrotonyl-CoA to 3-hydroxyisovaleryl-CoA. This step may be catalyzed by crotonase/3-hydroxybutyryl-CoA dehydratase (EC 4.2.1.55). The crotonase/3-hydroxybutyryl-CoA dehydratase may be, for example, Crt from *Clostridium beijerinckii* (ABR34202.1) (SEQ ID NO: 51), Crt from *Clostridium acetobutylicum* (NP_349318.1) (SEQ ID NO: 52), or LiuC from *Myxococcus xanthus* (WP_011553770.1). This step may also be catalyzed by crotonyl-CoA carboxylase-reductase (EC 1.3.1.86). The crotonyl-CoA carboxylase-reductase may be, for example, Ccr from *Treponema denticola* (NP_971211.1) (SEQ ID NO: 53). This step may also be catalyzed by crotonyl-CoA reductase (EC 1.3.1.44). The crotonyl-CoA reductase may be, for example, Ter from *Euglena gracilis* (AAW66853.1) (SEQ ID NO: 54). This step may also be catalyzed by a 3-hydroxypropionyl-CoA dehydratase (EC 4.2.1.116). This 3-hydroxypropionyl-CoA dehydratase may be, for example, Msed_2001 from *Metallosphaera sedula* (WP_012021928.1). This step may also be catalyzed by a enoyl-CoA hydratase. This enoyl-CoA hydratase (4.2.1.17) may be, for example, YngF from *Bacillus anthracis* (WP_000787371.1). *Clostridium autoethanogenum, Clostridium ljungdahlii,* and *Clostridium ragsdalei* do not have known native activity for this step. *Escherichia coli* does not have known native activity for this step.

Step 13 shows the conversion of acetoacetyl-CoA to 3-hydroxybutyryl-CoA. This step may be catalyzed by 3-hydroxybutyryl-CoA dehydrogenase (EC 1.1.1.157). The 3-hydroxybutyryl-CoA dehydrogenase may be, for example, Hbd from *Clostridium beijerinckii* (WP_011967675.1) (SEQ ID NO: 55), Hbd from *Clostridium acetobutylicum* (NP_349314.1) (SEQ ID NO: 56), or Hbd1 from *Clostridium kluyveri* (WP_011989027.1) (SEQ ID NO: 57). This step may also be catalyzed by acetoacetyl-CoA reductase (EC 4.2.1.36). The acetoacetyl-CoA reductase may be, for example, PhaB from *Cupriavidus necator* (WP_010810131.1) (SEQ ID NO: 58). This step may also be catalyzed by acetoacetyl-CoA hydratase (EC 4.2.1.119). Of note, PhaB is R-specific and Hbd is S-specific. Additionally, Hbd1 from *Clostridium kluyveri* is NADPH-dependent and Hbd from *Clostridium acetobutylicum* and *Clostridium beijerinckii* are NADH-dependent. *Clostridium autoethanogenum, Clostridium ljungdahlii,* and *Clostridium ragsdalei* do not have known native activity for this step. *Escherichia coli* does not have known native activity for this step.

Step 14 shows the conversion of 3-hydroxybutyryl-CoA to 3-hydroxybutyrate. This step may be catalyzed by thioesterase (EC 3.1.2.20). The thioesterase may be, for example, TesB from *Escherichia coli* (NP_414986.1) (SEQ ID NO: 7). This step may also be catalyzed by a putative thioesterase, e.g., from *Clostridium autoethanogenum* or *Clostridium ljungdahlii*. In particular, three putative thioesterases have been identified in *Clostridium autoethanogenum*: (1) "thioesterase 1" (AGY74947.1; annotated as palmitoyl-CoA hydrolase; SEQ ID NO: 8), (2) "thioesterase 2" (AGY75747.1; annotated as 4-hydroxybenzoyl-CoA thioesterase; SEQ ID NO: 9), and (3) "thioesterase 3" (AGY75999.1; annotated as putative thioesterase; SEQ ID NO: 10). Three putative thioesterases have also been identified in *Clostridium ljungdahlii*: (1) "thioesterase 1" (ADK15695.1; annotated as predicted acyl-CoA thioesterase 1; SEQ ID NO: 11), (2) "thioesterase 2" (ADK16655.1; annotated as predicted thioesterase; SEQ ID NO: 12), and (3) "thioesterase 3" (ADK16959.1; annotated as predicted thioesterase; SEQ ID NO: 13). This step may also be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum, Clostridium ljungdahlii,* and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 15 shows the conversion of 3-hydroxybutyrate to acetoacetate. This step may be catalyzed by 3-hydroxybutyrate dehydrogenase (EC 1.1.1.30). The 3-hydroxybutyrate dehydrogenase may be, for example, Bdh1 from *Ralstonia pickettii* (BAE72684.1) (SEQ ID NO: 60) or Bdh2 from *Ralstonia pickettii* (BAE72685.1) (SEQ ID NO: 61). The reverse reaction, the conversion of acetoacetate to 3-hydroxybutyrate, may be catalyzed by different 3-hydroxybutyrate dehydrogenase (EC 1.1.1.30) enzymes. For example, the conversion of acetoacetate to 3-hydroxybutyrate may be catalyzed by Bdh from *Clostridium autoethanogenum* (AGY75962) (SEQ ID NO: 62). *Clostridium ljungdahlii* and *Clostridium ragsdalei* likely have enzymes with similar activity. *Escherichia coli* does not have known native activity for this step.

Step 16 shows the conversion of 3-hydroxybutyrate to 3-hydroxybutyrylaldehyde. This step may be catalyzed by aldehyde:ferredoxin oxidoreductase (EC 1.2.7.5). The aldehyde:ferredoxin oxidoreductase (AOR) may be, for example, AOR from *Clostridium autoethanogenum* (WP_013238665.1; WP_013238675.1) (SEQ ID NOs: 63 and 64, respectively) or AOR from *Clostridium ljungdahlii* (ADK15073.1; ADK15083.1) (SEQ ID NOs: 65 and 66, respectively). In further embodiments, the aldehyde:ferredoxin oxidoreductase may be or may be derived, for example, from any of the following sources, the sequences of which are publically available:

| Description | Microrganism | Accession | GeneID |
| --- | --- | --- | --- |
| aldehyde:ferredoxin oxidoreductase | *Acidilobus saccharovorans* 345-15 | NC_014374.1 | 9498931 |
| aldehyde:ferredoxin oxidoreductase | *Acidilobus saccharovorans* 345-15 | NC_014374.1 | 9499504 |

-continued

| Description | Microrganism | Accession | GeneID |
|---|---|---|---|
| aldehyde:ferredoxin oxidoreductase | *Acidilobus saccharovorans* 345-15 | NC_014374.1 | 9499550 |
| aldehyde:ferredoxin oxidoreductase | *Acidilobus saccharovorans* 345-15 | NC_014374.1 | 9498997 |
| aldehyde:ferredoxin oxidoreductase | *Aciduliprofundum boonei* T469 | NC_013926.1 | 8828075 |
| aldehyde:ferredoxin oxidoreductase | *Aciduliprofundum boonei* T469 | NC_013926.1 | 8828511 |
| aldehyde:ferredoxin oxidoreductase | *Aciduliprofundum boonei* T469 | NC_013926.1 | 8828305 |
| aldehyde:ferredoxin oxidoreductase | *Aciduliprofundum boonei* T469 | NC_013926.1 | 8827762 |
| aldehyde:ferredoxin oxidoreductase | *Aciduliprofundum boonei* T469 | NC_013926.1 | 8827370 |
| aldehyde:ferredoxin oxidoreductase | *Aciduliprofundum* sp. MAR08-339 | NC_019942.1 | 14306579 |
| aldehyde:ferredoxin oxidoreductase | *Aciduliprofundum* sp. MAR08-339 | NC_019942.1 | 14306982 |
| aldehyde:ferredoxin oxidoreductase | *Aciduliprofundum* sp. MAR08-339 | NC_019942.1 | 14306639 |
| aldehyde:ferredoxin oxidoreductase | *Aciduliprofundum* sp. MAR08-339 | NC_019942.1 | 14307339 |
| aldehyde:ferredoxin oxidoreductase | *Aeropyrum pernix* K1 | NC_000854.2 | 1444491 |
| aldehyde:ferredoxin oxidoreductase | *Archaeoglobus fulgidus* DSM 4304 | NC_000917.1 | 1483287 |
| aldehyde:ferredoxin oxidoreductase | *Archaeoglobus fulgidus* DSM 4304 | NC_000917.1 | 1483233 |
| aldehyde:ferredoxin oxidoreductase | *Archaeoglobus fulgidus* DSM 4304 | NC_000917.1 | 1483554 |
| aldehyde:ferredoxin oxidoreductase | *Archaeoglobus fulgidus* DSM 4304 | NC_000917.1 | 1485513 |
| aldehyde:ferredoxin oxidoreductase | *Archaeoglobus profundus* DSM 5631 | NC_013741.1 | 8738726 |
| aldehyde:ferredoxin oxidoreductase | *Archaeoglobus profundus* DSM 5631 | NC_013741.1 | 8740019 |
| aldehyde:ferredoxin oxidoreductase | *Archaeoglobus sulfaticallidus* PM70-1 | NC_021169.1 | 15392228 |
| aldehyde:ferredoxin oxidoreductase | *Archaeoglobus sulfaticallidus* PM70-1 | NC_021169.1 | 15393814 |
| aldehyde:ferredoxin oxidoreductase | *Archaeoglobus sulfaticallidus* PM70-1 | NC_021169.1 | 15391826 |
| aldehyde:ferredoxin oxidoreductase | *Archaeoglobus sulfaticallidus* PM70-1 | NC_021169.1 | 15393763 |
| aldehyde:ferredoxin oxidoreductase | *Archaeoglobus sulfaticallidus* PM70-1 | NC_021169.1 | 15393491 |
| aldehyde:ferredoxin oxidoreductase | *Archaeoglobus veneficus* SNP6 | NC_015320.1 | 10393142 |
| aldehyde:ferredoxin oxidoreductase | *Archaeoglobus veneficus* SNP6 | NC_015320.1 | 10395048 |
| aldehyde:ferredoxin oxidoreductase | *Caldisphaera lagunensis* DSM 15908 | NC_019791.1 | 14212403 |
| aldehyde:ferredoxin oxidoreductase | *Caldisphaera lagunensis* DSM 15908 | NC_019791.1 | 14211524 |
| aldehyde:ferredoxin oxidoreductase | *Caldisphaera lagunensis* DSM 15908 | NC_019791.1 | 14212092 |
| aldehyde:ferredoxin oxidoreductase | *Caldisphaera lagunensis* DSM 15908 | NC_019791.1 | 14212561 |
| aldehyde:ferredoxin oxidoreductase | *Caldivirga maquilingensis* IC-167 | NC_009954.1 | 5710116 |
| aldehyde:ferredoxin oxidoreductase | *Caldivirga maquilingensis* IC-167 | NC_009954.1 | 5710117 |
| aldehyde:ferredoxin oxidoreductase | *Caldivirga maquilingensis* IC-167 | NC_009954.1 | 5709088 |
| aldehyde:ferredoxin oxidoreductase | *Caldivirga maquilingensis* IC-167 | NC_009954.1 | 5708891 |
| aldehyde:ferredoxin oxidoreductase | *Caldivirga maquilingensis* IC-167 | NC_009954.1 | 5710478 |
| aldehyde:ferredoxin oxidoreductase | *Caldivirga maquilingensis* IC-167 | NC_009954.1 | 5710457 |
| aldehyde:ferredoxin oxidoreductase | *Caldivirga maquilingensis* IC-167 | NC_009954.1 | 5709696 |
| aldehyde:ferredoxin oxidoreductase | *Candidatus Caldiarchaeum sub terraneum* | NC_022786.1 | 17602865 |
| aldehyde:ferredoxin oxidoreductase | *Candidatus Korarchaeum cryptofilum* OPF8 | NC_010482.1 | 6094361 |
| aldehyde:ferredoxin oxidoreductase | *Candidatus Korarchaeum cryptofilum* OPF8 | NC_010482.1 | 6094198 |
| aldehyde:ferredoxin oxidoreductase | *Candidatus Korarchaeum cryptofilum* OPF8 | NC_010482.1 | 6093546 |
| aldehyde:ferredoxin oxidoreductase | *Candidatus Korarchaeum cryptofilum* OPF8 | NC_010482.1 | 6093319 |
| aldehyde:ferredoxin oxidoreductase | *Candidatus Korarchaeum cryptofilum* OPF8 | NC_010482.1 | 6094057 |
| aldehyde:ferredoxin oxidoreductase | *Candidatus Korarchaeum cryptofilum* OPF8 | NC_010482.1 | 6093563 |
| aldehyde:ferredoxin oxidoreductase | *Chloroflexus aurantiacus* 11041 | NC_010175.1 | 5828639 |
| aldehyde:ferredoxin oxidoreductase | *Clostridium acetobutylicum* ATCC 824 | NC_003030.1 | 1118201 |
| aldehyde:ferredoxin oxidoreductase | *Clostridium botulinum* A sfr. ATCC 3502 | NC_009495.1 | 5187636 |
| aldehyde:ferredoxin oxidoreductase | *Clostridium botulinum* A str. Hall | NC_009698.1 | 5400593 |
| aldehyde:ferredoxin oxidoreductase | *Desulfovibrio vulgaris* sfr. Hildenborough | NC_002937.3 | 2796664 |
| aldehyde:ferredoxin oxidoreductase | *Desulfovibrio vulgaris* sfr. Hildenborough | NC_002937.3 | 2795337 |
| aldehyde:ferredoxin oxidoreductase | *Desulfurococcus fermentans* DSM 16532 | NC_018001.1 | 13061477 |
| aldehyde:ferredoxin oxidoreductase | *Desulfurococcus fermentans* DSM 16532 | NC_018001.1 | 13061068 |
| aldehyde:ferredoxin oxidoreductase | *Desulfurococcus fermentans* DSM 16532 | NC_018001.1 | 13062247 |

-continued

| Description | Microrganism | Accession | GeneID |
|---|---|---|---|
| aldehyde:ferredoxin oxidoreductase | *Desulfurococcus kamchatkensis* 1221n | NC_011766.1 | 7171099 |
| aldehyde:ferredoxin oxidoreductase | *Desulfurococcus kamchatkensis* 1221n | NC_011766.1 | 7171759 |
| aldehyde:ferredoxin oxidoreductase | *Desulfurococcus kamchatkensis* 1221n | NC_011766.1 | 7170725 |
| aldehyde:ferredoxin oxidoreductase | *Desulfurococcus mucosus* DSM 2162 | NC_014961.1 | 10152801 |
| aldehyde:ferredoxin oxidoreductase | *Ferroglobus placidus* DSM 10642 | NC_013849.1 | 8778536 |
| aldehyde:ferredoxin oxidoreductase | *Ferroglobus placidus* DSM 10642 | NC_013849.1 | 8779007 |
| aldehyde:ferredoxin oxidoreductase | *Ferroglobus placidus* DSM 10642 | NC_013849.1 | 8778940 |
| aldehyde:ferredoxin oxidoreductase | *Ferroglobus placidus* DSM 10642 | NC_013849.1 | 8779639 |
| aldehyde:ferredoxin oxidoreductase | *Ferroglobus placidus* DSM 10642 | NC_013849.1 | 8778820 |
| aldehyde:ferredoxin oxidoreductase | *Ferroglobus placidus* DSM 10642 | NC_013849.1 | 8778745 |
| aldehyde:ferredoxin oxidoreductase | *Ferroglobus placidus* DSM 10642 | NC_013849.1 | 8779874 |
| aldehyde:ferredoxin oxidoreductase | *Fervidicoccus fontis* Kam940 | NC_017461.1 | 12449263 |
| aldehyde:ferredoxin oxidoreductase | *Fervidicoccus fontis* Kam940 | NC_017461.1 | 12449994 |
| aldehyde:ferredoxin oxidoreductase | *Fervidicoccus fontis* Kam940 | NC_017461.1 | 12449294 |
| aldehyde:ferredoxin oxidoreductase | *Fervidicoccus fontis* Kam940 | NC_017461.1 | 12449682 |
| aldehyde:ferredoxin oxidoreductase | *Geobacter sulfurreducens* PCA | NC_002939.5 | 2685730 |
| aldehyde:ferredoxin oxidoreductase | *Geobacter sulfurreducens* PCA | NC_002939.5 | 2687039 |
| aldehyde:ferredoxin oxidoreductase | *Halalkalicoccus jeotgali* B3 | NC_014297.1 | 9418623 |
| aldehyde:ferredoxin oxidoreductase | *Halalkalicoccus jeotgali* B3 | NC_014297.1 | 9418760 |
| aldehyde:ferredoxin oxidoreductase | *Halalkalicoccus jeotgali* B3 | NC_014297.1 | 9420819 |
| aldehyde:ferredoxin oxidoreductase | *Halalkalicoccus jeotgali* B3 | NC_014297.1 | 9418748 |
| aldehyde:ferredoxin oxidoreductase | *Haloarcula hispanica* ATCC 33960 | NC_015948.1 | 11051410 |
| aldehyde:ferredoxin oxidoreductase | *Haloarcula hispanica* ATCC 33960 | NC_015948.1 | 11050783 |
| aldehyde:ferredoxin oxidoreductase | *Haloarcula hispanica* ATCC 33960 | NC_015948.1 | 11051433 |
| aldehyde:ferredoxin oxidoreductase | *Haloarcula hispanica* N601 | NC_023013.1 | 23805333 |
| aldehyde:ferredoxin oxidoreductase | *Haloarcula hispanica* N601 | NC_023013.1 | 23805138 |
| aldehyde:ferredoxin oxidoreductase | *Haloarcula hispanica* N601 | NC_023013.1 | 23804665 |
| aldehyde:ferredoxin oxidoreductase | *Haloarcula marismortui* ATCC 43049 | NC_006396.1 | 3127969 |
| aldehyde:ferredoxin oxidoreductase | *Haloarcula marismortui* ATCC 43049 | NC_006396.1 | 3129232 |
| aldehyde:ferredoxin oxidoreductase | *Haloferax mediterranei* ATCC 33500 | NC_017941.2 | 13028168 |
| aldehyde:ferredoxin oxidoreductase | *Haloferax mediterranei* ATCC 33500 | NC_017941.2 | 13028399 |
| aldehyde:ferredoxin oxidoreductase | *Haloferax volcanii* DS2 | NC_013964.1 | 8919329 |
| aldehyde:ferredoxin oxidoreductase | *Haloferax volcanii* DS2 | NC_013964.1 | 8919033 |
| aldehyde:ferredoxin oxidoreductase | *Haloferax volcanii* DS2 | NC_013967.1 | 8926544 |
| aldehyde:ferredoxin oxidoreductase | *Halogeomefricum borinquense* DSM 11551 | NC_014735.1 | 9989054 |
| aldehyde:ferredoxin oxidoreductase | *Halogeomefricum borinquense* DSM 11551 | NC_014729.1 | 9994424 |
| aldehyde:ferredoxin oxidoreductase | *Halogeomefricum borinquense* DSM 11551 | NC_014729.1 | 9992444 |
| aldehyde:ferredoxin oxidoreductase | halophilic archaeon DL31 | NC_015954.1 | 11095016 |
| aldehyde:ferredoxin oxidoreductase | halophilic archaeon DL31 | NC_015954.1 | 11095541 |
| aldehyde:ferredoxin oxidoreductase | halophilic archaeon DL31 | NC_015954.1 | 11094595 |
| aldehyde:ferredoxin oxidoreductase | halophilic archaeon DL31 | NC_015954.1 | 11096497 |
| aldehyde:ferredoxin oxidoreductase | halophilic archaeon DL31 | NC_015954.1 | 11094563 |
| aldehyde:ferredoxin oxidoreductase | halophilic archaeon DL31 | NC_015954.1 | 11095602 |
| aldehyde:ferredoxin oxidoreductase | *Halopiger xanaduensis* SH-6 | NC_015666.1 | 10799161 |
| aldehyde:ferredoxin oxidoreductase | *Halopiger xanaduensis* SH-6 | NC_015658.1 | 10795465 |
| aldehyde:ferredoxin oxidoreductase | *Halopiger xanaduensis* SH-6 | NC_015666.1 | 10798686 |
| aldehyde:ferredoxin oxidoreductase | *Halopiger xanaduensis* SH-6 | NC_015666.1 | 10796679 |
| aldehyde:ferredoxin oxidoreductase | *Halorubrum lacusprofundi* ATCC 49239 | NC_0 12029.1 | 7400122 |
| aldehyde:ferredoxin oxidoreductase | *Halorubrum lacusprofundi* ATCC 49239 | NC_0 12029.1 | 7400291 |
| aldehyde:ferredoxin oxidoreductase | *Halorubrum lacusprofundi* ATCC 49239 | NC_012029.1 | 7400689 |
| aldehyde:ferredoxin oxidoreductase | *Haloterrigena turkmenica* DSM 5511 | NC_013744.1 | 8744461 |
| aldehyde:ferredoxin oxidoreductase | *Haloterrigena turkmenica* DSM 5511 | NC_013744.1 | 8744695 |
| aldehyde:ferredoxin oxidoreductase | *Haloterrigena turkmenica* DSM 5511 | NC_013743.1 | 8740954 |
| aldehyde:ferredoxin oxidoreductase | *Haloterrigena turkmenica* DSM 5511 | NC_013745.1 | 8745418 |
| aldehyde:ferredoxin oxidoreductase | *Haloterrigena turkmenica* DSM 5511 | NC_013743.1 | 8742968 |
| aldehyde:ferredoxin oxidoreductase | *Haloterrigena turkmenica* DSM 5511 | NC_013743.1 | 8741246 |

| Description | Microrganism | Accession | GeneID |
| --- | --- | --- | --- |
| aldehyde:ferredoxin oxidoreductase | Haloterrigena turkmenica DSM 5511 | NC_013743.1 | 8741269 |
| aldehyde:ferredoxin oxidoreductase | Haloterrigena turkmenica DSM 5511 | NC_013745.1 | 8745313 |
| aldehyde:ferredoxin oxidoreductase | Hyperthermus butylicus DSM 5456 | NC_008818.1 | 4781896 |
| aldehyde:ferredoxin oxidoreductase | Hyperthermus butylicus DSM 5456 | NC_008818.1 | 4782266 |
| aldehyde:ferredoxin oxidoreductase | Hyperthermus butylicus DSM 5456 | NC_008818.1 | 4782804 |
| aldehyde:ferredoxin oxidoreductase | Hyperthermus butylicus DSM 5456 | NC_008818.1 | 4781774 |
| aldehyde:ferredoxin oxidoreductase | Ignicoccus hospitalis KIN4/I | NC_009776.1 | 5562477 |
| aldehyde:ferredoxin oxidoreductase | Ignicoccus hospitalis KIN4/I | NC_009776.1 | 5562774 |
| aldehyde:ferredoxin oxidoreductase | Ignisphaera aggregans DSM 17230 | NC_014471.1 | 9716798 |
| aldehyde:ferredoxin oxidoreductase | Methanocaldococcus jannaschii DSM 2661 | NC_000909.1 | 1452083 |
| aldehyde:ferredoxin oxidoreductase | Methanocella arvoryzae MRE50 | NC_009464.1 | 5142690 |
| aldehyde:ferredoxin oxidoreductase | Methanocella arvoryzae MRE50 | NC_009464.1 | 5143773 |
| aldehyde:ferredoxin oxidoreductase | Methanocella conradii HZ254 | NC_017034.1 | 11972399 |
| aldehyde:ferredoxin oxidoreductase | Methanocella conradii HZ254 | NC_017034.1 | 11971349 |
| aldehyde:ferredoxin oxidoreductase | Methanocella paludicola SANAE | NC_013665.1 | 8680711 |
| aldehyde:ferredoxin oxidoreductase | Methanocella paludicola SANAE | NC_013665.1 | 8680676 |
| aldehyde:ferredoxin oxidoreductase | Methanocorpusculum labreanum Z | NC_008942.1 | 4795790 |
| aldehyde:ferredoxin oxidoreductase | Methanoculleus marisnigri JR1 | NC_009051.1 | 4847673 |
| aldehyde:ferredoxin oxidoreductase | Methanohalobium evestigatum Z-7303 | NC_014253.1 | 9347460 |
| aldehyde:ferredoxin oxidoreductase | Methanohalobium evestigatum Z-7303 | NC_014253.1 | 9347022 |
| aldehyde:ferredoxin oxidoreductase | Methanolobus psychrophilus R15 | NC_018876.1 | 13845119 |
| aldehyde:ferredoxin oxidoreductase | Methanomethylovorans hollandica DSM 15978 | NC_019977.1 | 14408029 |
| aldehyde:ferredoxin oxidoreductase | Methanosaeta harundinacea 6Ac | NC_017527.1 | 12511443 |
| aldehyde:ferredoxin oxidoreductase | Methanosaeta thermophila PT | NC_008553.1 | 4462364 |
| aldehyde:ferredoxin oxidoreductase | Methanosalsum zhilinae DSM 4017 | NC_015676.1 | 10822365 |
| aldehyde:ferredoxin oxidoreductase | Methanosarcina acetivorans C2A | NC_003552.1 | 1475882 |
| aldehyde:ferredoxin oxidoreductase | Methanosarcina acetivorans C2A | NC_003552.1 | 1474856 |
| aldehyde:ferredoxin oxidoreductase | Methanosarcina acetivorans C2A | NC_003552.1 | 1473602 |
| aldehyde:ferredoxin oxidoreductase | Methanosarcina barkeri str. Fusaro | NC_007355.1 | 3625763 |
| aldehyde:ferredoxin oxidoreductase | Methanosarcina mazei Go1 | NC_003901.1 | 1479263 |
| aldehyde:ferredoxin oxidoreductase | Methanosarcina mazei Go1 | NC_003901.1 | 1481668 |
| aldehyde:ferredoxin oxidoreductase | Methanosarcina mazei Go1 | NC_003901.1 | 1480987 |
| aldehyde:ferredoxin oxidoreductase | Methanosarcina mazei Tuc01 | NC_020389.1 | 14656065 |
| aldehyde:ferredoxin oxidoreductase | Methanosarcina mazei Tuc01 | NC_020389.1 | 14656771 |
| aldehyde:ferredoxin oxidoreductase | Methanosarcina mazei Tuc01 | NC_020389.1 | 14654304 |
| aldehyde:ferredoxin oxidoreductase | Methanosphaerula palustris E1-9c | NC_011832.1 | 7271108 |
| aldehyde:ferredoxin oxidoreductase | Methanospirillum hungatei JF-1 | NC_007796.1 | 3924565 |
| aldehyde:ferredoxin oxidoreductase | Methylomicrobium alcaliphilum 20Z | NC_016112.1 | 11361147 |
| aldehyde:ferredoxin oxidoreductase | Moorella thermoacetica ATCC 39073 | NC_007644.1 | 3831332 |
| aldehyde:ferredoxin oxidoreductase | Moorella thermoacetica ATCC 39073 | NC_007644.1 | 3830998 |
| aldehyde:ferredoxin oxidoreductase | Moorella thermoacetica ATCC 39073 | NC_007644.1 | 3831866 |
| aldehyde:ferredoxin oxidoreductase | Natrialba magadii ATCC 43099 | NC_013922.1 | 8824961 |
| aldehyde:ferredoxin oxidoreductase | Natrialba magadii ATCC 43099 | NC_013922.1 | 8823392 |
| aldehyde:ferredoxin oxidoreductase | Natrialba magadii ATCC 43099 | NC_013923.1 | 8826737 |
| aldehyde:ferredoxin oxidoreductase | Natrialba magadii ATCC 43099 | NC_013922.1 | 8825516 |
| aldehyde:ferredoxin oxidoreductase | Natrinema pellirubrum DSM 15624 | NC_019962.1 | 14335278 |
| aldehyde:ferredoxin oxidoreductase | Natrinema pellirubrum DSM 15624 | NC_019962.1 | 14333050 |
| aldehyde:ferredoxin oxidoreductase | Natrinema pellirubrum DSM 15624 | NC_019962.1 | 14333754 |
| aldehyde:ferredoxin oxidoreductase | Natrinema sp. J7-2 | NC_018224.1 | 13349954 |
| aldehyde:ferredoxin oxidoreductase | Natronobacterium gregoryi SP2 | NC_019792.1 | 14210296 |
| aldehyde:ferredoxin oxidoreductase | Natronobacterium gregoryi SP2 | NC_019792.1 | 14207133 |
| aldehyde:ferredoxin oxidoreductase | Natronobacterium gregoryi SP2 | NC_019792.1 | 14209682 |
| aldehyde:ferredoxin oxidoreductase | Natronobacterium gregoryi SP2 | NC_019792.1 | 14207576 |
| aldehyde:ferredoxin oxidoreductase | Natronobacterium gregoryi SP2 | NC_019792.1 | 14206941 |
| aldehyde:ferredoxin oxidoreductase | Natronobacterium gregoryi SP2 | NC_019792.1 | 14206532 |
| aldehyde:ferredoxin oxidoreductase | Natronococcus occultus SP4 | NC_019974.1 | 14403316 |
| aldehyde:ferredoxin oxidoreductase | Natronococcus occultus SP4 | NC_019974.1 | 14405255 |
| aldehyde:ferredoxin oxidoreductase | Natronococcus occultus SP4 | NC_019974.1 | 14403781 |
| aldehyde:ferredoxin oxidoreductase | Natronococcus occultus SP4 | NC_019974.1 | 14402014 |
| aldehyde:ferredoxin oxidoreductase | Natronomonas moolapensis 8.8.11 | NC_020388.1 | 14651997 |
| aldehyde:ferredoxin oxidoreductase | Natronomonas moolapensis 8.8.11 | NC_020388.1 | 14652892 |
| aldehyde:ferredoxin oxidoreductase | Natronomonas moolapensis 8.8.11 | NC_020388.1 | 14651999 |
| aldehyde:ferredoxin oxidoreductase | Natronomonas pharaonis DSM 2160 | NC_007427.1 | 3694680 |
| aldehyde:ferredoxin oxidoreductase | Natronomonas pharaonis DSM 2160 | NC_007426.1 | 3702508 |
| aldehyde:ferredoxin oxidoreductase | Natronomonas pharaonis DSM 2160 | NC_007426.1 | 3702507 |
| aldehyde:ferredoxin oxidoreductase | Natronomonas pharaonis DSM 2160 | NC_007426.1 | 3702509 |
| aldehyde:ferredoxin oxidoreductase | Pyrobaculum aerophilum str.IM2 | NC_003364.1 | 1464236 |
| aldehyde:ferredoxin oxidoreductase | Pyrobaculum aerophilum str.IM2 | NC_003364.1 | 1464102 |

| Description | Microrganism | Accession | GeneID |
| --- | --- | --- | --- |
| aldehyde:ferredoxin oxidoreductase | Pyrobaculum aerophilum str.IM2 | NC_003364.1 | 1465126 |
| aldehyde:ferredoxin oxidoreductase | Pyrobaculum aerophilum str.IM2 | NC_003364.1 | 1465445 |
| aldehyde:ferredoxin oxidoreductase | Pyrobaculum arsenaticum DSM 13514 | NC_009376.1 | 5055904 |
| aldehyde:ferredoxin oxidoreductase | Pyrobaculum arsenaticum DSM 13514 | NC_009376.1 | 5055700 |
| aldehyde:ferredoxin oxidoreductase | Pyrobaculum arsenaticum DSM 13514 | NC_009376.1 | 5054881 |
| aldehyde:ferredoxin oxidoreductase | Pyrobaculum arsenaticum DSM 13514 | NC_009376.1 | 5054644 |
| aldehyde:ferredoxin oxidoreductase | Pyrobaculum arsenaticum DSM 13514 | NC_009376.1 | 5054547 |
| aldehyde:ferredoxin oxidoreductase | Pyrobaculum calidifontis JCM 11548 | NC_009073.1 | 4910224 |
| aldehyde:ferredoxin oxidoreductase | Pyrobaculum calidifontis JCM 11548 | NC_009073.1 | 4908822 |
| aldehyde:ferredoxin oxidoreductase | Pyrobaculum calidifontis JCM 11548 | NC_009073.1 | 4909927 |
| aldehyde:ferredoxin oxidoreductase | Pyrobaculum calidifontis JCM 11548 | NC_009073.1 | 4910099 |
| aldehyde:ferredoxin oxidoreductase | Pyrobaculum islandicum DSM 4184 | NC_008701.1 | 4617364 |
| aldehyde:ferredoxin oxidoreductase | Pyrobaculum islandicum DSM 4184 | NC_008701.1 | 4616724 |
| aldehyde:ferredoxin oxidoreductase | Pyrobaculum islandicum DSM 4184 | NC_008701.1 | 4617494 |
| aldehyde:ferredoxin oxidoreductase | Pyrobaculum neutrophilum V24Sta | NC_010525.1 | 6165427 |
| aldehyde:ferredoxin oxidoreductase | Pyrobaculum neutrophilum V24Sta | NC_010525.1 | 6164958 |
| aldehyde:ferredoxin oxidoreductase | Pyrobaculum neutrophilum V24Sta | NC_010525.1 | 6164976 |
| aldehyde:ferredoxin oxidoreductase | Pyrobaculum oguniense TE7 | NC_016885.1 | 11853778 |
| aldehyde:ferredoxin oxidoreductase | Pyrobaculum oguniense TE7 | NC_016885.1 | 11854024 |
| aldehyde:ferredoxin oxidoreductase | Pyrobaculum oguniense TE7 | NC_016885.1 | 11856490 |
| aldehyde:ferredoxin oxidoreductase | Pyrobaculum oguniense TE7 | NC_016885.1 | 11856176 |
| aldehyde:ferredoxin oxidoreductase | Pyrobaculum oguniense TE7 | NC_016885.1 | 11854908 |
| aldehyde:ferredoxin oxidoreductase | Pyrobaculum sp. 1860 | NC_016645.1 | 11594868 |
| aldehyde:ferredoxin oxidoreductase | Pyrobaculum sp. 1860 | NC_016645.1 | 11596631 |
| aldehyde:ferredoxin oxidoreductase | Pyrobaculum sp. 1860 | NC_016645.1 | 11594049 |
| aldehyde:ferredoxin oxidoreductase | Pyrococcus abyssi GE5 | NC_000868.1 | 1496313 |
| aldehyde:ferredoxin oxidoreductase | Pyrococcus abyssi GE5 | NC_000868.1 | 1495669 |
| aldehyde:ferredoxin oxidoreductase | Pyrococcus abyssi GE5 | NC_000868.1 | 1496580 |
| aldehyde:ferredoxin oxidoreductase | Pyrococcus abyssi GE5 | NC_000868.1 | 1495287 |
| aldehyde:ferredoxin oxidoreductase | Pyrococcus furiosus COM1 | NC_018092.1 | 13302148 |
| aldehyde:ferredoxin oxidoreductase | Pyrococcus furiosus COM1 | NC_018092.1 | 13301806 |
| aldehyde:ferredoxin oxidoreductase | Pyrococcus furiosus COM1 | NC_018092.1 | 13301219 |
| aldehyde:ferredoxin oxidoreductase | Pyrococcus furiosus COM1 | NC_018092.1 | 13300785 |
| aldehyde:ferredoxin oxidoreductase | Pyrococcus furiosus DSM 3638 | NC_003413.1 | 1468181 |
| aldehyde:ferredoxin oxidoreductase | Pyrococcus furiosus DSM 3638 | NC_003413.1 | 1469073 |
| aldehyde:ferredoxin oxidoreductase | Pyrococcus furiosus DSM 3638 | NC_003413.1 | 1469843 |
| aldehyde:ferredoxin oxidoreductase | Pyrococcus horikoshii OT3 | NC_000961.1 | 1443218 |
| aldehyde:ferredoxin oxidoreductase | Pyrococcus horikoshii OT3 | NC_000961.1 | 1443341 |
| aldehyde:ferredoxin oxidoreductase | Pyrococcus horikoshii OT3 | NC_000961.1 | 1443932 |
| aldehyde:ferredoxin oxidoreductase | Pyrococcus horikoshii OT3 | NC_000961.1 | 1443598 |
| aldehyde:ferredoxin oxidoreductase | Pyrococcus sp. NA2 | NC_015474.1 | 10555029 |
| aldehyde:ferredoxin oxidoreductase | Pyrococcus sp. NA2 | NC_015474.1 | 10554020 |
| aldehyde:ferredoxin oxidoreductase | Pyrococcus sp. NA2 | NC_015474.1 | 10555341 |
| aldehyde:ferredoxin oxidoreductase | Pyrococcus sp. ST04 | NC_017946.1 | 13022107 |
| aldehyde:ferredoxin oxidoreductase | Pyrococcus sp. ST04 | NC_017946.1 | 13022436 |
| aldehyde:ferredoxin oxidoreductase | Pyrococcus sp. ST04 | NC_017946.1 | 13021314 |
| aldehyde:ferredoxin oxidoreductase | Pyrococcus yayanosii CH1 | NC_015680.1 | 10837518 |
| aldehyde:ferredoxin oxidoreductase | Pyrococcus yayanosii CH1 | NC_015680.1 | 10837112 |
| aldehyde:ferredoxin oxidoreductase | Pyrococcus yayanosii CH1 | NC_015680.1 | 10837264 |
| aldehyde:ferredoxin oxidoreductase | Pyrolobus fumarii JA | NC_015931.1 | 11138144 |
| aldehyde:ferredoxin oxidoreductase | Pyrolobus fumarii JA | NC_015931.1 | 11138776 |
| aldehyde:ferredoxin oxidoreductase | Pyrolobus fumarii JA | NC_015931.1 | 11139127 |
| aldehyde:ferredoxin oxidoreductase | Rhodospirillum rubrum ATCC 11170 | NC_007643.1 | 3833668 |
| aldehyde:ferredoxin oxidoreductase | Staphylothermus hellenicus DSM 12710 | NC_014205.1 | 9234557 |
| aldehyde:ferredoxin oxidoreductase | Staphylothermus hellenicus DSM 12710 | NC_014205.1 | 9233414 |
| aldehyde:ferredoxin oxidoreductase | Staphylothermus hellenicus DSM 12710 | NC_014205.1 | 9234134 |
| aldehyde:ferredoxin oxidoreductase | Staphylothermus hellenicus DSM 12710 | NC_014205.1 | 9234110 |
| aldehyde:ferredoxin oxidoreductase | Staphylothermus marinus F1 | NC_009033.1 | 4907444 |
| aldehyde:ferredoxin oxidoreductase | Staphylothermus marinus F1 | NC_009033.1 | 4907343 |
| aldehyde:ferredoxin oxidoreductase | Thermanaerovibrio acidaminovorans DSM 6589 | NC_013522.1 | 8630284 |
| aldehyde:ferredoxin oxidoreductase | Thermanaerovibrio acidaminovorans DSM 6589 | NC_013522.1 | 8630027 |

| Description | Microrganism | Accession | GeneID |
| --- | --- | --- | --- |
| aldehyde:ferredoxin oxidoreductase | *Thermanaerovibrio acidaminovorans* DSM 6589 | NC_013522.1 | 8630623 |
| aldehyde:ferredoxin oxidoreductase | *Thermoanaerobacter wiegelii* Rt8.B1 | NC_015958.1 | 11082596 |
| aldehyde:ferredoxin oxidoreductase | *Thermococcus barophilus* MP | NC_014804.1 | 10041639 |
| aldehyde:ferredoxin oxidoreductase | *Thermococcus barophilus* MP | NC_014804.1 | 10041106 |
| aldehyde:ferredoxin oxidoreductase | *Thermococcus barophilus* MP | NC_014804.1 | 10042460 |
| aldehyde:ferredoxin oxidoreductase | *Thermococcus cleftensis* | NC_018015.1 | 13037745 |
| aldehyde:ferredoxin oxidoreductase | *Thermococcus cleftensis* | NC_018015.1 | 13038896 |
| aldehyde:ferredoxin oxidoreductase | *Thermococcus cleftensis* | NC_018015.1 | 13037242 |
| aldehyde:ferredoxin oxidoreductase | *Thermococcus gammatolerans* EJ3 | NC_012804.1 | 7988317 |
| aldehyde:ferredoxin oxidoreductase | *Thermococcus gammatolerans* EJ3 | NC_012804.1 | 7987451 |
| aldehyde:ferredoxin oxidoreductase | *Thermococcus kodakarensis* KOD1 | NC_006624.1 | 3233851 |
| aldehyde:ferredoxin oxidoreductase | *Thermococcus kodakarensis* KOD1 | NC_006624.1 | 3233735 |
| aldehyde:ferredoxin oxidoreductase | *Thermococcus litoralis* DSM 5473 | NC_022084.1 | 16550741 |
| aldehyde:ferredoxin oxidoreductase | *Thermococcus litoralis* DSM 5473 | NC_022084.1 | 16548761 |
| aldehyde:ferredoxin oxidoreductase | *Thermococcus litoralis* DSM 5473 | NC_022084.1 | 16550885 |
| aldehyde:ferredoxin oxidoreductase | *Thermococcus onnurineus* NA1 | NC_011529.1 | 7018383 |
| aldehyde:ferredoxin oxidoreductase | *Thermococcus onnurineus* NA1 | NC_011529.1 | 7016739 |
| aldehyde:ferredoxin oxidoreductase | *Thermococcus onnurineus* NA1 | NC_011529.1 | 7017051 |
| aldehyde:ferredoxin oxidoreductase | *Thermococcus onnurineus* NA1 | NC_011529.1 | 7017476 |
| aldehyde:ferredoxin oxidoreductase | *Thermococcus sibiricus* MM 739 | NC_012883.1 | 8096638 |
| aldehyde:ferredoxin oxidoreductase | *Thermococcus sibiricus* MM 739 | NC_012883.1 | 8096005 |
| aldehyde:ferredoxin oxidoreductase | *Thermococcus sibiricus* MM 739 | NC_012883.1 | 8096629 |
| aldehyde:ferredoxin oxidoreductase | *Thermococcus sibiricus* MM 739 | NC_012883.1 | 8095463 |
| aldehyde:ferredoxin oxidoreductase | *Thermococcus sibiricus* MM 739 | NC_012883.1 | 8096131 |
| aldehyde:ferredoxin oxidoreductase | *Thermococcus sibiricus* MM 739 | NC_012883.1 | 8096636 |
| aldehyde:ferredoxin oxidoreductase | *Thermococcus* sp. 4557 | NC_015865.1 | 11015504 |
| aldehyde:ferredoxin oxidoreductase | *Thermococcus* sp. 4557 | NC_015865.1 | 11015249 |
| aldehyde:ferredoxin oxidoreductase | *Thermococcus* sp. 4557 | NC_015865.1 | 11015571 |
| aldehyde:ferredoxin oxidoreductase | *Thermococcus* sp. AM4 | NC_016051.1 | 7419050 |
| aldehyde:ferredoxin oxidoreductase | *Thermococcus* sp. AM4 | NC_016051.1 | 7418514 |
| aldehyde:ferredoxin oxidoreductase | *Thermococcus* sp. AM4 | NC_016051.1 | 7420292 |
| aldehyde:ferredoxin oxidoreductase | *Thermodesulfovibrio yellowstonii* DSM 11347 | NC_011296.1 | 6941429 |
| aldehyde:ferredoxin oxidoreductase | *Thermodesulfovibrio yellowstonii* DSM 11347 | NC_011296.1 | 6943174 |
| aldehyde:ferredoxin oxidoreductase | *Thermodesulfovibrio yellowstonii* DSM 11347 | NC_011296.1 | 6941905 |
| aldehyde:ferredoxin oxidoreductase | *Thermofilum pendens* Hrk 5 | NC_008698.1 | 4602054 |
| aldehyde:ferredoxin oxidoreductase | *Thermofilum pendens* Hrk 5 | NC_008698.1 | 4601386 |
| aldehyde:ferredoxin oxidoreductase | *Thermofilum pendens* Hrk 5 | NC_008698.1 | 4600878 |
| aldehyde:ferredoxin oxidoreductase | *Thermofilum pendens* Hrk 5 | NC_008698.1 | 4600730 |
| aldehyde:ferredoxin oxidoreductase | *Thermofilum* sp. 1910b | NC_022093.1 | 16572780 |
| aldehyde:ferredoxin oxidoreductase | *Thermofilum* sp. 1910b | NC_022093.1 | 16572926 |
| aldehyde:ferredoxin oxidoreductase | *Thermofilum* sp. 1910b | NC_022093.1 | 16573009 |
| aldehyde:ferredoxin oxidoreductase | *Thermofilum* sp. 1910b | NC_022093.1 | 16574342 |
| aldehyde:ferredoxin oxidoreductase | *Thermogladius cellulolyticus* 1633 | NC_017954.1 | 13012904 |
| aldehyde:ferredoxin oxidoreductase | *Thermoplasma acidophilum* DSM 1728 | NC_002578.1 | 1456355 |
| aldehyde:ferredoxin oxidoreductase | *Thermoplasma acidophilum* DSM 1728 | NC_002578.1 | 1456646 |
| aldehyde:ferredoxin oxidoreductase | *Thermoplasma vokanium* GSS1 | NC_002689.2 | 1441901 |
| aldehyde:ferredoxin oxidoreductase | *Thermoplasma vokanium* GSS1 | NC_002689.2 | 1441379 |
| aldehyde:ferredoxin oxidoreductase | *Thermoproteus tenax* Kra 1 | NC_016070.1 | 11262174 |
| aldehyde:ferredoxin oxidoreductase | *Thermoproteus tenax* Kra 1 | NC_016070.1 | 11262275 |
| aldehyde:ferredoxin oxidoreductase | *Thermoproteus tenax* Kra 1 | NC_016070.1 | 11262652 |
| aldehyde:ferredoxin oxidoreductase | *Thermoproteus tenax* Kra 1 | NC_016070.1 | 11262926 |
| aldehyde:ferredoxin oxidoreductase | *Thermoproteus uzoniensis* 768-20 | NC_015315.1 | 10361668 |
| aldehyde:ferredoxin oxidoreductase | *Thermoproteus uzoniensis* 768-20 | NC_015315.1 | 10361250 |
| aldehyde:ferredoxin oxidoreductase | *Thermoproteus uzoniensis* 768-20 | NC_015315.1 | 10360972 |
| aldehyde:ferredoxin oxidoreductase | *Thermosphaera aggregans* DSM 11486 | NC_014160.1 | 9165115 |
| aldehyde:ferredoxin oxidoreductase | *Thermosphaera aggregans* DSM 11486 | NC_014160.1 | 9165462 |
| aldehyde:ferredoxin oxidoreductase | *Thermus thermophilus* HB8 | NC_006461.1 | 3168554 |
| aldehyde:ferredoxin oxidoreductase | *Thermus thermophilus* HB8 | NC_006461.1 | 3168612 |
| aldehyde:ferredoxin oxidoreductase | *Vulcanisaeta disfributa* DSM 14429 | NC_014537.1 | 9753145 |
| aldehyde:ferredoxin oxidoreductase | *Vulcanisaeta disfributa* DSM 14429 | NC_014537.1 | 9750947 |
| aldehyde:ferredoxin oxidoreductase | *Vulcanisaeta disfributa* DSM 14429 | NC_014537.1 | 9750989 |
| aldehyde:ferredoxin oxidoreductase | *Vulcanisaeta disfributa* DSM 14429 | NC_014537.1 | 9753486 |
| aldehyde:ferredoxin oxidoreductase | *Vulcanisaeta disfributa* DSM 14429 | NC_014537.1 | 9751414 |
| aldehyde:ferredoxin oxidoreductase | *Vulcanisaeta moutnovskia* 768-28 | NC_015151.1 | 10288238 |
| aldehyde:ferredoxin oxidoreductase | *Vulcanisaeta moutnovskia* 768-28 | NC_015151.1 | 10288894 |
| aldehyde:ferredoxin oxidoreductase | *Vulcanisaeta moutnovskia* 768-28 | NC_015151.1 | 10288574 |
| aldehyde:ferredoxin oxidoreductase | *Vulcanisaeta moutnovskia* 768-28 | NC_015151.1 | 10288827 |
| aldehyde:ferredoxin oxidoreductase | *Vulcanisaeta moutnovskia* 768-28 | NC_015151.1 | 10288607 |

| Description | Microorganism | Accession | GeneID |
| --- | --- | --- | --- |
| aldehyde:ferredoxin oxidoreductase | *Vulcanisaeta moutnovskia* 768-28 | NC_015151.1 | 10288523 |
| aldehyde:ferredoxin oxidoreductase | *Vulcanisaeta moutnovskia* 768-28 | NC_015151.1 | 10288815 |

AOR catalyzes the reaction of an acid and reduced ferredoxin to form an aldehyde and oxidized ferredoxin. In acetogens, this reaction can be coupled to oxidation CO (via CO dehydrogenase, EC 1.2.7.4) or hydrogen (via ferredoxin-dependent hydrogenase, EC 1.12.7.2 or 1.12.1.4) that both yield reduced ferredoxin (Köpke, *Curr Opin Biotechnol* 22: 320-325, 2011; Köpke, *PNAS USA*, 107: 13087-13092, 2010). *Clostridium autoethanogenum, Clostridium ljungdahlii*, and *Clostridium ragsdalei* have native activity for this step. However, overexpression of endogenous AOR or introduction of an exogenous AOR in *Clostridium autoethanogenum, Clostridium ljungdahlii*, or *Clostridium ragsdalei* may be desirable to enhance product yields. Alternatively, exogenous AOR may be introduced into a microorganism that does not natively comprise AOR, e.g., *E. coli*. In particular, the co-expression of Ptb-Buk and AOR (and, optionally, Adh) may enable such a microorganism to produce new non-native products.

Step 17 shows the conversion of 3-hydroxybutyrylaldehyde to 1,3-butanediol. This step may be catalyzed by alcohol dehydrogenase (EC 1.1.1.1. or 1.1.1.2.). Alcohol dehydrogenase can convert an aldehyde and NAD(P)H to an alcohol and NAD(P). The alcohol dehydrogenase may be, for example, Adh from *Clostridium autoethanogenum* (AGY76060.1) (SEQ ID NO: 67), *Clostridium ljungdahlii* (ADK17019.1) (SEQ ID NO: 68), or *Clostridium ragsdalei*, BdhB from *Clostridium acetobutylicum* (NP_349891.1) (SEQ ID NO: 69), Bdh from *Clostridium beijerinckii* (WP_041897187.1) (SEQ ID NO: 70), Bdh1 from *Clostridium ljungdahlii* (YP_003780648.1) (SEQ ID NO: 71), Bdh1 from *Clostridium autoethanogenum* (AGY76060.1) (SEQ ID NO: 72), Bdh2 from *Clostridium ljungdahlii* (YP_003782121.1) (SEQ ID NO: 73), Bdh2 from *Clostridium autoethanogenum* (AGY74784.1) (SEQ ID NO: 74), AdhE1 from *Clostridium acetobutylicum* (NP_149325.1) (SEQ ID NO: 75), AdhE2 from *Clostridium acetobutylicum* (NP_149199.1) (SEQ ID NO: 76), AdhE from *Clostridium beijerinckii* (WP_041893626.1) (SEQ ID NO: 77), AdhE1 from *Clostridium autoethanogenum* (WP_023163372.1) (SEQ ID NO: 78), or AdhE2 from *Clostridium autoethanogenum* (WP_023163373.1) (SEQ ID NO: 79). *Clostridium autoethanogenum, Clostridium ljungdahlii*, and *Clostridium ragsdalei* have native activity for this step. However, overexpression of endogenous alcohol dehydrogenase or introduction of an exogenous alcohol dehydrogenase in *Clostridium autoethanogenum, Clostridium ljungdahlii*, or *Clostridium ragsdalei* may be desirable to enhance product yields. *Escherichia coli* likely does not have native activity for this step.

Step 18 shows the conversion of 3-hydroxybutyryl-CoA to 3-hydroxybutyrylaldehyde. This step may be catalyzed by butyraldehyde dehydrogenase (EC 1.2.1.57). The butyraldehyde dehydrogenase may be, for example, Bld from *Clostridium saccharoperbutylacetonicum* (AAP42563.1) (SEQ ID NO: 80). *Clostridium autoethanogenum, Clostridium ljungdahlii*, and *Clostridium ragsdalei* do not have known native activity for this step. *Escherichia coli* does not have known native activity for this step.

Step 19 shows the conversion of 3-hydroxybutyryl-CoA to 2-hydroxyisobutyryl-CoA. This step may be catalyzed by 2-hydroxyisobutyryl-CoA mutase (EC 5.4.99.-). The 2-hydroxyisobutyryl-CoA mutase may be, for example, HcmAB from *Aquincola tertiaricarbonis* (AFK77668.1, large subunit; AFK77665.1, small subunit) (SEQ ID NOs: 81 and 82, respectively) or HcmAB from *Kyrpidia tusciae* (WP_013074530.1, large subunit; WP_013074531.1, small subunit) (SEQ ID NOs: 83 and 84, respectively). Chaperone MeaB (AFK77667.1, *Aquincola tertiaricarbonis*; WP_013074529.1, *Kyrpidia tusciae*) (SEQ ID NOs: 85 and 86, respectively) has been described to improve activity of HcmAB by reactivating HcmAB, although MeaB is not required for HcmAB function (Yaneva, *J Biol Chem*, 287: 15502-15511, 2012). *Clostridium autoethanogenum, Clostridium ljungdahlii*, and *Clostridium ragsdalei* do not have known native activity for this step. *Escherichia coli* does not have known native activity for this step.

Step 20 shows the conversion of 2-hydroxyisobutyryl-CoA to 2-hydroxyisobutyrate. This step may be catalyzed by phosphate butyryltransferase (EC 2.3.1.19)+butyrate kinase (EC 2.7.2.7). Exemplary sources for phosphate butyryltransferase and butyrate kinase are described elsewhere in this application. *Clostridium autoethanogenum, Clostridium ljungdahlii*, and *Clostridium ragsdalei* do not have known native activity for this step. *Escherichia coli* does not have known native activity for this step.

Step 21 shows the conversion of acetyl-CoA to succinyl-CoA. This step encompasses a number of enzymatic reactions involved in the reductive TCA pathway, which is natively present in many bacteria, including *Clostridium autoethanogenum, Clostridium ljungdahlii*, and *Clostridium ragsdalei* (and *Escherichia coli*) (Brown, *Biotechnol Biofuels*, 7: 40, 2014; U.S. Pat. No. 9,297,026). Enzymes involved in the conversion of acetyl-CoA to succinyl-CoA may include pyruvate:ferredoxin oxidoreductase (PFOR) (EC 1.2.7.1), pyruvate carboxylase (PYC) (EC 6.4.1.1), malic enzyme/malate dehydrogenase (EC 1.1.1.38, EC 1.1.1.40), pyruvate phosphate dikinase (PPDK) (EC:2.7.9.1), PEP carboxykinase (PCK) (EC 4.1.1.49), fumarate hydratase/fumerase (EC 4.2.1.2), fumarate reductase (EC 1.3.5.1)/succinate dehydrogenase (EC 1.3.5.4), and succinyl-CoA synthetase (EC 6.2.1.5). The pyruvate:ferredoxin oxidoreductase may be, for example, from *Clostridium autoethanogenum* (AGY75153, AGY77232) or *Escherichia coli* (NP_415896). The pyruvate carboxylase may be, for example, from *Clostridium autoethanogenum* (AGY75817). The malic enzyme/malate dehydrogenase may be, for example, from *Clostridium autoethanogenum* (AGY76687) or *Escherichia coli* (NP_416714, NP_417703). The pyruvate phosphate dikinase (PPDK) may be, for example, from *Clostridium autoethanogenum* (AGY76274, AGY77114). The PEP carboxykinase (PCK) may be, for example, from *Clostridium autoethanogenum* (AGY76928) or *Escherichia coli* (NP_417862). The fumarate hydratase/fumerase may be, for example, from *Clostridium autoethanogenum* (AGY76121, AGY76122) or *Escherichia coli* (NP_416128, NP_416129, NP_418546). The fumarate reductase/succinate dehydrogenase may be, for example, from *Clostridium*

*autoethanogenum* (AGY74573, AGY74575, AGY75257, AGY77166) or *Escherichia coli* (NP_415249, NP_415250, NP_415251, NP_415252, NP_418575, NP_418576, NP_418577, NP_418578). The succinyl-CoA synthetase may be, for example, from *Escherichia coli* (NP_415256, NP_415257).

Step 22 shows shows the conversion of acetyl-CoA and succinyl-CoA to 3-oxo-adipyl-CoA. This step may be catalyzed by β-ketoadipyl-CoA thiolase (EC 2.3.1.16). The ketoisovalerate oxidoreductase may be, for example, PaaJ from *Escherichia coli* (WP_001206190.1). *Clostridium autoethanogenum*, *Clostridium ljungdahlii*, and *Clostridium ragsdalei* do not have known native activity for this step. *Escherichia coli* does not have known native activity for this step.

Step 23 shows the conversion of 3-oxo-adipyl-CoA to 3-hydroxyadipyl-CoA. This step may be catalyzed by 3-hydroxybutyryl-CoA dehydrogenase (EC 1.1.1.157) or acetoacetyl-CoA hydratase (EC 4.2.1.119). The 3-hydroxybutyryl-CoA dehydrogenase or acetoacetyl-CoA hydratase may be, for example, Hbd from *Clostridium beijerinckii* (WP_011967675.1) (SEQ ID NO: 55), Hbd from *Clostridium acetobutylicum* (NP_349314.1) (SEQ ID NO: 56), Hbd1 from *Clostridium kluyveri* (WP_011989027.1) (SEQ ID NO: 57), or PaaH1 from *Cupriavidus necator* (WP_010814882.1). Of note, PhaB is R-specific and Hbd is S-specific. Additionally, Hbd1 from *Clostridium kluyveri* is NADPH-dependent and Hbd from *Clostridium acetobutylicum* and *Clostridium beijerinckii* are NADH-dependent. *Clostridium autoethanogenum*, *Clostridium ljungdahlii*, and *Clostridium ragsdalei* do not have known native activity for this step. *Escherichia coli* does not have known native activity for this step.

Step 24 shows the conversion of 3-hydroxyadipyl-CoA to 2,3-dehydroadipyl-CoA. This step may be catalyzed by an enoyl-CoA hydratase (EC: 4.2.1.17) or enoyl-CoA reductase (EC: 1.3.1.38). The enoyl-CoA hydratase or enoyl-CoA reductase may be, for example, Crt from *C. acetobutylicum* (NP_349318.1) or PhaJ from *Aeromonas caviae* (O32472) (Seq. ID No. 52). *Clostridium autoethanogenum*, *Clostridium ljungdahlii*, and *Clostridium ragsdalei* do not have known native activity for this step. *Escherichia coli* does not have known native activity for this step.

Step 25 shows the conversion of 2,3-dehydroadipyl-CoA to adipyl-CoA. This step may be catalyzed by trans-2-enoyl-CoA reductase (EC 1.3.8.1, EC 1.3.1.86, EC 1.3.1.85, EC 1.3.1.44). The trans-2-enoyl-CoA reductase may be, for example, Bcd from *C. acetobutylicum* (NP_349317.1) that forms a complex with electron flavoproteins EtfAB (NP_349315, NP_349316), Ccr from *Streptomyces collinus* (AAA92890), Ccr from *Rhodobacter sphaeroides* (YP_354044.1), Ter from *Treponema denticola* (NP_971211.1), or Ter from *Euglena gracilis* (AY741582.1). *Clostridium autoethanogenum*, *Clostridium ljungdahlii*, and *Clostridium ragsdalei* do not have known native activity for this step. *Escherichia coli* does not have known native activity for this step.

Step 26 shows the conversion of adipyl-CoA to adipic acid. This step may be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum*, *Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 27 shows the conversion of shows the conversion of 3-hydroxbutyryl-CoA to crotonyl-CoA. This step may be catalyzed by a crotonyl-CoA hydratase (crotonase) (EC 4.2.1.17) or crotonyl-CoA reductase (EC 1.3.1.38). The crotonyl-CoA hydratase (crotonase) or crotonyl-CoA reductase may be, for example, Crt from *C. acetobutylicum* (NP_349318.1) (SEQ ID NO: 52) or PhaJ from *Aeromonas caviae* (O32472). *Clostridium autoethanogenum*, *Clostridium ljungdahlii*, and *Clostridium ragsdalei* do not have known native activity for this step. *Escherichia coli* does not have known native activity for this step.

Step 28 shows the conversion of crotonyl-CoA to crotonate. This step may be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum*, *Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 29 shows the conversion of crotonate to crotonaldehyde. This step may be catalyzed by aldehyde:ferredoxin oxidoreductase (EC 1.2.7.5). Exemplary sources for aldehyde:ferredoxin oxidoreductases are described elsewhere in this application. AOR catalyzes the reaction of an acid and reduced ferredoxin to form an aldehyde and oxidized ferredoxin. In acetogens, this reaction can be coupled to oxidation CO (via CO dehydrogenase, EC 1.2.7.4) or hydrogen (via ferredoxin-dependent hydrogenase, EC 1.12.7.2 or 1.12.1.4) that both yield reduced ferredoxin (Köpke, *Curr Opin Biotechnol* 22: 320-325, 2011; Köpke, *PNAS USA*, 107: 13087-13092, 2010). *Clostridium autoethanogenum*, *Clostridium ljungdahlii*, and *Clostridium ragsdalei* have native activity for this step. However, overexpression of endogenous AOR or introduction of an exogenous AOR in *Clostridium autoethanogenum*, *Clostridium ljungdahlii*, or *Clostridium ragsdalei* may be desirable to enhance product yields. AOR of *Pyrococcus furiosus* has been demonstrated activity converting crotonaldehyde and crotonate (Loes, *J Bacteriol*, 187: 7056-7061, 2005). Alternatively, exogenous AOR may be introduced into a microorganism that does not natively comprise AOR, e.g., *E. coli*. In particular, the co-expression of Ptb-Buk and AOR (and, optionally, Adh) may enable such a microorganism to produce new non-native products.

Step 30 shows the conversion of crotonaldehyde to 2-buten-1-ol. This step may be catalyzed by alcohol dehydrogenase (EC 1.1.1.1. or 1.1.1.2.). Alcohol dehydrogenase can convert an aldehyde and NAD(P)H to an alcohol and NAD(P). The alcohol dehydrogenase may be, for example, Adh from *Clostridium autoethanogenum* (AGY76060.1) (SEQ ID NO: 67), *Clostridium ljungdahlii* (ADK17019.1) (SEQ ID NO: 68), or *Clostridium ragsdalei*, BdhB from *Clostridium acetobutylicum* (NP_349891.1) (SEQ ID NO:

69), Bdh from *Clostridium beijerinckii* (WP_041897187.1) (SEQ ID NO: 70), Bdh1 from *Clostridium ljungdahlii* (YP_003780648.1) (SEQ ID NO: 71), Bdh1 from *Clostridium autoethanogenum* (AGY76060.1) (SEQ ID NO: 72), Bdh2 from *Clostridium ljungdahlii* (YP_003782121.1) (SEQ ID NO: 73), Bdh2 from *Clostridium autoethanogenum* (AGY74784.1) (SEQ ID NO: 74), AdhE1 from *Clostridium acetobutylicum* (NP_149325.1) (SEQ ID NO: 75), AdhE2 from *Clostridium acetobutylicum* (NP_149199.1) (SEQ ID NO: 76), AdhE from *Clostridium beijerinckii* (WP_041893626.1) (SEQ ID NO: 77), AdhE1 from *Clostridium autoethanogenum* (WP_023163372.1) (SEQ ID NO: 78), or AdhE2 from *Clostridium autoethanogenum* (WP_023163373.1) (SEQ ID NO: 79). *Clostridium autoethanogenum*, *Clostridium ljungdahlii*, and *Clostridium ragsdalei* have native activity for this step. However, overexpression of endogenous alcohol dehydrogenase or introduction of an exogenous alcohol dehydrogenase in *Clostridium autoethanogenum*, *Clostridium ljungdahlii*, or *Clostridium ragsdalei* may be desirable to enhance product yields. *Escherichia coli* likely does not have native activity for this step.

Step 31 shows the conversion of crotonyl-CoA to butyryl-CoA. This step may be catalyzed by butyryl-CoA dehydrogenase or trans-2-enoyl-CoA reductase (EC 1.3.8.1, EC 1.3.1.86, EC 1.3.1.85, EC 1.3.1.44). The butyryl-CoA dehydrogenase or trans-2-enoyl-CoA reductase may be, for example, Bcd from *C. acetobutylicum* (NP_349317.1) that forms a complex with electron flavoproteins EtfAB (NP_349315, NP_349316), Ccr from *Streptomyces collinus* (AAA92890), Ccr from *Rhodobacter sphaeroides* (YP_354044.1), Ter from *Treponema denticola* (NP_971211.1), or Ter from *Euglena gracilis* (AY741582.1). *Clostridium autoethanogenum*, *Clostridium ljungdahlii*, and *Clostridium ragsdalei* do not have known native activity for this step. *Escherichia coli* does not have known native activity for this step.

Step 32 shows the conversion of butyryl-CoA to acetobutyryl-CoA. This step may be catalyzed by thiolase or acyl-CoA acetyltransferase (EC 2.3.1.9). The thiolase may be, for example, ThlA from *Clostridium acetobutylicum* (WP_010966157.1) (SEQ ID NO: 1), ThlA1 from *Clostridium kluyveri* (EDK35681), ThlA2 from *Clostridium kluyveri* (EDK35682), ThlA3 from *Clostridium kluyveri* (EDK35683), PhaA from *Cupriavidus necator* (WP_013956452.1) (SEQ ID NO: 2), BktB from *Cupriavidus necator* (WP_011615089.1) (SEQ ID NO: 3), or AtoB from *Escherichia coli* (NP_416728.1) (SEQ ID NO: 4). *Clostridium autoethanogenum*, *Clostridium ljungdahlii*, and *Clostridium ragsdalei* do not have known native activity for this step. *Escherichia coli* has native activity for this step.

Step 33 shows the conversion of acetobutyryl-CoA to acetobutyrate. This step may be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum*, *Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 34 shows the conversion of acetobutyrate to acetylacetone. This step may be catalyzed by an acetoacetate decarboxylase (EC 4.1.1.4). The acetoacetate decarboxylase may be, for example, Adc from *Clostridium beijerinckii* (WP_012059998.1) (SEQ ID NO: 14). This step may also be catalyzed by an alpha-ketoisovalerate decarboxylase (EC 4.1.1.74). The alpha-ketoisovalerate decarboxylase may be, for example, KivD from *Lactococcus lactis* (SEQ ID NO: 15). *Clostridium autoethanogenum*, *Clostridium ljungdahlii*, and *Clostridium ragsdalei* do not have known native activity for this step. Additionally, *Escherichia coli* does not have known native activity for this step. Rarely, conversion of acetoacetate to acetone may occur spontaneously. However, spontaneous conversion is highly inefficient and unlikely to result in the production of downstream products at desirable levels.

Step 35 shows the conversion of acetylacetone to 3-methyl-2-butanol. This step may be catalyzed by a primary:secondary alcohol dehydrogenase (EC 1.1.1.2). The primary:secondary alcohol dehydrogenase may be, for example, SecAdh from *Clostridium autoethanogenum* (AGY74782.1) (SEQ ID NO: 16), SecAdh from *Clostridium ljungdahlii* (ADK15544.1) (SEQ ID NO: 17), SecAdh from *Clostridium ragsdalei* (WP_013239134.1) (SEQ ID NO: 18), or SecAdh from *Clostridium beijerinckii* (WP_026889046.1) (SEQ ID NO: 19). This step may also be catalyzed by a primary:secondary alcohol dehydrogenase (EC 1.1.1.80), such as SecAdh from *Thermoanaerobacter brokii* (3FSR_A) (SEQ ID NO: 20). *Clostridium autoethanogenum*, *Clostridium ljungdahlii*, and *Clostridium ragsdalei* have native activity for this step (Köpke, *Appl Environ Microbiol*, 80: 3394-3403, 2014). However, *Escherichia coli* does not have known native activity for this step. Knocking down or knocking out this enzyme in *Clostridium autoethanogenum*, *Clostridium ljungdahlii*, or *Clostridium ragsdalei* results in the production and accumulation of acetylacetone rather than 3-methyl-2-butanol (WO 2015/085015).

Step 36 shows the conversion of acetobutyryl-CoA to 3-hydroxyhexanoyl-CoA. This step may be catalyzed by 3-hydroxybutyryl-CoA dehydrogenase (EC 1.1.1.157) or acetoacetyl-CoA hydratase (EC 4.2.1.119). The 3-hydroxybutyryl-CoA dehydrogenase or acetoacetyl-CoA hydratase may be, for example, Hbd from *Clostridium beijerinckii* (WP_011967675.1) (SEQ ID NO: 55), Hbd from *Clostridium acetobutylicum* (NP_349314.1) (SEQ ID NO: 56), Hbd1 from *Clostridium kluyveri* (WP_011989027.1) (SEQ ID NO: 57), Hbd2 from *Clostridium kluyveri* (EDK34807), or PaaH1 from *Cupriavidus necator* (WP_010814882.1). Of note, PhaB is R-specific and Hbd is S-specific. Additionally, Hbd1 from *Clostridium kluyveri* is NADPH-dependent and Hbd from *Clostridium acetobutylicum* and *Clostridium beijerinckii* are NADH-dependent. *Clostridium autoethanogenum*, *Clostridium ljungdahlii*, and *Clostridium ragsdalei* do not have known native activity for this step. *Escherichia coli* does not have known native activity for this step.

Step 37 shows the conversion of 3-hydroxyhexanoyl-CoA to 3-hydroxyhexanoate. This step may be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum*, *Clostridium ljungdahlii*, and *Clostridium ragsdalei* (or

*Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 38 shows the conversion of 3-hydroxyhexanoate to 1,3-hexaldehyde. This step may be catalyzed by aldehyde:ferredoxin oxidoreductase (EC 1.2.7.5). Exemplary sources for aldehyde:ferredoxin oxidoreductases are described elsewhere in this application. AOR catalyzes the reaction of an acid and reduced ferredoxin to form an aldehyde and oxidized ferredoxin. In acetogens, this reaction can be coupled to oxidation CO (via CO dehydrogenase, EC 1.2.7.4) or hydrogen (via ferredoxin-dependent hydrogenase, EC 1.12.7.2 or 1.12.1.4) that both yield reduced ferredoxin (Köpke, *Curr Opin Biotechnol* 22: 320-325, 2011; Köpke, *PNAS USA*, 107: 13087-13092, 2010). *Clostridium autoethanogenum*, *Clostridium ljungdahlii*, and *Clostridium ragsdalei* have native activity for this step. However, overexpression of endogenous AOR or introduction of an exogenous AOR in *Clostridium autoethanogenum*, *Clostridium ljungdahlii*, or *Clostridium ragsdalei* may be desirable to enhance product yields. Alternatively, exogenous AOR may be introduced into a microorganism that does not natively comprise AOR, e.g., *E. coli*. In particular, the co-expression of Ptb-Buk and AOR (and, optionally, Adh) may enable such a microorganism to produce new non-native products.

Step 39 shows the conversion of 1,3-hexaldehyde to 1,3-hexanediol. This step may be catalyzed by alcohol dehydrogenase (EC 1.1.1.1. or 1.1.1.2.). Alcohol dehydrogenase can convert an aldehyde and NAD(P)H to an alcohol and NAD(P). The alcohol dehydrogenase may be, for example, Adh from *Clostridium autoethanogenum* (AGY76060.1) (SEQ ID NO: 67), *Clostridium ljungdahlii* (ADK17019.1) (SEQ ID NO: 68), or *Clostridium ragsdalei*, BdhB from *Clostridium acetobutylicum* (NP_349891.1) (SEQ ID NO: 69), Bdh from *Clostridium beijerinckii* (WP_041897187.1) (SEQ ID NO: 70), Bdh1 from *Clostridium ljungdahlii* (YP_003780648.1) (SEQ ID NO: 71), Bdh1 from *Clostridium autoethanogenum* (AGY76060.1) (SEQ ID NO: 72), Bdh2 from *Clostridium ljungdahlii* (YP_003782121.1) (SEQ ID NO: 73), Bdh2 from *Clostridium autoethanogenum* (AGY74784.1) (SEQ ID NO: 74), AdhE1 from *Clostridium acetobutylicum* (NP_149325.1) (SEQ ID NO: 75), AdhE2 from *Clostridium acetobutylicum* (NP_149199.1) (SEQ ID NO: 76), AdhE from *Clostridium beijerinckii* (WP_041893626.1) (SEQ ID NO: 77), AdhE1 from *Clostridium autoethanogenum* (WP_023163372.1) (SEQ ID NO: 78), or AdhE2 from *Clostridium autoethanogenum* (WP_023163373.1) (SEQ ID NO: 79). *Clostridium autoethanogenum*, *Clostridium ljungdahlii*, and *Clostridium ragsdalei* have native activity for this step. However, overexpression of endogenous alcohol dehydrogenase or introduction of an exogenous alcohol dehydrogenase in *Clostridium autoethanogenum*, *Clostridium ljungdahlii*, or *Clostridium ragsdalei* may be desirable to enhance product yields. *Escherichia coli* likely does not have native activity for this step.

Step 40 shows the conversion of acetoacetyl-CoA to 3-hydroxy-3-methylglutaryl-CoA. This step may be catalyzed by a hydroxymethylglutaryl-CoA synthase (HMG-CoA synthase) (EC 2.3.3.10). HMG-CoA synthases are widespread across many genera and kingdoms of life and include, e.g., MvaS from *Staphylococcus aureus* (WP_053014863.1), ERG13 from *Saccharomyces cerevisiae* (NP_013580.1), HMGCS2 from *Mus musculus* (NP_032282.2), and many other members of the EC 2.3.3.10 group of enzymes. *Clostridium autoethanogenum*, *Clostridium ljungdahlii*, and *Clostridium ragsdalei* do not have known native activity for this step. *Escherichia coli* does not have known native activity for this step.

Step 41 shows the conversion of 3-hydroxy-3-methylglutanoyl-CoA to 3-methylgluconyl-CoA. This step may be catalyzed by a 3-hydroxybutyryl-CoA dehydratase (EC 4.2.1.55). The 3-hydroxybutyryl-CoA dehydratase may be, for example, LiuC from *Myxococcus xanthus* (WP_011553770.1). This step may also be catalyzed by a short-chain-enoyl-CoA hydratase (EC 4.2.1.150) or an enoyl-CoA hydratase (EC 4.2.1.17). *Clostridium autoethanogenum*, *Clostridium ljungdahlii*, and *Clostridium ragsdalei* do not have known native activity for this step. *Escherichia coli* does not have known native activity for this step.

Step 42 shows the conversion of 3-methylgluconyl-CoA to 2-methylcrotonyl-CoA. This step may be catalyzed by a methylcrotonyl-CoA decarboxylase (with high structural similarity to glutaconate-CoA transferase (EC 2.8.3.12)), e.g., aibAB from *Myxococcus xanthus* (WP_011554267.1 and WP_011554268.1). This step may also be catalyzed by a methylcrotonoyl-CoA carboxylase (EC 6.4.1.4), e.g., LiuDB from *Pseudomonas aeruginosa* (NP_250702.1 and NP_250704.1) or MCCA and MCCB from *Arabidopsis thaliana* (NP_563674.1 and NP_567950.1). *Clostridium autoethanogenum*, *Clostridium ljungdahlii*, and *Clostridium ragsdalei* do not have known native activity for this step. *Escherichia coli* does not have known native activity for this step.

Step 43 shows the conversion of methylcrotonyl-CoA to isovaleryl-CoA. This step may be catalyzed by an oxidoreductase, zinc-binding dehydrogenase. This oxidoreductase, zinc-binding dehydrogenase may be, for example, AibC from *Myxococcus xanthus* (WP_011554269.1). *Clostridium autoethanogenum*, *Clostridium ljungdahlii*, and *Clostridium ragsdalei* do not have known native activity for this step. *Escherichia coli* does not have known native activity for this step.

Step 44 shows the conversion of isovaleryl-CoA to isovalerate. This step may be catalyzed by CoA-transferase (i.e., acetyl-CoA:acetoacetyl-CoA transferase) (EC 2.8.3.9). The CoA-transferase may be, for example, CtfAB, a heterodimer comprising subunits CtfA and CtfB, from *Clostridium beijerinckii* (CtfA, WP_012059996.1) (SEQ ID NO: 5) (CtfB, WP_012059997.1) (SEQ ID NO: 6). This step may also be catalyzed by thioesterase (EC 3.1.2.20). The thioesterase may be, for example, TesB from *Escherichia coli* (NP_414986.1) (SEQ ID NO: 7). This step may also be catalyzed by a putative thioesterase, e.g., from *Clostridium autoethanogenum* or *Clostridium ljungdahlii*. In particular, three putative thioesterases have been identified in *Clostridium autoethanogenum*: (1) "thioesterase 1" (AGY74947.1; annotated as palmitoyl-CoA hydrolase; SEQ ID NO: 8), (2) "thioesterase 2" (AGY75747.1; annotated as 4-hydroxybenzoyl-CoA thioesterase; SEQ ID NO: 9), and (3) "thioesterase 3" (AGY75999.1; annotated as putative thioesterase; SEQ ID NO: 10). Three putative thioesterases have also been identified in *Clostridium ljungdahlii*: (1) "thioesterase 1" (ADK15695.1; annotated as predicted acyl-CoA thioesterase 1; SEQ ID NO: 11), (2) "thioesterase 2" (ADK16655.1; annotated as predicted thioesterase; SEQ ID NO: 12), and (3) "thioesterase 3" (ADK16959.1; annotated as predicted thioesterase; SEQ ID NO: 13). This step may also be catalyzed by phosphate butyryltransferase (EC 2.3.1.19)+butyrate kinase (EC 2.7.2.7). Exemplary sources for phosphate butyryltransferase and butyrate kinase are described elsewhere in this application. Native enzymes in *Clostridium autoethanogenum, Clostridium ljungdahlii*, and *Clostridium ragsdalei* (or *Escherichia coli*), such as thioesterases from *Clostridium autoethanogenum*, may catalyze this step and result in the production of some amount of downstream products. However, introduction of an exogenous enzyme or overexpression of an endogenous enzyme may be required to produce downstream products at desirable levels. Additionally, in certain embodiments, a disruptive mutation may be introduced to an endogenous enzyme, such as an endogenous thioesterase, to reduce or eliminate competition with introduced Ptb-Buk.

Step 45 shows the conversion of isovalerate to isovaleraldehyde. This step may be catalyzed by aldehyde:ferredoxin oxidoreductase (EC 1.2.7.5). The aldehyde:ferredoxin oxidoreductase (AOR) may be, for example, AOR from *Clostridium autoethanogenum* (WP_013238665.1; WP_013238675.1) (SEQ ID NOs: 63 and 64, respectively) or AOR from *Clostridium ljungdahlii* (ADK15073.1; ADK15083.1) (SEQ ID NOs: 65 and 66, respectively). Further exemplary sources for aldehyde:ferredoxin oxidoreductases are described elsewhere in this application. *Clostridium autoethanogenum, Clostridium ljungdahlii*, and *Clostridium ragsdalei* have native activity for this step. However, overexpression of endogenous AOR or introduction of an exogenous AOR in *Clostridium autoethanogenum, Clostridium ljungdahlii*, or *Clostridium ragsdalei* may be desirable to enhance product yields. Alternatively, exogenous AOR may be introduced into a microorganism that does not natively comprise AOR, e.g., *E. coli*. In particular, the co-expression of Ptb-Buk and AOR (and, optionally, Adh) may enable such a microorganism to produce new non-native products.

Step 46 shows the conversion of isovaleraldehyde to isoamyl alcohol. This step may be catalyzed by alcohol dehydrogenase (EC 1.1.1.1. or 1.1.1.2.). Alcohol dehydrogenase can convert an aldehyde and NAD(P)H to an alcohol and NAD(P). The alcohol dehydrogenase may be, for example, Adh from *Clostridium autoethanogenum* (AGY76060.1) (SEQ ID NO: 67), *Clostridium ljungdahlii* (ADK17019.1) (SEQ ID NO: 68), or *Clostridium ragsdalei*, BdhB from *Clostridium acetobutylicum* (NP_349891.1) (SEQ ID NO: 69), Bdh from *Clostridium beijerinckii* (WP_041897187.1) (SEQ ID NO: 70), Bdh1 from *Clostridium ljungdahlii* (YP_003780648.1) (SEQ ID NO: 71), Bdh1 from *Clostridium autoethanogenum* (AGY76060.1) (SEQ ID NO: 72), Bdh2 from *Clostridium ljungdahlii* (YP_003782121.1) (SEQ ID NO: 73), Bdh2 from *Clostridium autoethanogenum* (AGY74784.1) (SEQ ID NO: 74), AdhE1 from *Clostridium acetobutylicum* (NP_149325.1) (SEQ ID NO: 75), AdhE2 from *Clostridium acetobutylicum* (NP_149199.1) (SEQ ID NO: 76), AdhE from *Clostridium beijerinckii* (WP_041893626.1) (SEQ ID NO: 77), AdhE1 from *Clostridium autoethanogenum* (WP_023163372.1) (SEQ ID NO: 78), or AdhE2 from *Clostridium autoethanogenum* (WP_023163373.1) (SEQ ID NO: 79). *Clostridium autoethanogenum, Clostridium ljungdahlii*, and *Clostridium ragsdalei* have native activity for this step. However, overexpression of endogenous alcohol dehydrogenase or introduction of an exogenous alcohol dehydrogenase in *Clostridium autoethanogenum, Clostridium ljungdahlii*, or *Clostridium ragsdalei* may be desirable to enhance product yields. *Escherichia coli* likely does not have native activity for this step.

Step 47 shows the conversion of isovaleryl-CoA to isovaleraldehyde. This step may be catalyzed by butyraldehyde dehydrogenase (EC 1.2.1.57). The butyraldehyde dehydrogenase may be, for example, Bld from *Clostridium saccharoperbutylacetonicum* (AAP42563.1) (SEQ ID NO: 80). *Clostridium autoethanogenum, Clostridium ljungdahlii*, and *Clostridium ragsdalei* likely do not have native activity for this step. *Escherichia coli* does not have known native activity for this step.

Overview of Ptb-Buk

Figure 2:
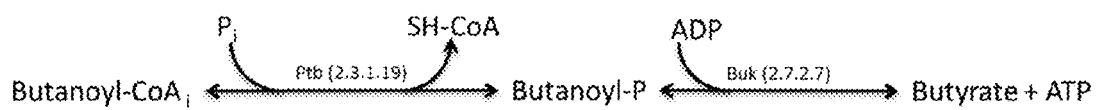
FIG. 2 is a diagram showing the reactions natively catalyzed by Ptb-Buk, namely the conversion of butanoyl-CoA to butyrate and the generation of one ATP.

The invention provides new pathways utilizing the Ptb-Buk enzyme system. In nature, this enzyme system is found in a range of butyrate producing microorganisms, such as butyrate-producing Clostridia or *Butyrivibrio*. In particular, phosphate butyryltransferase (Ptb) (EC 2.3.1.19) natively catalyzes the reaction of butanoyl-CoA+phosphate to form CoA+butanoyl phosphate and butyrate kinase (Buk) (EC 2.7.2.7) natively catalyzes the reaction of butanoyl phosphate and ADP to form butyrate (butanoate) and ATP. Accordingly, these enzymes together (Ptb-Buk) natively catalyze the conversion of butanoyl-CoA to butyrate and generate one ATP via substrate level-phosphorylation (FIG. 2). However, the inventors have discovered that Ptb is promiscuous and is capable of accepting a variety of acyl-CoAs and enoyl-CoAs as substrates, such that Ptb-Buk may be used to convert a number of acyl-CoAs and enoyl-CoAs to their corresponding acids or alkenates, respectively, while simultaneously generating ATP. It has been reported Ptb is active on a range of acyl-CoAs including acetoacetyl-CoA, in vitro (Thompson, *Appl Environ Microbiol*, 56: 607-613, 1990). It has not previously been shown that acetoacetyl-phosphate could be a substrate for Buk. Although Buk is known to accept a broad substrate range (Liu, *Appl Microbiol Biotechnol*, 53: 545-552, 2000), no activity has been shown in vivo.

Additionally, the inventors have discovered that the introduction of exogenous Ptb-Buk enables certain microorganisms to produce useful products, including acetone, isopropanol, isobutylene, 3-hydroxybutyrate, 1,3-butanediol, and 2-hydroxyisobutyrate, as well as other products such as propionate, caproate, and octonate.

Figure 3:
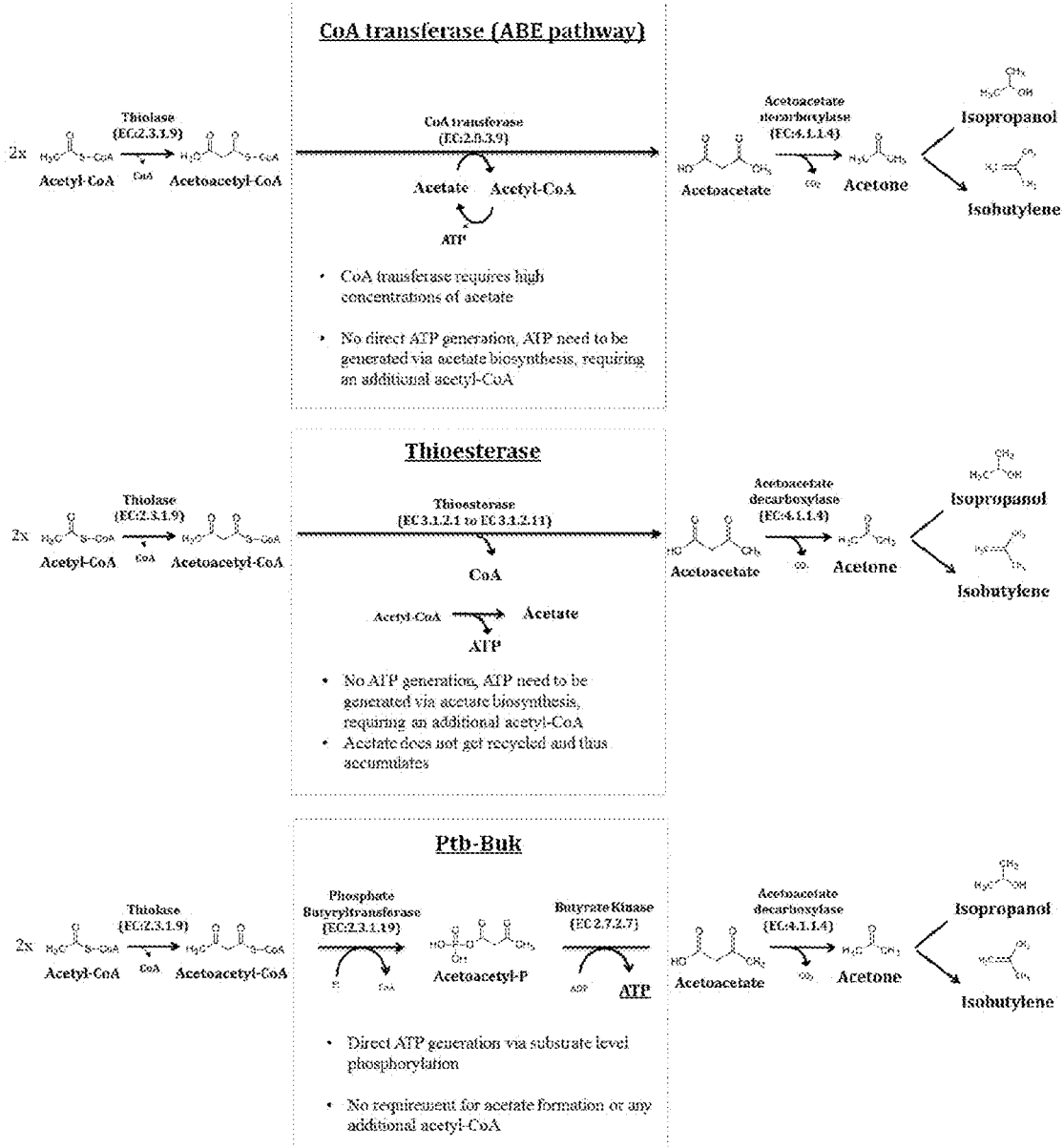
FIG. 3 is a diagram comparing the activities of CoA-transferase, thioesterase, and Ptb-Buk.

New pathways that rely on Ptb-Buk offer several major advantages over other known and existing pathway routes for production of products that rely on a CoA-transferase—as in the classic Clostridial acetone-butanol-ethanol (ABE) fermentation pathway—or a thioesterase (Jones, *Microbiol Rev*, 50: 484-524, 1986; Matsumoto, *Appl Microbiol Biotechnol*, 97: 205-210, 2013; May, *Metabol Eng*, 15: 218-225, 2013) (FIG. 3). In particular, these new pathways (1) are not dependent on the presence or production of particular molecules, such as organic acids, e.g., butyrate or acetate, required for the CoA-transferase reaction and (2) allow for generation of ATP via substrate level phosphorylation that would not be conserved in a thioesterase or CoA-transferase reaction. The same advantages also apply when using the Ptb-Buk system for other reactions, such as the conversion of 3-hydroxybutyryl-CoA to 3-hydroxybutyrate. Thus, these new pathways have the potential to yield much higher production titers and rates by generating additional energy and producing target products without co-production of undesired byproducts, such as acetate.

Particularly on a commercial scale, it is not desirable for microorganisms to produce acetate (or other organic acids required for the CoA transferase reaction) as byproduct, since acetate diverts carbon away from target products and thus affects the efficiency and yield of target products. Additionally, acetate may be toxic to microorganisms and/or may serve as a substrate for the growth of contaminating microorganisms. Furthermore, the presence of acetate makes it more difficult to recover and separate target products and to control fermentation conditions to favor the production of target products.

ATP generation through substrate level phosphorylation can be used as a driving force for product synthesis, especially in ATP-limited systems. In particular, acetogenic bacteria are known to live on the thermodynamic edge of life (Schuchmann, *Nat Rev Microbiol,* 12: 809-821, 2014). As such, all acetogenic microorganisms isolated to date have been described to produce acetate (Drake, Acetogenic Prokaryotes, In: *The Prokaryotes,* 3$^{rd}$ edition, pages 354-420, New York, N.Y., Springer, 2006) since the production of acetate provides the microorganism with an option to directly generate ATP from substrate level phosphorylation via Pta (phosphotransacetylase) (EC 2.3.1.8) and Ack (acetate kinase) (EC 2.7.2.1). Although mechanisms such as membrane gradients and electro bifurcation enzymes coupled to ion or proton translocating systems, e.g., the Rnf complex (Schuchmann, *Nat Rev Microbiol,* 12: 809-821, 2014), conserve ATP in these microorganisms, direct ATP generation remains critical for their survival. As a result, when introducing heterologous pathways that do not allow for ATP generation, acetate is produced as a byproduct (Schiel-Bengelsdorf, *FEBS Lett,* 586: 2191-2198, 2012). The Ptb-Buk pathways described herein, however, provide an alternative mechanism for the microorganism to generate ATP via substrate level phosphorylation and, therefore, avoid acetate production. In particular, acetate-forming enzymes, such as Pta-Ack, that would otherwise be essential (Nagarajan, *Microb Cell Factories,* 12: 118, 2013) can be replaced with Ptb-Buk as an alternative means of ATP generation. Since the microorganism can then rely on ATP generation via Ptb-Buk, this system provides a driving force that ensures maximum flux through the new pathways that use Ptb-Buk. The generation of ATP may also be crucial for downstream pathways that require ATP. For example, fermentative production of isobutylene from acetone requires ATP. While the complete pathway from acetyl-CoA to isobutylene is ATP-consuming when using a CoA-transferase or a thioesterase, the pathway is energy neutral when using Ptb-Buk.

Exemplary sources for Ptb and Buk are provided. However, it should be appreciated that other suitable sources for Ptb and Buk may be available. Additionally, Ptb and Buk may be engineered to improve activity and/or genes encoding Ptb-Buk may be codon-optimized for expression in particular host microorganisms.

The phosphate butyryltransferase may be or may be derived, for example, from any of the following sources, the sequences of which are publically available:

| Description | Microorganism | Accession |
| --- | --- | --- |
| phosphate butyryltransferase | *Clostridium* sp. | EKQ52186 |
| phosphate butyryltransferase | *Clostridium* sp. | WP_009167896 |
| phosphate butyryltransferase | *Clostridium saccharoperbutylacetonicum* | WP_015390396 |
| phosphate butyryltransferase | *Clostridium saccharobutylicum* | WP_022743598 |
| phosphate butyryltransferase | *Clostridium beijerinckii* | WP_026886639 |
| phosphate butyryltransferase | *Clostridium beijerinckii* | WP_041893500 |
| phosphate butyryltransferase | *Clostridium butyricum* | WP_003410761 |
| phosphate butyryltransferase | *Clostridium* sp. | CDB 14331 |
| phosphate butyryltransferase | *Clostridium botulinum* | WP_049180512 |
| phosphate butyryltransferase | *Clostridium* sp. | CDB74819 |
| phosphate butyryltransferase | *Clostridium paraputrificum* | WP_027098882 |
| phosphate butyryltransferase | *Clostridium* sp. | WP_024615655 |
| phosphate butyryltransferase | *Clostridium celatum* | WP_005211129 |
| phosphate butyryltransferase | *Clostridium baratii* | WP_039312969 |
| phosphate butyryltransferase | *Clostridium intestinale* | WP_021800215 |
| phosphate butyryltransferase | *Clostridium* sp. | WP_042402499 |
| phosphate butyryltransferase | *Clostridium* sp. | WP_032117069 |
| phosphate butyryltransferase | *Clostridium perfringens* | ABG85761 |
| phosphate butyryltransferase | *Clostridium botulinum* | WP_003374233 |
| phosphate butyryltransferase | *Clostridium perfringens* | WP_004460499 |
| phosphate butyryltransferase | *Clostridium perfringens* | WP_003454254 |
| phosphate butyryltransferase | *Clostridium perfringens* | WP_041707926 |
| phosphate butyryltransferase | *Clostridium perfringens* | BAB82054 |
| phosphate butyryltransferase | *Clostridium* sp. | WP_008681116 |
| phosphate butyryltransferase | *Clostridium chauvoei* | WP_021876993 |
| phosphate butyryltransferase | *Clostridium colicanis* | WP_002598839 |
| phosphate butyryltransferase | *Clostridium cadaveris* | WP_027637778 |
| phosphate butyryltransferase | *Clostridium acetobutylicum* | WP_010966357 |
| phosphate butyryltransferase | *Clostridium pasteurianum* | WP_015617430 |
| phosphate butyryltransferase | *Clostridium arbusti* | WP_010238988 |
| phosphate butyryltransferase | *Clostridium pasteurianum* | WP_003445696 |
| phosphate butyryltransferase | *Clostridium scatologenes* | WP_029160341 |
| phosphate butyryltransferase | *Clostridium* sp. | WP_032120461 |
| phosphate butyryltransferase | *Clostridium drakei* | WP_032078800 |
| phosphate butyryltransferase | *Clostridium* sp. | WP_021281241 |
| phosphate butyryltransferase | *Clostridium argentinense* | WP_039635970 |
| phosphate butyryltransferase | *Clostridium akagii* | WP_026883231 |
| phosphate butyryltransferase | *Clostridium* sp. | WP_053242611 |
| phosphate butyryltransferase | *Clostridium carboxidivorans* | WP_007063154 |
| phosphate butyryltransferase | *Clostridium* sp. | WP_035292411 |
| phosphate butyryltransferase | *Clostridium sulfidigenes* | WP_035133394 |
| phosphate butyryltransferase | *Clostridium tetanomorphum* | WP_035147564 |
| phosphate butyryltransferase | *Clostridium hydrogeniformans* | WP_027633206 |
| phosphate butyryltransferase | *Clostridium* sp. | WP_040212965 |

| Description | Microorganism | Accession |
| --- | --- | --- |
| phosphate butyryltransferase | Candidatus Clostridium | WP_040327613 |
| phosphate butyryltransferase | Clostridium sp. | WP_040192242 |
| phosphate butyryltransferase | Clostridium sp. | WP_050606427 |
| phosphate butyryltransferase | Clostridium lundense | WP_027625137 |
| phosphate butyryltransferase | Clostridium algidicarnis | WP_029451333 |
| phosphate butyryltransferase | Clostridium sp. | WP_035306567 |
| phosphate butyryltransferase | Clostridium acetobutylicum | AAA75486 |
| phosphate butyryltransferase | Clostridium botulinum | WP_025775938 |
| phosphate butyryltransferase | Clostridium botulinum | WP_045541062 |
| phosphate butyryltransferase | Clostridium botulinum | WP_003357252 |
| phosphate butyryltransferase | Clostridium botulinum | WP_030037192 |
| phosphate butyryltransferase | Clostridium bornimense | WP_044039341 |
| phosphate butyryltransferase | Clostridium botulinum | WP_041346554 |
| phosphate butyryltransferase | Clostridium sp. | WP_053468896 |
| phosphate butyryltransferase | Closfridiales bacterium | WP_034572261 |
| phosphate butyryltransferase | Clostridium tetani | WP_023439553 |
| phosphate butyryltransferase | Closfridiales bacterium | ERI95297 |
| phosphate butyryltransferase | Clostridium botulinum | WP_047403027 |
| phosphate butyryltransferase | Clostridium tetani | WP_011100667 |
| phosphate butyryltransferase | Clostridium tetani | WP_035111554 |
| phosphate butyryltransferase | Clostridium senegalense | WP_010295062 |
| phosphate butyryltransferase | Caloramator sp. | WP_027307587 |
| phosphate butyryltransferase | Thermobrachium celere | WP_018661036 |
| phosphate butyryltransferase | Clostridium cellulovorans | WP_010073683 |
| phosphate butyryltransferase | Coprococcus comes | CDB84786 |
| phosphate butyryltransferase | Coprococcus comes | WP_008371924 |
| phosphate butyryltransferase | Eubacterium sp. | CCZ03827 |
| phosphate butyryltransferase | Clostridium sp. | CCZ05442 |
| phosphate butyryltransferase | Caloramator australicus | WP_008907395 |
| phosphate butyryltransferase | Clostridium sp. | CCY59505 |
| phosphate butyryltransferase | Lachnospiraceae bacterium | WP_035626368 |
| phosphate butyryltransferase | Lachnospiraceae bacterium | WP_027440767 |
| phosphate butyryltransferase | Fervidicella metallireducens | WP_035381340 |
| phosphate butyryltransferase | Clostridium sp. | CCX89274 |
| phosphate butyryltransferase | Eubacterium xylanophilum | WP_026834525 |
| phosphate butyryltransferase | Roseburia sp. | CDF44203 |
| phosphate butyryltransferase | Butyrivibrio crossotus | WP_005600912 |
| phosphate butyryltransferase | Lachnospiraceae bacterium | WP_027117626 |
| phosphate butyryltransferase | Clostridium sp. | CDA68345 |
| phosphate butyryltransferase | Peptostreptococcaceae bacterium | WP_026899905 |
| phosphate butyryltransferase | Butyrivibrio crossotus | CCY77124 |
| phosphate butyryltransferase | Clostridium sp. | CDE44914 |
| phosphate butyryltransferase | Coprococcus eutactus | WP_004853197 |
| phosphate butyryltransferase | Firmicutes bacterium | CCY23248 |
| phosphate butyryltransferase | Lachnospiraceae bacterium | WP_027111007 |
| phosphate butyryltransferase | Lachnospiraceae bacterium | WP_016293387 |
| phosphate butyryltransferase | Clostridium sp. | WP_046822491 |

In a preferred embodiment, the phosphate butyryltransferase is Ptb from *Clostridium acetobutylicum* (WP_010966357; SEQ ID NO: 87) or *Clostridium beijerinckii* (WP_026886639; SEQ ID NO: 88) (WP_041893500; SEQ ID NO: 89). *Clostridium autoethanogenum*, *Clostridium ljungdahlii*, and *Clostridium ragsdalei* do not natively contain phosphate butyryltransferase.

The butyrate kinase may be or may be derived, for example, from any of the following sources, the sequences of which are publically available:

| Description | Microorganism | Accession |
| --- | --- | --- |
| butyrate kinase | Clostridium pasteurianum | ALB48406 |
| butyrate kinase | Clostridium sp. | CDB14330 |
| butyrate kinase | Clostridium sp. | CDB74820 |
| butyrate kinase | Clostridium sp. | EKQ52187 |
| butyrate kinase | Clostridium perfringens | Q0SQK0 |
| butyrate kinase | Clostridium sp. | WP_002582660 |
| butyrate kinase | Clostridium colicanis | WP_002598838 |
| butyrate kinase | Clostridium botulinum | WP_003371719 |
| butyrate kinase | Clostridium perfringens | WP_003454444 |
| butyrate kinase | Clostridium perfringens | WP_004459180 |
| butyrate kinase | Clostridium celatum | WP_005211128 |
| butyrate kinase | Clostridium sp. | WP_008681112 |
| butyrate kinase | Clostridium sp. | WP_008681114 |
| butyrate kinase | Clostridium sp. | WP_009167897 |
| butyrate kinase | Clostridium perfringens | WP_011010889 |
| butyrate kinase | Clostridium beijerinckii | WP_011967556 |
| butyrate kinase | Clostridium botulinum | WP_012422882 |
| butyrate kinase | Clostridium botulinum | WP_012450845 |
| butyrate kinase | Clostridium saccharoperbutylacetonicum | WP_015390397 |
| butyrate kinase | Clostridium beijerinckii | WP_017209677 |
| butyrate kinase | Clostridium botulinum | WP_017825911 |
| butyrate kinase | Clostridium chauvoei | WP_021876994 |
| butyrate kinase | Clostridium saccharobutylicum | WP_022743599 |
| butyrate kinase | Clostridium sp. | WP_024615656 |
| butyrate kinase | Clostridium perfringens | WP_025648345 |
| butyrate kinase | Clostridium beijerinckii | WP_026886638 |
| butyrate kinase | Clostridium paraputrificum | WP_027098883 |
| butyrate kinase | Clostridium sp. | WP_032117070 |
| butyrate kinase | Clostridium botulinum | WP_035786166 |
| butyrate kinase | Clostridium baratii | WP_039312972 |
| butyrate kinase | Clostridium diolis | WP_039772701 |
| butyrate kinase | Clostridium botulinum | WP_041082388 |
| butyrate kinase | Clostridium beijerinckii | WP_041893502 |

-continued

| Description | Microorganism | Accession |
| --- | --- | --- |
| butyrate kinase | Clostridium sp. | WP_042402497 |
| butyrate kinase | Clostridium baratii | WP_045725505 |
| butyrate kinase | Clostridium perfringens | WP_049039634 |
| butyrate kinase | Clostridium botulinum | WP_049180514 |
| butyrate kinase | Clostridium botulinum | WP_053341511 |
| butyrate kinase | Clostridium butyricum | ABU40948 |
| butyrate kinase | Clostridium sp. | CDE44915 |
| butyrate kinase | Clostridium senegalense | WP_010295059 |
| butyrate kinase | Clostridium intestinale | WP_021800216 |
| butyrate kinase | Eubacterium ventriosum | WP_005363839 |
| butyrate kinase | Closfridiales bacterium | WP_021657038 |
| butyrate kinase | Clostridium sp. | WP_021281242 |
| butyrate kinase | Clostridium sporogenes | WP_045520059 |
| butyrate kinase | Clostridium sp. | WP_050606428 |
| butyrate kinase | Clostridium botulinum | WP_012048334 |
| butyrate kinase | Clostridium botulinum | WP_012343352 |
| butyrate kinase | Clostridium botulinum | WP_003401518 |
| butyrate kinase | Clostridium argentinense | WP_039635972 |
| butyrate kinase | Clostridium botulinum | WP_003357547 |
| butyrate kinase | Clostridium hydrogeniformans | WP_027633205 |
| butyrate kinase | Clostridium botulinum | WP_033066487 |
| butyrate kinase | Roseburia sp. | CDF44202 |
| butyrate kinase | Lachnospiraceae bacterium | WP_027111008 |
| butyrate kinase | Clostridium sp. | CDA68344 |
| butyrate kinase | Lachnospiraceae bacterium | WP_022782491 |
| butyrate kinase | Clostridium botulinum | WP_012101111 |
| butyrate kinase | Clostridium carboxidivorans | WP_007063155 |
| butyrate kinase | Clostridium botulinum | WP_041346556 |
| butyrate kinase | Clostridium drakei | WP_032078801 |
| butyrate kinase | Clostridium sp. | WP_032120462 |
| butyrate kinase | Clostridium sp. | WP_053468897 |
| butyrate kinase | Firmicutes bacterium | CCZ27888 |
| butyrate kinase | Clostridium sp. | WP_035306569 |
| butyrate kinase | Coprococcus comes | CDB84787 |
| butyrate kinase | Clostridium sp. | WP_035292410 |
| butyrate kinase | Clostridium sp. | CCX89275 |
| butyrate kinase | Clostridium sp. | WP_040212963 |
| butyrate kinase | Clostridium pasteurianum | WP_003445697 |
| butyrate kinase | Clostridium sp. | WP_053242610 |
| butyrate kinase | Lachnospiraceae bacterium | WP_016299320 |
| butyrate kinase | Lachnospiraceae bacterium | WP_022785085 |
| butyrate kinase | Lachnospiraceae bacterium | WP_016281561 |
| butyrate kinase | Eubacterium sp. | CDA28786 |
| butyrate kinase | Clostridium scatologenes | WP_029160342 |
| butyrate kinase | Lachnospiraceae bacterium | WP_016228168 |
| butyrate kinase | Clostridium pasteurianum | WP_015617429 |
| butyrate kinase | Clostridium algidicarnis | WP_029451332 |
| butyrate kinase | Lachnospiraceae bacterium | WP_016293388 |
| butyrate kinase | Clostridium sulfidigenes | WP_035133396 |
| butyrate kinase | Clostridium tetani | WP_011100666 |
| butyrate kinase | Clostridium tetanomorphum | WP_035147567 |
| butyrate kinase | Subdoligranulum variabile | WP_007045828 |
| butyrate kinase | Eubacterium sp. | CCZ03826 |
| butyrate kinase | Firmicutes bacterium | CDF07483 |
| butyrate kinase | Eubacterium sp. | CDB13677 |
| butyrate kinase | Clostridium sp. | WP_008400594 |
| butyrate kinase | Clostridium tetani | WP_023439552 |
| butyrate kinase | Closfridiales bacterium | WP_022787536 |
| butyrate kinase | Lachnospiraceae bacterium | WP_027434709 |
| butyrate kinase | Firmicutes bacterium | CCY23249 |
| butyrate kinase | Clostridium acetobutylicum | WP_010966356 |

In a preferred embodiment, the butyrate kinase is Buk from *Clostridium acetobutylicum* (WP_010966356; SEQ ID NO: 90) or *Clostridium beijerinckii* (WP_011967556; SEQ ID NO: 91) (WP_017209677; SEQ ID NO: 92) (WP_026886638; SEQ ID NO: 93) (WP_041893502; SEQ ID NO: 94). *Clostridium autoethanogenum*, *Clostridium ljungdahlii*, and *Clostridium ragsdalei* do not natively contain butyrate kinase.

Since Ptb-Buk has been shown to function on a broad range of substrates it is reasonable to assume that if Ptb-Buk does not exhibit any activity and a desired substrate it can be engineered to achieve activity on the substrate in question. A strategy could be (but would not be limited to) rational design based on available crystal structures of Ptb and Buk with and without a bound substrate where the binding pocket would be changed to accommodate the new substrate or through saturation mutagenesis. When activity is obtained, it can be further improved through iterative cycles of enzyme engineering. These engineering efforts would be combined with assays to test enzyme activity. These types of strategies have previously proven effective (see, e.g., Huang, *Nature*, 537: 320-327, 2016; Khoury, *Trends Biotechnol*, 32: 99-109, 2014; Packer, *Nature Rev Genetics*, 16: 379-394, 2015; Privett, *PNAS USA*, 109: 3790-3795, 2012).

Figure 33:
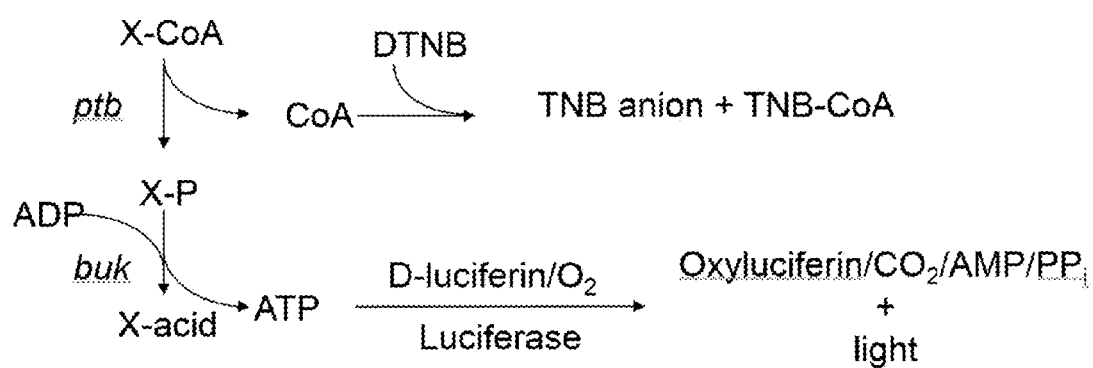
FIG. 33 is a diagram showing the coupling firefly luciferase (Luc) to the Ptb-Buk system to characterize Ptb-Buk variants.

To improve substrate specificity of Ptb-Buk towards a specific acyl-CoA substrate, Ptb-Buk variants from public databases or generated Ptb-Buk mutants (for example, from directed evolution) can be screened using a high throughput assay, namely overexpressing Ptb-Buk enzyme pairs in *E. coli*, adding a test substrate, and screening for ATP production with a bioluminescence assay. The assay can use the well-established practice of correlating ATP concentration with firefly luciferase enzyme bioluminescence. The amenability of this assay to multi-well plate formats would facilitate efficient screening of substrate preference across new Ptb-Buk combinations (FIG. 33).

By screening for ATP production rather than depletion of substrate or accumulation of product, the assay avoids measuring spontaneous hydrolysis of the CoA group. However, an alternative approach described in literature, is to use free CoA can be measured using the established assay using Ellman's reagent (5,5'-dithiobis-(2-nitrobenzoic acid) or DTNB) (Thompson, Appl Environ Microbiol, 56: 607-613, 1990.) in order to estimate the coupling efficiency of the Ptb-Buk reactions (FIG. 33). Acyl-CoAs and corresponding free acids and phospho-intermediates can also be measured during the validation phase using LC-MS/MS.

In a high-throughput screening approach, it is difficult gather kinetic data due to the labor involved in protein quantification. Instead, for each preparation of *E. coli* lysate containing Ptb-Buk enzymes, the activity against each substrate of interest (measured as luminescence per unit time) can be compared to the activity against the positive control substrate (butyryl-CoA) and against acetyl-CoA (the physiological substrate that will likely provide the greatest competition for enzyme active sites against target acyl-CoA).

In order to ensure that the assay is not biased due to native phosphotransacetylase (Pta) and/or acetate kinase (Ack) activity, the assay can also be evaluated in an *E. coli* strain where pta and/or ack genes have been knocked out.

Production of Acetone and Isopropanol

Acetone and isopropanol are important industrial solvents with a combined market size of 8 million tons and a global market value of $8.5-11 billion. In addition, acetone and isopropanol are precursors to valuable downstream products, including polymethyl methacrylate (PMMA), which has a global market value of $7 billion, isobutylene, which has a global market value of $25-29 billion, and propylene, which has a global market value of $125 billion. Additionally, a route from acetone to jet fuel has recently been reported. Currently, industrial acetone production is directly linked to petrochemical phenol production, as it is a by-product of the cumene process. Around 92% of acetone output by volume is a co-product of phenol production from cumene. This has significant implications on both environment and market. In the cumene process, per mol phenol produced one mol of sodium sulfite accumulates posing a serious waste management problem and a challenge to natural environments and human health. The world market demand for phenol is expected to stagnate or decline, while the demand for acetone is predicted to rise. Alternative phenol production routes from direct oxidation of benzene are in development and expected to commercialize soon; this could result in a complete elimination of acetone production.

Acetone has been produced at industrial scale for almost 100 years, as a by-product of butanol in ABE fermentation. While industrial ABE fermentation declined in the second half of the 20$^{th}$ century due to low oil prices and high sugar costs, it has recently revived, with several commercial plants built during the last few years. Multiple groups have also demonstrated acetone production from sugar in heterologous hosts that express the corresponding enzymes from ABE fermentation organisms, in particular *E. coli* and yeast through metabolic engineering and synthetic biology approaches by several academic groups. However, low yields and high costs associated the pre-treatment needed to release the polysaccharide-component of biomass make the production of acetone via standard fermentation uneconomic as current biochemical conversion technologies do not utilize the lignin component of biomass, which can constitute up to 40% of this material.

The invention provides a microorganism capable of producing acetone or precursors thereof from a substrate. The invention further provides a method of producing acetone or precursors thereof by culturing such a microorganism in the presence of a substrate. In preferred embodiments, the microorganism is derived from a parental microorganism selected from the group consisting of *Clostridium autoethanogenum, Clostridium ljungdahlii*, or *Clostridium ragsdalei*. However, the microorganism may also be derived from an entirely different microorganism, e.g., *Eschericia coli*. The enzymatic pathways described for the production of acetone may comprise endogenous enzymes and, where endogenous enzyme activity is absent or low, exogenous enzymes.

Acetone via steps 1, 2, and 3: In one embodiment, the invention provides a microorganism comprising enzymes for steps 1, 2, and 3, whereby the microorganism is capable of producing acetone or precursors thereof from a substrate, such as a gaseous substrate. Typically, at least one of the enzymes in this pathway is exogenous to the microorganism. In a preferred embodiment, step 2 is catalyzed by Ptb-Buk. Exemplary types and sources of enzymes for steps 1, 2, and 3 are described elsewhere in this application. If the microorganism is derived from a parental microorganism that natively contains a primary:secondary alcohol dehydrogenase capable of converting acetone to isopropanol (step 4) (e.g., *Clostridium autoethanogenum, Clostridium ljungdahlii*, or *Clostridium ragsdalei*), the microorganism may be modified to knock down or knock out the expression of primary:secondary alcohol dehydrogenase (e.g., by disrupting the gene encoding the primary:secondary alcohol dehydrogenase), such that the microorganism produces acetone without converting it to isopropanol (WO 2015/085015).

Acetone via steps 1, 13, 14, 15, and 3: In one embodiment, the invention provides a microorganism comprising exogenous enzymes for steps 1, 13, 14, 15, and 3, whereby the microorganism is capable of producing acetone or precursors thereof from a substrate, such as a gaseous substrate. Typically, at least one of the enzymes in this pathway is exogenous to the microorganism. In a preferred embodiment, step 14 is catalyzed by Ptb-Buk. Exemplary types and sources of enzymes for steps 1, 13, 14, 15, and 3 are described elsewhere in this application. If the microorganism is derived from a parental microorganism that natively contains a primary:secondary alcohol dehydrogenase capable of converting acetone to isopropanol (step 4) (e.g., *Clostridium autoethanogenum, Clostridium ljungdahlii*, or *Clostridium ragsdalei*), the microorganism may be modified to knock down or knock out the expression of primary:secondary alcohol dehydrogenase (e.g., by disrupting the gene encoding the primary:secondary alcohol dehydrogenase), such that the microorganism produces acetone without converting it to isopropanol (WO 2015/085015).

In one embodiment, the microorganism may comprise more than one pathway for the production of acetone.

The invention provides a microorganism capable of producing isopropanol or precursors thereof from a substrate. The invention further provides a method of producing isopropanol or precursors thereof by culturing such a microorganism in the presence of a substrate. In preferred embodiments, the microorganism is derived from a parental microorganism selected from the group consisting of *Clostridium autoethanogenum, Clostridium ljungdahlii*, or *Clostridium ragsdalei*. However, the microorganism may also be derived from an entirely different microorganism, e.g., *Eschericia coli*. The enzymatic pathways described for the production of isopropanol may comprise endogenous enzymes and, where endogenous enzyme activity is absent or low, exogenous enzymes.

Isopropanol via steps 1, 2, 3, and 4: In one embodiment, the invention provides a microorganism comprising enzymes for steps 1, 2, 3, and 4, whereby the microorganism is capable of producing isopropanol or precursors thereof from a substrate, such as a gaseous substrate. Typically, at least one of the enzymes in this pathway is exogenous to the microorganism. In a preferred embodiment, step 2 is catalyzed by Ptb-Buk. Exemplary types and sources of enzymes for steps 1, 2, 3, and 4 are described elsewhere in this application. If the microorganism is derived from a parental microorganism that natively contains a primary:secondary alcohol dehydrogenase capable of converting acetone to isopropanol (step 4) (e.g., *Clostridium autoethanogenum, Clostridium ljungdahlii*, or *Clostridium ragsdalei*), introduction of an exogenous enzyme for step 4 is not required to produce isopropanol. However, modification of the microorganism, for example, to overexpress a native primary:secondary alcohol dehydrogenase may result in enhanced production of isopropanol.

Isopropanol via steps 1, 13, 14, 15, 3, and 4: In one embodiment, the invention provides a microorganism comprising enzymes for steps 1, 13, 14, 15, 3, and 4, whereby the microorganism is capable of producing isopropanol or precursors thereof from a substrate, such as a gaseous substrate. Typically, at least one of the enzymes in this pathway is exogenous to the microorganism. In a preferred embodiment, step 14 is catalyzed by Ptb-Buk. Exemplary types and sources of enzymes for steps 1, 13, 14, 15, 3, and 4 are described elsewhere in this application. If the microorganism is derived from a parental microorganism that natively contains a primary:secondary alcohol dehydrogenase capable of converting acetone to isopropanol (step 4) (e.g., *Clostridium autoethanogenum, Clostridium ljungdahlii*, or *Clostridium ragsdalei*), introduction of an exogenous enzyme for step 4 is not required to produce isopropanol. However, modification of the microorganism, for example, to overexpress a native primary:secondary alcohol dehydrogenase may result in enhanced production of isopropanol.

In one embodiment, the microorganism may comprise more than one pathway for the production of isopropanol.

Production of Isobutylene

Isobutylene is a major chemical building block with a market size of over 15 million tons and a global market value of $25-29 billion. Beyond its use in chemistry and as a fuel additive (15 Mt/yr), isobutylene may be converted to isooctane, a high performance, drop-in fuel for gasoline cars. Global Bioenergies has filed patent applications on the fermentative production of isobutene (i.e., isobutylene) from acetone, but none of the disclosed routes involve Ptb-Buk (WO 2010/001078; EP 2295593; WO 2011/076691; van Leeuwen, *Appl Microbiol Biotechnol*, 93: 1377-1387, 2012).

The invention provides a microorganism capable of producing isobutylene or precursors thereof from a substrate. The invention further provides a method of producing isobutylene or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of isobutylene may comprise endogenous enzymes and, where endogenous enzyme activity is absent or low, exogenous enzymes.

FIG. 1 shows two alternative routes to isobutylene. The first involves the production of isobutylene via steps 1, 2, 3, 5, and 6. The second involves the production of isobutylene via steps 1, 2, 3, 7, 8, and 6. Steps 2 and 8 may be catalyzed by Ptb-Buk. Accordingly, each route may involve Ptb-Buk.

Isobutylene via steps 1, 2, 3, 5, and 6: In one embodiment, the invention provides a microorganism comprising enzymes for steps 1, 2, 3, 5, and 6, whereby the microorganism is capable of producing isobutylene or precursors thereof from a substrate, such as a gaseous substrate. Typically, at least one of the enzymes in this pathway is exogenous to the microorganism. In a preferred embodiment, step 2 is catalyzed by Ptb-Buk. Exemplary types and sources of enzymes for steps 1, 2, 3, 5, and 6 are described elsewhere in this application. If the microorganism is derived from a parental microorganism that natively contains a primary:secondary alcohol dehydrogenase capable of converting acetone to isopropanol (step 4) (e.g., *Clostridium autoethanogenum*, *Clostridium ljungdahlii*, or *Clostridium ragsdalei*), the microorganism may be modified to knock down or knock out the expression of primary:secondary alcohol dehydrogenase (e.g., by disrupting the gene encoding the primary:secondary alcohol dehydrogenase) to prevent the conversion of acetone to isopropanol and maximize the conversion of acetone to isobutylene.

Isobutylene via steps 1, 2, 3, 7, 8, and 6: In one embodiment, the invention provides a microorganism comprising enzymes for steps 1, 2, 3, 7, 8, and 6, whereby the microorganism is capable of producing isobutylene or precursors thereof from a substrate, such as a gaseous substrate. Typically, at least one of the enzymes in this pathway is exogenous to the microorganism. In a preferred embodiment, step 2 and/or step 8 are catalyzed by Ptb-Buk. Exemplary types and sources of enzymes for steps 1, 2, 3, 7, 8, and 6 are described elsewhere in this application. If the microorganism is derived from a parental microorganism that natively contains a primary:secondary alcohol dehydrogenase capable of converting acetone to isopropanol (step 4) (e.g., *Clostridium autoethanogenum*, *Clostridium ljungdahlii*, or *Clostridium ragsdalei*), the microorganism may be modified to knock down or knock out the expression of primary: secondary alcohol dehydrogenase (e.g., by disrupting the gene encoding the primary:secondary alcohol dehydrogenase) to prevent the conversion of acetone to isopropanol and maximize the conversion of acetone to isobutylene.

Production of 3-Hydroxybutyrate

3-Hydroxybutyrate (3-HB) is a four carbon carboxylic acid in the family of betahydroxy acids. 3-hydroxybutyrate is a cosmetic ingredient for oily skin clarification, an intermediate for anti-aging cream formulations, an intermediate for polyhydroxybutyrate (PHB), a biodegradable polymer resin, and co-monomer with other polyhydroxy acids for novel bioplastics. Additionally, 3-hydroxybutyrate has specialty applications in biocompatible and biodegradable nanocomposites, particularly for medical implants, intermediate for C3/C4 chemicals, chiral building blocks, and fine chemicals. Although the production of (R)- and (S)-3-hydroxybutyrate by recombinant *E. coli* grown on glucose, the production of 3-hydroxybutyrate has not been demonstrated from microorganisms grown on gaseous substrates (Tseng, *Appl Environ Microbiol*, 75: 3137-3145, 2009). Notably, the system previously demonstrated in *E. coli* was not directly transferable to acetogens, including *C. autoethanogenum*, due to the presence of native thioesterases in acetogens. Although *E. coli* also has a thioesterase TesB that can act on 3-HB-CoA, Tseng showed that background activity is minimal (<0.1 g/L). While in *E. coli* production of stereopure isomers were reported, the inventors surprisingly found that a mix of isomers were produced in *C. autoethanogenum*. Without being bound to this theory, this is likely a result of native isomerase activity. This enables the combination of an (S)-specific 3-hydroxybutyryl-CoA dehydrogenase (Hbd) to be combined with the (R)-specific Ptb-Buk for optimized production. To produce stereopure isomers, this activity can be knocked-out. Taken together, it this invention enables to produce several g/L of 3-HB compared to low production in *E. coli* and using Ptb-Buk any combination of (R)- or (S)-specific 3-hydroxybutyryl-CoA dehydrogenase and native *Clostridium autoethanogenum* thioesterase.

The invention provides a microorganism capable of producing 3-hydroxybutyrate or precursors thereof from a substrate. The invention further provides a method of producing 3-hydroxybutyrate or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of 3-hydroxybutyrate may comprise endogenous enzymes and, where endogenous enzyme activity is absent or low, exogenous enzymes.

FIG. 1 shows two alternative routes to 3-hydroxybutyrate. The first involves the production of 3-hydroxybutyrate via steps 1, 2, and 15. The second involves the production of 3-hydroxybutyrate via steps 1, 13, and 14. Steps 2 and 14 may be catalyzed by Ptb-Buk. Accordingly, each route may involve Ptb-Buk. In one embodiment, the microorganism may comprise more than one pathway for the production of 3-hydroxybutyrate, wherein Ptb-Buk may catalyze more than one step (e.g., steps 2 and 14).

3-Hydroxybutyrate via steps 1, 2, and 15: In one embodiment, the invention provides a microorganism comprising enzymes for steps 1, 2, and 15, whereby the microorganism is capable of producing 3-hydroxybutyrate or precursors thereof from a substrate, such as a gaseous substrate. Typically, at least one of the enzymes in this pathway is exogenous to the microorganism. In a preferred embodiment, step 2 is catalyzed by Ptb-Buk. Exemplary types and sources of enzymes for steps 1, 2, and 15 are described elsewhere in this application.

3-Hydroxybutyrate via steps 1, 13, and 14: In one embodiment, the invention provides a microorganism comprising enzymes for steps 1, 13, and 14, whereby the microorganism is capable of producing 3-hydroxybutyrate or precursors thereof from substrate, such as a gaseous substrate. Typically, at least one of the enzymes in this pathway is exogenous to the microorganism. In a preferred embodiment, step 14 is catalyzed by Ptb-Buk. Exemplary types and sources of enzymes for steps 1, 13, and 14 are described elsewhere in this application.

Production of 1,3-Butanediol 1,3-Butanediol (1,3-BDO) is commonly used as a solvent for food flavoring agents and is a co-monomer used in certain polyurethane and polyester resins. More importantly, 1,3-butanediol may be catalytically converted to 1,3-butadiene (Makshina, *Chem Soc Rev,* 43: 7917-7953, 2014). Butadiene is used to produce rubber, plastics, lubricants, latex, and other products. While much of the butadiene produced today is used for the rubber in automobile tires, it can also be used to produce adiponitrile, which can be used in the manufacture of nylon 6,6. Global demand for butadiene is on the rise. In 2011, there was an estimated 10.5 million tons of demand, valued at $40 billion.

The invention provides a microorganism capable of producing 1,3-butanediol or precursors thereof from a substrate. The invention further provides a method of producing 1,3-butanediol or precursors thereof by culturing such a microorganism in the presence of substrate. In preferred embodiments, the microorganism is derived from a parental microorganism selected from the group consisting of *Clostridium autoethanogenum, Clostridium ljungdahlii,* or *Clostridium ragsdalei*. However, the microorganism may also be derived from an entirely different microorganism, e.g., *Eschericia coli*. The enzymatic pathways described for the production of 1,3-butanediol may comprise endogenous enzymes and, where endogenous enzyme activity is absent or low, exogenous enzymes.

In certain embodiments, the microorganism may produce 1,3-butanediol without co-production of ethanol (or with production of only a small amount of ethanol, e.g., less than 0.1-1.0 g/L ethanol or less than 1-10 g/L ethanol).

FIG. 1 shows three alternative routes to 1,3-butanediol. The first involves the production of 1,3-butanediol via steps 1, 2, 15, 16, and 17. The second involves the production of 1,3-butanediol via steps 1, 13, 14, 16, and 17. The third involves the production of 1,3-butanediol via steps 1, 13, 18, and 17. Steps 2 and 14 may be catalyzed by Ptb-Buk. Accordingly, at least the first and second routes may involve Ptb-Buk. In one embodiment, the microorganism may comprise more than one pathway for the production of 1,3-butanediol. In a related embodiment, the Ptb-Buk may catalyze more than one step (e.g., steps 2 and 14).

1,3-Butanediol via steps 1, 2, 15, 16, and 17: In one embodiment, the invention provides a microorganism comprising enzymes for steps 1, 2, 15, 16, and 17, whereby the microorganism is capable of producing 1,3-butanediol or precursors thereof from a substrate, such as a gaseous substrate. Typically, at least one of the enzymes in this pathway is exogenous to the microorganism. In a preferred embodiment, step 2 is catalyzed by Ptb-Buk. Exemplary types and sources of enzymes for steps 1, 2, 15, 16, and 17 are described elsewhere in this application.

1,3-Butanediol via steps 1, 13, 14, 16, and 17: In one embodiment, the invention provides a microorganism comprising enzymes for steps 1, 13, 14, 16, and 17, whereby the microorganism is capable of producing 1,3-butanediol or precursors thereof from a substrate, such as a gaseous substrate. Typically, at least one of the enzymes in this pathway is exogenous to the microorganism. In a preferred embodiment, step 14 is catalyzed by Ptb-Buk. Exemplary types and sources of enzymes for steps 1, 13, 14, 16, and 17 are described elsewhere in this application.

Figure 11:
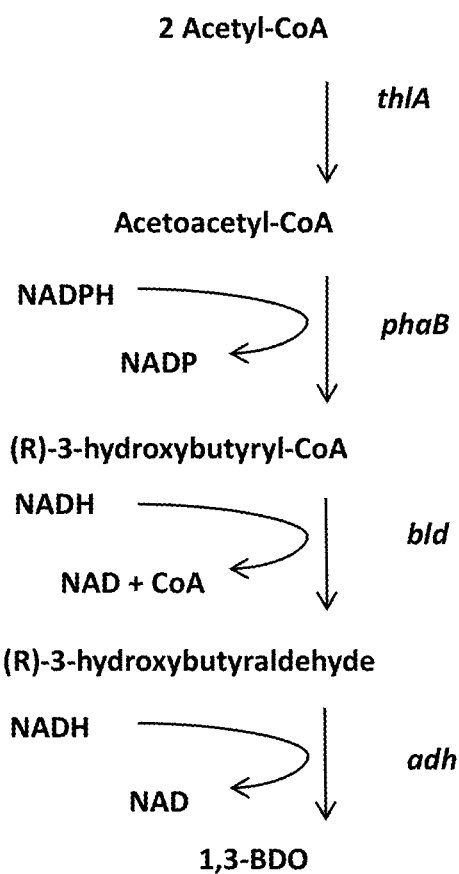
FIG. 11 is a diagram showing the production of 1,3-butanediol via 3-butyraldehyde dehydrogenase (Bld).

1,3-Butanediol via steps 1, 13, 18, and 17: In one embodiment, the invention provides a microorganism comprising enzymes for steps 1, 13, 18, and 17, whereby the microorganism is capable of producing 1,3-butanediol or precursors thereof from a substrate, such as a gaseous substrate (FIG. 11). Typically, at least one of the enzymes in this pathway is exogenous to the microorganism. Exemplary types and sources of enzymes for steps 1, 13, 18, and 17 are described elsewhere in this application. A similar route has been demonstrated in *E. coli*, but not in acetogens such as *Clostridium autoethanogenum, Clostridium ljungdahlii,* and *Clostridium ragsdalei* (Kataoka, *J Biosci Bioeng,* 115: 475-480, 2013). Although the use of Ptb-Buk results in the production of (R)-1,3-butanediol, this route, which does not require the use of Ptb-Buk, may result in the production of (S)-1,3-butanediol.

Production of 2-Hydroxyisobutyrate

2-Hydroxyisobutyrate (2-HIB) is a four carbon carboxylic acid that may serve as a building block for many types of polymers. The methyl ester of methacrylic acid, which can be synthesized by dehydration of 2-hydroxyisobutyrate or via the corresponding amide, is polymerized to polymethylmethacrylate (PMMA) for the production of acrylic glass, durable coatings, and inks. For this compound alone, the global market exceeds 3 million tons. Other branched C4 carboxylic acids, e.g., chloro- and amino-derivatives of 2-hydroxyisobutyrate, as well as isobutylene glycol and its oxide, are also used in polymers and for many other applications.

Figure 8:
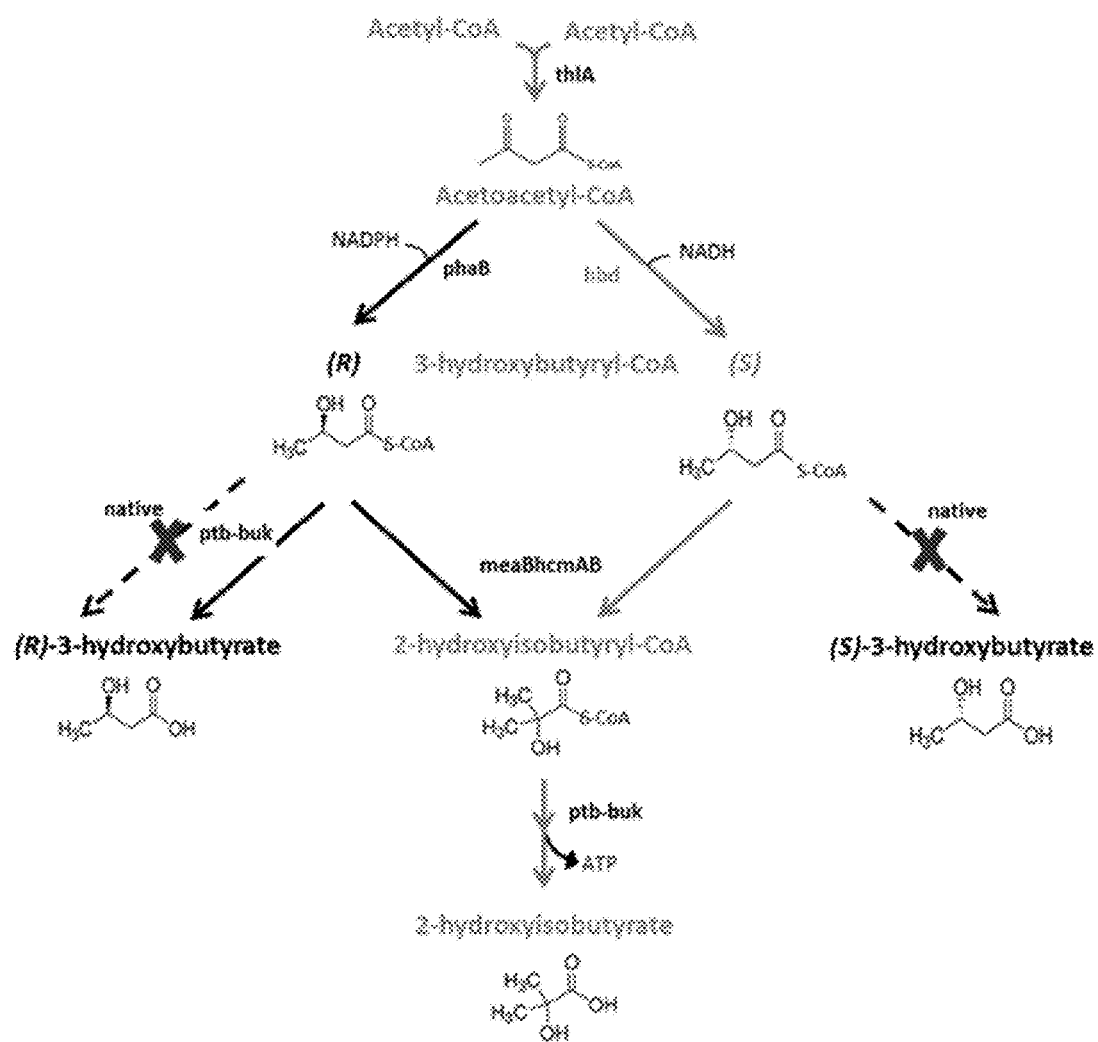
FIG. 8 is a diagram showing the stereospecificity of Ptb-Buk for the production of (R)-3-hydroxybutyrate and 2-hydroxyisobutyrate. The term "native" in FIG. 8 refers to native thioesterase.

The stereospecificity of the Ptb-Buk system is particularly useful in overcoming the limitations of the current state of art with respect to the production of 2-hydroxyisobutyrate. Both Ptb-Buk and thioesterases are promiscuous, such that side activity with 3-hydroxybutyryl-CoA may divert resources away from target pathways for the production of 2-hydroxyisobutyryl-CoA (see, e.g., FIG. 1 and FIG. 8). However, Ptb-Buk is able to distinguish between stereoisomers and will act on (R)-3-hydroxybutyryl-CoA, but not on (S)-3-hydroxybutyryl-CoA. In contrast, thioesterases are not able to distinguish between 3-hydroxybutyryl-CoA stereoisomers. In a preferred embodiment, an (S)-specific acetoacetyl-CoA hydratase (EC 4.2.1.119) (step 13) is chosen in combination with the Ptb-Buk (step 20) to avoid losses to 3-hydroxybutyrate and maximize 2-hydroxyisobutyrate yield (FIG. 8). The (S)-specific form of 3-hydroxybutyryl-CoA is also the preferred substrate for the 2-hydroxyisobutyryl-CoA mutase (EC 5.4.99.-) (step 19) (Yaneva, *J Biol Chem,* 287: 15502-15511, 2012).

The invention provides a microorganism capable of producing 2-hydroxyisobutyrate or precursors thereof from a substrate. The invention further provides a method of producing 2-hydroxyisobutyrate or precursors thereof by culturing such a microorganism in the presence of a substrate. In preferred embodiments, the microorganism is derived from a parental microorganism selected from the group consisting of *Clostridium autoethanogenum, Clostridium ljungdahlii,* or *Clostridium ragsdalei*. However, the microorganism may also be derived from an entirely different microorganism, e.g., *Eschericia coli*. The enzymatic pathways described for the production of 2-hydroxyisobutyrate may comprise endogenous enzymes and, where endogenous enzyme activity is absent or low, exogenous enzymes.

2-Hydroxyisobutyrate via steps 1, 13, 19, and 20: In one embodiment, the invention provides a microorganism comprising enzymes for steps 1, 13, 19, and 20, whereby the microorganism is capable of producing 2-hydroxyisobutyrate or precursors thereof from a substrate, such as a gaseous substrate. Typically, at least one of the enzymes in this pathway is exogenous to the microorganism. In a preferred embodiment, step 20 is catalyzed by Ptb-Buk. Exemplary types and sources of enzymes for steps 1, 13, 19, and 20 are described elsewhere in this application.

In certain embodiments, the invention also provides a microorganism capable of producing 2-hydroxybutyrate (2-HB) or precursors thereof from a substrate. The invention further provides a method of producing 2-hydroxybutyrate or precursors thereof by culturing such a microorganism in the presence of a substrate. Without wishing to be bound by any particular theory, the inventors believe the observed production of 2-hydroxybutyrate is attributable to nonspecific mutase activity in microorganisms such as *Clostridium autoethanogenum*, *Clostridium ljungdahlii*, and *Clostridium ragsdalei*.

Production of Adipic Acid

Adipic acid is the most important dicarboxylic acid with an estimated market of greater US $4.5 billion with about 2.5 billion kgs produced annually. Over 60% of produced adipic acid is being used as monomer precursor for the production of nylon and the global market for adipic acid is expected to reach US $7.5 billion by 2019. Currently, adipic acid is almost exclusively produced petrochemically, e.g. by carbonylation of butadiene.

Figure 34:
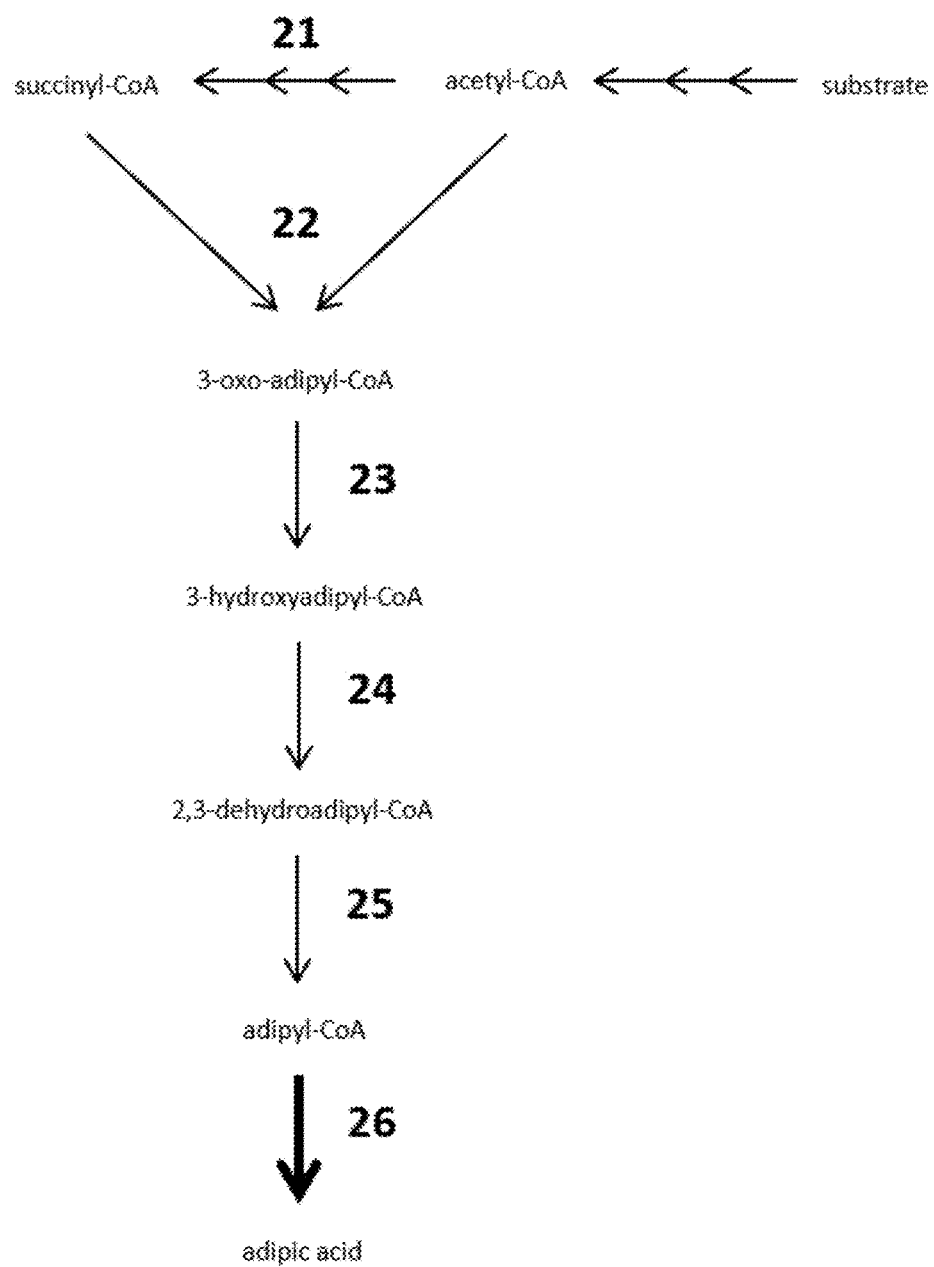
FIG. 34 is a diagram of metabolic pathways for the production of various products, including adipic acid. Bold arrows indicate steps that may be catalyzed by Ptb-Buk.

The invention provides a microorganism capable of producing adipic acid or precursors thereof from a substrate (FIG. 34). The invention further provides a method of producing adipic acid or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of adipic acid may comprise endogenous enzymes and, where endogenous enzyme activity is absent or low, exogenous enzymes.

Adipic acid via steps 22, 23, 24, 25, and 26: In one embodiment, the invention provides a microorganism comprising enzymes for steps 22, 23, 24, 25, and 26, whereby the microorganism is capable of producing adipic acid or precursors thereof from a substrate, such as a gaseous substrate. Typically, at least one of the enzymes in this pathway is exogenous to the microorganism. In a preferred embodiment, step 26 is catalyzed by Ptb-Buk. Exemplary types and sources of enzymes for steps 22, 23, 24, 25, and 26 are described elsewhere in this application.

Adipic acid via steps 21, 22, 23, 24, 25, and 26: In one embodiment, the invention provides a microorganism comprising enzymes for steps 21, 22, 23, 24, 25, and 26, whereby the microorganism is capable of producing adipic acid or precursors thereof from a substrate, such as a gaseous substrate. Typically, at least one of the enzymes in this pathway is exogenous to the microorganism. In a preferred embodiment, step 26 is catalyzed by Ptb-Buk. Exemplary types and sources of enzymes for steps 21, 22, 23, 24, 25, and 26 are described elsewhere in this application.

In one embodiment, the microorganism may comprise more than one pathway for the production of adipic acid.

Production of 1,3-Hexanediol

Figure 35:
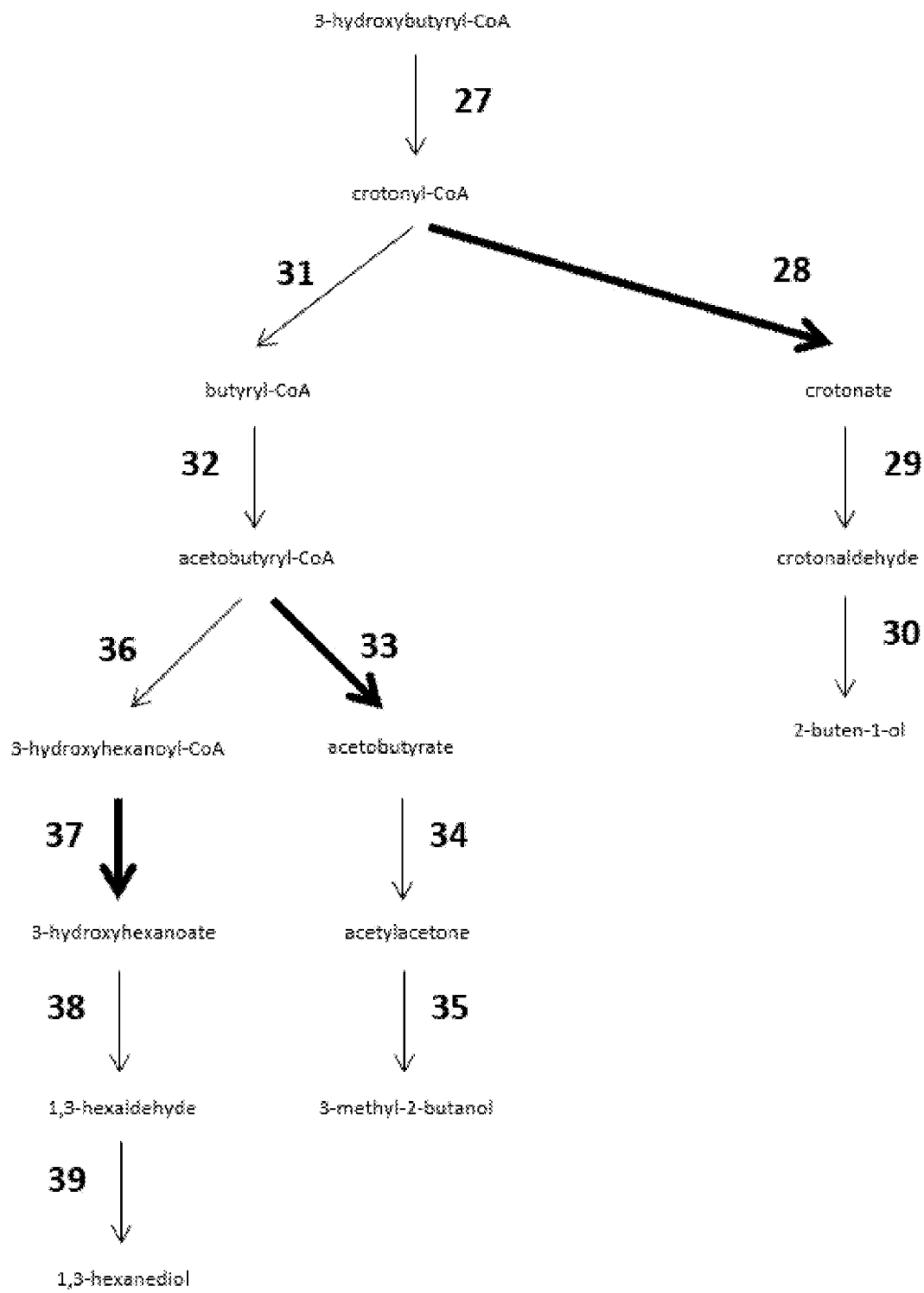
FIG. 35 is a diagram of metabolic pathways for the production of various products, including 1,3-hexanediol, 2-methyl-2-butanol, and 2-buten-1-ol. Bold arrows indicate steps that may be catalyzed by Ptb-Buk.

The invention provides a microorganism capable of producing 1,3-hexanediol or precursors thereof from a substrate (FIG. 35). The invention further provides a method of producing 1,3-hexanediol or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of 1,3-hexanediol may comprise endogenous enzymes and, where endogenous enzyme activity is absent or low, exogenous enzymes.

The pathways depicted in FIG. 35 begin with 3-hydroxybutyryl-CoA, which may be produced via steps 1 and 13, as depicted in FIG. 1.

1,3-Hexanediol via steps 1, 13, 27, 31, 32, 36, 37, 38, and 39: In one embodiment, the invention provides a microorganism comprising enzymes for steps 1, 13, 27, 31, 32, 36, 37, 38, and 39, whereby the microorganism is capable of producing 1,3-hexanediol or precursors thereof from a substrate, such as a gaseous substrate. Typically, at least one of the enzymes in this pathway is exogenous to the microorganism. In a preferred embodiment, step 37 is catalyzed by Ptb-Buk. Exemplary types and sources of enzymes for steps 1, 13, 27, 31, 32, 36, 37, 38, and 39 are described elsewhere in this application.

Production of 3-Methyl-2-Butanol

The invention provides a microorganism capable of producing 3-methyl-2-butanol or precursors thereof from a substrate (FIG. 35). The invention further provides a method of producing 3-methyl-2-butanol or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of 3-methyl-2-butanol may comprise endogenous enzymes and, where endogenous enzyme activity is absent or low, exogenous enzymes.

The pathways depicted in FIG. 35 begin with 3-hydroxybutyryl-CoA, which may be produced via steps 1 and 13, as depicted in FIG. 1.

3-Methyl-2-butanol via steps 1, 13, 27, 31, 32, 33, 34, and 35: In one embodiment, the invention provides a microorganism comprising enzymes for steps 1, 13, 27, 31, 32, 33, 34, and 35, whereby the microorganism is capable of producing 3-methyl-2-butanol or precursors thereof from a substrate, such as a gaseous substrate. Typically, at least one of the enzymes in this pathway is exogenous to the microorganism. In a preferred embodiment, step 33 is catalyzed by Ptb-Buk. Exemplary types and sources of enzymes for steps 1, 13, 27, 31, 32, 33, 34, and 35 are described elsewhere in this application.

Production of 2-Buten-1-ol

The invention provides a microorganism capable of producing 2-buten-1-ol or precursors thereof from a substrate (FIG. 35). The invention further provides a method of producing 2-buten-1-ol or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of 2-buten-1-ol may comprise endogenous enzymes and, where endogenous enzyme activity is absent or low, exogenous enzymes.

The pathways depicted in FIG. 35 begin with 3-hydroxy-butyryl-CoA, which may be produced via steps 1 and 13, as depicted in FIG. 1.

2-Buten-1-ol via steps 1, 13, 27, 28, 29, and 30: In one embodiment, the invention provides a microorganism comprising enzymes for steps 1, 13, 27, 28, 29, and 30, whereby the microorganism is capable of producing 2-buten-1-ol or precursors thereof from a substrate, such as a gaseous substrate. Typically, at least one of the enzymes in this pathway is exogenous to the microorganism. In a preferred embodiment, step 28 is catalyzed by Ptb-Buk. Exemplary types and sources of enzymes for steps 1, 13, 27, 28, 29, and 30 are described elsewhere in this application.

Production of Isovalerate

Figure 36:
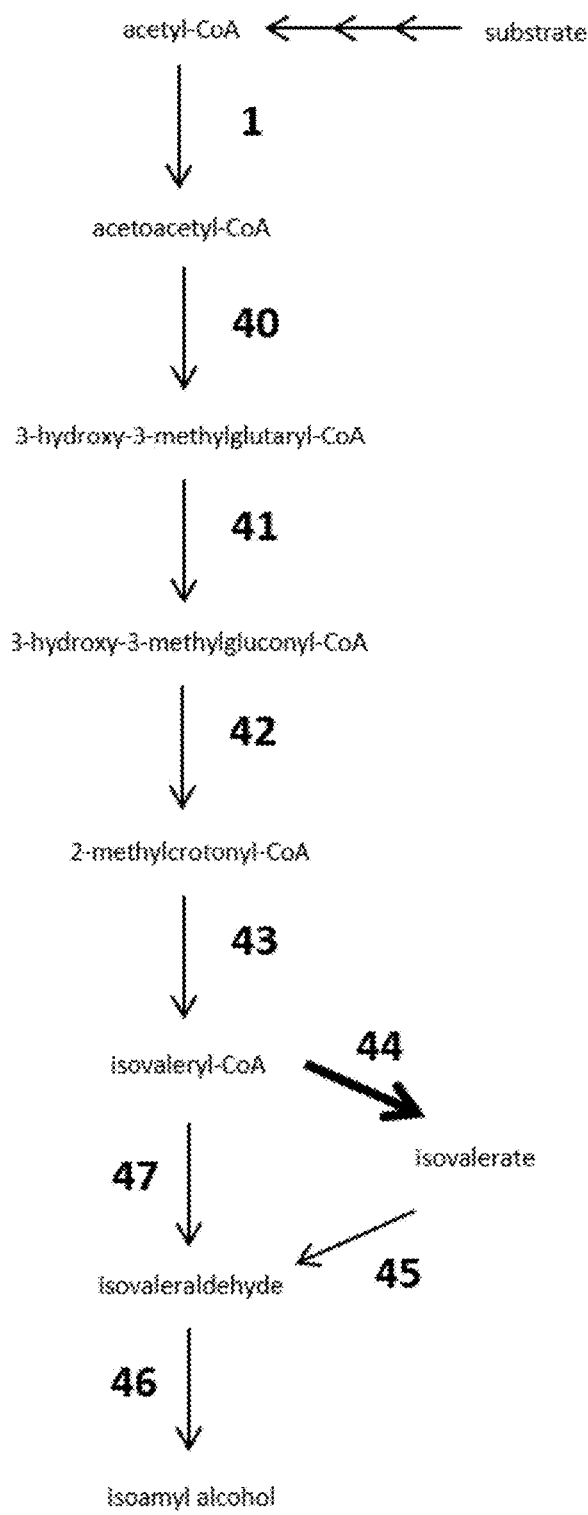
FIG. 36 is a diagram of metabolic pathways for the production of various products, including isovalerate and isoamyl alcohol. Bold arrows indicate steps that may be catalyzed by Ptb-Buk.

The invention provides a microorganism capable of producing isovalerate or precursors thereof from a substrate (FIG. 36). The invention further provides a method of producing isovalerate or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of isovalerate may comprise endogenous enzymes and, where endogenous enzyme activity is absent or low, exogenous enzymes.

Isovalerate via steps 1, 40, 41, 42, 43, and 44: In one embodiment, the invention provides a microorganism comprising enzymes for steps 1, 40, 41, 42, 43, and 44, whereby the microorganism is capable of producing isovalerate or precursors thereof from a substrate, such as a gaseous substrate. Typically, at least one of the enzymes in this pathway is exogenous to the microorganism. In a preferred embodiment, step 44 is catalyzed by Ptb-Buk. Exemplary types and sources of enzymes for steps 1, 40, 41, 42, 43, and 44 are described elsewhere in this application.

Production of Isoamyl Alcohol

The invention provides a microorganism capable of producing isoamyl alcohol or precursors thereof from a substrate (FIG. 36). The invention further provides a method of producing isoamyl alcohol or precursors thereof by culturing such a microorganism in the presence of a substrate. In preferred embodiments, the microorganism is derived from a parental microorganism selected from the group consisting of *Clostridium autoethanogenum*, *Clostridium ljungdahlii*, or *Clostridium ragsdalei*. However, the microorganism may also be derived from an entirely different microorganism, e.g., *Eschericia coli*. The enzymatic pathways described for the production of isoamyl alcohol may comprise endogenous enzymes and, where endogenous enzyme activity is absent or low, exogenous enzymes.

Isoamyl alcohol via steps 1, 40, 41, 42, 43, 44, 45, and 46: In one embodiment, the invention provides a microorganism comprising enzymes for steps 1, 40, 41, 42, 43, 44, 45, and 46, whereby the microorganism is capable of producing isoamyl alcohol or precursors thereof from a substrate, such as a gaseous substrate. Typically, at least one of the enzymes in this pathway is exogenous to the microorganism. In a preferred embodiment, step 44 is catalyzed by Ptb-Buk. Exemplary types and sources of enzymes for steps 1, 40, 41, 42, 43, 44, 45, and 46 are described elsewhere in this application.

Isoamyl alcohol via steps 1, 40, 41, 42, 43, 47 and 46: In one embodiment, the invention provides a microorganism comprising enzymes for steps 1, 40, 41, 42, 43, 47 and 46, whereby the microorganism is capable of producing isoamyl alcohol or precursors thereof from a substrate, such as a gaseous substrate. Typically, at least one of the enzymes in this pathway is exogenous to the microorganism. Exemplary types and sources of enzymes for steps 1, 40, 41, 42, 43, 47 and 46 are described elsewhere in this application.

In one embodiment, the microorganism may comprise more than one pathway for the production of isoamyl alcohol.

Production of Additional Products

Figure 32:
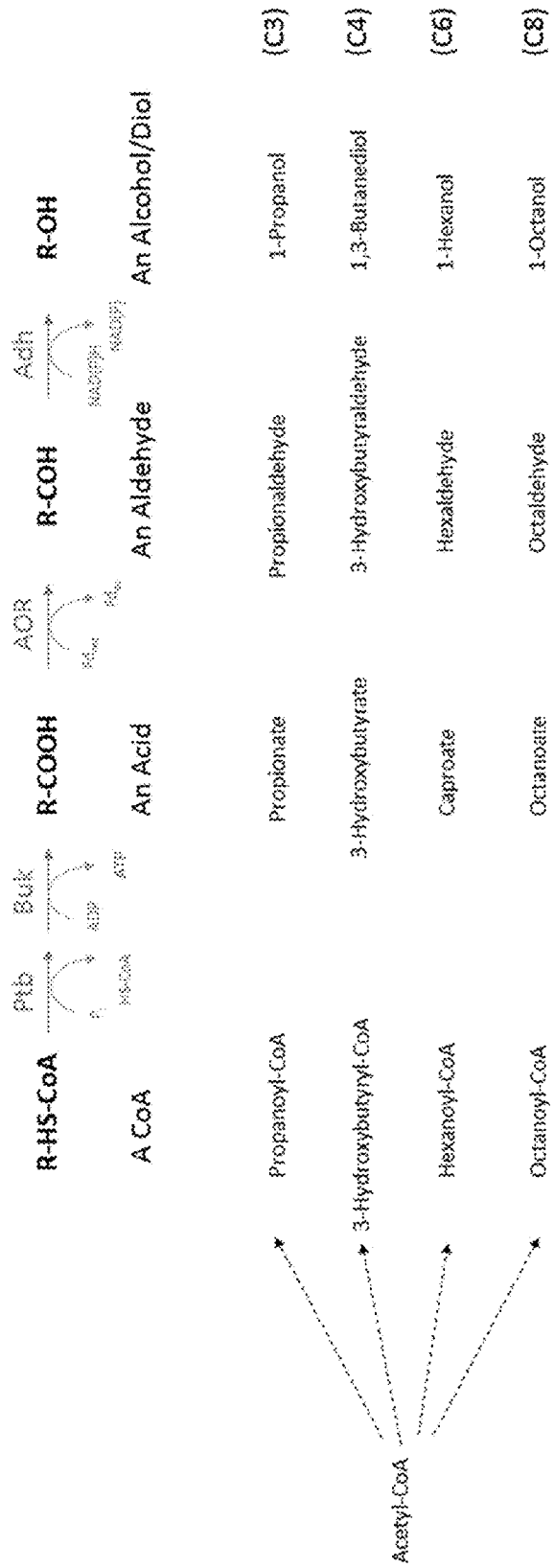
FIG. 32 is a diagram showing the production of various products in a microorganism comprising Ptb-Buk, AOR, and Adh.

The invention provides a microorganism comprising exogenous Ptb-Buk and exogenous or endogenous aldehyde:ferredoxin oxidoreductase (AOR). Such a microorganism may produce, for example, 1-propanol, 1-butanol, 1-hexanol, and 1-octanol or precursors thereof from acetyl-CoA generated, for example, from a gaseous substrate (FIG. 32). The invention further provides a method of producing 1-propanol, 1-butanol, 1-hexanol, and 1-octanol or precursors thereof by culturing such a microorganism in the presence of a gaseous substrate. *Clostridium autoethanogenum*, *Clostridium ljungdahlii*, and *Clostridium ragsdalei* natively comprise AOR. However, AOR may be overexpressed in such microorganisms in combination with expression of exogenous Ptb-Buk. Alternatively, exogenous AOR and exogenous Ptb-Buk may be expressed in a microorganism other than *Clostridium autoethanogenum*, *Clostridium ljungdahlii*, and *Clostridium ragsdalei*, such as *Escherichia coli*.

Production of Precursors and Intermediates

The pathways depicted in FIGS. 1, 34, 35, and 36 may be modified to produce precursors or intermediates of the aforementioned products. In particular, partial enzymatic pathways for any of the pathways described herein may be inserted in a host microorganism to obtain production of precursors or intermediates.

Definitions and Background

The term "genetic modification" or "genetic engineering" broadly refers to manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

With respect to enzyme activity, a "substrate" is a molecule upon which an enzyme acts and a "product" is a molecule produced by the action of an enzyme. A "native substrate," therefore, is a molecule upon which an enzyme natively acts in a wild-type microorganism and a "native product" is a molecule natively produced by the action of the enzyme in the wild-type microorganism. For example, butanoyl-CoA is the native substrate of Ptb and butanoyl phosphate and is the native substrate of Buk. Additionally, butanoyl phosphate is the native product of Ptb and butyrate (butanoate) is the native product of Buk. Likewise, a "non-native substrate" is a molecule upon which an enzyme does not natively act in a wild-type microorganism and a "non-native product" is a molecule not natively produced by the action of the enzyme in the wild-type microorganism. An enzyme that is capable of acting on multiple different substrates, whether native or non-native, is typically referred to as a "promiscuous" enzyme. The inventors have discovered that Ptb is promiscuous and is capable of accepting a variety of acyl-CoAs and enoyl-CoAs as substrates, such that Ptb-Buk may be used to convert a number of acyl-CoAs and enoyl-CoAs to their corresponding acids or alkenates, respectively, while simultaneously generating ATP. Thus, in preferred embodiments, the Ptb-Buk of the invention acts on non-native substrates (i.e., substrates other than butanoyl-CoA and/or butanoyl phosphate) to produce non-native products (i.e., products other than butanoyl phosphate and/or butyrate (butanoate)).

The term "butyryl-CoA" may be used interchangeably herein with "butanoyl-CoA."

The term "energy-generating" or the like may be used interchangeably herein with "energy-conserving" or the like. Both of these terms are commonly used in the literature.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the invention that produces no target product or substantially no target product or a reduced amount of target product compared to the parental microorganism from which the microorganism of the invention is derived. For example, the microorganism of the invention may produce no target product or at least about 1%, 3%, 5%, 10%, 20%, 30%, 40%, 50%, 60%, 70%, 80%, 90%, or 95% less target product than the parental microorganism. For example, the microorganism of the invention may produce less than about 0.001, 0.01, 0.10, 0.30, 0.50, or 1.0 g/L target product.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum*, *Clostridium ljungdahlii*, or *Clostridium ragsdalei*. In a further preferred embodiment, the genes of the invention are codon optimized for expression in *Clostridium autoethanogenum* LZ1561, which is deposited under DSMZ accession number DSM23693.

"Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum, Clostridium ljungdahlii*, or *Clostridium ragsdalei*. In a preferred embodiment, the parental microorganism is *Clostridium autoethanogenum* LZ1561, which is deposited under DSMZ accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum, Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/−[1] | − | − | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[2] | − |
| *Clostridium ragsdalei* | + | + | + | + | + | + | − |

TABLE 1-continued

|  | C1-fixing | Anaerobe | Acetogen | Ethanologen | Autotroph | Carboxydotroph | Methanotroph |
|---|---|---|---|---|---|---|---|
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | −[3] | + | + | − |
| *Oxobacter pfennigii* | + | + | + | − | + | + | − |
| *Sporomusa ovata* | + | + | + | − | + | +/−[4] | − |
| *Sporomusa silvacetica* | + | + | + | − | + | +/−[5] | − |
| *Sporomusa sphaeroides* | + | + | + | − | + | +/−[6] | − |
| *Thermoanaerobacter kiuvi* | + | + | + | − | + | − | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and

*Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

In some embodiments, however, the microorganism of the invention is a microorganism other than *Clostridium autoethanogenum*, *Clostridium ljungdahlii*, or *Clostridium ragsdalei*. For example, the microorganism may be selected from the group consisting of *Escherichia coli*, *Saccharomyces cerevisiae*, *Clostridium acetobutylicum*, *Clostridium beijerinckii*, *Clostridium saccharbutyricum*, *Clostridium saccharoperbutylacetonicum*, *Clostridium butyricum*, *Clostridium diolis*, *Clostridium kluyveri*, *Clostridium pasterianium*, *Clostridium novyi*, *Clostridium difficile*, *Clostridium thermocellum*, *Clostridium cellulolyticum*, *Clostridium cellulovorans*, *Clostridium phytofermentans*, *Lactococcus lactis*, *Bacillus subtilis*, *Bacillus licheniformis*, *Zymomonas mobilis*, *Klebsiella oxytoca*, *Klebsiella pneumonia*, *Corynebacterium glutamicum*, *Trichoderma reesei*, *Cupriavidus necator*, *Pseudomonas putida*, *Lactobacillus plantarum*, and *Methylobacterium extorquens*.

"Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of $CO$ or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/

180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol. In certain embodiments, microbial biomass itself may be considered a product.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

The terms "intermediate" and "precursor," which may be referred to interchangeably herein, refer to a molecular entity in an enzymatic pathway upstream of an observed or target product.

"Selectivity" refers to the ratio of the production of a target product to the production of all fermentation products produced by a microorganism. The microorganism of the invention may be engineered to produce products at a certain selectivity or at a minimum selectivity. In one embodiment, a target product account for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the invention is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example demonstrates the ability of Ptb-Buk to convert acetoacetyl-CoA to acetoacetate in *E. coli* in vivo and its use in production of acetone, isopropanol, 3-hydroxybutyrate, and isobutylene Pathways that rely on the Ptb-Buk system for acetoacetate production from acetoacetyl-CoA were designed and constructed. This was done in a modular fashion using a pDUET vector system (Novagen). One module contained ptb-buk genes from *C. beijerinckii* NCIMB8052 (GenBank NC_009617, position 232027 . . . 234147; Cbei_0203-204; NCBI-GeneID 5291437-38) on plasmid pACYC. Another module contained the thiolase gene thlA of *C. acetobutylicum* (Genbank NC_001988, position 82040 . . . 83218; CA_P0078; NCBI-GeneID 1116083) and the acetoacetate decarboxylase gene adc of *C. beijerinckii* NCIMB8052 (Genbank NC_009617, position 4401916 . . . 4402656; Cbei_3835; NCBI-GeneID 5294996) on plasmid pCOLA. Ptb and buk genes were amplified from genomic DNA of *C. beijerinckii* NCIMB8052 and thlA and adc genes from an existing acetone plasmid pMTL85147-thlA-ctfAB-adc (WO 2012/115527) and cloned under control of the T7 promoter present in the pDUET vectors via restriction independent cloning with the circular polymerase extension cloning (CPEC) method (Quan, *PloS One,* 4:e6441, 2009).

Oligonucleotides used for amplification of ptb and buk genes:

| SEQ ID NO: | Name | Sequence | Direction |
|---|---|---|---|
| 95 | pACYCDuet-ptb-buk - pACYC-ptb-R1 | AAGTTTTTACTCATATGTATATC TCCTTCTTATACTTAAC | reverse |
| 96 | pACYCDuet-ptb-buk- ptb-pACYC-F1 | AGAAGGAGATATACATATGAGT AAAAACTTTGATGAGTTA | forward |
| 97 | pACYCDuet-ptb-buk - buk-pACYC-R1 | ACCAGACTCGAGGGTACCTAGT AAACCTTAGCTTGTTC | reverse |
| 98 | pACYCDuet-ptb-buk - pACYC-buk-F1 | TAAGGTTTACTAGGTACCCTCG AGTCTGGTAAAGAAAC | forward |

Oligonucleotides used for amplification of thlA and adc genes:

| SEQ ID NO: | Name | Sequence | Direction |
|---|---|---|---|
| 99 | pCOLADuet-thlA-adc thlA-adc-R1 | -ACATATGTATATCTCCTTCTTAC TAGCACTTTTCTAGCAATATTG | reverse |
| 100 | pCOLADuet-thlA-adc adc-ThlA-F1 | -AGTAAGAAGGAGATATACATAT GTTAGAAAGTGAAGTATCTAAAC | forward |
| 101 | pCOLADuet-thlA-adc adc-pCOLA-R1 | -CAGACTCGAGGGTACCTTATTT TACTGAAAGATAATCATGTAC | reverse |
| 102 | pCOLADuet-thlA-adc pCOLA-adc-F1 | -TCTTTCAGTAAAATAAGGTACC CTCGAGTCTGGTAAAGAAAC | forward |
| 103 | pCOLADuet-thlA-adc thlA-pCOLA-F1 | -GAAGGAGATATACATATGAAA GAAGTTGTAATAGCTAGTG | forward |
| 104 | pCOLADuet-thlA-adc pCOLA-thlA-R1 | -ACAACTTCTTTCATATGTATATC TCCTTCTTATACTTAAC | reverse |

Figure 4:
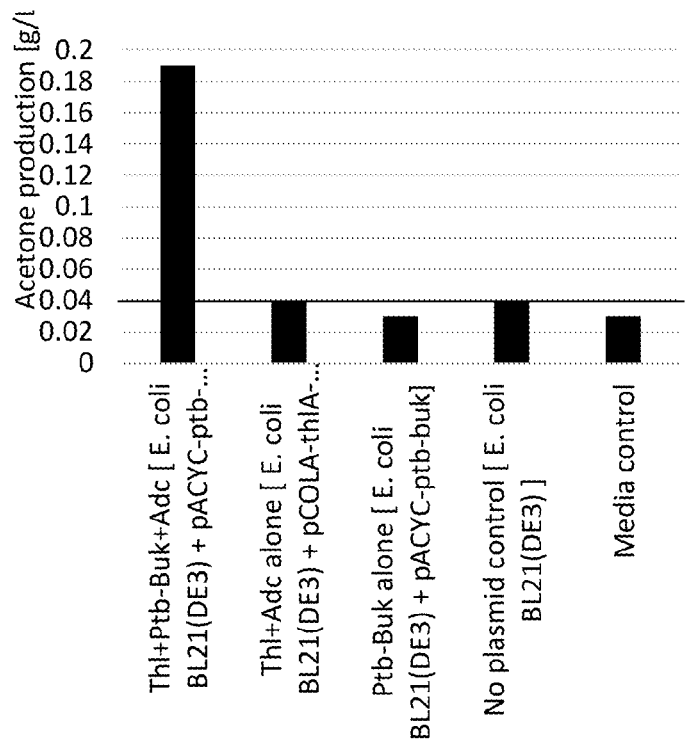
FIG. 4 is a graph showing average acetone production in *E. coli* BL21 (D3) modified with plasmids comprising exogenous genes. This data demonstrates the ability of Ptb-Buk to convert acetoacetyl-CoA to acetoacetate in *E. coli* in vivo.
Figure 5:
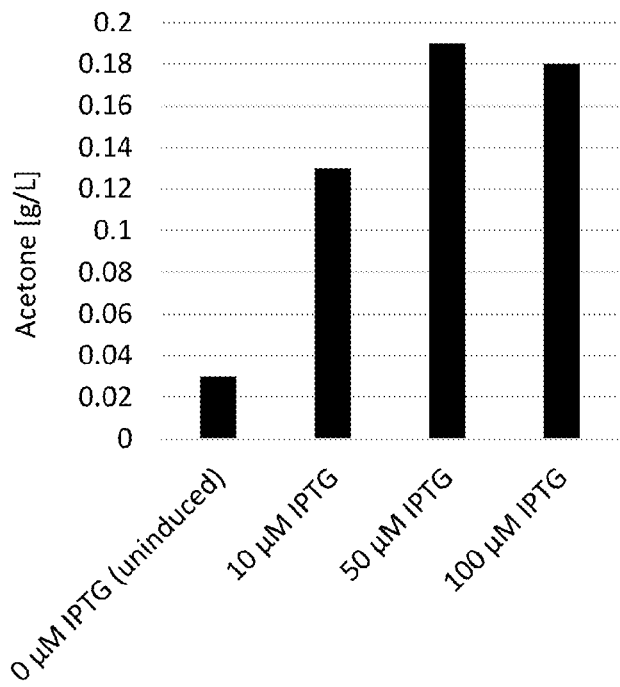
FIG. 5 is a graph showing the effect of induction of *E. coli* BL21 (DE3) carrying both the pACYC-ptb-buk and pCOLA-thlA-adc plasmids (expressing thiolase, Ptb-Buk, and acetoacate decarboxylase).

After the plasmids pACYC-ptb-buk (SEQ ID NO: 105) and pCOLA-thlA-adc (SEQ ID NO: 106) were constructed, they were transformed individually and together into *E. coli* BL21 (DE3) (Novagen) and growth experiments carried out in quadruplicates in 1.5 mL cultures in 12-well plates at 28° C. with 160 rpm orbital shaking using M9 minimal medium (Sambrook, Molecular Cloning: A Laboratory Manual, Vol 3, Cold Spring Harbour Press, 1989) with glucose (FIG. 4). The cultures were inoculated at an OD600 nm of 0.1 and induced with different concentrations of IPTG (0, 50, 100 µM) after 2 h of growth (FIG. 5). The plates were sealed using plate tape strips and each well was pierced with a green tipped needle to provide micro-aerobic conditions. Growth was carried out for another 64 h of induction. The experiment was repeated in triplicate.

Acetone concentrations, as well as the concentrations of other metabolites such as isobutylene, were measured using gas chromatography (GC) analysis, employing an Agilent 6890N headspace GC equipped with a Supelco polyethylene glycol (PEG) 60-µm solid-phase microextraction fiber, a Restek Rtx-1 (30 m×0.32 µm×5 µm) column, and a flame ionization detector (FID). Samples (4 ml) were transferred into a 20-ml headspace vial, upon which the fiber was incubated (exposed) for 10 min at 50° C. The sample was desorbed in the injector at 250° C. for 9 min. Chromatography was performed with an oven program of 40° C. (5-min hold) and 10° C./min to 200° C., followed by a 5-min hold at 220° C. The column flow rate was 1 ml/min, with hydrogen as the carrier gas. The FID was kept at 250° C., with hydrogen at 40 ml/min, air at 450 ml/min, and nitrogen at 15 ml/min as the makeup gas.

It was immediately obvious that acetone was produced in the strain carrying both the pACYC-ptb-buk and pCOLA-thlA-adc plamids (expressing thiolase, Ptb-Buk, and acetoacetate decarboxylase). Average final acetone production of 0.19 g/L was measured, whereas no acetone was produced in a no plasmid control, media control, and single plasmid controls pACYC-ptb-buk (expressing Ptb-Buk) or pCOLA-thlA-adc plamid (expressing thiolase and acetoacetate decarboxylase) (below reliable detection limit). The uninduced culture of the strain carrying both the pACYC-ptb-buk and pCOLA-thlA-adc plamids (expressing thiolase, Ptb-Buk, and acetoacetate decarboxylase) did not produce appreciable amounts of acetone.

Average Acetone Production in *E. coli* BL21 (DE3):

| Strain | Acetone (g/L) |
|---|---|
| Thl + Ptb-Buk + Adc [*E. coil* BL21 (DE3) + pACYC-ptb-buk + pCOLA-thlA-adc] | 0.19 ± 0.04 |
| Thl + Adc alone [*E. coil* BL21 (DE3) + pCOLA-thlA-adc] | 0.04 ± 0.01 |
| Ptb-Buk alone [*E. coil* BL21 (DE3) + pACYC-ptb-buk] | 0.03 ± 0.01 |

| Strain | Acetone (g/L) |
|---|---|
| No plasmid control [*E. coli* BL21 (DE3)] | 0.04 ± 0.01 |
| Media control | 0.03 ± 0.01 |

This experiment clearly demonstrates that Ptb-Buk is able to perform the conversion of acetoacetyl-CoA to acetoacetate can be used in place of a CoA-transferase or a thioesterase for the production of acetone, exemplified using a route that comprises steps 1, 2, and 3 of FIG. 1.

It is well known that isopropanol can be produced from acetone by addition of a primary:secondary alcohol dehydrogenase (Köpke, *Appl Environ Microbiol*, 80: 3394-3403, 2014) (step 4 in FIG. 1) and that isobutylene can be produced from acetone via addition of a hydroxyisovalerate synthase (step 5 in FIG. 1) and decarboxylase (step 6 in FIG. 1) (van Leeuwen, *Appl Microbiol Biotechnol*, 93: 1377-1387, 2012). A pathway can be constructed that includes the above-demonstrated acetone route via Ptb-Buk with the genes thlA, ptb-buk, and adc and a primary:secondary alcohol dehydrogenase gene (e.g., Genbank accession number NC_022592, pos. 609711 ... 610766; CAETHG 0553; NCBI-GeneID: 17333984) that would allow isopropanol production via the Ptb-Buk system in *E. coli* comprising steps 1, 2, 3, and 4 of FIG. 1. Similarly, a pathway can be constructed that includes the above-demonstrated acetone route via Ptb-Buk conversion of acetoacetyl-CoA to acetoacetate with the genes thlA, ptb-buk, and adc and genes for a hydroxyisovalerate synthase and decarboxylase that would allow isobutylene production via the Ptb-Buk system in *E. coli* comprising of steps 1, 2, 3, 5, and 6 of FIG. 1. Acetoacetete can also be converted to 3-hydroxybutyrate via a 3-hydroxybutyrate dehydrogenase Bdh. This can be combined with Ptb-Buk conversion of acetoacetyl-CoA to acetoacetate for 3-hydroxybutyrate production in a strain expressing genes thlA, ptb-buk, and bdh resulting in a pathway comprising steps 1, 2, and 15 of FIG. 1.

Example 2

This example demonstrates the ability of Ptb-Buk to convert acetoacetyl-CoA to acetoacetate in *C. autoethanogenum* in vivo and the use of Ptb-Buk in the production of acetone, isopropanol, 3-hydroxybutyrate, and isobutylene from a gaseous substrate.

To demonstrate that the Ptb-Buk system also allows acetone, isopropanol, or isobutylene synthesis from gaseous substrates, a plasmid was constructed that contains the same genes as in Example 1, thl+ptb-buk+adc under control of a clostridial promoter on a shuttle vector that allows expression in acetogens such as *C. autoethanogenum, C. ljungdahlii* or *C. ragsdalei*.

The pMTL plasmid is a shuttle plasmid system for introducing circular dna into Clostridia via *E. coli* conjugation (Heap, *J Microbiol Methods*, 78: 79-85, 2009. The genes of interest (i.e., hbd, phaB, thlA, ptb, buk, and aor1) were cloned into the lacZ region of the plasmids using common techniques in molecular biology including dna restriction digestion followed by ligation, and the golden gate dna assembly technology when more than one pieces of dna fragments were to be cloned simultaneously into the plasmid. The constructed plasmids are verified by DNA sequencing.

Production of acetone and isopropanol was previously demonstrated in *C. autoethanogenum* using a plasmid pMTL85147-thlA-ctfAB-adc encoding thl+ctfAB+adc (WO 2012/115527) under the control of a clostridial promoter from the Wood-Ljungdahl gene cluster. In this plasmid the ctfAB genes encoding the CoA transferase were replaced directly with ptb-buk genes encoding the Ptb-Buk system. This was done as described in Example 1 using the CPEC method. The resulting plasmid is pMTL85147-thlA-ptb-buk-adc.

Oligonucleotides used for the amplification of ptb-buk and cloning into pMTL8317-thl-ptb-buk-adc are described below.

| SEQ ID NO: | Name | Sequence | Direction |
|---|---|---|---|
| 107 | thlA-ptb-R1 | ATTTCCTCCCTTTCTAGCACTTT TCTAGCAATATTG | reverse |
| 108 | adc-buk-F1 | TAAGGTTTACTAAGGAGGTTGT TTTATGTTAGAAAG | forward |
| 109 | thlA-ptb-F1 | GCTAGAAAAGTGCTAGAAAGG GAGGAAATGAACATG | forward |
| 110 | Buk-adc-R1 | AAAACAACCTCCTTAGTAAACC TTAGCTTGTTCTTC | reverse |

*C. autoethanogenum* DSM10061 and DSM23693 (a derivate of DSM10061) were sourced from DSMZ (The German Collection of Microorganisms and Cell Cultures, Inhoffenstraβe 7 B, 38124 Braunschweig, Germany).

Strains were grown at 37° C. in PETC medium at pH 5.6 using standard anaerobic techniques (Hungate, *Meth Microbiol*, 3B: 117-132, 1969; Wolfe, *Adv Microb Physiol*, 6: 107-146, 1971). 30 psi CO-containing steel mill gas (collected from New Zealand Steel site in Glenbrook, NZ) or a synthetic gas blend with same composition of 44% CO, 32% $N_2$, 22% $CO_2$, 2% $H_2$ was used as substrate for autotrophic growth. For solid media, 1.2% bacto agar (BD, Franklin Lakes, N.J. 07417, USA) was added.

The construct was synthesized and then transformed into *C. autoethanogenum* via conjugation. For this, the expression vector was first introduced into the conjugative donor strain *E. coli* HB101+R702 (CA434) (Williams, *J Gen Microbiol*, 1136: 819-826, 1990) (the donor) using standard heat shock transformation. Donor cells were recovered in SOC medium (Sambrook, Molecular Cloning: A Laboratory Manual, Vol 3, Cold Spring Harbour Press, 1989) at 37° C. for 1 h before being plated on to LB medium (Sambrook, Molecular Cloning: A Laboratory Manual, Vol 3, Cold Spring Harbour Press, 1989) plates containing 100 µg/ml spectinomycin and 25 µg/ml chloramphenicol. LB plates were incubated at 37° C. overnight. The next day, 5 ml LB aliquots containing 100 µg/ml spectinomycin and 25 µg/ml chloramphenicol were inoculated with several donor colonies and incubated at 37° C., shaking for approximately 4 h, or until the culture was visibly dense but had not yet entered stationary phase. 1.5 ml of the donor culture was harvested in a microcentrifuge tube at room temperature by centrifugation at 4000 rpm for 2 min, and the supernatant was discarded. The donor cells were gently resuspended in 500 µl sterile PBS buffer (Sambrook, Molecular Cloning: A Laboratory Manual, Vol 3, Cold Spring Harbour Press, 1989) and centrifuged at 4000 rpm for 2 min and the PBS supernatant was discarded. The pellet was introduced into an anaerobic chamber and gently resuspended in 200 µl during late exponential phase *C. autoethanogenum* culture (the recipient). The conjugation mixture (the mix of donor and recipient cells) was spotted onto PETC-MES+fructose agar plates and left to dry. When the spots were no longer visibly wet, the plates were introduced into a pressure jar, pressurized with syngas to 25-30 psi and incubated at 37° C. for ~24 h. After 24 h incubation, the conjugation mixture was removed from the plates by gently scraping it off using a 10 µl inoculation loop. The removed mixture was suspended in 200-300 µl PETC medium. 100 µl aliquots of the conjugation mixture were plated on to PETC medium agar plates supplemented 15 µg/ml thiamphenicol to select for transformants bearing the plasmid, which confers resistance to thiamphenicol via expression of chloramphenicol acetyltransferase.

Three distinct colonies of C. autoethanogenum bearing the pMTL85147-thlA-ptb-buk-adc plasmid were inoculated into 2 mL of PETC-MES medium with 15 µg/ml thiamphenicol and grown autotrophically at 37° C. with 100 rpm orbital shaking for three days. Cultures were diluted to $OD_{600\,nm}$=0.05 in 10 mL PETC-MES medium with 15 µg/ml thiamphenicol in serum bottles and grown autotrophically at 37° C. with 100 rpm orbital shaking for five days, sampling daily to measure biomass and metabolites. In parallel a control strain was examined where the expression plasmid encoded only thl and adc under the control of the Wood-Ljungdahl cluster promoter, with no ctfAB or ptb-buk genes to catalyse the formation of acetoacetate from acetoacetyl-CoA (pMTL85147-thlA-adc). Cultures were sampled for five days in order to monitor metabolites and biomass accumulation.

Isopropanol concentrations as well as concentrations of ethanol, acetic acid, 2,3-butanediol and lactic acid were measured by high-performance liquid chromatography (HPLC) on an Agilent LC with refractive index (RI) detection at 35° C. Samples were prepared by diluting 400 µL with 100 µL of 5-sulfosalicylic acid solution (1% w/v in 1 M sulphuric acid), followed by a 3 minute centrifugation at 14,000 rpm; the supernatant was transferred to a glass vial for analysis. Separation was carried out with a 10 µL injection on to an Alltech IOA-2000 column (150 mm×6.5 mm×8 µm) at 0.7 mL/min and 65° C. under isocratic conditions, using 5 mM sulphuric acid mobile phase.

In some instances, a longer HPLC method was used to improve peak separation. In this method, isopropanol, ethanol, acetate, 2,3-butanediol, and also 3-hydroxybutyrate (which is not separated using the shorter method) concentrations were measured by high-performance liquid chromatography (HPLC) on an Agilent 1260 Infinity LC with refractive index (RI) detection at 35° C. Samples were prepared by diluting 400 µL with 100 µL of 5-sulfosalicylic acid solution (1% w/v in 1 M sulphuric acid), followed by a 3 minute centrifugation at 14,000 rpm; the supernatant was transferred to a glass vial for analysis. Separation was carried out with a 10 µL injection on to an Aminex HPX-87H column (300 mm×7.8 mm×9 µm) at 0.6 mL/min and 35° C. under isocratic conditions, using 5 mM sulphuric acid mobile phase.

Figure 12:
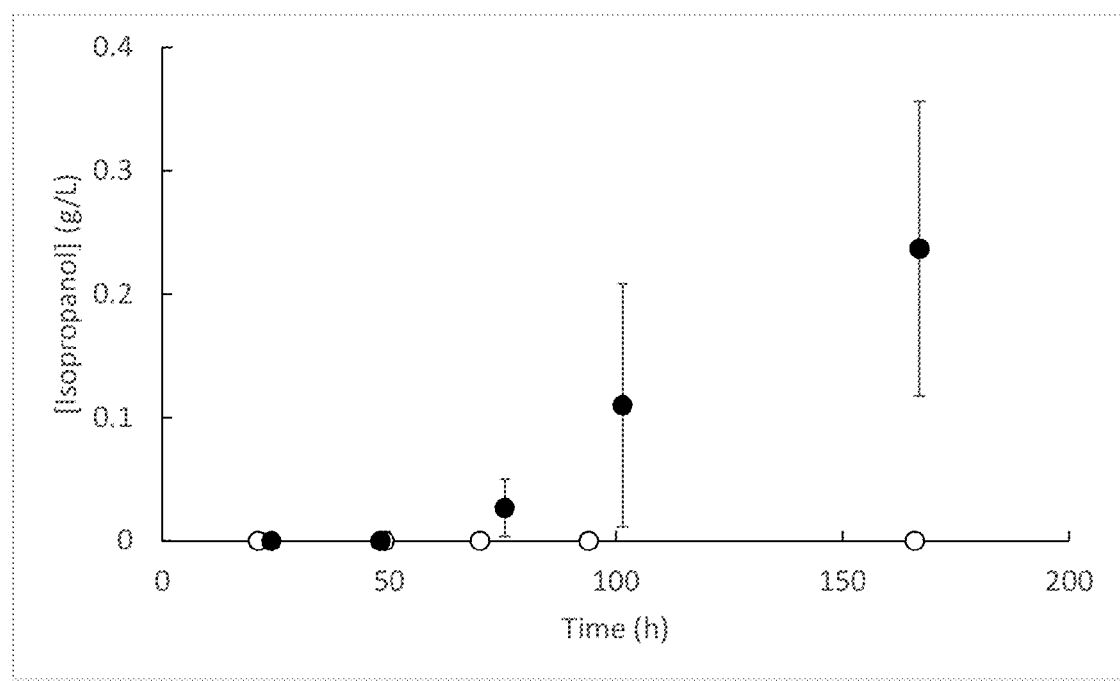
FIG. 12 is a graph showing isopropanol production in *C. autoethanogenum* using the Ptb-Buk system over a control. ○ pMTL85147-thlA-adc, • pMTL85147-thlA-ptb-buk-adc.
Figure 13A:
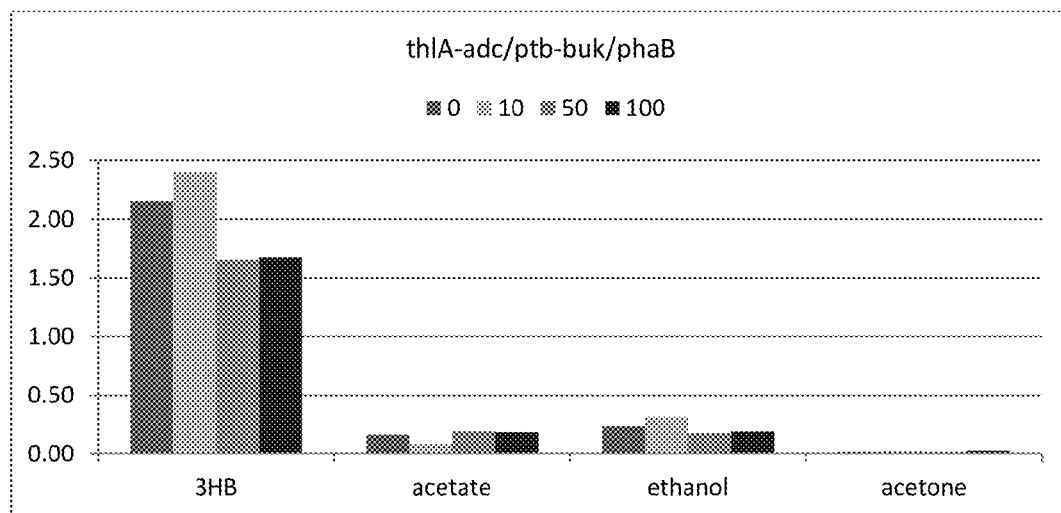
FIGS. 13A-F are graphs showing production of 3-hydroxybutyrate, acetate, ethanol, and acetone with modular plasmids in *E. coli* with different concentrations of inducer IPTG (0, 50, 100 μM).
Figure 13B:
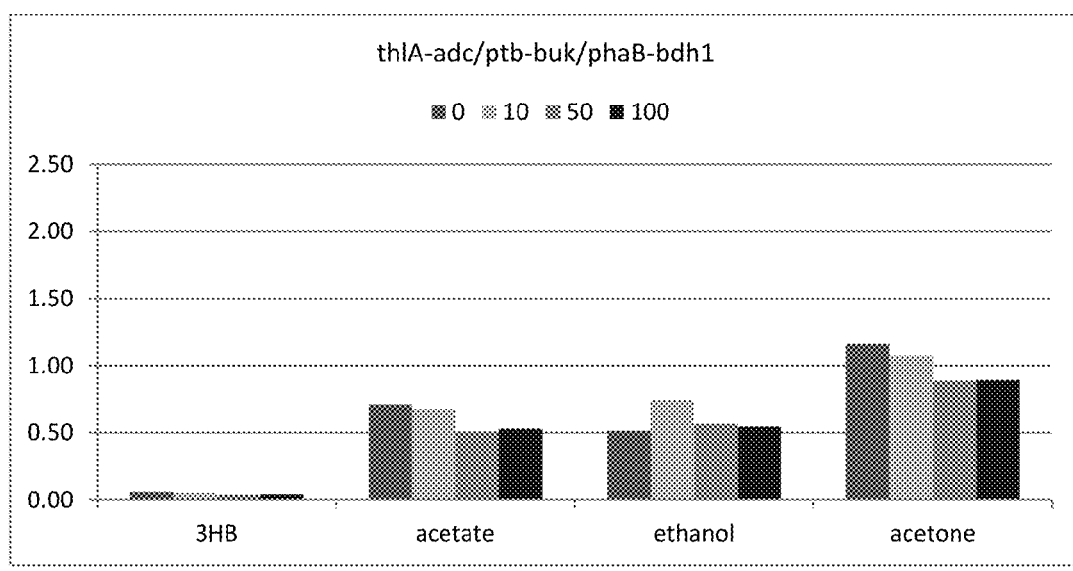
Figure 13C:
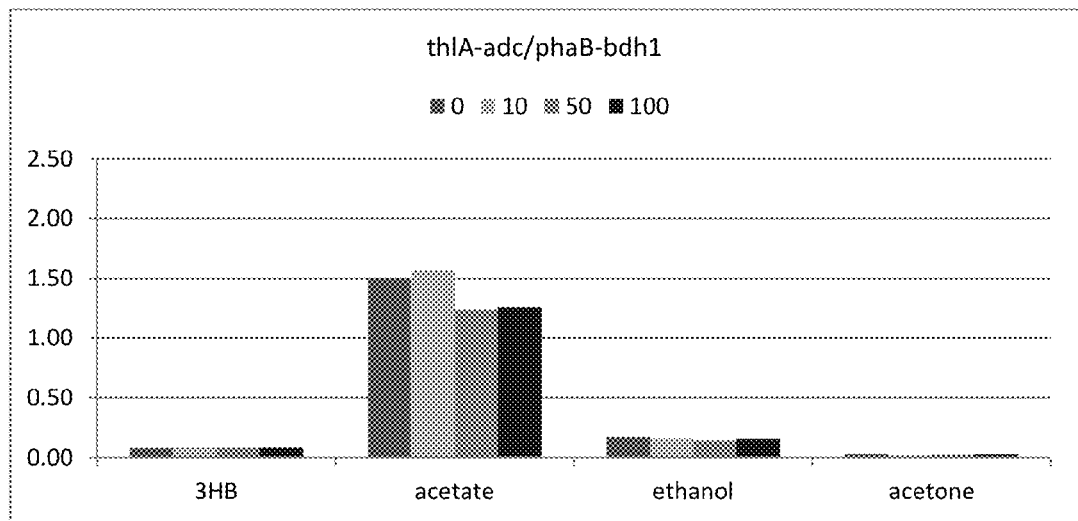
Figure 13D:
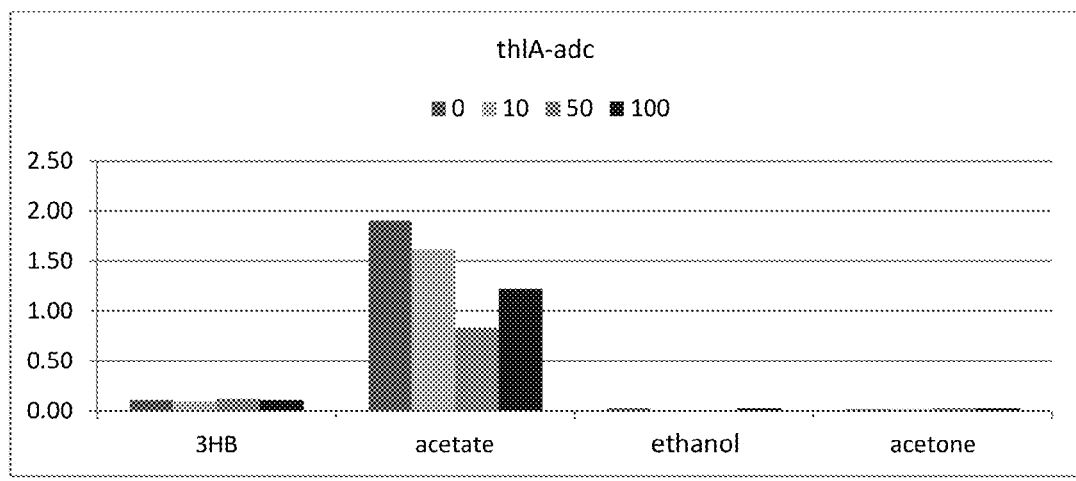
Figure 13E:
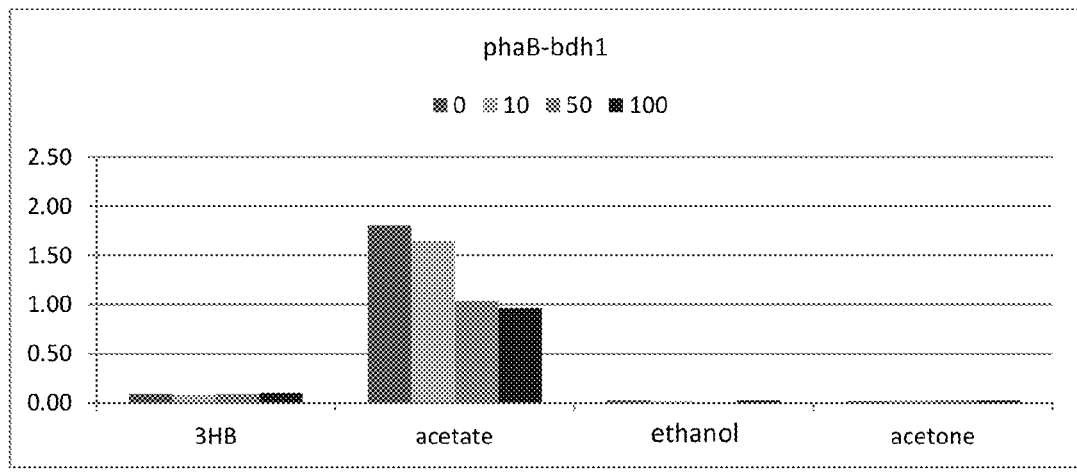
Figure 13F:
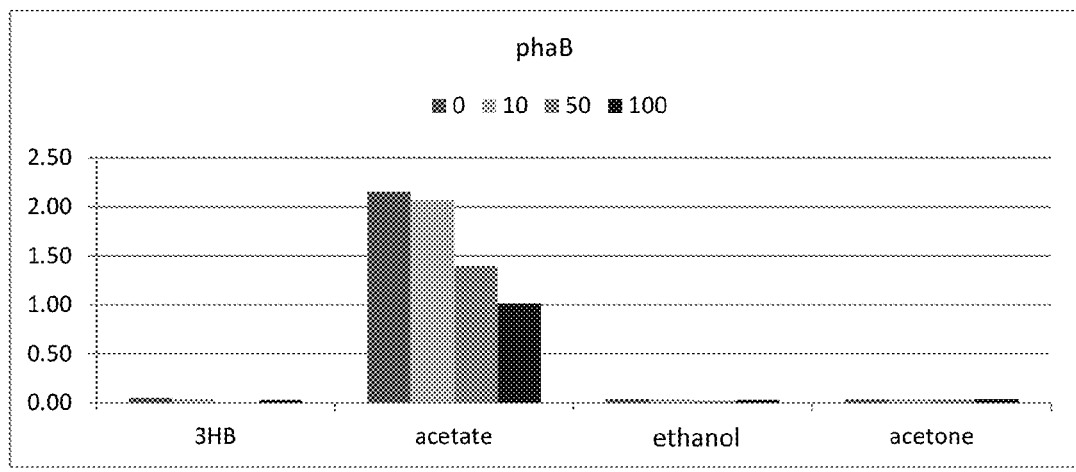

C. autoethanogenum bearing the pMTL85147-thlA-ptb-buk-adc produced isopropanol up to 0.804 g IPA/g of biomass, whereas control strain C. autoethanogenum with pMTL85147-thlA-adc that does not contain Ptb-Buk produced no IPA (FIG. 12).

This experiment clearly demonstrates that Ptb-Buk is able to perform the conversion of acetoacetyl-CoA to acetoacetate in the isopropanol pathway when using a gaseous substrate. Ptb-Buk can be used in place of a CoA transferase or a thioesterase in a gas-fermenting acetogen such as C. autoethanogenum, exemplified using a route that comprises steps 1, 2, 3, and 4 of FIG. 1.

C. autoethanogenum contains a native primary:secondary alcohol dehydrogenase that converts acetone to isopropanol (Köpke, Appl Environ Microbiol, 80: 3394-3403, 2014). It has been demonstrated that knock-out of this gene eliminates conversion of acetone to isopropanol in C. autoethanogenum (WO 2015/085015). In background of this knock-out, it becomes possible to produce acetone (rather than isopropanol) via the Ptb-Buk system from a gaseous feedstock, using the same genes comprising steps 1, 2, and 3 of FIG. 1. Addition of hydroxyisovalerate synthase and decarboxylase genes (van Leeuwen, Appl Microbiol Biotechnol, 93: 1377-1387, 2012) to this strain would enable isobutylene production from gas in C. autoethanogenum or similar bacteria comprising of steps 1, 2, 3, 5, and 6 of FIG. 1.

Acetoacetate can also be converted to 3-hydroxybutyrate via a 3-hydroxybutyrate dehydrogenase Bdh. A 3-hydroxybutyrate dehydrogenase was identified in the genome of C. autoethanogenum (AGY75962) and other acetogens as C. ljungdahlii (ADK16920.1). This activity can be combined with Ptb-Buk (or CoA transferase) conversion of acetoacetyl-CoA to acetoacetate for 3-hydroxybutyrate production in a strain expressing genes thlA, ptb-buk (or ctfAB) and bdh resulting a pathway comprising steps 1, 2, and 15 of FIG. 1. Low levels of 3-hydroxybutyrate formation (up to 2 g/L) via this route have been demonstrated in C. autoethanogenum. These levels could be enhanced by overexpressing the Bdh gene that is only expressed in at low levels natively.

Figure 37:
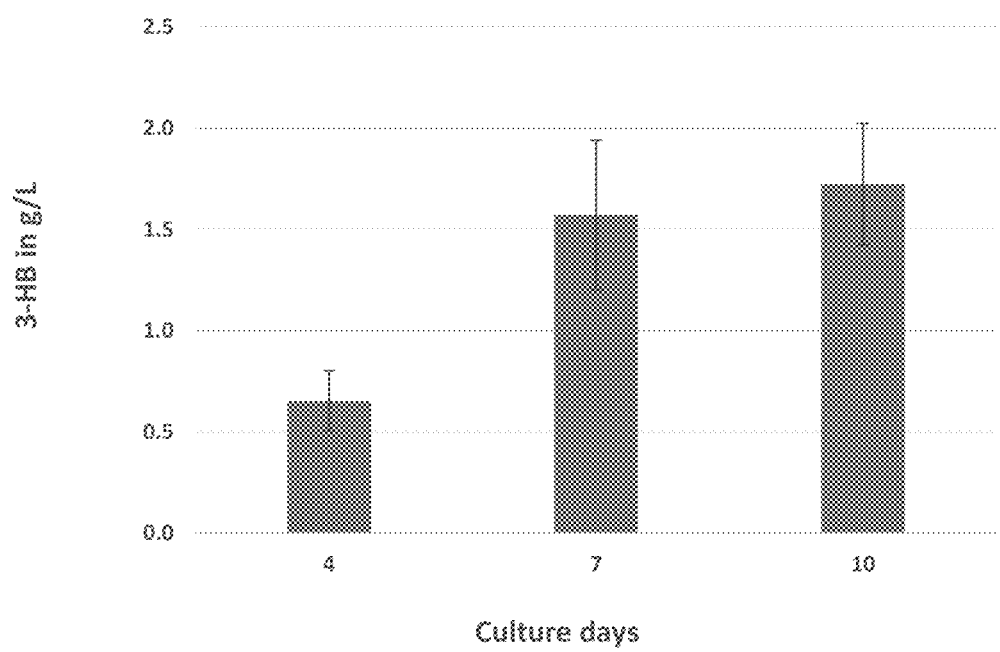
FIG. 37 is a graph of 3-HB production in *C. autoethanogenum* containing plasmid pMTL82256-thlA-ctfAB at various points of growth.
Figure 38A:
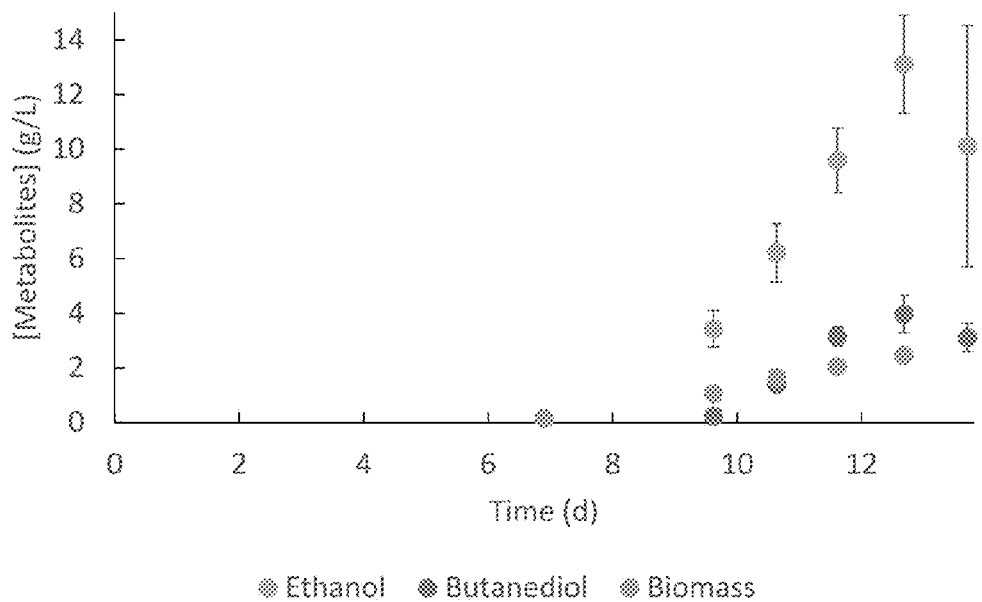
FIG. 38A is a graph showing the growth and ethanol and 2,3-butanediol production profile of strain *C. autoethanogenum* pta-ack::ptb-buk+pMTL85147-thlA-ptb-buk-adc.
Figure 38B:
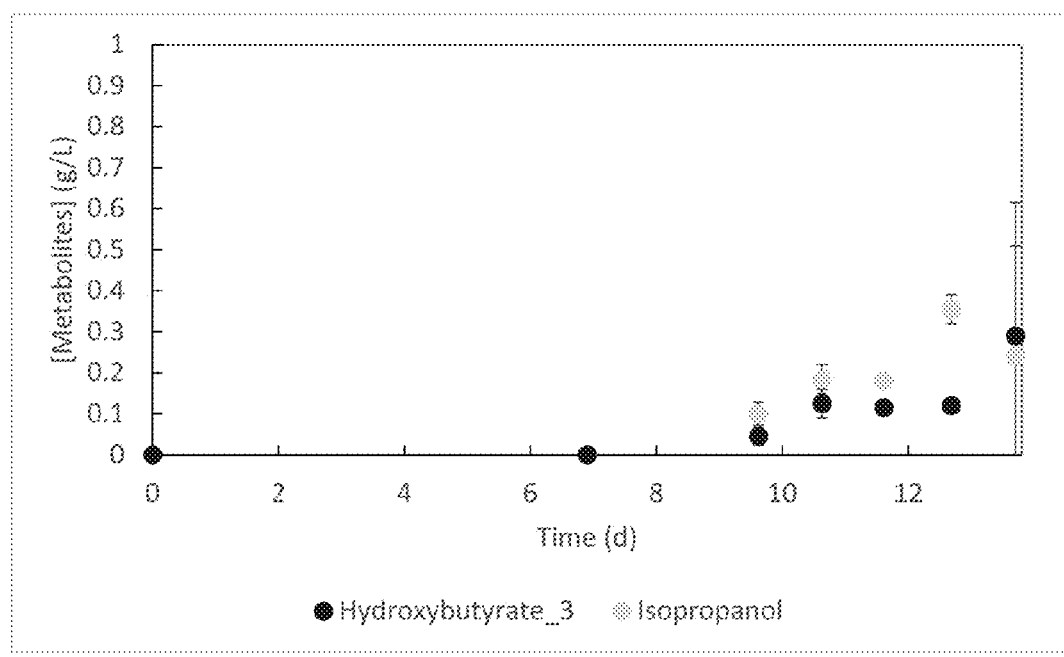
FIG. 38B is a graph showing the isopropanol and 3-HB production profile of strain *C. autoethanogenum* pta-ack::ptb-buk+pMTL85147-thlA-ptb-buk-adc.

In one experiment, C. autoethanogenum was transformed with plasmid pMTL82256-thlA-ctfAB as described in Example 2. The production was monitored for 10 days from six biological replicates under autotrophic conditions as described in Example 2. The average of 3-HB after 10 days was 1.86±0.14 g/L. At day 10, 1,3-butanediol was produced (from 3-HB) at an average titer of 0.38±0.05 g/L (FIG. 37). No acetone or isopropanol was formed. This demonstrates that 3-HB can be produced efficiently via acetoacetate through native enzymes.

In certain embodiments, it may be desirable to knock out or knock down expression of 3-hydroxybutyrate dehydrogenases, such as Bdh, to prevent carbon drain to 3-HB and therefore boost production of products such as acetone, isopropanol, and isobutylene.

Example 3

This example demonstrates the ability of Ptb-Buk to convert (R)-3-hydroxybutyryl-CoA to (R)-3-hydroxybutyryrate in E. coli in vivo for production of (R)-hydroxybutyrate, acetone, isopropanol, or isobutylene.

Figure 6:
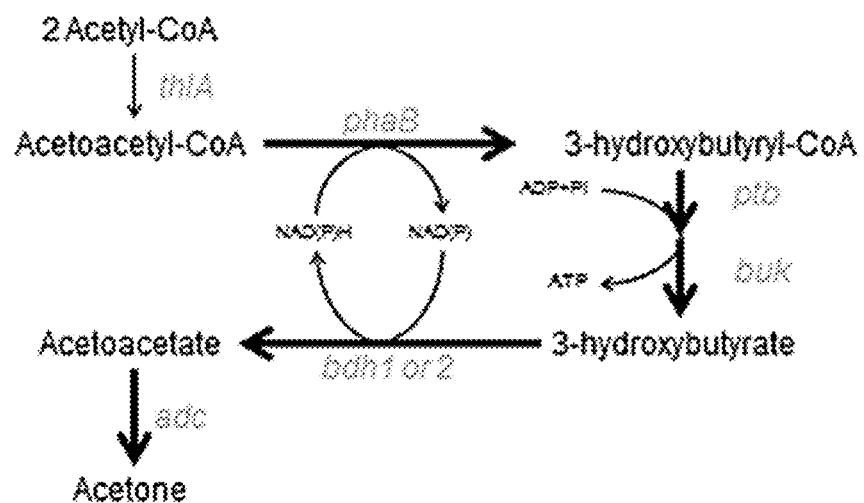
FIG. 6 is a diagram of a pathway designed to use Ptb-Buk for acetone production, while recycling the reducing equivalents produced in the production of (R)-3-hydroxybutyryl-CoA and the ATP generated by Ptb-Buk.

Pathways were designed and constructed that rely on the Ptb-Buk system for (R)-3-hydroxybutyrate production from (R)-3-hydroxybutyryl-CoA. Additionally, a 3-hydroxybutyrate dehydrogenase (Bdh) was utilized for conversion of (R)-3-HB to acetoacetate. It has been reported that Ralstonia pickettii have two 3-hydroxybutyrate dehydrogenases Bdh1 and Bdh2 that are able to convert 3-hydroxybutyrate to acetoacetate in vitro (Takanashi, J Biosci Bioeng, 101: 501-507, 2006). One pathway was designed making use of this enzyme for acetone production (steps 1, 13, 14, 15, 3 of FIG. 1), while recycling the reducing equivalents produced in the production of (R)-3-hydroxybutyryl-CoA and the ATP generated by Ptb-Buk (FIG. 6).

The pathways were constructed in a modular fashion using the pDUET vector system (Novagen). The two modules described in example above (pACYC-ptb-buk for expression of Ptb-Buk and pCOLA-thlA-adc for expression of thiolase and acetoacetate decarboxylase) were used together with two additional modules containing either (R)-specific 3-hydroxybutyrate dehydrogenase phaB of *Cupravidus necator* (WP_010810131.1) alone (pCDF-phaB) and one with 3-hydroxybutyrate dehydrogenase bdh1 gene of *Rasltonia pickettii* (BAE72684.1) (pCDF-phaB-bdh1) in vector pCDF. Both phaB and bdh1 gene were synthesized from GeneArt and cloned under control of the T7 promoter present in via restriction independent cloning with the circular polymerase extension cloning (CPEC) method (Quan, PloS One, 4:e6441, 2009).

Oligonucleotides used for amplification of bdh1 gene:

| SEQ ID NO: | Name | Sequence | Direction |
|---|---|---|---|
| 111 | pDuet-insert2-R1 | CATATGTATATCTCCTTCTTATA-CTTAAC | forward |
| 112 | insert2-pDuet-F1 | GTTAAGTATAAGAAGGAGATAT ACATATG | forward |
| 113 | pDuet-insert2-F1 | CCTCGAGTCTGGTAAAGAAAC | forward |
| 114 | insert2-pDuet-R1 | GTTTCTTTACCAGACTCGAGG | forward |

Oligonucleotides used for amplification of phaB gene:

| SEQ ID NO: | Name | Sequence | Direction |
|---|---|---|---|
| 115 | pCDF-phaB - pACYC-phaB-R1 | CTATTCTTTGTGTCATGGTATAT CTCCTTATTAAAG | forward |
| 116 | pCDF-phaB - phaB-pACYC-F1 | ATAAGGAGATATACCATGACAC AAAGAATAGCATAC | forward |
| 117 | pCDF-phaB - pACYC-phaB-F1 | TGGTTTACACATGGGATAAGAT CCGAATTCGAGCTC | forward |
| 118 | pCDF-phaB - phaB-pACYC-R1 | AGCTCGAATTCGGATCTTATCC CATGTGTAAACCAC | forward |

After the plasmids pACYC-ptb-buk (SEQ ID NO: 105), pCOLA-thlA-adc (SEQ ID NO: 106), pCDF-phaB (SEQ ID NO: 119) and pCDF-phaB-bdh1 (SEQ ID NO: 120) were constructed, they were transformed individually and in combinations into *E. coli* BL21 (DE3) (Novagen) and growth experiments were carried out in quadruplicate in 1.5 mL cultures in 12-well plates at 28° C. with 160 rpm orbital shaking using M9 minimal medium with glucose. The cultures were inoculated at an OD600 nm of 0.1 and after 2 h of growth induced with different concentrations of IPTG (0, 50, 100 µM). The plates were sealed using BioRad plate tape strips and each well pierced with a green tipped needle to provide micro-aerobic conditions. Growth was carried out for another 64 h of induction. The experiment was repeated 3 times. Metabolites were measured as described in previous examples.

Cultures containing a combination of plasmids pACYC-ptb-buk, pCOLA-thlA-adc and pCDF-phaB produced between 1.65-2.4 g/L (R)-3-hydroxybutyrate (depending on level of inducer), with only very small amounts of byproducts (FIGS. 13A-F), demonstrating the efficiency of the Ptb-Buk system to convert (R)-3-hydroxybutyryl-CoA to (R)-3-hydroxybutyryrate and support growth (FIG. 13A-F). In cultures that also expressed bdh1 (containing a combination of plasmids pACYC-ptb-buk, pCOLA-thlA-adc, and pCDF-phaB-bdh1) only small amounts of (R)-3-hydroxybutyryrate were found in the culture media, while between 0.89-1.16 g/L acetone was found (depending on level of inducer), indicating that bdh1 gene is efficient in converting (R)-3-hydroxybutyrate to acetoacetate and further to acetone. In all plasmid combinations that lack Ptb-Buk, no 3-hydroxybutyrate or acetone was found (FIG. 13A-F). In these cultures, acetate levels were significantly higher.

This experiment clearly demonstrates that Ptb-Buk is able to perform the conversion of (R)-3-hydroxybutyrate-CoA to 3-hydroxybutyrate and also that Bdh1 is able in vivo to convert 3-hydroxybutyrate further to acetoacetate by recycling the reducing equivalents produced in the production of (R)-3-hydroxybutyryl-CoA. The experiment also highlights that Ptb-Buk is able to support growth and therefore acetate production becomes unnecessary. Production of (R)-3-hydroxybutyrate formation was exemplified in a strain that comprises steps 1, 13, and 14 of FIG. 1. Production of acetone was exemplified via a route that comprises steps 1, 13, 14, 15, and 3 of FIG. 1.

It is well known that isopropanol can be produced from acetone by addition of a primary:secondary alcohol dehydrogenase (step 4 in FIG. 1) (Köpke, *Appl Environ Microbiol*, 80: 3394-3403, 2014) and that isobutylene can be produced from acetone via addition of a hydroxyisovalerate synthase (step 5 in FIG. 1) and decarboxylase (step 6 in FIG. 1) (van Leeuwen, *Appl Microbiol Biotechnol*, 93: 1377-1387, 2012). A pathway can be constructed that includes the above-demonstrated acetone route via Ptb-Buk with the genes thlA, ptb-buk, and adc and a primary:secondary alcohol dehydrogenase gene (e.g., Genbank NC_022592, pos. 609711 ... 610766; CAETHG_0553; NCBI-GeneID: 17333984) that would allow isopropanol production via the Ptb-Buk system in *E. coli* (steps 1, 13, 14, 15, 3, and 4 of FIG. 1). Similarly, a pathway can be constructed that includes the above-demonstrated acetone route via Ptb-Buk with the genes thlA, ptb-buk, and adc and genes for a hydroxyisovalerate synthase and decarboxylase that would allow isobutylene production via the Ptb-Buk system in *E. coli* (steps 1, 13, 14, 15, 3, 5, and 6 of FIG. 1).

Example 4

This example demonstrates the production of (R)-3-hydroxybutyrate and 1,3-butanediol in *C. autoethanogenum*. It also demonstrates production of 1,3-butanediol in absence of 2,3-butanediol.

A strain of *C. autoethanogenum* was constructed in which the native pathway for 2,3-butanediol production was inactivated and replaced with genes for (R)-3-hydroxybutyryl-CoA formation. This was achieved by replacing the acetolactate decarboxylase gene (budA) on genome of *C. autoethanogenum* with genes for thiolase (thlA of *C. acetobutylicum*; GenBank NC_001988, position 82040 ... 83218; CA_P0078; NCBI-GeneID 1116083) and (R)-specific 3-hydroxybutyrate dehydrogenase (phaB of *Cupravidus necator*; GenBank WP_010810131.1) resulting in strain *C. autoethanogenum* budA::thlAphaB.

Figure 14:
FIG. 14 is a plasmid map of plasmid pMTL8225-budA::thlA-phaB.

To replace budA gene with thlA and phaB genes a plasmid, pMTL8225-budA::thlA-phaB (FIG. 14), with *E. coli* toxin gene mazF under tet3n0 tetracycline inducible promoter (for counter selection), ~1 kb upstream homology arm of budA gene, thlA, phaB, ermB cassette flanked by loxP sites and ~1 kb downstream homology arm of budA gene were assembled on plasmid pMTL-tet3no.

The ~1 kb upstream and downstream homology arms of budA were PCR amplified from *C. autoethanogenum* with primers SN01/SN02 and SN07/SN08. thlA and phaB genes were PCR amplified from genomic DNA of *Cupriavidus necator* using primers SN03/SN04mod. The ermB cassette flanked with loxP sites was PCR amplified using primers SN05mod/SN06. tet3no promoter flanked by FseI and PmeI was synthesized and treated with restriction enzymes FseI and PmeI and cleaned. The PCR products and digested vector were assembled using GeneArt Seamless cloning kit from Life Technologies and plasmid pMTL8225-budA::thlA-phaB (SEQ ID NO: 121) with no mutations in the inserted fragments was used to transform *C. autoethanogenum* by conjugation as described in previous examples.

Figure 15:
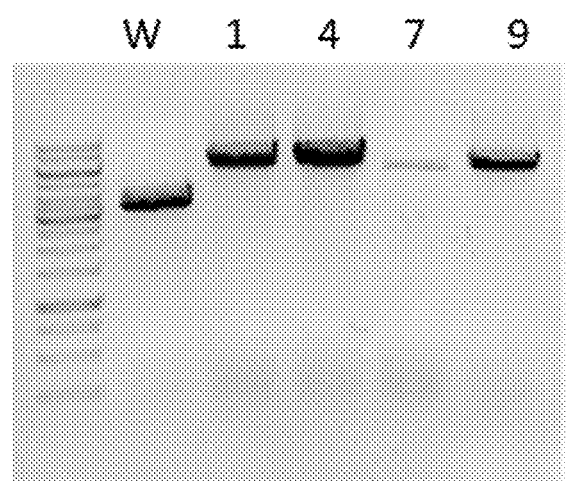
FIG. 15 is a gel image of PCR verification of replacement of acetolactate synthase (budA) genes with thiolase (thlA) and 3-hydroxybutyryl-CoA dehydrogenase (phaB) genes in *C. autoethanogenum* for 4 clones (1, 4, 7, 9) compared to wild-type (W). All clones are positive as seen by a larger PCR fragment size compared to wild-type.

Following conjugation and selection on trimethoprim and clarithromycin, 9 colonies were streaked twice on PETC-MES agar plates with clarithromycin and anhydrotetracycline to induce the expression of mazF genes. The colonies from clarithromycin and anhydrotetracycline should have the budA genes replaced with thlA and phaB genes and ermB cassette. This was verified by PCR using primers Og31f/Og32r flanking the homology arms and KAPA polymerase (FIG. 15).

While a band of ~3.3 kb is amplified from the wild type strain, bands of ~5.7 kb were amplified from colonies 1,4, 7 and 9 indicating the replacement of budA gene with thlA, phaB and ermB cassette. The above event was further confirmed by sequencing the PCR products of all 4 clones. With the resulting modification the expression of thlA and phaB genes is driven by the promoter upstream of budA gene.

detector (FID). Samples were prepared by diluting 400 µL of sample with 400 µL of acetonitrile, followed by a 3 minute centrifugation at 14,000 rpm; the supernatant was transferred to a glass vial and the sample was dried in a Thermo SpeedVac. Once dry, the samples were then suspended in a solution of 400 µL of N,O-Bistrifluoroacetamide (BSTFA) and pyridine (3:1 ratio) and heated in a sealed glass vial for 60 minutes at 60° C. Samples were transferred to an autosampler for analysis using a 1 µL injection, a split ration of 30 to 1, and an inlet temperature of 250° C. Chromatography was performed with an oven program of 70° C. (no hold) to a ramp of 3° C./min to 110° C. to a ramp of 15° C./min to 230° C., followed by a final ramp of 40° C./min to 310° C. with a 3-min hold. The column flow rate was 1.8 ml/min, with helium as the carrier gas. The FID was kept at 320° C., with hydrogen at 40 ml/min, air at 400 ml/min, and helium at 20 ml/min as the makeup gas.

Figure 16:
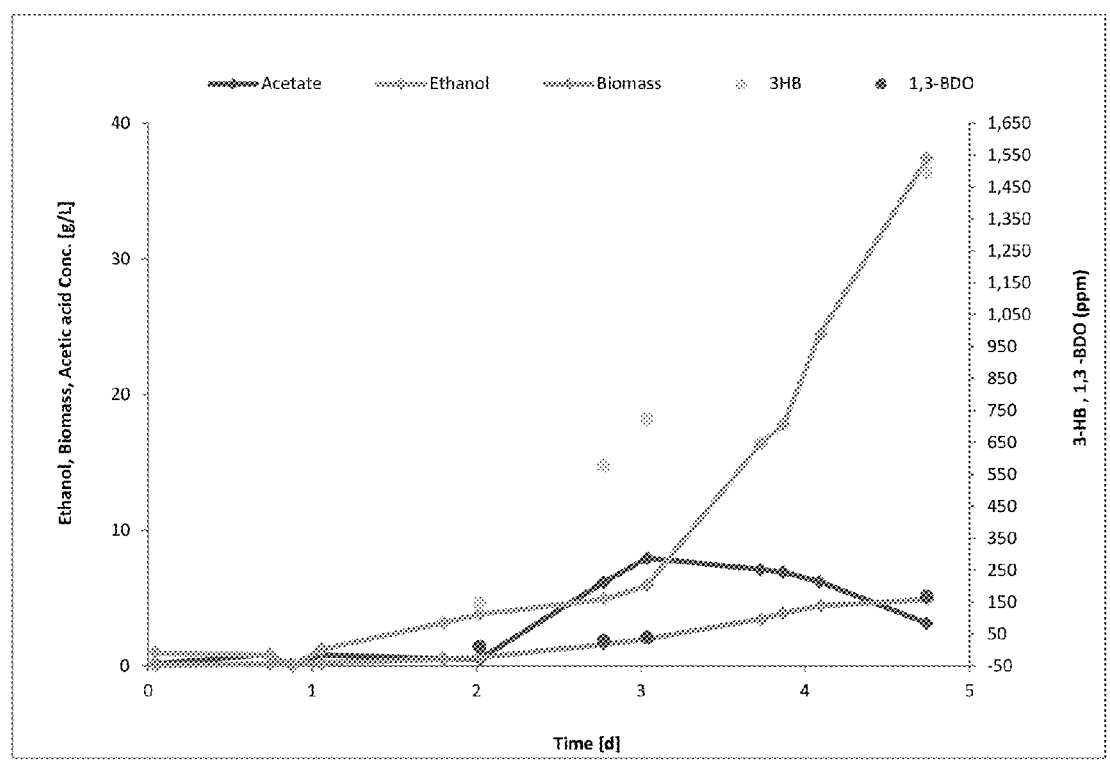
FIG. 16 is a graph showing fermentation profile of a batch fermentation *C. autoethanogenum* budA::thlAphaB strain and demonstrating 3-hydroxybutyrate and 1,3-butanediol formation from gas.

Surprisingly, up to 1.55 g/L 3-hydroxybutyrate was produced from gas in a *C. autoethanogenum* budA::thlA-phaB strain expressing thlA and phaB (FIG. 16). A native thioesterase may convert the formed 3-hydroxybutyryl-CoA to 3-hydroxybutyrate. In the genome sequence, three putative thioesterases were identified.

Figure 7:
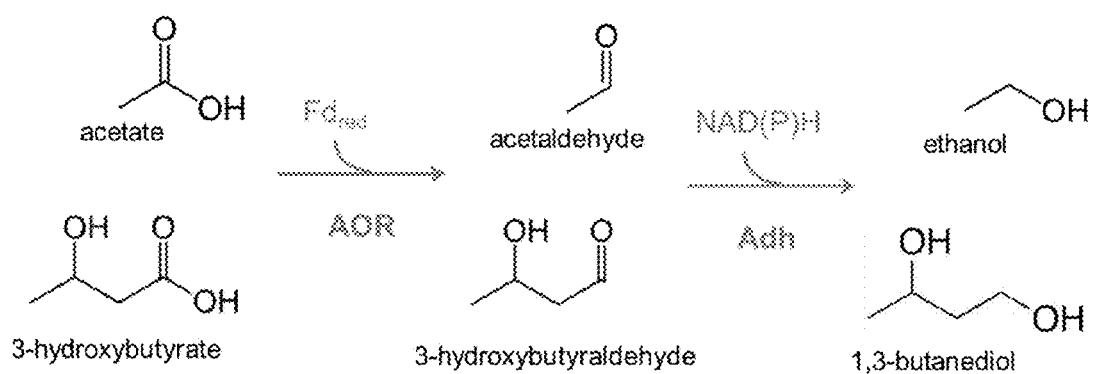
FIG. 7 is a diagram showing the role of aldehyde: ferredoxin oxidoreductase (AOR), ferredoxin, and Adh in the production of 1,3-butanediol in *C. autoethanogenum*. More generally, AOR may be used to catalyze the conversion of an acid to an aldehyde and Adh may be used to catalyze the conversion of the aldehyde to an alcohol/diol.

Even more surprising, it was also found that, along 3-hydroxybutyrate formation, there was also 1,3-butanediol formation of up to 150 mg/L (FIG. 16). This may be due to native aldehyde:ferredoxin oxidoreductase (AOR) and alcohol dehydrogenase activity. Two AOR genes and several alcohol dehydrogenases are present in the genome of *C. autoethanogenum* (Mock, *J Bacteriol*, 197: 2965-2980, 2015). This reduction of 3-hydroxybutyrate is powered by reduced ferredoxin and thus can be directly coupled to CO oxidation, which provides reduced ferredoxin (CO+ $Fd_{ox} \rightarrow CO_2 + Fd_{red}$) (FIG. 7).

| SEQ ID NO: | Description | Sequence |
|---|---|---|
| 122 | SN01 | ATTTACAAATTCGGCCGGCCTACCTCCTCGTATAAATAAGATG |
| 123 | 5N02 | CTAGCTATTACAACTTCTTTCATATTACATTCACCTCTATGTC |
| 124 | 5N03 | GACATAGAGGTGAATGTAATATGAAAGAAGTTGTAATAGCTAG |
| 125 | SN04mod | GTATAGCATACATTATACGAACGGTATTATCCCATGTGTAAACCACCGT |
| 126 | SN05mod | TTCGTATAATGTATGCTATACGAAGTTATCCTTAGAAGCAAACTTAAG |
| 127 | SN06 | GTCTAGTGTTTTTTTCTATCAATACTCTAGATACCGTTCGTATAGC |
| 128 | SN07 | TGTATGCTATACGAACGGTAAGTATTGATAGAAAAAAACACTAGAC |
| 129 | SN08 | CAAAAAGGAGTTTAAACAAAAAGTCATAAACCTGGATAAC |
| 130 | Og31f | CCGTTTCTCACAACAACAATACCAG |
| 131 | Og32r | AAACCACCTTGACGATGAAACCATA |

A fermentation with *C. autoethanogenum* budA::thlA-phaB strain was carried out. The culture was grown at 37° C. under synthetic gas (50% CO, 18% CO$_2$, 2% H$_2$, and 30% N$_2$) that was continuously fed into the bioreactor. The gas flow was initially set at 50 ml/min, increasing to 400 ml/min over the course of the experiment, while the agitation was increased from 200 rpm to 500 rpm. The fermentation was carried out for close to 5 days. Metabolites were measured as described in examples above.

The concentration of 1,3-butanediol and other metabolites, such as 2-hydroxyisobutyric acid, were measured using gas chromatography (GC) analysis, employing an Agilent 6890N GC equipped a Agilent CP-SIL 5CB-MS (50 m×0.25 µm×0.25 µm) column, autosampler and a flame ionization 1,3-BDO production was also demonstrated from gas via an alternative route using a butyraldehyde dehydrogenase Bld from *Clostridium saccharoperbutylacetonicum* (AAP42563.1) (SEQ ID NO: 80). The bld gene was synthesized and cloned together with the same thiolase (thlA of *C. acetobutylicum*) and (R)-specific 3-hydroxybutyrate dehydrogenase (phaB of *Cupravidus necator*) into a plasmid pMTL8315-Pfdx-thlA-phaB-bld (SEQ ID NO: 132). Bld and phaB genes were amplified from the above plasmid via primers in table below and cloned into existing plasmid pMTL85147-thlA (WO 2012/115527).

| SEQ ID NO: | Primer | Sequence | Direction |
|---|---|---|---|
| 133 | bld-phaB-F1 | ACATGGGATAAGAAGGAGATATACATATGAT AAAAG | forward |
| 134 | bld-pMTL-R1 | CGTCGACTCTAGATTAACCTGCTAAAACA CATCTTC | forward |
| 135 | pMTL-bld-F1 | GTGTTTTAGCAGGTTAATCTAGAGTC GACGTCACGC | forward |

The resulting construct was transformed into *C. autoethanogenum* as described above and a growth experiment was conducted in serum bottles with 50-mL PETC media and pressurized at 30 psi with CO-containing steel mill gas (collected from New Zealand Steel site in Glenbrook, NZ) or a synthetic gas blend with same composition of 44% CO, 32% $N_2$, 22% $CO_2$, 2% $H_2$.

Scientific). The operon P-hbd1-rbs2-thlA was cloned in between restriction sites NotI and XhoI found in the multiple cloning region of the plasmid. P is the constitutive promoter which contains an intact ribosome binding site (rbs). rbs2 (SEQ ID NO: 140) is the ribosome binding site for expressing thlA. The stepwise procedures were amplification of the P, hbd1, and thlA from existing templates with primers listed below.

| SEQ ID NO: | Name | Sequence | Direction |
|---|---|---|---|
| 141 | Pfdx-F1 | AAAGGTCTCCGGCCGCGCTCACTATCTGCG GAACC | forward |
| 142 | Pfdx-R1 | TTTGGTCTCGAATTCTGTAACACCTCCTTAA TTTTTAG | reverse |
| 143 | Ppfor-F1 | AAAGGTCTCCGGCCGCAAAATAGTTGATAA TAATGCAGAG | forward |
| 144 | Ppfor-R1 | TTTGGTCTCGAATTCCTCTC CTTTTCAAGCATATA | reverse |
| 145 | hbd1-F1 | AAAGGTCTCGAATTCAAAGATCTATGTCTAT TAAATCAGTTGCAG | forward |
| 146 | hbd1-R1 | TTTGGTCTCCCTCCTTTCT ATTTCTAATATGCGAAAAATCCTTTACC | reverse |
| 147 | thlA-F1 | AAAGGTCTCAGGAGGTGTTACATATGAAAG AAGTTGTAATAGCTAGTGC | forward |
| 148 | thlA-R1 | TTTGGTCTCCTCGAGTATGGATCCCTAGCAC TTTTCTAGCAATATTGC | reverse |

Figure 17A:
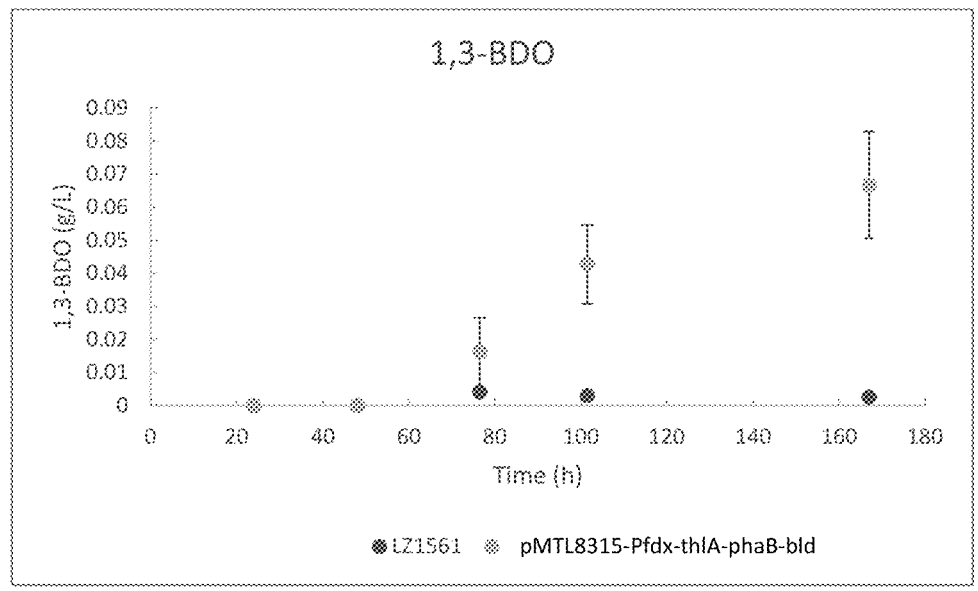
FIG. 17A is a graph showing production of 1,3-BDO via thiolase, 3-hydroxybutyryl-CoA dehydrogenase (Bld), and butyraldehyde dehydrogenase.
Figure 17B:
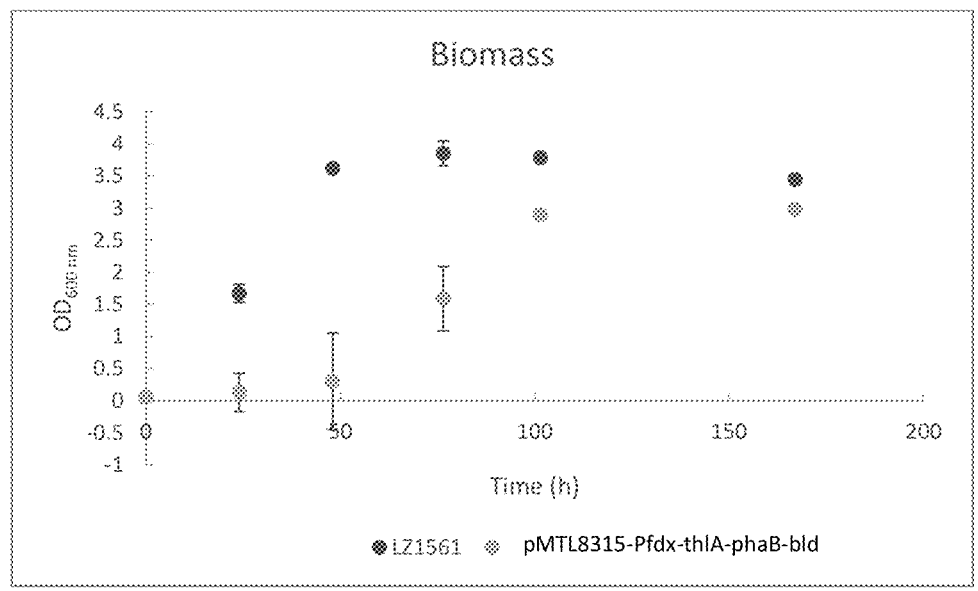
FIG. 17B is a graph showing the impact of bld expression on growth.

1,3-BDO production was demonstrated via this route from gas (FIG. 17A), but production was less (up to 67 mg/L 1,3-BDO) than via the AOR route and, in contrast to the AOR route, growth was impacted when expressing the bld gene comparing to the *C. autoethanogenum* wild-type (FIG. 17B).

Figure 40:
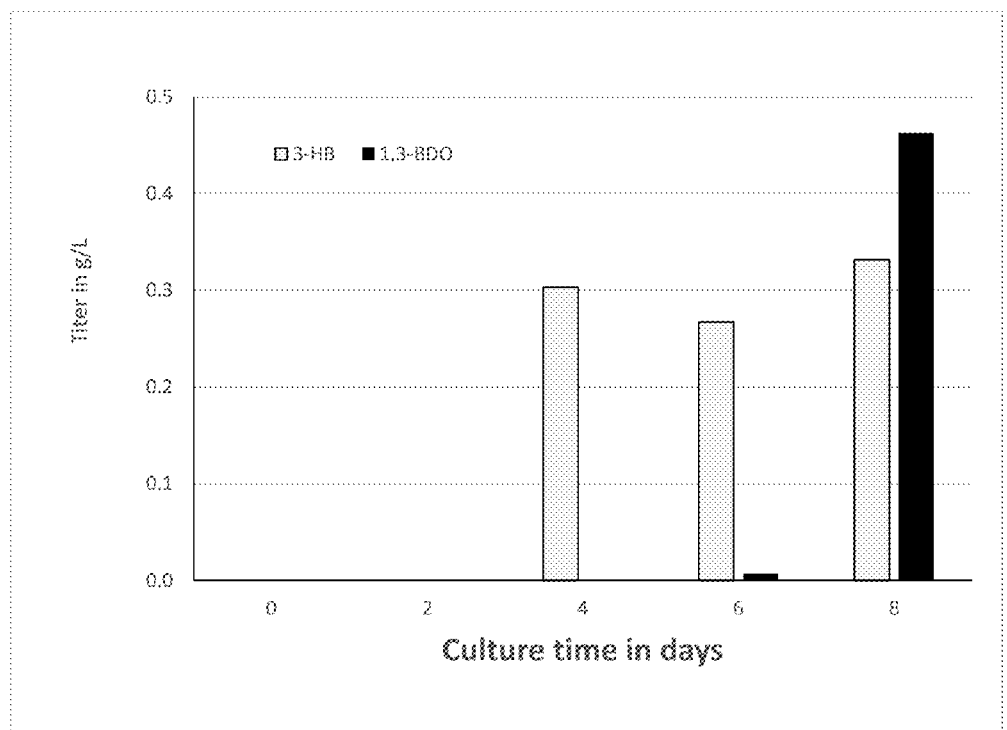
FIG. 40 is a graph showing production of 3-HB and 1,3-BDO by *C. autoethanogenum* transformed with plasmid pMTL83159-phaB-thlA at various points of growth.

In another experiment, *C. autoethanogenum* transformed with plasmid pMTL83159-phaB-thlA as described in Example 2 produced 0.33 and 0.46 g/L of 3-HB and 1,3-BDO, respectively, in a bottle experiment under autotrophic conditions as described in Example 2 (FIG. 40).

Example 5

This example demonstrates the production of (S)-3-hydroxybutyrate and 1,3-butanediol in *C. autoethanogenum*.

A plasmid was constructed that expresses a thiolase (thlA from *C. acetobutylicum*; SEQ ID NO: 136) and an (S)-specific 3-hydroxybutyrate dehydrogenase (hbd1 from *C. kluyveri*; SEQ ID NO: 137) under either a ferredoxin promoter ($P_{fdx}$ isolated from *C. autoethanogenum*; SEQ ID NO: 138) or a pyruvate-ferredoxin oxidoreductase promoter ($P_{pfor}$ isolated from *C. autoethanogenum*; SEQ ID NO: 139). The plasmid was constructed as follows: P-hbd1-rbs2-thlA and pieced together and cloned into the pMTL83151 vector (Heap, *J Microbiol Meth*, 78: 79-85, 2009) by routine methods in molecular cloning, including restrictive enzyme digestion followed by ligation, overlap extension polymerase chain reaction, seamless cloning (Thermo Fisher Scientific), and GeneArt Type IIs (Thermo Fisher The polymerase chain reactions were performed as follow using Kapa Taq PCR Kit (Kapa Biosystems). Set annealing temperature at 56° C., and extension for 1 minute. Repeat PCR reaction for 30 cycles. Afterwards, PCR products were desalted using the DNA Clean & Concentrator Kit (Zymo Research Corporation).

pMTL83151 plasmid backbone was prepared by carrying out the NotI/XhoI double digestion using the FastDigest NotI and FastDigest XhoI (Thermo Fisher Scientific) following the protocol provided, followed by treatment with alkaline phosphate, using the FastAP Alkaline Phosphatase (Thermo Fisher Scientific) and the protocols provided. The digested backbone was then desalted with the DNA Clean & Concentrator Kit (Zymo Research Corporation).

The assembly of the PCR products and the plasmid backbone was carried out using the GeneArt Type IIs Kit (Thermo Fisher Scientific). The resulting plasmid was then isolated from the *E. coli* plasmid expression host using the QIAprep Spin Miniprep Kit (Qiagen).

To introduce the assembled plasmids pMTL8315-Pfdx-hbd1-thlA and pMTL8315-Ppfor-hbd1-thlA consisting of the operons, the plasmid was first introduced into the *E. coli* CA434 strain by chemical transformation. Afterwards, conjugation was performed by mixing the transformed CA434 strain with a *C. autoethanogenum* production host on a solid LB-agar media, and incubation in an anaerobic environment under pressure with a mix consisting of carbon monoxide and hydrogen as described in Example 2. *C. autoethanogenum*, after conjugation, was selected by successive growth on the solid media containing the proper antibiotic and trimethroprim to remove the remaining E. coli CA434 strain, under the anaerobic conditions.

The C. autoethanogenum strains carrying the introduced pMTL8315-Pfdx-hbd1-thlA or pMTL8315-Ppfor-hbd1-thlA plasmids consisting of the operon P-hbd1-rbs2-thlA were grown in a 10-mL PETC media in a 250-mL Schott bottle, sealed tight with rubber septum and cap, and pressurized at 30 psi with CO-containing steel mill gas (collected from New Zealand Steel site in Glenbrook, NZ) or a synthetic gas blend with same composition of 44% CO, 32% $N_2$, 22% $CO_2$, 2% $H_2$. Metabolites were measured as described in previous examples.

Figure 18A:
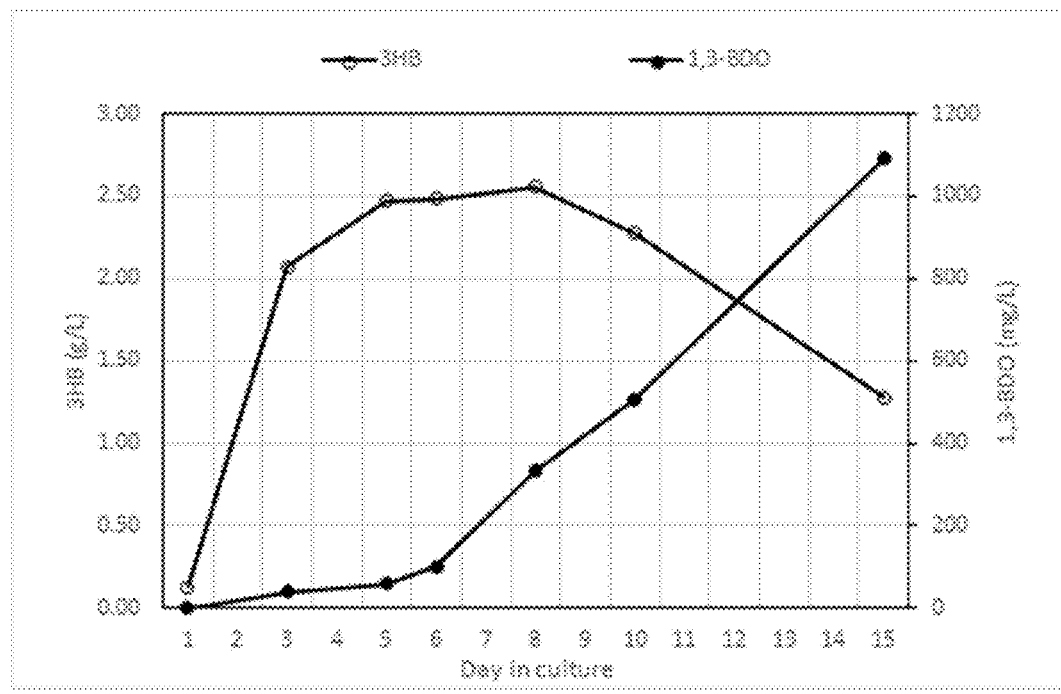
FIG. 18A is a graph showing the formation of 3-hydroxybutyrate and 1,3-butanediol from gaseous substrate in *C. autoethanogenum* pMTL8315-Pfdx-hbd1-thlA.

Surprisingly, there was 3-hydroxybutyrate produced from gas in C. autoethanogenum cultures expressing thlA and hbd1 (FIG. 18A). A native thioesterase may convert the formed 3-hydroxybutyryl-CoA to 3-hydroxybutyrate. In the genome sequence, three putative thioesterases were identified. In the strain carrying pMTL8315-Pfdx-hbd1-thlA up to 2.55 g/L 3-hydroxybutyrate was found (FIG. 18A).

Figure 18B:
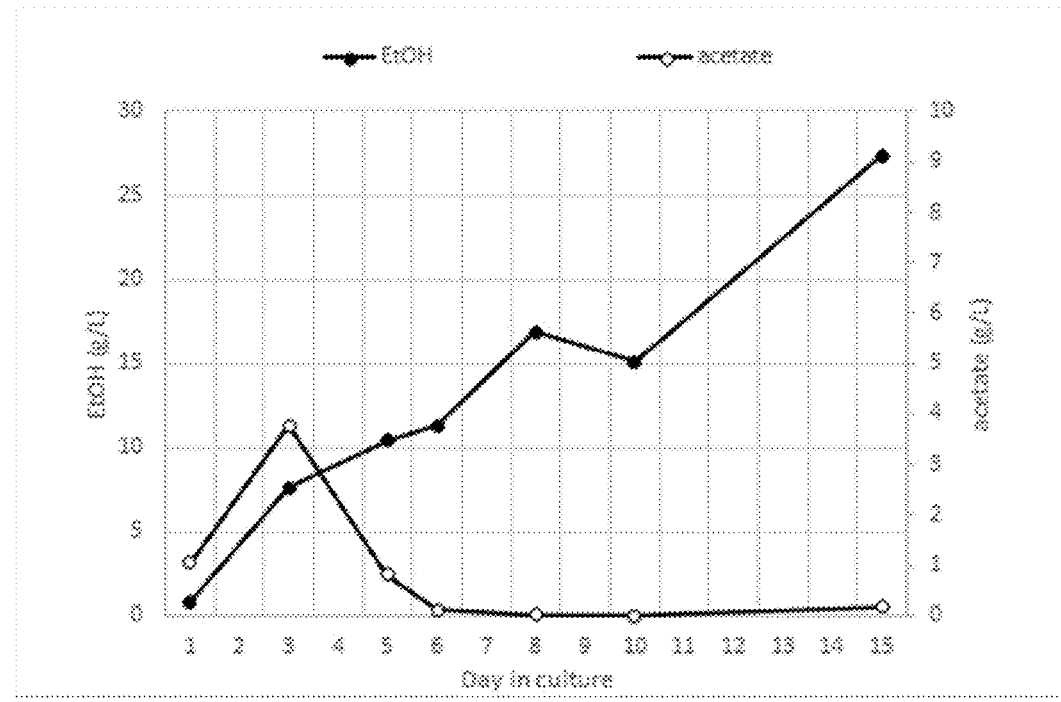
FIG. 18B is a graph showing the reduction of acetate to ethanol in the same culture.
Figure 19:
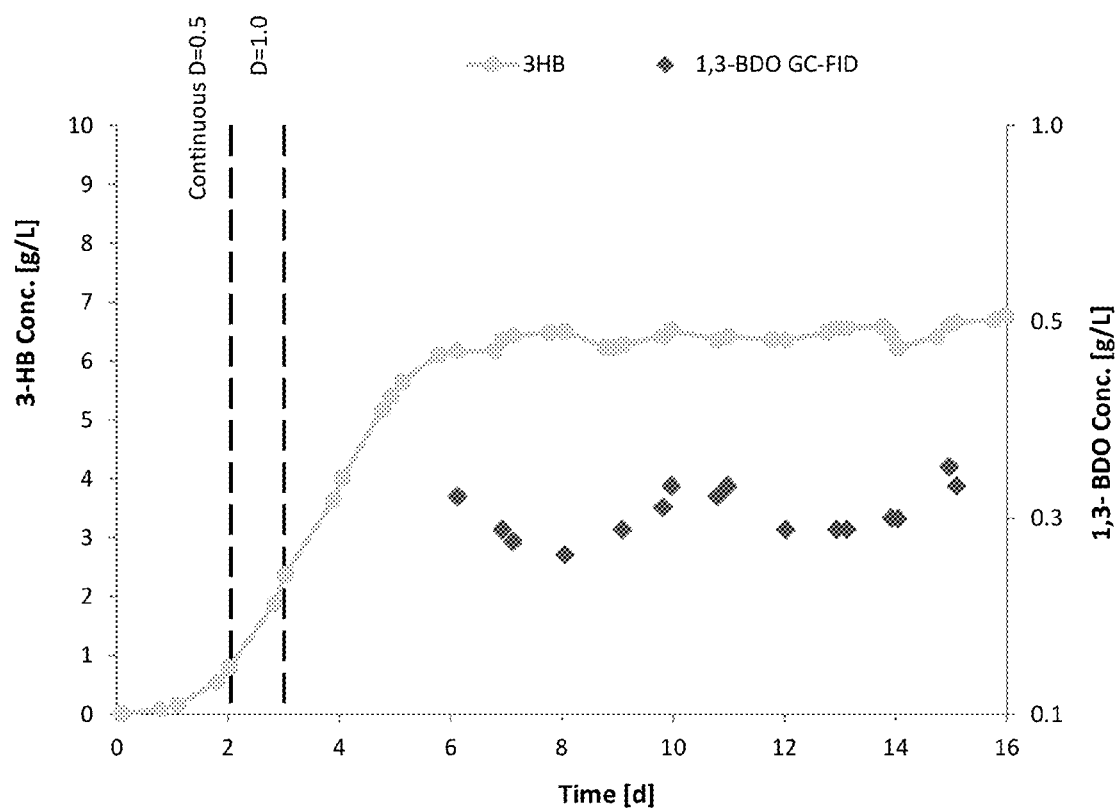
FIG. 19 is a graph showing the fermentation profile for strain *C. autoethanogenum* pMTL8315-Pfdx-hbd1-thlA demonstrating formation of 3-hydroxybutyrate and 1,3-butanediol from gaseous substrate in continuous culture (where indicated, media was replenished continuously with given dilution rate D).

Even more surprising, it was also found that 3-hydroxybutyrate is over time converted to 1,3-butanediol, at the end of growth up to 1.1 g/L 1,3-butanediol was produced in strain carrying plasmid pMTL8315-Pfdx-hbd1-thlA (FIG. 18A). This may be due to native aldehyde:ferredoxin oxidoreductase (AOR) and alcohol dehydrogenase activity. Two AOR genes and several alcohol dehydrogenases are present in the genome of C. autoethanogenum (Mock, J Bacteriol, 197: 2965-2980, 2015). This reduction of 3-hydroxybutyrate (and reduction of acetate to ethanol; FIG. 18B) is powered by reduced ferredoxin and thus can be directly coupled to CO oxidation, which provides reduced ferredoxin ($CO+Fd_{ox} \rightarrow CO_2+Fd_{red}$) (FIG. 7).

The same strain of C. autoethanogenum carrying plasmid pMTL8315-Pfdx-hbd1-thlA was also tested in continuous fermentation. Fermentation was carried out as described in previous example, but the culture was turned continuous with a dilution rate with fresh media of around 0.05 at day 2 and then increased to 1.0 at day 3. High 3-hydroxybutyrate production of up to 7 g/L was observed with 1,3-BDO production of 0.5 g/L.

Figure 41:
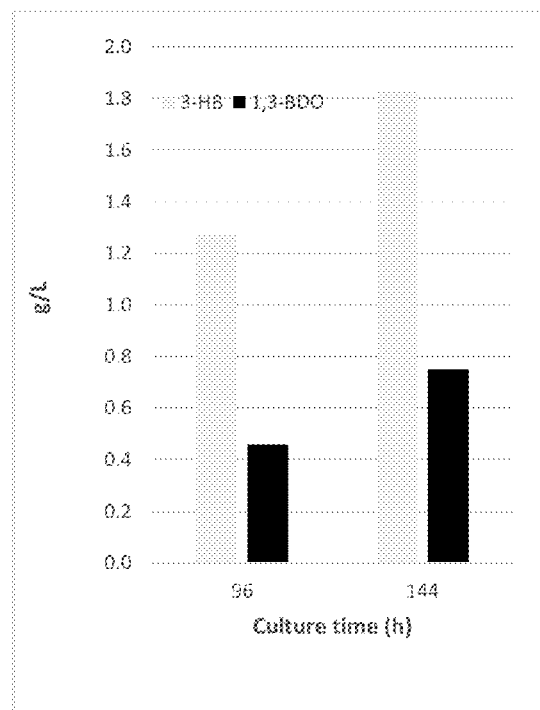
FIG. 41 is a graph showing production of 3-HB and 1,3-BDO by *C. autoethanogenum* comprising budA knockout and pMTL-HBD-ThlA at various points of growth.

To improve production of (S)-3-hydroxybutyrate and 1,3-butanediol and avoid synthesis of another form of butanediol (2,3-butanediol), plasmid pMTL-HBD-ThlA was introduced into a strain that has an inactivated 2,3-butanediol pathway where the acetolactate decarboxylase gene BudA has been deleted (U.S. Pat. No. 9,297,026). This budA knockout eliminated the major pathway to 2,3-BDO, increasing the specificity for 3-HB and 1,3-BDO production. When pMTL-HBD-ThlA was expressed in the budA deletion strain, a total of 15% C-mol was achieved for both 3-HB and 1,3-BDO (FIG. 41).

|           | Selectivity (C-mol %) |
|-----------|-----------------------|
| Acetate   | 14.7                  |
| Ethanol   | 64.9                  |
| 2,3-BDO   | 1.3                   |
| Biomass   | 3.7                   |
| 3-HB      | 10.4                  |
| 1,3-BDO   | 5.0                   |

As a comparison, in a strain expressing the same plasmid, pMTL83159-hbd-thlA without budA knockout, the total specificity for the production of 3-HB and 1,3-BDO at the steady state was only 6.9%

|           | Selectivity (C-mol%) |
|-----------|----------------------|
| Acetate   | 0.4                  |
| Ethanol   | 84.3                 |
| 2,3-BDO   | 6.2                  |
| Biomass   | 2.2                  |
| 3-HB      | 3.5                  |
| 1,3-BDO   | 3.4                  |

Example 6

This example demonstrates that the Ptb-Buk system is efficient in C. autoethanogenum on a range of acyl-CoAs including acetoacetyl-CoA, 3-hydroxybutyryl-CoA, and 2-hydroxyisobutyryl-CoA The Ptb-Buk system was expressed from a plasmid in C. autoethanogenum and its activity measured using a CoA hydrolysis assay. For this, ptb-buk genes from C. beijerinckii NCIMB8052 (GenBank NC_009617, position 232027 . . . 234147; Cbei_0203-204; NCBI-GeneID 5291437-38) were amplified from genomic DNA of C. beijerinckii NCIMB8052 and cloned under control of a pyruvate-ferredoxin oxidoreductase promoter ($P_{pfor}$ isolated from C. autoethanogenum; SEQ ID NO: 139) into pMTL82251 vector ((Heap, J Microbiol Meth, 78: 79-85, 2009) by routine methods in molecular cloning, including restrictive enzyme digestion followed by ligation, overlap extension polymerase chain reaction, seamless cloning (Thermo Fisher Scientific), and GeneArt Type IIs (Thermo Fisher Scientific) as described in Example 5. Oligonucleotides are described below.

| SEQ ID NO: | Name       | Sequence                                  | Direction |
|------------|------------|-------------------------------------------|-----------|
| 149        | Ppfor-F2   | aaacagctatgaccgcGGCCGCAAAATAGT            | forward   |
| 150        | Ppfor-R2   | ttactcatTGGATTCCTCTCCITT                  | reverse   |
| 151        | Ptb-Buk-F2 | ggaatccaATGAGTAAAAACTTTGATGAG             | forward   |
| 152        | Ptb-Buk-R2 | caggcctcgagatctcCTAGTAAACCTTAGCTTGTTC     | reverse   |

The resulting plasmid pMTL82256-ptb-buk (SEQ ID NO: 153) was introduced into C. autoethanogenum as described in previous examples.

Acyl-CoA hydrolysis assays were performed as follows. C. autoethanogenum cells were harvested at OD 2 (late exponential phase) by centrifugation (14,000 rpm for 1 min at 4° C.). Cells were re-suspended in 500 μl lysis buffer (potassium phosphate buffer, pH 8). Cells were lysed using a freeze thaw cycle (optional), sonication 6×30 s at amplitude 20 on ice. Samples were centrifuged for 10 min at 14,000 rpm at 4° C. and the supernatant with soluble proteins was removed. The protein concentration was measured, e.g., with a Bradford assay.

The assay mix contained: 484 µl of potassium phosphate buffer pH 8.0, 1 µl of DTNB (final concentration of 0.1 mM), 10 µl of cell lysate, and 5 µl of CoA (final concentration of 500 µM). All the components were mixed in a quartz cuvette (1 ml cuvette with a read length of 1 cm) except the protein. The assay was started by adding the cell lysate and following the reaction in a spectrophotometer at 405 nm, 30° C. for 3 min. A control without lysate was run to measure autolysis of the acyl-CoA.

To determine activity, slope on the linear part of the curve (usually in the first 30 s), was calculated. The protein amount was normalized and slope was divided by protein amount. An extinction coefficient (14,150 $M^{-1}$ $cm^{-1}$) was used to calculate the specific activity in M/s/mg. The activity of the negative control was subtracted.

The assay was performed with acetoacetyl-CoA, a racemic mix of 3-hydroxybutyryl-CoA (3-HB-CoA) and 2-hydroxyisobutyryl-CoA (2-HIB-CoA). The possibility of artificially low hydrolysis rates for 3-HB-CoA and 2-HIB-CoA due to potential substrate limitation was addressed by repeating the hydrolysis assays for *C. autoethanogenum* lysates using different concentrations of acyl-CoA, 500 µM and 200 µM.

Figure 20A:
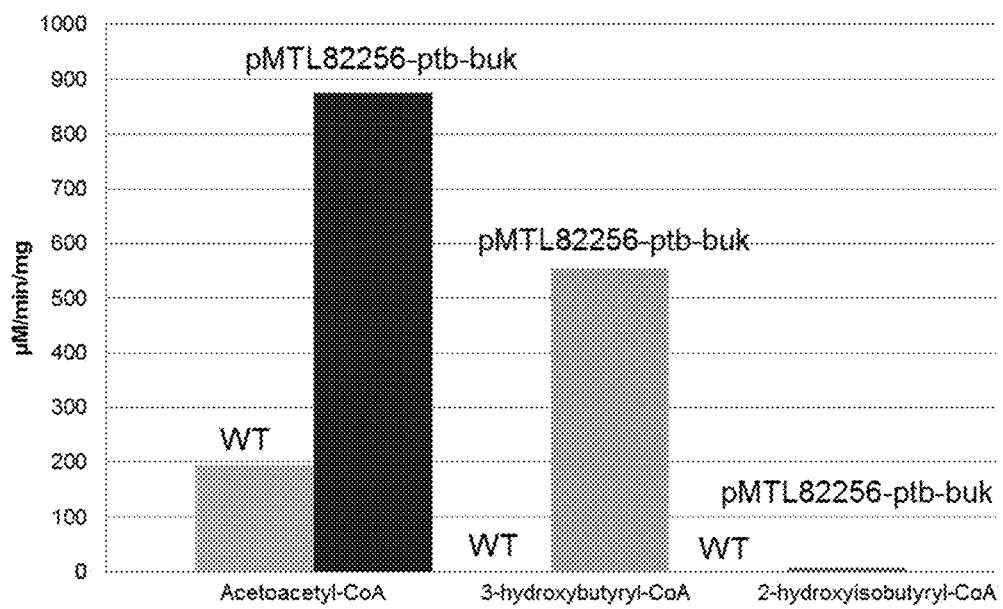
FIG. 20A and FIG. 20B are graphs showing increased CoA hydrolysis activity on a range of acyl-CoAs (acetoacetyl-CoA, 3-hydroxybutyryl-CoA and 2-hydroxyisobutyryl-CoA) in *C. autoethanogenum* expressing the Ptb-Buk system from plasmid pMTL82256-ptb-buk compared to wild-type (WT).
Figure 20B:
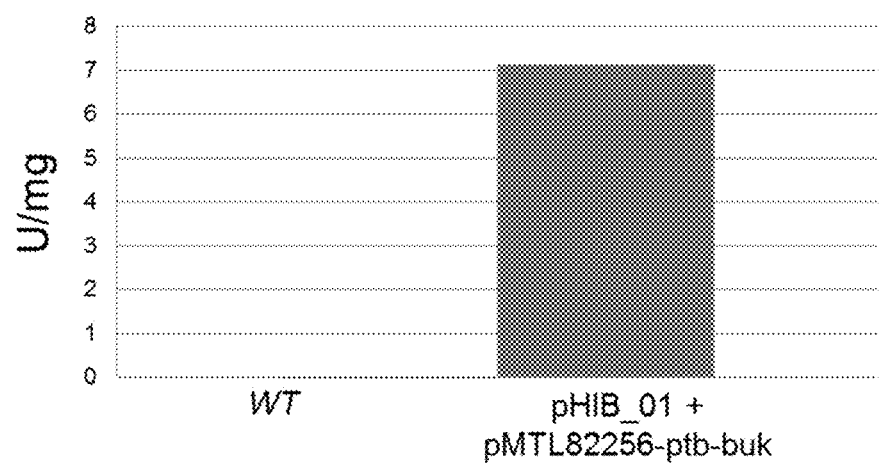

The results of the assay show significantly increased CoA hydrolysis in lysates of *C. autoethanogenum* carrying plasmid pMTL82256-ptb-buk expressing the Ptb-Buk system on a range of acyl-CoAs including acetoacetyl-CoA, 3-hydroxybutyryl-CoA and 2-hydroxyisobutyryl-CoA (FIGS. 20A-B). Notably, there is also CoA hydrolysis for acyl-CoAs as 2-hydroxyisobutyryl-CoA that are not hydrolysed by the *C. autoethanogenum* wild-type. With acetoacetyl-CoA and 3-hydroxybutyryl-CoA some native CoA hydrolysis activity was observed.

Example 7

This example demonstrates the disruption of identified native thioesterase genes improve efficiency of the Ptb-Buk and CoA transferase system by increasing the pool of available acyl-CoAs such as acetoacetyl-CoA, 3-hydroxybutyryl-CoA or 2-hydroxyisobutyryl-CoA.

In contrast to the Ptb-Buk system, where energy is conserved in the form of ATP during conversion of acyl-CoAs to their respective acids, no energy is conserved if the CoAs are simply hydrolyzed.

In hydrolase assays it was found that there is native hydrolysis activity for acetoacetyl-CoA and 3-hydroxybutyryl-CoA in *C. autoethanogenum*.

Acyl-CoA hydrolysis assays with acetoacetyl-CoA, a racemic mix of 3-hydroxybutyryl-CoA (3-HB-CoA) and 2-hydroxyisobutyryl-CoA (2-HIB-CoA were performed as described in previous example. The results of the assay show cleavage of acetoacetyl-CoA and 3-HB-CoA, but not 2-HIB-CoA, and confirm native activity is present in *C. autoethanogenum* (FIG. 11).

An analysis of the genome of *C. autoethanogenum* led to identification of three putative CoA-thioesterases (thioesterhydrolases) that could be responsible for to the cleavage of acetoacetyl-CoA or 3-hydroxybutyryl-CoA thioester bond. These are also present in other acetogens such as *C. ljungdahlii*.

| Description | Annotation | *C. autoethanogenum* | SEQ ID NO: | *C. ljungdahlii* | SEQ ID NO: |
| --- | --- | --- | --- | --- | --- |
| thioesterase 1 (CAETHG_0718) | Palmitoyl-CoA hydrolase | AGY74947.1 | 154 | ADK15695.1 | 157 |
| thioesterase 2 (CAETHG_1524) | 4-Hydroxybenzoyl-CoA thioesterase | AGY75747.1 | 155 | ADK16655.1 | 158 |
| thioesterase 3 (CAETHG_1780) | Putative Thioesterase | AGY75999.1 | 156 | ADK16959.1 | 159 |

Inactivation of these three putative CoA-thioesterases lead to higher product titers, improving efficiency of the Ptb-Buk system. The three putative thioesterases were inactivated using ClosTron technology. In brief, the targeting domain of the type II Ltr was reprogrammed using the ClosTron website and the retargeted ClosTron plasmids were ordered from DNA 2.0. The ClosTron knock out vectors pMTL007C-E2-Cau-2640-571s targeting the thioesterase 1 (CAETHG_0718), pMTL007C-E2-PBor3782-166s targeting the thioesterase 2 (CAETHG_1524), and pMTL007C-E2-PBor4039-199s targeting the thioesterase 3 (CAETHG_1780) were introduced into *C. autoethanogenum* using conjugation.

Selection for integration was done by selecting PETC supplemented with 5 µg/ml clarithromycin and successful inactivation by integration of the type II intron was confirmed by PCR across the insertion site.

Figure 21A:
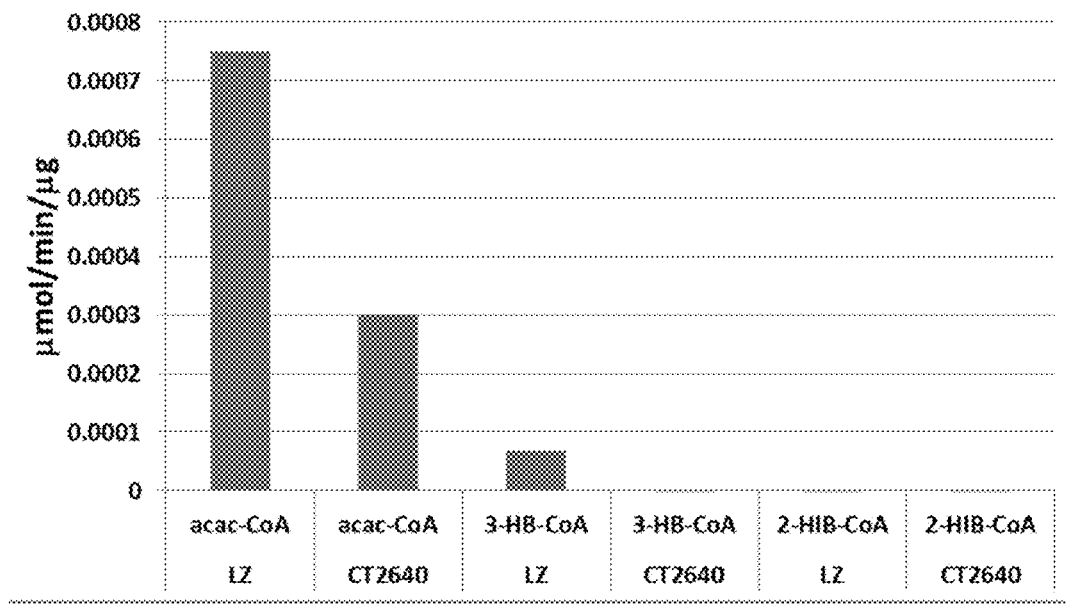
FIG. 21A and FIG. 21B are graphs showing reduced acyl-CoA hydrolysis activity of *C. autoethanogenum* strains with inactivated thioesterases (CT2640=thioesterase 1, CT1524=thioesterase 2, CT1780=thioesterase 3) compared to activity found in *C. autoethanogenum* LZ1560 or LZ1561.
Figure 21B:
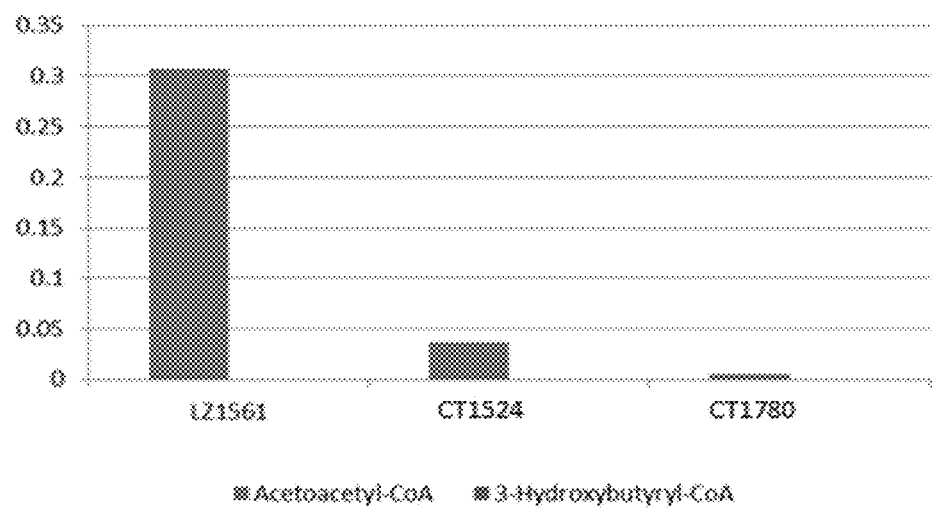
Figure 22:
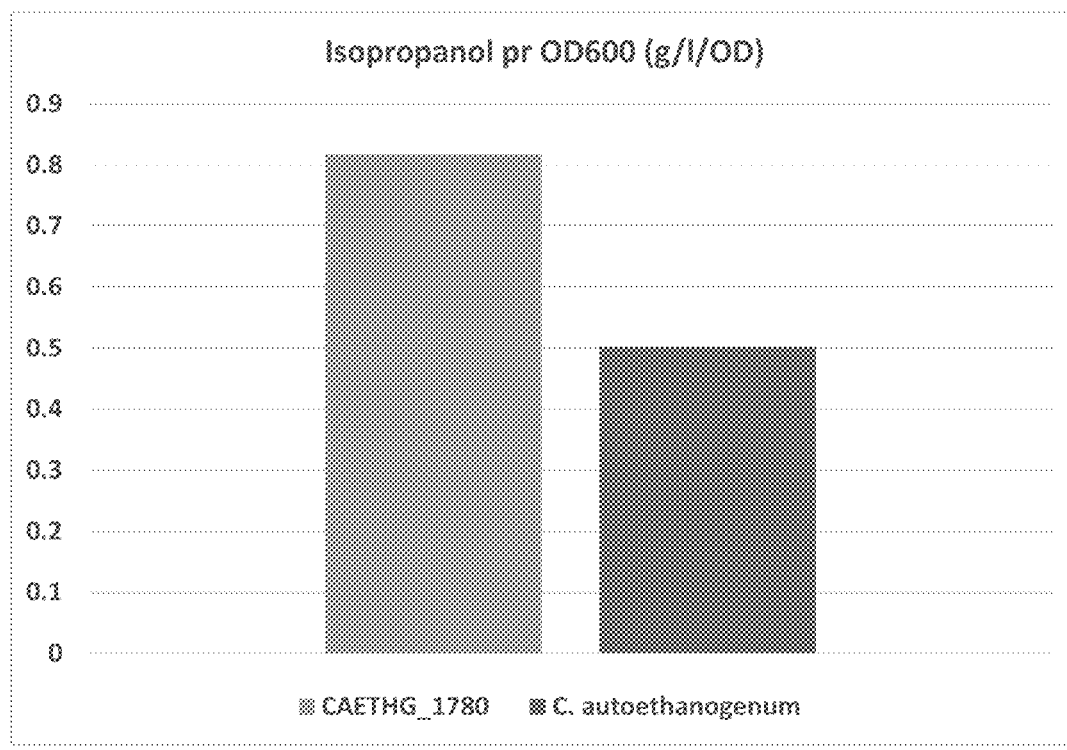
FIG. 22 is a graph showing increased specific isopropanol production in a *C. autoethanogenum* strain with disrupted thioesterase 3 CAETHG_1780 compared to wild-type *C. autoethanogenum*.
Figure 23A:
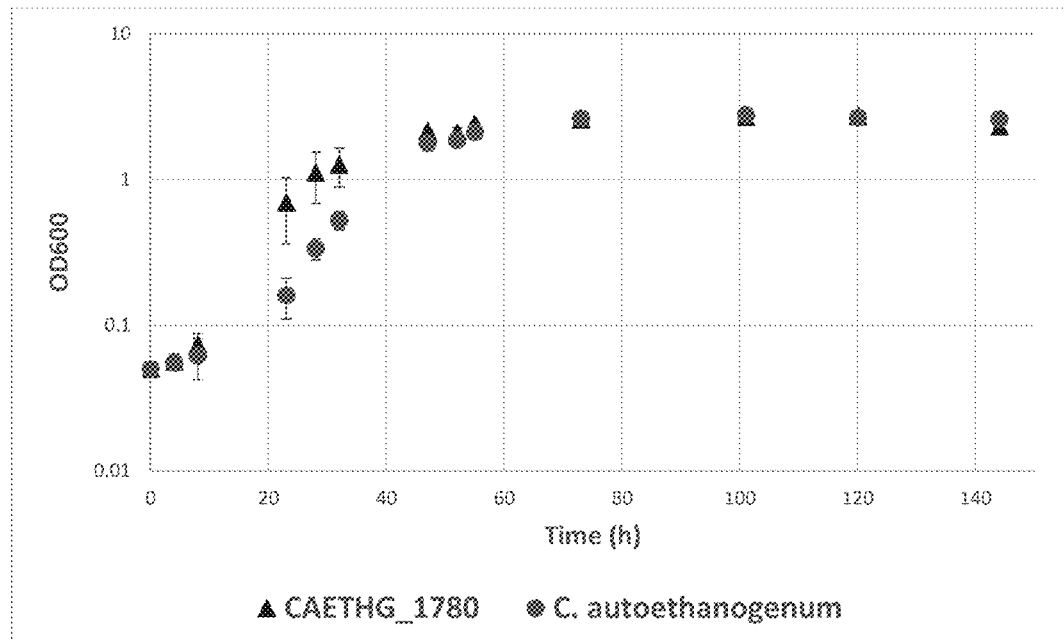
FIGS. 23A-D are graphs showing growth (FIG. 23A) and isopropanol (FIG. 23B), acetate (FIG. 23C), and ethanol (FIG. 23D) production profiles of *C. autoethanogenum* wild-type and strain with disrupted thioesterase 3 (CAETHG_1780) compared to wild-type *C. autoethanogenum*.
Figure 23B:
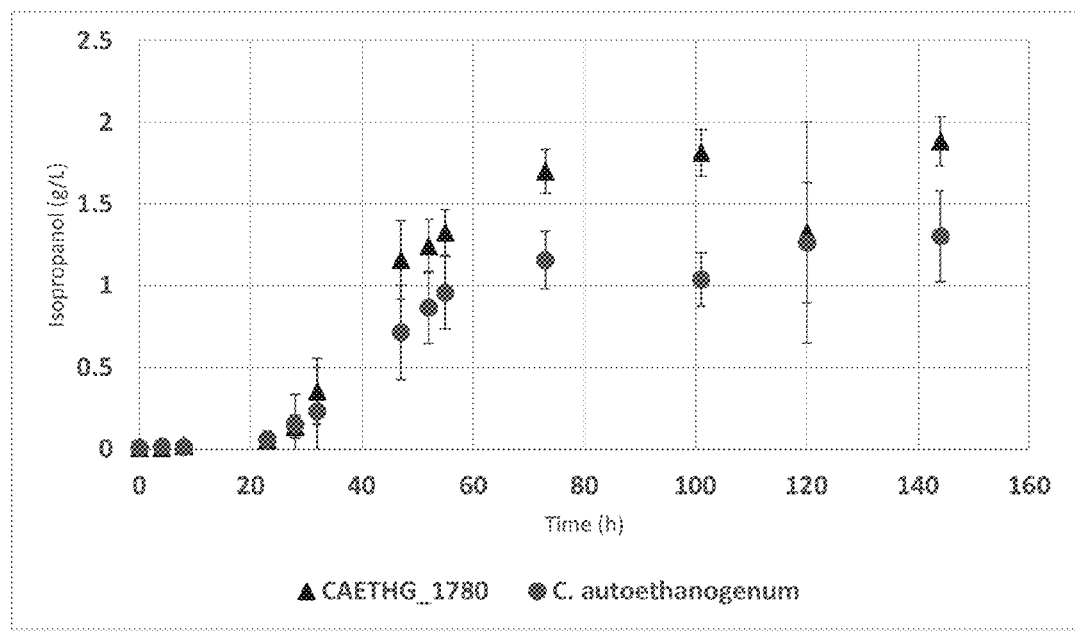
Figure 23C:
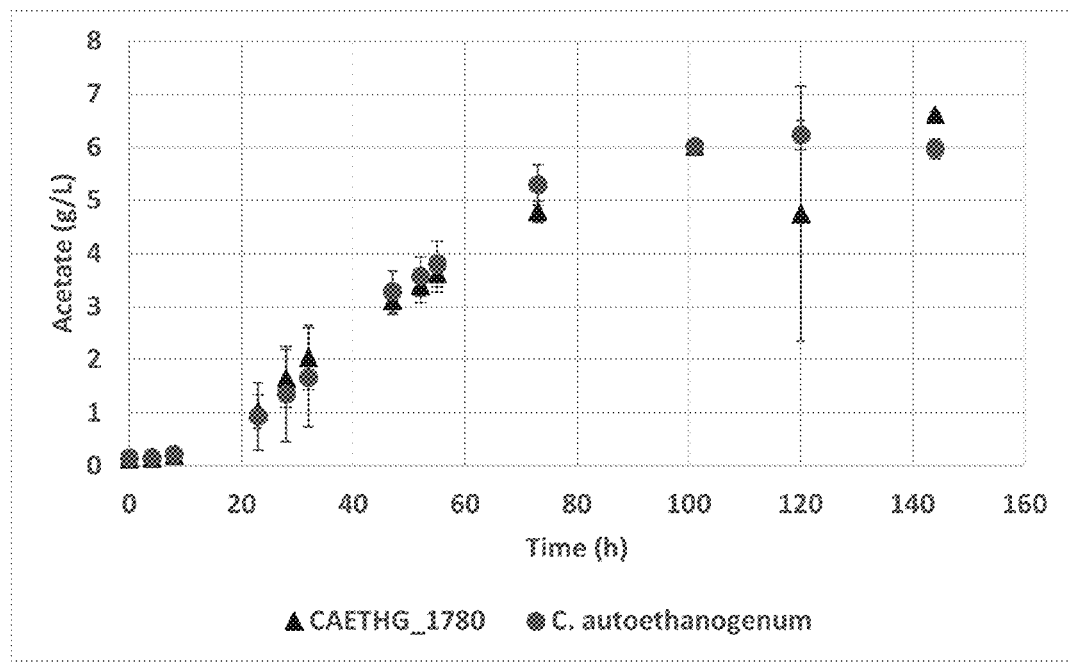
Figure 23D:
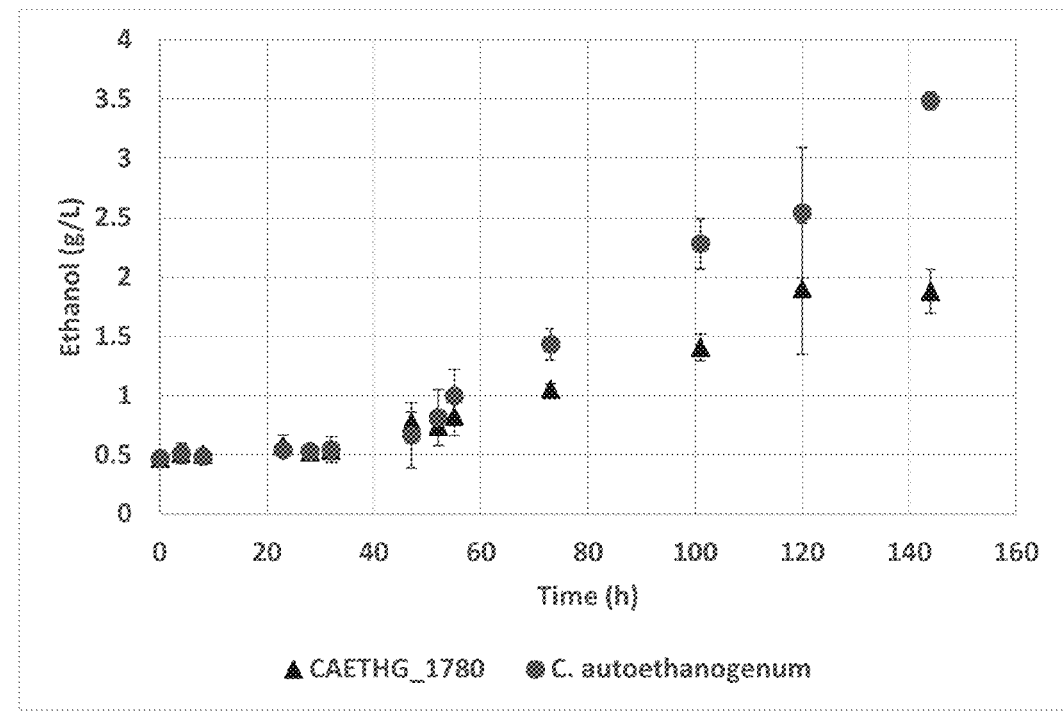

The CoA hydrolase activity on acetoacetyl-CoA of both wild type *C. autoethanogenum* and each of the *C. autoethanogenum* with one of the putative genes inactivated was measured using the assay described above. It was shown that all three strains with the inactivated putative thioesterases showed less hydrolysis activity on acetoacetyl-CoA and 3-hydroxybutyryl-CoA (FIGS. 21A-B).

To demonstrate that the decreased CoA hydrolase activity, and thus an increased pool in acetoacetyl-CoA, is beneficial for production of acetoacetyl-CoA derived products, the isopropanol plasmid pMTL85147-thlA-ctfAB-adc encoding thl+ctfAB+adc (WO 2012/115527) was introduced into the *C. autoethanogenum* wild-type strain and the strain with inactivated thioesterase 1. A growth experiment was carried out 40 ml PETC medium in 1 L Schott bottles in technical triplicates with Co gas at 37° C. at 110 rpm shaking. Synthetic gas (50% CO, 18% $CO_2$, 2% $H_2$, and 30% $N_2$) was used as sole energy and carbon source. Headspace exchanged once and gassed to 21 psi (1.5 bar) at 37° C. under synthetic gas (50% CO, 18% $CO_2$, 2% $H_2$, and 30% $N_2$). Samples for OD and analytics were taken twice a day.

The strain with inactivated thioesterase 3 CAETHG 1780 produced significantly higher levels of isopropanol than the wild-type (FIG. 22 and FIGS. 23A-D).

Similarly, knockout of thioesterases in *C. autoethanogenum* would increase the pool of 3-hydroxybutyryl-CoA, allowing more efficient utilization of 3-hydroxybutyryl-CoA by Ptb-Buk and leading to higher production of acetone, isopropanol, isobutylene, (R)-3-hydroxybutyrate, 1,3-butanediol, and/or 2-hydroxyisobutyric acid. When plasmid pMTL8315-Pfdx-hbd1-thlA of Example 5 was introduced into *C. autoethanogenum* strain with interrupted thioesterase 2 CAETHG_1524, 3-hydroxybutyrate synthesis was abolished (compared to the up to 2.55 g/L 3-hydroxybutyrate that were found when expressing this plasmid in the *C. autoethanogenum* wild type strain). No competing activity for 3-hydroxybutyryl-CoA is present in this strain.

These results demonstrate that by reducing thioesterase activity, a higher CoA pool for the Ptb-Buk system and product synthesis is available.

Figure 42A:
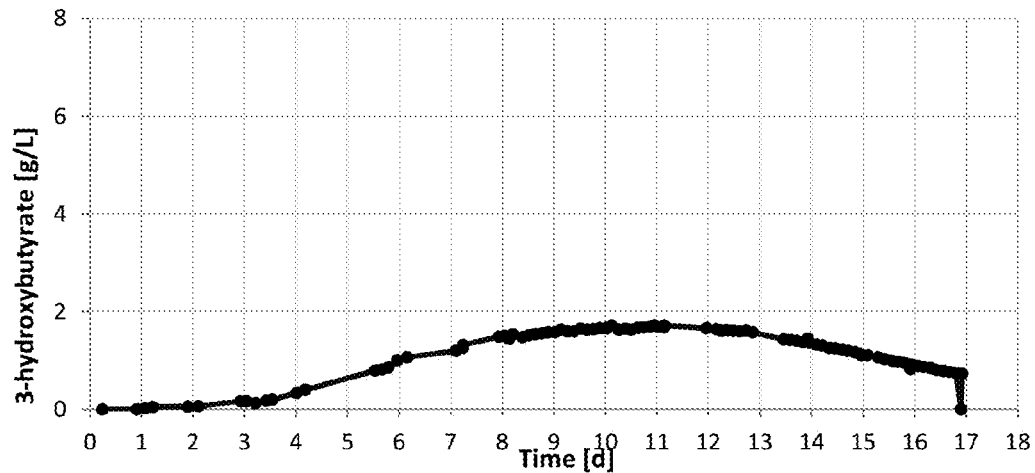
FIG. 42A is a graph showing production of 3-HB in a *C. autoethanogenum* pMTL83159-phaB-thlA+pMTL82256 fermentation.
Figure 42B:
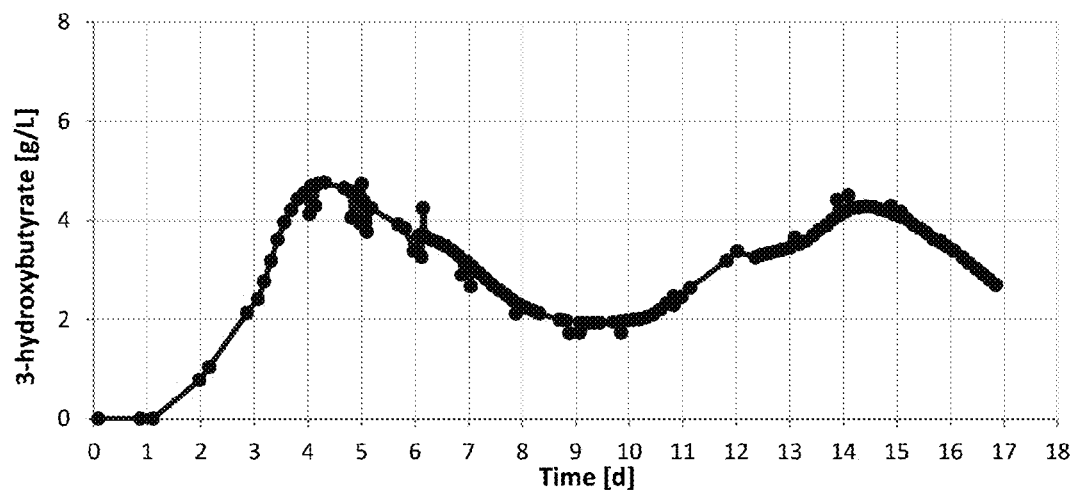
FIG. 42B is a graph showing production of 3-HB in a *C. autoethanogenum* pMTL83159-phaB-thlA+pMTL82256-buk-ptb fermentation.

Additionally, the production of 3-HB and 1,3-BDO can be increased by overexpression of ptb-buk. In a control experiment, whereby *C. autoethanogenum* as described in Example 2 was transformed with plasmids pMTL83159-phaB-thlA from Example 4 plus pMTL82256 (Heap, *J Microbiol Methods*, 78: 79-85, 2009), in which the latter is an empty plasmid used as a background control, the fermentation of such strain resulted in a production of 3-HB with highest titer at 1.68 g/L at day 10 (FIG. 42A). When pMTL82256-buk-ptb, instead of the empty plasmid pMTL82256, was coexpressed with pMTL83159-phaB-thlA in *C. autoethanogenum*, the fermentation resulted in a higher titter of 3-HB, at 4.76 g/L, at an earlier time, day 4 (FIG. 42B).

Deletion of native thioesterases enhances the efficiency of the ptb-buk system, which has preference for (R)-3-HB-CoA. The locus of the thioesterase gene in the genome was deleted and replaced with the buk-ptb dna fragment via the common molecular biology technique known as homologous recombination. The substitution of the thioesterase gene by the buk-ptb was confirmed by PCR, followed by agarose gel electrophoresis and dna sequencing.

Figure 43:
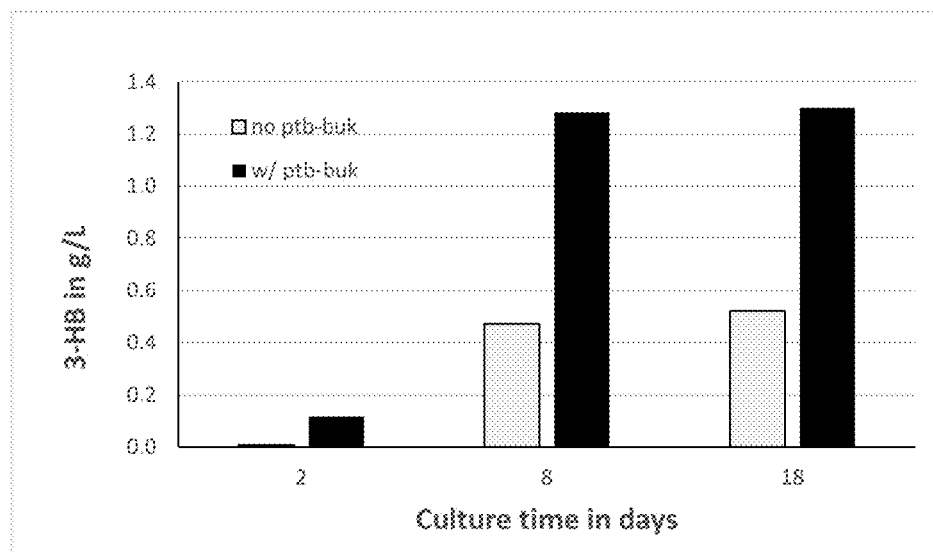
FIG. 43 is a graph showing the production of 3-HB in a *C. autoethanogenum* strain with thioesterase knockout (ACAETHG_1524) expressing plasmid pMTL83156-phaB-thlA with and without Ptb-Buk expression plasmid pMTL82256-buk-ptb.

In a bottle experiment, when pMTL83156-phaB-thlA was expressed without ptb-buk in the thioesterase deletion mutant, described above, the average maximum titer of 3-HB produced was 0.50±0.05 g/L, similar to the titer obtained using an unmodified *C. autoethanogenum* strain. When pMTL82256-buk-ptb was coexpressed with the pMTL83156-phaB-thlA plasmid in a thioesterase knockout strain, the production of 3-HB increased to 1.29±0.10 g/L (FIG. 43).

Example 8

This example demonstrates that it is possible to eliminate acetate production system in an acetogen *C. autoethanogenum* with the Ptb-buk system.

All acetogenic microorganisms are described to produce acetate (Drake, Acetogenic Prokaryotes, In: *The Prokaryotes*, 3$^{rd}$ edition, pages 354-420, New York, N.Y., Springer, 2006) as the production of acetate provides the microorganism with an option to directly generate ATP from substrate level phosphorylation via Pta (phosphotransacetylase) and Ack (phosphotransacetylase-acetate kinase). Native acetate-forming enzymes such as Pta-Ack are therefore considered to be essential in acetogens (Nagarajan, *Microb Cell Factories*, 12: 118, 2013). Since Ptb-Buk provides an alternative means for energy generation, it becomes possible to replace the native Pta-Ack system with Ptb-Buk.

Figure 24:
FIG. 24 is a plasmid map of pMTL8225-pta-ack::ptb-buk.

The pta and ack genes in *C. autoethanogenum* are in one operon. To replace pta and ack genes with ptb and buk genes a plasmid, pMTL8225-pta-ack::ptb-buk (FIG. 24), with mazF counter selection marker that is under tetracycline inducible promoter, ~1 kb upstream homology arm, ptb, buk, ermB cassette flanked by loxP sites and ~1 kb downstream homology arm was assembled (SEQ ID NO: 160).

The ~1 kb upstream and downstream homology arms were PCR amplified from *C. autoethanogenum* with primers SN22f/SN23r and SN28f/SN29r. Ptb and buk genes were PCR amplified from pIPA_16 plasmid using primers SN24f/SN25r. The ermB cassette with loxP sites was PCR amplified using primers SN26f/SN27r. The plasmid backbone was PCR amplified with primers SN30f/SN31r. KAPA polymerase was used for all PCR amplifications. The PCR products were assembled using GeneArt Seamless cloning kit from Life Technologies and plasmid with no mutations in the insert fragments was used to transform *C. autoethanogenum* by conjugation as described earlier.

Figure 25:
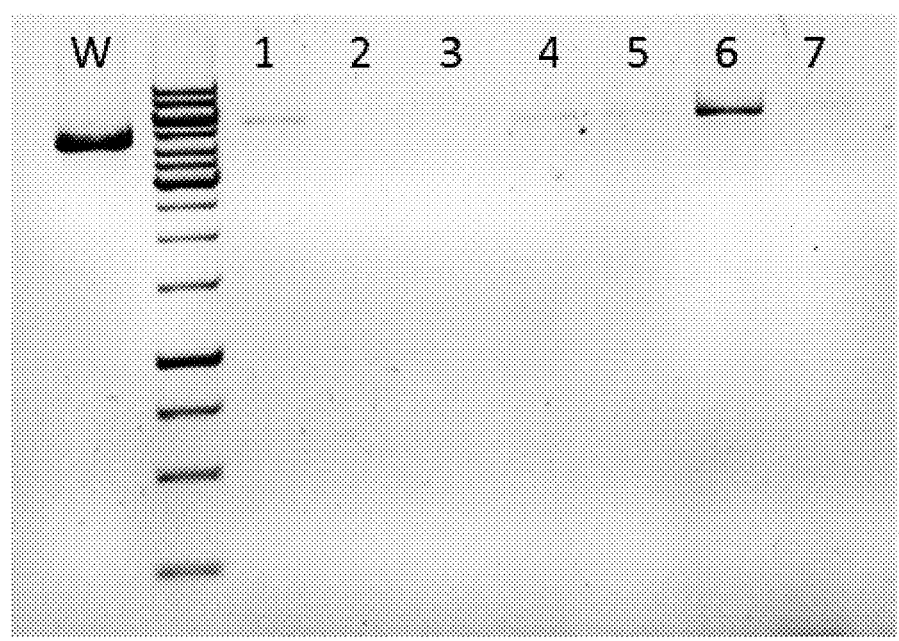
FIG. 25 is a gel image indicating the replacement of pta and ack genes replaced with ptb and buk genes and ermB cassette.
Figure 26:
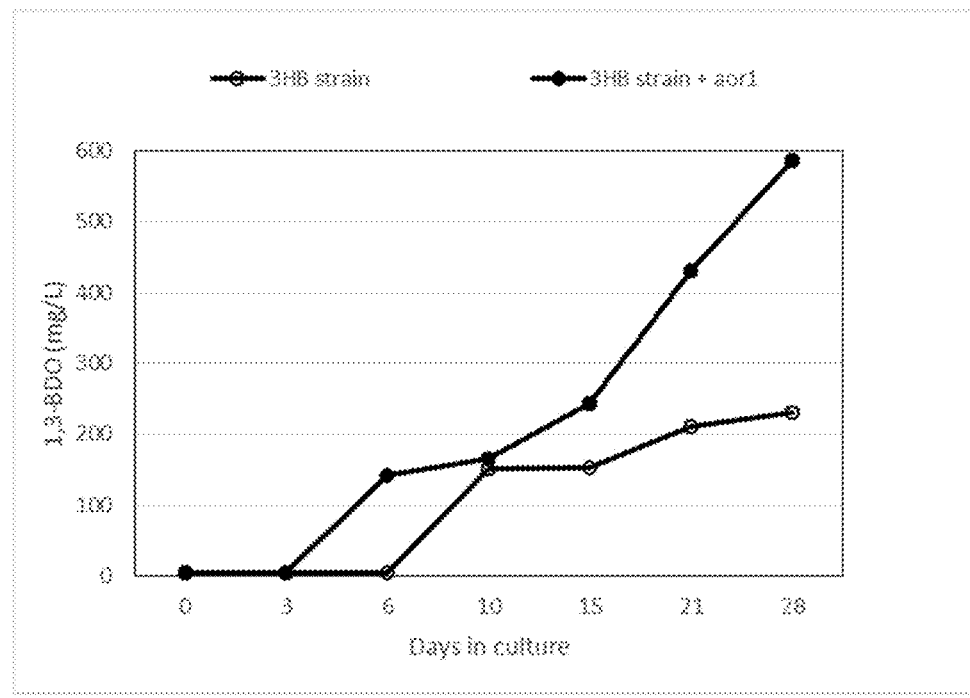
FIG. 26 is a graph showing increased conversion 3-hydroxybutyrate to 1,3-BDO by overexpression of the aldehyde:ferredoxin oxidoreductase gene aor1.

Following conjugation and selection on trimethoprim and clarithromycin, 7 colonies were streaked twice on PETC-MES agar plates with clarithromycin and anhydrotetracycline to induce the expression of mazF genes. The colonies from clarithromycin and anhydrotetracycline should have the pta and ack genes replaced with ptb and buk genes and ermB cassette. This was verified by PCR using primers Og29f/Og30r flanking the homology arms and KAPA polymerase (FIG. 25). While a band of ~4.6 kb is amplified from the wildtype strain, bands of ~5.7 kb was amplified from colonies 1 and 4-7, indicating the replacement of pta and ack genes replaced with ptb and buk genes and ermB cassette. The above event was further confirmed by sequencing the PCR products from clones 4-7.

With the resulting modification the expression of ptb and buk genes is driven by the promoter upstream of pta gene.

| SEQ ID NO: | Name | Sequence |
| --- | --- | --- |
| 161 | SN22f | TTTACAAATTCGGCCGGCCAAAGATTGCTCTATGTTTAAGCT |
| 162 | SN23r | CATCAAAGTTTTTACTCATCAATTTCATGTTCATTTCCTCCCT |
| 163 | SN24f | AGGGAGGAAATGAACATGAAATTGATGAGTAAAAACTTTGATGAGT |
| 164 | SN25 r | GTATAGCATACATTATACGAACGGTACTAGTAAACCTTAGCTTGTTCTTC |
| 165 | SN26f | GAAGAACAAGCTAAGGTTTACTAGTACCGTTCGTATAATGTATGCTATAC |
| 166 | SN27r | AGAGATGAGCATTAAAAGTCAAGTCTACCGTTCGTATAGCATACA |
| 167 | SN28f | TGTATGCTATACGAACGGTAGACTTGACTTTTAATGCTCATCTCT |
| 168 | SN29r | CATGAGATTATCAAAAGGAGTTTAAATATCTATTTTGTCCTTAGGA |

| SEQ ID NO: | Name | Sequence |
|---|---|---|
| 169 | SN3 0f | TCCTAAGGACAAAATAGATATTTAAACTCCTTTTTGATAATCTCATG |
| 170 | SN31r | AGCTTAAACATAGAGCAATCTTTGGCCGGCCGAATTTGTAAA |
| 171 | 0g29f | AGCCACATCCAGTAGATTGAACTTT |
| 172 | 0g3 0r | AATTCGCCCTACGATTAAAGTGGAA |

The resulting strain *C. autoethanogenum* pta-ack::ptb-buk, in which the pta-ack operon was replaced by the ptb-buk operon was transformed as described above with the isopropanol production plasmid pMTL85147-thlA-adc from Example 2. A growth study was carried out under autotrophic conditions and analyzed for metabolic end products. No acetate production was observed, while isopropanol (up to 0.355 g/L) and 3-HB (up to 0.29 g/L) was still produced alongside ethanol and 2,3-butanediol (FIGS. 39A and 39B). This demonstrates that it is possible to produce isopropanol and 3-HB without acetate production from gaseous substrates CO and/or $CO_2$ and $H_2$ using the Ptb-Buk system.

If acetone rather than isopropanol is the target product, the primary:secondary alcohol dehydrogenase gene (SEQ ID NO: 17) can be further knocked out this strain *C. autoethanogenum* pta-ack::ptb-buk using methods described above and in detail in WO 2015/085015. Introducing plasmid pMTL85147-thlA-adc into this strain results in production of acetone at similar levels as described above for isopropanol without co-production of acetate. Ethanol, 2,3-butanediol and 3-HB may be further products.

By further knock-outs it is possible to eliminate these products as well, e.g., knock-out of the acetolactate decarboxylase gene BudA results in a strain unable to produce 2,3-butanediol (U.S. Pat. No. 9,297,026). 3-HB production may be reduced or eliminated by deletion of 3-hydroxybutyrate dehydrogenase gene Bdh (SEQ ID NO: 62).

Example 9

This example demonstrates improvement of conversion of 3-hydroxybutyrate to 1,3-BDO by overexpression of the aldehyde:ferredoxin oxidoreductase gene aor1.

The pMTL82251 plasmid backbone was used for overexpression of the *C. autoethanogenum* aor1 gene. The pMTL82251 plasmid was selected since it has a different replication origin and antibiotic marker, but could be co-expressed with, the plasmid used in Example 5 that contained hbd1 and thlA. Preparation of the plasmid backbone and the assembly reaction were carried out following the procedures listed above, first generating plasmid pMTL82256 by introducing the *C. autoethanogenum* ferredoxin promoter into plasmid pMTL82251 and then adding the aor1 genes to form plasmid pMTL82256-aor1. The following primers were used.

| SEQ ID NO: | Name | Sequence | Direction |
|---|---|---|---|
| 173 | Pfdx-F1 | AAAGGTCTCCGGCCGCGCTCACTATCTGCGGAACC | forward |
| 174 | Pfdx-R1 | TTTGGTCTCGAATTCTGTAACACCTCCTTAATTTTreverseTAG | reverse |
| 175 | aor1-F1 | AAAGGTCTCGAATTCAAAGATCTATGTATGGTTATGATGGTAAAGTATTAAG | forward |
| 176 | aor1-R1 | TTTGGTCTCCTCGAGTATGGATCCCTAGAACTTACreverseCTATATATTCATCTAATCC | reverse |

After transforming the resulting plasmid pMTL82256-aor1 into the *E. coli* CA434 strain, conjugation was performed on the previous *C. autoethanogenum* 1,3-BDO production host. Thus, the resulting *C. autoethanogenum* strain carried two plasmids, one for overexpressing hbd1 and thlA, and another for aor1, under different replication origins and selection marker. The production for 1,3-BDO was characterized and quantified following the procedures above.

The results clearly show that 1,3-BDO production can be improved by overexpressing aor1. Likewise other aldehyde: ferredoxin oxidoreductase genes could be expressed in *C. autoethanogenum* to facilitate conversion of 3-hydroxybutyrate to 1,3-butanediol.

Figure 44:
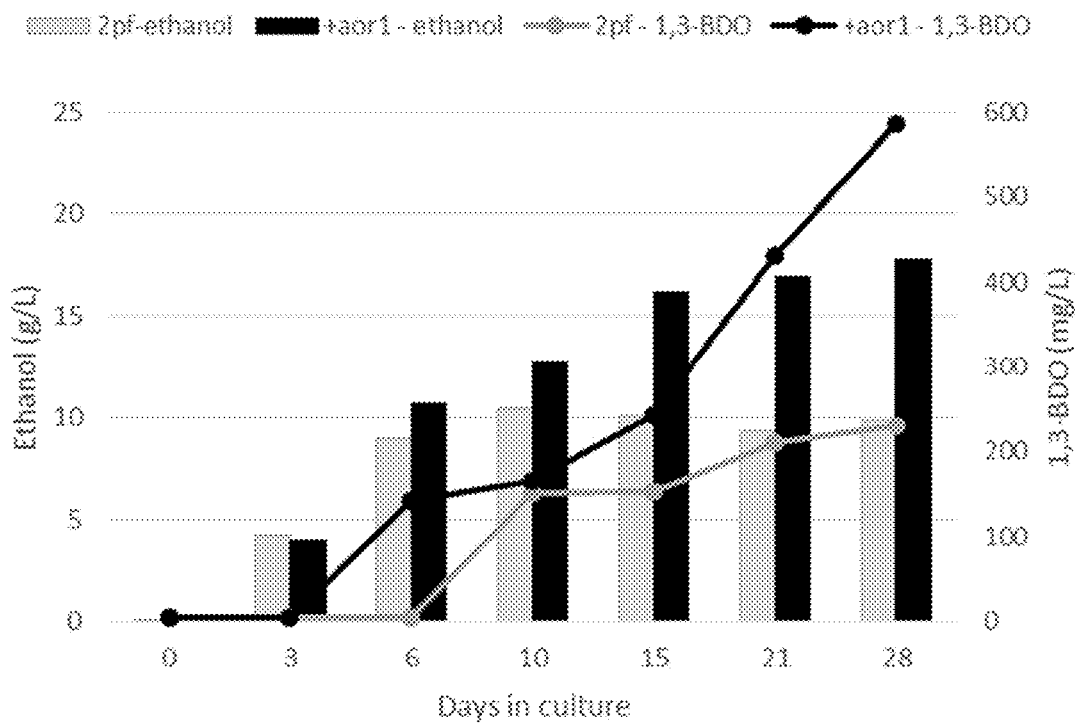
FIG. 44 is a graph showing showing ethanol and 1,3-BDO production in a *C. autoethanogenum* strain expressing plasmid pMTL82256-hbd-thlA (2pf) with and without AOR overexpression plasmid pMTL83159-aor1 (+aor1).

To improve of 1,3-BDO production, AOR was overexpressed to improve conversion of 3-HB to 3-HB-aldehyde. To do this, pMTL82256-hbd-thlA and pMTL83159-aor1 were coexpressed in *C. autoethanogenum*. As compared to the strain that carried pMTL82256-hbd-thlA alone, the aor1-coexpressed strain produced higher ethanol and 1,3-BDO (FIG. 44).

Example 10

This example demonstrates the stereospecificity of Ptb-Buk that allows for the production of 2-hydroxyisobutyric acid without the production of unwanted byproducts.

2-hydroxyisobutyic acid can be produced in *E. coli* and *C. autoethanogenum* by introduction of a thiolase and a 3-hydroxybutyryl-CoA dehydrogenase to convert acetyl-CoA to 3-hydroxybutyryl-CoA, a 2-hydroxyisobutyryl-CoA mutase enzyme for conversion of 3-hydroxybutyryl-CoA to 2-hydroxyisobutyryl-CoA and an enzyme that can hydrolyse the CoA to form 2-hydroxyisobutyric acid. The 3-hydroxybutyryl-CoA dehydrogenase can either be (R)- or (S)-specific and the enzyme converting 2-hydroxyisobutyryl-CoA to 2-hydroxybutyrate according to steps 1, 13, 19, and 20 of FIG. 1. This last step can either be done via a thioesterase or the Ptb-Buk system.

Three potential candidate genes, *E. coli* thioesterase type II TesB, the *C. autoethanogenum* phosphate acetyltransferase/acetate kinase pair and the *C. beijerinckii* butyryltransferase/butyrate kinase pair were cloned into *E. coli* pDUET T7 expression vectors via methods described above and primers below.

| SEQ ID NO: | Primer | Sequence |
|---|---|---|
| 177 | pETDuet-pta-ack - ack-DuetI2-R1 | GGGTACCTTATTTATTTTCAACTATTTCTTTTGTATC |
| 178 | pETDuet-pta-ack - DuetI2-ack-F1 | TTGAAAATAAATAAGGTACCCTCGAGTCTGGTAAAG |
| 179 | pETDuet-pta-ack - DuetI2-pta-R1 | TTTTTTCCATATGTATATCTCCTTCTTATACTTAAC |
| 180 | pETDuet-pta-ack - pta-DuetI2-F 1 | AGGAGATATACATATGGAAAAAATTTGGAGTAAGGC |
| 181 | pETDuet-tesB - DuetI2-tesB-F1 | GAAATCATAATTAAGGTA CC CTCGAGTCTGGTAAAG |
| 182 | pETDuet-tesB - DuetI2-tesB-R1 | CCTGACTCATATGTATATCTCCTTCTTATACTTAAC |
| 183 | pETDuet-tesB - DuetI2-F1 | tesB-AAGAAGGAGATATACATATGAGTCAGGCACTTAAAA |
| 184 | pETDuet-tesB - testB-DuetI2-R1 | AGGGTACCTTAATTATGATTTCTCATAACACCTTC |

Figure 27:
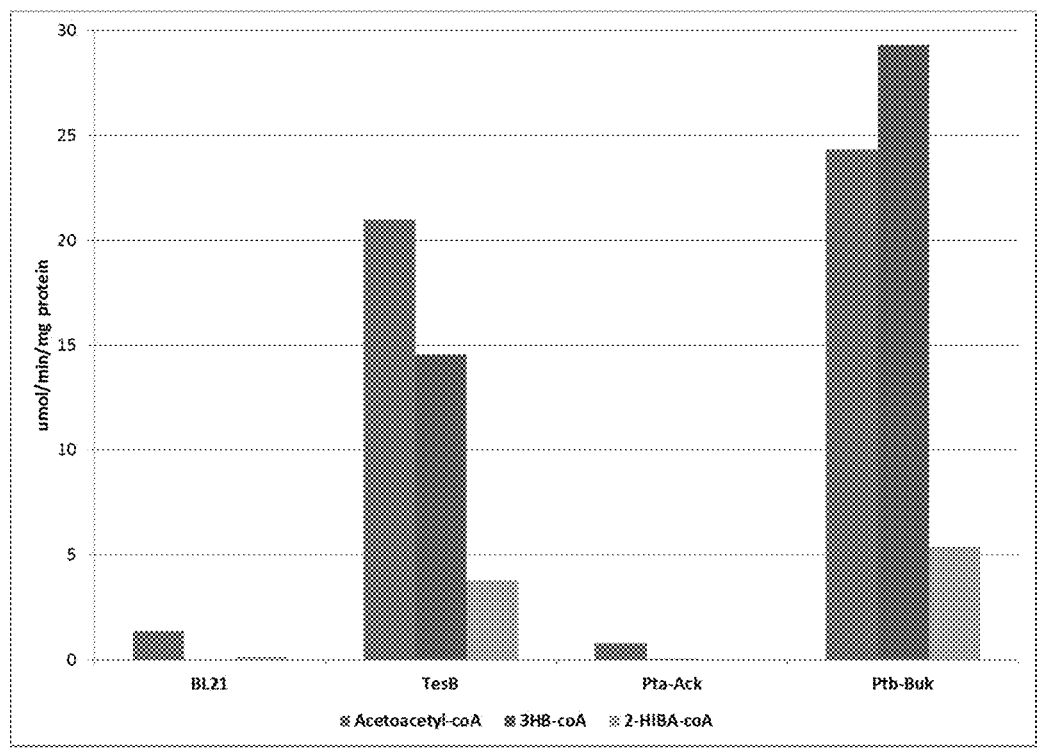
FIG. 27 is a graph showing the activity of thioesterase TesB, Pta-Ack, and Ptb-Buk system on CoA hydrolysis of acetoacetyl-CoA, 3-hydroxybutyryl-CoA and 2-hydroxyisobutyryl-CoA compared to control (BL21 strain). Ptb-Buk shows highest activity, while Pta-Ack shows no activity.

The obtained plasmids pDUET-pta-ack (SEQ ID NO: 185), pDUET-ptb-buk (SEQ ID NO: 186), pDUET-tesB (SEQ ID NO: 187) and introduced into *E. coli* BL21(DE3) for expression and then assayed for their activity on acetoacetyl-CoA, 3-hydroxybutyryl-CoA and 2-hydroxyisobutyryl-CoA. The results are shown in FIG. 27. *E. coli* BL21 has a small but measurable amount of activity on all three substrates. Pta-Ack resulted in no activity above background, while both thioesterase TesB and Ptb-Buk showed high activity on all three substrates, including 2-hydroxyisobutyryl-CoA.

The activity of both thioesterase TesB and Ptb-Buk was higher on linear acetoacetyl-CoA, 3-hydroxybutyryl-CoA than on branched 2-hydroxyisobutyryl-CoA. This creates a problem in the pathway as it results in early termination of the pathway at 3-hydroxybutyryl-CoA, in particular as activities are higher than activities on the 2-hydroxyisobutyryl-CoA mutase enzyme.

Figure 28A:
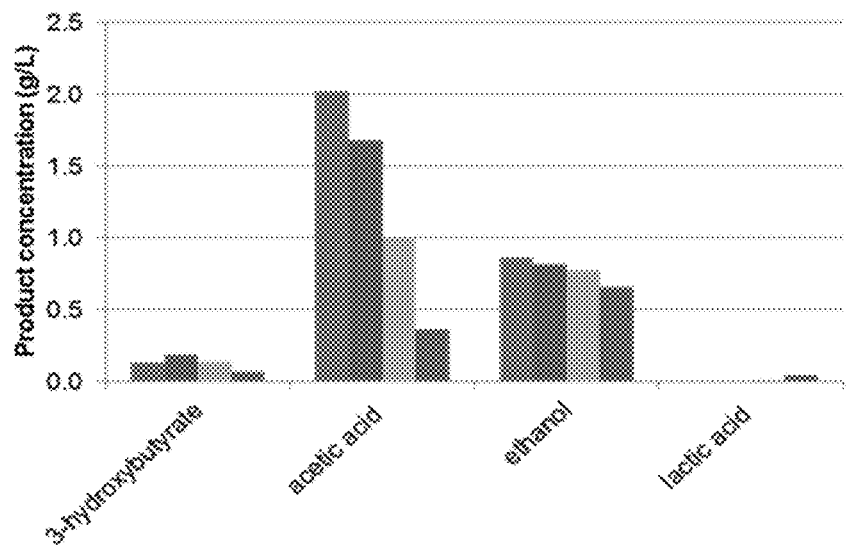
FIGS. 28A and 28B are graphs showing production of 3-hydroxybutyrate via Ptb-Buk in combination with an (S)-specific (Hbd) (FIG. 28A) or (R)-specific 3-hydroxybutyrate (PhaB) (FIG. 28B) dehydrogenase.
Figure 28B:
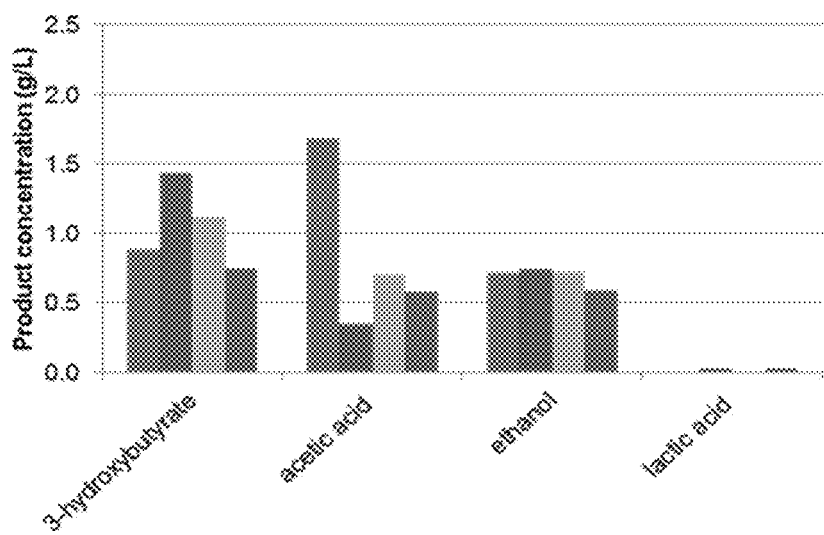
Figure 29A:
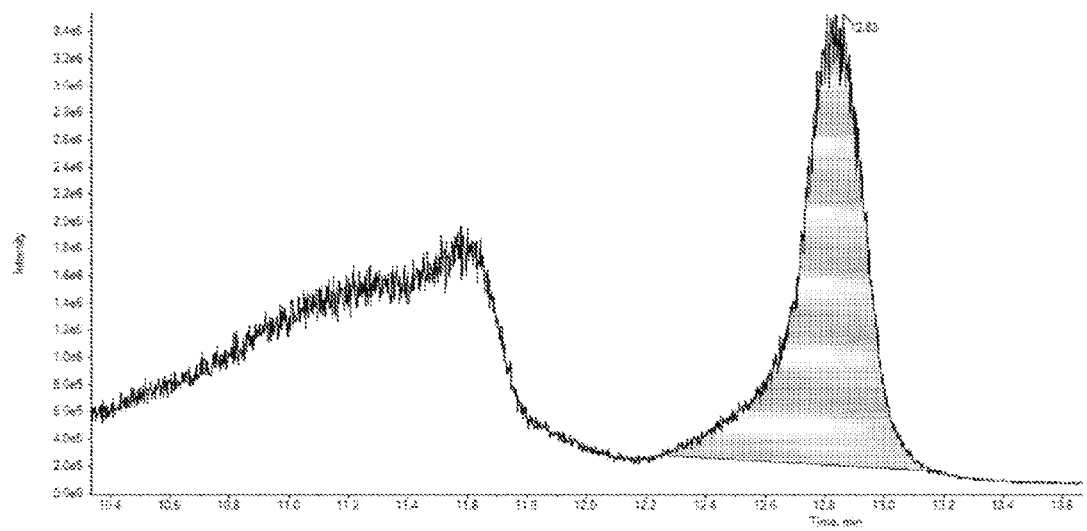
FIGS. 29A-D are graphs showing LC-MS/MS detection of 2-hydroxyisobutyric acid (2-HIB) and 2-hydroxybutyrate (2-HB).
Figure 29B:
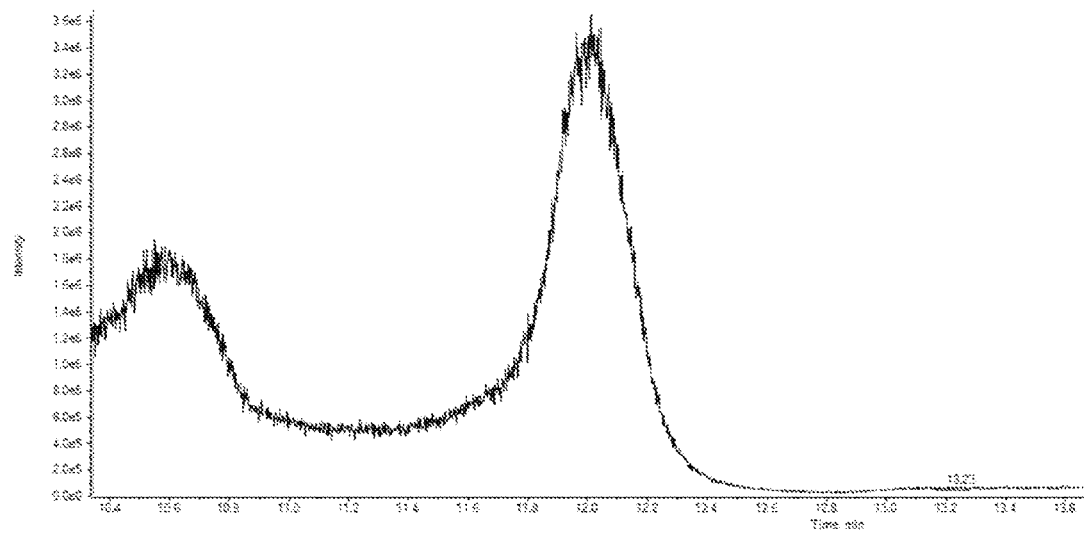
Figure 29C:
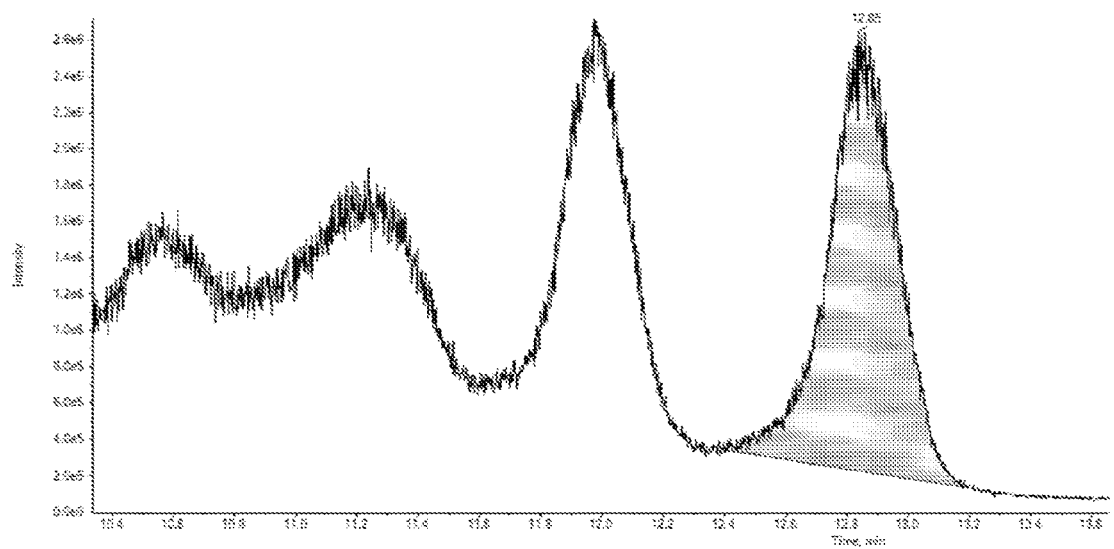
Figure 29D:
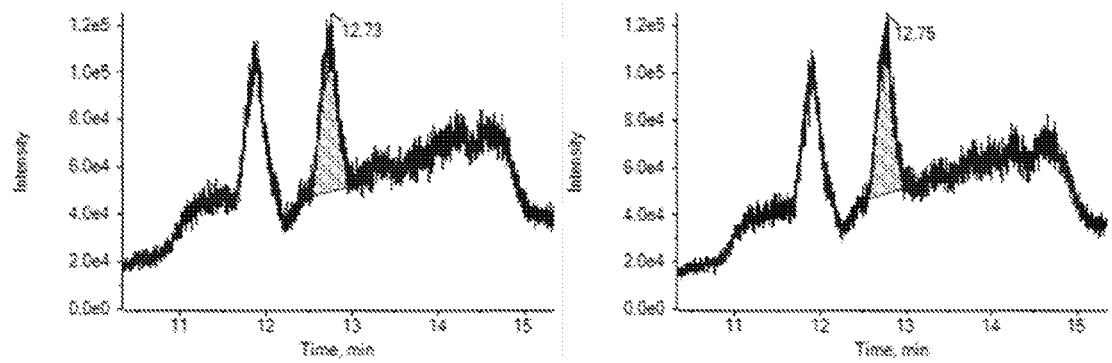

However, Ptb-Buk in contrast to thioesterases is able to distinguish between stereoisomers and will only (or preferentially) act on (R)-3-hydroxybutyryl-CoA but not on (S)-3-hydroxybutyryl-CoA. This was demonstrated by expressing the Ptb-Buk system either with ThlA and (S)-specific Hbd (FIG. 28A) or (R)-specific phaB (FIG. 28B) in the pDuet system in *E. coli*. The constructs were constructed as described in Examples 1 and 3. Growth studies confirmed that appreciable amounts of 3-hydroxybutyrate were only formed when Ptb-Buk was expressed in combination with the (S)-specific Hbd but not the (R)-specific phaB.

Therefore, a route via an (S)-specific 3-hydroxybutyryl-CoA dehydrogenase and the Ptb-Buk provides significant advantages, as the Ptb-Buk system (unlike thioesterases) is not active on (S)-3-hydroxybutyryl-CoA but (S)-3-hydroxybutyryl-CoA is also the preferred isomer of the 2-hydroxyisobutyryl-CoA mutase (Yaneva, *J Biol Chem*, 287: 15502-15511, 2012). The produced 2-hydroxyisobutyryl-CoA can then be used via the Ptb-Buk to produce 2-hydroxyisobutyric acid and (unlike thioesterases) 2-hydroxyisobutyryl-CoA hydrolysis provides additional energy (FIG. 8).

Modular constructs were designed to compare performance of the pathway. A gene cassette containing the Wood-Ljungdahl promoter in front of the genes meaB, hcmA and hcmB was codon optimized and synthesized (SEQ ID NO: 188). HcmA and hcmB encode a 2-hydroxyisobutyryl-CoA mutase and meaB a chaperon from *Aquincola tertiaricarbonis*, in the construct hcmA and meaB genes were fused together as one protein as described (SEQ ID NO: 189) (Yaneva, *J Biol Chem*, 287: 15502-15511, 2012). The gene cassette was cloned into either a plasmid containing thiolase (thlA from *C. acetobutylicum*; SEQ ID NO: 136) and an (S)-specific 3-hydroxybutyrate dehydrogenase (hbd from *C. acetobutylicum*; SEQ ID NO: 190) (pMTL83155-thlA-hbd) or an (R)-specific 3-hydroxybutyrate dehydrogenase (phaB from *R. eutropha*) (pMTL83155-thlA-phaB) using the restriction enzymes KpnI and NcoI to form plasmids pMTL83155-thlA-hbd-Pwl-meaBhcmA-hcmB (SEQ ID NO: 191) and pMTL83155-thlA-phaB-Pwl-meaBhcmA-hcmB (SEQ ID NO: 192), respectively. Sub-cloning of the codon optimized 2-hydroxyisobutyryl-CoA mutase casette in *E. coli* Top-10 was only successful after some initial cloning complications; it was found that the 2-hydroxyisobutyryl-CoA mutase casette could only be cloned into the plasmid at a lower temperature (28° C.).

Vector pMTL83155-thlA-hbd and pMTL83155-thlA-phaB were created by first amplifying a promoter region of the phosphate acetyltransferase of *C. autoethanogenum* (SEQ ID NO: 193) and cloning into vector pMTL83151 (FJ797647.1; Heap, *J Microbiol Meth*, 78: 79-85, 2009) using NotI and NdeI restriction sites before introducing genes thlA and hbd or respectively phaB via NdeI and KpnI in a double ligation reaction.

In addition, compatible plasmid modules for expressing ptb-buk or tesB were built. For this, the respective genes were amplified from genomic DNA and introduced into plasmid pMTL82256 described in Example 9 and then introducing either ptb-buk or phaB using NdeI and NcoI and Seamless Cloning kit (Life technologies) to form plasmids pMTL82256-ptb-buk (SEQ ID NO: 194) and pMTL82256-tesB (SEQ ID NO: 195).

Plasmids pMTL83155-thlA-hbd-Pwl-meaBhcmA-hcmB, pMTL83155-thlA-phaB-Pwl-meaBhcmA-hcmB, pMTL82256-ptb-buk and pMTL82256-tesB were introduced into *E. coli* Top-10 (all steps at 28° C.) and *C. autoethanogenum* by transformation as described in previous examples in the following combinations: pMTL83155-thlA-hbd-Pwl-meaBhcmA-hcmB+pMTL82256-ptb-buk, pMTL83155-thlA-hbd-Pwl-meaBhcmA-hcmB+ pMTL82256-tesB, pMTL83155-thlA-phaB-Pwl-meaBhcmA-hcmB+pMTL82256-ptb-buk and pMTL83155-thlA-phaB-Pwl-meaBhcmA-hcmB+pMTL82256-tesB.

Growth experiments were carried out with E. coli in LB medium at 30° C. for 4 days and C. autoethanogenum in PETC medium with 30 psi CO-containing steel mill gas (collected from New Zealand Steel site in Glenbrook, NZ) at 30° C. and 37° C. for 6 days. Metabolites were measured as described above. In addition to measurement by GC-MS, 2-Hydroxyisobutyric acid production was also confirmed using liquid chromatography tandem mass spectrometry (LC-MS/MS) and $^1$H nuclear magnetic resonance (NMR) spectroscopy.

Liquid chromatography tandem mass spectrometry (LC-MS/MS) data was acquired on a Dionex UltiMate 3000 liquid chromatography system (Dionex, California, USA) coupled to an ABSciex 4000 QTRAP mass spectrometer (ABSciex, Concord, Canada). The liquid chromatography system was controlled by Chromeleon software (Dionex), and chromatographic separation was achieved by injecting 10 μl onto a Gemini-NX C18 150 mm×2 mm I.D., 3 μm 110 Å particle column (Phenomenex, Aschaffenburg, Germany) equipped with a pre-column Security Guard Gemini-NX C18 4 mm×2 mm I.D. cartridge. The column oven temperature was controlled and maintained at 55° C. throughout the acquisition and the mobile phases were as follows: 7.5 mM aqueous tributylamine adjusted to pH 4.95 (±0.05) with glacial acetic acid (eluent A) and acetonitrile (eluent B). The mobile phase flow rate was maintained at 300 μL/min throughout a gradient profile and was introduced directly into the mass spectrometer with no split. The mass spectrometer was controlled by Analyst 1.5.2 software (AB-Sciex) and was equipped with a TurboV electrospray source operated in negative ionisation mode. The following previously optimized (and therefore general) parameters were used to acquire scheduled Multiple Reaction Monitoring (MRM) data: ionspray voltage −4500V, nebulizer (GS1), auxiliary (GS2), curtain (CUR) and collision (CAD) gases were 60, 60, 20 and medium (arbitrary units), respectively, generated via a N300DR nitrogen generator (Peak Scientific, Massachusetts, USA). The auxiliary gas temperature was maintained at 350° C. The entrance potential (EP) was −10 volts. This method is also able to detect and separate 2-hydroxybutyric acid.

$^1$H nuclear magnetic resonance (NMR) spectroscopy at a field strength of 400 MHz. Samples were prepared by diluting 400 μL of sample with 400 μL of 20 mM phosphate buffer prepared with $D_2O$ and containing trimethylsilyl proprionic acid (TMSP) as internal standard (pH of 7). The samples were then transferred glass NMR tube (5 mm×8 inches) and analysed by $^1$H NMR using presaturation for water suppression with a 30° excitation pulse, 15 second relaxation delay and 64 scans at a temperature of 27° C. Once acquired the spectrum was transformed, flattened and integrated using Agilent VnmrJ software. The known concentration of TMSP was used for quantitation of 2-hydroxyisobutyric using the resonance at 1.36 ppm (singlet).

Figure 30:
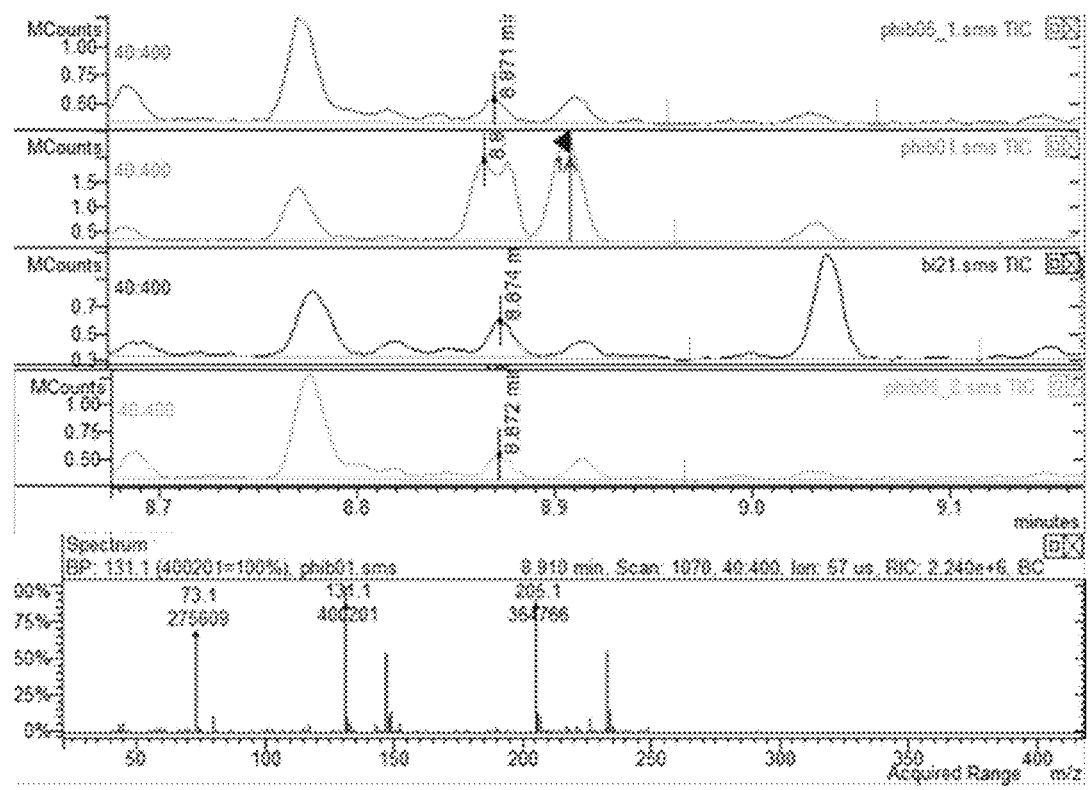
FIG. 30 is a set of graphs showing GC-MS confirmation of 2-hydroxyisobutyric acid (8.91 min) production. First panel: *C. autoethanogenum*+pMTL83155-thlA-hbd-Pwl-meaBhcmA-hcmB+pMTL82256-tesB. Second panel: *C. autoethanogenum*+pMTL83155-thlA-hbd-Pwl-meaBhcmA-hcmB+pMTL82256-ptb-buk (spectrum). Third panel: *E. coli*+pMTL83155-thlA-hbd-Pwl-meaBhcmA-hcmB+pMTL82256-tesB. Fourth panel: *E. coli*+pMTL83155-thlA-hbd-Pwl-meaBhcmA-hcmB+pMTL82256-ptb-buk.

In both E. coli growing heterotrophically as well as C. autoethanogenum growing autotrophically, 2-hydroxyisobutyric acid could be detected in constructs pMTL83155-thlA-hbd-Pwl-meaBhcmA-hcmB+pMTL82256-tesB (1.5 mg/L in LC-MS/MS method and 8 mg/L in GC-MS in C. autoethanogenum; 0.5 mg/L in LC-MS/MS method and 2 mg/L in GC-MS in E. coli) and pMTL83155-thlA-phaB-Pwl-meaBhcmA-hcmB+pMTL82256-ptb-buk (15 mg/L in LC-MS/MS method and 75 mg/L in GC-MS in C. autoethanogenum; 1.1 mg/L in LC-MS/MS method and 8.5 mg/L in GC-MS in E. coli), but not in constructs all other constructs including the control. By far the highest production occurred in strain carrying plasmid pMTL83155-thlA-hbd-Pwl-meaBhcmA-hcmB+pMTL82256-ptb-buk (10× higher than all other routes), that has the optimal pathway with thiolase, (S)-specific (S)-specific 3-hydroxybutyryl-CoA dehydrogenase, the 2-hydroxyisobutyryl-CoA mutase, and the Ptb-Buk system (FIGS. 29A-D). Surprisingly, also production of 2-hydroxybutyrate (2-HB) (up to 64 mg/L by LC-MS/MS and 50 mg/L by GC-MS in C. autoethanogenum; 12 mg/L by LC-MS/MS and 9.5 mg/L by GC-MS in E. coli) was found in this strain, indicating unspecific mutase activity (FIG. 30). This was also found in the tesB strain, but again at significant lower levels (18 mg/L in LC-MS-MS and 9 mg/L in GC-MS in C. autoethanogenum). Production of 2-hydroxyisobutyric acid was also confirmed by NMR.

Figure 31:
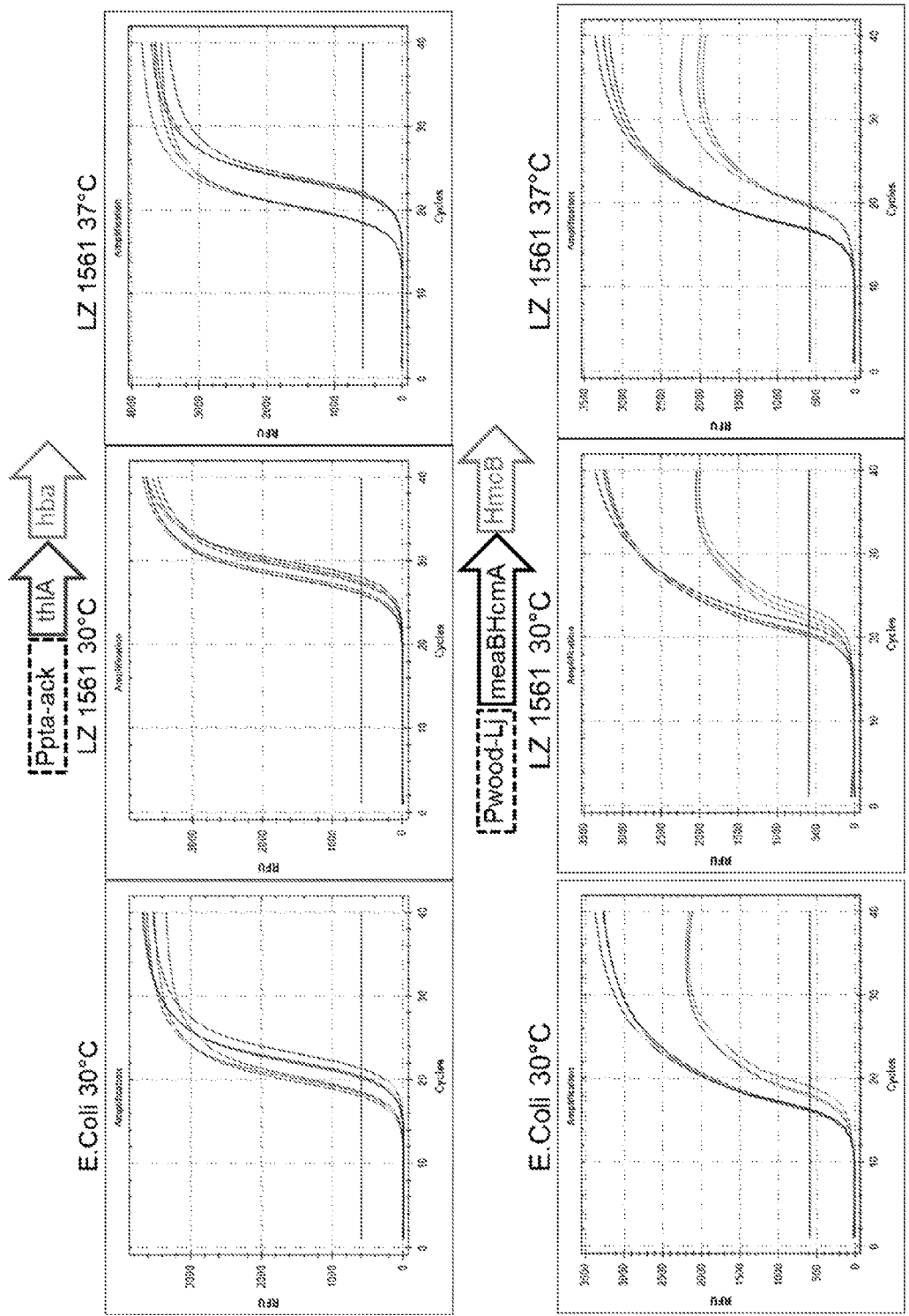
FIG. 31 is a set of graphs of real time PCR showing expression of genes of the 2-HIBA pathway (thlA, hba, meaBhcmA, hcmB from pta-ack promoter and respectively Wood-Ljungdahl operon promoter) in *E. coli*, *C. autoethanogenum* LZ1561 at 30° C., and *C. autoethanogenum* LZ1561 at 37° C.

In addition, also qRT-PCR was carried out to confirm expression of the genes thlA, hbd, meaBhcmA and hcmB (FIG. 31).

The RT-PCR graphs show that thlA gene product is expressed to slightly higher levels with the $P_{pta-ack}$ promoter than hbd (as expected with a second gene in an operon) and that hmcB shows slightly lower expression levels than meaBhcmA. Also there is lower expression in C. autoethanogenum at 30° C. than at 37° C. and E. coli at 30° C. For specific cycle numbers see below.

| Condition | Target | Cq Mean | Cq Std Dev |
|---|---|---|---|
| E. coli/30° C. | thlA | 18.26 | 0.243 |
| | hbd | 20.6 | 0.603 |
| | meaBhcmA | 16.20 | 0.108 |
| | hmcB | 18.30 | 0.666 |
| C. autoethanogenum/30° C. | thlA | 26.10 | 0.169 |
| | Hbd | 27.54 | 0.415 |
| | meaBhcmA | 20.63 | 0.604 |
| | hmcB | 22.64 | 0.697 |
| C. autoethanogenum/37° C. | thlA | 18.48 | 0.069 |
| | hbd | 21.85 | 0.222 |
| | meaBhcmA | 16.72 | 0.119 |
| | hmcB | 19.62 | 0.173 |

The ratio of (S)-3-hydroxybutyric acid to (R)-3-hydroxybutyric acid was measured by high-performance liquid chromatography (HPLC) on an Agilent 1260 Infinity LC with UV detection at 210 nm. Samples were prepared by centrifugation at 14,000 rpm for 3 minutes, followed by evaporation of 200 μL of supernatant to dryness. The pellet was then re-suspended in 100% Isopropanol and sonicated under heat for 1 hour. Centrifugation was repeated and the supernatant transferred to an HPLC vial for analysis. Separation was achieved with a 5 μL injection on to a TCI Chiral MB-S column (250 mm×4.6 mm×3 μm) at 1.5 mL/min and 40° C. under isocratic conditions, using 95-5 hexane-isopropanol mobile phase containing 0.1% trifluoracetic acid.

A stereospecific analysis of produce 3-HB has been performed. Surprisingly it was found that in C. autoethanogenum, a mix of isomers was produced. Enzymes Hbd and PhaB are described to be stereospecific, PhaB is R-specific and Hbd is S-specific and when expressing these enzymes in E. coli a stereopure product has been observed (Tseng, Appl Environ Microbiol, 75: 3137-3145, 2009).

The following table indicates the distribution of (R)- and (S)-form of 3-HB at equilibrium produced via three different routes in C. autoethanogenum. These data suggest the presence of isomerase in the C. autoethanogenum.

| Route | % R-form | % S-form |
|---|---|---|
| ThlA - PhaB | 55 ± 7 | 53 ± 5 |
| ThlA - HBD | 12 ± 3 | 88 ± 3 |
| ThlA - ctfAB | 16 ± 7 | 84 ± 7 |

Knockout of native isomerases may prevent interconversion of (R) and (S) forms of 3-HB. Alternatively, expression or overexpression of isomerases could enable new ptb-buk routes. For example, Hbd could be used to generate (S)-3-HB, isomerase could convert (S)-3-HB to (R)-3-HB, and ptb-buk could act on (R)-3-HB to produce products of interest.

Example 11

This example demonstrates the production of isobutylene via Ptb-Buk conversion of 3-hydroxyisovaleryl-CoA and 3-hydroxyisovalerate.

Different routes for production of isobutylene have been described, for example the conversion of acetone to isobutylene via a hydroxyisovalerate synthase and decarboxylase (van Leeuwen, Appl Microbiol Biotechnol, 93: 1377-1387, 2012). However, the hydroxyisovalerate decarboxylase step is an ATP requiring step and kinetics of this enzyme may not be ideal. Two alternative routes to isobutylene using the Ptb-Buk system have been identified through 3-hydroxyisovaleryl-CoA which has been shown in vitro to be a viable substrate for the Ptb-Buk system (Liu, Appl Microbiol Biotechnol, 53: 545-552, 2000).

Figure 9:
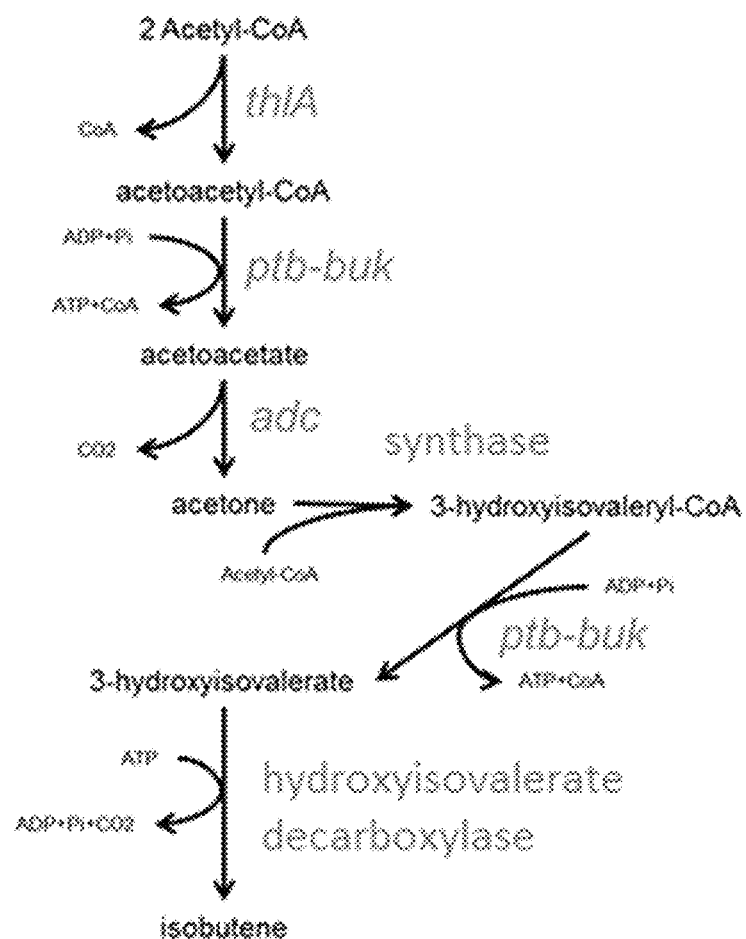
FIG. 9 is a diagram showing the production of isobutene via Ptb-Buk conversion of 3-hydroxyisovaleryl-CoA and 3-hydroxyisovalerate using alternative pathway 1.

Alternative pathway 1 consists of a synthase that converts acetone into 3-hydroxyisovaleryl-CoA (FIG. 9).

Figure 10:
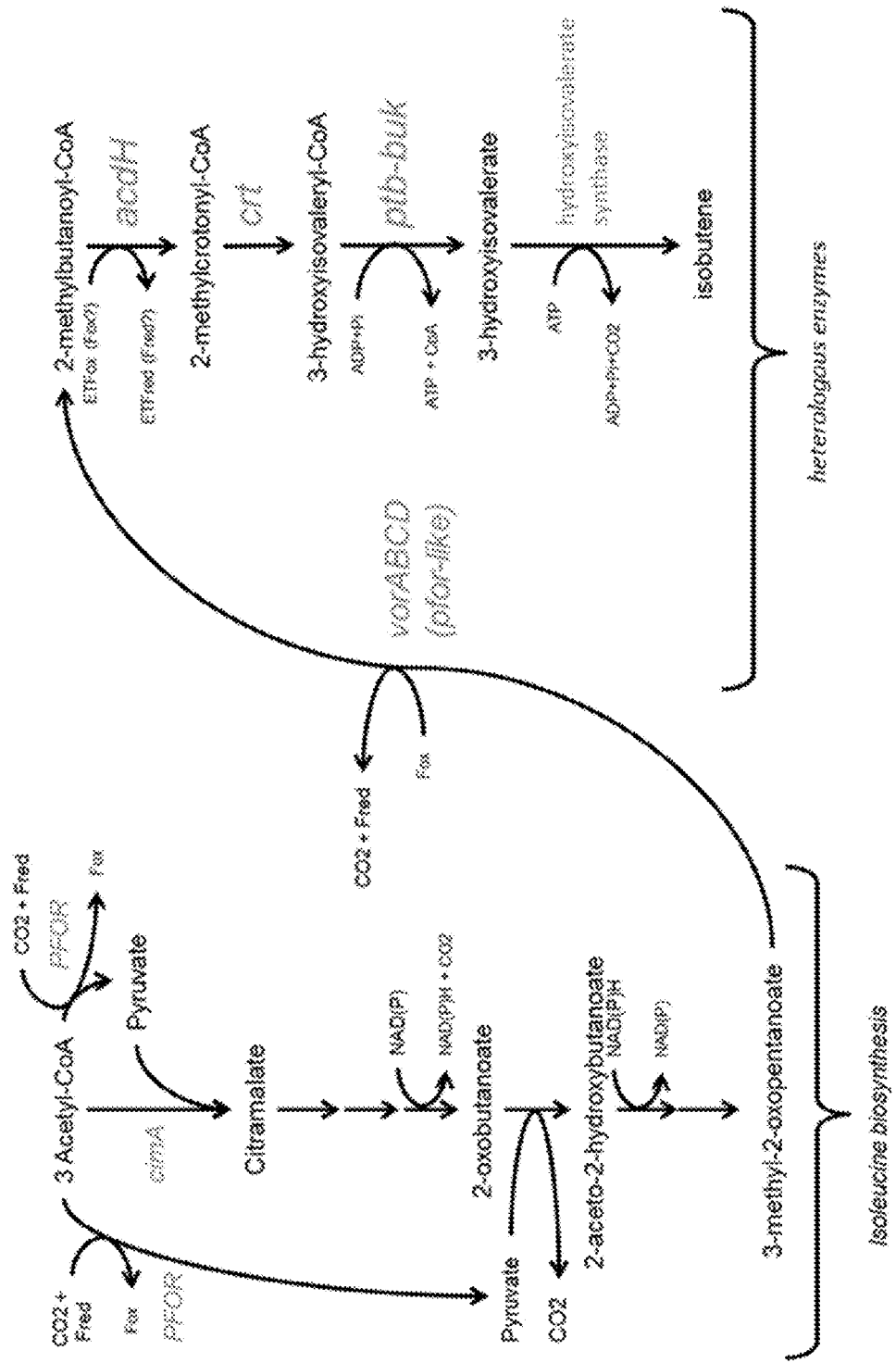
FIG. 10 is a diagram showing the production of isobutene via Ptb-Buk conversion of 3-hydroxyisovaleryl-CoA and 3-hydroxyisovalerate using alternative pathway 2.

Alternative pathway 2 proceeds via known intermediate 3-methyl-2-oxopentanoate of the isoleucine biosynthesis that is common to bacteria such as E. coli or C. autoethanogenum (FIG. 10).

Example 12

This example describes methods for characterizing Ptb-Buk variants.

Given the substrate promiscuity of Ptb-Buk, it is likely that Ptb-Buk systems of varying amino acid sequences will possess varying preferences for given substrates. In order to identify a Ptb-Buk system that favors a desired substrate (e.g. acetoacetyl-CoA, 3-hydroxybutyryl-CoA, 2-hydroxyisobutyryl-CoA, acetyl-CoA, and/or butyryl-CoA), a high-throughput screen is desirable. Such a screen can be accomplished by coupling firefly luciferase (Luc) to the Ptb-Buk system (FIG. 33). Luc reacts with D-luciferin, generating oxyluciferin, carbon dioxide, and light. In addition to magnesium and molecular oxygen, Luc requires ATP for the reaction to proceed. ATP is a product generated by Ptb-Buk when provided an appropriate acyl-CoA or enoyl-CoA substrate. Therefore, Ptb-Buk reaction rates and preferences can be compared for varying substrates by quantifying the amount of light generated by a reaction containing Ptb-Buk, Luc, d-luciferin, magnesium, molecular oxygen, phosphate, ADP, and an acyl-CoA or enoyl-CoA.

Example 13

This example uses genome-scale modeling to demonstrate that high non-native product selectivities can be achieved using Ptb-Buk. Furthermore, it shows that the use of Ptb-Buk could permit the coupling of cellular growth with product production, allowing the construction of stable and high-yielding fermentation strains.

A genome-scale metabolic model of C. autoethanogenum similar to the one described by Marcellin, Green Chem, 18: 3020-3028, 2006 was utilized. Variants of this model were created that incorporate additional metabolic reactions, each one representing a different genetically modified microorganism for non-native product formation. Three model versions were created for each non-native product pathway, incorporating either a thioesterase, acetate CoA-transferase or Ptb-Buk reaction.

Maximum selectivities were calculated using flux balance analysis (FBA), using scripts from the COBRA Toolbox v2.0 in MATLAB R2014a (The Mathworks, Inc.) with Gurobi version 6.0.4 as the solver (Gurobi Optimization, Inc.). Exchange reactions were constrained to represent a chemically defined minimal growth medium with CO as the source of carbon and energy. An evolutionary algorithm was used to search for the existence of strain designs incorporating up to ten gene knockouts that couple target non-native chemical production with growth.

FBA predicts that pathways using Ptb-Buk or CoA transferase offer the highest product selectivities due to ATP gain through substrate level phosphorylation. The results are illustrated in Table 2. However, it should be noted that one limitation of Genome-scale models and FBA analysis is that enzyme kinetics are not captured. The CoA transferase reaction requires a certain base level of acetate for functionality, therefore in reality the maximum selectivity using a CoA transferase would be less than 100% due to a base level of acetate required to be present.

| Non-native product | Maximum selectivity % (C in target product/C in all fermentation products) | | |
|---|---|---|---|
| | Thioesterase | CoA-transferase | Ptb-Buk |
| Acetone | 82.0 | 100 | 100 |
| Isopropanol | 82.1 | 100 | 100 |
| Isobutylene | 55.9 | 80.2 | 80.2 |
| 3-Hydroxybutyrate | 86.0 | 100 | 100 |
| 1,3-Butanediol | 88.6 | 100 | 100 |
| 2-Hydroxyisobutyrate | 86.0 | 100 | 100 |

Table 2. Flux balance analysis (FBA) showing the maximum possible non-native product selectivities in C. autoethanogenum for a set of products and candidate enzymes.

It is desirable to construct strains where the target non-native chemical must be produced for cell growth. FBA predicts that in most cases it would be difficult to couple target chemical production with growth when using a thioesterase or a CoA transferase; instead, native products acetate and ethanol would be favored. However, when using Ptb-Buk, many growth-coupled chemical production strain designs exist, often incorporating a disruption of the phosphotransacetylase-acetate kinase reactions. Table 3 summarizes the growth coupling ability of each strain.

| Non-native product | Ability to couple non-native chemical production with growth | | |
|---|---|---|---|
| | Thioesterase | CoA-transferase | Ptb-Buk |
| Acetone | No | No | Yes |
| Isopropanol | No | No | Yes |
| Isobutylene | No | No | No |

-continued

| Non-native product | Ability to couple non-native chemical production with growth | | |
|---|---|---|---|
| | Thioesterase | CoA-transferase | Ptb-Buk |
| 3-Hydroxybutyrate | No | No | Yes |
| 1,3-Butanediol | No | Yes | Yes |
| 2-Hydroxyisobutyrate | No | No | Yes |

Table 3. Potential to couple non-native chemical production with growth in C. autoethanogenum during growth on CO when reconfiguring the metabolic network with up to ten gene knockouts.

While both Ptb-Buk and CoA transferase can support high selectivities, flux balance analysis predicts that in most cases, only Ptb-Buk would allow the construction of stable, high-yielding fermentation strains that couple non-native chemical production with growth.

Example 14

This example demonstrates the production of adipic acid via Ptb-Buk from gaseous feedstock.

Production of adipic acid in E. coli from sugar has been described by a pathway utilizing Ptb-Buk (Yu, Biotechnol Bioeng, 111: 2580-2586, 2014). However production was low, in the μg/L range. Without wishing to be bound by any particular theory, the inventors believe that this is likely a function of lacking driving force in forms of reducing power and surplus ATP. Using a reduced gaseous substrate as CO and $H_2$ and an acetogenic bacterium such as C. autoethanogenum, this current limitation can be overcome. CO and $H_2$ oxidation provide sufficient driving force for reduction of 3-oxo-adipyl-CoA to 3-hydroxyadipyl-CoA by 3-hydroxybutyryl-CoA dehydrogenase or acetoacetyl-CoA hydratase and 2,3-dehydroadipyl-CoA to adipyl-CoA by enoyl-CoA hydrolase or enoyl-CoA reductase (FIG. 34, steps 23 and 25), in contrast to E. coli growing heterotrophically on more oxidized sugars. Acetogenic bacteria live on the energetic limit of life and therefore ATP generating reactions like the Ptb-Buk system have a strong driving force, ensuring efficient conversion of adipyl-CoA to adipic acid (FIG. 34, step 26), in contrast to E. coli growing heterotrophically on sugars generating surplus ATP from glycolysis.

To produce adipic acid from gas in C. autoethanogenum, genes encoding a succinyl-CoA synthetase from E. coli (NP_415256, NP_415257), a ketoisovalerate oxidoreductase PaaJ from E. coli (WP_001206190.1), a 3-hydroxybutyryl-CoA dehydrogenase Hbd from Clostridium beijerinckii (WP_011967675.1), a trans-2-enoyl-CoA reductase Crt from C. acetobutylicum (NP_349318.1), trans-2-enoyl-CoA reductase Bcd from C. acetobutylicum (NP_349317.1) and electron flavoproteins EtfAB (NP_349315, NP_349316) are cloned on an expression plasmid and then transformed as described above in C. autoethanogenum strains pta-ack::ptb-buk or CAETHG_1524::ptb-buk from previous examples. Adipic acid is produce according to the steps depicted in FIG. 34.

Example 15

This example demonstrates the production of various products including 2-buten-1-ol, 3-methyl-2-butanol, 1,3-hexanediol (HDO) via Ptb-Buk and AOR.

As demonstrated in Example 6, Ptb-Buk is highly promiscuous and acts on a wide range of CoAs as substrates or can be engineered to use a range of non-natural CoAs as substrates. Likewise AOR enzyme has been shown to act on a wide range of substrates. Together these two enzymes can convert a wide range of CoAs via their acids into aldehydes, which then can be further converted to alcohols, ketones or enols via alcohol dehdydrogeneses, for which a wide variety exists in nature. While under standard conditions the reduction of acids with ferredoxin to aldehydes via the AOR is endergonic (Thauer, Bacteriol Rev, 41: 100-180, 1977) and as such not feasible, it surprisingly is in carboxydotrophic acetogens such as C. autoethanogenum that operate at low pH and with CO or $H_2$ as substrate (Mock, J Bacteriol, 197: 2965-2980, 2015). One common limitation working with acetogens is that they are ATP-limited, living on the thermodynamic edge of life (Schuchmann, Nat Rev Microbiol, 12: 809-821, 2014), which can be overcome by coupling this acid reduction to ATP-linked formation of acids from CoAs via the Ptb-Buk system.

The Ptb-Buk system and AOR system has been demonstrated in above examples for several different products, but can be extended to further products, for example production of 2-buten-1-ol, 3-methyl-2-butanol, 1,3-hexanediol (HDO). 2-Buten-1-ol can be produced via Ptb-Buk, AOR and an alcohol dehydrogenase from crotonyl-CoA (FIG. 35). 1,3-Hexanediol can be produced via Ptb-Buk, AOR and an alcohol dehydrogenase from 3-hydroxy-hexanoyl-CoA (FIG. 35). By combining Ptb-Buk, Adc and an alcohol dehydrogenase (such as native primary: secondary alcohol dehydrogenase), 3-methyl-2-butanol can be formed from acetobutyryl-CoA.

All of these precursors, crotonyl-CoA, 3-hydroxy-hexanoyl-CoA, or acetobutyryl-CoA can be formed by reduction and elongation of acetyl-CoA, acetoacetyl-CoA and 3-HB-CoA which are described in previous examples via known fermentation pathways of, for example, Clostridium kluyveri (Barker, PNAS USA, 31: 373-381, 1945; Seedorf, PNAS USA, 105: 2128-2133, 2008) and other Clostridia. Involved enzymes include crotonyl-CoA hydratase (crotonase) or crotonyl-CoA reductase, butyryl-CoA dehydrogenase or trans-2-enoyl-CoA reductase, thiolase or acyl-CoA acetyltransferase and 3-hydroxybutyryl-CoA dehydrogenase or acetoacetyl-CoA hydratase (FIG. 35). Respective genes from C. kluyveri or other Clostridia have be cloned on an expression plasmid (U.S. 2011/0236941) and and then transformed as described above in C. autoethanogenum strains pta-ack::ptb-buk or CAETHG_1524::ptb-buk from previous examples for production of 2-buten-1-ol, 3-methyl-2-butanol, 1,3-hexanediol (HDO). 2-Buten-1-ol, 3-methyl-2-butanol, and 1,3-hexanediol (HDO) may be precursors for further downstream products.

Figure 39:
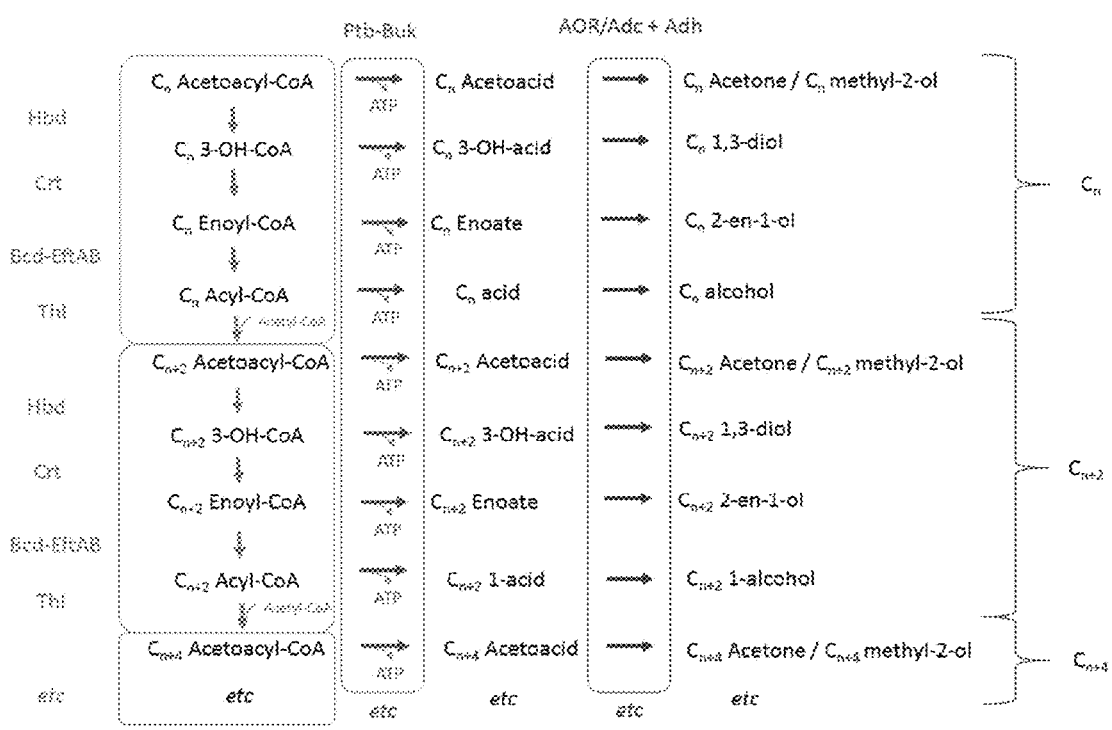
FIG. 39 is a diagram of a pathway scheme for producing a range of $C_4$, $C_6$, $C_8$, $C_{10}$, $C_{12}$, $C_{14}$ alcohols, ketones, enols or diols via combining known chain elongation pathway (Hbd, Crt, Bcd-EtfAB, Thl) with Ptb-Buk+AOR/Adc-Adh.

While these are only a few examples, it should be clear that this pathway can be further extended using the same enzymes or engineered variants thereof that have specificity for higher chain length to produce a range of C4, C6, C8, C10, C12, C14 alcohols, ketones, enols or diols (FIG. 39). Different type of molecules can be obtained also by using primer or extender units different than acetyl-CoA in the thiolase step as been described elsewhere (Cheong, Nature Biotechnol, 34: 556-561, 2016).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A genetically engineered C1-fixing bacterium comprising:
   (a) an enzyme that converts acetyl-CoA to acetoacetyl-CoA,
   (b) an enzyme that converts acetoacetyl-CoA to 3-hydroxybutyryl-CoA, and
   (c) an enzyme that converts 3-hydroxybutyryl-CoA to 3-hydroxybutyrate,
wherein at least one of the enzymes is exogenous to the bacterium.

2. The bacterium of claim 1, wherein the enzyme that converts acetyl-CoA to acetoacetyl-CoA is thiolase (EC 2.3.1.9).

3. The bacterium of claim 1, wherein the enzyme that converts acetoacetyl-CoA to 3-hydroxybutyryl-CoA is 3-hydroxybutyryl-CoA dehydrogenase (EC 1.1.1.157) or acetoacetyl-CoA reductase (EC 4.2.1.36).

4. The bacterium of claim 1, wherein the enzyme that converts 3-hydroxybutyryl-CoA to 3-hydroxybutyrate is thioesterase (EC 3.1.2.20), phosphate butyryltransferase (EC 2.3.1.19) and butyrate kinase (EC 2.7.2.7), or CoA-transferase (EC 2.8.3.9).

5. The bacterium of claim 1, wherein the enzyme that converts 3-hydroxybutyryl-CoA to 3-hydroxybutyrate is stereospecific.

6. The bacterium of claim 1, wherein the 3-hydroxybutyrate is (R)-3-hydroxybutyrate, (S)-3-hydroxybutyrate, or a combination thereof.

7. The bacterium of claim 1, wherein the bacterium further comprises an isomerase that interconverts (R)-3-hydroxybutyrate and (S)-3-hydroxybutyrate.

8. The bacterium of claim 1, wherein the bacterium further comprises an enzyme that converts 3-hydroxybutyrate to 3-hydroxybutyryaldehyde.

9. The bacterium of claim 8, wherein the enzyme that converts 3-hydroxybutyrate to 3-hydroxybutyryaldehyde is aldehyde:ferredoxin oxidoreductase (EC 1.2.7.5).

10. The bacterium of claim 8, wherein the bacterium further comprises an enzyme that converts 3-hydroxybutyryaldehyde to 1,3-butanediol.

11. The bacterium of claim 10, wherein the enzyme that converts 3-hydroxybutyryaldehyde to 1,3-butanediol is alcohol dehydrogenase (EC 1.1.1.1. or 1.1.1.2.).

12. The bacterium of claim 1, wherein the bacterium is derived from a parental bacterium selected from the group consisting of *Acetobacterium woodii, Alkalibaculum bacchii, Blautia product, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kiuvi*.

13. The bacterium of claim 1, wherein the bacterium further comprises exogenous or endogenous aldehyde:ferredoxin oxidoreductase (AOR).

14. The bacterium of claim 1, wherein the bacterium further comprises a disruptive mutation in a phosphotransacetylase (Pta) and an acetate kinase (Ack).

15. The bacterium of claim 1, wherein the bacterium further comprises a disruptive mutation in a thioesterase.

16. A method of producing 3-hydroxybutyrate comprising culturing the bacterium of claim 1 in the presence of a substrate, whereby the bacterium produces 3-hydroxybutyrate.

17. The method of claim 16, wherein the substrate is a gaseous substrate comprising one or more of CO, $CO_2$, and $H_2$.

18. The method of claim 16, wherein the substrate comprises syngas or industrial waste gas.

19. A method of producing 3-hydroxybutyryaldehyde comprising culturing the bacterium of claim 8 in the presence of a substrate, whereby the bacterium produces 3-hydroxybutyryaldehyde.

20. A method of producing 1,3-butanediol comprising culturing the bacterium of claim 10 in the presence of a substrate, whereby the bacterium produces 1,3-butanediol.

* * * * *

SEQUENCE LISTING

```
<160> NUMBER OF SEQ ID NOS: 195

<210> SEQ ID NO 1
<211> LENGTH: 392
<212> TYPE: PRT
<213> ORGANISM: Clostridium acetobutylicum
<220> FEATURE:
<221> NAME/KEY: MISC_FEATURE
<223> OTHER INFORMATION: ThlA, WP_010966157.1

<400> SEQUENCE: 1

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
            35                  40                  45

Asn Glu Val Ile Leu Gly Asn Val Leu Gln Ala Gly Leu Gly Gln Asn
        50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
```

```
              210                 215                 220
Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
                275                 280                 285

Gly Tyr Gly Pro Phe Tyr Ala Thr Lys Ala Ala Ile Glu Lys Ala Gly
            290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
            370                 375                 380

Thr Ala Ile Leu Leu Glu Lys Cys
385                 390

<210> SEQ ID NO 2
<211> LENGTH: 393
<212> TYPE: PRT
<213> ORGANISM: Cupriavidus necator
<220> FEATURE:
<221> NAME/KEY: MISC_FEATURE
<223> OTHER INFORMATION: PhaA, WP_013956452.1

<400> SEQUENCE: 2

Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175
```

```
Glu Leu Ala Val Gly Ser Gln Asn Lys Ala Glu Ala Ala Gln Lys Ala
                180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
        210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
        290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
370                 375                 380

Gly Val Ala Leu Ala Val Glu Arg Lys
385                 390

<210> SEQ ID NO 3
<211> LENGTH: 394
<212> TYPE: PRT
<213> ORGANISM: Cupriavidus necator
<220> FEATURE:
<221> NAME/KEY: MISC_FEATURE
<223> OTHER INFORMATION: BktB, WP_011615089.1

<400> SEQUENCE: 3

Met Thr Arg Glu Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140
```

```
Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390

<210> SEQ ID NO 4
<211> LENGTH: 394
<212> TYPE: PRT
<213> ORGANISM: Escherichia coli
<220> FEATURE:
<221> NAME/KEY: MISC_FEATURE
<223> OTHER INFORMATION: AtoB, NP_416728.1

<400> SEQUENCE: 4

Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
                20                  25                  30

Val Ile Lys Ala Ala Ile Glu Arg Ala Lys Ile Asp Ser Gln His Val
            35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
```

```
            100                 105                 110
Gly Gly Met Glu Asn Met Ser Leu Ala Pro Tyr Leu Leu Asp Ala Lys
                115                 120                 125

Ala Arg Ser Gly Tyr Arg Leu Gly Asp Gly Gln Val Tyr Asp Val Ile
            130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Val Thr Arg
            195                 200                 205

Lys Lys Thr Phe Val Phe Ser Gln Asp Glu Phe Pro Lys Ala Asn Ser
            210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
            275                 280                 285

Met Gly Met Gly Pro Val Pro Ala Thr Gln Lys Ala Leu Gln Leu Ala
            290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
            355                 360                 365

Arg Asp Lys Thr Leu Gly Leu Ala Thr Leu Cys Ile Gly Gly Gly Gln
            370                 375                 380

Gly Ile Ala Met Val Ile Glu Arg Leu Asn
385                 390

<210> SEQ ID NO 5
<211> LENGTH: 217
<212> TYPE: PRT
<213> ORGANISM: Clostridium beijerinckii
<220> FEATURE:
<221> NAME/KEY: MISC_FEATURE
<223> OTHER INFORMATION: CtfA, WP_012059996.1

<400> SEQUENCE: 5

Met Asn Lys Leu Val Lys Leu Thr Asp Leu Lys Arg Ile Phe Lys Asp
1               5                   10                  15

Gly Met Thr Ile Met Val Gly Gly Phe Leu Asp Cys Gly Thr Pro Glu
            20                  25                  30

Asn Ile Ile Asp Met Leu Val Asp Leu Asn Ile Lys Asn Leu Thr Ile
        35                  40                  45

Ile Ser Asn Asp Thr Ala Phe Pro Asn Lys Gly Ile Gly Lys Leu Ile
50                  55                  60
```

```
Val Asn Gly Gln Val Ser Lys Val Ile Ala Ser His Ile Gly Thr Asn
 65                  70                  75                  80

Pro Glu Thr Gly Lys Lys Met Ser Ser Gly Glu Leu Lys Val Glu Leu
                 85                  90                  95

Ser Pro Gln Gly Thr Leu Ile Glu Arg Ile Arg Ala Ala Gly Ser Gly
            100                 105                 110

Leu Gly Gly Val Leu Thr Pro Thr Gly Leu Gly Thr Ile Val Glu Glu
        115                 120                 125

Gly Lys Lys Lys Val Thr Ile Asp Gly Lys Glu Tyr Leu Leu Glu Leu
    130                 135                 140

Pro Leu Ser Ala Asp Val Ser Leu Ile Lys Gly Ser Ile Val Asp Glu
145                 150                 155                 160

Phe Gly Asn Thr Phe Tyr Arg Ala Ala Thr Lys Asn Phe Asn Pro Tyr
                165                 170                 175

Met Ala Met Ala Ala Lys Thr Val Ile Val Glu Ala Glu Asn Leu Val
            180                 185                 190

Lys Cys Glu Asp Leu Lys Arg Asp Ala Ile Met Thr Pro Gly Val Leu
        195                 200                 205

Val Asp Tyr Ile Val Lys Glu Ala Ala
    210                 215

<210> SEQ ID NO 6
<211> LENGTH: 221
<212> TYPE: PRT
<213> ORGANISM: Clostridium beijerinckii
<220> FEATURE:
<221> NAME/KEY: MISC_FEATURE
<223> OTHER INFORMATION: CtfB, WP_012059997.1

<400> SEQUENCE: 6

Met Ile Val Asp Lys Val Leu Ala Lys Glu Ile Ile Ala Lys Arg Val
  1               5                  10                  15

Ala Lys Glu Leu Lys Lys Asp Gln Leu Val Asn Leu Gly Ile Gly Leu
                 20                  25                  30

Pro Thr Leu Val Ala Asn Tyr Val Pro Lys Glu Met Asn Ile Thr Phe
             35                  40                  45

Glu Ser Glu Asn Gly Met Val Gly Met Ala Gln Met Ala Ser Ser Gly
 50                  55                  60

Glu Asn Asp Pro Asp Ile Ile Asn Ala Gly Gly Glu Tyr Val Thr Leu
 65                  70                  75                  80

Leu Pro Gln Gly Ser Phe Phe Asp Ser Ser Met Ser Phe Ala Leu Ile
                 85                  90                  95

Arg Gly Gly His Val Asp Val Ala Val Leu Gly Ala Leu Glu Val Asp
            100                 105                 110

Glu Lys Gly Asn Leu Ala Asn Trp Ile Val Pro Asn Lys Ile Val Pro
        115                 120                 125

Gly Met Gly Gly Ala Met Asp Leu Ala Ile Gly Ala Lys Lys Ile Ile
    130                 135                 140

Val Ala Met Gln His Thr Gly Lys Ser Lys Pro Lys Ile Val Lys Lys
145                 150                 155                 160

Cys Thr Leu Pro Leu Thr Ala Lys Ala Gln Val Asp Leu Ile Val Thr
                165                 170                 175

Glu Leu Cys Val Ile Asp Val Thr Asn Asp Gly Leu Leu Leu Lys Glu
            180                 185                 190

Ile His Lys Asp Thr Thr Ile Asp Glu Ile Lys Phe Leu Thr Asp Ala
        195                 200                 205
```

Asp Leu Ile Ile Pro Asp Asn Leu Lys Ile Met Asp Ile
    210             215             220

<210> SEQ ID NO 7
<211> LENGTH: 286
<212> TYPE: PRT
<213> ORGANISM: Escherichia coli
<220> FEATURE:
<221> NAME/KEY: MISC_FEATURE
<223> OTHER INFORMATION: TesB, NP_414986.1

<400> SEQUENCE: 7

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 8
<211> LENGTH: 436
<212> TYPE: PRT
<213> ORGANISM: Clostridium autoethanogenum
<220> FEATURE:
<221> NAME/KEY: MISC_FEATURE
<223> OTHER INFORMATION: putative thioesterase 1, AGY74947.1

<400> SEQUENCE: 8

```
Met Asn Asn Asp Asn Cys Thr Ile Lys Ile Thr Pro Glu Val Ser Arg
1               5                   10                  15

Val Asp Glu Pro Val Asp Ile Lys Ile Asn Gly Leu Pro Lys Asn Glu
            20                  25                  30

Lys Val Ile Ile Arg Ala Val Ser Ser Asp Tyr Tyr Cys Ile Asn Ala
        35                  40                  45

Ser Ile Leu Glu Ile Gly Asp Asn Thr Leu Trp Glu Ser Tyr Ala Val
    50                  55                  60

Phe Glu Thr Asp Glu Cys Gly Asn Ile Asn Phe Glu Asn Ala Val Pro
65                  70                  75                  80

Val Asp Gly Thr Tyr Ser Asn Cys Asp Lys Met Gly Leu Phe Tyr Ser
                85                  90                  95

Met Arg Pro Lys Gln Ile Arg Lys Ser Lys Leu Ile Gln Lys Leu Ser
            100                 105                 110

Ser Ile Asn Glu Asn Arg Lys Tyr Lys Ile Thr Phe Thr Val Glu Lys
        115                 120                 125

Asn Gly Lys Ile Ile Gly Ser Lys Glu His Thr Arg Val Tyr Cys Asp
    130                 135                 140

Asp Thr Ile Lys Ser Ile Asp Val Val Glu Lys Asn Leu Leu Ala Arg
145                 150                 155                 160

Tyr Phe Thr Ser Lys Asp Asn Ile Lys His Pro Ala Ile Val Leu
                165                 170                 175

Ser Gly Ser Asp Gly Arg Ile Glu Lys Ala Gln Ala Ile Ala Glu Leu
            180                 185                 190

Phe Ala Met Arg Gly Tyr Ser Ala Leu Ala Val Cys Tyr Phe Gly Leu
            195                 200                 205

Glu Gly Thr Pro Glu Asp Leu Asn Met Ile Pro Leu Glu Tyr Val Glu
    210                 215                 220

Asn Ala Val Lys Trp Leu Lys Arg Gln Asp Thr Val Asp Glu Asn Lys
225                 230                 235                 240

Ile Ala Ile Tyr Gly Arg Ser Lys Gly Gly Glu Leu Val Leu Leu Ala
                245                 250                 255

Ala Ser Met Phe Lys Asp Ile Ala Cys Val Ile Ala Asn Thr Pro Ser
            260                 265                 270

Cys Tyr Val Tyr Glu Gly Ile Lys Ser Asn Lys Leu Pro Ser His His
        275                 280                 285

Ser Ser Trp Met Tyr Arg Gly Arg Glu Ile Pro Tyr Leu Lys Phe Asn
    290                 295                 300

Phe His Ile Ile Leu Arg Leu Ile Ile Lys Met Lys Lys Glu Lys
305                 310                 315                 320

Gly Ala Leu Ala Trp Met Tyr Lys Lys Leu Ile Glu Glu Gly Asp Arg
            325                 330                 335

Asp Lys Ala Thr Ile Ala Leu Asp Lys Ile Asn Gly Ser Val Leu Met
            340                 345                 350

Ile Ser Ser Ala Ala Asp Glu Ile Trp Pro Ser Lys Met His Ser Glu
        355                 360                 365

Thr Val Cys Ser Ile Phe Glu Lys Ser His Lys His Glu Tyr Lys
    370                 375                 380

His Ile Thr Phe Ala Lys Ser Gly His Ile Leu Thr Val Pro Phe Gln
385                 390                 395                 400

Ser Ile Tyr Pro Ser Glu Lys Tyr Pro Tyr Asp Val Glu Ser Trp Ala
                405                 410                 415
```

```
Lys Ala Asn Met Asp Ser Trp Asn Glu Thr Ile Lys Phe Leu Glu Lys
            420                 425                 430

Trp Ala Ser Lys
        435

<210> SEQ ID NO 9
<211> LENGTH: 137
<212> TYPE: PRT
<213> ORGANISM: Clostridium autoethanogenum
<220> FEATURE:
<221> NAME/KEY: MISC_FEATURE
<223> OTHER INFORMATION: putative thioesterase 2, AGY75747.1

<400> SEQUENCE: 9

Met Tyr Ile Asn Glu Thr Lys Val Val Arg Tyr Ala Glu Thr Asp
1               5                   10                  15

Lys Met Gly Ile Val His His Ser Asn Tyr Tyr Ile Tyr Phe Glu Glu
            20                  25                  30

Ala Arg Thr Gln Phe Ile Lys Lys Thr Gly Ile Ser Tyr Ser Gln Met
        35                  40                  45

Glu Lys Asp Gly Ile Met Phe Pro Leu Val Glu Ser Asn Cys Arg Tyr
50                  55                  60

Leu Gln Gly Ala Lys Tyr Glu Asp Glu Leu Leu Ile Lys Thr Trp Ile
65                  70                  75                  80

Lys Glu Leu Thr Pro Val Lys Ala Glu Phe Asn Tyr Ser Val Ile Arg
                85                  90                  95

Glu Asn Asp Gln Lys Glu Ile Ala Lys Gly Ser Thr Leu His Ala Phe
            100                 105                 110

Val Asn Asn Asn Phe Lys Ile Ile Asn Leu Lys Lys Asn His Thr Glu
        115                 120                 125

Leu Phe Lys Lys Leu Gln Ser Leu Ile
        130                 135

<210> SEQ ID NO 10
<211> LENGTH: 128
<212> TYPE: PRT
<213> ORGANISM: Clostridium autoethanogenum
<220> FEATURE:
<221> NAME/KEY: MISC_FEATURE
<223> OTHER INFORMATION: putative thioesterase 3, AGY75999.1

<400> SEQUENCE: 10

Met Asp Phe Ser Lys Leu Phe Lys Val Gly Ser Thr Tyr Val Ser Glu
1               5                   10                  15

Tyr Ile Val Lys Pro Glu Asp Thr Ala Asn Phe Ile Gly Asn Asn Gly
            20                  25                  30

Val Val Met Leu Ser Thr Pro Ala Met Ile Lys Tyr Met Glu Tyr Thr
        35                  40                  45

Thr Leu His Ile Val Asp Asn Val Ile Pro Lys Asn Tyr Arg Pro Val
50                  55                  60

Gly Thr Lys Ile Asp Val Glu His Ile Lys Pro Ile Pro Ala Asn Met
65                  70                  75                  80

Lys Val Val Val Lys Val Thr Leu Ile Ser Ile Glu Gly Lys Lys Leu
                85                  90                  95

Arg Tyr Asn Val Glu Ala Phe Asn Glu Lys Asn Cys Lys Val Gly Phe
            100                 105                 110

Gly Ile Tyr Glu Gln Gln Ile Val Asn Leu Glu Gln Phe Leu Asn Arg
        115                 120                 125
```

```
<210> SEQ ID NO 11
<211> LENGTH: 436
<212> TYPE: PRT
<213> ORGANISM: Clostridium ljungdahlii
<220> FEATURE:
<221> NAME/KEY: MISC_FEATURE
<223> OTHER INFORMATION: putative thioesterase 1, ADK15695.1

<400> SEQUENCE: 11
```

| | | | | | | | | | | | | | | |
|---|---|---|---|---|---|---|---|---|---|---|---|---|---|---|
| Met | Asn | Asp | Asn | Cys | Thr | Ile | Lys | Ile | Thr | Pro | Glu | Val | Ser | Arg |
| 1 | | | | 5 | | | | | 10 | | | | | 15 |
| Val | Asp | Glu | Pro | Val | Asp | Ile | Lys | Ile | Asn | Gly | Leu | Pro | Lys | Asn | Glu |
| | | | 20 | | | | | 25 | | | | | 30 | | |
| Lys | Val | Ile | Ile | Arg | Ala | Val | Ser | Ser | Asp | Tyr | Tyr | Cys | Ile | Asn | Ala |
| | | | 35 | | | | | 40 | | | | | 45 | | |
| Ser | Ile | Leu | Glu | Ile | Gly | Asp | Asn | Thr | Leu | Trp | Glu | Ser | Tyr | Ala | Val |
| | 50 | | | | | 55 | | | | | 60 | | | | |
| Phe | Glu | Thr | Asp | Glu | Cys | Gly | Asn | Ile | Asn | Phe | Glu | Asn | Ala | Val | Pro |
| 65 | | | | | 70 | | | | | 75 | | | | | 80 |
| Val | Asp | Gly | Thr | Tyr | Ser | Asn | Cys | Asp | Lys | Met | Gly | Leu | Phe | Tyr | Ser |
| | | | | 85 | | | | | 90 | | | | | 95 | |
| Met | Arg | Pro | Lys | Gln | Ile | Arg | Lys | Ser | Lys | Leu | Ile | Gln | Lys | Leu | Ser |
| | | | 100 | | | | | 105 | | | | | 110 | | |
| Ser | Ile | Asn | Glu | Asn | Arg | Lys | Tyr | Lys | Ile | Thr | Phe | Thr | Val | Glu | Lys |
| | | | 115 | | | | | 120 | | | | | 125 | | |
| Asn | Gly | Lys | Ile | Ile | Gly | Ser | Lys | Glu | His | Thr | Arg | Val | Tyr | Cys | Asp |
| | 130 | | | | | 135 | | | | | 140 | | | | |
| Asp | Thr | Ile | Lys | Ser | Ile | Asp | Val | Val | Glu | Lys | Asn | Leu | Leu | Ala | Arg |
| 145 | | | | | 150 | | | | | 155 | | | | | 160 |
| Tyr | Phe | Thr | Ser | Lys | Asp | Asn | Ile | Lys | His | Pro | Ala | Ile | Ile | Val | Leu |
| | | | | 165 | | | | | 170 | | | | | 175 | |
| Ser | Gly | Ser | Asp | Gly | Arg | Ile | Glu | Lys | Ala | Gln | Ala | Ile | Ala | Glu | Leu |
| | | | 180 | | | | | 185 | | | | | 190 | | |
| Phe | Ala | Met | Arg | Gly | Tyr | Ser | Ala | Leu | Ala | Val | Cys | Tyr | Phe | Gly | Leu |
| | | | 195 | | | | | 200 | | | | | 205 | | |
| Glu | Gly | Thr | Pro | Glu | Asp | Leu | Asn | Met | Ile | Pro | Leu | Glu | Tyr | Val | Glu |
| | 210 | | | | | 215 | | | | | 220 | | | | |
| Asn | Ala | Val | Lys | Trp | Leu | Lys | Arg | Gln | Asp | Thr | Val | Asp | Glu | Asn | Lys |
| 225 | | | | | 230 | | | | | 235 | | | | | 240 |
| Ile | Ala | Ile | Tyr | Gly | Arg | Ser | Lys | Gly | Gly | Glu | Leu | Val | Leu | Leu | Ala |
| | | | | 245 | | | | | 250 | | | | | 255 | |
| Ala | Ser | Met | Phe | Lys | Asp | Ile | Ala | Cys | Val | Ile | Ala | Asn | Thr | Pro | Ser |
| | | | 260 | | | | | 265 | | | | | 270 | | |
| Cys | Tyr | Val | Tyr | Glu | Gly | Ile | Lys | Ser | Asn | Lys | Leu | Pro | Ser | His | His |
| | | | 275 | | | | | 280 | | | | | 285 | | |
| Ser | Ser | Trp | Met | Tyr | Arg | Gly | Arg | Glu | Ile | Pro | Tyr | Leu | Lys | Phe | Asn |
| | 290 | | | | | 295 | | | | | 300 | | | | |
| Phe | His | Ile | Ile | Leu | Arg | Leu | Ile | Ile | Lys | Met | Met | Lys | Lys | Glu | Lys |
| 305 | | | | | 310 | | | | | 315 | | | | | 320 |
| Gly | Ala | Leu | Ala | Trp | Met | Tyr | Lys | Leu | Ile | Glu | Glu | Gly | Asp | Arg |
| | | | | 325 | | | | | 330 | | | | | 335 |
| Asp | Lys | Ala | Thr | Ile | Ala | Leu | Asp | Lys | Ile | Asn | Gly | Ser | Val | Leu | Met |
| | | | 340 | | | | | 345 | | | | | 350 | | |
| Ile | Ser | Ser | Ala | Ala | Asp | Glu | Ile | Trp | Pro | Ser | Lys | Met | His | Ser | Glu |
| | | | 355 | | | | | 360 | | | | | 365 | | |

```
Thr Val Cys Ser Ile Phe Glu Lys Ser His Phe Lys His Glu Tyr Lys
    370                 375                 380

His Ile Thr Phe Ala Lys Ser Gly His Ile Leu Thr Val Pro Phe Gln
385                 390                 395                 400

Ser Ile Tyr Pro Ser Glu Lys Tyr Pro Tyr Asp Val Glu Ser Trp Ala
                405                 410                 415

Lys Ala Asn Met Asp Ser Trp Asn Glu Thr Ile Lys Phe Leu Glu Lys
            420                 425                 430

Trp Ala Ser Lys
        435

<210> SEQ ID NO 12
<211> LENGTH: 137
<212> TYPE: PRT
<213> ORGANISM: Clostridium ljungdahlii
<220> FEATURE:
<221> NAME/KEY: MISC_FEATURE
<223> OTHER INFORMATION: putative thioesterase 2, ADK16655.1

<400> SEQUENCE: 12

Met Tyr Ile Asn Glu Thr Lys Val Val Arg Tyr Ala Glu Thr Asp
1               5                   10                  15

Lys Met Gly Ile Val His His Ser Asn Tyr Ile Tyr Phe Glu Glu
            20                  25                  30

Ala Arg Thr Gln Phe Ile Lys Lys Thr Gly Ile Ser Tyr Ser Gln Met
            35                  40                  45

Glu Lys Asp Gly Ile Met Phe Pro Leu Val Glu Ser Asn Cys Arg Tyr
50                  55                  60

Leu Gln Gly Ala Lys Tyr Glu Asp Glu Leu Leu Ile Lys Thr Trp Ile
65                  70                  75                  80

Lys Glu Leu Thr Pro Val Lys Ala Glu Phe Asn Tyr Ser Val Ile Arg
                85                  90                  95

Glu Asn Asp Gln Lys Glu Ile Ala Lys Gly Ser Thr Leu His Ala Phe
            100                 105                 110

Val Asn Asn Asn Phe Lys Ile Ile Asn Leu Lys Lys Asn His Thr Glu
            115                 120                 125

Leu Phe Lys Lys Leu Gln Ser Leu Ile
        130                 135

<210> SEQ ID NO 13
<211> LENGTH: 128
<212> TYPE: PRT
<213> ORGANISM: Clostridium ljungdahlii
<220> FEATURE:
<221> NAME/KEY: MISC_FEATURE
<223> OTHER INFORMATION: putative thioesterase 3, ADK16959.1

<400> SEQUENCE: 13

Met Asp Phe Ser Lys Leu Phe Lys Val Gly Ser Thr Tyr Val Ser Glu
1               5                   10                  15

Tyr Ile Val Lys Pro Glu Asp Thr Ala Asn Phe Ile Gly Asn Asn Gly
            20                  25                  30

Val Val Met Leu Ser Thr Pro Ala Met Ile Lys Tyr Met Glu Tyr Thr
            35                  40                  45

Thr Leu His Ile Val Asp Asn Val Ile Pro Lys Asn Tyr Arg Pro Val
        50                  55                  60

Gly Thr Lys Ile Asp Val Glu His Ile Lys Pro Ile Pro Ala Asn Met
65                  70                  75                  80
```

-continued

```
Lys Val Val Lys Val Thr Leu Ile Ser Ile Glu Gly Lys Lys Leu
                85                  90                  95

Arg Tyr Asn Val Glu Ala Phe Asn Glu Lys Asn Cys Lys Val Gly Phe
            100                 105                 110

Gly Ile Tyr Glu Gln Gln Ile Val Asn Leu Glu Gln Phe Leu Asn Arg
        115                 120                 125

<210> SEQ ID NO 14
<211> LENGTH: 246
<212> TYPE: PRT
<213> ORGANISM: Clostridium beijerinckii
<220> FEATURE:
<221> NAME/KEY: MISC_FEATURE
<223> OTHER INFORMATION: Adc, WP_012059998.1

<400> SEQUENCE: 14

Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245

<210> SEQ ID NO 15
<211> LENGTH: 548
<212> TYPE: PRT
<213> ORGANISM: Lactococcus lactis
<220> FEATURE:
<221> NAME/KEY: MISC_FEATURE
<223> OTHER INFORMATION: KivD

<400> SEQUENCE: 15
```

-continued

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
        290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415
```

```
Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 16
<211> LENGTH: 351
<212> TYPE: PRT
<213> ORGANISM: Clostridium autoethanogenum
<220> FEATURE:
<221> NAME/KEY: MISC_FEATURE
<223> OTHER INFORMATION: SecAdh, AGY74782.1

<400> SEQUENCE: 16

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
            35                  40                  45

Leu Gly Asn Arg Glu Asn Met Ile Leu Gly His Glu Ala Val Gly Glu
        50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220
```

```
Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
            245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
        290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 17
<211> LENGTH: 351
<212> TYPE: PRT
<213> ORGANISM: Clostridium ljungdahlii
<220> FEATURE:
<221> NAME/KEY: MISC_FEATURE
<223> OTHER INFORMATION: SecAdh, ADK15544.1

<400> SEQUENCE: 17

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
```

```
                225                 230                 235                 240
Met Ala Gly Gly Gly Ala Glu Thr Leu Ala Gln Ala Val Thr Met Val
                    245                 250                 255
Lys Pro Gly Gly Val Ile Ser Asn Ile Asn Tyr His Gly Ser Gly Asp
                260                 265                 270
Thr Leu Pro Ile Pro Arg Val Gln Trp Gly Cys Gly Met Ala His Lys
                275                 280                 285
Thr Ile Arg Gly Gly Leu Cys Pro Gly Gly Arg Leu Arg Met Glu Met
290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                    325                 330                 335
Met Lys Asn Lys Pro Lys Asp Leu Ile Lys Ser Val Val Thr Phe
                340                 345                 350
```

<210> SEQ ID NO 18
<211> LENGTH: 351
<212> TYPE: PRT
<213> ORGANISM: Clostridium ragsdalei
<220> FEATURE:
<221> NAME/KEY: MISC_FEATURE
<223> OTHER INFORMATION: SecAdh, WP_013239134.1

<400> SEQUENCE: 18

```
Met Lys Gly Phe Ala Met Leu Gly Ile Asn Lys Leu Gly Trp Ile Glu
1                 5                  10                 15
Lys Lys Asn Pro Val Pro Gly Pro Tyr Asp Ala Ile Val His Pro Leu
                20                  25                  30
Ala Val Ser Pro Cys Thr Ser Asp Ile His Thr Val Phe Glu Gly Ala
                35                  40                  45
Leu Gly Asn Arg Glu Asn Met Ile Leu Gly His Glu Ala Val Gly Glu
            50                  55                  60
Ile Ala Glu Val Gly Ser Glu Val Lys Asp Phe Lys Val Gly Asp Arg
65                  70                  75                  80
Val Ile Val Pro Cys Thr Thr Pro Asp Trp Arg Ser Leu Glu Val Gln
                85                  90                  95
Ala Gly Phe Gln Gln His Ser Asn Gly Met Leu Ala Gly Trp Lys Phe
                100                 105                 110
Ser Asn Phe Lys Asp Gly Val Phe Ala Asp Tyr Phe His Val Asn Asp
            115                 120                 125
Ala Asp Met Asn Leu Ala Ile Leu Pro Asp Glu Ile Pro Leu Glu Ser
130                 135                 140
Ala Val Met Met Thr Asp Met Met Thr Thr Gly Phe His Gly Ala Glu
145                 150                 155                 160
Leu Ala Asp Ile Lys Met Gly Ser Ser Val Val Ile Gly Ile Gly
                165                 170                 175
Ala Val Gly Leu Met Gly Ile Ala Gly Ser Lys Leu Arg Gly Ala Gly
                180                 185                 190
Arg Ile Ile Gly Val Gly Ser Arg Pro Val Cys Val Glu Thr Ala Lys
            195                 200                 205
Phe Tyr Gly Ala Thr Asp Ile Val Asn Tyr Lys Asn Gly Asp Ile Val
        210                 215                 220
Glu Gln Ile Met Asp Leu Thr His Gly Lys Gly Val Asp Arg Val Ile
225                 230                 235                 240
```

```
Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 19
<211> LENGTH: 351
<212> TYPE: PRT
<213> ORGANISM: Clostridium beijerinckii
<220> FEATURE:
<221> NAME/KEY: MISC_FEATURE
<223> OTHER INFORMATION: SecAdh

```
Lys Pro Gly Gly Ile Ile Ser Asn Ile Asn Tyr His Gly Ser Gly Asp
                260                 265                 270

Ala Leu Leu Ile Pro Arg Val Glu Trp Gly Cys Gly Met Ala His Lys
            275                 280                 285

Thr Ile Lys Gly Gly Leu Cys Pro Gly Gly Arg Leu Arg Ala Glu Met
290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Ala Leu Leu Leu
                325                 330                 335

Met Lys Asp Lys Pro Lys Asp Leu Ile Lys Ala Val Val Ile Leu
            340                 345                 350

<210> SEQ ID NO 20
<211> LENGTH: 352
<212> TYPE: PRT
<213> ORGANISM: Thermoanaerobacter brokii
<220> FEATURE:
<221> NAME/KEY: MISC_FEATURE
<223> OTHER INFORMATION: SecAdh, 3FSR_A

<400> SEQUENCE: 20

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
                20                  25                  30

Ala Val Ala Pro Cys Thr Ser Asp Ile His Thr Val Phe Glu Gly Ala
            35                  40                  45

Ile Gly Glu Arg His Asn Met Ile Leu Gly His Glu Ala Val Gly Glu
        50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
                100                 105                 110

Ser Asn Val Lys Asp Gly Val Phe Gly Glu Phe Phe His Val Asn Asp
            115                 120                 125

Ala Asp Met Asn Leu Ala His Leu Pro Lys Glu Ile Pro Leu Glu Ala
        130                 135                 140

Ala Val Met Ile Pro Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
```

```
                260                 265                 270
Ala Leu Leu Ile Pro Arg Val Glu Trp Gly Cys Gly Met Ala His Lys
            275                 280                 285
Thr Ile Lys Gly Gly Leu Cys Pro Gly Gly Arg Leu Arg Met Glu Arg
            290                 295                 300
Leu Ile Asp Leu Val Phe Tyr Lys Arg Val Asp Pro Ser Lys Leu Val
305                 310                 315                 320
Thr His Val Phe Arg Gly Phe Asp Asn Ile Glu Lys Ala Phe Met Leu
            325                 330                 335
Met Lys Asp Lys Pro Lys Asp Leu Ile Lys Pro Val Val Ile Leu Ala
            340                 345                 350

<210> SEQ ID NO 21
<211> LENGTH: 520
<212> TYPE: PRT
<213> ORGANISM: Mus musculus
<220> FEATURE:
<221> NAME/KEY: MISC_FEATURE
<223> OTHER INFORMATION: HMG-CoA synthase

<400> SEQUENCE: 21

Met Pro Gly Ser Leu Pro Leu Asn Ala Glu Ala Cys Trp Pro Lys Asp
1               5                   10                  15
Val Gly Ile Val Ala Leu Glu Ile Tyr Phe Pro Ser Gln Tyr Val Asp
            20                  25                  30
Gln Ala Glu Leu Glu Lys Tyr Asp Gly Val Asp Ala Gly Lys Tyr Thr
            35                  40                  45
Ile Gly Leu Gly Gln Ala Arg Met Gly Phe Cys Thr Asp Arg Glu Asp
        50                  55                  60
Ile Asn Ser Leu Cys Leu Thr Val Val Gln Lys Leu Met Glu Arg His
65                  70                  75                  80
Ser Leu Ser Tyr Asp Cys Ile Gly Arg Leu Glu Val Gly Thr Glu Thr
                85                  90                  95
Ile Ile Asp Lys Ser Lys Ser Val Lys Ser Lys Leu Met Gln Leu Phe
            100                 105                 110
Glu Glu Ser Gly Asn Thr Asp Ile Glu Gly Ile Asp Thr Thr Asn Ala
            115                 120                 125
Cys Tyr Gly Gly Thr Ala Ala Val Phe Asn Ala Val Asn Trp Val Glu
        130                 135                 140
Ser Ser Ser Trp Asp Gly Arg Tyr Ala Leu Val Val Ala Gly Asp Ile
145                 150                 155                 160
Ala Ile Tyr Ala Thr Gly Asn Ala Arg Pro Thr Gly Gly Val Gly Ala
                165                 170                 175
Val Ala Leu Leu Ile Gly Pro Asn Ala Pro Leu Ile Phe Asp Arg Gly
            180                 185                 190
Leu Arg Gly Thr His Met Gln His Ala Tyr Asp Phe Tyr Lys Pro Asp
            195                 200                 205
Met Leu Ser Glu Tyr Pro Val Val Asp Gly Lys Leu Ser Ile Gln Cys
        210                 215                 220
Tyr Leu Ser Ala Leu Asp Arg Cys Tyr Ser Val Tyr Arg Lys Lys Ile
225                 230                 235                 240
Arg Ala Gln Trp Gln Lys Glu Gly Lys Asp Lys Asp Phe Thr Leu Asn
                245                 250                 255
Asp Phe Gly Phe Met Ile Phe His Ser Pro Tyr Cys Lys Leu Val Gln
            260                 265                 270
```

-continued

```
Lys Ser Leu Ala Arg Met Phe Leu Asn Asp Phe Leu Asn Asp Gln Asn
            275                 280                 285

Arg Asp Lys Asn Ser Ile Tyr Ser Gly Leu Glu Ala Phe Gly Asp Val
        290                 295                 300

Lys Leu Glu Asp Thr Tyr Phe Asp Arg Asp Val Glu Lys Ala Phe Met
305                 310                 315                 320

Lys Ala Ser Ser Glu Leu Phe Asn Gln Lys Thr Lys Ala Ser Leu Leu
                325                 330                 335

Val Ser Asn Gln Asn Gly Asn Met Tyr Thr Ser Val Tyr Gly Ser
            340                 345                 350

Leu Ala Ser Val Leu Ala Gln Tyr Ser Pro Gln Gln Leu Ala Gly Lys
            355                 360                 365

Arg Val Gly Val Phe Ser Tyr Gly Ser Gly Leu Ala Ala Thr Leu Tyr
        370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Cys Val Ala Pro Asp Val Phe Ala Glu Asn Met Lys Leu Arg Glu Asp
            420                 425                 430

Thr His His Leu Ala Asn Tyr Ile Pro Gln Cys Ser Ile Asp Ser Leu
        435                 440                 445

Phe Glu Gly Thr Trp Tyr Leu Val Arg Val Asp Glu Lys His Arg Arg
    450                 455                 460

Thr Tyr Ala Arg Arg Pro Phe Thr Asn Asp His Ser Leu Asp Glu Gly
465                 470                 475                 480

Met Gly Leu Val His Ser Asn Thr Ala Thr Glu His Ile Pro Ser Pro
                485                 490                 495

Ala Lys Lys Val Pro Arg Leu Pro Ala Thr Ser Ala Glu Ser Glu Ser
            500                 505                 510

Ala Val Ile Ser Asn Gly Glu His
            515                 520

<210> SEQ ID NO 22
<211> LENGTH: 396
<212> TYPE: PRT
<213> ORGANISM: Saccharomyces cerevisiae
<220> FEATURE:
<221> NAME/KEY: MISC_FEATURE
<223> OTHER INFORMATION: Mdd, CAA96324.1

<400> SEQUENCE: 22

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110
```

Pro Thr Ala Ala Gly Leu Ala Ser Ser Ala Gly Phe Ala Ala Leu
        115                 120                 125

Val Ser Ala Ile Ala Lys Leu Tyr Gln Leu Pro Gln Ser Thr Ser Glu
        130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
                180                 185                 190

Lys Ala Cys Val Leu Val Ser Asp Ile Lys Lys Asp Val Ser Ser
        195                 200                 205

Thr Gln Gly Met Gln Leu Thr Val Ala Thr Ser Glu Leu Phe Lys Glu
        210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
        260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
        290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
        340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
        370                 375                 380

Ser Leu Ile Asp Ala Lys Thr Gly Leu Pro Lys Glu
385                 390                 395

<210> SEQ ID NO 23
<211> LENGTH: 324
<212> TYPE: PRT
<213> ORGANISM: Picrophilus torridus
<220> FEATURE:
<221> NAME/KEY: MISC_FEATURE
<223> OTHER INFORMATION: Mdd, WP_011178157.1

<400> SEQUENCE: 23

Met Glu Asn Tyr Asn Val Lys Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
        35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp

```
                65                  70                  75                  80
Lys Phe Lys His Glu Ile Leu Met Arg Val Asn Leu Asp Asp Glu Asn
                    85                  90                  95

Asn Leu Ser Ile Asp Ser Arg Asn Phe Asn Ile Leu Ser Gly Ser Ser
                100                 105                 110

Asp Ser Gly Ala Ala Leu Gly Glu Cys Ile Glu Ser Ile Phe Glu
            115                 120                 125

Tyr Asn Ile Asn Ile Phe Thr Phe Glu Asn Asp Leu Gln Arg Ile Ser
            130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
                180                 185                 190

Ser Asn Glu Ile His Glu Asn Ile Ile Lys His Glu Asn Tyr Arg Glu
                195                 200                 205

Arg Ile Lys Ser Ala Glu Arg Lys Ala Lys Lys Leu Glu Glu Leu Ser
            210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Ile Asn
                245                 250                 255

Asp Arg Met Glu Asn Leu Ile Glu Arg Val Lys Glu Met Lys Asn Asn
                260                 265                 270

Phe Trp Asn Ser Tyr Ile Val Thr Gly Gly Pro Asn Val Phe Val Ile
                275                 280                 285

Thr Glu Lys Lys Asp Val Asp Lys Ala Met Glu Gly Leu Asn Asp Leu
            290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 24
<211> LENGTH: 460
<212> TYPE: PRT
<213> ORGANISM: Clostridium autoethanogenum
<220> FEATURE:
<221> NAME/KEY: MISC_FEATURE
<223> OTHER INFORMATION: CimA, AGY76958.1

<400> SEQUENCE: 24

Met Lys Lys Ser Ser Tyr Glu Tyr Lys Leu Asn Asn Val Asp Ser Pro
1               5                   10                  15

Asn Phe Tyr Lys Asn Ile Phe Pro Tyr Asp Glu Ile Pro Lys Ile Asn
                20                  25                  30

Phe Asn Gly Val Gln Ile Pro Lys Asp Leu Pro Glu Asn Ile Tyr Ile
            35                  40                  45

Thr Asp Thr Thr Phe Arg Asp Gly Gln Gln Ser Met Pro Pro Tyr Thr
            50                  55                  60

Thr Glu Gln Ile Ile Arg Ile Phe Asp Tyr Leu His Asn Leu Asp Asn
65                  70                  75                  80

Asn Ser Gly Ile Ile Lys Gln Thr Glu Phe Phe Leu Tyr Thr Glu Lys
                85                  90                  95

Asp Arg Lys Ala Ala Gln Val Cys Met Glu Arg Gly Tyr Glu Phe Pro
```

```
            100                 105                 110
Glu Val Thr Ser Trp Ile Arg Ala Asn Lys Glu Asp Phe Lys Leu Val
            115                 120                 125

Lys Gln Met Gly Ile Lys Glu Thr Gly Met Leu Met Ser Cys Ser Asp
    130                 135                 140

Tyr His Ile Phe Lys Lys Leu Arg Lys Thr Arg Lys Glu Thr Met Asp
145                 150                 155                 160

Met Tyr Leu Gly Ile Val Lys Glu Ala Leu Asp Asn Gly Ile Arg Pro
                165                 170                 175

Arg Cys His Leu Glu Asp Ile Thr Arg Ala Asp Phe Tyr Gly Phe Val
            180                 185                 190

Val Pro Leu Val Asn Lys Leu Met Glu Leu Ser Lys Gln Ser Gly Ile
        195                 200                 205

Pro Ile Lys Ile Arg Ala Cys Asp Thr Leu Gly Leu Gly Val Ser Tyr
    210                 215                 220

Ser Gly Val Glu Leu Pro Arg Ser Val Gln Ala Ile Met Tyr Gly Leu
225                 230                 235                 240

Arg Asn Asn Cys Gly Val Pro Ser Glu Cys Ile Glu Trp His Gly His
                245                 250                 255

Asn Asp Phe Tyr Ala Val Val Asn Asn Ser Thr Thr Ala Trp Leu Tyr
            260                 265                 270

Gly Ala Ser Ala Val Asn Thr Ser Phe Leu Gly Ile Gly Glu Arg Thr
        275                 280                 285

Gly Asn Cys Pro Leu Glu Ala Met Ile Phe Glu Tyr Gly Gln Ile Lys
    290                 295                 300

Gly Asn Thr Lys Asn Met Lys Leu Glu Val Ile Thr Glu Leu Ser Glu
305                 310                 315                 320

Tyr Phe Lys Lys Glu Met Glu Tyr Ala Val Pro Pro Arg Thr Pro Phe
                325                 330                 335

Val Gly Lys Glu Phe Asn Val Thr Arg Ala Gly Ile His Ala Asp Gly
            340                 345                 350

Ile Leu Lys Asp Glu Glu Ile Tyr Asn Ile Phe Asp Thr Asp Lys Ile
        355                 360                 365

Leu Gly Arg Pro Val Val Val Ala Val Asn Gln Tyr Ser Gly His Ala
    370                 375                 380

Gly Ile Ala Ala Trp Ile Asn Thr Tyr Tyr Arg Leu Lys Asp Glu Glu
385                 390                 395                 400

Lys Ile Asp Lys Trp Asp Thr Arg Ile Ala Lys Ile Lys Glu Trp Val
                405                 410                 415

Asp Glu Gln Tyr Lys Ala Gly Arg Thr Ser Ile Ile Gly Asn Asp Glu
            420                 425                 430

Leu Glu Leu Leu Val Asp Lys Met Leu Pro Asp Ile Ser Gln Lys Lys
        435                 440                 445

Lys Lys Glu Leu Ala Arg Val Asp Thr Arg Phe Ile
    450                 455                 460

<210> SEQ ID NO 25
<211> LENGTH: 491
<212> TYPE: PRT
<213> ORGANISM: Methanocaldococcus jannaschii
<220> FEATURE:
<221> NAME/KEY: MISC_FEATURE
<223> OTHER INFORMATION: CimA, NP_248395.1

<400> SEQUENCE: 25
```

```
Met Met Val Arg Ile Phe Asp Thr Thr Leu Arg Asp Gly Glu Gln Thr
1               5                   10                  15
Pro Gly Val Ser Leu Thr Pro Asn Asp Lys Leu Glu Ile Ala Lys Lys
            20                  25                  30
Leu Asp Glu Leu Gly Val Asp Val Ile Glu Ala Gly Ser Ala Ile Thr
        35                  40                  45
Ser Lys Gly Glu Arg Glu Gly Ile Lys Leu Ile Thr Lys Glu Gly Leu
50                  55                  60
Asn Ala Glu Ile Cys Ser Phe Val Arg Ala Leu Pro Val Asp Ile Asp
65                  70                  75                  80
Ala Ala Leu Glu Cys Asp Val Asp Ser Val His Leu Val Val Pro Thr
                85                  90                  95
Ser Pro Ile His Met Lys Tyr Lys Leu Arg Lys Thr Glu Asp Glu Val
            100                 105                 110
Leu Glu Thr Ala Leu Lys Ala Val Glu Tyr Ala Lys Glu His Gly Leu
        115                 120                 125
Ile Val Glu Leu Ser Ala Glu Asp Ala Thr Arg Ser Asp Val Asn Phe
    130                 135                 140
Leu Ile Lys Leu Phe Asn Glu Gly Lys Val Gly Ala Asp Arg Val
145                 150                 155                 160
Cys Val Cys Asp Thr Val Gly Val Leu Thr Pro Gln Lys Ser Gln Glu
                165                 170                 175
Leu Phe Lys Lys Ile Thr Glu Asn Val Asn Leu Pro Val Ser Val His
            180                 185                 190
Cys His Asn Asp Phe Gly Met Ala Thr Ala Asn Thr Cys Ser Ala Val
        195                 200                 205
Leu Gly Gly Ala Val Gln Cys His Val Thr Val Asn Gly Ile Gly Glu
    210                 215                 220
Arg Ala Gly Asn Ala Ser Leu Glu Glu Val Val Ala Ala Leu Lys Ile
225                 230                 235                 240
Leu Tyr Gly Tyr Asp Thr Lys Ile Lys Met Glu Lys Leu Tyr Glu Val
                245                 250                 255
Ser Arg Ile Val Ser Arg Leu Met Lys Leu Pro Val Pro Pro Asn Lys
            260                 265                 270
Ala Ile Val Gly Asp Asn Ala Phe Ala His Glu Ala Gly Ile His Val
        275                 280                 285
Asp Gly Leu Ile Lys Asn Thr Glu Thr Tyr Glu Pro Ile Lys Pro Glu
    290                 295                 300
Met Val Gly Asn Arg Arg Ile Ile Leu Gly Lys His Ser Gly Arg
305                 310                 315                 320
Lys Ala Leu Lys Tyr Lys Leu Asp Leu Met Gly Ile Asn Val Ser Asp
                325                 330                 335
Glu Gln Leu Asn Lys Ile Tyr Glu Arg Val Lys Glu Phe Gly Asp Leu
            340                 345                 350
Gly Lys Tyr Ile Ser Asp Ala Asp Leu Leu Ala Ile Val Arg Glu Val
        355                 360                 365
Thr Gly Lys Leu Val Glu Glu Lys Ile Lys Leu Asp Glu Leu Thr Val
    370                 375                 380
Val Ser Gly Asn Lys Ile Thr Pro Ile Ala Ser Val Lys Leu His Tyr
385                 390                 395                 400
Lys Gly Glu Asp Ile Thr Leu Ile Glu Thr Ala Tyr Gly Val Gly Pro
                405                 410                 415
Val Asp Ala Ala Ile Asn Ala Val Arg Lys Ala Ile Ser Gly Val Ala
```

```
            420                 425                 430
Asp Ile Lys Leu Val Glu Tyr Arg Val Glu Ala Ile Gly Gly Gly Thr
            435                 440                 445

Asp Ala Leu Ile Glu Val Val Lys Leu Arg Lys Gly Thr Glu Ile
450                 455                 460

Val Glu Val Arg Lys Ser Asp Ala Asp Ile Ile Arg Ala Ser Val Asp
465                 470                 475                 480

Ala Val Met Glu Gly Ile Asn Met Leu Leu Asn
                485                 490

<210> SEQ ID NO 26
<211> LENGTH: 421
<212> TYPE: PRT
<213> ORGANISM: Clostridium autoethanogenum
<220> FEATURE:
<221> NAME/KEY: MISC_FEATURE
<223> OTHER INFORMATION: LeuC, WP_023162955.1

<400> SEQUENCE: 26

Met Gly Met Thr Met Thr Gln Lys Ile Leu Ala His His Ala Lys Met
1               5                   10                  15

Asp Glu Val Lys Ala Gly Gln Leu Ile Lys Val Lys Leu Asp Leu Val
            20                  25                  30

Leu Gly Asn Asp Ile Thr Thr Pro Val Ala Ile Asn Glu Phe Asn Lys
        35                  40                  45

Ile Gly Leu Asn Asn Val Phe Asp Lys Asn Lys Ile Ala Ile Val Pro
    50                  55                  60

Asp His Phe Thr Pro Asn Lys Asp Ile Lys Ser Ala Glu Gln Cys Lys
65                  70                  75                  80

Tyr Val Arg Glu Phe Val Lys Lys Met Glu Ile Lys Asn Tyr Phe Glu
                85                  90                  95

Val Gly Arg Met Gly Ile Glu His Ala Leu Ile Pro Glu Lys Gly Leu
            100                 105                 110

Ala Val Cys Gly Asp Val Val Ile Gly Ala Asp Ser His Thr Cys Thr
        115                 120                 125

Tyr Gly Ala Leu Gly Ala Phe Ser Thr Gly Ile Gly Ser Thr Asp Met
    130                 135                 140

Ala Ala Gly Met Ala Thr Gly Glu Ala Trp Phe Lys Val Pro Glu Ala
145                 150                 155                 160

Ile Lys Phe Val Leu Lys Gly Lys Leu Thr Lys Trp Val Ser Gly Lys
                165                 170                 175

Asp Val Ile Leu His Ile Ile Gly Met Ile Gly Val Asp Gly Ala Leu
            180                 185                 190

Tyr Lys Ser Met Glu Phe Thr Gly Glu Gly Val Ser Ser Leu Thr Met
        195                 200                 205

Asp Asp Arg Phe Thr Ile Cys Asn Met Ala Ile Glu Ala Gly Ala Lys
    210                 215                 220

Asn Gly Ile Phe Pro Val Asp Glu Asn Thr Ile Asn Tyr Val Lys Glu
225                 230                 235                 240

His Ser Lys Lys Asn Tyr Thr Val Tyr Glu Ala Asp Ser Asp Ala Glu
                245                 250                 255

Tyr Ser Gln Val Ile Glu Ile Asp Leu Ser Lys Ile Arg Pro Thr Val
            260                 265                 270

Ala Phe Pro His Ile Pro Glu Asn Thr Lys Thr Ile Asp Glu Val Gly
        275                 280                 285
```

```
Asp Ile Arg Ile Asp Gln Val Val Ile Gly Ser Cys Thr Asn Gly Arg
    290                 295                 300

Ile Gly Asp Leu Arg Ala Ala Ser Ile Leu Lys Gly Arg Lys Val
305                 310                 315                 320

Asn Glu Asn Val Arg Ala Ile Ile Phe Pro Ala Thr Gln Ala Ile Tyr
                325                 330                 335

Leu Gln Ala Met Lys Glu Gly Leu Ile Glu Ile Phe Ile Glu Ala Gly
                340                 345                 350

Ala Val Val Ser Thr Pro Thr Cys Gly Pro Cys Leu Gly Gly His Met
                355                 360                 365

Gly Ile Leu Ala Glu Gly Glu Arg Ala Val Ser Thr Thr Asn Arg Asn
370                 375                 380

Phe Val Gly Arg Met Gly His Val Lys Ser Glu Val Tyr Leu Ala Ser
385                 390                 395                 400

Pro Glu Val Ala Ala Ser Ala Val Thr Gly Lys Ile Ser Ser Pro
                405                 410                 415

Glu Glu Val Val Lys
            420

<210> SEQ ID NO 27
<211> LENGTH: 164
<212> TYPE: PRT
<213> ORGANISM: Clostridium autoethanogenum
<220> FEATURE:
<221> NAME/KEY: MISC_FEATURE
<223> OTHER INFORMATION: LeuD, AGY77204.1

<400> SEQUENCE: 27

Met Ile Lys Gly Lys Ala Ile Lys Tyr Gly Asp Asn Val Asp Thr Asp
1               5                   10                  15

Val Ile Ile Pro Ala Arg Tyr Leu Asn Thr Ser Asp His Lys Glu Leu
                20                  25                  30

Ala Ser His Cys Met Glu Asp Ile Asp Lys Asp Phe Ser Lys Lys Ile
                35                  40                  45

Ser Lys Gly Asp Ile Met Ile Ala Gly Lys Asn Phe Gly Cys Gly Ser
50                  55                  60

Ser Arg Glu His Ala Pro Ile Ala Ile Lys Ala Ser Gly Ile Ser Cys
65                  70                  75                  80

Ile Ile Ala Glu Thr Phe Ala Arg Ile Phe Phe Arg Asn Ser Ile Asn
                85                  90                  95

Ile Gly Leu Pro Ile Met Glu Cys Glu Glu Ala Ala Lys Asp Ile Asp
                100                 105                 110

Glu Lys Asp Glu Val Ser Val Asp Thr Val Ser Gly Val Ile Thr Asn
            115                 120                 125

Ile Thr Lys Asn Lys Thr Tyr Lys Ala Val Pro Phe Pro Glu Phe Met
            130                 135                 140

His Lys Ile Ile Lys Ser Glu Gly Leu Ile Asn Tyr Ile Lys Glu Glu
145                 150                 155                 160

Val Glu Asn Lys

<210> SEQ ID NO 28
<211> LENGTH: 466
<212> TYPE: PRT
<213> ORGANISM: Escherichia coli
<220> FEATURE:
<221> NAME/KEY: MISC_FEATURE
<223> OTHER INFORMATION: LeuC, NP_414614.1
```

<400> SEQUENCE: 28

```
Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415
```

```
Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
            435                 440                 445

Met Ala Ala Ala Ala Val Thr Gly His Phe Ala Asp Ile Arg Asn
450                 455                 460

Ile Lys
465

<210> SEQ ID NO 29
<211> LENGTH: 201
<212> TYPE: PRT
<213> ORGANISM: Escherichia coli
<220> FEATURE:
<221> NAME/KEY: MISC_FEATURE
<223> OTHER INFORMATION: LeuD, NP_414613.1

<400> SEQUENCE: 29

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 30
<211> LENGTH: 354
<212> TYPE: PRT
<213> ORGANISM: Clostridium autoethanogenum
<220> FEATURE:
<221> NAME/KEY: MISC_FEATURE
<223> OTHER INFORMATION: LeuB, WP_023162957.1

<400> SEQUENCE: 30

Met Lys Ile Ala Ile Ile Pro Gly Asp Gly Ile Gly Lys Glu Ile Ile
1               5                   10                  15

Glu Gln Ala Lys Lys Val Leu Lys Ala Ala Ser Ala Lys Tyr Asn Phe
            20                  25                  30
```

```
Asp Phe Glu Cys Glu Val Leu Leu Gly Gly Ala Ala Val Asp Ala
            35                  40                  45

Thr Gly Val Pro Leu Pro Asp Lys Thr Val Glu Val Cys Lys Lys Ser
 50                  55                  60

Asp Ala Val Leu Leu Gly Ala Val Gly Gly Pro Lys Trp Asp Ser Leu
 65                  70                  75                  80

Pro Ser Lys Leu Arg Pro Glu Ala Gly Leu Leu Gly Ile Arg Lys Ala
                 85                  90                  95

Leu Gly Val Phe Ala Asn Leu Arg Pro Ala Ile Leu Phe Pro Glu Leu
            100                 105                 110

Ile Ala Ala Ser Asn Leu Lys Pro Glu Val Leu Gly Gly Leu Asp
            115                 120                 125

Ile Met Ile Val Arg Glu Leu Ile Gly Gly Ala Tyr Phe Gly Glu Lys
            130                 135                 140

Asn Arg Ile Asp Ile Glu Gly Gly Lys Lys Ala Trp Asp Thr Ile Ser
145                 150                 155                 160

Tyr Thr Ser Phe Glu Ile Asp Arg Ile Thr Arg Lys Ala Phe Glu Ile
                165                 170                 175

Ala Arg Lys Arg Ser Asn Arg Leu Thr Leu Val Asp Lys Ala Asn Val
            180                 185                 190

Leu Glu Ser Ser Lys Leu Trp Arg Glu Val Val Gly Asn Ile Ala Lys
            195                 200                 205

Glu Tyr Glu Asp Val Glu Ile Asn Tyr Met Tyr Val Asp Asn Ala Ser
            210                 215                 220

Met Gln Leu Ile Arg Asp Pro Lys Gln Phe Asp Val Ile Leu Thr Glu
225                 230                 235                 240

Asn Met Phe Gly Asp Ile Leu Ser Asp Glu Ala Ser Met Leu Thr Gly
                245                 250                 255

Ser Leu Gly Met Leu Pro Ser Ala Ser Val Arg Gly Asp Ser Phe Gly
            260                 265                 270

Leu Tyr Glu Pro Val His Gly Ser Ala Pro Asp Ile Ala Gly Gln Asn
            275                 280                 285

Lys Ala Asn Pro Ile Gly Thr Ile Met Ser Val Ala Met Met Leu Lys
290                 295                 300

Tyr Ser Phe Asp Met Glu Gln Ala Tyr Val Asp Ile Lys Asn Ala Ile
305                 310                 315                 320

Ser Lys Val Leu Lys Glu Gly Tyr Arg Thr Gly Asp Ile Ala Lys Glu
                325                 330                 335

Asp Ser Lys Leu Val Gly Thr Glu Glu Met Gly Asp Leu Ile Val Lys
            340                 345                 350

Asn Leu

<210> SEQ ID NO 31
<211> LENGTH: 363
<212> TYPE: PRT
<213> ORGANISM: Escherichia coli
<220> FEATURE:
<221> NAME/KEY: MISC_FEATURE
<223> OTHER INFORMATION: LeuB, NP_414615.4

<400> SEQUENCE: 31

Met Ser Lys Asn Tyr His Ile Ala Val Leu Pro Gly Asp Gly Ile Gly
 1               5                  10                  15

Pro Glu Val Met Thr Gln Ala Leu Lys Val Leu Asp Ala Val Arg Asn
                 20                  25                  30
```

Arg Phe Ala Met Arg Ile Thr Thr Ser His Tyr Asp Val Gly Gly Ala
            35                  40                  45

Ala Ile Asp Asn His Gly Gln Pro Leu Pro Pro Ala Thr Val Glu Gly
 50                  55                  60

Cys Glu Gln Ala Asp Ala Val Leu Phe Gly Ser Val Gly Gly Pro Lys
 65                  70                  75                  80

Trp Glu His Leu Pro Pro Asp Gln Gln Pro Glu Arg Gly Ala Leu Leu
                 85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
            115                 120                 125

Ala Asn Gly Phe Asp Ile Leu Cys Val Arg Glu Leu Thr Gly Gly Ile
130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
            195                 200                 205

Val Asn Glu Ile Ala Thr Glu Tyr Pro Asp Val Glu Leu Ala His Met
210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
            275                 280                 285

Asp Ile Ala Gly Lys Asn Ile Ala Asn Pro Ile Ala Gln Ile Leu Ser
290                 295                 300

Leu Ala Leu Leu Leu Arg Tyr Ser Leu Asp Ala Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Val Ser Thr Asp Glu Met Gly
            340                 345                 350

Asp Ile Ile Ala Arg Tyr Val Ala Glu Gly Val
            355                 360

<210> SEQ ID NO 32
<211> LENGTH: 536
<212> TYPE: PRT
<213> ORGANISM: Clostridium autoethanogenum
<220> FEATURE:
<221> NAME/KEY: MISC_FEATURE
<223> OTHER INFORMATION: IlvB, AGY74359.1

<400> SEQUENCE: 32

Met Lys Ala Ala Glu Ala Val Ile Gln Cys Leu Lys Lys Glu Asn Val
1               5                   10                  15

Asn Met Val Phe Gly Tyr Pro Gly Ala Ala Val Val Pro Ile Tyr Glu

```
                  20                  25                  30
Ala Leu Arg Lys Ser Asp Val Lys His Ile Leu Val Arg Gln Glu Gln
                 35                  40                  45
Ala Ala Gly His Ser Ala Ser Gly Tyr Ala Arg Ser Thr Gly Glu Val
 50                  55                  60
Gly Val Cys Ile Val Thr Ser Gly Pro Gly Ala Thr Asn Leu Ile Thr
 65                  70                  75                  80
Ala Ile Ala Ala Ala Tyr Met Asp Ser Ile Pro Leu Val Val Ile Thr
                 85                  90                  95
Gly Gln Val Lys Ser Thr Leu Ile Gly Arg Asp Val Phe Gln Glu Leu
                100                 105                 110
Asp Ile Thr Gly Ala Thr Glu Ser Phe Thr Lys Tyr Asn Phe Leu Val
                115                 120                 125
Arg Asp Ala Lys Ser Ile Pro Lys Thr Ile Lys Glu Ala Phe Tyr Ile
                130                 135                 140
Ala Glu Thr Gly Arg Lys Gly Pro Val Leu Val Asp Ile Pro Met Asp
145                 150                 155                 160
Ile Met Glu Glu Asp Ile Asp Phe Glu Tyr Pro Glu Ser Val Asn Ile
                165                 170                 175
Arg Gly Tyr Lys Pro Thr Val Lys Gly His Ser Gly Gln Ile Lys Lys
                180                 185                 190
Ile Ile Asp Arg Ile Lys Val Ser Lys Arg Pro Leu Ile Cys Ala Gly
                195                 200                 205
Gly Gly Val Ile Leu Ala Asn Ala Gln Lys Glu Leu Glu Gln Phe Val
                210                 215                 220
Lys Lys Ser His Ile Pro Val Val His Thr Leu Met Gly Lys Gly Cys
225                 230                 235                 240
Ile Asn Glu Asn Ser Asp Tyr Tyr Val Gly Leu Ile Gly Thr His Gly
                245                 250                 255
Phe Ala Tyr Ala Asn Lys Val Val Gln Asn Ala Asp Val Leu Ile Leu
                260                 265                 270
Ile Gly Ala Arg Ala Ser Asp Arg Thr Val Ser Gly Val Lys Ser Phe
                275                 280                 285
Ala Lys Asp Ala Asp Ile Ile His Ile Asp Ile Asp Pro Ala Glu Ile
                290                 295                 300
Gly Lys Ile Leu Asn Thr Tyr Ile Pro Val Val Gly Asp Cys Gly Ser
305                 310                 315                 320
Val Leu Ser Asp Leu Asn Lys Glu Ile Val Ala Pro Gln Thr Glu Lys
                325                 330                 335
Trp Met Glu Glu Ile Lys Asn Trp Lys Lys Asp Leu Tyr Ile Glu Arg
                340                 345                 350
Lys Pro Thr Asp Lys Val Asn Pro Lys Tyr Val Leu Lys Thr Val Ser
                355                 360                 365
Asp Thr Leu Gly Glu Glu Val Ile Leu Thr Ala Asp Val Gly Gln Asn
                370                 375                 380
Gln Leu Trp Cys Ala Arg Asn Phe Arg Met Thr Gly Asn Arg Lys Phe
385                 390                 395                 400
Leu Thr Ser Gly Gly Leu Gly Thr Met Gly Tyr Ser Leu Pro Ala Ala
                405                 410                 415
Ile Gly Ala Lys Ile Ala Cys Pro Asp Lys Gln Val Ile Ala Phe Ala
                420                 425                 430
Gly Asp Gly Gly Phe Gln Met Ser Leu Phe Glu Leu Gly Thr Ile Ala
                435                 440                 445
```

```
Glu Asn Asn Leu Asn Ile Ile Ile Val Leu Phe Asn Ser Gly Leu
    450                 455                 460

Gly Met Val Arg Glu Ile Gln Asp Asn Lys Tyr Ser Gly Glu Phe Gly
465                 470                 475                 480

Val Asn Phe Arg Thr Asn Pro Asp Phe Val Lys Leu Ala Glu Ala Tyr
                485                 490                 495

Gly Leu Lys Ala Lys Arg Val Glu Asn Asp Ser Glu Phe Asn Gly Val
                500                 505                 510

Phe Arg Glu Ala Leu Asp Ser Ser Lys Ala Phe Leu Ile Glu Cys Ile
                515                 520                 525

Val Asp Pro His Glu Arg Thr Phe
    530                 535

<210> SEQ ID NO 33
<211> LENGTH: 558
<212> TYPE: PRT
<213> ORGANISM: Clostridium autoethanogenum
<220> FEATURE:
<221> NAME/KEY: MISC_FEATURE
<223> OTHER INFORMATION: IlvB, AGY74635.1

<400> SEQUENCE: 33

Met Lys Ile Lys Gly Ala Glu Val Leu Leu Lys Cys Met Met Glu Gln
1               5                   10                  15

Gly Val Asp Thr Val Phe Gly Tyr Pro Gly Ala Val Leu Pro Ile
                20                  25                  30

Tyr Asp Ala Leu Tyr Ala Ala Lys Gly Lys Ile Thr His Ile Ser Thr
                35                  40                  45

Ser His Glu Gln Gly Ala Ala His Ala Ala Asp Gly Tyr Ala Arg Ser
            50                  55                  60

Thr Gly Lys Val Gly Val Val Ile Ala Thr Ser Gly Pro Gly Ala Thr
65              70                  75                  80

Asn Thr Val Thr Ala Ile Ala Thr Ala Tyr Met Asp Ser Val Pro Ile
                85                  90                  95

Val Val Phe Thr Gly Gln Val Ala Arg Ser Leu Leu Gly Lys Asp Ser
            100                 105                 110

Phe Gln Glu Val Asn Ile Lys Asp Ile Thr Ala Ser Ile Thr Lys Lys
            115                 120                 125

Ser Cys Ile Val Glu Lys Val Glu Asp Leu Ala Asp Thr Val Arg Glu
        130                 135                 140

Ala Phe Gln Ile Ala Val Ser Gly Arg Pro Gly Pro Val Val Val Asp
145                 150                 155                 160

Ile Pro Lys Asp Val Gln Ser Ala Glu Val Glu Tyr Glu Pro Phe Arg
                165                 170                 175

Ser Lys Leu Ser Glu Ile Lys Glu Lys Lys Tyr Phe Asn Leu Asn Glu
            180                 185                 190

Tyr Gly Asp Ser Leu Asn Lys Ala Ile Asp Met Ile Asn Arg Ser Glu
        195                 200                 205

Arg Pro Val Ile Tyr Ser Gly Gly Thr Val Thr Ser Gly Ala Gln
    210                 215                 220

Asn Glu Leu Met Glu Leu Val Glu Lys Ile Asp Ser Pro Ile Thr Cys
225                 230                 235                 240

Ser Leu Met Gly Ile Gly Ala Phe Pro Gly Asn Asn Glu Tyr Tyr Met
                245                 250                 255

Gly Met Val Gly Met His Gly Ser Arg Cys Ser Asn Tyr Ala Val Ser
```

```
                260             265             270
Asn Cys Asp Leu Leu Ile Ala Ile Gly Ala Arg Phe Ser Asp Arg Val
            275                 280                 285

Ile Ser Lys Val Ser Ala Phe Ala Pro Lys Ala Arg Ile Ile His Ile
        290                 295                 300

Asp Ile Asp Pro Lys Glu Phe Gly Lys Asn Val Asp Ile Asp Val Ala
305                 310                 315                 320

Ile Lys Gly Asp Val Lys Glu Val Leu Gln Lys Ile Asn Cys Lys Leu
                325                 330                 335

Glu Lys Ala Asp His Arg Asp Trp Met Glu Lys Ile Lys Gln Trp Lys
            340                 345                 350

Ser Glu Gln Cys Glu Pro Phe Lys Glu Cys Lys Leu Ser Pro Lys Phe
        355                 360                 365

Ile Met Asp Thr Leu Tyr Asn Leu Thr Gly Gly Glu Cys Ile Ile Thr
    370                 375                 380

Thr Glu Val Gly Gln Asn Gln Ile Trp Thr Ala Gln Tyr Phe Lys Phe
385                 390                 395                 400

Leu Lys Pro Arg Thr Phe Val Ser Ser Gly Leu Gly Thr Met Gly
                405                 410                 415

Phe Gly Leu Gly Ala Ser Ile Gly Ala Ser Met Gly Asn Pro Gly Lys
            420                 425                 430

Lys Val Ile Asn Val Ala Gly Asp Gly Ser Phe Lys Met Asn Ser Thr
        435                 440                 445

Glu Leu Ala Thr Val Ala Lys Tyr Lys Leu Pro Ile Val Gln Leu Leu
    450                 455                 460

Leu Asn Asn Arg Ala Leu Gly Met Val Tyr Gln Trp Gln Asp Met Phe
465                 470                 475                 480

Tyr Gly Lys Arg Phe Ser Asn Thr Glu Leu Gly Pro Asp Val Asp Phe
                485                 490                 495

Met Lys Leu Gly Glu Ala Tyr Gly Ile Lys Thr Phe Lys Ile Glu Asp
            500                 505                 510

Asn Ser Gln Val Glu Lys Cys Leu Lys Glu Ala Leu Asp Leu Asn Glu
        515                 520                 525

Pro Val Ile Ile Glu Cys Asp Ile Asp Arg Lys Glu Lys Val Phe Pro
    530                 535                 540

Ile Val Pro Pro Gly Ala Ala Ile Ser Asp Leu Val Glu Glu
545                 550                 555
```

<210> SEQ ID NO 34
<211> LENGTH: 158
<212> TYPE: PRT
<213> ORGANISM: Clostridium autoethanogenum
<220> FEATURE:
<221> NAME/KEY: MISC_FEATURE
<223> OTHER INFORMATION: IlvN, AGY74360.1

<400> SEQUENCE: 34

```
Met Ser Val Leu Val Glu Asn His Ser Gly Val Leu Ser Lys Val Ala
1               5                   10                  15

Gly Leu Phe Ser Arg Arg Gly Tyr Asn Ile His Ser Leu Thr Val Gly
            20                  25                  30

Val Thr Gly Asp Pro Glu Ile Ser Arg Met Thr Ile Val Ser Ile Gly
        35                  40                  45

Asp Asp Tyr Met Phe Glu Gln Ile Ser Lys Gln Leu Asn Lys Leu Ile
    50                  55                  60
```

```
Glu Val Ile Lys Val Ile Glu Leu Asn Pro Asp Ala Ser Val Tyr Arg
 65                  70                  75                  80

Glu Leu Ser Leu Ile Lys Val Ser Ala Glu Ser Asn Asn Lys Leu Leu
                 85                  90                  95

Ile Met Glu Ser Val Asn Thr Phe Arg Gly Lys Ile Val Asp Met Asn
            100                 105                 110

Glu Lys Ser Met Ile Ile Glu Ile Thr Gly Asn Glu Lys Lys Ile Ser
        115                 120                 125

Ala Phe Ile Glu Leu Met Lys Pro Tyr Gly Ile Lys Glu Ile Ile Arg
    130                 135                 140

Thr Gly Leu Thr Ala Leu Gln Arg Gly Ser Lys Leu Glu Asp
145                 150                 155
```

<210> SEQ ID NO 35
<211> LENGTH: 562
<212> TYPE: PRT
<213> ORGANISM: Escherichia coli
<220> FEATURE:
<221> NAME/KEY: MISC_FEATURE
<223> OTHER INFORMATION: IlvB, NP_418127.1

<400> SEQUENCE: 35

```
Met Ala Ser Ser Gly Thr Thr Ser Thr Arg Lys Arg Phe Thr Gly Ala
  1               5                  10                  15

Glu Phe Ile Val His Phe Leu Glu Gln Gln Gly Ile Lys Ile Val Thr
                 20                  25                  30

Gly Ile Pro Gly Gly Ser Ile Leu Pro Val Tyr Asp Ala Leu Ser Gln
             35                  40                  45

Ser Thr Gln Ile Arg His Ile Leu Ala Arg His Glu Gln Gly Ala Gly
 50                  55                  60

Phe Ile Ala Gln Gly Met Ala Arg Thr Asp Gly Lys Pro Ala Val Cys
 65                  70                  75                  80

Met Ala Cys Ser Gly Pro Gly Ala Thr Asn Leu Val Thr Ala Ile Ala
                 85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
        195                 200                 205

Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270
```

-continued

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
        290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
        340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
        370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
        420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
                500                 505                 510

Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
        530                 535                 540

Lys Val Tyr Pro Met Val Pro Pro Gly Ala Ala Asn Thr Glu Met Val
545                 550                 555                 560

Gly Glu

<210> SEQ ID NO 36
<211> LENGTH: 96
<212> TYPE: PRT
<213> ORGANISM: Escherichia coli
<220> FEATURE:
<221> NAME/KEY: MISC_FEATURE
<223> OTHER INFORMATION: IlvN, NP_418126.1

<400> SEQUENCE: 36

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
                20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

```
Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95
```

<210> SEQ ID NO 37
<211> LENGTH: 337
<212> TYPE: PRT
<213> ORGANISM: Clostridium autoethanogenum
<220> FEATURE:
<221> NAME/KEY: MISC_FEATURE
<223> OTHER INFORMATION: IlvC, WP_013238693.1

<400> SEQUENCE: 37

```
Met Glu Lys Leu Lys Val Tyr Tyr Asp Glu Asp Ala Asp Leu Asn Leu
1               5                   10                  15

Leu Lys Gly Lys Lys Ile Ala Ile Leu Gly Phe Gly Ser Gln Gly His
                20                  25                  30

Ala His Ala Leu Asn Leu Lys Glu Ser Gly Leu Asp Val Ile Val Gly
            35                  40                  45

Leu Tyr Lys Gly Ser Lys Ser Trp Lys Lys Ala Glu Asp Tyr Gly Phe
50                  55                  60

Lys Val Tyr Glu Ile Ala Glu Ala Val Lys Gln Ala Asp Ile Ile Thr
65                  70                  75                  80

Val Leu Leu Pro Asp Glu Lys Gln Lys Gln Ile Tyr Asp Glu Ser Ile
                85                  90                  95

Lys Asp Asn Leu Ser Glu Gly Asn Ala Leu Phe Phe Ala His Gly Phe
            100                 105                 110

Asn Ile His Phe Asn Gln Ile Val Pro Pro Lys Phe Val Asp Val Leu
        115                 120                 125

Met Ile Ala Pro Lys Gly Pro Gly His Ile Val Arg Arg Glu Tyr Thr
130                 135                 140

Leu Gly Asn Gly Val Pro Cys Leu Tyr Ala Val Tyr Gln Asp Tyr Ser
145                 150                 155                 160

Gly Lys Gly Lys Glu Ile Ala Leu Ala Tyr Gly Lys Gly Ile Gly Gly
                165                 170                 175

Thr Arg Ala Gly Val Met Thr Thr Thr Phe Lys Val Glu Thr Glu Thr
            180                 185                 190

Asp Leu Phe Gly Glu Gln Val Val Leu Cys Gly Gly Val Ala Glu Leu
        195                 200                 205

Ile Lys Ala Gly Phe Asp Thr Leu Val Glu Ala Gly Tyr Ala Pro Glu
210                 215                 220

Asn Ala Tyr Phe Glu Cys Leu His Glu Met Lys Leu Ile Val Asp Leu
225                 230                 235                 240

Ile Tyr Glu Gly Gly Leu Ala Arg Met Arg Tyr Ser Val Ser Asp Thr
                245                 250                 255

Ala Glu Tyr Gly Asp Tyr Lys Ile Gly Lys Arg Ile Ile Asn Asp Asn
            260                 265                 270

Thr Arg Ala Glu Met Lys Lys Val Leu Thr Glu Ile Gln Asp Gly Thr
        275                 280                 285

Phe Ala Arg Glu Trp Leu Leu Glu Asn Gln Thr Gly Arg Pro Gly Phe
290                 295                 300

Thr Ala Arg Arg Arg Met Glu Lys Asp Ala Pro Ile Glu Lys Val Gly
305                 310                 315                 320

Lys Glu Leu Arg Ser Met Met Ser Trp Ile Asn Glu Asn Pro Asp Asn
```

```
                325                 330                 335

Glu

<210> SEQ ID NO 38
<211> LENGTH: 491
<212> TYPE: PRT
<213> ORGANISM: Escherichia coli
<220> FEATURE:
<221> NAME/KEY: MISC_FEATURE
<223> OTHER INFORMATION: IlvC, NP_418222.1

<400> SEQUENCE: 38

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
    35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
```

```
                340             345             350
Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 39
<211> LENGTH: 552
<212> TYPE: PRT
<213> ORGANISM: Clostridium autoethanogenum
<220> FEATURE:
<221> NAME/KEY: MISC_FEATURE
<223> OTHER INFORMATION: IlvD, WP_013238694.1

<400> SEQUENCE: 39

Met Lys Ser Asp Ser Val Lys Lys Gly Ile Lys Ala Ala Pro Ala Arg
1               5                   10                  15

Ala Leu Met Tyr Gly Met Gly Tyr Thr Lys Glu Glu Ile Glu Arg Pro
            20                  25                  30

Leu Ile Gly Ile Val Asn Ser Gln Asn Glu Ile Val Ala Gly His Met
        35                  40                  45

His Leu Asp Glu Ile Ala Lys Ala Ala Lys Leu Gly Val Ala Met Ser
    50                  55                  60

Gly Gly Thr Pro Ile Glu Phe Pro Ala Ile Ala Val Cys Asp Gly Ile
65                  70                  75                  80

Ala Met Gly His Val Gly Met Lys Tyr Ser Leu Ala Ser Arg Glu Leu
                85                  90                  95

Ile Ala Asp Ser Ile Glu Ala Met Ala Thr Ala His Gly Phe Asp Gly
            100                 105                 110

Leu Val Leu Ile Pro Asn Cys Asp Lys Ile Val Pro Gly Met Leu Met
        115                 120                 125

Ala Ala Ala Arg Leu Asn Ile Pro Ala Val Val Val Ser Gly Gly Pro
    130                 135                 140

Met Arg Ala Gly Lys Leu Asn Asn Lys Ala Leu Asp Phe Ser Thr Cys
145                 150                 155                 160

Ile Glu Lys Val Ala Ala Cys Ser Asp Gly Lys Val Thr Glu Glu Glu
                165                 170                 175

Leu Glu Glu Glu Ala Lys Arg Ala Cys Pro Gly Cys Gly Ser Cys Ser
            180                 185                 190

Gly Leu Phe Thr Ala Asn Ser Met Asn Ser Leu Thr Glu Val Leu Gly
        195                 200                 205
```

```
Met Gly Leu Pro Leu Asn Gly Ser Ala Leu Ala Gln Thr Gly Glu Arg
    210                 215                 220

Asn Gln Leu Ala Lys Tyr Ala Gly Met Tyr Val Met Asp Cys Val Lys
225                 230                 235                 240

Asn Asp Arg Arg Pro Arg Asp Ile Leu Thr Leu Asp Ala Phe Lys Asn
                245                 250                 255

Ala Ile Thr Val Asp Met Ala Met Ala Gly Ser Thr Asn Thr Val Leu
                260                 265                 270

His Leu Pro Ala Ile Ala His Glu Ala Gly Ile Glu Leu Asn Leu Asp
            275                 280                 285

Leu Phe His Glu Ile Ser Lys His Thr Pro Cys Leu Thr Lys Leu Ser
    290                 295                 300

Pro Ser Gly Lys His His Met Glu Asp Leu His Leu Ala Gly Gly Ile
305                 310                 315                 320

Pro Ala Leu Met Asn Glu Leu Ser Lys Lys Gly Leu Ile Asn Glu Asp
                325                 330                 335

Ala Leu Thr Val Thr Gly Lys Thr Val Gly Glu Thr Ile Lys Asp Phe
                340                 345                 350

Lys Val Leu Asp Tyr Glu Val Ile Arg Ser Val Asp Asn Ala Tyr Ser
            355                 360                 365

Ser Glu Gly Gly Ile Ala Ile Leu Arg Gly Asn Leu Ala Pro Asp Gly
    370                 375                 380

Ala Val Val Lys Glu Ser Ala Val Ser Lys Glu Met Met Val His Glu
385                 390                 395                 400

Gly Pro Ala Arg Val Tyr Asn Ser Glu Glu Ala Ala Val Lys Ala Ile
                405                 410                 415

Phe Gly Asn Glu Ile Asn Lys Gly Asp Val Ile Val Ile Arg Tyr Glu
                420                 425                 430

Gly Pro Lys Gly Gly Pro Gly Met Arg Glu Met Leu Ser Pro Thr Ser
            435                 440                 445

Ala Ile Ala Gly Met Gly Leu Asp Lys Asp Val Ala Leu Leu Thr Asp
    450                 455                 460

Gly Arg Phe Ser Gly Ala Thr Arg Gly Ala Ser Ile Gly His Val Ser
465                 470                 475                 480

Pro Glu Ala Met Glu Gly Gly Leu Ile Gly Leu Val Glu Glu Gly Asp
                485                 490                 495

Thr Ile Phe Val Asp Ile Thr Asn Lys Lys Leu Glu Leu Lys Val Ser
                500                 505                 510

Glu Glu Glu Leu Glu Lys Arg Arg Lys Asn Tyr Val Lys Pro Glu Pro
            515                 520                 525

Lys Ile Lys Thr Gly Tyr Leu Ser Arg Tyr Ala Lys Leu Val Thr Ser
    530                 535                 540

Ala Asn Thr Gly Ala Val Leu Lys
545                 550
```

<210> SEQ ID NO 40
<211> LENGTH: 616
<212> TYPE: PRT
<213> ORGANISM: Escherichia coli
<220> FEATURE:
<221> NAME/KEY: MISC_FEATURE
<223> OTHER INFORMATION: IlvD, YP_026248.1

<400> SEQUENCE: 40

```
Met Pro Lys Tyr Arg Ser Ala Thr Thr Thr His Gly Arg Asn Met Ala
1               5                   10                  15
```

-continued

Gly Ala Arg Ala Leu Trp Arg Ala Thr Gly Met Thr Asp Ala Asp Phe
                20                  25                  30
Gly Lys Pro Ile Ile Ala Val Val Asn Ser Phe Thr Gln Phe Val Pro
            35                  40                  45
Gly His Val His Leu Arg Asp Leu Gly Lys Leu Val Ala Glu Gln Ile
        50                  55                  60
Glu Ala Ala Gly Gly Val Ala Lys Glu Phe Asn Thr Ile Ala Val Asp
 65                  70                  75                  80
Asp Gly Ile Ala Met Gly His Gly Gly Met Leu Tyr Ser Leu Pro Ser
                85                  90                  95
Arg Glu Leu Ile Ala Asp Ser Val Glu Tyr Met Val Asn Ala His Cys
            100                 105                 110
Ala Asp Ala Met Val Cys Ile Ser Asn Cys Asp Lys Ile Thr Pro Gly
        115                 120                 125
Met Leu Met Ala Ser Leu Arg Leu Asn Ile Pro Val Ile Phe Val Ser
130                 135                 140
Gly Gly Pro Met Glu Ala Gly Lys Thr Lys Leu Ser Asp Gln Ile Ile
145                 150                 155                 160
Lys Leu Asp Leu Val Asp Ala Met Ile Gln Gly Ala Asp Pro Lys Val
                165                 170                 175
Ser Asp Ser Gln Ser Asp Gln Val Glu Arg Ser Ala Cys Pro Thr Cys
            180                 185                 190
Gly Ser Cys Ser Gly Met Phe Thr Ala Asn Ser Met Asn Cys Leu Thr
        195                 200                 205
Glu Ala Leu Gly Leu Ser Gln Pro Gly Asn Gly Ser Leu Leu Ala Thr
    210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
            260                 265                 270
Ile Ala Met Gly Gly Ser Thr Asn Thr Val Leu His Leu Leu Ala Ala
        275                 280                 285
Ala Gln Glu Ala Glu Ile Asp Phe Thr Met Ser Asp Ile Asp Lys Leu
    290                 295                 300
Ser Arg Lys Val Pro Gln Leu Cys Lys Val Ala Pro Ser Thr Gln Lys
305                 310                 315                 320
Tyr His Met Glu Asp Val His Arg Ala Gly Gly Val Ile Gly Ile Leu
                325                 330                 335
Gly Glu Leu Asp Arg Ala Gly Leu Leu Asn Arg Asp Val Lys Asn Val
            340                 345                 350
Leu Gly Leu Thr Leu Pro Gln Thr Leu Glu Gln Tyr Asp Val Met Leu
        355                 360                 365
Thr Gln Asp Asp Ala Val Lys Asn Met Phe Arg Ala Gly Pro Ala Gly
    370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
            420                 425                 430

-continued

```
Gly Cys Ile Val Lys Thr Ala Gly Val Asp Asp Ser Ile Leu Lys Phe
            435                 440                 445

Thr Gly Pro Ala Lys Val Tyr Glu Ser Gln Asp Ala Val Glu Ala
450                 455                 460

Ile Leu Gly Gly Lys Val Val Ala Gly Asp Val Val Ile Arg Tyr
465                 470                 475                 480

Glu Gly Pro Lys Gly Pro Gly Met Gln Glu Met Leu Tyr Pro Thr
            485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
            515                 520                 525

Ser Pro Glu Ala Ala Ser Gly Gly Ser Ile Gly Leu Ile Glu Asp Gly
530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
            565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
            595                 600                 605

Arg Asp Lys Ser Lys Leu Gly Gly
        610                 615
```

<210> SEQ ID NO 41
<211> LENGTH: 477
<212> TYPE: PRT
<213> ORGANISM: Methanothermobacter thermautotrophicus
<220> FEATURE:
<221> NAME/KEY: MISC_FEATURE
<223> OTHER INFORMATION: VorA, WP_010876344.1

<400> SEQUENCE: 41

```
Met Thr Lys Lys Val Ile Arg Lys Pro Asp Ser Leu His Asp Val Phe
1               5                   10                  15

Glu Arg Lys Gly Gly Ser Ala Pro Thr Ala Thr His Tyr Cys Ala Gly
            20                  25                  30

Cys Gly His Gly Ile Leu His Lys Leu Ile Gly Glu Ala Met Asp Glu
        35                  40                  45

Leu Gly Ile Gln Glu Arg Ala Val Met Ile Ser Pro Val Gly Cys Ala
    50                  55                  60

Val Phe Ala Tyr Tyr Tyr Phe Asp Cys Gly Asn Val Gln Val Ala His
65                  70                  75                  80

Gly Arg Ala Pro Ala Val Gly Thr Gly Ile Ser Arg Ala Glu Asp Asp
                85                  90                  95

Ala Val Val Ile Leu Tyr Gln Gly Asp Gly Asp Leu Ala Ser Ile Gly
            100                 105                 110

Leu Asn Glu Thr Ile Gln Ala Ala Asn Arg Gly Glu Lys Leu Ala Val
        115                 120                 125

Phe Phe Val Asn Asn Thr Val Tyr Gly Met Thr Gly Gly Gln Met Ala
    130                 135                 140

Pro Thr Thr Leu Val Gly Glu Val Thr Val Thr Cys Pro Thr Gly Arg
145                 150                 155                 160

Asp Pro Arg Tyr Ala Gly Tyr Pro Leu His Met Cys Glu Leu Leu Asp
                165                 170                 175
```

```
Asn Leu Gln Ala Pro Val Phe Ile Glu Arg Val Ser Leu Ala Asp Pro
            180                 185                 190

Lys Arg Ile Arg Arg Ala Arg Arg Ala Ile Lys Arg Ala Leu Glu Ile
        195                 200                 205

Gln Arg Asp Gly Lys Gly Tyr Ala Phe Val Glu Val Leu Ser Pro Cys
    210                 215                 220

Pro Thr Asn Leu Arg Gln Asp Ala Glu Gly Ala Glu Arg Phe Leu Lys
225                 230                 235                 240

Glu Glu Met Glu Lys Glu Phe Pro Val Lys Asn Phe Arg Asp Arg Ser
            245                 250                 255

Ala Glu Thr Glu Pro Leu Ile Arg Ser Glu Ser Asp Phe Ser Arg Glu
        260                 265                 270

Ser Leu Asp Arg Ile Phe Gln Ile Arg Glu Asp Ser Val Pro Asp Pro
    275                 280                 285

Val Asp Asp Pro Glu Phe Pro Glu Val Arg Val Lys Ile Ala Gly Phe
290                 295                 300

Gly Gly Gln Gly Val Leu Ser Met Gly Leu Thr Leu Ala Gln Ala Ala
305                 310                 315                 320

Cys Ser Glu Gly Arg His Thr Ser Trp Tyr Pro Ala Tyr Gly Pro Glu
            325                 330                 335

Gln Arg Gly Gly Thr Ser Ser Cys Gly Val Val Ile Ser Gly Glu Arg
        340                 345                 350

Val Gly Ser Pro Ala Val Asp Thr Pro Asp Val Leu Val Ala Leu Asn
    355                 360                 365

Gln Pro Ser Leu Asp Glu Phe Ala Asp Val Ala Asp Gly Gly Ile
    370                 375                 380

Ile Leu Tyr Asp Ser Thr Thr Ala Ser Phe Ser Gly Gly Ala Val Arg
385                 390                 395                 400

Ala Met Gly Val Pro Ala Leu Glu Ile Ala Arg Lys His Gly Thr Ala
            405                 410                 415

Arg Ala Ala Asn Thr Val Met Leu Gly Val Met Met Ala Leu Gly Leu
        420                 425                 430

Thr Gly Leu Asp Glu Glu Ser Phe Arg Glu Ala Ile Lys Phe Thr Phe
    435                 440                 445

Ala Gly Lys Glu Lys Ile Ile Asp Met Asn Leu Arg Ile Leu Glu Ala
    450                 455                 460

Gly Ala Glu Trp Ala Arg Glu Asn Ile Glu Gly Glu Leu
465                 470                 475

<210> SEQ ID NO 42
<211> LENGTH: 352
<212> TYPE: PRT
<213> ORGANISM: Methanothermobacter thermautotrophicus
<220> FEATURE:
<221> NAME/KEY: MISC_FEATURE
<223> OTHER INFORMATION: VorB, WP_010876343.1

<400> SEQUENCE: 42

Met Ala Thr Gln Met Val Lys Gly Asn Thr Ala Val Ile Ile Gly Ala
1               5                   10                  15

Met Tyr Ala Gly Cys Asp Cys Tyr Phe Gly Tyr Pro Ile Thr Pro Ala
            20                  25                  30

Ser Glu Ile Leu His Glu Ala Ser Arg Tyr Phe Pro Met Val Gly Arg
        35                  40                  45

Lys Phe Val Gln Ala Glu Ser Glu Glu Ala Ala Ile Asn Met Val Tyr
```

```
            50                  55                  60
Gly Ala Ala Ala Gly His Arg Val Met Thr Ala Ser Ser Gly Pro
 65                  70                  75                  80

Gly Ile Ser Leu Lys Gln Glu Gly Ile Ser Phe Leu Ala Gly Ala Glu
                 85                  90                  95

Leu Pro Ala Val Ile Val Asp Val Met Arg Ala Gly Pro Gly Leu Gly
                100                 105                 110

Asn Ile Gly Pro Glu Gln Gly Asp Tyr Asn Gln Ile Val Lys Gly Gly
                115                 120                 125

Gly His Gly Asn Tyr Arg Asn Met Val Leu Ala Pro Ser Ser Val Gln
            130                 135                 140

Glu Met Cys Asp Leu Thr Met Glu Ala Phe Glu Leu Ala Asp Lys Tyr
145                 150                 155                 160

Arg Asn Pro Val Val Leu Thr Asp Ala Val Leu Gly Gln Met Ala
                165                 170                 175

Glu Pro Leu Arg Phe Pro Glu Glu Ala Val Glu His Arg Pro Asp Thr
                180                 185                 190

Ser Trp Ala Val Cys Gly Asn Arg Glu Thr Met Lys Asn Leu Val Thr
            195                 200                 205

Ser Ile Phe Leu Asp Phe Asp Glu Leu Glu Glu Phe Asn Phe Tyr Leu
            210                 215                 220

Gln Glu Lys Tyr Ala Arg Ile Glu Glu Asn Glu Val Arg Tyr Glu Glu
225                 230                 235                 240

Tyr Leu Val Asp Asp Ala Glu Ile Val Met Val Ala Tyr Gly Ile Ser
                245                 250                 255

Ser Arg Val Ala Arg Ser Ala Val Glu Thr Ala Arg Ala Glu Gly Ile
            260                 265                 270

Asn Val Gly Leu Leu Arg Pro Ile Thr Leu Phe Pro Phe Pro Ser Asp
            275                 280                 285

Arg Ile Arg Glu Leu Ala Asp Gly Gly Cys Arg Phe Ile Ser Val Glu
            290                 295                 300

Met Ser Ser Gly Gln Met Arg Glu Asp Ile Arg Met Ala Ser Gly Cys
305                 310                 315                 320

Arg Asp Val Glu Leu Val Asn Arg Met Gly Gly Asn Leu Ile Glu Leu
                325                 330                 335

Arg Asp Val Leu Glu Lys Ile Arg Glu Val Ala Gly Asp Ser Ser Asp
            340                 345                 350

<210> SEQ ID NO 43
<211> LENGTH: 79
<212> TYPE: PRT
<213> ORGANISM: Methanothermobacter thermautotrophicus
<220> FEATURE:
<221> NAME/KEY: MISC_FEATURE
<223> OTHER INFORMATION: VorC, WP_010876342.1

<400> SEQUENCE: 43

Met Lys Lys Ala Tyr Pro Val Ile Asn Ser Val Glu Cys Lys Ala Cys
 1                5                  10                  15

Glu Arg Cys Ile Ile Ala Cys Pro Arg Lys Val Leu Gln Met Ser Ser
                 20                  25                  30

Lys Ile Asn Glu Arg Gly Tyr His Tyr Val Glu Tyr Arg Gly Glu Gly
             35                  40                  45

Cys Asn Gly Cys Gly Asn Cys Tyr Tyr Thr Cys Pro Glu Ile Asn Ala
 50                  55                  60
```

Ile Glu Val His Ile Glu Arg Cys Glu Asp Gly Asn Thr Asp Gly
65                  70                  75

<210> SEQ ID NO 44
<211> LENGTH: 124
<212> TYPE: PRT
<213> ORGANISM: Methanothermobacter thermautotrophicus
<220> FEATURE:
<221> NAME/KEY: MISC_FEATURE
<223> OTHER INFORMATION: VorD, WP_010876341.1

<400> SEQUENCE: 44

Met Asp Glu Asp Gly Tyr Met Trp Phe Val Gly Arg Thr Asp Ile
1               5                   10                  15

Ile Lys Ser Ser Gly Tyr Arg Ile Gly Pro Phe Glu Val Glu Ser Ala
                20                  25                  30

Ile Ile Ser His Pro Ser Val Leu Glu Cys Ala Val Thr Gly Tyr Pro
            35                  40                  45

Asp Pro Ile Arg Gly Gln Val Val Lys Ala Thr Ile Val Leu Ala Arg
        50                  55                  60

Gly Tyr Glu Pro Ser Glu Glu Leu Lys Lys Glu Ile Gln Asp His Val
65                  70                  75                  80

Lys Arg Val Thr Ala Pro Tyr Lys Tyr Pro Arg Ile Val Glu Phe Val
                85                  90                  95

Asp Glu Leu Pro Lys Thr Ile Ser Gly Lys Ile Arg Arg Val Glu Ile
            100                 105                 110

Arg Glu His Asp Leu Glu Gly Asp Gly Glu Asn Pro
        115                 120

<210> SEQ ID NO 45
<211> LENGTH: 394
<212> TYPE: PRT
<213> ORGANISM: Pyrococcus furiosus
<220> FEATURE:
<221> NAME/KEY: MISC_FEATURE
<223> OTHER INFORMATION: VorA, WP_011012106.1

<400> SEQUENCE: 45

Met Glu Tyr Lys Pro Ile Arg Lys Val Val Ser Gly Asn Tyr Ala Ala
1               5                   10                  15

Ala Tyr Ala Ala Leu His Ala Arg Val Gln Val Val Ala Ala Tyr Pro
                20                  25                  30

Ile Thr Pro Gln Thr Ser Ile Ile Glu Lys Ile Ala Glu Phe Ile Ala
            35                  40                  45

Asn Gly Glu Ala Asp Ile Gln Tyr Ile Pro Val Glu Ser Glu His Ser
        50                  55                  60

Ala Met Ala Ala Cys Ile Gly Ala Ser Ala Thr Gly Ala Arg Thr Phe
65                  70                  75                  80

Thr Ala Thr Ser Ala Gln Gly Leu Ala Leu Met His Glu Met Leu His
                85                  90                  95

Trp Ala Ala Gly Ala Arg Leu Pro Ile Val Met Val Asp Val Asn Arg
            100                 105                 110

Ala Met Ala Pro Pro Trp Ser Val Trp Asp Asp Gln Thr Asp Ser Leu
        115                 120                 125

Ser Gln Arg Asp Thr Gly Trp Met Gln Phe Tyr Ala Glu Asn Asn Gln
        130                 135                 140

Glu Val Tyr Asp Gly Val Leu Met Ala Tyr Lys Val Ala Glu Thr Val
145                 150                 155                 160

-continued

Asn Val Pro Ala Met Val Glu Ser Ala Phe Ile Leu Ser His Thr
            165                 170                 175

Tyr Asp Val Val Glu Met Ile Pro Gln Glu Leu Val Asp Glu Phe Leu
        180                 185                 190

Pro Pro Arg Lys Pro Leu Tyr Ser Leu Ala Asn Phe Asp Glu Pro Ile
    195                 200                 205

Ala Val Gly Ala Leu Ala Thr Pro Asn Asp Tyr Tyr Glu Phe Arg Tyr
210                 215                 220

Lys Leu Ala Lys Ala His Glu Glu Ala Lys Lys Val Ile Lys Glu Val
225                 230                 235                 240

Gly Lys Glu Phe Gly Glu Arg Phe Gly Arg Asp Tyr Ser Gln Met Ile
            245                 250                 255

Glu Thr Gly Tyr Ile Asp Asp Ala Asp Phe Val Phe Met Gly Met Gly
        260                 265                 270

Ser Leu Met Gly Thr Val Lys Glu Ala Val Asp Leu Leu Arg Lys Glu
    275                 280                 285

Gly Tyr Lys Val Gly Tyr Ala Lys Val Arg Trp Phe Arg Pro Phe Pro
290                 295                 300

Lys Glu Glu Leu Val Glu Ile Ala Glu Ser Val Lys Gly Ile Ala Val
305                 310                 315                 320

Leu Asp Arg Asn Phe Ser Phe Gly Gln Glu Gly Ile Leu Phe Thr Glu
            325                 330                 335

Ser Lys Gly Ala Leu Tyr Asn Ser Ser Ala His Pro Leu Met Lys Asn
        340                 345                 350

Tyr Ile Val Gly Leu Gly Gly Arg Asp Val Thr Val Lys Asp Ile Lys
    355                 360                 365

Ala Ile Ala Asp Asp Met Lys Lys Val Ile Glu Ser Gly Lys Val Asp
370                 375                 380

Lys Glu Val Val Trp Tyr His Leu Lys Arg
385                 390

<210> SEQ ID NO 46
<211> LENGTH: 311
<212> TYPE: PRT
<213> ORGANISM: Pyrococcus furiosus
<220> FEATURE:
<221> NAME/KEY: MISC_FEATURE
<223> OTHER INFORMATION: VorB, WP_011012105.1

<400> SEQUENCE: 46

Met Glu Val Pro Glu Asn Ile Lys Lys Arg Val Thr Ile Pro Phe Glu
1               5                   10                  15

Glu His Phe Tyr Ala Gly His Thr Ala Cys Gln Gly Cys Gly Ala Ser
            20                  25                  30

Leu Gly Leu Arg Tyr Val Leu Lys Ala Tyr Gly Lys Lys Thr Ile Leu
        35                  40                  45

Val Ile Pro Ala Cys Cys Ser Thr Ile Ile Ala Gly Pro Trp Pro Tyr
    50                  55                  60

Ser Ala Ile Asp Ala Asn Leu Phe His Thr Ala Phe Glu Thr Thr Gly
65                  70                  75                  80

Ala Val Ile Ser Gly Ile Glu Ala Leu Lys Ala Met Gly Tyr Lys
            85                  90                  95

Val Lys Gly Glu Asp Gly Ile Met Val Val Gly Trp Ala Gly Asp Gly
        100                 105                 110

Gly Thr Ala Asp Ile Gly Leu Gln Ala Leu Ser Gly Phe Leu Glu Arg
    115                 120                 125

```
Gly His Asp Ala Val Tyr Ile Met Tyr Asp Asn Glu Ala Tyr Met Asn
            130                 135                 140

Thr Gly Ile Gln Arg Ser Ser Thr Pro Tyr Gly Ala Trp Thr Thr
145                 150                 155                 160

Asn Thr Pro Gly Gly Arg Arg His Phe Leu Glu Lys Arg His Lys Lys
                165                 170                 175

Lys Val Ile Asp Ile Val Ile Ala His Arg Ile Pro Tyr Ala Ala Thr
            180                 185                 190

Ala Ser Ile Ala Tyr Pro Glu Asp Phe Ile Arg Lys Leu Lys Lys Ala
            195                 200                 205

Gln Lys Ile Ser Gly Pro Ser Phe Ile Gln Leu Phe Ala Pro Cys Pro
    210                 215                 220

Thr Gly Trp Arg Ala Pro Thr Asp Lys Ser Ile Glu Ile Ala Arg Leu
225                 230                 235                 240

Ala Val Gln Thr Ala Tyr Phe Pro Leu Phe Glu Tyr Glu Asn Gly Lys
                245                 250                 255

Tyr Lys Ile Asn Met Pro Asn Pro Lys Glu Pro Lys Pro Ile Glu
                260                 265                 270

Glu Phe Leu Lys Leu Gln Gly Arg Phe Lys Tyr Met Thr Lys Glu Asp
    275                 280                 285

Ile Glu Thr Leu Gln Lys Trp Val Leu Glu Trp Glu Arg Leu Lys
    290                 295                 300

Lys Leu Ala Glu Val Phe Gly
305                 310

<210> SEQ ID NO 47
<211> LENGTH: 185
<212> TYPE: PRT
<213> ORGANISM: Pyrococcus furiosus
<220> FEATURE:
<221> NAME/KEY: MISC_FEATURE
<223> OTHER INFORMATION: VorC, WP_011012108.1

<400> SEQUENCE: 47

Met Ile Glu Val Arg Phe His Gly Arg Gly Gln Gly Ala Val Thr
1               5                   10                  15

Ala Ala Asn Ile Leu Ala Glu Ala Ala Phe Leu Glu Gly Lys Tyr Val
                20                  25                  30

Gln Ala Phe Pro Phe Gly Val Glu Arg Arg Gly Ala Pro Val Thr
            35                  40                  45

Ala Phe Thr Arg Ile Asp Asn Lys Pro Ile Arg Ile Lys Thr Gln Ile
    50                  55                  60

Tyr Glu Pro Asp Val Val Val Leu Asp Pro Ser Leu Leu Asp Ala
65                  70                  75                  80

Val Asp Val Thr Ala Gly Leu Lys Asp Glu Gly Ile Val Ile Val Asn
                85                  90                  95

Thr Glu Lys Ser Lys Glu Glu Val Leu Glu Lys Leu Lys Lys Pro
            100                 105                 110

Lys Lys Leu Ala Ile Val Asp Ala Thr Thr Ile Ala Leu Glu Ile Leu
    115                 120                 125

Gly Leu Pro Ile Thr Asn Thr Ala Ile Leu Gly Ala Val Ala Lys Ala
            130                 135                 140

Thr Gly Leu Val Lys Ile Glu Ser Ile Glu Glu Ala Ile Lys Asp Thr
145                 150                 155                 160

Phe Ser Gly Glu Leu Gly Glu Lys Asn Ala Arg Ala Ala Arg Glu Ala
```

```
                        165                 170                 175

Tyr Glu Lys Thr Glu Val Phe Glu Leu
                180                 185

<210> SEQ ID NO 48
<211> LENGTH: 105
<212> TYPE: PRT
<213> ORGANISM: Pyrococcus furiosus
<220> FEATURE:
<221> NAME/KEY: MISC_FEATURE
<223> OTHER INFORMATION: VorD, WP_011012107.1

<400> SEQUENCE: 48

Met Asn Thr Leu Phe Gly Lys Thr Lys Glu Glu Ala Lys Pro Ile Val
1               5                   10                  15

Leu Lys Ser Val Asp Glu Tyr Pro Glu Ala Pro Ile Ser Leu Gly Thr
                20                  25                  30

Thr Leu Val Asn Pro Thr Gly Asp Trp Arg Thr Phe Lys Pro Val Val
            35                  40                  45

Asn Glu Glu Lys Cys Val Lys Cys Tyr Ile Cys Trp Lys Tyr Cys Pro
    50                  55                  60

Glu Pro Ala Ile Tyr Ile Lys Pro Asp Gly Tyr Val Ala Ile Asp Tyr
65                  70                  75                  80

Asp Tyr Cys Lys Gly Cys Gly Ile Cys Ala Asn Glu Cys Pro Thr Lys
                85                  90                  95

Ala Ile Thr Met Ile Lys Glu Glu Lys
                100                 105

<210> SEQ ID NO 49
<211> LENGTH: 386
<212> TYPE: PRT
<213> ORGANISM: Streptomyces avermitilis
<220> FEATURE:
<221> NAME/KEY: MISC_FEATURE
<223> OTHER INFORMATION: AcdH, AAD44196.1 or BAB69160.1

<400> SEQUENCE: 49

Met Asp His Arg Leu Thr Pro Glu Leu Glu Glu Leu Arg Arg Thr Val
1               5                   10                  15

Glu Glu Phe Ala His Asp Val Val Ala Pro Lys Ile Gly Asp Phe Tyr
                20                  25                  30

Glu Arg His Glu Phe Pro Tyr Glu Ile Val Arg Glu Met Gly Arg Met
            35                  40                  45

Gly Leu Phe Gly Leu Pro Phe Pro Glu Glu Tyr Gly Gly Met Gly Gly
    50                  55                  60

Asp Tyr Leu Ala Leu Gly Ile Ala Leu Glu Glu Leu Ala Arg Val Asp
65                  70                  75                  80

Ser Ser Val Ala Ile Thr Leu Glu Ala Gly Val Ser Leu Gly Ala Met
                85                  90                  95

Pro Ile His Leu Phe Gly Thr Asp Ala Gln Lys Ala Glu Trp Leu Pro
                100                 105                 110

Arg Leu Cys Ser Gly Glu Ile Leu Gly Ala Phe Gly Leu Thr Glu Pro
            115                 120                 125

Asp Gly Gly Ser Asp Ala Gly Ala Thr Arg Thr Thr Ala Arg Leu Asp
    130                 135                 140

Glu Ser Thr Asn Glu Trp Val Ile Asn Gly Thr Lys Cys Phe Ile Thr
145                 150                 155                 160

Asn Ser Gly Thr Asp Ile Thr Gly Leu Val Thr Val Thr Ala Val Thr
```

```
                165                 170                 175
Gly Arg Lys Pro Asp Gly Lys Pro Leu Ile Ser Ser Ile Ile Val Pro
            180                 185                 190

Ser Gly Thr Pro Gly Phe Thr Val Ala Ala Pro Tyr Ser Lys Val Gly
        195                 200                 205

Trp Asn Ala Ser Asp Thr Arg Glu Leu Ser Phe Ala Asp Val Arg Val
    210                 215                 220

Pro Ala Ala Asn Leu Leu Gly Glu Gln Gly Arg Gly Tyr Ala Gln Phe
225                 230                 235                 240

Leu Arg Ile Leu Asp Glu Gly Arg Ile Ala Ile Ser Ala Leu Ala Thr
                245                 250                 255

Gly Leu Ala Gln Gly Cys Val Asp Glu Ser Val Lys Tyr Ala Gly Glu
            260                 265                 270

Arg His Ala Phe Gly Arg Asn Ile Gly Ala Tyr Gln Ala Ile Gln Phe
        275                 280                 285

Lys Ile Ala Asp Met Glu Met Lys Ala His Met Ala Arg Val Gly Trp
    290                 295                 300

Arg Asp Ala Ala Ser Arg Leu Val Ala Gly Glu Pro Phe Lys Lys Glu
305                 310                 315                 320

Ala Ala Ile Ala Lys Leu Tyr Ser Ser Thr Val Ala Val Asp Asn Ala
                325                 330                 335

Arg Glu Ala Thr Gln Ile His Gly Gly Tyr Gly Phe Met Asn Glu Tyr
            340                 345                 350

Pro Val Ala Arg Met Trp Arg Asp Ser Lys Ile Leu Glu Ile Gly Glu
        355                 360                 365

Gly Thr Ser Glu Val Gln Arg Met Leu Ile Ala Arg Glu Leu Gly Leu
    370                 375                 380

Val Gly
385
```

<210> SEQ ID NO 50
<211> LENGTH: 386
<212> TYPE: PRT
<213> ORGANISM: Streptomyces coelicolor
<220> FEATURE:
<221> NAME/KEY: MISC_FEATURE
<223> OTHER INFORMATION: AcdH, AAD44195.1

<400> SEQUENCE: 50

```
Met Asp His Lys Leu Ser Pro Glu Leu Glu Glu Leu Arg Arg Thr Val
1               5                   10                  15

Glu Gln Phe Ala His Asp Val Val Ala Pro Lys Ile Gly Asp Phe Tyr
            20                  25                  30

Glu Arg His Glu Phe Pro Tyr Glu Ile Val Arg Glu Met Gly Arg Met
        35                  40                  45

Gly Leu Phe Gly Leu Pro Phe Pro Glu Glu Tyr Gly Gly Met Gly Gly
    50                  55                  60

Asp Tyr Phe Ala Leu Gly Val Ala Leu Glu Glu Leu Ala Arg Val Asp
65                  70                  75                  80

Ser Ser Val Ala Ile Thr Leu Glu Ala Gly Val Ser Leu Gly Ala Met
                85                  90                  95

Pro Leu His Leu Phe Gly Thr Glu Glu Gln Lys Arg Glu Trp Leu Pro
            100                 105                 110

Arg Leu Cys Ser Gly Glu Ile Leu Gly Ala Phe Gly Leu Thr Glu Pro
        115                 120                 125
```

-continued

Asp Gly Gly Ser Asp Ala Gly Ala Thr Arg Thr Thr Ala Arg Leu Asp
    130                 135                 140

Glu Ala Thr Asn Glu Trp Val Ile Asn Gly Thr Lys Cys Phe Ile Thr
145                 150                 155                 160

Asn Ser Gly Thr Asp Ile Thr Gly Leu Val Thr Val Thr Ala Val Thr
                165                 170                 175

Gly Arg Lys Pro Asp Gly Arg Pro Leu Ile Ser Ser Ile Ile Val Pro
            180                 185                 190

Ser Gly Thr Pro Gly Phe Thr Val Ala Ala Pro Tyr Ser Lys Val Gly
        195                 200                 205

Trp Asn Ala Ser Asp Thr Arg Glu Leu Ser Phe Ala Asp Val Arg Val
    210                 215                 220

Pro Ala Ala Asn Leu Leu Gly Glu Leu Gly Arg Gly Tyr Ala Gln Phe
225                 230                 235                 240

Leu Arg Ile Leu Asp Glu Gly Arg Val Ala Ile Ala Ala Leu Gly Thr
                245                 250                 255

Gly Leu Ala Gln Gly Cys Val Asp Glu Ser Val Ala Tyr Ala Lys Glu
            260                 265                 270

Arg His Ala Phe Gly Arg Pro Ile Gly Ala Asn Gln Ala Ile Gln Phe
        275                 280                 285

Lys Ile Ala Asp Met Glu Met Lys Ala His Thr Ala Arg Leu Ala Trp
290                 295                 300

Arg Asp Ala Ala Ser Arg Leu Val Ala Gly Glu Pro Phe Lys Lys Glu
305                 310                 315                 320

Ala Ala Leu Ala Lys Leu Tyr Ser Ser Thr Val Ala Val Asp Asn Ala
                325                 330                 335

Arg Asp Ala Thr Gln Val His Gly Gly Tyr Gly Phe Met Asn Glu Tyr
            340                 345                 350

Pro Val Ala Arg Met Trp Arg Asp Ala Lys Ile Leu Glu Ile Gly Glu
        355                 360                 365

Gly Thr Ser Glu Val Gln Arg Met Leu Ile Ala Arg Glu Leu Gly Leu
    370                 375                 380

Val Gly
385

<210> SEQ ID NO 51
<211> LENGTH: 261
<212> TYPE: PRT
<213> ORGANISM: Clostridium beijerinckii
<220> FEATURE:
<221> NAME/KEY: MISC_FEATURE
<223> OTHER INFORMATION: Crt, ABR34202.1

<400> SEQUENCE: 51

Met Glu Leu Lys Asn Val Ile Leu Glu Lys Glu Gly His Leu Ala Ile
1               5                   10                  15

Val Thr Ile Asn Arg Pro Lys Ala Leu Asn Ala Leu Asn Ser Glu Thr
                20                  25                  30

Leu Lys Asp Leu Asp Ala Val Leu Glu Asp Leu Glu Lys Asp Ser Asn
            35                  40                  45

Met Tyr Thr Val Ile Val Thr Gly Ala Gly Glu Lys Ser Phe Val Ala
        50                  55                  60

Gly Ala Asp Ile Ser Glu Met Lys Asp Leu Asn Glu Glu Gln Gly Lys
65                  70                  75                  80

Glu Phe Gly Ile Leu Gly Asn Asn Val Phe Arg Arg Leu Glu Arg Leu
                85                  90                  95

```
Asp Lys Pro Val Ile Ala Ala Ile Ser Gly Phe Ala Leu Gly Gly Gly
            100                 105                 110

Cys Glu Leu Ala Met Ser Cys Asp Ile Arg Ile Ala Ser Val Lys Ala
        115                 120                 125

Lys Phe Gly Gln Pro Glu Ala Gly Leu Gly Ile Thr Pro Gly Phe Gly
    130                 135                 140

Gly Thr Gln Arg Leu Ala Arg Ile Val Gly Pro Gly Lys Ala Lys Glu
145                 150                 155                 160

Leu Ile Tyr Thr Cys Asp Leu Ile Asn Ala Glu Ala Tyr Arg Ile
                165                 170                 175

Gly Leu Val Asn Lys Val Val Glu Leu Glu Lys Leu Met Glu Glu Ala
            180                 185                 190

Lys Ala Met Ala Asn Lys Ile Ala Ala Asn Ala Pro Lys Ala Val Ala
        195                 200                 205

Tyr Cys Lys Asp Ala Ile Asp Arg Gly Met Gln Val Asp Ile Asp Ala
    210                 215                 220

Ala Ile Leu Ile Glu Ala Glu Asp Phe Gly Lys Cys Phe Ala Thr Glu
225                 230                 235                 240

Asp Gln Thr Glu Gly Met Thr Ala Phe Leu Glu Arg Arg Ala Glu Lys
                245                 250                 255

Asn Phe Gln Asn Lys
            260

<210> SEQ ID NO 52
<211> LENGTH: 261
<212> TYPE: PRT
<213> ORGANISM: Clostridium acetobutylicum
<220> FEATURE:
<221> NAME/KEY: MISC_FEATURE
<223> OTHER INFORMATION: Crt, NP_349318.1

<400> SEQUENCE: 52

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
```

```
                180                 185                 190
Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
        210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 53
<211> LENGTH: 397
<212> TYPE: PRT
<213> ORGANISM: Treponema denticola
<220> FEATURE:
<221> NAME/KEY: MISC_FEATURE
<223> OTHER INFORMATION: Ccr, NP_971211.1

<400> SEQUENCE: 53

Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
    210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270
```

```
Asn Lys Gly Leu Val Thr Arg Ala Ser Ala Val Ile Pro Val Ile Pro
            275                 280                 285

Leu Tyr Leu Ala Ser Leu Phe Lys Val Met Lys Glu Lys Gly Asn His
        290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Asn Arg Ile Arg Ile
                325                 330                 335

Asp Asp Trp Glu Leu Glu Asp Val Gln Lys Ala Val Ser Ala Leu
                340                 345                 350

Met Glu Lys Val Thr Gly Glu Asn Ala Glu Ser Leu Thr Asp Leu Ala
        355                 360                 365

Gly Tyr Arg His Asp Phe Leu Ala Ser Asn Gly Phe Asp Val Glu Gly
        370                 375                 380

Ile Asn Tyr Glu Ala Glu Val Glu Arg Phe Asp Arg Ile
385                 390                 395

<210> SEQ ID NO 54
<211> LENGTH: 539
<212> TYPE: PRT
<213> ORGANISM: Euglena gracilis
<220> FEATURE:
<221> NAME/KEY: MISC_FEATURE
<223> OTHER INFORMATION: Ter, AAW66853.1

<400> SEQUENCE: 54

Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

Gly Val Asp Arg Gly Leu Met Arg Pro Thr Thr Ala Ala Ala Leu Thr
    50                  55                  60

Thr Met Arg Glu Val Pro Gln Met Ala Glu Gly Phe Ser Gly Glu Ala
65                  70                  75                  80

Thr Ser Ala Trp Ala Ala Ala Gly Pro Gln Trp Ala Pro Leu Val
                85                  90                  95

Ala Ala Ala Ser Ser Ala Leu Ala Leu Trp Trp Ala Ala Arg Arg
            100                 105                 110

Ser Val Arg Arg Pro Leu Ala Ala Leu Ala Glu Leu Pro Thr Ala Val
        115                 120                 125

Thr His Leu Ala Pro Pro Met Ala Met Phe Thr Thr Ala Lys Val
    130                 135                 140

Ile Gln Pro Lys Ile Arg Gly Phe Ile Cys Thr Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
            180                 185                 190

Thr Gly Tyr Gly Leu Ser Thr Arg Ile Thr Ala Ala Phe Gly Tyr Gln
        195                 200                 205

Ala Ala Thr Leu Gly Val Phe Leu Ala Gly Pro Pro Thr Lys Gly Arg
    210                 215                 220

Pro Ala Ala Ala Gly Trp Tyr Asn Thr Val Ala Phe Glu Lys Ala Ala
225                 230                 235                 240
```

-continued

```
Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
            260                 265                 270

Thr Val Asp Leu Val Val Tyr Ser Ile Ala Ala Pro Lys Arg Thr Asp
        275                 280                 285

Pro Ala Thr Gly Val Leu His Lys Ala Cys Leu Lys Pro Ile Gly Ala
    290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Ile Ala Asp Thr Val Lys
                325                 330                 335

Val Met Gly Gly Glu Asp Trp Glu Leu Trp Ile Gln Ala Leu Ser Glu
                340                 345                 350

Ala Gly Val Leu Ala Glu Gly Ala Lys Thr Val Ala Tyr Ser Tyr Ile
            355                 360                 365

Gly Pro Glu Met Thr Trp Pro Val Tyr Trp Ser Gly Thr Ile Gly Glu
        370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
            420                 425                 430

Val Met Lys Glu Lys Gly Thr His Glu Gly Cys Ile Glu Gln Met Val
        435                 440                 445

Arg Leu Leu Thr Thr Lys Leu Tyr Pro Glu Asn Gly Ala Pro Ile Val
    450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
                485                 490                 495

Leu Lys Asp Ile Ser Asp Phe Ala Gly Tyr Gln Thr Glu Phe Leu Arg
            500                 505                 510

Leu Phe Gly Phe Gly Ile Asp Gly Val Asp Tyr Asp Gln Pro Val Asp
        515                 520                 525

Val Glu Ala Asp Leu Pro Ser Ala Ala Gln Gln
    530                 535

<210> SEQ ID NO 55
<211> LENGTH: 282
<212> TYPE: PRT
<213> ORGANISM: Clostridium beijerinckii
<220> FEATURE:
<221> NAME/KEY: MISC_FEATURE
<223> OTHER INFORMATION: Hbd, WP_011967675.1

<400> SEQUENCE: 55

Met Lys Lys Ile Phe Val Leu Gly Ala Gly Thr Met Gly Ala Gly Ile
1               5                   10                  15

Val Gln Ala Phe Ala Gln Lys Gly Cys Glu Val Ile Val Arg Asp Ile
            20                  25                  30

Lys Glu Glu Phe Val Asp Arg Gly Ile Ala Gly Ile Thr Lys Gly Leu
        35                  40                  45

Glu Lys Gln Val Ala Lys Gly Lys Met Ser Glu Glu Asp Lys Glu Ala
```

```
            50                  55                  60
Ile Leu Ser Arg Ile Ser Gly Thr Thr Asp Met Lys Leu Ala Ala Asp
 65                  70                  75                  80

Cys Asp Leu Val Val Glu Ala Ala Ile Glu Asn Met Lys Ile Lys Lys
                 85                  90                  95

Glu Ile Phe Ala Glu Leu Asp Gly Ile Cys Lys Pro Glu Ala Ile Leu
                100                 105                 110

Ala Ser Asn Thr Ser Ser Leu Ser Ile Thr Glu Val Ala Ser Ala Thr
                115                 120                 125

Lys Arg Pro Asp Lys Val Ile Gly Met His Phe Phe Asn Pro Ala Pro
            130                 135                 140

Val Met Lys Leu Val Glu Ile Ile Lys Gly Ile Ala Thr Ser Gln Glu
145                 150                 155                 160

Thr Phe Asp Ala Val Lys Glu Leu Ser Val Ala Ile Gly Lys Glu Pro
                165                 170                 175

Val Glu Val Ala Glu Ala Pro Gly Phe Val Val Asn Arg Ile Leu Ile
                180                 185                 190

Pro Met Ile Asn Glu Ala Ser Phe Ile Leu Gln Glu Gly Ile Ala Ser
                195                 200                 205

Val Glu Asp Ile Asp Thr Ala Met Lys Tyr Gly Ala Asn His Pro Met
            210                 215                 220

Gly Pro Leu Ala Leu Gly Asp Leu Ile Gly Leu Asp Val Cys Leu Ala
225                 230                 235                 240

Ile Met Asp Val Leu Phe Thr Glu Thr Gly Asp Asn Lys Tyr Arg Ala
                245                 250                 255

Ser Ser Ile Leu Arg Lys Tyr Val Arg Ala Gly Trp Leu Gly Arg Lys
                260                 265                 270

Ser Gly Lys Gly Phe Tyr Asp Tyr Ser Lys
            275                 280

<210> SEQ ID NO 56
<211> LENGTH: 282
<212> TYPE: PRT
<213> ORGANISM: Clostridium acetobutylicum
<220> FEATURE:
<221> NAME/KEY: MISC_FEATURE
<223> OTHER INFORMATION: Hbd, NP_349314.1

<400> SEQUENCE: 56

Met Lys Lys Val Cys Val Ile Gly Ala Gly Thr Met Gly Ser Gly Ile
 1                5                  10                  15

Ala Gln Ala Phe Ala Ala Lys Gly Phe Glu Val Val Leu Arg Asp Ile
                 20                  25                  30

Lys Asp Glu Phe Val Asp Arg Gly Leu Asp Phe Ile Asn Lys Asn Leu
             35                  40                  45

Ser Lys Leu Val Lys Lys Gly Lys Ile Glu Glu Ala Thr Lys Val Glu
 50                  55                  60

Ile Leu Thr Arg Ile Ser Gly Thr Val Asp Leu Asn Met Ala Ala Asp
 65                  70                  75                  80

Cys Asp Leu Val Ile Glu Ala Ala Val Glu Arg Met Asp Ile Lys Lys
                 85                  90                  95

Gln Ile Phe Ala Asp Leu Asp Asn Ile Cys Lys Pro Glu Thr Ile Leu
                100                 105                 110

Ala Ser Asn Thr Ser Ser Leu Ser Ile Thr Glu Val Ala Ser Ala Thr
                115                 120                 125
```

-continued

```
Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
                195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
                260                 265                 270

Ser Gly Lys Gly Phe Tyr Asp Tyr Ser Lys
                275                 280
```

<210> SEQ ID NO 57
<211> LENGTH: 282
<212> TYPE: PRT
<213> ORGANISM: Clostridium kluyveri
<220> FEATURE:
<221> NAME/KEY: MISC_FEATURE
<223> OTHER INFORMATION: Hbd1, WP_011989027.1

<400> SEQUENCE: 57

```
Met Ser Ile Lys Ser Val Ala Val Leu Gly Ser Gly Thr Met Ser Arg
1               5                   10                  15

Gly Ile Val Gln Ala Phe Ala Glu Ala Gly Ile Asp Val Ile Ile Arg
                20                  25                  30

Gly Arg Thr Glu Gly Ser Ile Gly Lys Gly Leu Ala Ala Val Lys Lys
            35                  40                  45

Ala Tyr Asp Lys Lys Val Ser Lys Gly Lys Ile Ser Gln Glu Asp Ala
50                  55                  60

Asp Lys Ile Val Gly Arg Val Ser Thr Thr Thr Glu Leu Glu Lys Leu
65                  70                  75                  80

Ala Asp Cys Asp Leu Ile Ile Glu Ala Ala Ser Glu Asp Met Asn Ile
                85                  90                  95

Lys Lys Asp Tyr Phe Gly Lys Leu Glu Glu Ile Cys Lys Pro Glu Thr
                100                 105                 110

Ile Phe Ala Thr Asn Thr Ser Ser Leu Ser Ile Thr Glu Val Ala Thr
                115                 120                 125

Ala Thr Lys Arg Pro Asp Lys Phe Ile Gly Met His Phe Phe Asn Pro
130                 135                 140

Ala Asn Val Met Lys Leu Val Glu Ile Ile Arg Gly Met Asn Thr Ser
145                 150                 155                 160

Gln Glu Thr Phe Asp Ile Ile Lys Glu Ala Ser Ile Lys Ile Gly Lys
                165                 170                 175

Thr Pro Val Glu Val Ala Glu Ala Pro Gly Phe Val Val Asn Lys Ile
                180                 185                 190

Leu Val Pro Met Ile Asn Glu Ala Val Gly Ile Leu Ala Glu Gly Ile
                195                 200                 205
```

```
Ala Ser Ala Glu Asp Ile Asp Thr Ala Met Lys Leu Gly Ala Asn His
        210                 215                 220

Pro Met Gly Pro Leu Ala Leu Gly Asp Leu Ile Gly Leu Asp Val Val
225                 230                 235                 240

Leu Ala Val Met Asp Val Leu Tyr Ser Glu Thr Gly Asp Ser Lys Tyr
                245                 250                 255

Arg Ala His Thr Leu Leu Arg Lys Tyr Val Arg Ala Gly Trp Leu Gly
        260                 265                 270

Arg Lys Ser Gly Lys Gly Phe Phe Ala Tyr
        275                 280

<210> SEQ ID NO 58
<211> LENGTH: 246
<212> TYPE: PRT
<213> ORGANISM: Cupriavidus necator
<220> FEATURE:
<221> NAME/KEY: MISC_FEATURE
<223> OTHER INFORMATION: PhaB, WP_010810131.1

<400> SEQUENCE: 58

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
                20                  25                  30

Gly Cys Gly Pro Asn Ser Pro Arg Arg Glu Lys Trp Leu Glu Gln Gln
            35                  40                  45

Lys Ala Leu Gly Phe Asp Phe Ile Ala Ser Glu Gly Asn Val Ala Asp
        50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
                100                 105                 110

Leu Thr Ser Leu Phe Asn Val Thr Lys Gln Val Ile Asp Gly Met Ala
            115                 120                 125

Asp Arg Gly Trp Gly Arg Ile Val Asn Ile Ser Ser Val Asn Gly Gln
        130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 59
<211> LENGTH: 134
<212> TYPE: PRT
```

<213> ORGANISM: Aeromonas caviae
<220> FEATURE:
<221> NAME/KEY: MISC_FEATURE
<223> OTHER INFORMATION: PhaJ, O32472

<400> SEQUENCE: 59

Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
                35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
                100                 105                 110

Thr Thr Arg Ile Phe Thr Gln Gly Gly Ala Leu Ala Val Thr Gly Glu
            115                 120                 125

Ala Val Val Lys Leu Pro
            130

<210> SEQ ID NO 60
<211> LENGTH: 260
<212> TYPE: PRT
<213> ORGANISM: Ralstonia pickettii
<220> FEATURE:
<221> NAME/KEY: MISC_FEATURE
<223> OTHER INFORMATION: Bdh1, BAE72684.1

<400> SEQUENCE: 60

Met Gln Leu Lys Gly Lys Ser Ala Ile Val Thr Gly Ala Ala Ser Gly
1               5                   10                  15

Ile Gly Lys Ala Ile Ala Glu Leu Leu Ala Lys Glu Gly Ala Ala Val
                20                  25                  30

Ala Ile Ala Asp Leu Asn Leu Glu Ala Ala Arg Ala Ala Ala Ala Gly
            35                  40                  45

Ile Glu Ala Ala Gly Gly Lys Ala Ile Ala Val Ala Met Asp Val Thr
    50                  55                  60

Ser Glu Ala Ser Val Asn Gln Leu Thr Asp Glu Val Ala Gln Ala Phe
65                  70                  75                  80

Gly Asn Ile Asp Ile Leu Val Ser Asn Ala Gly Ile Gln Ile Val Asn
                85                  90                  95

Pro Ile Gln Asn Tyr Ala Phe Ser Asp Trp Lys Lys Met Gln Ala Ile
                100                 105                 110

His Val Asp Gly Ala Phe Leu Thr Thr Lys Ala Ala Leu Lys Tyr Met
            115                 120                 125

Tyr Arg Asp Lys Arg Gly Gly Thr Val Ile Tyr Met Gly Ser Val His
    130                 135                 140

Ser His Glu Ala Ser Pro Leu Lys Ser Ala Tyr Val Ala Ala Lys His
145                 150                 155                 160

Ala Leu Leu Gly Leu Ala Arg Val Leu Ala Lys Glu Gly Ala Glu Phe
                165                 170                 175

Asn Val Arg Ser His Val Ile Cys Pro Gly Phe Val Arg Thr Pro Leu

```
                180             185             190
Val Asp Lys Gln Ile Pro Glu Gln Ala Lys Glu Leu Gly Ile Ser Glu
            195                 200                 205
Glu Glu Val Val Arg Arg Val Met Leu Gly Gly Thr Val Asp Gly Val
        210                 215                 220
Phe Thr Thr Val Asp Asp Val Ala Arg Thr Ala Leu Phe Leu Cys Ala
225                 230                 235                 240
Phe Pro Ser Ala Ala Leu Thr Gly Gln Ser Phe Ile Val Ser His Gly
                245                 250                 255
Trp Tyr Met Gln
            260

<210> SEQ ID NO 61
<211> LENGTH: 256
<212> TYPE: PRT
<213> ORGANISM: Ralstonia pickettii
<220> FEATURE:
<221> NAME/KEY: MISC_FEATURE
<223> OTHER INFORMATION: Bdh2, BAE72685.1

<400> SEQUENCE: 61

Met Leu Gln Gly Lys Thr Ala Leu Val Thr Gly Ser Thr Cys Gly Ile
1               5                   10                  15
Gly Leu Gly Ile Ala Gln Ala Leu Ala Ala Gln Gly Ala Asn Ile Ile
            20                  25                  30
Val Asn Gly Phe Arg Arg Ala Asp Gly Ala Arg Gln Gln Ile Ala Ala
        35                  40                  45
Ala Gly Gln Val Ile Arg Leu Gly Tyr His Gly Ala Asp Met Ser Lys
    50                  55                  60
Ala Ser Glu Ile Glu Asp Met Met Arg Tyr Ala Glu Ala Glu Phe Ala
65                  70                  75                  80
Ala Asp Ile Leu Val Asn Asn Ala Gly Ile Gln His Val Ala Ser Ile
                85                  90                  95
Glu Asp Phe Pro Pro Glu Arg Trp Asp Ala Ile Ile Ala Ile Asn Leu
            100                 105                 110
Thr Ser Ala Phe His Thr Thr Arg Leu Ala Leu Pro Gly Met Arg Gln
        115                 120                 125
Lys Asn Trp Gly Arg Val Ile Asn Ile Ala Ser Thr His Gly Leu Val
    130                 135                 140
Ala Ser Ala Gln Lys Ser Ala Tyr Val Ala Ala Lys His Gly Ile Val
145                 150                 155                 160
Gly Leu Thr Lys Val Thr Ala Leu Glu Thr Ala Gln Asn Arg Val Thr
                165                 170                 175
Ala Asn Ala Ile Cys Pro Gly Trp Val Leu Thr Pro Leu Val Gln Lys
            180                 185                 190
Gln Val Gln Ala Arg Pro Ala His Gly Ile Ser Val Glu Gln Ala Lys
        195                 200                 205
Arg Glu Leu Val Ile Glu Lys Gln Pro Ser Gly Gln Phe Val Thr Pro
    210                 215                 220
Asp Glu Leu Gly Ala Leu Ala Val Phe Leu Ala Ser Glu Ala Gly Arg
225                 230                 235                 240
Gln Val Arg Gly Ala Ile Trp Asn Met Ala Gly Gly Trp Phe Ala Gln
                245                 250                 255

<210> SEQ ID NO 62
<211> LENGTH: 254
```

```
<212> TYPE: PRT
<213> ORGANISM: Clostridium autoethanogenum
<220> FEATURE:
<221> NAME/KEY: MISC_FEATURE
<223> OTHER INFORMATION: Bdh, AGY75962

<400> SEQUENCE: 62

Met Arg Leu Glu Asn Lys Val Ala Ile Val Thr Gly Ser Ala Met Gly
1               5                   10                  15

Ile Gly Lys Ala Ile Val Arg Asp Phe Val Asn Glu Gly Ala Lys Val
            20                  25                  30

Ile Ile Ser Asp Ile Leu Glu Ala Glu Gly Gln Ala Leu Glu Glu Glu
        35                  40                  45

Leu Gln Lys Lys Gly His Ser Val Tyr Phe Phe Lys Thr Asp Val Ser
    50                  55                  60

Ser Glu Lys Asn Ile Lys Glu Leu Val Lys Phe Thr Leu Glu Lys Phe
65                  70                  75                  80

Gly Thr Ile Asn Ile Leu Cys Asn Asn Ala Ala Val Asn Ile Pro Gly
                85                  90                  95

Ser Val Leu Glu Leu Thr Glu Asp Ile Trp Asn Lys Thr Met Asp Val
            100                 105                 110

Asn Val Lys Ser His Phe Leu Val Ser Lys His Val Ile Pro Val Met
        115                 120                 125

Gln Lys Ala Gly Gly Ser Ile Val Asn Thr Ala Ser Ala Asn Ser
    130                 135                 140

Phe Val Ala Glu Pro Arg Leu Ser Ala Tyr Val Ala Ser Lys Gly Ala
145                 150                 155                 160

Ile Leu Met Leu Thr Arg Ala Met Ala Leu Asp Phe Ala Lys Asp Asn
                165                 170                 175

Ile Arg Val Asn Cys Ile Cys Pro Gly Trp Val Asp Thr Thr Phe Asn
            180                 185                 190

Asp Ala His Ala Glu Leu Phe Gly Gly Arg Glu Ala Val Leu Lys Asp
        195                 200                 205

Leu Ala Ser Val Gln Pro Ile Gly Arg Pro Ile Ala Pro Met Glu Ile
    210                 215                 220

Ala Lys Ile Ala Thr Phe Leu Ala Ser Asp Asp Ser Ser Cys Met Thr
225                 230                 235                 240

Gly Ser Pro Val Ile Ala Asp Gly Gly Ile Thr Ala Gly Val
                245                 250

<210> SEQ ID NO 63
<211> LENGTH: 607
<212> TYPE: PRT
<213> ORGANISM: Clostridium autoethanogenum
<220> FEATURE:
<221> NAME/KEY: MISC_FEATURE
<223> OTHER INFORMATION: AOR, WP_013238665.1

<400> SEQUENCE: 63

Met Tyr Gly Tyr Asp Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60
```

```
Pro Leu Thr Gly Ala Pro Val Pro Thr Ser Gly Arg Phe Met Val Val
 65                  70                  75                  80

Thr Lys Ala Pro Leu Thr Gly Thr Ile Gly Ile Ser Asn Ser Gly Gly
                 85                  90                  95

Lys Trp Gly Val Asp Leu Lys Lys Ala Gly Trp Asp Met Ile Ile Val
                100                 105                 110

Glu Asp Lys Ala Asp Ser Pro Val Tyr Ile Glu Ile Val Asp Asp Lys
                115                 120                 125

Val Glu Ile Lys Asp Ala Ser Gln Leu Trp Gly Lys Val Thr Ser Glu
                130                 135                 140

Thr Thr Lys Glu Leu Glu Lys Ile Thr Glu Asn Lys Ser Lys Val Leu
145                 150                 155                 160

Cys Ile Gly Pro Ala Gly Glu Arg Leu Ser Leu Met Ala Ala Val Met
                165                 170                 175

Asn Asp Val Asp Arg Thr Ala Ala Arg Gly Gly Val Gly Ala Val Met
                180                 185                 190

Gly Ser Lys Asn Leu Lys Ala Ile Thr Val Lys Gly Thr Gly Lys Ile
            195                 200                 205

Ala Leu Ala Asp Lys Glu Lys Val Lys Val Ser Val Glu Lys Ile
210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Lys Asn Phe Gln Glu Ser Tyr Thr Asn Gln Ala Asp Lys Ile Ser
                260                 265                 270

Gly Glu Thr Leu Thr Ala Asn Gln Leu Val Arg Lys Asn Pro Cys Tyr
            275                 280                 285

Ser Cys Pro Ile Gly Cys Gly Arg Trp Val Arg Leu Lys Asp Gly Thr
            290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
                325                 330                 335

Asn Glu Tyr Gly Ile Asp Thr Ile Thr Cys Gly Ala Thr Ile Ala Ala
                340                 345                 350

Ala Met Glu Leu Tyr Gln Arg Gly Tyr Ile Lys Asp Glu Ile Ala
            355                 360                 365

Gly Asp Asn Leu Ser Leu Lys Trp Gly Asp Thr Glu Ser Met Ile Gly
            370                 375                 380

Trp Ile Lys Arg Met Val Tyr Ser Glu Gly Phe Gly Ala Lys Met Thr
385                 390                 395                 400

Asn Gly Ser Tyr Arg Leu Cys Glu Gly Tyr Gly Ala Pro Glu Tyr Ser
                405                 410                 415

Met Thr Val Lys Lys Gln Glu Ile Pro Ala Tyr Asp Pro Arg Gly Ile
                420                 425                 430

Gln Gly His Gly Ile Thr Tyr Ala Val Asn Asn Arg Gly Gly Cys His
            435                 440                 445

Ile Lys Gly Tyr Met Ile Asn Pro Glu Ile Leu Gly Tyr Pro Glu Lys
            450                 455                 460

Leu Asp Arg Phe Ala Leu Asp Gly Lys Ala Ala Tyr Ala Lys Leu Phe
465                 470                 475                 480

His Asp Leu Thr Ala Val Ile Asp Ser Leu Gly Leu Cys Ile Phe Thr
```

```
                      485                 490                 495
Thr Phe Gly Leu Gly Ile Gln Asp Tyr Val Asp Met Tyr Asn Ala Val
                500                 505                 510

Val Gly Glu Ser Thr Tyr Asp Ala Asp Ser Leu Leu Glu Ala Gly Asp
            515                 520                 525

Arg Ile Trp Thr Leu Glu Lys Leu Phe Asn Leu Ala Ala Gly Ile Asp
        530                 535                 540

Ser Ser Gln Asp Thr Leu Pro Lys Arg Leu Leu Glu Glu Pro Ile Pro
545                 550                 555                 560

Asp Gly Pro Ser Lys Gly Glu Val His Arg Leu Asp Val Leu Leu Pro
                565                 570                 575

Glu Tyr Tyr Ser Val Arg Gly Trp Ser Lys Glu Gly Ile Pro Thr Glu
                580                 585                 590

Glu Thr Leu Lys Lys Leu Gly Leu Asp Glu Tyr Ile Gly Lys Phe
                595                 600                 605

<210> SEQ ID NO 64
<211> LENGTH: 607
<212> TYPE: PRT
<213> ORGANISM: Clostridium autoethanogenum
<220> FEATURE:
<221> NAME/KEY: MISC_FEATURE
<223> OTHER INFORMATION: AOR, WP_013238675.1

<400> SEQUENCE: 64

Met Tyr Gly Tyr Lys Gly Lys Val Leu Arg Ile Asn Leu Ser Ser Lys
1               5                   10                  15

Thr Tyr Ile Val Glu Glu Leu Lys Ile Asp Lys Ala Lys Lys Phe Ile
                20                  25                  30

Gly Ala Arg Gly Leu Gly Val Lys Thr Leu Phe Asp Glu Val Asp Pro
            35                  40                  45

Lys Val Asp Pro Leu Ser Pro Asp Asn Lys Phe Ile Ile Ala Ala Gly
        50                  55                  60

Pro Leu Thr Gly Ala Pro Val Pro Thr Ser Gly Arg Phe Met Val Val
65                  70                  75                  80

Thr Lys Ser Pro Leu Thr Gly Thr Ile Ala Ile Ala Asn Ser Gly Gly
                85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175

Asn Asp Val Asp Arg Thr Ala Gly Arg Gly Gly Val Gly Ala Val Met
            180                 185                 190

Gly Ser Lys Asn Leu Lys Ala Ile Val Val Lys Gly Ser Gly Lys Val
        195                 200                 205

Lys Leu Phe Asp Glu Gln Lys Val Lys Glu Val Ala Leu Glu Lys Thr
    210                 215                 220

Asn Ile Leu Arg Lys Asp Pro Val Ala Gly Gly Gly Leu Pro Thr Tyr
225                 230                 235                 240
```

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
            260                 265                 270

Gly Glu Thr Leu Thr Lys Asp Cys Leu Val Arg Lys Asn Pro Cys Tyr
        275                 280                 285

Arg Cys Pro Ile Ala Cys Gly Arg Trp Val Lys Leu Asp Asp Gly Thr
    290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
            340                 345                 350

Ala Met Glu Leu Tyr Gln Arg Gly Tyr Ile Lys Asp Glu Ile Ala
        355                 360                 365

Ala Asp Gly Leu Ser Leu Asn Trp Gly Asp Ala Lys Ser Met Val Glu
    370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Leu Pro Ala Tyr Asp Pro Arg Gly Ile
            420                 425                 430

Gln Gly His Gly Ile Thr Tyr Ala Val Asn Asn Arg Gly Gly Cys His
        435                 440                 445

Ile Lys Gly Tyr Met Val Ser Pro Glu Ile Leu Gly Tyr Pro Glu Lys
    450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
            500                 505                 510

Val Gly Gly Glu Leu His Asp Val Asn Ser Leu Met Leu Ala Gly Asp
        515                 520                 525

Arg Ile Trp Thr Leu Glu Lys Ile Phe Asn Leu Lys Ala Gly Ile Asp
    530                 535                 540

Ser Ser Gln Asp Thr Leu Pro Lys Arg Leu Leu Glu Glu Gln Ile Pro
545                 550                 555                 560

Glu Gly Pro Ser Lys Gly Glu Val His Lys Leu Asp Val Leu Leu Pro
                565                 570                 575

Glu Tyr Tyr Ser Val Arg Gly Trp Asp Lys Asn Gly Ile Pro Thr Glu
            580                 585                 590

Glu Thr Leu Lys Lys Leu Gly Leu Asp Glu Tyr Val Gly Lys Leu
        595                 600                 605

<210> SEQ ID NO 65
<211> LENGTH: 607
<212> TYPE: PRT
<213> ORGANISM: Clostridium ljungdahlii
<220> FEATURE:
<221> NAME/KEY: MISC_FEATURE
<223> OTHER INFORMATION: AOR, ADK15073.1

<400> SEQUENCE: 65

```
Met Tyr Gly Tyr Asp Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
                20                  25                  30

Gly Cys Arg Gly Leu Gly Val Lys Thr Leu Phe Asp Glu Ile Asp Pro
            35                  40                  45

Lys Ile Asp Ala Leu Ser Pro Glu Asn Lys Phe Ile Ile Val Thr Gly
50                      55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
                100                 105                 110

Glu Asp Lys Ala Asp Ser Pro Val Tyr Ile Glu Ile Val Asp Asp Lys
            115                 120                 125

Val Glu Ile Lys Asp Ala Ser Gln Leu Trp Gly Lys Val Thr Ser Glu
130                 135                 140

Thr Thr Lys Glu Leu Glu Lys Ile Thr Glu Asn Lys Ser Lys Val Leu
145                 150                 155                 160

Cys Ile Gly Pro Ala Gly Glu Arg Leu Ser Leu Met Ala Ala Val Met
                165                 170                 175

Asn Asp Val Asp Arg Thr Ala Ala Arg Gly Val Gly Ala Val Met
            180                 185                 190

Gly Ser Lys Asn Leu Lys Ala Ile Thr Val Lys Gly Thr Gly Lys Ile
            195                 200                 205

Ala Leu Ala Asp Lys Glu Lys Val Lys Val Ser Val Glu Lys Ile
210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Lys Asn Phe Gln Glu Ser Tyr Thr Asn Gln Ala Asp Lys Ile Ser
                260                 265                 270

Gly Glu Thr Leu Thr Ala Asn Gln Leu Val Arg Lys Asn Pro Cys Tyr
            275                 280                 285

Ser Cys Pro Ile Gly Cys Gly Arg Trp Val Arg Leu Lys Asp Gly Thr
            290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
                325                 330                 335

Asn Glu Tyr Gly Ile Asp Thr Ile Thr Cys Gly Ala Thr Ile Ala Ala
                340                 345                 350

Ala Met Glu Leu Tyr Gln Arg Gly Tyr Ile Lys Asp Glu Ile Ala
            355                 360                 365

Gly Asp Asn Leu Ser Leu Lys Trp Gly Asp Thr Glu Ser Met Ile Gly
370                 375                 380

Trp Ile Lys Arg Met Val Tyr Ser Glu Gly Phe Gly Ala Lys Met Thr
385                 390                 395                 400

Asn Gly Ser Tyr Arg Leu Cys Glu Gly Tyr Gly Ala Pro Glu Tyr Ser
                405                 410                 415
```

```
Met Thr Val Lys Lys Gln Glu Ile Pro Ala Tyr Asp Pro Arg Gly Ile
                420                 425                 430

Gln Gly His Gly Ile Thr Tyr Ala Val Asn Asn Arg Gly Gly Cys His
            435                 440                 445

Ile Lys Gly Tyr Met Ile Asn Pro Glu Ile Leu Gly Tyr Pro Glu Lys
        450                 455                 460

Leu Asp Arg Phe Ala Leu Asp Gly Lys Ala Ala Tyr Ala Lys Leu Phe
465                 470                 475                 480

His Asp Leu Thr Ala Val Ile Asp Ser Leu Gly Leu Cys Ile Phe Thr
                485                 490                 495

Thr Phe Gly Leu Gly Ile Gln Asp Tyr Val Asp Met Tyr Asn Ala Val
            500                 505                 510

Val Gly Glu Ser Thr Tyr Asp Ala Asp Ser Leu Leu Glu Ala Gly Asp
        515                 520                 525

Arg Ile Trp Thr Leu Glu Lys Leu Phe Asn Leu Ala Ala Gly Ile Asp
                535                 540

Ser Ser Gln Asp Thr Leu Pro Lys Arg Leu Leu Glu Pro Ile Pro
545                 550                 555                 560

Asp Gly Pro Ser Lys Gly Glu Val His Arg Leu Asp Val Leu Leu Pro
                565                 570                 575

Glu Tyr Tyr Ser Val Arg Gly Trp Ser Lys Glu Gly Ile Pro Thr Glu
            580                 585                 590

Glu Thr Leu Lys Lys Leu Gly Leu Asp Glu Tyr Ile Gly Lys Phe
                595                 600                 605

<210> SEQ ID NO 66
<211> LENGTH: 607
<212> TYPE: PRT
<213> ORGANISM: Clostridium ljungdahlii
<220> FEATURE:
<221> NAME/KEY: MISC_FEATURE
<223> OTHER INFORMATION: AOR, ADK15083.1

<400> SEQUENCE: 66

Met Tyr Gly Tyr Lys Gly Lys Val Leu Arg Ile Asn Leu Ser Ser Lys
1               5                   10                  15

Thr Tyr Ile Val Glu Glu Leu Lys Ile Asp Lys Ala Lys Lys Phe Ile
                20                  25                  30

Gly Ala Arg Gly Leu Gly Val Lys Thr Leu Phe Asp Glu Val Asp Pro
            35                  40                  45

Lys Val Asp Pro Leu Ser Pro Asp Asn Lys Phe Ile Ile Ala Ala Gly
        50                  55                  60

Pro Leu Thr Gly Ala Pro Val Pro Thr Ser Gly Arg Phe Met Val Val
65                  70                  75                  80

Thr Lys Ser Pro Leu Thr Gly Thr Ile Ala Ile Ala Asn Ser Gly Gly
                85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175
```

```
Asn Asp Val Asp Arg Thr Ala Gly Arg Gly Val Gly Ala Val Met
            180                 185                 190

Gly Ser Lys Asn Leu Lys Ala Ile Val Val Lys Gly Ser Gly Lys Val
            195                 200                 205

Lys Leu Phe Asp Glu Gln Lys Val Lys Glu Val Ala Leu Glu Lys Thr
210                 215                 220

Asn Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
            260                 265                 270

Gly Glu Thr Leu Thr Lys Asp Cys Leu Val Arg Lys Asn Pro Cys Tyr
            275                 280                 285

Arg Cys Pro Ile Ala Cys Gly Arg Trp Val Lys Leu Asp Asp Gly Thr
            290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
            340                 345                 350

Ala Met Glu Leu Tyr Gln Arg Gly Tyr Ile Lys Asp Glu Glu Ile Ala
            355                 360                 365

Ala Asp Gly Leu Ser Leu Asn Trp Gly Asp Ala Lys Ser Met Val Glu
            370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Leu Pro Ala Tyr Asp Pro Arg Gly Ile
            420                 425                 430

Gln Gly His Gly Ile Thr Tyr Ala Val Asn Asn Arg Gly Gly Cys His
            435                 440                 445

Ile Lys Gly Tyr Met Val Ser Pro Glu Ile Leu Gly Tyr Pro Glu Lys
            450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
            500                 505                 510

Val Gly Gly Glu Leu His Asp Val Asn Ser Leu Met Leu Ala Gly Asp
            515                 520                 525

Arg Ile Trp Thr Leu Glu Lys Ile Phe Asn Leu Lys Ala Gly Ile Asp
            530                 535                 540

Ser Ser Gln Asp Thr Leu Pro Lys Arg Leu Leu Glu Glu Gln Ile Pro
545                 550                 555                 560

Glu Gly Pro Ser Lys Gly Val His Lys Leu Asp Val Leu Leu Pro
                565                 570                 575

Glu Tyr Tyr Ser Val Arg Gly Trp Asp Lys Asn Gly Ile Pro Thr Glu
            580                 585                 590
```

Glu Thr Leu Lys Lys Leu Gly Leu Asp Glu Tyr Val Gly Lys Leu
            595                 600                 605

<210> SEQ ID NO 67
<211> LENGTH: 405
<212> TYPE: PRT
<213> ORGANISM: Clostridium autoethanogenum
<220> FEATURE:
<221> NAME/KEY: MISC_FEATURE
<223> OTHER INFORMATION: Adh, AGY76060.1

<400> SEQUENCE: 67

Met Lys Tyr Met Gly Ile Lys Ile Tyr Gly Asn Lys Ile Arg Gly Ile
1               5                   10                  15

Ile Met Glu Arg Phe Thr Leu Pro Arg Asp Ile Tyr Phe Gly Glu Asp
            20                  25                  30

Ala Leu Gly Ala Leu Lys Thr Leu Lys Gly Lys Ala Val Val
            35                  40                  45

Val Gly Gly Gly Ser Met Lys Arg Phe Gly Phe Leu Asp Lys Val Glu
        50                  55                  60

Glu Tyr Leu Lys Glu Ala Asn Ile Glu Val Lys Leu Ile Glu Gly Val
65                  70                  75                  80

Glu Pro Asp Pro Ser Val Glu Thr Val Met Lys Gly Ala Lys Ile Met
                85                  90                  95

Thr Glu Phe Gly Pro Asp Trp Ile Val Ala Ile Gly Gly Gly Ser Pro
            100                 105                 110

Ile Asp Ala Ala Lys Ala Met Trp Leu Phe Tyr Glu Tyr Pro Asp Phe
            115                 120                 125

Thr Phe Lys Gln Ala Ile Val Pro Phe Gly Leu Pro Glu Leu Arg Gln
        130                 135                 140

Lys Ala Lys Phe Val Ala Ile Ala Ser Thr Ser Gly Thr Ala Thr Glu
145                 150                 155                 160

Val Thr Ser Phe Ser Val Ile Thr Asp Tyr Lys Ala Lys Ile Lys Tyr
                165                 170                 175

Pro Leu Ala Asp Phe Asn Leu Thr Pro Asp Ile Ala Ile Val Asp Pro
            180                 185                 190

Ala Leu Ala Gln Thr Met Pro Pro Lys Leu Thr Ala His Thr Gly Met
        195                 200                 205

Asp Ala Leu Thr His Ala Leu Glu Ala Tyr Val Ala Ser Ala Arg Ser
    210                 215                 220

Asp Ile Ser Asp Pro Leu Ala Ile His Ser Ile Ile Met Thr Arg Asp
225                 230                 235                 240

Asn Leu Leu Lys Ser Tyr Lys Gly Asp Lys Asp Ala Arg Asn Lys Met
                245                 250                 255

His Ile Ser Gln Cys Leu Ala Gly Met Ala Phe Ser Asn Ala Leu Leu
            260                 265                 270

Gly Ile Thr His Ser Leu Ala His Lys Thr Gly Ala Val Trp His Ile
        275                 280                 285

Pro His Gly Cys Ala Asn Ala Ile Tyr Leu Pro Tyr Val Leu Asp Phe
    290                 295                 300

Asn Lys Lys Ala Cys Ser Asp Arg Tyr Ala Asn Ile Ala Lys Ile Leu
305                 310                 315                 320

Gly Leu Lys Gly Thr Thr Glu Asp Glu Leu Val Asp Ser Leu Val Lys
                325                 330                 335

Met Val Gln Asp Met Asp Lys Glu Leu Asn Ile Pro Leu Thr Leu Lys
            340                 345                 350

```
Asp Tyr Gly Ile Ser Lys Asp Asp Phe Asn Ser Asn Val Asp Phe Ile
        355                 360                 365

Ala Lys Asn Ala Leu Leu Asp Ala Cys Thr Gly Ala Asn Pro Arg Pro
370                 375                 380

Ile Asp Phe Asp Gln Met Lys Lys Ile Leu Gln Cys Ile Tyr Asp Gly
385                 390                 395                 400

Lys Lys Val Thr Phe
            405

<210> SEQ ID NO 68
<211> LENGTH: 388
<212> TYPE: PRT
<213> ORGANISM: Clostridium ljungdahlii
<220> FEATURE:
<221> NAME/KEY: MISC_FEATURE
<223> OTHER INFORMATION: Adh, ADK17019.1

<400> SEQUENCE: 68

Met Glu Arg Phe Thr Leu Pro Arg Asp Ile Tyr Phe Gly Glu Asp Ala
1               5                   10                  15

Leu Gly Ala Leu Lys Thr Leu Lys Gly Lys Ala Val Val Val
            20                  25                  30

Gly Gly Gly Ser Met Lys Arg Phe Gly Phe Leu Asp Lys Val Glu Glu
        35                  40                  45

Tyr Leu Lys Glu Ala Asn Ile Glu Val Lys Leu Ile Glu Gly Val Glu
    50                  55                  60

Pro Asp Pro Ser Val Glu Thr Val Met Lys Gly Ala Lys Ile Met Thr
65                  70                  75                  80

Glu Phe Gly Pro Asp Trp Ile Val Ala Ile Gly Gly Gly Ser Pro Ile
                85                  90                  95

Asp Ala Ala Lys Ala Met Trp Leu Phe Tyr Glu Tyr Pro Asp Phe Thr
            100                 105                 110

Phe Lys Gln Ala Ile Val Pro Phe Gly Leu Pro Glu Leu Arg Gln Lys
        115                 120                 125

Ala Lys Phe Val Ala Ile Ala Ser Thr Ser Gly Thr Ala Thr Glu Val
130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Val Asp Pro Ala
                165                 170                 175

Leu Ala Gln Thr Met Pro Pro Lys Leu Thr Ala His Thr Gly Met Asp
            180                 185                 190

Ala Leu Thr His Ala Leu Glu Ala Tyr Val Ala Ser Ala Arg Ser Asp
        195                 200                 205

Ile Ser Asp Pro Leu Ala Ile His Ser Ile Ile Met Thr Arg Asp Asn
    210                 215                 220

Leu Leu Lys Ser Tyr Lys Gly Asp Lys Asp Ala Arg Asn Lys Met His
225                 230                 235                 240

Ile Ser Gln Cys Leu Ala Gly Met Ala Phe Ser Asn Ala Leu Leu Gly
                245                 250                 255

Ile Thr His Ser Leu Ala His Lys Thr Gly Ala Val Trp His Ile Pro
            260                 265                 270

His Gly Cys Ala Asn Ala Ile Tyr Leu Pro Tyr Val Leu Asp Phe Asn
        275                 280                 285

Lys Lys Ala Cys Ser Asp Arg Tyr Ala Asn Ile Ala Lys Ile Leu Gly
```

```
                    290                 295                 300
Leu Lys Gly Thr Thr Glu Asp Glu Leu Val Asp Ser Leu Val Lys Met
305                 310                 315                 320

Val Gln Asp Met Asp Lys Glu Leu Asn Ile Pro Leu Thr Leu Lys Asp
                325                 330                 335

Tyr Gly Ile Ser Lys Asp Phe Asn Ser Asn Val Asp Phe Ile Ala
                340                 345                 350

Lys Asn Ala Leu Leu Asp Ala Cys Thr Gly Ala Asn Pro Arg Pro Ile
                355                 360                 365

Asp Phe Asp Gln Met Lys Lys Ile Leu Gln Cys Ile Tyr Asp Gly Lys
            370                 375                 380

Lys Val Thr Phe
385

<210> SEQ ID NO 69
<211> LENGTH: 390
<212> TYPE: PRT
<213> ORGANISM: Clostridium acetobutylicum
<220> FEATURE:
<221> NAME/KEY: MISC_FEATURE
<223> OTHER INFORMATION: BdhB, NP_349891.1

<400> SEQUENCE: 69

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
                20                  25                  30

Val Leu Ile Val Tyr Gly Gly Ser Ile Lys Arg Asn Gly Ile Tyr
            35                  40                  45

Asp Lys Ala Val Ser Ile Leu Glu Lys Asn Ser Ile Lys Phe Tyr Glu
50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
            115                 120                 125

Arg Val Leu Pro Ile Ala Ser Ile Leu Thr Ile Ala Ala Thr Gly Ser
        130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
                180                 185                 190

Ala Asp Ile Met Ser His Ile Phe Glu Val Tyr Phe Ser Asn Thr Lys
            195                 200                 205

Thr Ala Tyr Leu Gln Asp Arg Met Ala Glu Ala Leu Leu Arg Thr Cys
        210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255
```

```
Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 70
<211> LENGTH: 387
<212> TYPE: PRT
<213> ORGANISM: Clostridium beijerinckii
<220> FEATURE:
<221> NAME/KEY: MISC_FEATURE
<223> OTHER INFORMATION: Bdh, WP_041897187.1

<400> SEQUENCE: 70

Met Glu Asn Phe Asn Tyr Ser Ile Pro Thr Lys Val Tyr Phe Gly Lys
1               5                   10                  15

Gly Gln Ile Lys Asn Leu Ala Ala Ile Ile Lys Glu Tyr Gly Asn Lys
            20                  25                  30

Ile Phe Ile Ala Tyr Gly Gly Gly Ser Ile Lys Lys Ile Gly Leu Tyr
        35                  40                  45

Asp Glu Met Ile Lys Ile Leu Asn Asp Asn Ser Ile Ser Tyr Val Glu
    50                  55                  60

Leu Ser Gly Ile Glu Pro Asn Pro Arg Ile Glu Thr Val Arg Lys Gly
65                  70                  75                  80

Ile Lys Ile Cys Lys Glu Asn Asn Val Glu Val Val Leu Ala Val Gly
                85                  90                  95

Gly Gly Ser Thr Ile Asp Cys Ala Lys Val Ile Ala Ala Gly Val Lys
            100                 105                 110

Tyr Glu Gly Asp Pro Trp Asp Leu Val Thr Ser Pro Gln Lys Ile Asn
        115                 120                 125

Glu Val Leu Pro Ile Val Thr Ile Leu Thr Leu Ser Ala Thr Gly Ser
    130                 135                 140

Glu Met Asp Pro His Ala Val Ile Ser Asp Met Thr Thr Asn Gln Lys
145                 150                 155                 160

Leu Gly Thr Gly His Glu Asn Met Lys Pro Lys Ala Ser Ile Leu Asp
                165                 170                 175

Pro Glu Tyr Thr Tyr Ser Val Pro Lys Asn Gln Thr Ala Ala Gly Thr
            180                 185                 190

Ala Asp Ile Met Ser His Ile Phe Glu Thr Tyr Phe Asn His Thr Lys
        195                 200                 205

Gly Val Asp Ile Gln Asp Ser Thr Ala Glu Gly Leu Leu Arg Ala Cys
    210                 215                 220
```

```
Ile Lys Tyr Gly Lys Ile Ala Ile Glu Asn Pro Lys Asp Tyr Asp Ala
225                 230                 235                 240

Arg Ala Asn Leu Met Trp Ala Ser Ser Trp Ala Ile Asn Gly Leu Ile
            245                 250                 255

Ser Tyr Gly Thr Asn Ser Pro Trp Val Val His Pro Met Glu His Glu
        260                 265                 270

Leu Ser Ala Phe Tyr Asp Ile Thr His Gly Val Gly Leu Ala Ile Leu
        275                 280                 285

Thr Pro His Trp Met Lys Tyr Ser Leu Asp Asp Thr Thr Val Phe Lys
        290                 295                 300

Phe Ala Gln Tyr Gly Ile Asn Val Trp Gly Ile Asp Lys Asn Leu Asp
305                 310                 315                 320

Lys Phe Glu Ile Ala Asn Lys Ala Ile Glu Lys Thr Ser Glu Phe Phe
            325                 330                 335

Lys Glu Leu Gly Ile Pro Ser Thr Leu Arg Glu Val Gly Ile Glu Glu
            340                 345                 350

Glu Lys Leu Glu Leu Met Ala Lys Ala Met Asn Pro Tyr Phe Lys
            355                 360                 365

Tyr Ala Phe Lys Pro Leu Asp Glu Asn Asp Ile Leu Lys Ile Phe Lys
    370                 375                 380

Ala Ala Leu
385

<210> SEQ ID NO 71
<211> LENGTH: 388
<212> TYPE: PRT
<213> ORGANISM: Clostridium ljungdahlii
<220> FEATURE:
<221> NAME/KEY: MISC_FEATURE
<223> OTHER INFORMATION: Bdh1, YP_003780648.1

<400> SEQUENCE: 71

Met Gly Arg Phe Thr Leu Pro Arg Asp Ile Tyr Phe Gly Glu Asn Ala
1               5                   10                  15

Leu Glu Asn Leu Lys Asn Leu Asp Gly Asn Lys Ala Val Val Val Val
            20                  25                  30

Gly Gly Gly Ser Met Lys Arg Phe Gly Phe Leu Ala Lys Val Glu Lys
        35                  40                  45

Tyr Leu Lys Glu Thr Gly Met Glu Val Lys Leu Ile Glu Gly Val Glu
    50                  55                  60

Pro Asp Pro Ser Val Asp Thr Val Met Asn Gly Ala Lys Ile Met Arg
65                  70                  75                  80

Asp Phe Asn Pro Asp Trp Ile Val Ser Ile Gly Gly Gly Ser Pro Ile
                85                  90                  95

Asp Ala Ala Lys Ala Met Trp Ile Phe Tyr Glu Tyr Pro Asp Phe Thr
            100                 105                 110

Phe Glu Lys Ala Val Val Pro Phe Gly Ile Pro Lys Leu Arg Gln Lys
        115                 120                 125

Ala Gln Phe Val Ala Ile Pro Ser Thr Ser Gly Thr Ala Thr Glu Val
    130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Ile Asp Pro Ser
                165                 170                 175

Leu Ala Glu Thr Met Pro Lys Lys Leu Thr Ala His Thr Gly Met Asp
```

```
                    180                 185                 190
Ala Leu Thr His Ala Ile Glu Ala Tyr Val Ala Ser Leu His Ser Asp
                195                 200                 205
Phe Ser Asp Pro Leu Ala Met His Ala Ile Thr Met Ile His Lys Tyr
            210                 215                 220
Leu Leu Lys Ser Tyr Glu Asp Lys Glu Ala Arg Gly His Met His
225                 230                 235                 240
Ile Ala Gln Cys Leu Ala Gly Met Ala Phe Ser Asn Ala Leu Leu Gly
                245                 250                 255
Ile Thr His Ser Ile Ala His Lys Thr Gly Ala Val Phe His Ile Pro
            260                 265                 270
His Gly Cys Ala Asn Ala Ile Tyr Leu Pro Tyr Val Ile Asp Phe Asn
        275                 280                 285
Lys Lys Ala Cys Ser Glu Arg Tyr Ala Lys Ile Ala Lys Lys Leu His
        290                 295                 300
Leu Ser Gly Asn Ser Glu Asp Glu Leu Ile Asp Ser Leu Thr Glu Met
305                 310                 315                 320
Ile Arg Thr Met Asn Lys Lys Met Asp Ile Pro Leu Thr Ile Lys Asp
                325                 330                 335
Tyr Gly Ile Ser Glu Asn Asp Phe Asn Glu Asn Leu Asp Phe Ile Ala
                340                 345                 350
His Asn Ala Met Met Asp Ala Cys Thr Gly Ser Asn Pro Arg Ala Ile
            355                 360                 365
Thr Glu Glu Glu Met Lys Lys Leu Leu Gln Tyr Met Tyr Asn Gly Gln
        370                 375                 380
Lys Val Asn Phe
385

<210> SEQ ID NO 72
<211> LENGTH: 405
<212> TYPE: PRT
<213> ORGANISM: Clostridium autoethanogenum
<220> FEATURE:
<221> NAME/KEY: MISC_FEATURE
<223> OTHER INFORMATION: Bdh1, AGY76060.1

<400> SEQUENCE: 72

Met Lys Tyr Met Gly Ile Lys Ile Tyr Gly Asn Lys Ile Arg Gly Ile
1               5                   10                  15
Ile Met Glu Arg Phe Thr Leu Pro Arg Asp Ile Tyr Phe Gly Glu Asp
                20                  25                  30
Ala Leu Gly Ala Leu Lys Thr Leu Lys Gly Lys Lys Ala Val Val Val
            35                  40                  45
Val Gly Gly Gly Ser Met Lys Arg Phe Gly Phe Leu Asp Lys Val Glu
        50                  55                  60
Glu Tyr Leu Lys Glu Ala Asn Ile Glu Val Lys Leu Ile Glu Gly Val
65                  70                  75                  80
Glu Pro Asp Pro Ser Val Glu Thr Val Met Lys Gly Ala Lys Ile Met
                85                  90                  95
Thr Glu Phe Gly Pro Asp Trp Ile Val Ala Ile Gly Gly Gly Ser Pro
                100                 105                 110
Ile Asp Ala Ala Lys Ala Met Trp Leu Phe Tyr Glu Tyr Pro Asp Phe
            115                 120                 125
Thr Phe Lys Gln Ala Ile Val Pro Phe Gly Leu Pro Glu Leu Arg Gln
        130                 135                 140
```

Lys Ala Lys Phe Val Ala Ile Ala Ser Thr Ser Gly Thr Ala Thr Glu
145                 150                 155                 160

Val Thr Ser Phe Ser Val Ile Thr Asp Tyr Lys Ala Lys Ile Lys Tyr
                165                 170                 175

Pro Leu Ala Asp Phe Asn Leu Thr Pro Asp Ile Ala Ile Val Asp Pro
            180                 185                 190

Ala Leu Ala Gln Thr Met Pro Pro Lys Leu Thr Ala His Thr Gly Met
        195                 200                 205

Asp Ala Leu Thr His Ala Leu Glu Ala Tyr Val Ala Ser Ala Arg Ser
    210                 215                 220

Asp Ile Ser Asp Pro Leu Ala Ile His Ser Ile Ile Met Thr Arg Asp
225                 230                 235                 240

Asn Leu Leu Lys Ser Tyr Lys Gly Asp Lys Asp Ala Arg Asn Lys Met
                245                 250                 255

His Ile Ser Gln Cys Leu Ala Gly Met Ala Phe Ser Asn Ala Leu Leu
            260                 265                 270

Gly Ile Thr His Ser Leu Ala His Lys Thr Gly Ala Val Trp His Ile
        275                 280                 285

Pro His Gly Cys Ala Asn Ala Ile Tyr Leu Pro Tyr Val Leu Asp Phe
    290                 295                 300

Asn Lys Lys Ala Cys Ser Asp Arg Tyr Ala Asn Ile Ala Lys Ile Leu
305                 310                 315                 320

Gly Leu Lys Gly Thr Thr Glu Asp Glu Leu Val Asp Ser Leu Val Lys
                325                 330                 335

Met Val Gln Asp Met Asp Lys Glu Leu Asn Ile Pro Leu Thr Leu Lys
            340                 345                 350

Asp Tyr Gly Ile Ser Lys Asp Phe Asn Ser Asn Val Asp Phe Ile
        355                 360                 365

Ala Lys Asn Ala Leu Leu Asp Ala Cys Thr Gly Ala Asn Pro Arg Pro
    370                 375                 380

Ile Asp Phe Asp Gln Met Lys Lys Ile Leu Gln Cys Ile Tyr Asp Gly
385                 390                 395                 400

Lys Lys Val Thr Phe
                405

<210> SEQ ID NO 73
<211> LENGTH: 388
<212> TYPE: PRT
<213> ORGANISM: Clostridium ljungdahlii
<220> FEATURE:
<221> NAME/KEY: MISC_FEATURE
<223> OTHER INFORMATION: Bdh2, YP_003782121.1

<400> SEQUENCE: 73

Met Glu Arg Phe Thr Leu Pro Arg Asp Ile Tyr Phe Gly Glu Asp Ala
1               5                   10                  15

Leu Gly Ala Leu Lys Thr Leu Lys Gly Lys Lys Ala Val Val Val Val
            20                  25                  30

Gly Gly Gly Ser Met Lys Arg Phe Gly Phe Leu Asp Lys Val Glu Glu
        35                  40                  45

Tyr Leu Lys Glu Ala Asn Ile Glu Val Lys Leu Ile Glu Gly Val Glu
    50                  55                  60

Pro Asp Pro Ser Val Glu Thr Val Met Lys Gly Ala Lys Ile Met Thr
65                  70                  75                  80

Glu Phe Gly Pro Asp Trp Ile Val Ala Ile Gly Gly Gly Ser Pro Ile
                85                  90                  95

Asp Ala Ala Lys Ala Met Trp Leu Phe Tyr Glu Tyr Pro Asp Phe Thr
            100                 105                 110

Phe Lys Gln Ala Ile Val Pro Phe Gly Leu Pro Glu Leu Arg Gln Lys
            115                 120                 125

Ala Lys Phe Val Ala Ile Ala Ser Thr Ser Gly Thr Ala Thr Glu Val
            130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Val Asp Pro Ala
                165                 170                 175

Leu Ala Gln Thr Met Pro Pro Lys Leu Thr Ala His Thr Gly Met Asp
            180                 185                 190

Ala Leu Thr His Ala Leu Glu Ala Tyr Val Ala Ser Ala Arg Ser Asp
            195                 200                 205

Ile Ser Asp Pro Leu Ala Ile His Ser Ile Ile Met Thr Arg Asp Asn
            210                 215                 220

Leu Leu Lys Ser Tyr Lys Gly Asp Lys Asp Ala Arg Asn Lys Met His
225                 230                 235                 240

Ile Ser Gln Cys Leu Ala Gly Met Ala Phe Ser Asn Ala Leu Leu Gly
                245                 250                 255

Ile Thr His Ser Leu Ala His Lys Thr Gly Ala Val Trp His Ile Pro
            260                 265                 270

His Gly Cys Ala Asn Ala Ile Tyr Leu Pro Tyr Val Leu Asp Phe Asn
            275                 280                 285

Lys Lys Ala Cys Ser Asp Arg Tyr Ala Asn Ile Ala Lys Ile Leu Gly
            290                 295                 300

Leu Lys Gly Thr Thr Glu Asp Glu Leu Val Asp Ser Leu Val Lys Met
305                 310                 315                 320

Val Gln Asp Met Asp Lys Glu Leu Asn Ile Pro Leu Thr Leu Lys Asp
                325                 330                 335

Tyr Gly Ile Ser Lys Asp Asp Phe Asn Ser Asn Val Asp Phe Ile Ala
                340                 345                 350

Lys Asn Ala Leu Leu Asp Ala Cys Thr Gly Ala Asn Pro Arg Pro Ile
            355                 360                 365

Asp Phe Asp Gln Met Lys Lys Ile Leu Gln Cys Ile Tyr Asp Gly Lys
            370                 375                 380

Lys Val Thr Phe
385

<210> SEQ ID NO 74
<211> LENGTH: 388
<212> TYPE: PRT
<213> ORGANISM: Clostridium autoethanogenum
<220> FEATURE:
<221> NAME/KEY: MISC_FEATURE
<223> OTHER INFORMATION: Bdh2, AGY74784.1

<400> SEQUENCE: 74

Met Gly Arg Phe Thr Leu Pro Arg Asp Ile Tyr Phe Gly Glu Asn Ala
1               5                   10                  15

Leu Glu Asn Leu Lys Asn Leu Asp Gly Asn Lys Ala Val Val Val Val
            20                  25                  30

Gly Gly Gly Ser Met Lys Arg Phe Gly Phe Leu Ala Lys Val Glu Lys
            35                  40                  45

Tyr Leu Lys Glu Thr Gly Met Glu Val Lys Leu Ile Glu Gly Val Glu

```
            50                  55                  60
Pro Asp Pro Ser Val Asp Thr Val Met Asn Gly Ala Lys Ile Met Arg
 65                  70                  75                  80

Asp Phe Asn Pro Asp Trp Ile Val Ser Ile Gly Gly Ser Pro Ile
                 85                  90                  95

Asp Ala Ala Lys Ala Met Trp Ile Phe Tyr Glu Tyr Pro Asp Phe Thr
                100                 105                 110

Phe Glu Lys Ala Val Val Pro Phe Gly Ile Pro Lys Leu Arg Gln Lys
                115                 120                 125

Ala Gln Phe Val Ala Ile Pro Ser Thr Ser Gly Thr Ala Thr Glu Val
                130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Ile Asp Pro Ser
                165                 170                 175

Leu Ala Glu Thr Met Pro Lys Lys Leu Thr Ala His Thr Gly Met Asp
                180                 185                 190

Ala Leu Thr His Ala Ile Glu Ala Tyr Val Ala Ser Leu His Ser Asp
                195                 200                 205

Phe Ser Asp Pro Leu Ala Met His Ala Ile Thr Met Ile His Lys Tyr
                210                 215                 220

Leu Leu Lys Ser Tyr Glu Glu Asp Lys Glu Ala Arg Gly His Met His
225                 230                 235                 240

Ile Ala Gln Cys Leu Ala Gly Met Ala Phe Ser Asn Ala Leu Leu Gly
                245                 250                 255

Ile Thr His Ser Ile Ala His Lys Thr Gly Ala Val Phe His Ile Pro
                260                 265                 270

His Gly Cys Ala Asn Ala Ile Tyr Leu Pro Tyr Val Ile Asp Phe Asn
                275                 280                 285

Lys Lys Ala Cys Ser Glu Arg Tyr Ala Lys Ile Ala Lys Lys Leu His
                290                 295                 300

Leu Ser Gly Asn Ser Glu Asp Glu Leu Ile Asp Ser Leu Thr Glu Met
305                 310                 315                 320

Ile Arg Thr Met Asn Lys Lys Met Asp Ile Pro Leu Thr Ile Lys Asp
                325                 330                 335

Tyr Gly Ile Ser Glu Asn Asp Phe Asn Glu Asn Leu Asp Phe Ile Ala
                340                 345                 350

His Asn Ala Met Met Asp Ala Cys Thr Gly Ser Asn Pro Arg Ala Ile
                355                 360                 365

Thr Glu Glu Glu Met Lys Lys Leu Leu Gln Tyr Met Tyr Asn Gly Gln
                370                 375                 380

Lys Val Asn Phe
385

<210> SEQ ID NO 75
<211> LENGTH: 862
<212> TYPE: PRT
<213> ORGANISM: Clostridium acetobutylicum
<220> FEATURE:
<221> NAME/KEY: MISC_FEATURE
<223> OTHER INFORMATION: AdhE1, NP_149325.1

<400> SEQUENCE: 75

Met Lys Val Thr Thr Val Lys Glu Leu Asp Glu Lys Leu Lys Val Ile
 1               5                  10                  15
```

-continued

```
Lys Glu Ala Gln Lys Lys Phe Ser Cys Tyr Ser Gln Glu Met Val Asp
            20                  25                  30
Glu Ile Phe Arg Asn Ala Ala Met Ala Ala Ile Asp Ala Arg Ile Glu
        35                  40                  45
Leu Ala Lys Ala Ala Val Leu Glu Thr Gly Met Gly Leu Val Glu Asp
 50                  55                  60
Lys Val Ile Lys Asn His Phe Ala Gly Glu Tyr Ile Tyr Asn Lys Tyr
 65                  70                  75                  80
Lys Asp Glu Lys Thr Cys Gly Ile Ile Glu Arg Asn Glu Pro Tyr Gly
                85                  90                  95
Ile Thr Lys Ile Ala Glu Pro Ile Gly Val Val Ala Ala Ile Ile Pro
            100                 105                 110
Val Thr Asn Pro Thr Ser Thr Thr Ile Phe Lys Ser Leu Ile Ser Leu
        115                 120                 125
Lys Thr Arg Asn Gly Ile Phe Phe Ser Pro His Pro Arg Ala Lys Lys
130                 135                 140
Ser Thr Ile Leu Ala Ala Lys Thr Ile Leu Asp Ala Ala Val Lys Ser
145                 150                 155                 160
Gly Ala Pro Glu Asn Ile Ile Gly Trp Ile Asp Glu Pro Ser Ile Glu
                165                 170                 175
Leu Thr Gln Tyr Leu Met Gln Lys Ala Asp Ile Thr Leu Ala Thr Gly
            180                 185                 190
Gly Pro Ser Leu Val Lys Ser Ala Tyr Ser Ser Gly Lys Pro Ala Ile
        195                 200                 205
Gly Val Gly Pro Gly Asn Thr Pro Val Ile Ile Asp Glu Ser Ala His
    210                 215                 220
Ile Lys Met Ala Val Ser Ser Ile Ile Leu Ser Lys Thr Tyr Asp Asn
225                 230                 235                 240
Gly Val Ile Cys Ala Ser Glu Gln Ser Val Ile Val Leu Lys Ser Ile
                245                 250                 255
Tyr Asn Lys Val Lys Asp Glu Phe Gln Glu Arg Gly Ala Tyr Ile Ile
            260                 265                 270
Lys Lys Asn Glu Leu Asp Lys Val Arg Glu Val Ile Phe Lys Asp Gly
        275                 280                 285
Ser Val Asn Pro Lys Ile Val Gly Gln Ser Ala Tyr Thr Ile Ala Ala
290                 295                 300
Met Ala Gly Ile Lys Val Pro Lys Thr Thr Arg Ile Leu Ile Gly Glu
305                 310                 315                 320
Val Thr Ser Leu Gly Glu Glu Pro Phe Ala His Glu Lys Leu Ser
                325                 330                 335
Pro Val Leu Ala Met Tyr Glu Ala Asp Asn Phe Asp Asp Ala Leu Lys
            340                 345                 350
Lys Ala Val Thr Leu Ile Asn Leu Gly Gly Leu Gly His Thr Ser Gly
        355                 360                 365
Ile Tyr Ala Asp Glu Ile Lys Ala Arg Asp Lys Ile Asp Arg Phe Ser
    370                 375                 380
Ser Ala Met Lys Thr Val Arg Thr Phe Val Asn Ile Pro Thr Ser Gln
385                 390                 395                 400
Gly Ala Ser Gly Asp Leu Tyr Asn Phe Arg Ile Pro Pro Ser Phe Thr
                405                 410                 415
Leu Gly Cys Gly Phe Trp Gly Gly Asn Ser Val Ser Glu Asn Val Gly
            420                 425                 430
Pro Lys His Leu Leu Asn Ile Lys Thr Val Ala Glu Arg Arg Glu Asn
```

```
              435                 440                 445
Met Leu Trp Phe Arg Val Pro His Lys Val Tyr Phe Lys Phe Gly Cys
    450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
                500                 505                 510

Lys Val Gly Arg Glu Ala Asp Leu Lys Thr Ile Lys Lys Ala Thr Glu
                515                 520                 525

Glu Met Ser Ser Phe Met Pro Asp Thr Ile Ile Ala Leu Gly Gly Thr
    530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
                580                 585                 590

Ile Thr Thr Ser Ala Gly Ser Gly Ser Glu Val Thr Pro Phe Ala Leu
                595                 600                 605

Val Thr Asp Asn Asn Thr Gly Asn Lys Tyr Met Leu Ala Asp Tyr Glu
    610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

Ile Glu Ala Tyr Thr Ser Val Tyr Ala Ser Glu Tyr Thr Asn Gly Leu
                660                 665                 670

Ala Leu Glu Ala Ile Arg Leu Ile Phe Lys Tyr Leu Pro Glu Ala Tyr
                675                 680                 685

Lys Asn Gly Arg Thr Asn Glu Lys Ala Arg Glu Lys Met Ala His Ala
    690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
                725                 730                 735

Ile Ala Asn Ala Leu Leu Ile Glu Glu Val Ile Lys Phe Asn Ala Val
                740                 745                 750

Asp Asn Pro Val Lys Gln Ala Pro Cys Pro Gln Tyr Lys Tyr Pro Asn
                755                 760                 765

Thr Ile Phe Arg Tyr Ala Arg Ile Ala Asp Tyr Ile Lys Leu Gly Gly
                770                 775                 780

Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
                805                 810                 815

Leu Glu Glu Asn Phe Tyr Ser Ser Leu Asp Arg Ile Ser Glu Leu Ala
                820                 825                 830

Leu Asp Asp Gln Cys Thr Gly Ala Asn Pro Arg Phe Pro Leu Thr Ser
                835                 840                 845

Glu Ile Lys Glu Met Tyr Ile Asn Cys Phe Lys Lys Gln Pro
                850                 855                 860
```

```
<210> SEQ ID NO 76
<211> LENGTH: 858
<212> TYPE: PRT
<213> ORGANISM: Clostridium acetobutylicum
<220> FEATURE:
<221> NAME/KEY: MISC_FEATURE
<223> OTHER INFORMATION: AdhE2, NP_149199.1

<400> SEQUENCE: 76
```

| | | | | | | | | | | | | | | |
|---|---|---|---|---|---|---|---|---|---|---|---|---|---|---|
| Met | Lys | Val | Thr | Asn | Gln | Lys | Glu | Leu | Lys | Gln | Lys | Leu | Asn | Glu | Leu |
| 1 | | | | 5 | | | | | 10 | | | | | 15 | |
| Arg | Glu | Ala | Gln | Lys | Lys | Phe | Ala | Thr | Tyr | Thr | Gln | Glu | Gln | Val | Asp |
| | | | 20 | | | | | 25 | | | | | 30 | | |
| Lys | Ile | Phe | Lys | Gln | Cys | Ala | Ile | Ala | Ala | Lys | Glu | Arg | Ile | Asn |
| | | 35 | | | | | 40 | | | | | 45 | | |
| Leu | Ala | Lys | Leu | Ala | Val | Glu | Glu | Thr | Gly | Ile | Gly | Leu | Val | Glu | Asp |
| | 50 | | | | | 55 | | | | | 60 | | | | |
| Lys | Ile | Ile | Lys | Asn | His | Phe | Ala | Ala | Glu | Tyr | Ile | Tyr | Asn | Lys | Tyr |
| 65 | | | | | 70 | | | | | 75 | | | | | 80 |
| Lys | Asn | Glu | Lys | Thr | Cys | Gly | Ile | Ile | Asp | His | Asp | Asp | Ser | Leu | Gly |
| | | | | 85 | | | | | 90 | | | | | 95 | |
| Ile | Thr | Lys | Val | Ala | Glu | Pro | Ile | Gly | Ile | Val | Ala | Ala | Ile | Val | Pro |
| | | | 100 | | | | | 105 | | | | | 110 | | |
| Thr | Thr | Asn | Pro | Thr | Ser | Thr | Ala | Ile | Phe | Lys | Ser | Leu | Ile | Ser | Leu |
| | | 115 | | | | | 120 | | | | | 125 | | | |
| Lys | Thr | Arg | Asn | Ala | Ile | Phe | Phe | Ser | Pro | His | Pro | Arg | Ala | Lys | Lys |
| 130 | | | | | 135 | | | | | 140 | | | | | |
| Ser | Thr | Ile | Ala | Ala | Ala | Lys | Leu | Ile | Leu | Asp | Ala | Ala | Val | Lys | Ala |
| 145 | | | | | 150 | | | | | 155 | | | | | 160 |
| Gly | Ala | Pro | Lys | Asn | Ile | Ile | Gly | Trp | Ile | Asp | Glu | Pro | Ser | Ile | Glu |
| | | | | 165 | | | | | 170 | | | | | 175 | |
| Leu | Ser | Gln | Asp | Leu | Met | Ser | Glu | Ala | Asp | Ile | Ile | Leu | Ala | Thr | Gly |
| | | | 180 | | | | | 185 | | | | | 190 | | |
| Gly | Pro | Ser | Met | Val | Lys | Ala | Ala | Tyr | Ser | Ser | Gly | Lys | Pro | Ala | Ile |
| | | 195 | | | | | 200 | | | | | 205 | | | |
| Gly | Val | Gly | Ala | Gly | Asn | Thr | Pro | Ala | Ile | Ile | Asp | Glu | Ser | Ala | Asp |
| 210 | | | | | 215 | | | | | 220 | | | | | |
| Ile | Asp | Met | Ala | Val | Ser | Ser | Ile | Ile | Leu | Ser | Lys | Thr | Tyr | Asp | Asn |
| 225 | | | | | 230 | | | | | 235 | | | | | 240 |
| Gly | Val | Ile | Cys | Ala | Ser | Glu | Gln | Ser | Ile | Leu | Val | Met | Asn | Ser | Ile |
| | | | | 245 | | | | | 250 | | | | | 255 | |
| Tyr | Glu | Lys | Val | Lys | Glu | Glu | Phe | Val | Lys | Arg | Gly | Ser | Tyr | Ile | Leu |
| | | | 260 | | | | | 265 | | | | | 270 | | |
| Asn | Gln | Asn | Glu | Ile | Ala | Lys | Ile | Lys | Glu | Thr | Met | Phe | Lys | Asn | Gly |
| | | 275 | | | | | 280 | | | | | 285 | | | |
| Ala | Ile | Asn | Ala | Asp | Ile | Val | Gly | Lys | Ser | Ala | Tyr | Ile | Ile | Ala | Lys |
| | 290 | | | | | 295 | | | | | 300 | | | | |
| Met | Ala | Gly | Ile | Glu | Val | Pro | Gln | Thr | Thr | Lys | Ile | Leu | Ile | Gly | Glu |
| 305 | | | | | 310 | | | | | 315 | | | | | 320 |
| Val | Gln | Ser | Val | Glu | Lys | Ser | Glu | Leu | Phe | Ser | His | Glu | Lys | Leu | Ser |
| | | | | 325 | | | | | 330 | | | | | 335 | |
| Pro | Val | Leu | Ala | Met | Tyr | Lys | Val | Lys | Asp | Phe | Asp | Glu | Ala | Leu | Lys |
| | | | 340 | | | | | 345 | | | | | 350 | | |
| Lys | Ala | Gln | Arg | Leu | Ile | Glu | Leu | Gly | Gly | Ser | Gly | His | Thr | Ser | Ser |

```
            355                 360                 365
Leu Tyr Ile Asp Ser Gln Asn Asn Lys Asp Lys Val Lys Glu Phe Gly
370                 375                 380
Leu Ala Met Lys Thr Ser Arg Thr Phe Ile Asn Met Pro Ser Ser Gln
385                 390                 395                 400
Gly Ala Ser Gly Asp Leu Tyr Asn Phe Ala Ile Ala Pro Ser Phe Thr
                405                 410                 415
Leu Gly Cys Gly Thr Trp Gly Gly Asn Ser Val Ser Gln Asn Val Glu
            420                 425                 430
Pro Lys His Leu Leu Asn Ile Lys Ser Val Ala Glu Arg Arg Glu Asn
            435                 440                 445
Met Leu Trp Phe Lys Val Pro Gln Lys Ile Tyr Phe Lys Tyr Gly Cys
            450                 455                 460
Leu Arg Phe Ala Leu Lys Glu Leu Lys Asp Met Asn Lys Lys Arg Ala
465                 470                 475                 480
Phe Ile Val Thr Asp Lys Asp Leu Phe Lys Leu Gly Tyr Val Asn Lys
                485                 490                 495
Ile Thr Lys Val Leu Asp Glu Ile Asp Ile Lys Tyr Ser Ile Phe Thr
                500                 505                 510
Asp Ile Lys Ser Asp Pro Thr Ile Asp Ser Val Lys Lys Gly Ala Lys
            515                 520                 525
Glu Met Leu Asn Phe Glu Pro Asp Thr Ile Ile Ser Ile Gly Gly Gly
            530                 535                 540
Ser Pro Met Asp Ala Ala Lys Val Met His Leu Leu Tyr Glu Tyr Pro
545                 550                 555                 560
Glu Ala Glu Ile Glu Asn Leu Ala Ile Asn Phe Met Asp Ile Arg Lys
                565                 570                 575
Arg Ile Cys Asn Phe Pro Lys Leu Gly Thr Lys Ala Ile Ser Val Ala
                580                 585                 590
Ile Pro Thr Thr Ala Gly Thr Gly Ser Glu Ala Thr Pro Phe Ala Val
            595                 600                 605
Ile Thr Asn Asp Glu Thr Gly Met Lys Tyr Pro Leu Thr Ser Tyr Glu
            610                 615                 620
Leu Thr Pro Asn Met Ala Ile Ile Asp Thr Glu Leu Met Leu Asn Met
625                 630                 635                 640
Pro Arg Lys Leu Thr Ala Ala Thr Gly Ile Asp Ala Leu Val His Ala
                645                 650                 655
Ile Glu Ala Tyr Val Ser Val Met Ala Thr Asp Tyr Thr Asp Glu Leu
                660                 665                 670
Ala Leu Arg Ala Ile Lys Met Ile Phe Lys Tyr Leu Pro Arg Ala Tyr
            675                 680                 685
Lys Asn Gly Thr Asn Asp Ile Glu Ala Arg Glu Lys Met Ala His Ala
            690                 695                 700
Ser Asn Ile Ala Gly Met Ala Phe Ala Asn Ala Phe Leu Gly Val Cys
705                 710                 715                 720
His Ser Met Ala His Lys Leu Gly Ala Met His His Val Pro His Gly
                725                 730                 735
Ile Ala Cys Ala Val Leu Ile Glu Glu Val Ile Lys Tyr Asn Ala Thr
            740                 745                 750
Asp Cys Pro Thr Lys Gln Thr Ala Phe Pro Gln Tyr Lys Ser Pro Asn
            755                 760                 765
Ala Lys Arg Lys Tyr Ala Glu Ile Ala Glu Tyr Leu Asn Leu Lys Gly
            770                 775                 780
```

-continued

```
Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
            805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
            835                 840                 845

Glu Leu Lys Asp Ile Tyr Ile Lys Ser Phe
        850                 855

<210> SEQ ID NO 77
<211> LENGTH: 860
<212> TYPE: PRT
<213> ORGANISM: Clostridium beijerinckii
<220> FEATURE:
<221> NAME/KEY: MISC_FEATURE
<223> OTHER INFORMATION: AdhE, WP_041893626.1

<400> SEQUENCE: 77

Met Arg Val Thr Asn Pro Glu Glu Leu Thr Lys Arg Ile Glu Gln Ile
1               5                   10                  15

Arg Glu Ala Gln Arg Glu Phe Ala Lys Phe Ser Gln Glu Glu Val Asp
            20                  25                  30

Glu Ile Phe Arg Gln Ala Ala Met Ala Ala Asn Asp Ala Arg Ile Thr
        35                  40                  45

Leu Ala Lys Met Ala Val Glu Glu Ser Gly Met Gly Ile Val Glu Asp
50                  55                  60

Lys Val Ile Lys Asn His Phe Ala Ala Glu Tyr Ile Tyr Asn Gln Tyr
65                  70                  75                  80

Lys Asp Thr Lys Thr Cys Gly Val Ile Glu Arg Asp Glu Met Phe Gly
                85                  90                  95

Ile Thr His Ile Ala Glu Pro Ile Gly Val Ile Ala Ala Ile Val Pro
            100                 105                 110

Thr Thr Asn Pro Thr Ser Thr Ala Ile Phe Lys Thr Leu Ile Ala Leu
        115                 120                 125

Lys Thr Arg Asn Gly Ile Ile Ile Ser Pro His Pro Arg Ala Lys Asn
130                 135                 140

Ser Thr Ile Ala Ala Ala Lys Ile Val Leu Glu Ala Ala Glu Arg Ala
145                 150                 155                 160

Gly Ala Pro Lys Gly Ile Ile Gly Trp Ile Asp Glu Pro Ser Ile Glu
                165                 170                 175

Leu Ser Arg Asn Val Met Ser Glu Ser Asp Ile Ile Leu Ala Thr Gly
            180                 185                 190

Gly Pro Gly Met Val Arg Ala Ala Tyr Ser Ser Gly Lys Pro Ala Ile
        195                 200                 205

Gly Val Gly Ala Gly Asn Thr Pro Ala Ile Ile Asp Asp Thr Ala His
    210                 215                 220

Ile Lys Met Ala Val Asn Ser Ile Leu Leu Ser Lys Thr Phe Asp Asn
225                 230                 235                 240

Gly Val Val Cys Ala Ser Glu Gln Ser Ile Ile Ala Met Glu Ser Val
                245                 250                 255

Tyr Asp Glu Val Arg Lys Glu Leu Asp Glu Arg Gly Ala Tyr Ile Leu
            260                 265                 270

Lys Gly Asp Glu Val Asp Lys Val Arg Ser Ile Ile Leu Asp Pro Lys
```

-continued

```
            275                 280                 285
Gly Ser Leu Asn Ser Glu Ile Val Gly Gln Ser Ala Tyr Lys Ile Ala
290                 295                 300
Lys Met Ala Gly Val Glu Val Ser Glu Ala Val Lys Val Leu Ile Gly
305                 310                 315                 320
Glu Val Glu Ser Pro Glu Leu Glu Pro Phe Ser His Glu Lys Leu
                325                 330                 335
Ser Pro Ile Leu Gly Met Tyr Lys Ala Lys Thr Phe Asp Asp Ala Leu
                340                 345                 350
Arg Leu Ala Ser Arg Met Ile Glu Leu Gly Gly Phe Gly His Thr Ser
                355                 360                 365
Ile Leu Tyr Thr Asn Gln Val Glu Ser Val Asp Arg Ile Glu Lys Phe
370                 375                 380
Gly Val Ala Met Lys Thr Ala Arg Thr Leu Ile Asn Met Pro Ala Ser
385                 390                 395                 400
Gln Gly Ala Ile Gly Asp Ile Tyr Asn Phe Lys Leu Ala Pro Ser Leu
                405                 410                 415
Thr Leu Gly Cys Gly Ser Trp Gly Gly Asn Ser Ile Ser Glu Asn Val
                420                 425                 430
Gly Pro Lys His Leu Ile Asn Val Lys Arg Ile Ala Glu Arg Arg Glu
                435                 440                 445
Asn Met Leu Trp Phe Arg Val Pro Asp Lys Ile Tyr Phe Lys Phe Gly
                450                 455                 460
Cys Leu Pro Ile Ala Leu Glu Glu Leu Asn Ala Met Lys Lys Lys Arg
465                 470                 475                 480
Ala Phe Ile Val Thr Asp Arg Val Leu Phe Asp Leu Gly Tyr Thr His
                485                 490                 495
Lys Ile Thr Asp Ile Leu Ser Glu Asn His Ile Glu Tyr Lys Ile Phe
                500                 505                 510
Ser Asp Val Glu Pro Asp Pro Thr Leu Lys Ala Ala Lys Leu Gly Ala
                515                 520                 525
Asp Ala Met Arg Asp Phe Asn Pro Asp Val Ile Ile Ala Ile Gly Gly
530                 535                 540
Gly Ser Pro Met Asp Ala Ala Lys Ile Met Trp Val Met Tyr Glu His
545                 550                 555                 560
Pro Asp Val Arg Phe Glu Asp Leu Ala Met Arg Phe Met Asp Ile Arg
                565                 570                 575
Lys Arg Val Tyr Glu Phe Pro Pro Met Gly Glu Arg Ala Ile Leu Val
                580                 585                 590
Ala Ile Pro Thr Ser Ala Gly Thr Gly Ser Glu Val Thr Pro Phe Ala
                595                 600                 605
Val Ile Thr Asp Gln Gln Thr Gly Val Lys Tyr Pro Leu Ala Asp Tyr
610                 615                 620
Ala Leu Thr Pro Asn Met Ala Ile Ile Asp Ala Glu Leu Met Met Ser
625                 630                 635                 640
Met Pro Lys Gly Leu Thr Ala Ala Ser Gly Ile Asp Ala Leu Val His
                645                 650                 655
Ala Ile Glu Ala Tyr Val Ser Val Leu Ala Ser Glu Tyr Thr Asn Gly
                660                 665                 670
Leu Ala Leu Glu Ala Ile Arg Leu Thr Phe Lys Tyr Leu Pro Asp Ala
                675                 680                 685
Tyr Asn Gly Gly Thr Thr Asn Ile Lys Ala Arg Glu Lys Met Ala His
                690                 695                 700
```

-continued

```
Ala Ser Ser Val Ala Gly Met Ala Phe Ala Asn Ala Phe Leu Gly Ile
705                 710                 715                 720

Cys His Ser Met Ala His Lys Leu Gly Ala Phe His His Val Pro His
            725                 730                 735

Gly Ile Ala Asn Ala Leu Leu Ile Asp Glu Val Ile Arg Phe Asn Ala
        740                 745                 750

Thr Asp Ala Pro Arg Lys Gln Ala Ala Phe Pro Gln Tyr Lys Tyr Pro
            755                 760                 765

Asn Ala Gly Trp Arg Tyr Ala Arg Ile Ala Asp Tyr Leu Asn Leu Gly
    770                 775                 780

Gly Asn Thr Glu Glu Lys Val Glu Leu Leu Ile Lys Ala Ile Asp
785                 790                 795                 800

Asp Leu Lys Val Lys Val Arg Ile Pro Lys Ser Ile Lys Glu Phe Gly
                805                 810                 815

Val Ser Glu Glu Lys Phe Tyr Asp Ser Met Asp Glu Met Val Glu Gln
                820                 825                 830

Ala Phe Asp Asp Gln Cys Thr Gly Ala Asn Pro Arg Tyr Pro Leu Met
                835                 840                 845

Ser Glu Ile Lys Glu Met Tyr Ile Lys Ser Tyr Asn
    850                 855                 860
```

<210> SEQ ID NO 78
<211> LENGTH: 870
<212> TYPE: PRT
<213> ORGANISM: Clostridium autoethanogenum
<220> FEATURE:
<221> NAME/KEY: MISC_FEATURE
<223> OTHER INFORMATION: AdhE1, WP_023163372.1

<400> SEQUENCE: 78

```
Met Lys Val Thr Asn Val Glu Glu Leu Met Lys Arg Leu Glu Glu Ile
1               5                   10                  15

Lys Asp Ala Gln Lys Lys Phe Ala Thr Tyr Thr Gln Glu Gln Val Asp
                20                  25                  30

Glu Ile Phe Arg Gln Ala Ala Met Ala Ala Asn Ser Ala Arg Ile Glu
            35                  40                  45

Leu Ala Lys Met Ala Val Glu Glu Ser Gly Met Gly Ile Val Glu Asp
50                  55                  60

Lys Val Ile Lys Asn His Phe Ala Ser Glu Tyr Ile Tyr Asn Lys Tyr
65                  70                  75                  80

Lys Asp Glu Lys Thr Cys Gly Val Leu Glu Arg Asp Ala Gly Phe Gly
                85                  90                  95

Ile Val Arg Ile Ala Glu Pro Val Gly Val Ile Ala Ala Val Val Pro
            100                 105                 110

Thr Thr Asn Pro Thr Ser Thr Ala Ile Phe Lys Ser Leu Ile Ala Leu
        115                 120                 125

Lys Thr Arg Asn Gly Ile Ile Phe Ser Pro His Pro Arg Ala Lys Lys
    130                 135                 140

Ser Thr Ile Ala Ala Lys Ile Val Leu Asp Ala Val Lys Ala
145                 150                 155                 160

Gly Ala Pro Glu Gly Ile Ile Gly Trp Ile Asp Glu Pro Ser Ile Glu
                165                 170                 175

Leu Ser Gln Val Val Met Gly Glu Ala Asn Leu Ile Leu Ala Thr Gly
            180                 185                 190

Gly Pro Gly Met Val Lys Ala Ala Tyr Ser Ser Gly Lys Pro Ala Val
```

-continued

```
            195                 200                 205
Gly Val Gly Pro Gly Asn Thr Pro Ala Val Ile Asp Glu Ser Ala Asp
    210                 215                 220
Ile Lys Met Ala Val Asn Ser Ile Leu Leu Ser Lys Thr Phe Asp Asn
225                 230                 235                 240
Gly Met Ile Cys Ala Ser Glu Gln Ser Val Ile Val Leu Asp Ser Ile
                245                 250                 255
Tyr Glu Glu Val Lys Lys Glu Phe Ala Tyr Arg Gly Ala Tyr Ile Leu
            260                 265                 270
Ser Lys Asp Glu Thr Asp Lys Val Gly Lys Ile Ile Leu Lys Asn Gly
        275                 280                 285
Ala Leu Asn Ala Gly Ile Val Gly Gln Pro Ala Phe Lys Ile Ala Gln
    290                 295                 300
Leu Ala Gly Val Asp Val Pro Glu Lys Ala Lys Val Leu Ile Gly Glu
305                 310                 315                 320
Val Glu Ser Val Glu Leu Glu Glu Pro Phe Ser His Glu Lys Leu Ser
                325                 330                 335
Pro Val Leu Ala Met Tyr Arg Ala Arg Asn Phe Glu Asp Ala Ile Ala
            340                 345                 350
Lys Thr Asp Lys Leu Val Arg Ala Gly Gly Phe Gly His Thr Ser Ser
        355                 360                 365
Leu Tyr Ile Asn Pro Met Thr Glu Lys Ala Lys Val Gly Lys Phe Ser
    370                 375                 380
Thr Met Met Lys Thr Ser Arg Thr Ile Ile Asn Thr Pro Ser Ser Gln
385                 390                 395                 400
Gly Gly Ile Gly Asp Ile Tyr Asn Phe Lys Leu Ala Pro Ser Leu Thr
                405                 410                 415
Leu Gly Cys Gly Ser Trp Gly Gly Asn Ser Val Ser Glu Asn Val Gly
            420                 425                 430
Pro Lys His Leu Leu Asn Ile Lys Ser Val Ala Glu Arg Arg Glu Asn
        435                 440                 445
Met Leu Trp Phe Arg Val Pro Glu Lys Val Tyr Phe Lys Tyr Gly Ser
    450                 455                 460
Leu Gly Val Ala Leu Lys Glu Leu Lys Val Met Asn Lys Lys Lys Val
465                 470                 475                 480
Phe Ile Val Thr Asp Lys Val Leu Tyr Gln Leu Gly Tyr Val Asp Lys
                485                 490                 495
Val Thr Lys Val Leu Glu Glu Leu Lys Ile Ser Tyr Lys Val Phe Thr
            500                 505                 510
Asp Val Glu Pro Asp Pro Thr Leu Ala Thr Ala Lys Lys Gly Ala Ala
        515                 520                 525
Glu Leu Leu Ser Tyr Glu Pro Asp Thr Ile Ile Ser Val Gly Gly Gly
    530                 535                 540
Ser Ala Met Asp Ala Ala Lys Ile Met Trp Val Met Tyr Glu His Pro
545                 550                 555                 560
Glu Val Lys Phe Glu Asp Leu Ala Met Arg Phe Met Asp Ile Arg Lys
                565                 570                 575
Arg Val Tyr Val Phe Pro Lys Met Gly Glu Lys Ala Met Met Ile Ser
            580                 585                 590
Val Ala Thr Ser Ala Gly Thr Gly Ser Glu Val Thr Pro Phe Ala Val
        595                 600                 605
Ile Thr Asp Glu Lys Thr Gly Ala Lys Tyr Pro Leu Ala Asp Tyr Glu
    610                 615                 620
```

Leu Thr Pro Asp Met Ala Ile Val Asp Ala Glu Leu Met Met Gly Met
625                 630                 635                 640

Pro Arg Gly Leu Thr Ala Ala Ser Gly Ile Asp Ala Leu Thr His Ala
            645                 650                 655

Leu Glu Ala Tyr Val Ser Ile Met Ala Thr Glu Phe Thr Asn Gly Leu
        660                 665                 670

Ala Leu Glu Ala Val Lys Leu Ile Phe Glu Tyr Leu Pro Lys Ala Tyr
    675                 680                 685

Thr Glu Gly Thr Thr Asn Val Lys Ala Arg Glu Lys Met Ala His Ala
690                 695                 700

Ser Cys Ile Ala Gly Met Ala Phe Ala Asn Ala Phe Leu Gly Val Cys
705                 710                 715                 720

His Ser Met Ala His Lys Leu Gly Ala Gln His His Ile Pro His Gly
                725                 730                 735

Ile Ala Asn Ala Leu Met Ile Asp Glu Val Ile Lys Phe Asn Ala Val
            740                 745                 750

Asp Asp Pro Ile Lys Gln Ala Ala Phe Pro Gln Tyr Glu Tyr Pro Asn
        755                 760                 765

Ala Arg Tyr Arg Tyr Ala Gln Ile Ala Asp Cys Leu Asn Leu Gly Gly
    770                 775                 780

Asn Thr Glu Glu Glu Lys Val Gln Leu Leu Ile Asn Ala Ile Asp Asp
785                 790                 795                 800

Leu Lys Ala Lys Leu Asn Ile Pro Gly Thr Ile Lys Glu Ala Gly Val
                805                 810                 815

Ser Glu Asp Lys Phe Tyr Ala Thr Leu Asp Lys Met Ser Glu Leu Ala
            820                 825                 830

Phe Asp Asp Gln Cys Thr Gly Ala Asn Pro Arg Tyr Pro Leu Ile Ser
        835                 840                 845

Glu Ile Lys Gln Met Tyr Ile Asn Val Phe Asp Lys Thr Glu Pro Ile
    850                 855                 860

Val Glu Asp Glu Glu Lys
865                 870

<210> SEQ ID NO 79
<211> LENGTH: 877
<212> TYPE: PRT
<213> ORGANISM: Clostridium autoethanogenum
<220> FEATURE:
<221> NAME/KEY: MISC_FEATURE
<223> OTHER INFORMATION: AdhE2, WP_023163373.1

<400> SEQUENCE: 79

Met Lys Val Thr Lys Val Thr Asn Val Glu Glu Leu Met Lys Lys Leu
1               5                   10                  15

Asp Glu Val Thr Ala Ala Gln Lys Lys Phe Ser Ser Tyr Thr Gln Glu
            20                  25                  30

Gln Val Asp Glu Ile Phe Arg Gln Ala Met Ala Ala Asn Ser Ala
        35                  40                  45

Arg Ile Asp Leu Ala Lys Met Ala Val Glu Glu Ser Gly Met Gly Ile
    50                  55                  60

Val Glu Asp Lys Val Ile Lys Asn His Phe Ala Glu Tyr Ile Tyr
65                  70                  75                  80

Asn Lys Tyr Lys Gly Glu Lys Thr Cys Gly Val Leu Glu Gln Asp Glu
                85                  90                  95

Gly Phe Gly Met Val Arg Ile Ala Glu Pro Val Gly Val Ile Ala Ala

```
            100                 105                 110
Val Val Pro Thr Thr Asn Pro Thr Ser Thr Ala Ile Phe Lys Ser Leu
            115                 120             125
Ile Ala Leu Lys Thr Arg Asn Gly Ile Val Phe Ser Pro His Pro Arg
            130             135             140
Ala Lys Lys Ser Thr Ile Ala Ala Lys Ile Val Leu Asp Ala Ala
145                 150             155                 160
Val Lys Ala Gly Ala Pro Glu Gly Ile Ile Gly Trp Ile Asp Glu Pro
                165                 170                 175
Ser Ile Glu Leu Ser Gln Val Val Met Lys Glu Ala Asp Leu Ile Leu
                180                 185             190
Ala Thr Gly Gly Pro Gly Met Val Lys Ala Ala Tyr Ser Ser Gly Lys
            195                 200             205
Pro Ala Ile Gly Val Gly Pro Gly Asn Thr Pro Ala Val Ile Asp Glu
            210                 215             220
Ser Ala Asp Ile Lys Met Ala Val Asn Ser Ile Leu Leu Ser Lys Thr
225             230                 235                 240
Phe Asp Asn Gly Met Ile Cys Ala Ser Glu Gln Ser Val Ile Val Ala
                245                 250             255
Ser Ser Ile Tyr Asp Glu Val Lys Lys Glu Phe Ala Asp Arg Gly Ala
            260                 265                 270
Tyr Ile Leu Ser Lys Asp Glu Thr Asp Lys Val Gly Lys Thr Ile Met
            275                 280             285
Ile Asn Gly Ala Leu Asn Ala Gly Ile Val Gly Gln Ser Ala Phe Lys
            290                 295             300
Ile Ala Gln Met Ala Gly Val Ser Val Pro Glu Asp Ala Lys Ile Leu
305                 310                 315             320
Ile Gly Glu Val Lys Ser Val Glu Pro Glu Glu Pro Phe Ala His
                325                 330                 335
Glu Lys Leu Ser Pro Val Leu Ala Met Tyr Lys Ala Lys Asp Phe Asp
            340                 345             350
Glu Ala Leu Leu Lys Ala Gly Arg Leu Val Glu Arg Gly Gly Ile Gly
            355                 360             365
His Thr Ser Val Leu Tyr Val Asn Ser Met Thr Glu Lys Val Lys Val
            370             375             380
Glu Lys Phe Arg Glu Thr Met Lys Thr Gly Arg Thr Leu Ile Asn Met
385             390                 395                 400
Pro Ser Ala Gln Gly Ala Ile Gly Asp Ile Tyr Asn Phe Lys Leu Ala
                405                 410             415
Pro Ser Leu Thr Leu Gly Cys Gly Ser Trp Gly Gly Asn Ser Val Ser
                420             425             430
Glu Asn Val Gly Pro Lys His Leu Leu Asn Ile Lys Ser Val Ala Glu
            435                 440             445
Arg Arg Glu Asn Met Leu Trp Phe Arg Val Pro Glu Lys Val Tyr Phe
450             455                 460
Lys Tyr Gly Ser Leu Gly Val Ala Leu Lys Glu Leu Arg Ile Met Glu
465             470                 475             480
Lys Lys Lys Ala Phe Ile Val Thr Asp Lys Val Leu Tyr Gln Leu Gly
                485                 490                 495
Tyr Val Asp Lys Ile Thr Lys Asn Leu Asp Glu Leu Arg Val Ser Tyr
            500             505                 510
Lys Ile Phe Thr Asp Val Glu Pro Asp Pro Thr Leu Ala Thr Ala Lys
            515                 520             525
```

-continued

Lys Gly Ala Ala Glu Leu Leu Ser Tyr Glu Pro Asp Thr Ile Ile Ala
530                 535                 540

Val Gly Gly Gly Ser Ala Met Asp Ala Ala Lys Ile Met Trp Val Met
545                 550                 555                 560

Tyr Glu His Pro Glu Val Arg Phe Glu Asp Leu Ala Met Arg Phe Met
            565                 570                 575

Asp Ile Arg Lys Arg Val Tyr Val Phe Pro Lys Met Gly Glu Lys Ala
            580                 585                 590

Met Met Ile Ser Val Ala Thr Ser Ala Gly Thr Gly Ser Glu Val Thr
            595                 600                 605

Pro Phe Ala Val Ile Thr Asp Glu Arg Thr Gly Ala Lys Tyr Pro Leu
610                 615                 620

Ala Asp Tyr Glu Leu Thr Pro Asn Met Ala Ile Val Asp Ala Glu Leu
625                 630                 635                 640

Met Met Gly Met Pro Lys Gly Leu Thr Ala Ala Ser Gly Ile Asp Ala
            645                 650                 655

Leu Thr His Ala Leu Glu Ala Tyr Val Ser Ile Met Ala Ser Glu Tyr
            660                 665                 670

Thr Asn Gly Leu Ala Leu Glu Ala Thr Arg Leu Val Phe Lys Tyr Leu
            675                 680                 685

Pro Ile Ala Tyr Thr Glu Gly Thr Ile Asn Val Lys Ala Arg Glu Lys
690                 695                 700

Met Ala His Ala Ser Cys Ile Ala Gly Met Ala Phe Ala Asn Ala Phe
705                 710                 715                 720

Leu Gly Val Cys His Ser Met Ala His Lys Leu Gly Ala Gln His His
            725                 730                 735

Ile Pro His Gly Ile Ala Asn Ala Leu Met Ile Asp Glu Val Ile Lys
            740                 745                 750

Phe Asn Ala Val Glu Ala Pro Arg Lys Gln Ala Ala Phe Pro Gln Tyr
            755                 760                 765

Lys Tyr Pro Asn Val Lys Arg Arg Tyr Ala Arg Ile Ala Asp Tyr Leu
770                 775                 780

Asn Leu Gly Gly Ser Thr Asp Glu Lys Val Gln Leu Leu Ile Asn
785                 790                 795                 800

Ala Ile Asp Asp Leu Lys Thr Lys Leu Asn Ile Pro Lys Thr Ile Lys
            805                 810                 815

Glu Ala Gly Val Ser Glu Asp Lys Phe Tyr Ala Thr Leu Asp Thr Met
            820                 825                 830

Ser Glu Leu Ala Phe Asp Asp Gln Cys Thr Gly Ala Asn Pro Arg Tyr
            835                 840                 845

Pro Leu Ile Gly Glu Ile Lys Gln Met Tyr Ile Asn Ala Phe Asp Thr
850                 855                 860

Pro Lys Ala Thr Val Glu Lys Thr Arg Lys Lys
865                 870                 875

<210> SEQ ID NO 80
<211> LENGTH: 468
<212> TYPE: PRT
<213> ORGANISM: Clostridium saccharoperbutylacetonicum
<220> FEATURE:
<221> NAME/KEY: MISC_FEATURE
<223> OTHER INFORMATION: Bld, AAP42563.1

<400> SEQUENCE: 80

Met Ile Lys Asp Thr Leu Val Ser Ile Thr Lys Asp Leu Lys Leu Lys

-continued

```
  1               5                  10                 15
Thr Asn Val Glu Asn Ala Asn Leu Lys Asn Tyr Lys Asp Asp Ser Ser
             20                  25                 30
Cys Phe Gly Val Phe Glu Asn Val Glu Asn Ala Ile Ser Asn Ala Val
             35                  40                 45
His Ala Gln Lys Ile Leu Ser Leu His Tyr Thr Lys Glu Gln Arg Glu
             50                  55                 60
Lys Ile Ile Thr Glu Ile Arg Lys Ala Ala Leu Glu Asn Lys Glu Ile
 65                  70                  75                 80
Leu Ala Thr Met Ile Leu Glu Glu Thr His Met Gly Arg Tyr Glu Asp
                 85                  90                 95
Lys Ile Leu Lys His Glu Leu Val Ala Lys Tyr Thr Pro Gly Thr Glu
                100                 105                110
Asp Leu Thr Thr Thr Ala Trp Ser Gly Asp Asn Gly Leu Thr Val Val
                115                 120                125
Glu Met Ser Pro Tyr Gly Val Ile Gly Ala Ile Thr Pro Ser Thr Asn
                130                 135                140
Pro Thr Glu Thr Val Ile Cys Asn Ser Ile Gly Met Ile Ala Ala Gly
145                 150                 155                160
Asn Thr Val Val Phe Asn Gly His Pro Gly Ala Lys Lys Cys Val Ala
                165                 170                175
Phe Ala Val Glu Met Ile Asn Lys Ala Ile Ile Ser Cys Gly Gly Pro
                180                 185                190
Glu Asn Leu Val Thr Thr Ile Lys Asn Pro Thr Met Asp Ser Leu Asp
                195                 200                205
Ala Ile Ile Lys His Pro Ser Ile Lys Leu Leu Cys Gly Thr Gly Gly
210                 215                 220
Pro Gly Met Val Lys Thr Leu Leu Asn Ser Gly Lys Lys Ala Ile Gly
225                 230                 235                240
Ala Gly Ala Gly Asn Pro Pro Val Ile Val Asp Asp Thr Ala Asp Ile
                245                 250                255
Glu Lys Ala Gly Lys Ser Ile Ile Glu Gly Cys Ser Phe Asp Asn Asn
                260                 265                270
Leu Pro Cys Ile Ala Glu Lys Glu Val Phe Val Phe Glu Asn Val Ala
                275                 280                285
Asp Asp Leu Ile Ser Asn Met Leu Lys Asn Asn Ala Val Ile Ile Asn
                290                 295                300
Glu Asp Gln Val Ser Lys Leu Ile Asp Leu Val Leu Gln Lys Asn Asn
305                 310                 315                320
Glu Thr Gln Glu Tyr Ser Ile Asn Lys Lys Trp Val Gly Lys Asp Ala
                325                 330                335
Lys Leu Phe Leu Asp Glu Ile Asp Val Glu Ser Pro Ser Ser Val Lys
                340                 345                350
Cys Ile Ile Cys Glu Val Ser Ala Arg His Pro Phe Val Met Thr Glu
                355                 360                365
Leu Met Met Pro Ile Leu Pro Ile Val Arg Val Lys Asp Ile Asp Glu
                370                 375                380
Ala Ile Glu Tyr Ala Lys Ile Ala Glu Gln Asn Arg Lys His Ser Ala
385                 390                 395                400
Tyr Ile Tyr Ser Lys Asn Ile Asp Asn Leu Asn Arg Phe Glu Arg Glu
                405                 410                415
Ile Asp Thr Thr Ile Phe Val Lys Asn Ala Lys Ser Phe Ala Gly Val
                420                 425                430
```

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 81
<211> LENGTH: 562
<212> TYPE: PRT
<213> ORGANISM: Aquincola tertiaricarbonis
<220> FEATURE:
<221> NAME/KEY: MISC_FEATURE
<223> OTHER INFORMATION: HcmAB, large subunit, AFK77668.1

<400> SEQUENCE: 81

Met Thr Trp Leu Glu Pro Gln Ile Lys Ser Gln Leu Gln Ser Glu Arg
1               5                   10                  15

Lys Asp Trp Glu Ala Asn Glu Val Gly Ala Phe Leu Lys Lys Ala Pro
            20                  25                  30

Glu Arg Lys Glu Gln Phe His Thr Ile Gly Asp Phe Pro Val Gln Arg
        35                  40                  45

Thr Tyr Thr Ala Ala Asp Ile Ala Asp Thr Pro Leu Glu Asp Ile Gly
    50                  55                  60

Leu Pro Gly Arg Tyr Pro Phe Thr Arg Gly Pro Tyr Pro Thr Met Tyr
65                  70                  75                  80

Arg Ser Arg Thr Trp Thr Met Arg Gln Ile Ala Gly Phe Gly Thr Gly
                85                  90                  95

Glu Asp Thr Asn Lys Arg Phe Lys Tyr Leu Ile Ala Gln Gly Gln Thr
            100                 105                 110

Gly Ile Ser Thr Asp Phe Asp Met Pro Thr Leu Met Gly Tyr Asp Ser
        115                 120                 125

Asp His Pro Met Ser Asp Gly Glu Val Gly Arg Glu Gly Val Ala Ile
    130                 135                 140

Asp Thr Leu Ala Asp Met Glu Ala Leu Leu Ala Asp Ile Asp Leu Glu
145                 150                 155                 160

Lys Ile Ser Val Ser Phe Thr Ile Asn Pro Ser Ala Trp Ile Leu Leu
                165                 170                 175

Ala Met Tyr Val Ala Leu Gly Glu Lys Arg Gly Tyr Asp Leu Asn Lys
            180                 185                 190

Leu Ser Gly Thr Val Gln Ala Asp Ile Leu Lys Glu Tyr Met Ala Gln
        195                 200                 205

Lys Glu Tyr Ile Tyr Pro Ile Ala Pro Ser Val Arg Ile Val Arg Asp
    210                 215                 220

Ile Ile Thr Tyr Ser Ala Lys Asn Leu Lys Arg Tyr Asn Pro Ile Asn
225                 230                 235                 240

Ile Ser Gly Tyr His Ile Ser Glu Ala Gly Ser Ser Pro Leu Gln Glu
                245                 250                 255

Ala Ala Phe Thr Leu Ala Asn Leu Ile Thr Tyr Val Asn Glu Val Thr
            260                 265                 270

Lys Thr Gly Met His Val Asp Glu Phe Ala Pro Arg Leu Ala Phe Phe
        275                 280                 285

Phe Val Ser Gln Gly Asp Phe Phe Glu Glu Val Ala Lys Phe Arg Ala
    290                 295                 300

Leu Arg Arg Cys Tyr Ala Lys Ile Met Lys Glu Arg Phe Gly Ala Arg

```
                305                 310                 315                 320
Asn Pro Glu Ser Met Arg Leu Arg Phe His Cys Gln Thr Ala Ala Ala
            325                 330                 335
Thr Leu Thr Lys Pro Gln Tyr Met Val Asn Val Val Arg Thr Ser Leu
            340                 345                 350
Gln Ala Leu Ser Ala Val Leu Gly Ala Gln Ser Leu His Thr Asn
            355                 360                 365
Gly Tyr Asp Glu Ala Phe Ala Ile Pro Thr Glu Asp Ala Met Lys Met
            370                 375                 380
Ala Leu Arg Thr Gln Gln Ile Ile Ala Glu Glu Ser Gly Val Ala Asp
385                 390                 395                 400
Val Ile Asp Pro Leu Gly Gly Ser Tyr Tyr Val Glu Ala Leu Thr Thr
                405                 410                 415
Glu Tyr Glu Lys Lys Ile Phe Glu Ile Leu Glu Glu Val Glu Lys Arg
            420                 425                 430
Gly Gly Thr Ile Lys Leu Ile Glu Gln Gly Trp Phe Gln Lys Gln Ile
            435                 440                 445
Ala Asp Phe Ala Tyr Glu Thr Ala Leu Arg Lys Gln Ser Gly Gln Lys
            450                 455                 460
Pro Val Ile Gly Val Asn Arg Phe Val Glu Asn Glu Asp Val Lys
465                 470                 475                 480
Ile Glu Ile His Pro Tyr Asp Asn Thr Thr Ala Glu Arg Gln Ile Ser
                485                 490                 495
Arg Thr Arg Arg Val Arg Ala Glu Arg Asp Glu Ala Lys Val Gln Ala
            500                 505                 510
Met Leu Asp Gln Leu Val Ala Val Ala Lys Asp Glu Ser Gln Asn Leu
            515                 520                 525
Met Pro Leu Thr Ile Glu Leu Val Lys Ala Gly Ala Thr Met Gly Asp
            530                 535                 540
Ile Val Glu Lys Leu Lys Gly Ile Trp Gly Thr Tyr Arg Glu Thr Pro
545                 550                 555                 560
Val Phe

<210> SEQ ID NO 82
<211> LENGTH: 136
<212> TYPE: PRT
<213> ORGANISM: Aquincola tertiaricarbonis
<220> FEATURE:
<221> NAME/KEY: MISC_FEATURE
<223> OTHER INFORMATION: HcmAB, small subunit, AFK77665.1

<400> SEQUENCE: 82

Met Asp Gln Thr Pro Ile Arg Val Leu Leu Ala Lys Val Gly Leu Asp
1               5                   10                  15
Gly His Asp Arg Gly Val Lys Val Val Ala Arg Ala Leu Arg Asp Ala
            20                  25                  30
Gly Met Asp Val Ile Tyr Ser Gly Leu His Arg Thr Pro Glu Glu Val
            35                  40                  45
Val Asn Thr Ala Ile Gln Glu Asp Val Asp Val Leu Gly Val Ser Leu
            50                  55                  60
Leu Ser Gly Val Gln Leu Thr Val Phe Pro Lys Ile Phe Lys Leu Leu
65                  70                  75                  80
Asp Glu Arg Gly Ala Gly Asp Leu Ile Val Ile Ala Gly Gly Val Met
                85                  90                  95
Pro Asp Glu Asp Ala Ala Ala Ile Arg Lys Leu Gly Val Arg Glu Val
```

```
                 100                 105                 110

Leu Leu Gln Asp Thr Pro Pro Gln Ala Ile Ile Asp Ser Ile Arg Ser
             115                 120                 125

Leu Val Ala Ala Arg Gly Ala Arg
         130                 135

<210> SEQ ID NO 83
<211> LENGTH: 563
<212> TYPE: PRT
<213> ORGANISM: Kyrpidia tusciae
<220> FEATURE:
<221> NAME/KEY: MISC_FEATURE
<223> OTHER INFORMATION: HcmAB, large subunit, WP_013074530.1

<400> SEQUENCE: 83

Met Ala Asp Gln Glu Lys Leu Phe Asn Gly Asp Glu Ile Arg Arg Ile
1               5                   10                  15

Arg Gln Glu Lys Glu Arg Trp Tyr Arg Glu Thr Val Lys Gly Asn Asp
            20                  25                  30

Gly Gly Asn Asp Tyr Val Thr Asp Ser Gly Ile Pro Val Asn Leu Ile
        35                  40                  45

Tyr Gly Pro Asp Asp Ile Ala Asp Phe Asp Tyr Leu Lys Glu Ser Gly
    50                  55                  60

Phe Ser Gly Glu Pro Pro Tyr Val Arg Gly Val Tyr Pro Asn Met Tyr
65                  70                  75                  80

Arg Gly Arg Leu Phe Thr Ile Arg Gln Ile Ala Gly Phe Gly Thr Pro
                85                  90                  95

Glu Asp Thr Asn Arg Arg Phe Lys Phe Leu Leu Glu Asn Gly Ala Thr
            100                 105                 110

Gly Thr Ser Val Val Leu Asp Leu Pro Thr Ile Arg Gly Tyr Asp Ser
        115                 120                 125

Asp Asp Pro Lys Ala Glu Gly His Val Gly Ala Ala Gly Val Ala Ile
    130                 135                 140

Asp Ser Leu Glu Asp Met Glu Ala Leu Tyr Asp Gly Ile Pro Ile Asp
145                 150                 155                 160

Gln Val Ser Ser Asn Ile Val Thr His Leu Pro Ser Thr Thr Val Val
                165                 170                 175

Leu Met Ala Met Phe Val Ala Met Ala Glu Lys Arg Gly Leu Pro Leu
            180                 185                 190

Glu Lys Leu Ser Gly Thr Asn Gln Asn Asp Phe Leu Met Glu Thr Thr
        195                 200                 205

Ile Gly Ser Ser Leu Glu Ile Leu Pro Pro Lys Ala Ser Phe Arg Leu
    210                 215                 220

Gln Cys Asp Ser Ile Glu Tyr Ala Ser Lys Arg Leu Pro Arg Trp Asn
225                 230                 235                 240

Pro Val Ser Tyr Asn Gly Tyr Asn Leu Arg Glu Ala Gly Thr Thr Ala
                245                 250                 255

Val Gln Glu Val Gly Cys Ala Ile Ala Asn Ala Ile Ala Thr Thr Glu
            260                 265                 270

Glu Leu Ile Arg Arg Gly Asn Asp Val Asp Asp Phe Ala Lys Arg Leu
        275                 280                 285

Ser Phe Phe Trp Asn Leu Phe Asn Asp Phe Phe Glu Glu Ile Ala Lys
    290                 295                 300

Cys Arg Ala Ser Arg Leu Val Trp Tyr Asp Val Met Lys Asn Arg Phe
305                 310                 315                 320
```

-continued

```
Gly Ala Lys Asn Pro Arg Ser Tyr Leu Met Arg Phe His Val Gln Thr
            325                 330                 335

Gly Gly Ile Thr Leu Thr Lys Val Glu Pro Leu Asn Asn Ile Ala Arg
            340                 345                 350

Ser Ala Ile Gln Gly Leu Ala Ala Val Leu Gly Gly Ala Gln Ser Leu
            355                 360                 365

His Ile Asp Ser Tyr Asp Glu Ala Tyr Ser Ala Pro Thr Glu Gln Ala
            370                 375                 380

Ala Leu Val Ser Leu Arg Thr Gln Gln Ile Ile Gln Val Glu Thr Gly
385                 390                 395                 400

Val Val Asn Thr Val Asp Pro Leu Ala Gly Ser Tyr Tyr Val Glu Tyr
            405                 410                 415

Leu Thr Arg Glu Met Ala Glu His Ile Arg Ala Tyr Ile Asp Gln Ile
            420                 425                 430

Glu Ser Arg Gly Gly Ile Ile Ala Val Val Glu Ser Gly Trp Leu His
            435                 440                 445

Arg Glu Ile Ala Glu Phe Ala Tyr Arg Thr Gln Gln Asp Ile Glu Thr
            450                 455                 460

Gly Lys Arg Lys Val Val Gly Leu Asn Tyr Phe Pro Ser Lys Glu Ala
465                 470                 475                 480

Glu Thr Lys Val Glu Val Phe Arg Tyr Pro Glu Asp Ala Glu Arg Met
            485                 490                 495

Gln Lys Glu Lys Leu Ala Lys Leu Arg Ala Arg Arg Asp Pro Val Lys
            500                 505                 510

Val Glu Gln Thr Leu Arg Val Leu Arg Glu Lys Cys His Glu Asp Val
            515                 520                 525

Asn Ile Leu Pro Tyr Val Lys Asp Ala Val Glu Ala Tyr Cys Thr Leu
            530                 535                 540

Gly Glu Ile Gln Asn Val Phe Arg Glu Glu Phe Gly Leu Trp Gln Phe
545                 550                 555                 560

Pro Leu Val

<210> SEQ ID NO 84
<211> LENGTH: 132
<212> TYPE: PRT
<213> ORGANISM: Kyrpidia tusciae
<220> FEATURE:
<221> NAME/KEY: MISC_FEATURE
<223> OTHER INFORMATION: HcmAB, small subunit, WP_013074531.1

<400> SEQUENCE: 84

Met Glu Lys Lys Ile Lys Val Ile Met Val Lys Leu Gly Leu Asp Ile
1               5                   10                  15

His Trp Arg Gly Ala Leu Val Val Ser Lys Met Leu Arg Asp Arg Gly
            20                  25                  30

Met Glu Val Val Tyr Leu Gly Asn Leu Phe Pro Glu Gln Ile Val Gln
            35                  40                  45

Ala Ala Val Gln Glu Gly Ala Asp Val Val Gly Leu Ser Thr Leu Gly
            50                  55                  60

Gly Asn His Leu Thr Leu Gly Pro Lys Val Val Glu Leu Leu Arg Ala
65                  70                  75                  80

Lys Gly Met Glu Glu Val Leu Val Ile Met Gly Gly Val Ile Pro Glu
            85                  90                  95

Glu Asp Val Pro Ala Leu Lys Glu Ala Gly Ile Ala Glu Val Phe Gly
            100                 105                 110
```

```
Pro Glu Thr Pro Ile Asp Ala Ile Glu Ser Phe Ile Arg Ser Arg Phe
            115                 120                 125

Pro Asp Arg Asp
    130
```

<210> SEQ ID NO 85
<211> LENGTH: 327
<212> TYPE: PRT
<213> ORGANISM: Aquincola tertiaricarbonis
<220> FEATURE:
<221> NAME/KEY: MISC_FEATURE
<223> OTHER INFORMATION: MeaB, AFK77667.1

<400> SEQUENCE: 85

```
Met Thr Tyr Val Pro Ser Ser Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Asp Ser Gly Val
            100                 105                 110

Phe Ile Arg Ser Met Ala Thr Arg Gly Ala Thr Gly Gly Met Ala Arg
        115                 120                 125

Ala Ala Leu Asp Ala Val Asp Leu Leu Asp Val Ala Gly Tyr His Thr
    130                 135                 140

Ile Ile Leu Glu Thr Val Gly Val Gly Gln Asp Glu Val Glu Val Ala
145                 150                 155                 160

His Ala Ser Asp Thr Thr Val Val Ser Ala Pro Gly Leu Gly Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Ala Asn Arg Thr Leu Thr Asp
        195                 200                 205

Leu Lys Gln Met Leu Thr Leu Gly Thr Met Val Gly Pro Lys Arg Ala
    210                 215                 220

Trp Ala Ile Pro Val Val Gly Val Ser Ser Tyr Thr Gly Glu Gly Val
225                 230                 235                 240

Asp Asp Leu Leu Gly Arg Ile Ala Ala His Arg Gln Ala Thr Ala Asp
                245                 250                 255

Thr Glu Leu Gly Arg Glu Arg Arg Arg Val Ala Glu Phe Arg Leu
            260                 265                 270

Gln Lys Thr Ala Glu Thr Leu Leu Leu Glu Arg Phe Thr Thr Gly Ala
    275                 280                 285

Gln Pro Phe Ser Pro Ala Leu Ala Asp Ser Leu Ser Asn Arg Ala Ser
    290                 295                 300

Asp Pro Tyr Ala Ala Arg Glu Leu Ile Ala Arg Thr Ile Arg Lys
305                 310                 315                 320

Glu Tyr Ser Asn Asp Leu Ala
                325
```

-continued

<210> SEQ ID NO 86
<211> LENGTH: 312
<212> TYPE: PRT
<213> ORGANISM: Kyrpidia tusciae
<220> FEATURE:
<221> NAME/KEY: MISC_FEATURE
<223> OTHER INFORMATION: MeaB, WP_013074529.1

<400> SEQUENCE: 86

Met Gln Glu Leu Leu Ser Arg Phe Asp Ala Gly Asp Pro Val Ala Leu
1               5                   10                  15

Gly Lys Leu Leu Lys Glu Val Glu Asn Gly Thr Ser Ser Gly Lys Glu
            20                  25                  30

Ala Leu Arg Cys Thr Ala Ser Arg Gln Gly Arg Ala His Val Val Gly
        35                  40                  45

Ile Thr Gly Pro Pro Gly Ala Gly Lys Ser Thr Leu Thr Ala Lys Leu
    50                  55                  60

Ser Lys Arg Trp Ala Glu Ala Gly Arg Glu Val Gly Ile Val Cys Val
65                  70                  75                  80

Asp Pro Thr Ser Pro Phe Ser Gly Gly Ala Leu Leu Gly Asp Arg Ile
                85                  90                  95

Arg Met Leu Glu Leu Ser Ser Phe Pro Asn Val Phe Ile Lys Ser Leu
            100                 105                 110

Ala Thr Arg Gly Ser Leu Gly Gly Met Ala Ala Ser Thr Ala Asp Ile
        115                 120                 125

Ile Gln Leu Met Asp Ala Tyr Gly Lys Glu Val Val Val Glu Thr
    130                 135                 140

Val Gly Val Gly Gln Val Glu Phe Asp Val Met Asp Leu Ser Asp Thr
145                 150                 155                 160

Val Val Leu Val Asn Val Pro Gly Leu Gly Asp Ser Ile Gln Ala Leu
                165                 170                 175

Lys Ala Gly Ile Leu Glu Ile Ala Asp Ile Phe Val Ile Asn Gln Ala
            180                 185                 190

Asp Arg Pro Gly Ala Glu Asp Ser Val Arg Asp Leu Arg Gln Met Leu
        195                 200                 205

Ala Asp Arg Lys Glu Thr Gly Trp Leu Trp Pro Val Val Lys Thr Val
    210                 215                 220

Ala Thr Arg Gly Glu Gly Ile Asp Arg Leu Ala Glu Ala Ile Glu Ser
225                 230                 235                 240

His Arg Ala Tyr Leu Lys Arg Glu Gln Leu Trp Glu Glu Lys Arg Cys
                245                 250                 255

Arg Arg Asn Arg Gln Arg Leu Met Gln Glu Met Asp Arg Leu Phe Arg
            260                 265                 270

Gln His Val Leu Thr Arg Ile Arg Thr Asp Pro Thr Ala Arg Ala Leu
        275                 280                 285

Phe Glu Glu Val Glu Lys Gly Thr Gln Asp Pro Tyr Ser Ala Ala Arg
    290                 295                 300

His Leu Phe Gln Glu Ile Val Asn
305                 310

<210> SEQ ID NO 87
<211> LENGTH: 301
<212> TYPE: PRT
<213> ORGANISM: Clostridium acetobutylicum
<220> FEATURE:
<221> NAME/KEY: MISC_FEATURE
<223> OTHER INFORMATION: Ptb, WP_010966357.1

<400> SEQUENCE: 87

```
Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Met Val Met
                85                  90                  95

Lys Gly Leu Val Asn Thr Ala Thr Phe Leu Arg Ser Val Leu Asn Lys
            100                 105                 110

Glu Val Gly Leu Arg Thr Gly Lys Thr Met Ser His Val Ala Val Phe
        115                 120                 125

Glu Thr Glu Lys Phe Asp Arg Leu Leu Phe Leu Thr Asp Val Ala Phe
130                 135                 140

Asn Thr Tyr Pro Glu Leu Lys Glu Lys Ile Asp Ile Val Asn Asn Ser
145                 150                 155                 160

Val Lys Val Ala His Ala Ile Gly Ile Glu Asn Pro Lys Val Ala Pro
                165                 170                 175

Ile Cys Ala Val Glu Val Ile Asn Pro Lys Met Pro Ser Thr Leu Asp
            180                 185                 190

Ala Ala Met Leu Ser Lys Met Ser Asp Arg Gly Gln Ile Lys Gly Cys
        195                 200                 205

Val Val Asp Gly Pro Leu Ala Leu Asp Ile Ala Leu Ser Glu Glu Ala
210                 215                 220

Ala His His Lys Gly Val Thr Gly Glu Val Ala Gly Lys Ala Asp Ile
225                 230                 235                 240

Phe Leu Met Pro Asn Ile Glu Thr Gly Asn Val Met Tyr Lys Thr Leu
                245                 250                 255

Thr Tyr Thr Thr Asp Ser Lys Asn Gly Gly Ile Leu Val Gly Thr Ser
            260                 265                 270

Ala Pro Val Val Leu Thr Ser Arg Ala Asp Ser His Glu Thr Lys Met
        275                 280                 285

Asn Ser Ile Ala Leu Ala Ala Leu Val Ala Gly Asn Lys
        290                 295                 300
```

<210> SEQ ID NO 88
<211> LENGTH: 302
<212> TYPE: PRT
<213> ORGANISM: Clostridium beijerinckii
<220> FEATURE:
<221> NAME/KEY: MISC_FEATURE
<223> OTHER INFORMATION: Ptb

<400> SEQUENCE: 88

```
Met Ser Lys Asn Phe Asp Glu Leu Leu Ser Arg Leu Lys Glu Val Pro
1               5                   10                  15

Thr Lys Lys Val Ala Val Ala Val Ala Gln Asp Glu Pro Val Leu Glu
            20                  25                  30

Ala Ile Lys Glu Ala Thr Glu Asn Asn Ile Ala Glu Ala Ile Leu Val
```

```
            35                  40                  45
Gly Asp Lys Gln Gln Ile His Glu Ile Ala Lys Lys Ile Asn Leu Asp
 50                  55                  60

Leu Ser Asp Tyr Glu Ile Met Asp Ile Lys Asp Pro Lys Lys Ala Thr
 65                  70                  75                  80

Leu Glu Ala Val Lys Leu Val Ser Ser Gly His Ala Asp Met Leu Met
                 85                  90                  95

Lys Gly Leu Val Asp Thr Ala Thr Phe Leu Arg Ser Val Leu Asn Lys
                100                 105                 110

Glu Val Gly Leu Arg Thr Gly Lys Leu Met Ser His Val Ala Val Phe
            115                 120                 125

Asp Val Glu Gly Trp Asp Arg Leu Leu Phe Leu Thr Asp Ala Ala Phe
        130                 135                 140

Asn Thr Tyr Pro Glu Phe Lys Asp Lys Val Gly Met Ile Asn Asn Ala
145                 150                 155                 160

Val Val Val Ala His Ala Cys Gly Ile Asp Val Pro Arg Ile Ala Pro
                165                 170                 175

Ile Cys Pro Val Glu Val Val Asn Thr Ser Met Gln Ser Thr Val Asp
                180                 185                 190

Ala Ala Leu Leu Ala Lys Met Ser Asp Arg Gly Gln Ile Lys Gly Cys
            195                 200                 205

Ile Ile Asp Gly Pro Phe Ala Leu Asp Asn Ala Ile Ser Glu Glu Ala
        210                 215                 220

Ala His His Lys Gly Val Thr Gly Ser Val Ala Gly Lys Ala Asp Ile
225                 230                 235                 240

Leu Leu Leu Pro Asn Ile Glu Ala Ala Asn Val Met Tyr Lys Thr Leu
                245                 250                 255

Thr Tyr Phe Ser Lys Ser Arg Asn Gly Gly Leu Leu Val Gly Thr Ser
                260                 265                 270

Ala Pro Val Ile Leu Thr Ser Arg Ala Asp Ser Phe Glu Thr Lys Val
            275                 280                 285

Asn Ser Ile Ala Leu Ala Ala Leu Val Ala Ala Arg Asn Lys
        290                 295                 300

<210> SEQ ID NO 89
<211> LENGTH: 302
<212> TYPE: PRT
<213> ORGANISM: Clostridium beijerinckii
<220> FEATURE:
<221> NAME/KEY: MISC_FEATURE
<223> OTHER INFORMATION: Ptb, WP_041893500

```
Lys Gly Leu Val Asp Thr Ala Thr Phe Leu Arg Ser Val Leu Asn Lys
                100                 105                 110

Glu Val Gly Leu Arg Thr Gly Lys Leu Met Ser His Val Ala Val Phe
            115                 120                 125

Asp Val Glu Gly Trp Asp Arg Leu Leu Phe Leu Thr Asp Ala Ala Phe
        130                 135                 140

Asn Thr Tyr Pro Glu Phe Lys Asp Lys Val Gly Met Ile Asn Asn Ala
145                 150                 155                 160

Val Val Val Ala His Ala Cys Gly Ile Asp Val Pro Arg Ile Ala Pro
                165                 170                 175

Ile Cys Pro Val Glu Val Val Asn Thr Ser Met Gln Ser Thr Val Asp
            180                 185                 190

Ala Ala Leu Leu Ala Lys Met Ser Asp Arg Gly Gln Ile Lys Gly Cys
        195                 200                 205

Val Ile Asp Gly Pro Phe Ala Leu Asp Asn Ala Ile Ser Glu Glu Ala
    210                 215                 220

Ala His His Lys Gly Val Thr Gly Ser Val Ala Gly Lys Ala Asp Ile
225                 230                 235                 240

Leu Leu Leu Pro Asn Ile Glu Ala Ala Asn Val Met Tyr Lys Thr Leu
                245                 250                 255

Thr Tyr Phe Ser Lys Ser Arg Asn Gly Gly Leu Leu Val Gly Thr Ser
            260                 265                 270

Ala Pro Val Ile Leu Thr Ser Arg Ala Asp Ser Phe Glu Thr Lys Val
        275                 280                 285

Asn Ser Ile Ala Leu Ala Ala Leu Val Ala Ala Arg Asn Lys
    290                 295                 300

<210> SEQ ID NO 90
<211> LENGTH: 355
<212> TYPE: PRT
<213> ORGANISM: Clostridium acetobutylicum
<220> FEATURE:
<221> NAME/KEY: MISC_FEATURE
<223> OTHER INFORMATION: Buk, WP_010966356.1

<400> SEQUENCE: 90

Met Tyr Arg Leu Leu Ile Ile Asn Pro Gly Ser Thr Ser Thr Lys Ile
1               5                   10                  15

Gly Ile Tyr Asp Asp Glu Lys Glu Ile Phe Glu Lys Thr Leu Arg His
            20                  25                  30

Ser Ala Glu Glu Ile Glu Lys Tyr Asn Thr Ile Phe Asp Gln Phe Gln
        35                  40                  45

Phe Arg Lys Asn Val Ile Leu Asp Ala Leu Lys Glu Ala Asn Ile Glu
    50                  55                  60

Val Ser Ser Leu Asn Ala Val Val Gly Arg Gly Gly Leu Leu Lys Pro
65                  70                  75                  80

Ile Val Ser Gly Thr Tyr Ala Val Asn Gln Lys Met Leu Glu Asp Leu
                85                  90                  95

Lys Val Gly Val Gln Gly Gln His Ala Ser Asn Leu Gly Gly Ile Ile
            100                 105                 110

Ala Asn Glu Ile Ala Lys Glu Ile Asn Val Pro Ala Tyr Ile Val Asp
        115                 120                 125

Pro Val Val Val Asp Glu Leu Asp Glu Val Ser Arg Ile Ser Gly Met
    130                 135                 140

Ala Asp Ile Pro Arg Lys Ser Ile Phe His Ala Leu Asn Gln Lys Ala
145                 150                 155                 160
```

-continued

Val Ala Arg Arg Tyr Ala Lys Glu Val Gly Lys Lys Tyr Glu Asp Leu
                165                 170                 175

Asn Leu Ile Val Val His Met Gly Gly Gly Thr Ser Val Gly Thr His
            180                 185                 190

Lys Asp Gly Arg Val Ile Glu Val Asn Asn Thr Leu Asp Gly Glu Gly
        195                 200                 205

Pro Phe Ser Pro Glu Arg Ser Gly Gly Val Pro Ile Gly Asp Leu Val
    210                 215                 220

Arg Leu Cys Phe Ser Asn Lys Tyr Thr Tyr Glu Val Met Lys Lys
225                 230                 235                 240

Ile Asn Gly Lys Gly Gly Val Val Ser Tyr Leu Asn Thr Ile Asp Phe
                245                 250                 255

Lys Ala Val Val Asp Lys Ala Leu Glu Gly Asp Lys Lys Cys Ala Leu
            260                 265                 270

Ile Tyr Glu Ala Phe Thr Phe Gln Val Ala Lys Glu Ile Gly Lys Cys
        275                 280                 285

Ser Thr Val Leu Lys Gly Asn Val Asp Ala Ile Ile Leu Thr Gly Gly
    290                 295                 300

Ile Ala Tyr Asn Glu His Val Cys Asn Ala Ile Glu Asp Arg Val Lys
305                 310                 315                 320

Phe Ile Ala Pro Val Val Arg Tyr Gly Gly Glu Asp Glu Leu Leu Ala
                325                 330                 335

Leu Ala Glu Gly Gly Leu Arg Val Leu Arg Gly Glu Glu Lys Ala Lys
            340                 345                 350

Glu Tyr Lys
        355

<210> SEQ ID NO 91
<211> LENGTH: 355
<212> TYPE: PRT
<213> ORGANISM: Clostridium beijerinckii
<220> FEATURE:
<221> NAME/KEY: MISC_FEATURE
<223> OTHER INFORMATION: Buk, WP_011967556

<400> SEQUENCE: 91

Met Ser Tyr Lys Leu Leu Ile Ile Asn Pro Gly Ser Thr Ser Thr Lys
1               5                   10                  15

Ile Gly Val Tyr Glu Gly Glu Lys Glu Leu Phe Glu Thr Leu Arg
                20                  25                  30

His Thr Asn Glu Glu Ile Lys Arg Tyr Asp Thr Ile Tyr Asp Gln Phe
            35                  40                  45

Glu Phe Arg Lys Glu Val Ile Leu Asn Val Leu Lys Glu Lys Asn Phe
    50                  55                  60

Asp Ile Lys Thr Leu Ser Ala Ile Val Gly Arg Gly Met Leu Arg
65                  70                  75                  80

Pro Val Glu Gly Gly Thr Tyr Ala Val Asn Asp Ala Met Val Glu Asp
                85                  90                  95

Leu Lys Val Gly Val Gln Gly Pro His Ala Ser Asn Leu Gly Gly Ile
            100                 105                 110

Ile Ala Lys Ser Ile Gly Asp Glu Leu Asn Ile Pro Ser Phe Ile Val
        115                 120                 125

Asp Pro Val Val Thr Asp Glu Leu Ala Asp Val Ala Arg Leu Ser Gly
    130                 135                 140

Val Pro Glu Leu Pro Arg Lys Ser Lys Phe His Ala Leu Asn Gln Lys

```
145                 150                 155                 160
Ala Val Ala Lys Arg Tyr Gly Lys Glu Ser Gly Gln Gly Tyr Glu Asn
                165                 170                 175

Leu Asn Leu Val Val His Met Gly Gly Val Ser Val Gly Ala
            180                 185                 190

His Asn His Gly Lys Val Val Asp Val Asn Asn Ala Leu Asp Gly Asp
        195                 200                 205

Gly Pro Phe Ser Pro Glu Arg Ala Gly Ser Val Pro Ile Gly Asp Leu
    210                 215                 220

Val Lys Met Cys Phe Ser Gly Lys Tyr Ser Glu Ala Glu Val Tyr Gly
225                 230                 235                 240

Lys Ala Val Gly Lys Gly Phe Val Gly Tyr Leu Asn Thr Asn Asp
                245                 250                 255

Val Lys Gly Val Ile Asp Lys Met Glu Glu Gly Asp Lys Glu Cys Glu
            260                 265                 270

Ser Ile Tyr Lys Ala Phe Val Tyr Gln Ile Ser Lys Ala Ile Gly Glu
        275                 280                 285

Met Ser Val Val Leu Glu Gly Lys Val Asp Gln Ile Ile Phe Thr Gly
    290                 295                 300

Gly Ile Ala Tyr Ser Pro Thr Leu Val Pro Asp Leu Lys Ala Lys Val
305                 310                 315                 320

Glu Trp Ile Ala Pro Val Thr Val Tyr Pro Gly Glu Asp Glu Leu Leu
                325                 330                 335

Ala Leu Ala Gln Gly Ala Ile Arg Val Leu Asp Gly Glu Gln Ala
            340                 345                 350

Lys Val Tyr
        355

<210> SEQ ID NO 92
<211> LENGTH: 355
<212> TYPE: PRT
<213> ORGANISM: Clostridium beijerinckii
<220> FEATURE:
<221> NAME/KEY: MISC_FEATURE
<223> OTHER INFORMATION: Buk, WP_017209677

```
Val Pro Glu Leu Pro Arg Lys Ser Lys Phe His Ala Leu Asn Gln Lys
145                 150                 155                 160

Ala Val Ala Lys Arg Tyr Gly Lys Glu Ser Gly Gln Gly Tyr Glu Asn
                165                 170                 175

Leu Asn Leu Val Val His Met Gly Gly Val Ser Val Gly Ala
            180                 185                 190

His Asn His Gly Lys Val Val Asp Val Asn Asn Ala Leu Asp Gly Asp
            195                 200                 205

Gly Pro Phe Ser Pro Glu Arg Ala Gly Ser Val Pro Ile Gly Asp Leu
            210                 215                 220

Val Lys Met Cys Phe Ser Gly Lys Tyr Ser Glu Ala Glu Val Tyr Gly
225                 230                 235                 240

Lys Val Val Gly Lys Gly Phe Val Gly Tyr Leu Asn Thr Asn Asp
                245                 250                 255

Val Lys Gly Val Ile Asp Lys Met Glu Gly Asp Lys Glu Cys Gly
            260                 265                 270

Ser Ile Tyr Lys Ala Phe Val Tyr Gln Ile Ser Lys Ala Ile Gly Glu
            275                 280                 285

Met Ser Val Val Leu Glu Gly Lys Val Asp Gln Ile Ile Phe Thr Gly
290                 295                 300

Gly Ile Ala Tyr Ser Pro Thr Leu Val Pro Asp Leu Lys Ala Lys Val
305                 310                 315                 320

Glu Trp Ile Ala Pro Val Thr Val Tyr Pro Gly Glu Asp Glu Leu Leu
                325                 330                 335

Ala Leu Ala Gln Gly Ala Ile Arg Val Leu Asp Gly Glu Glu Gln Ala
                340                 345                 350

Lys Val Tyr
        355

<210> SEQ ID NO 93
<211> LENGTH: 355
<212> TYPE: PRT
<213> ORGANISM: Clostridium beijerinckii
<220> FEATURE:
<221> NAME/KEY: MISC_FEATURE
<223> OTHER INFORMATION: Buk, WP_026886638

<400> SEQUENCE: 93

Met Ser Tyr Lys Leu Leu Ile Ile Asn Pro Gly Ser Thr Ser Thr Lys
1               5                   10                  15

Ile Gly Val Tyr Glu Gly Glu Lys Glu Leu Phe Glu Glu Thr Leu Arg
                20                  25                  30

His Thr Asn Glu Glu Ile Lys Arg Tyr Asp Thr Ile Tyr Asp Gln Phe
            35                  40                  45

Glu Phe Arg Lys Glu Val Ile Leu Asn Val Leu Lys Glu Lys Asn Phe
        50                  55                  60

Asp Ile Lys Thr Leu Ser Ala Ile Val Gly Arg Gly Met Leu Arg
65                  70                  75                  80

Pro Val Glu Gly Gly Thr Tyr Ala Val Asn Asp Ala Met Val Glu Asp
                85                  90                  95

Leu Lys Val Gly Val Gln Gly Pro His Ala Ser Asn Leu Gly Gly Ile
            100                 105                 110

Ile Ala Lys Ser Ile Gly Asp Glu Leu Asn Ile Pro Ser Phe Ile Val
            115                 120                 125

Asp Pro Val Val Thr Asp Glu Leu Ala Asp Val Ala Arg Leu Ser Gly
            130                 135                 140
```

Val Pro Glu Leu Pro Arg Lys Ser Lys Phe His Ala Leu Asn Gln Lys
145                 150                 155                 160

Ala Val Ala Lys Arg Tyr Gly Lys Glu Ser Gly Gln Gly Tyr Glu Asn
                165                 170                 175

Leu Asn Leu Val Val His Met Gly Gly Gly Val Ser Val Gly Ala
            180                 185                 190

His Asn His Gly Lys Val Val Asp Val Asn Asn Ala Leu Asp Gly Asp
                195                 200                 205

Gly Pro Phe Ser Pro Glu Arg Ala Gly Ser Val Pro Ile Gly Asp Leu
        210                 215                 220

Val Lys Met Cys Phe Ser Gly Lys Tyr Ser Glu Ala Glu Val Tyr Gly
225                 230                 235                 240

Lys Val Val Gly Lys Gly Gly Phe Val Gly Tyr Leu Asn Thr Asn Asp
                245                 250                 255

Val Lys Gly Val Ile Asp Asn Met Glu Ser Gly Asp Lys Glu Cys Glu
                260                 265                 270

Ser Ile Tyr Lys Ala Phe Val Tyr Gln Ile Ser Lys Ala Ile Gly Glu
        275                 280                 285

Met Ser Val Val Leu Gly Lys Val Asp Gln Ile Ile Phe Thr Gly
        290                 295                 300

Gly Ile Ala Tyr Ser Pro Thr Leu Val Pro Asp Leu Lys Glu Lys Val
305                 310                 315                 320

Glu Trp Ile Ala Pro Val Thr Val Tyr Pro Gly Glu Asp Glu Leu Leu
                325                 330                 335

Ala Leu Ala Gln Gly Ala Ile Arg Val Leu Asp Gly Glu Glu Gln Ala
            340                 345                 350

Lys Val Tyr
        355

<210> SEQ ID NO 94
<211> LENGTH: 355
<212> TYPE: PRT
<213> ORGANISM: Clostridium beijerinckii
<220> FEATURE:
<221> NAME/KEY: MISC_FEATURE
<223> OTHER INFORMATION: Buk, WP_041893502

<400> SEQUENCE: 94

Met Ser Tyr Lys Leu Ile Ile Asn Pro Gly Ser Thr Ser Thr Lys
1               5                   10                  15

Ile Gly Val Tyr Glu Gly Glu Lys Glu Leu Phe Glu Glu Thr Leu Arg
            20                  25                  30

His Thr Asn Glu Glu Ile Lys Arg Tyr Asp Thr Ile Tyr Asp Gln Phe
        35                  40                  45

Glu Phe Arg Lys Glu Val Ile Leu Asn Val Leu Lys Glu Lys Asn Phe
    50                  55                  60

Asp Ile Lys Thr Leu Ser Ala Ile Val Gly Arg Gly Met Leu Arg
65                  70                  75                  80

Pro Val Glu Gly Gly Thr Tyr Ala Val Asn Asp Ala Met Val Glu Asp
                85                  90                  95

Leu Lys Val Gly Val Gln Gly Pro His Ala Ser Asn Leu Gly Gly Ile
            100                 105                 110

Ile Ala Lys Ser Ile Gly Asp Glu Leu Ser Ile Pro Ser Phe Ile Val
        115                 120                 125

Asp Pro Val Val Thr Asp Glu Leu Ala Asp Val Ala Arg Leu Ser Gly 130                 135                 140
Val Pro Glu Leu Pro Arg Lys Ser Lys Phe His Ala Leu Asn Gln Lys
145                 150                 155                 160

Ala Val Ala Lys Arg Tyr Gly Lys Glu Ser Gly Gln Gly Tyr Glu Asn
                165                 170                 175

Leu Asn Leu Val Val His Met Gly Gly Val Ser Val Gly Ala
                180                 185                 190

His Asn His Gly Lys Val Val Asp Val Asn Asn Ala Leu Asp Gly Asp
                195                 200                 205

Gly Pro Phe Ser Pro Glu Arg Ala Gly Ser Val Pro Ile Gly Asp Leu
                210                 215                 220

Val Lys Met Cys Phe Ser Gly Lys Tyr Ser Glu Ala Glu Val Tyr Gly
225                 230                 235                 240

Lys Val Val Gly Lys Gly Gly Phe Val Gly Tyr Leu Asn Thr Asn Asp
                245                 250                 255

Val Lys Gly Val Ile Asp Lys Met Glu Glu Gly Asp Lys Glu Cys Gly
                260                 265                 270

Ser Ile Tyr Lys Ala Phe Val Tyr Gln Ile Ser Lys Ala Ile Gly Glu
                275                 280                 285

Met Ser Val Val Leu Glu Gly Lys Val Asp Gln Ile Ile Phe Thr Gly
290                 295                 300

Gly Ile Ala Tyr Ser Pro Thr Leu Val Pro Asp Leu Lys Ala Lys Val
305                 310                 315                 320

Glu Trp Ile Ala Pro Val Thr Val Tyr Pro Gly Glu Asp Glu Leu Leu
                325                 330                 335

Ala Leu Ala Gln Gly Ala Ile Arg Val Leu Asp Gly Glu Glu Gln Ala
                340                 345                 350

Lys Val Tyr
        355

<210> SEQ ID NO 95
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pACYCDuet-ptb-buk - pACYC-ptb-R1, reverse

<400> SEQUENCE: 95 aagttttac tcatatgtat atctccttct tatacttaac          40

<210> SEQ ID NO 96
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pACYCDuet-ptb-buk - ptb-pACYC-F1, forward

<400> SEQUENCE: 96
agaaggagat atacatatga gtaaaaactt tgatgagtta          40

<210> SEQ ID NO 97
<211> LENGTH: 38
<212> TYPE: DNA
<213> ORGANISM: Artificial sequence

```
<220> FEATURE:
<223> OTHER INFORMATION: Synthetic polynucleotide
<220> FEATURE:
<221> NAME/KEY: misc_feature
<223> OTHER INFORMATION: pACYCDuet-ptb-buk - buk-pACYC-R1, reverse

<400> SEQUENCE: 97
accagactcg agggtaccta gtaaaccttta gcttgttc                              38

<210> SEQ ID NO 98
<211> LENGTH: 38
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pACYCDuet-ptb-buk - pACYC-buk-F1, forward

<400> SEQUENCE: 98
taaggtttac taggtaccct cgagtctggt aaagaaac                              38

<210> SEQ ID NO 99
<211> LENGTH: 45
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLADuet-thlA-adc - thlA-adc-R1, reverse

<400> SEQUENCE: 99
acatatgtat atctccttct tactagcact tttctagcaa tattg                      45

<210> SEQ ID NO 100
<211> LENGTH: 45
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLADuet-thlA-adc - adc-ThlA-F1, forward

<400> SEQUENCE: 100
agtaagaagg agatatacat atgttagaaa gtgaagtatc taaac                      45

<210> SEQ ID NO 101
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLADuet-thlA-adc - adc-pCOLA-R1, reverse

<400> SEQUENCE: 101
cagactcgag ggtaccttat tttactgaaa gataatcatg tac                        43

<210> SEQ ID NO 102
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: pCOLADuet-thlA-adc - pCOLA-adc-F1, forward

<400> SEQUENCE: 102

| tctttcagta aaataaggta ccctcgagtc tggtaaagaa ac | 42 |
|---|---|

<210> SEQ ID NO 103
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLADuet-thlA-adc - thlA-pCOLA-F1, forward

<400> SEQUENCE: 103

| gaaggagata tacatatgaa agaagttgta atagctagtg | 40 |
|---|---|

<210> SEQ ID NO 104
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLADuet-thlA-adc - pCOLA-thlA-R1, reverse

<400> SEQUENCE: 104

| acaacttctt tcatatgtat atctccttct tatacttaac | 40 |
|---|---|

<210> SEQ ID NO 105
<211> LENGTH: 5791
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pACYC-ptb-buk, plasmid

<400> SEQUENCE: 105

| ggggaattgt gagcggataa caattcccct gtagaaataa ttttgtttaa ctttaataag | 60 |
|---|---|
| gagatatacc atgggcagca gccatcacca tcatcaccac agccaggatc cgaattcgag | 120 |
| ctcggcgcgc ctgcaggtcg acaagcttgc ggccgcataa tgcttaagtc gaacagaaag | 180 |
| taatcgtatt gtacacggcc gcataatcga aattaatacg actcactata ggggaattgt | 240 |
| gagcggataa caattcccca tcttagtata ttagttaagt ataagaagga gatatacata | 300 |
| tgagtaaaaa ctttgatgag ttattatcaa gattaaagga agttccaaca aaaaagtgg | 360 |
| ctgtagccgt agcacaagat gaaccagtat tagaggctat aaaagaagct acagaaaata | 420 |
| acatcgcaca agcaatattg gttggtgata acaacaaat ccatgaaatc gcaaagaaaa | 480 |
| taaacttgga cttatctgat tatgaaataa tggatattaa agatccaaag aaagcaacat | 540 |
| tagaagcagt aaaattagtt tctagtggtc atgcagatat gttaatgaaa ggtctagttg | 600 |
| atactgcaac attcctaaga agcgtattaa acaagaggt tggtcttaga acaggaaaat | 660 |
| taatgtccca tgtagctgtg tttgatgtgg aaggttggga tagactgtta tttttaactg | 720 |
| atgcagcatt taatacatat ccagaattta aggataaagt tggaatgata ataatgcag | 780 |
| ttgtagttgc tcatgcatgt ggaatagatg ttccaagagt agcacctata tgcccagttg | 840 |
| aagttgtaaa tacaagtatg caatcaacag ttgatgcagc attgttagct aaaatgagtg | 900 |

```
acaggggggca aattaaagga tgcgtaattg atggaccttt tgccttagat aatgcaatat      960
cagaagaagc agctcatcat aaaggtgtta caggatcagt agcaggtaaa gctgatatat     1020
tattattacc aaatatagaa gcagcaaatg taatgtataa aacattaaca tatttctcta     1080
aatcaagaaa tggtggactt ttagtaggta catcagcacc agtaatttta acttcaagag     1140
cagattcatt cgaaactaaa gttaattcaa ttgctcttgc agcattagtt gcagcaagaa     1200
ataagtaata aatcaatcca taataattaa tgcataatta atggagagat ttatatggaa     1260
tttgcaatgc actattagat tctataataa tttcttctga aaattatgca ttatgactgt     1320
atagaatgca ttaaatttaa gggggattca gaatgtcata taagctatta ataatcaatc     1380
caggttcaac atcaacaaag attggtgttt acgaaggaga aaaggaacta tttgaagaaa     1440
ctttgagaca cacaaatgaa gaaataaaga gatatgatac aatatatgat caatttgaat     1500
ttagaaaaga agttatatta aatgttctta agaaaagaa ttttgatata aagactctaa      1560
gtgctattgt tggtagaggt ggaatgctta gaccagttga aggtggaaca tatgcagtaa     1620
atgatgcaat ggttgaagat ttaaaagttg gagttcaagg acctcatgct tctaaccttg     1680
gcggaataat tgccaagtca attggagatg aattaaatat tccatcattt atagtagatc     1740
cagttgttac agatgagtta gcagatgtag caagactatc tggagtacca gaactaccaa     1800
gaaaaagtaa attccatgct ttaaatcaaa aagcggtagc taaaagatat ggaaaagaaa     1860
gtggacaagg atatgaaaac ctaaatcttg tagttgtaca tatgggtgga ggcgtttcag     1920
ttggtgctca caatcatggg aaagttgtcg atgtaaataa tgcattagat ggagatggcc     1980
cattctcacc agaaagagct ggatcagttc caattggtga tttagttaaa atgtgtttta     2040
gtggaaaata tagtgaagca gaagtatatg gcaaggctgt aggaaaaggt ggatttgttg     2100
gttatctaaa cacaaatgat gtaaaaggtg ttattgataa gatggaagaa ggagataaag     2160
aatgtgaatc aatatacaaa gcatttgttt atcaaatttc aaaagcaatc ggagaaatgt     2220
cagttgtatt agaaggtaaa gttgatcaaa ttattttttac cggaggaatt gcatactcac     2280
caacacttgt tccagacctt aaagcaaaag ttgaatggat agccccagtt acagtttatc     2340
ctggagaaga tgaattactt gctctagctc aaggtgctat aagagtactt gatggagaag     2400
aacaagctaa ggtttactag gtaccctcga gtctggtaaa gaaaccgctg ctgcgaaatt     2460
tgaacgccag cacatggact cgtctactag cgcagcttaa ttaacctagg ctgctgccac     2520
cgctgagcaa taactagcat aaccccttgg ggcctctaaa cgggtcttga ggggttttt     2580 gctgaaacct caggcatttg agaagcacac ggtcacactg cttccggtag tcaataaacc     2640
ggtaaaccag caatagacat aagcggctat ttaacgaccc tgccctgaac cgacgacaag     2700
ctgacgaccg ggtctccgca agtggcactt tcggggaaa tgtgcgcgga acccctatttt    2760 gtttatttt ctaaatacat tcaaatatgt atccgctcat gaattaattc ttagaaaaac     2820
tcatcgagca tcaaatgaaa ctgcaattta ttcatatcag gattatcaat accatatttt     2880
tgaaaaagcc gtttctgtaa tgaaggagaa aactcaccga ggcagttcca taggatggca     2940
agatcctggt atcggtctgc gattccgact cgtccaacat caatacaacc tattaatttc     3000
ccctcgtcaa aaataaggtt atcaagtgag aaatcaccat gagtgacgac tgaatccggt     3060
gagaatggca aaagtttatg catttctttc cagacttgtt caacaggcca gccattacgc     3120
tcgtcatcaa aatcactcgc atcaaccaaa ccgttattca ttcgtgattg cgcctgagcg     3180
agacgaaata cgcggtcgct gttaaaagga caattacaaa caggaatcga atgcaaccgg     3240
cgcaggaaca ctgccagcgc atcaacaata ttttcacctg aatcaggata ttcttctaat     3300
```

```
acctggaatg ctgttttccc ggggatcgca gtggtgagta accatgcatc atcaggagta    3360
cggataaaat gcttgatggt cggaagaggc ataaattccg tcagccagtt tagtctgacc    3420
atctcatctg taacatcatt ggcaacgcta cctttgccat gtttcagaaa caactctggc    3480
gcatcgggct tcccatacaa tcgatagatt gtcgcacctg attgcccgac attatcgcga    3540
gcccatttat acccatataa atcagcatcc atgttggaat ttaatcgcgg cctagagcaa    3600
gacgtttccc gttgaatatg gctcatactc ttccttttc aatattattg aagcattat     3660
cagggttatt gtctcatgag cggatacata tttgaatgta tttagaaaaa taaacaaata    3720
ggcatgctag cgcagaaacg tcctagaaga tgccaggagg atacttagca gagagacaat    3780
aaggccggag cgaagccgtt tttccatagg ctccgccccc ctgacgaaca tcacgaaatc    3840
tgacgctcaa atcagtggtg gcgaaacccg acaggactat aaagatacca ggcgtttccc    3900
cctgatggct ccctcttgcg ctctcctgtt cccgtcctgc ggcgtccgtg ttgtggtgga    3960
ggctttaccc aaatcaccac gtcccgttcc gtgtagacag ttcgctccaa gctgggctgt    4020
gtgcaagaac cccccgttca gcccgactgc tgcgccttat ccggtaacta tcatcttgag    4080
tccaacccgg aaagacacga caaaacgcca ctggcagcag ccattggtaa ctgagaatta    4140
gtggatttag atatcgagag tcttgaagtg gtggcctaac agaggctaca ctgaaaggac    4200
agtatttggt atctgcgctc cactaaagcc agttaccagg ttaagcagtt ccccaactga    4260
cttaaccttc gatcaaaccg cctccccagg cggttttttc gtttacagag caggagatta    4320
cgacgatcgt aaaaggatct caagaagatc ctttacggat tcccgacacc atcactctag    4380
atttcagtgc aatttatctc ttcaaatgta gcacctgaag tcagccccat acgatataag    4440
ttgtaattct catgttagtc atgccccgcg cccaccggaa ggagctgact gggttgaagg    4500
ctctcaaggg catcggtcga gatcccggtg cctaatgagt gagctaactt acattaattg    4560
cgttgcgctc actgcccgct ttccagtcgg gaaacctgtc gtgccagctg cattaatgaa    4620
tcggccaacg cgcggggaga gcggtttgc gtattgggcg ccagggtggt ttttcttttc    4680
accagtgaga cgggcaacag ctgattgccc ttcaccgcct ggccctgaga gagttgcagc    4740
aagcggtcca cgctggtttg ccccagcagg cgaaaatcct gtttgatggt ggttaacggc    4800
gggatataac atgagctgtc ttcggtatcg tcgtatccca ctaccgagat gtccgcacca    4860
acgcgcagcc cggactcgt aatggcgcgc attgcgccca cgccatctg atcgttggca    4920
accagcatcg cagtgggaac gatgccctca ttcagcattt gcatggtttg ttgaaaaccg    4980
gacatggcac tccagtcgcc ttcccgttcc gctatcggct gaatttgatt gcgagtgaga    5040
tatttatgcc agccagccag acgcagacgc gccgagacag aacttaatgg gcccgctaac    5100
agcgcgattt gctggtgacc caatgcgacc agatgctcca cgcccagtcg cgtaccgtct    5160
tcatgggaga aaataatact gttgatgggt gtctggtcag agacatcaag aaataacgcc    5220
ggaacattag tgcaggcagc ttccacagca atggcatcct ggtcatccag cggatagtta    5280
atgatcagcc cactgacgcg ttgcgcgaga agattgtgca ccgccgcttt acaggcttcg    5340
acgccgcttc gttctaccat cgacaccacc acgctggcac ccagttgatc ggcgcgagat    5400
ttaatcgccg cgacaatttg cgacggcgcg tgcagggcca gactggaggt ggcaacgcca    5460
atcagcaacg actgtttgcc cgccagttgt tgtgccacgc ggttgggaat gtaattcagc    5520
tccgccatcg ccgcttccac ttttcccgc gttttcgcag aaacgtggct ggcctggttc    5580
accacgcggg aaacggtctg ataagagaca ccggcatact ctgcgacatc gtataacgtt    5640
```

-continued

| | |
|---|---|
| actggtttca cattcaccac cctgaattga ctctcttccg ggcgctatca tgccataccg | 5700 |
| cgaaaggttt tgcgccattc gatggtgtcc gggatctcga cgctctccct tatgcgactc | 5760 |
| ctgcattagg aaattaatac gactcactat a | 5791 |

<210> SEQ ID NO 106
<211> LENGTH: 5609
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCOLA-thlA-adc, plasmid

<400> SEQUENCE: 106

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggcgcgc ctgcaggtcg acaagcttgc ggccgcataa tgcttaagtc gaacagaaag | 180 |
| taatcgtatt gtacacggcc gcataatcga aattaatacg actcactata ggggaattgt | 240 |
| gagcggataa caattcccca tcttagtata ttagttaagt ataagaagga gatatacata | 300 |
| tgaaagaagt tgtaatagct agtgcagtaa gaacagcgat tggatcttat ggaaagtctc | 360 |
| ttaaggatgt accagcagta gatttaggag ctacagctat aaaggaagca gttaaaaaag | 420 |
| caggaataaa accagaggat gttaatgaag tcatttttagg aaatgttctt caagcaggtt | 480 |
| taggacagaa tccagcaaga caggcatctt ttaaagcagg attaccagtt gaaattccag | 540 |
| ctatgactat taataaggtt tgtggttcag acttagaac agttagctta gcagcacaaa | 600 |
| ttataaaagc aggagatgct gacgtaataa tagcaggtgg tatggaaaat atgtctagag | 660 |
| ctccttactt agcgaataac gctagatggg gatatagaat gggaaacgct aaatttgttg | 720 |
| atgaaatgat cactgacgga ttgtgggatg catttaatga ttaccacatg ggaataacag | 780 |
| cagaaaacat agctgagaga tggaacattt caagagaaga acaagatgag tttgctcttg | 840 |
| catcacaaaa aaaagctgaa gaagctataa aatcaggtca atttaaagat gaaatagttc | 900 |
| ctgtagtaat taaaggcaga aagggagaaa ctgtagttga tacagatgag caccctagat | 960 |
| ttggatcaac tatagaagga cttgcaaaat aaaacctgc cttcaaaaaa gatggaacag | 1020 |
| ttacagctgg taatgcatca ggattaaatg actgtgcagc agtacttgta atcatgagtg | 1080 |
| cagaaaaagc taaagagctt ggagtaaaac cacttgctaa gatagtttct tatggttcag | 1140 |
| caggagttga cccagcaata atgggatatg gacctttcta tgcaacaaaa gcagctattg | 1200 |
| aaaaagcagg ttggacagtt gatgaattag atttaataga atcaaatgaa gcttttgcag | 1260 |
| ctcaaagttt agcagtagca aaagatttaa aatttgatat gaataaagta aatgtaaatg | 1320 |
| gaggagctat tgcccttggt catccaattg gagcatcagg tgcaagaata ctcgttactc | 1380 |
| ttgtacacgc aatgcaaaaa agagatgcaa aaaaaggctt agcaacttta tgtataggtg | 1440 |
| gcggacaagg aacagcaata ttgctagaaa agtgctagta agaaggagat atacatatgt | 1500 |
| tagaaagtga agtatctaaa caaattacaa ctccacttgc tgctccagcg tttcctagag | 1560 |
| gaccatatag gtttcacaat agagaatatc taaacattat ttatcgaact gatttagatg | 1620 |
| ctcttcgaaa aatagtacca gagccacttg aattagatag agcatatgtt agatttgaaa | 1680 |
| tgatggctat gcctgataca accggactag gctcatatac agaatgtggt caagctattc | 1740 |
| cagtaaaata taatggtgtt aagggtgact acttgcatat gatgtatcta gataatgaac | 1800 |

-continued

```
ctgctattgc tgttggaaga gaaagtagcg cttatccaaa aaagcttggc tatccaaagc      1860
tatttgttga ttcagatact ttagttggga cacttaaata tggtacatta ccagtagcta      1920
ctgcaacaat gggatataag cacgagcctc tagatcttaa agaagcctat gctcaaattg      1980
caagacccaa ttttatgcta aaaatcattc aaggttacga tggtaagcca agaatttgtg      2040
aactaatatg tgcagaaaat actgatataa ctattcacgg tgcttggact ggaagtgcac      2100
gtctacaatt atttagccat gcactagctc ctcttgctga tttacctgta ttagagattg      2160
tatcagcatc tcatatcctc acagatttaa ctcttggaac acctaaggtt gtacatgatt      2220
atctttcagt aaaataaggt accctcgagt ctggtaaaga aaccgctgct gcgaaatttg      2280
aacgccagca catggactcg tctactagcg cagcttaatt aacctaggct gctgccaccg      2340
ctgagcaata actagcataa ccccttgggg cctctaaacg ggtcttgagg ggttttttgc      2400
tgaaacctca ggcatttgag aagcacacgg tcacactgct tccggtagtc aataaaccgg      2460
taaaccagca atagacataa gcggctattt aacgaccctg ccctgaaccg acgacaagct      2520
gacgaccggg tctccgcaag tggcactttt cggggaaatg tgcgcggaac ccctatttgt      2580
ttatttttct aaatacattc aaatatgtat ccgctcatga attaattctt agaaaaactc      2640
atcgagcatc aaatgaaact gcaatttatt catatcagga ttatcaatac catattttg       2700 aaaaagccgt ttctgtaatg aaggagaaaa ctcaccgagg cagttccata ggatggcaag      2760
atcctggtat cggtctgcga ttccgactcg tccaacatca atacaaccta ttaatttccc      2820
ctcgtcaaaa ataaggttat caagtgagaa atcaccatga gtgacgactg aatccggtga      2880
gaatggcaaa agtttatgca tttctttcca gacttgttca acaggccagc cattacgctc      2940
gtcatcaaaa tcactcgcat caaccaaacc gttattcatt cgtgattgcg cctgagcgag      3000
acgaaatacg cggtcgctgt taaaaggaca attacaaaca ggaatcgaat gcaaccggcg      3060
caggaacact gccagcgcat caacaatatt ttcacctgaa tcaggatatt cttctaatac      3120
ctggaatgct gttttcccgg ggatcgcagt ggtgagtaac catgcatcat caggagtacg      3180
gataaaatgc ttgatggtcg gaagaggcat aaattccgtc agccagttta gtctgaccat      3240
ctcatctgta acatcattgg caacgctacc tttgccatgt ttcagaaaca actctggcgc      3300
atcgggcttc ccatacaatc gatagattgt cgcacctgat tgcccgacat tatcgcgagc      3360
ccatttatac ccatataaat cagcatccat gttggaattt aatcgcggcc tagagcaaga      3420
cgtttcccgt tgaatatggc tcatactctt ccttttttcaa tattattgaa gcatttatca      3480
gggttattgt ctcatgagcg gatacatatt tgaatgtatt tagaaaaata acaaataggg      3540
catgctagcg cagaaacgtc ctagaagatg ccaggaggat acttagcaga gagacaataa      3600
ggccggagcg aagccgtttt tccataggct ccgcccccct gacgaacatc acgaaatctg      3660
acgctcaaat cagtggtggc gaaacccgac aggactataa agataccagg cgtttccccc      3720
tgatggctcc ctcttgcgct ctcctgttcc cgtcctgcgg cgtccgtgtt gtggtggagg      3780
ctttacccaa atcaccacgt cccgttccgt gtagacagtt cgctccaagc tgggctgtgt      3840
gcaagaaccc cccgttcagc ccgactgctg cgccttatcc ggtaactatc atcttgagtc      3900
caacccggaa agacacgaca aaacgccact ggcagcagcc attggtaact gagaattagt      3960
ggatttagat atcgagagtc ttgaagtggt ggcctaacag aggctacact gaaaggacag      4020
tatttggtat ctgcgctcca ctaaagccag ttaccaggtt aagcagttcc ccaactgact      4080
taaccttcga tcaaaccgcc tccccaggcg gttttttcgt ttacagagca ggagattacg      4140
acgatcgtaa aaggatctca agaagatcct ttacggattc ccgacaccat cactctagat      4200
```

```
ttcagtgcaa tttatctctt caaatgtagc acctgaagtc agccccatac gatataagtt    4260
gtaattctca tgttagtcat gccccgcgcc caccggaagg agctgactgg gttgaaggct    4320
ctcaagggca tcggtcgaga tcccggtgcc taatgagtga gctaacttac attaattgcg    4380
ttgcgctcac tgcccgcttt ccagtcggga acctgtcgt gccagctgca ttaatgaatc     4440
ggccaacgcg cggggagagg cggtttgcgt attgggcgcc agggtggttt tcttttcac     4500 cagtgagacg gcaacagct gattgccctt caccgcctgg ccctgagaga gttgcagcaa    4560
gcggtccacg ctggtttgcc ccagcaggcg aaaatcctgt ttgatggtgg ttaacggcgg    4620
gatataacat gagctgtctt cggtatcgtc gtatcccact accgagatgt ccgcaccaac    4680
gcgcagcccg gactcggtaa tggcgcgcat tgcgcccagc gccatctgat cgttggcaac    4740
cagcatcgca gtgggaacga tgccctcatt cagcatttgc atggtttgtt gaaaaccgga    4800
catggcactc cagtcgcctt cccgttccgc tatcggctga atttgattgc gagtgagata    4860
tttatgccag ccagcagac gcagacgcgc cgagacagaa cttaatgggc cgctaacag     4920 cgcgatttgc tggtgaccca atgcgaccag atgctccacg cccagtcgcg taccgtcttc    4980
atgggagaaa ataatactgt tgatgggtgt ctggtcagag acatcaagaa ataacgccgg    5040
aacattagtg caggcagctt ccacagcaat ggcatcctgg tcatccagcg gatagttaat    5100
gatcagccca ctgacgcgtt gcgcgagaag attgtgcacc gccgctttac aggcttcgac    5160
gccgcttcgt tctaccatcg acaccaccac gctggcaccc agttgatcgg cgcgagattt    5220
aatcgccgcg acaatttgcg acggcgcgtg cagggccaga ctggaggtgg caacgccaat    5280
cagcaacgac tgtttgcccg ccagttgttg tgccacgcgg ttgggaatgt aattcagctc    5340
cgccatcgcc gcttccactt ttcccgcgt tttcgcagaa acgtggctgg cctggttcac      5400
cacgcgggaa acggtctgat aagagacacc ggcatactct gcgacatcgt ataacgttac    5460
tggtttcaca ttcaccaccc tgaattgact ctcttccggg cgctatcatg ccataccgcg    5520
aaaggttttg cgccattcga tggtgtccgg gatctcgacg ctctccctta tgcgactcct    5580
gcattaggaa attaatacga ctcactata                                      5609
```

<210> SEQ ID NO 107
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: thlA-ptb-R1, reverse

<400> SEQUENCE: 107
atttcctccc tttctagcac ttttctagca atattg                              36

<210> SEQ ID NO 108
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: adc-buk-F1, forward

<400> SEQUENCE: 108
taaggtttac taaggaggtt gttttatgtt agaaag                              36

<210> SEQ ID NO 109
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: thlA-ptb-F1, forward

<400> SEQUENCE: 109
gctagaaaag tgctagaaag ggaggaaatg aacatg                36

<210> SEQ ID NO 110
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Buk-adc-R1, reverse

<400> SEQUENCE: 110
aaaacaacct ccttagtaaa ccttagcttg ttcttc                36

<210> SEQ ID NO 111
<211> LENGTH: 29
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pDuet-insert2-R1, forward

<400> SEQUENCE: 111
catatgtata tctccttctt atacttaac                 29

<210> SEQ ID NO 112
<211> LENGTH: 29
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: insert2-pDuet-F1, forward

<400> SEQUENCE: 112
gttaagtata agaaggagat atacatatg                 29

<210> SEQ ID NO 113
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pDuet-insert2-F1, forward

<400> SEQUENCE: 113
cctcgagtct ggtaaagaaa c                     21

<210> SEQ ID NO 114
<211> LENGTH: 21
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: insert2-pDuet-R1, forward

<400> SEQUENCE: 114
gtttctttac cagactcgag g                                        21

<210> SEQ ID NO 115
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCDF-phaB - pACYC-phaB-R1, forward

<400> SEQUENCE: 115
ctattctttg tgtcatggta tatctcctta ttaaag                        36

<210> SEQ ID NO 116
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCDF-phaB - phaB-pACYC-F1, forward

<400> SEQUENCE: 116
ataaggagat ataccatgac acaaagaata gcatac                        36

<210> SEQ ID NO 117
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pcdf-phab - pacyc-phab-f1, forward

<400> SEQUENCE: 117
tggtttacac atgggataag atccgaattc gagctc                        36

<210> SEQ ID NO 118
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCDF-phaB - phaB-pACYC-R1, forward

<400> SEQUENCE: 118
agctcgaatt cggatcttat cccatgtgta aaccac                        36

<210> SEQ ID NO 119
<211> LENGTH: 4486
<212> TYPE: DNA
<213> ORGANISM: Artificial sequence
<220> FEATURE:
<223> OTHER INFORMATION: Synthetic polynucleotide
<220> FEATURE:
```

<221> NAME/KEY: misc_feature
<223> OTHER INFORMATION: pCDF-phaB, plasmid

<400> SEQUENCE: 119

```
ggggaattgt gagcggataa caattcccct gtagaaataa ttttgtttaa ctttaataag      60
gagatatacc atgacacaaa gaatagcata cgtaacaggt ggtatgggtg gtataggaac     120
tgcaatatgt caaagattag caaaagatgg atttagagtt gtagctggat gcggaccaaa     180
tagtcctaga agagaaaagt ggttagaaca acaaaaagca cttggatttg atttcatagc     240
ttctgaaggt aacgtagcag attgggactc aactaaaact gcttttgata aagttaaatc     300
tgaagttggt gaagttgatg tattaataaa taatgcaggt attactagag atgtagtatt     360
tagaaagatg acaagagctg actgggatgc agtaatagat actaatctta ctagtctttt     420
caatgtaact aagcaggtaa ttgatggtat ggcagataga ggttgggggta gaatagtaaa      480
tattagttca gttaatggac aaaaaggtca gtttggacag acaaattatt ctacagctaa     540
agcaggtctt catggttttta caatggcttt agcacaggaa gttgctacaa aaggtgttac     600
agttaacact gttagtccag gatatattgc tactgacatg gtaaaggcta aagacaaga      660
tgttcttgat aaaattgttg ctacaatacc agtaaagaga ttaggacttc ctgaagagat     720
agcatctatt tgtgcatggt tatcaagtga agaatcagga ttctcaactg gtgctgatttt     780
ttcattaaac ggtggtttac acatgggata agatccgaat tcgagctcgg cgcgcctgca     840
ggtcgacaag cttgcggccg cataatgctt aagtcgaaca gaaagtaatc gtattgtaca     900
cggccgcata tcgaaatta atacgactca ctatagggga attgtgagcg gataacaatt     960
ccccatctta gtatattagt taagtataag aaggagatat acatatggca gatctcaatt    1020
ggatatcggc cggccacgcg atcgctgacg tcggtaccct cgagtctggt aaagaaaccg    1080
ctgctgcgaa atttgaacgc cagcacatgg actcgtctac tagcgcagct taattaacct    1140
aggctgctgc caccgctgag caataactag cataacccct tggggcctct aaacgggtct    1200
tgaggggttt tttgctgaaa cctcaggcat ttgagaagca cacggtcaca ctgcttccgg    1260
tagtcaataa accggtaaac cagcaataga cataagcggc tatttaacga ccctgccctg    1320
aaccgacgac cgggtcatcg tggccggatc ttgcggcccc tcggcttgaa cgaattgtta    1380
gacattattt gccgactacc ttggtgatct cgcctttcac gtagtggaca aattcttcca    1440
actgatctgc gcgcgaggcc aagcgatctt cttcttgtcc aagataagcc tgtctagctt    1500
caagtatgac gggctgatac tgggccggca ggcgctccat tgcccagtcg gcagcgacat    1560
ccttcggcgc gattttgccg gttactgcgc tgtaccaaat gcgggacaac gtaagcacta    1620
catttcgctc atcgccagcc cagtcgggcg gcgagttcca tagcgttaag gtttcattta    1680
gcgcctcaaa tagatcctgt tcaggaaccg gatcaaagag ttcctccgcc gctggaccta    1740
ccaaggcaac gctatgttct cttgcttttg tcagcaagat agccagatca atgtcgatcg    1800
tggctggctc gaagatacct gcaagaatgt cattgcgctg ccattctcca aattgcagtt    1860
cgcgcttagc tggataacgc cacggaatga tgtcgtcgtg cacaacaatg gtgacttcta    1920
cagcgcggag aatctcgctc tctccagggg aagccgaagt ttccaaaagg tcgttgatca    1980
aagctcgccg cgttgtttca tcaagcctta cggtcaccgt aaccagcaaa tcaatatcac    2040
tgtgtggctt caggccgcca tccactgcgg agccgtacaa atgtacggcc agcaacgtcg    2100
gttcgagatg cgctcgatg acgccaacta ccctctgatag ttgagtcgat acttcggcga    2160
tcaccgcttc cctcatactc ttcctttttc aatattattg aagcatttat cagggttatt    2220
```

```
gtctcatgag cggatacata tttgaatgta tttagaaaaa taaacaaata gctagctcac    2280
tcggtcgcta cgctccgggc gtgagactgc ggcgggcgct gcggacacat acaaagttac    2340
ccacagattc cgtggataag caggggacta acatgtgagg caaaacagca gggccgcgcc    2400
ggtggcgttt ttccataggc tccgccctcc tgccagagtt cacataaaca gacgcttttc    2460
cggtgcatct gtgggagccg tgaggctcaa ccatgaatct gacagtacgg gcgaaacccg    2520
acaggactta agatccccca ccgtttccgg cgggtcgctc cctcttgcgc tctcctgttc    2580
cgaccctgcc gtttaccgga tacctgttcc gcctttctcc cttacgggaa gtgtggcgct    2640
ttctcatagc tcacacactg gtatctcggc tcggtgtagg tcgttcgctc caagctgggc    2700
tgtaagcaag aactccccgt tcagcccgac tgctgcgcct tatccggtaa ctgttcactt    2760
gagtccaacc cggaaaagca cggtaaaacg ccactggcag cagccattgg taactgggag    2820
ttcgcagagg atttgtttag ctaaacacgc ggttgctctt gaagtgtgcg ccaaagtccg    2880
gctacactgg aaggacagat ttggttgctg tgctctgcga agccagttta ccacggttaa    2940
gcagttcccc aactgactta accttcgatc aaaccacctc cccaggtggt tttttcgttt    3000
acagggcaaa agattacgcg cagaaaaaaa ggatctcaag aagatccttt gatcttttct    3060
actgaaccgc tctagatttc agtgcaattt atctcttcaa atgtagcacc tgaagtcagc    3120
cccatacgat ataagttgta attctcatgt tagtcatgcc ccgcgcccac cggaaggagc    3180
tgactgggtt gaaggctctc aagggcatcg gtcgagatcc cggtgcctaa tgagtgagct    3240
aacttacatt aattgcgttg cgctcactgc ccgctttcca gtcgggaaac ctgtcgtgcc    3300
agctgcatta atgaatcggc caacgcgcgg ggagaggcgg tttgcgtatt gggcgccagg    3360
gtggtttttc ttttcaccag tgagacgggc aacagctgat tgcccttcac cgcctggccc    3420
tgagagagtt gcagcaagcg gtccacgctg gtttgcccca gcaggcgaaa atcctgtttg    3480
atggtggtta acggcgggat ataacatgag ctgtcttcgg tatcgtcgta tcccactacc    3540
gagatgtccg caccaacgcg cagcccggac tcggtaatgg cgcgcattgc gcccagcgcc    3600
atctgatcgt tggcaaccag catcgcagtg gaacgatgc cctcattcag catttgcatg    3660
gtttgttgaa aaccggacat ggcactccag tcgccttccc gttccgctat cggctgaatt    3720
tgattgcgag tgagatattt atgccagcca gccagacgca gacgcgccga cagaacttt    3780 aatgggcccg ctaacagcgc gatttgctgg tgacccaatg cgaccagatg ctccacgccc    3840
agtcgcgtac cgtcttcatg ggagaaaata atactgttga tgggtgtctg gtcagagaca    3900
tcaagaaata acgccggaac attagtgcag gcagcttcca cagcaatggc atcctggtca    3960
tccagcggat agttaatgat cagcccactg acgcgttgcg cgagaagatt gtgcaccgcc    4020
gctttacagg cttcgacgcc gcttcgttct accatcgaca ccaccacgct ggcacccagt    4080
tgatcggcgc gagatttaat cgccgcgaca atttgcgacg cgcgtgcag gccagactg    4140 gaggtggcaa cgccaatcag caacgactgt ttgcccgcca gttgttgtgc cacgcggttg    4200
ggaatgtaat tcagctccgc catcgccgct tccactttt ccgcgttttt cgcagaaacg    4260
tggctggcct ggttcaccac gcgggaaacg gtctgataag agacaccggc atactctgcg    4320
acatcgtata cgttactggt ttcacattc accaccctga attgactctc ttccgggcgc    4380
tatcatgcca taccgcgaaa ggttttgcgc cattcgatgg tgtccgggat ctcgacgctc    4440
tcccttatgc gactcctgca ttaggaaatt aatacgactc actata         4486
```

<210> SEQ ID NO 120
<211> LENGTH: 5221

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCDF-phaB-bdh1, plasmid

<400> SEQUENCE: 120

```
ggggaattgt gagcggataa caattcccct gtagaaataa ttttgtttaa ctttaataag      60
gagatatacc atgacacaaa gaatagcata cgtaacaggt ggtatgggtg gtataggaac     120
tgcaatatgt caaagattag caaaagatgg atttagagtt gtagctggat gcggaccaaa     180
tagtcctaga agagaaaagt ggttagaaca acaaaaagca cttggatttg atttcatagc     240
ttctgaaggt aacgtagcag attgggactc aactaaaact gcttttgata agttaaatc      300
tgaagttggt gaagttgatg tattaataaa taatgcaggt attactagag atgtagtatt     360
tagaaagatg acaagagctg actgggatgc agtaatagat actaatctta ctagtctttt     420
caatgtaact aagcaggtaa ttgatggtat ggcagataga ggttggggta gaatagtaaa     480
tattagttca gttaatggac aaaaaggtca gtttggacag acaaattatt ctacagctaa     540
agcaggtctt catggtttta caatggcttt agcacaggag ttgctacaa aaggtgttac      600
agttaacact gttagtccag gatatattgc tactgacatg gtaaaggcta aagacaaga     660
tgttcttgat aaaattgttg ctacaatacc agtaaagaga ttaggacttc ctgaagagat     720
agcatctatt tgtgcatggt tatcaagtga agaatcagga ttctcaactg gtgctgattt     780
ttcattaaac ggtggtttac acatgggata agatccgaat tcgagctcgg cgcgcctgca     840
ggtcgacaag cttgcggccg cataatgctt aagtcgaaca gaaagtaatc gtattgtaca     900
cggccgcata atcgaaatta atacgactca ctataggga attgtgagcg ataacaatt      960
ccccatctta gtatattagt taagtataag aaggagatat acatatgcaa ttaaaaggta    1020
aaagtgcaat agtaactggt gcagcaagtg gaataggaaa agcaatagca gaattacttg    1080
caaaagaagg tgcagcagta gcaatagctg atttaaattt agaagcagca agagcagcag    1140
cagctggaat agaagcagct ggcggaaaag ctatagctgt agcaatggat gtaactagtg    1200
aagcaagtgt aaatcaagca actgatgaag tagcacaagc atttggaaat atagatatat    1260
tagtaagtaa tgctggaata caaatagtaa atcctataca aaattatgca tttagtgatt    1320
ggaaaaaaat gcaagcaata catgtagatg gtgcattttt aactactaaa gcagcattga    1380
aatatatgta tagagataaa agaggtggaa ctgtaatata tatgggaagt gtacattctc    1440
atgaagcaag tccttttaaaa agtgcttatg tagcagcaaa acatgcatta ttaggattag    1500
caagagtatt agctaaagaa ggtgctgaat tcaacgtaag atctcacgtt atatgtcctg    1560
gatttgtaag aactcccttta gtagataaac aaataccgtga acaagcaaaa gaattaggaa    1620
taagtgaaga agaagtagtt agaagagtaa tgttaggtgg aacagtagac ggtgtattta    1680
ctactgtaga tgatgtagca agaactgcat tattttatg tgcatttcct agtgcagcat    1740
taactggaca agttttata gtaagtcatg gatggtatat gcaataaggt accctcgagt    1800
ctggtaaaga aaccgctgct gcgaaatttg aacgccagca catggactcg tctactagcg    1860
cagcttaatt aacctaggct gctgccaccg ctgagcaata actagcataa ccccttgggg    1920
cctctaaacg ggtcttgagg ggttttttgc tgaaacctca ggcatttgag aagcacacgg    1980
tcacactgct tccggtagtc aataaaccgg taaaccagca atagacataa gcggctattt    2040
aacgaccctg ccctgaaccg acgaccgggt catcgtggcc ggatcttgcg gcccctcggc    2100
```

```
ttgaacgaat tgttagacat tatttgccga ctaccttggt gatctcgcct ttcacgtagt   2160
ggacaaattc ttccaactga tctgcgcgcg aggccaagcg atcttcttct tgtccaagat   2220
aagcctgtct agcttcaagt atgacgggct gatactgggc cggcaggcgc tccattgccc   2280
agtcggcagc gacatccttc ggcgcgattt tgccggttac tgcgctgtac caaatgcggg   2340
acaacgtaag cactacattt cgctcatcgc cagcccagtc gggcggcgag ttccatagcg   2400
ttaaggtttc atttagcgcc tcaaatagat cctgttcagg aaccggatca aagagttcct   2460
ccgccgctgg acctaccaag gcaacgctat gttctcttgc ttttgtcagc aagatagcca   2520
gatcaatgtc gatcgtggct ggctcgaaga tacctgcaag aatgtcattg cgctgccatt   2580
ctccaaattg cagttcgcgc ttagctggat aacgccacgg aatgatgtcg tcgtgcacaa   2640
caatggtgac ttctacagcg cggagaatct cgctctctcc aggggaagcc gaagtttcca   2700
aaaggtcgtt gatcaaagct cgccgcgttg tttcatcaag ccttacggtc accgtaacca   2760
gcaaatcaat atcactgtgt ggcttcaggc cgccatccac tgcggagccg tacaaatgta   2820
cggccagcaa cgtcggttcg agatggcgct cgatgacgcc aactacctct gatagttgag   2880
tcgatacttc ggcgatcacc gcttccctca tactcttcct ttttcaatat tattgaagca   2940
tttatcaggg ttattgtctc atgagcggat acatatttga atgtatttag aaaaataaac   3000
aaatagctag ctcactcggt cgctacgctc cgggcgtgag actgcggcgg cgctgcggga   3060
cacatacaaa gttacccaca gattccgtgg ataagcaggg gactaacatg tgaggcaaaa   3120
cagcagggcc gcgccggtgg cgttttttcca taggctccgc cctcctgcca gagttcacat   3180
aaacagacgc ttttccggtg catctgtggg agccgtgagg ctcaaccatg aatctgacag   3240
tacgggcgaa acccgacagg acttaaagat ccccaccgtt tccggcgggt cgctccctct   3300
tgcgctctcc tgttccgacc ctgccgttta ccggatacct gttccgcctt tctcccttac   3360
gggaagtgtg gcgctttctc atagctcaca cactggtatc tcggctcggt gtaggtcgtt   3420
cgctccaagc tgggctgtaa gcaagaactc cccgttcagc ccgactgctg cgccttatcc   3480
ggtaactgtt cacttgagtc caacccggaa aagcacggta aaacgccact ggcagcagcc   3540
attggtaact gggagttcgc agaggatttg tttagctaaa cacgcggttg ctcttgaagt   3600
gtgcgccaaa gtccggctac actggaagga cagatttggt tgctgtgctc tgcgaaagcc   3660
agttaccacg gttaagcagt tccccaactg acttaacctt cgatcaaacc cctccccag   3720
gtggtttttt cgtttacagg gcaaaagatt acgcgcagaa aaaaggatc tcaagaagat   3780
cctttgatct tttctactga accgctctag atttcagtgc aatttatctc ttcaaatgta   3840
gcacctgaag tcagccccat acgatataag ttgtaattct catgttagtc atgccccgcg   3900
cccaccggaa ggagctgact gggttgaagg ctctcaaggg catcggtcga gatcccggtg   3960
cctaatgagt gagctaactt acattaattg cgttgcgctc actgcccgct ttccagtcgg   4020
gaaacctgtc gtgccagctg cattaatgaa tcggccaacg cgcggggaga ggcggtttgc   4080
gtattgggcg ccagggtggt ttttcttttc accagtgaga cgggcaacag ctgattgccc   4140
ttcaccgcct ggccctgaga gagttgcagc aagcggtcca cgctggtttg ccccagcagg   4200
cgaaaatcct gtttgatggt ggttaacggc gggatataac atgagctgtc ttcggtatcg   4260
tcgtatccca ctaccgagat gtccgcacca acgcgcagcc cggactcggt aatggcgcgc   4320
attgcgccca cgccatctg atcgttggca accagcatcg cagtgggaac gatgccctca   4380
ttcagcattt gcatggtttg ttgaaaaccg gacatggcac tccagtcgcc ttcccgttcc   4440
```

```
gctatcggct gaatttgatt gcgagtgaga tatttatgcc agccagccag acgcagacgc    4500
gccgagacag aacttaatgg gcccgctaac agcgcgattt gctggtgacc caatgcgacc    4560
agatgctcca cgcccagtcg cgtaccgtct tcatgggaga aaataatact gttgatgggt    4620
gtctggtcag agacatcaag aaataacgcc ggaacattag tgcaggcagc ttccacagca    4680
atggcatcct ggtcatccag cggatagtta atgatcagcc cactgacgcg ttgcgcgaga    4740
agattgtgca ccgccgcttt acaggcttcg acgccgcttc gttctaccat cgacaccacc    4800
acgctggcac ccagttgatc ggcgcgagat ttaatcgccg cgacaatttg cgacggcgcg    4860
tgcagggcca gactggaggt ggcaacgcca atcagcaacg actgtttgcc cgccagttgt    4920
tgtgccacgc ggttgggaat gtaattcagc tccgccatcg ccgcttccac ttttcccgc     4980 gttttcgcag aaacgtggct ggcctggttc accacgcggg aaacggtctg ataagagaca    5040
ccggcatact ctgcgacatc gtataacgtt actggtttca cattcaccac cctgaattga    5100
ctctcttccg ggcgctatca tgccataccg cgaaaggttt tgcgccattc gatggtgtcc    5160
gggatctcga cgctctccct tatgcgactc ctgcattagg aaattaatac gactcactat    5220
a                                                                   5221
```

<210> SEQ ID NO 121
<211> LENGTH: 10922
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL8225-budA::thlA-phaB, plasmid

<400> SEQUENCE: 121

```
aaactccttt ttgataatct catgaccaaa atcccttaac gtgagttttc gttccactga      60
gcgtcagacc ccgtagaaaa gatcaaagga tcttcttgag atcctttttt tctgcgcgta     120
atctgctgct tgcaaacaaa aaaaccaccg ctaccagcgg tggtttgttt gccggatcaa     180
gagctaccaa ctctttttcc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg gctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
cgtgagctat gagaaagcgc cacgcttccc gaagggagaa aggcggacag gtatccggta     540
agcggcaggg tcggaacagg agagcgcacg agggagcttc caggggaaa cgcctggtat      600 ctttatagtc ctgtcgggtt tcgccacctc tgacttgagc gtcgattttt gtgatgctcg     660 tcagggggggc ggagcctatg gaaaaacgcc agcaacgcgg ccttttttacg gttcctggcc   720 ttttgctggc cttttgctca catgttcttt cctgcgttat cccctgattc tgtggataac     780
cgtattaccg cctttgagtg agctgatacc gctcgccgca gccgaacgac cgagcgcagc    840
gagtcagtga gcgaggaagc ggaagagcgc ccaatacgca gggccccctg cttcggggtc    900
attatagcga ttttttcggt atatccatcc ttttcgcac gatatacagg attttgccaa     960
agggttcgtg tagactttcc ttggtgtatc caacggcgtc agccgggcag gataggtgaa   1020
gtaggcccac ccgcgagcgg gtgttccttc ttcactgtcc cttattcgca cctggcggtg   1080
ctcaacggga atcctgctct gcgaggctgg ccggctaccg ccggcgtaac agatgagggc   1140
```

```
aagcggatgg ctgatgaaac caagccaacc aggaagggca gcccacctat caaggtgtac    1200
tgccttccag acgaacgaag agcgattgag gaaaaggcgg cggcggccgg catgagcctg    1260
tcggcctacc tgctggccgt cggccagggc tacaaaatca cgggcgtcgt ggactatgag    1320
cacgtccgcg agctggcccg catcaatggc gacctgggcc gctgggcgg cctgctgaaa    1380 ctctggctca ccgacgaccc gcgcacggcg cggttcggtg atgccacgat cctcgccctg    1440
ctggcgaaga tcgaagagaa gcaggacgag cttggcaagg tcatgatggg cgtggtccgc    1500
ccgagggcag agccatgact tttttagccg ctaaaacggc cggggggtgc gcgtgattgc    1560
caagcacgtc cccatgcgct ccatcaagaa gagcgacttc gcggagctgg tgaagtacat    1620
caccgacgag caaggcaaga ccgatcgggc cccctgcagg ataaaaaaat tgtagataaa    1680
ttttataaaa tagtttttatc tacaattttt ttatcaggaa acagctatga ccgcggccgc    1740
ggcgccaagc ttagaaaaat ataaataaga agtagcttta agagaattaa attattaaga    1800
aaagcaaagg tgtttaaaaa ataaatttttt aaacaccttt gcttttctta aattataaat    1860
aagataaaaa agaatcctga ataaaataaa aaggggtgtc tcaaaatttt atttttgagac    1920 gaccccttt tattctatat gtcgatgcta tagctgagat cgtggaattc ttgttagcta    1980
ccagattcac atttaagttg tttctctaaa ccacagatta tcaattcaag tccaaaagaa    2040
aatgctggtt ctgcgccttg atgatcaaat aactctattg cttgtcttaa caatggaggc    2100
attgaatctg ttgttggtgt ttctctttcc tcttttgcaa cttgatgttc ttgatcctcc    2160
aatacgcaac ctaaagtaaa atgtcctaca gcacttagtg cgtataaggc attttctaaa    2220
ctaaaaccct gttgacataa gaatgctaat tgattttcta atgttcata ttgttttca    2280 gttggtctag ttcctaaatg tactttagcc ccatctctat gtgataatag agcacaacga    2340
aaagatttag cgttattcct aagaaaatct tgccatgatt caccttctaa aggacaaaag    2400
tgagtgtgat gtctatctaa catttcaata gctaaggcgt caagtaaagc tctcttattc    2460
ttcacatgcc aatacaacgt aggttgttct actccaagtt tctgagctaa ctttcttgta    2520
gttagtcctt ctattccaac ttcatttagt aattccaatg cactattgat aactttactt    2580
ttatcaagtc tagacatcat ttaatatcct cctcttcaat atatttaagt cgactgatcg    2640
gatcctgatc ggagctccca tggcggccgg tcgatatcga tgtgtagtag cctgtgaaat    2700
aagtaaggaa aaaaagaag taagtgttat atatgatgat tattttgtag atgtagatag    2760
gataatagaa tccatagaaa atataggtta tacagttata taaaaattac tttaaaatct    2820
atcattgata gggtaaaata taaatcgtat aaagttgtgt aattttttaag gaggtgtgtt    2880 acagacgtcc gcgagagacc ttaaatatat tgaagaggag gaaatacata tggtttcaag    2940
atatgttcca gatatgggag atttaatatg ggttgatttt gatccaacaa aaggatcaga    3000
acaagcagga catagaccag cagttgtttt atcaccattt atgtataata ataaaacagg    3060
aatgtgttta tgtgttccat gtacaacaca atcaaaagga tatccatttg aagttgtttt    3120
atcaggacaa gaaagagatg gagttgcatt agcagatcaa gttaaatcaa tagcatggag    3180
agcaagagga gcaacaaaaa aaggaacagt tgcaccagaa gaattacaat taataaaagc    3240
aaaaataaat gttttaatag gataatgtta ttaagctagc ataaaaataa gaagcctgca    3300
tttgcaggct tcttattttt atggcgcgcc gttctgaatc cttagctaat ggttcaacag    3360
gtaactatga cgaagatagc accctggata agtctgtaat ggattctaag gcatttaatg    3420
aagacgtgta tataaaatgt gctaatgaaa aagaaaatgc gttaaagag cctaaaatga    3480 gttcaaatgg ttttgaaatt gattggtagt ttaatttaat atatttttc tattggctat    3540
```

```
ctcgatacct atagaatctt ctgttcactt ttgtttttga aatataaaaa ggggctttt    3600
agccccttt ttttaaaact ccggaggagt ttcttcattc ttgatactat acgtaactat    3660
tttcgatttg acttcattgt caattaagct agtaaaatca atggttaaaa aacaaaaaac   3720
ttgcattttt ctacctagta atttataatt ttaagtgtcg agtttaaaag tataatttac   3780
caggaaagga gcaagttttt taataaggaa aaattttcc ttttaaaatt ctatttcgtt    3840
atatgactaa ttataatcaa aaaaatgaaa ataaacaaga ggtaaaaact gcttagaga    3900
aatgtactga taaaaaaaga aaaaatccta gatttacgtc atacatagca cctttaacta   3960
ctaagaaaaa tattgaaagg acttccactt gtggagatta tttgtttatg ttgagtgatg   4020
cagacttaga acatttaaa ttacataaag gtaattttg cggtaataga ttttgtccaa    4080
tgtgtagttg gcgacttgct tgtaaggata gtttagaaat atctattctt atggagcatt   4140
taagaaaaga agaaaataaa gagtttatat ttttaactct tacaactcca aatgtaaaaa   4200
gttatgatct taattattct attaaacaat ataataaatc ttttaaaaaa ttaatggagc   4260
gtaaggaagt taaggatata actaaaggtt atataagaaa attagaagta acttaccaaa   4320
aggaaaaata cataacaaag gatttatgga aaataaaaaa agattattat caaaaaaag   4380
gacttgaaat tggtgattta gaacctaatt ttgatactta taatcctcat tttcatgtag   4440
ttattgcagt taataaaagt tatttttacag ataaaaatta ttatataaat cgagaaagat   4500
ggttggaatt atggaagttt gctactaagg atgattctat aactcaagtt gatgttagaa   4560
aagcaaaaat taatgattat aaagaggttt acgaacttgc gaaatattca gctaaagaca   4620
ctgattattt aatatcgagg ccagtatttg aattttta taaagcatta aaaggcaagc   4680
aggtattagt ttttagtgga ttttttaaag atgcacacaa attgtacaag caaggaaaac   4740
ttgatgttta taaaagaaa gatgaaatta aatatgtcta tatagtttat tataattggt    4800
gcaaaaaca atatgaaaaa actagaataa gggaacttac ggaagatgaa aaagaagaat   4860
taaatcaaga tttaatagat gaaatagaaa tagattaaag tgtaactata ctttatatat   4920
atatgattaa aaaaataaaa aacaacagcc tattaggttg ttgtttttta ttttctttat   4980
taatttttt aattttagt ttttagttct tttttaaaat aagtttcagc ctcttttca    5040
atatttttta aagaaggagt atttgcatga attgcctttt ttctaacaga cttaggaaat   5100
attttaacag tatcttcttg cgccggtgat tttggaactt cataacttac taattttaaa   5160
ttattatttt ctttttaat tgtaacagtt gcaaagaag ctgaacctgt tccttcaact    5220
agtttatcat cttcaatata atattcttga cctatatagt ataaatatat ttttattata   5280
ttttactt tttctgaatc tattatttta taatcataaa agttttacc accaaaagaa    5340
ggttgtactc cttctggtcc aacatatttt tttactatat tatctaaata atttttggga   5400
actggtgttg taatttgatt aatcgaacaa ccagttatac ttaaaggaat tataactata   5460
aaatatata ggattatctt tttaaatttc attattggcc tcctttttat taaatttatg    5520
ttaccataaa aaggacataa cgggaatatg tagaatattt ttaatgtaga caaaattta    5580
cataaatata aagaaggaa gtgtttgttt aaatttata gcaaactatc aaaaattagg    5640
gggataaaaa tttatgaaaa aaaggttttc gatgttattt ttatgtttaa ctttaatagt   5700
ttgtggttta tttacaaatt cggccggcct acctcctcgt ataaataaga tgttttgtt    5760
ttgcttgata ctacttttc ttcacaggaa aatatacttc agtaacaaga tctttaggaa    5820
tggtgacttg gtgggggtca gttacatata cttcatatgg tgggtttgta agtttatatc   5880
```

```
cttcatttc  tacccattcc  ctcaacttag  catatacaga  gatgttaatt  ctgaatatga   5940
gccccttaaa  acagacttcg  cacaaaggac  tccaggcaag  tatcttgttc  cctttacaat   6000
ctcctttatc  ggaatggcaa  gttctgtatc  attgccagaa  ggattgtatt  cagcgctgtg   6060
ataaatagtt  attggcttac  caagaaagtc  aattacaaaa  atatatataa  agaaagcaaa   6120
gctacatata  ttaaagcatt  taaggtaaaa  ctaaaaatat  tataaaaatg  aaattatttt   6180
ttctcatagc  taaagttaca  taatacgagg  aggatttata  atgaaaaaag  taataggaat   6240
tataagtatt  gtactatttg  tactcgtagc  acttcaatcc  tgtgctgcag  gagtaggaaa   6300
tgcattaagt  aataacaaag  aagctagtgg  atctgctgga  ttatttttat  ctgtatgtat   6360
gcttattgct  ggaataatag  caataatatc  aaaatatagt  aaaggtatga  ctataacagc   6420
tatagtattt  tatttgttag  cttttgttgt  agggattgct  aatgtgggc   attttttcaga  6480
tttgcaaatt  tggtcaatca  ttaacttgat  atttgctgga  ctattgatat  ttcatttgct   6540
taaaaataag  caattatata  atagcagtgg  gaaaaagtag  aatcatatat  tgtaattatt   6600
tttaattatg  ttggcaaaat  tgaaattgtc  actgaaacac  ctctaaatgt  tttaaataca   6660
tatgtttaat  tattgtgaca  gattctaata  gtagaaagta  gaaatttgct  atgttataat   6720
gacatagagg  tgaatgtaat  atgaaagaag  ttgtaatagc  tagtgcagta  agaacagcga   6780
ttggatctta  tggaaagtct  cttaaggatg  taccagcagt  agatttagga  gctacagcta   6840
taaaggaagc  agttaaaaaa  gcaggaataa  aaccagagga  tgttaatgaa  gtcatttttag  6900
gaaatgttct  tcaagcaggt  ttaggacaga  atccagcaag  acaggcatct  tttaaagcag   6960
gattaccagt  tgaaattcca  gctatgacta  ttaataaggt  ttgtggttca  ggacttagaa   7020
cagttagctt  agcagcacaa  attataaaag  caggagatgc  tgacgtaata  atagcaggtg   7080
gtatggaaaa  tatgtctaga  gctccttact  tagcgaataa  cgctagatgg  ggatatagaa   7140
tgggaaacgc  taaatttgtt  gatgaaatga  tcactgacgg  attgtgggat  gcatttaatg   7200
attaccacat  gggaataaca  gcagaaaaca  tagctgagag  atggaacatt  tcaagagaag   7260
aacaagatga  gtttgctctt  gcatcacaaa  aaaaagctga  agaagctata  aaatcaggtc   7320
aatttaaaga  tgaaatagtt  cctgtagtaa  ttaaaggcag  aaagggagaa  actgtagttg   7380
atacagatga  gcaccctaga  tttggatcaa  ctatagaagg  acttgcaaaa  ttaaaacctg   7440
ccttcaaaaa  agatggaaca  gttacagctg  gtaatgcatc  aggattaaat  gactgtgcag   7500
cagtacttgt  aatcatgagt  gcagaaaaag  ctaaagagct  tggagtaaaa  ccacttgcta   7560
agatagtttc  ttatggttca  gcaggagttg  acccagcaat  aatgggatat  ggacctttct   7620
atgcaacaaa  agcagctatt  gaaaaagcag  gttggacagt  tgatgaatta  gatttaatag   7680
aatcaaatga  agcttttgca  gctcaaagtt  tagcagtagc  aaaagattta  aaatttgata   7740
tgaataaagt  aaatgtaaat  ggaggagcta  ttgcccttgg  tcatccaatt  ggagcatcag   7800
gtgcaagaat  actcgttact  cttgtacacg  caatgcaaaa  aagagatgca  aaaaaaggct   7860
tagcaacttt  atgtataggt  ggcggacaag  gaacagcaat  attgctagaa  aagtgctagg   7920
aattcaggag  gtatagcata  tgacacaaag  aatagcatac  gtaacaggtg  gtatgggtgg   7980
tataggaact  gcaatatgtc  aaagattagc  aaaagatgga  tttagagttg  tagctggatg   8040
cggaccaaat  agtcctagaa  gagaaaagtg  gttagaacaa  caaaaagcac  ttggatttga   8100
tttcatagct  tctgaaggta  acgtagcaga  ttgggactca  actaaaactg  cttttgataa   8160
agttaaatct  gaagttggtg  aagttgatgt  attaataaat  aatgcaggta  ttactagaga   8220
tgtagtattt  agaaagatga  caagagctga  ctgggatgca  gtaatagata  ctaatcttac   8280
```

```
tagtcttttc aatgtaacta agcaggtaat tgatggtatg gcagatagag gttggggtag      8340
aatagtaaat attagttcag ttaatggaca aaaaggtcag tttggacaga caaattattc      8400
tacagctaaa gcaggtcttc atggttttac aatggcttta gcacaggaag ttgctacaaa      8460
aggtgttaca gttaacactg ttagtccagg atatattgct actgacatgg taaaggctat      8520
aagacaagat gttcttgata aaattgttgc tacaatacca gtaaagagat taggacttcc      8580
tgaagagata gcatctattt gtgcatggtt atcaagtgaa gaatcaggat tctcaactgg      8640
tgctgatttt tcattaaacg gtggtttaca catgggataa taccgttcgt ataatgtatg      8700
ctatacgaag ttatccttag aagcaaactt aagagtgtgt tgatagtgca gtatcttaaa      8760
attttgtgta taataggaat tgaagttaaa ttagatgcta aaaatttgta attaagaagg      8820
agggattcgt catgttggta ttccaaatgc gtaatgtaga taaaacatct actgttttga      8880
aacagactaa aaacagtgat tacgcagata aataaatacg ttagattaat tcctaccagt      8940
gactaatctt atgactttt aaacagataa ctaaaattac aaacaaatcg tttaacttct      9000
gtatttattt acagatgtaa tcacttcagg agtaattaca tgaacaaaaa tataaaatat      9060
tctcaaaact ttttaacgag tgaaaaagta ctcaaccaaa taataaaaca attgaattta      9120
aaagaaaccg ataccgttta cgaaattgga acaggtaaag ggcatttaac gacgaaactg      9180
gctaaaataa gtaaacaggt aacgtctatt gaattagaca gtcatctatt caacttatcg      9240
tcagaaaaat taaaactgaa cattcgtgtc actttaattc accaagatat tctacagttt      9300
caattcccta acaaacagag gtataaaatt gttgggagta ttccttacca tttaagcaca      9360
caaattatta aaaaagtggt ttttgaaagc catgcgtctg acatctatct gattgttgaa      9420
gaaggattct acaagcgtac cttggatatt caccgaacac tagggttgct cttgcacact      9480
caagtctcga ttcagcaatt gcttaagctg ccagcggaat gctttcatcc taaaccaaaa      9540
gtaaacagtg tcttaataaa acttacccgc cataccacag atgttccaga taaatattgg      9600
aagctatata cgtactttgt ttcaaaatgg gtcaatcgag aatatcgtca actgtttact      9660
aaaaatcagt ttcatcaagc aatgaaacac gccaaagtaa acaatttaag taccattact      9720
tatgagcaag tattgtctat ttttaatagt tatctattat ttaacgggag gaaataattc      9780
tatgagtcgc ttttttaaat ttggaaagtt acacgttact aaagggaatg gagataaatt      9840
attagatata ctactgacag cttccaagaa gctaaagagg tcataacttc gtataatgta      9900
tgctatacga acggtaagta ttgatagaaa aaaacactag acagtgctaa taacaatgtc      9960
tagtgctttt tatcttgctc aattttttca ttgagttcat ttaagtaagt ccacctgtcc     10020 atctttcgt ctagctcttt ttccagtgaa ttcttttcgg ataagagatc ttcaagaagt     10080
gcataatcag atgaagcagc ttccatttct attttctttt cagatataga ttttctaga     10140 tgttcaatta cctcatctat tttgtcaaac tccatttgtt ctgcataggt aaattttaga     10200
ggcttttctt tttgcaactt atagttgttt ttagctgtat ttttcttaga gcttattttt     10260
tcctctgata tttttgcagt tttgtgaaaa taggaatagt ttcctgtata ttgagtgatt     10320
ttaccgtttc cttcaaaaga aaatatttta tcaactgttt tgtcaaggaa gtacctgtca     10380
tgagatacag ctataacagc tccttcaaaa tcgttaatat aatcttctag gattgtaagt     10440
gtttctatat ccagatcatt tgttggttcg tccagcaaaa gtacattagg gtaattcatc     10500
agtattttta gaagatataa tcttcttcgt tctcctcctg aaagttttcc aaggggagtc     10560
cattgaactg aaggttcaaa taaaaaattt tcaagtacag cagaagcact tatttttca     10620
```

-continued

```
cccgatgaag ttgacgcata ttctgatgtc ccacgtatgt attcaattac cctttcgttc    10680
atatccatat cagaaattcc ctgagaatag tatcctatct ttactgtttc acctatatct    10740
atagtgccgc tgtccggcag aattttttga actaaaatat tcataagagt ggatttacca    10800
cttccattag gtccaataat acctattctg tcattattta gtatgttata agtgaaattt    10860
ttaattaatg tcttttcacc aaaacttttg cttatgttat ccaggtttat gacttttgt     10920 tt                                                                    10922
```

<210> SEQ ID NO 122
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN01

<400> SEQUENCE: 122

```
atttacaaat tcggccggcc tacctcctcg tataaataag atg                         43
```

<210> SEQ ID NO 123
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN02

<400> SEQUENCE: 123

```
ctagctatta caacttcttt catattacat tcacctctat gtc                         43
```

<210> SEQ ID NO 124
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN03

<400> SEQUENCE: 124

```
gacatagagg tgaatgtaat atgaaagaag ttgtaatagc tag                         43
```

<210> SEQ ID NO 125
<211> LENGTH: 49
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN04mod
<400> SEQUENCE: 125

```
gtatagcata cattatacga acggtattat cccatgtgta aaccaccgt                   49
```

<210> SEQ ID NO 126
<211> LENGTH: 48
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN05mod

<400> SEQUENCE: 126
ttcgtataat gtatgctata cgaagttatc cttagaagca aacttaag            48

<210> SEQ ID NO 127
<211> LENGTH: 46
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN06

<400> SEQUENCE: 127
gtctagtgtt tttctatc aatactctag ataccgttcg tatagc                46

<210> SEQ ID NO 128
<211> LENGTH: 46
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN07

<400> SEQUENCE: 128
tgtatgctat acgaacggta agtattgata gaaaaaaaca ctagac              46

<210> SEQ ID NO 129
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN08

<400> SEQUENCE: 129
caaaaaggag tttaaacaaa aagtcataaa cctggataac                     40

<210> SEQ ID NO 130
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Og31f

<400> SEQUENCE: 130
ccgtttctca caacaacaat accag                                     25

<210> SEQ ID NO 131
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Og32r

```
<400> SEQUENCE: 131
aaaccacctt gacgatgaaa ccata                                           25

<210> SEQ ID NO 132
<211> LENGTH: 7951
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL8315-Pfdx-thlA-phaB-bld, plasmid

<400> SEQUENCE: 132
cctgcaggat aaaaaaattg tagataaatt ttataaaata gttttatcta caattttttt     60
atcaggaaac agctatgacc gcggccgctc actatctgcg gaacctgcct ccttatctga    120
taaaaaatat tcgctgcatc tttgacttgt tattttcttt caaatgccta aaattatctt    180
ttaaaattat aacaaatgtg ataaaataca ggggatgaaa acattatcta aaaattaagg    240
aggtgttaca tatgaaagaa gttgtaatag ctagtgcagt aagaacagcg attggatctt    300
atggaaagtc tcttaaggat gtaccagcag tagatttagg agctacagct ataaaggaag    360
cagttaaaaa agcaggaata aaaccagagg atgttaatga agtcatttta ggaaatgttc    420
ttcaagcagg tttaggacag aatccagcaa gacaggcatc ttttaaagca ggattaccag    480
ttgaaattcc agctatgact attaataagg tttgtggttc aggacttaga acagttagct    540
tagcagcaca aattataaaa gcaggagatg ctgacgtaat aatagcaggt ggtatggaaa    600
atatgtctag agctccttac ttagcgaata acgctagatg gggatataga atgggaaacg    660
ctaaatttgt tgatgaaatg atcactgacg gattgtggga tgcatttaat gattaccaca    720
tgggaataac agcagaaaac atagctgaga gatggaacat ttcaagagaa gaacaagatg    780
agtttgctct tgcatcacaa aaaaagctg aagaagctat aaaatcaggt caatttaaag    840
atgaaatagt tcctgtagta attaaaggca gaaagggaga actgtagtt gatacagatg    900 agcaccctag atttggatca actatagaag acttgcaaa attaaaacct gccttcaaaa    960
aagatggaac agttacagct ggtaatgcat caggattaaa tgactgtgca gcagtacttg   1020
taatcatgag tgcagaaaaa gctaaagagc ttggagtaaa accacttgct aagatagttt   1080
cttatggttc agcaggagtt gacccagcaa taatgggata tggacctttc tatgcaacaa   1140
aagcagctat tgaaaaagca ggttggacag ttgatgaatt agatttaata gaatcaaatg   1200
aagcttttgc agctcaaagt ttagcagtag caaaagatt aaaatttgat atgaataaag   1260
taaatgtaaa tggaggagct attgcccttg gtcatccaat tggagcatca ggtgcaagaa   1320
tactcgttac tcttgtacac gcaatgcaaa aagagatgc aaaaaaggc ttagcaactt   1380 tatgtatagg tggcggacaa ggaacagcaa tattgctaga aaagtgctag gaattcagga   1440
ggtatagcat atgacacaaa gaatagcata cgtaacaggt ggtatgggtg gtataggaac   1500
tgcaatatgt caaagattag caaaagatgg atttagagtt gtagctggat gcggaccaaa   1560
tagtcctaga agagaaaagt ggttagaaca acaaaaagca cttggatttg atttcatagc   1620
ttctgaaggt aacgtagcag attgggactc aactaaaact gcttttgata agttaaatc   1680 tgaagttggt gaagttgatg tattaataaa taatgcaggt attactagag atgtagtatt   1740
tagaaagatg acaagagctg actgggatgc agtaatagat actaatctta ctagtctttt   1800
caatgtaact aagcaggtaa ttgatggtat ggcagataga ggttgggta gaatagtaaa   1860
```

```
tattagttca gttaatggac aaaaaggtca gtttggacag acaaattatt ctacagctaa    1920
agcaggtctt catggttta caatggcttt agcacaggaa gttgctacaa aaggtgttac    1980
agttaacact gttagtccag gatatattgc tactgacatg gtaaaggcta aagacaaga    2040 tgttcttgat aaaattgttg ctacaatacc agtaaagaga ttaggacttc ctgaagagat    2100
agcatctatt tgtgcatggt tatcaagtga agaatcagga ttctcaactg gtgctgattt    2160
ttcattaaac ggtggtttac acatgggata agaaggagat atacatatga taaaagatac    2220
acttgttagt attacaaaag atttaaaact taaaactaat gttgaaaatg caaatcttaa    2280
aaattataaa gatgatagtt cttgttttgg agtatttgaa atgttgaaa atgcaataag    2340 taatgcagta catgctcaaa aaattttatc tcttcattat acaaaagaac agagagaaaa    2400
aattataact gaaattagaa aagcagcttt agaaaataaa gaaatattag ctacaatgat    2460
tcttgaagaa actcacatgg gaagatatga agataaaata cttaaacatg aacttgtagc    2520
aaaatataca cctggaactg aagatttaac tacaactgct tggtcaggtg ataatggact    2580
tacagtagtt gaaatgagtc cttatggagt tataggagca attacaccttt ctactaatcc    2640 aacagaaact gtaatatgta attcaattgg tatgattgca gctggaaata ctgtagtttt    2700
taatggtcat cctggagcta aaaaatgtgt agcatttgct gttgaaatga ttaataaagc    2760
tataattagt tgtggaggtc ctgaaaatct tgttacaact ataaaaaatc caacaatgga    2820
ttctcttgat gcaataatta acatccttc aattaaactt ctttgtggta caggaggtcc    2880
aggaatggta aaaactcttc ttaattctgg taaaaaagct ataggagcag gtgctggaaa    2940
tcctccagta attgttgatg atacagcaga tatagaaaaa gctggtaaat caattattga    3000
aggatgtagt tttgataata atttaccatg tatagcagaa aaagaagtat tgttttttga    3060
aaatgttgct gatgattta ttagtaatat gcttaaaaat aatgcagtaa taattaatga    3120
agatcaagtt tctaaactta gatttagt attacagaaa aataatgaaa cacaggaata    3180
ttctattaat aaaaaatggg taggaaaaga tgcaaaatta tttcttgatg aaatagatgt    3240
agaatcacct tcaagtgtta aatgtataat ttgtgaagtt tctgcttcac atccatttgt    3300
aatgactgaa ttaatgatgc ctatacttcc aattgtaaga gttaaagata tagatgaagc    3360
aatagaatat gcaaaattg ctgaacagaa tagaaaacat agtgcttata tttattctaa    3420
aaatatagat aatttaaata gatttgaaag agaaatagat acaactattt ttgttaaaaa    3480
tgcaaaatca tttgctggtg taggatatga agcagaaggt tttacaactt ttacaatagc    3540
tggaagtact ggtgaaggta ttacaagtgc aagaaatttt acaagacaga gaagatgtgt    3600
tttagcaggt taatctagag tcgacgtcac gcgtccatgg agatctcgag gcctgcagac    3660
atgcaagctt ggcactggcc gtcgttttac aacgtcgtga ctgggaaaac cctggcgtta    3720
cccaacttaa tcgccttgca gcacatcccc ctttcgccag ctggcgtaat agcgaagagg    3780
cccgcaccga tcgcccttcc caacagttgc gcagcctgaa tggcgaatgg cgctagcata    3840
aaaataagaa gcctgcattt gcaggcttct tatttttatg gcgcgccgcc attatttttt    3900
tgaacaattg acaattcatt tcttattttt tattaagtga tagtcaaaag gcataacagt    3960
gctgaataga aagaaattta cagaaaagaa aattatagaa tttagtatga ttaattatac    4020
tcatttatga atgtttaatt gaatacaaaa aaaaatactt gttatgtatt caattacggg    4080
ttaaaatata gacaagttga aaatttaat aaaaaaataa gtcctcagct cttatatatt    4140
aagctaccaa cttagtatat aagccaaaac ttaaatgtgc taccaacaca tcaagccgtt    4200
agagaactct atctatagca atatttcaaa tgtaccgaca tacaagagaa acattaacta    4260
```

```
tatatattca atttatgaga ttatcttaac agatataaat gtaaattgca ataagtaaga    4320
tttagaagtt tatagccttt gtgtattgga agcagtacgc aaaggctttt ttatttgata    4380
aaaattagaa gtatatttat tttttcataa ttaatttatg aaaatgaaag ggggtgagca    4440
aagtgacaga ggaaagcagt atcttatcaa ataacaaggt attagcaata tcattattga    4500
ctttagcagt aaacattatg acttttatag tgcttgtagc taagtagtac gaaaggggga    4560
gctttaaaaa gctccttgga atacatagaa ttcataaatt aatttatgaa agaagggcg     4620
tatatgaaaa cttgtaaaaa ttgcaaagag tttattaaag atactgaaat atgcaaaata    4680
cattcgttga tgattcatga taaaacagta gcaacctatt gcagtaaata caatgagtca    4740
agatgtttac ataaagggaa agtccaatgt attaattgtt caaagatgaa ccgatatgga    4800
tggtgtgcca taaaaatgag atgttttaca gaggaagaac agaaaaaaga acgtacatgc    4860
attaaatatt atgcaaggag ctttaaaaaa gctcatgtaa agaagagtaa aagaaaaaa     4920
taatttattt attaatttaa tattgagagt gccgacacag tatgcactaa aaaatatatc    4980
tgtggtgtag tgagccgata caaaaggata gtcactcgca ttttcataat acatcttatg    5040
ttatgattat gtgtcggtgg gacttcacga cgaaaaccca caataaaaaa agagttcggg    5100
gtagggttaa gcatagttga ggcaactaaa caatcaagct aggatatgca gtagcagacc    5160
gtaaggtcgt tgtttaggtg tgttgtaata catacgctat taagatgtaa aaatacggat    5220
accaatgaag ggaaaagtat aattttttgga tgtagtttgt ttgttcatct atgggcaaac    5280
tacgtccaaa gccgtttcca aatctgctaa aaagtatatc ctttctaaaa tcaaagtcaa    5340
gtatgaaatc ataaataaag tttaattttg aagttattat gatattatgt ttttctatta    5400
aaataaatta agtatataga atagtttaat aatagtatat acttaatgtg ataagtgtct    5460
gacagtgtca cagaaaggat gattgttatg gattataagc ggccggccag tgggcaagtt    5520
gaaaaattca caaaaatgtg gtataatatc tttgttcatt agagcgataa acttgaattt    5580
gagagggaac ttagatggta tttgaaaaaa ttgataaaaa tagttggaac agaaaagagt    5640
attttgacca ctactttgca agtgtaccct gtacctacag catgaccgtt aaagtggata    5700
tcacacaaat aaaggaaaag ggaatgaaac tatatcctgc aatgctttat tatattgcaa    5760
tgattgtaaa ccgccattca gagtttagga cggcaatcaa tcaagatggt gaattgggga    5820
tatatgatga gatgatacca agctatacaa tatttcacaa tgatactgaa acattttcca    5880
gcctttggac tgagtgtaag tctgacttta aatcattttt agcagattat gaaagtgata    5940
cgcaacggta tggaaacaat catagaatgg aaggaaagcc aaatgctccg gaaaacattt    6000
ttaatgtatc tatgataccg tggtcaacct tcgatggctt taatctgaat ttgcagaaag    6060
gatatgatta tttgattcct attttactaa tggggaaata ttataaagaa gataacaaaa    6120
ttatacttcc tttggcaatt caagttcatc acgcagtatg tgacggattt cacatttgcc    6180
gttttgtaaa cgaattgcag gaattgataa atagttaact tcaggtttgt ctgtaactaa    6240
aaacaagtat ttaagcaaaa acatcgtaga aatacggtgt ttttgttac  cctaagttta    6300
aactcctttt tgataatctc atgaccaaaa tcccttaacg tgagttttcg ttccactgag    6360
cgtcagaccc cgtagaaaag atcaaaggat cttcttgaga tcctttttttt ctgcgcgtaa    6420
tctgctgctt gcaaacaaaa aaaccaccgc taccagcggt ggtttgtttg ccggatcaag    6480
agctaccaac tctttttccg aaggtaactg gcttcagcag agcgcagata ccaaatactg    6540
ttcttctagt gtagccgtag ttaggccacc acttcaagaa ctctgtagca ccgcctacat    6600
```

```
acctcgctct gctaatcctg ttaccagtgg ctgctgccag tggcgataag tcgtgtctta      6660
ccgggttgga ctcaagacga tagttaccgg ataaggcgca gcggtcgggc tgaacggggg      6720
gttcgtgcac acagcccagc ttggagcgaa cgacctacac cgaactgaga tacctacagc      6780
gtgagctatg agaaagcgcc acgcttcccg aagggagaaa ggcggacagg tatccggtaa      6840
gcggcagggt cggaacagga gagcgcacga gggagcttcc agggggaaac gcctggtatc      6900
tttatagtcc tgtcgggttt cgccacctct gacttgagcg tcgattttg tgatgctcgt       6960 cagggggcg gagcctatgg aaaaacgcca gcaacgcggc cttttacgg ttcctggcct         7020 tttgctggcc ttttgctcac atgttctttc ctgcgttatc ccctgattct gtggataacc       7080
gtattaccgc ctttgagtga gctgataccg ctcgccgcag ccgaacgacc gagcgcagcg      7140
agtcagtgag cgaggaagcg gaagagcgcc caatacgcag gccccctgc ttcgggtca        7200 ttatagcgat ttttcggta tatccatcct ttttcgcacg atatacagga ttttgccaaa       7260
gggttcgtgt agactttcct tggtgtatc aacggcgtca gccggcaggg ataggtgaag       7320
taggcccacc cgcgagcggg tgttccttct tcactgtccc ttattcgcac ctggcggtgc      7380
tcaacgggaa tcctgctctg cgaggctggc cggctaccgc cggcgtaaca gatgagggca      7440
agcggatggc tgatgaaacc aagccaacca ggaagggcag cccacctatc aaggtgtact      7500
gccttccaga cgaacgaaga gcgattgagg aaaaggcggc ggcggccggc atgagcctgt      7560
cggcctacct gctggccgtc ggccaggct acaaaatcac gggcgtcgtg gactatgagc      7620
acgtccgcga gctggcccgc atcaatggcg acctgggccg cctgggcggc ctgctgaaac     7680
tctggctcac cgacgacccg cgcacggcgc ggttcggtga tgccacgatc ctcgccctgc      7740
tggcgaagat cgaagagaag caggacgagc ttggcaaggt catgatgggc gtggtccgcc      7800
cgagggcaga gccatgactt tttagccgc taaaacggcc gggggtgcg cgtgattgcc         7860 aagcacgtcc ccatgcgctc catcaagaag agcgacttcg cggagctggt gaagtacatc      7920
accgacgagc aaggcaagac cgatcgggcc c                                     7951
```

<210> SEQ ID NO 133
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: bld-phaB-F1, forward

<400> SEQUENCE: 133
acatgggata agaaggagat atacatatga taaaag                                36

<210> SEQ ID NO 134
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: bld-pMTL-R1, forward

<400> SEQUENCE: 134
cgtcgactct agattaacct gctaaaacac atcttc                                36

<210> SEQ ID NO 135
<211> LENGTH: 36

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL-bld-F1, forward

<400> SEQUENCE: 135
gtgttttagc aggttaatct agagtcgacg tcacgc                               36

<210> SEQ ID NO 136
<211> LENGTH: 1179
<212> TYPE: DNA
<213> ORGANISM: Clostridium acetobutylicum
<220> FEATURE:
<221> NAME/KEY: misc_feature
<223> OTHER INFORMATION: thlA

<400> SEQUENCE: 136
atgaaagaag ttgtaatagc tagtgcagta agaacagcga ttggatctta tggaaagtct     60
cttaaggatg taccagcagt agatttagga gctacagcta taaaggaagc agttaaaaaa    120
gcaggaataa aaccagagga tgttaatgaa gtcatttttag gaaatgttct tcaagcaggt   180
ttaggacaga atccagcaag acaggcatct tttaaagcag gattaccagt gaaaattcca    240
gctatgacta ttaataaggt ttgtggttca ggacttagaa cagttagctt agcagcacaa    300
attataaaag caggagatgc tgacgtaata atagcaggtg gtatggaaaa tatgtctaga    360
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaagctga agaagctata aaatcaggtc aatttaaaga tgaaatagtt    600
cctgtagtaa ttaaaggcag aaaggggaga actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta gatagtttc ttatggttca    840 gcaggagttg acccagcaat aatgggatat ggaccttctt atgcaacaaa agcagctatt    900
gaaaaagcag gttggacagt tgatgaatta gatttaatag aatcaaatga agcttttgca    960
gctcaaagtt tagcagtagc aaaagatta aaatttgata tgaataaagt aaatgtaaat   1020
ggaggagcta ttgcccttgg tcatccaatt ggagcatcag gtgcaagaat actcgttact   1080
cttgtacacg caatgcaaaa agagatgca aaaaaaggct tagcaacttt atgtataggt   1140
ggcggacaag gaacagcaat attgctagaa aagtgctag                         1179

<210> SEQ ID NO 137
<211> LENGTH: 849
<212> TYPE: DNA
<213> ORGANISM: Clostridium kluyveri
<220> FEATURE:
<221> NAME/KEY: misc_feature
<223> OTHER INFORMATION: hbd1

<400> SEQUENCE: 137
atgagtatta aaagtgtagc ggttttaggt agtggaacta tgtctcgtgg aattgtgcag    60
gcttttgcag aagcaggtat agatgtaatt atccgtggaa gaactgaagg tagtattgga   120
aaaggtctag cagcagtaaa gaaagcttat gataaaaaag tatcaaaggg gaaaatttcc    180
```

```
caggaagatg ctgataaaat agttggaaga gtaagtacaa caactgaact tgaaaaattg    240
gctgattgtg atcttataat agaagcagca tcagaggata tgaatataaa gaaagactat    300
tttggaaaat tagaagaaat atgcaagcct gaaacaattt ttgctactaa tacttcttca    360
ttatctataa ctgaagtagc aacagctaca aagagaccag ataaattcat aggaatgcat    420
ttctttaatc cagcaaatgt tatgaaatta gttgaaatca taagaggtat gaatacttca    480
caagaaactt ttgatattat aaaagaagct tccattaaaa taggaaaaac tcctgtagaa    540
gttgcagaag ctccaggatt tgttgtaaac aagatattag taccaatgat caatgaagca    600
gtaggaattt tggcagaagg aatagcttca gcagaagata tcgatacagc tatgaaatta    660
ggcgctaatc acccaatggg tcctttagca ttaggagatc ttattggact tgatgtagtt    720
cttgcagtta tggatgtact ttatagtgaa actggagatt caaaatatag agctcataca    780
ttacttagaa aatatgtaag agcaggatgg cttggaagaa aatcaggaaa aggattcttc    840
gcttattaa                                                            849

<210> SEQ ID NO 138
<211> LENGTH: 176
<212> TYPE: DNA
<213> ORGANISM: Clostridium autoethanogenum
<220> FEATURE:
<221> NAME/KEY: misc_feature
<223> OTHER INFORMATION: ferredoxin promoter

<400> SEQUENCE: 138
ggccgcgctc actatctgcg gaacctgcct cctatctga taaaaatat tcgctgcatc    60 tttgacttgt tattttcttt caaatgccta aaattatctt ttaaaattat aacaaatgtg    120
ataaaataca ggggatgaaa acattatcta aaaattaagg aggtgttaca gaattc       176

<210> SEQ ID NO 139
<211> LENGTH: 474
<212> TYPE: DNA
<213> ORGANISM: Clostridium autoethanogenum
<220> FEATURE:
<221> NAME/KEY: misc_feature
<223> OTHER INFORMATION: pyruvate-ferredoxin oxidoreductase promoter

<400> SEQUENCE: 139
aaaatagttg ataataatgc agagttataa acaaaggtga aaagcattac ttgtattctt    60
ttttatatat tattataaat taaaatgaag ctgtattaga aaaatacac acctgtaata    120 taaaatttta aattaatttt taattttttc aaaatgtatt ttcatgtttt agaatttga    180 tgtatattaa aatagtagaa tacataagat acttaattta attaaagata gttaagtact    240
tttcaatgtg ctttttttaga tgtttaatac aaatctttaa ttgtaaaaga aatgctgtac    300
tatttactgt actagtgacg ggattaaact gtattaatta taaataaaaa ataagtacag    360
ttgtttaaaa ttatattttg tattaaatct aatagtacga tgtaagttat tttatactat    420
tgctagttta ataaaaagat ttaattatat gcttgaaaag gagaggaatt cata          474

<210> SEQ ID NO 140
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ribosome binding site rbs2
```

-continued

<400> SEQUENCE: 140
aaatagaaag gaggtgttac at    22

<210> SEQ ID NO 141
<211> LENGTH: 35
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Pfdx-F1, forward

<400> SEQUENCE: 141
aaaggtctcc ggccgcgctc actatctgcg gaacc    35

<210> SEQ ID NO 142
<211> LENGTH: 38
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Pfdx-R1, reverse

<400> SEQUENCE: 142
tttggtctcg aattctgtaa cacctcctta atttttag    38

<210> SEQ ID NO 143
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ppfor-F1, forward

<400> SEQUENCE: 143
aaaggtctcc ggccgcaaaa tagttgataa taatgcagag    40

<210> SEQ ID NO 144
<211> LENGTH: 35
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ppfor-R1, reverse

<400> SEQUENCE: 144
tttggtctcg aattcctctc cttttcaagc atata    35

<210> SEQ ID NO 145
<211> LENGTH: 45
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hbd1-F1, forward

<400> SEQUENCE: 145
aaaggtctcg aattcaaaga tctatgtcta ttaaatcagt tgcag    45

<210> SEQ ID NO 146
<211> LENGTH: 47
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hbd1-R1, reverse

<400> SEQUENCE: 146
tttggtctcc ctcctttcta tttctaatat gcgaaaaatc ctttacc    47

<210> SEQ ID NO 147
<211> LENGTH: 49
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: thlA-F1, forward

<400> SEQUENCE: 147
aaaggtctca ggaggtgtta catatgaaag aagttgtaat agctagtgc    49

<210> SEQ ID NO 148
<211> LENGTH: 48
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: thlA-R1, reverse

<400> SEQUENCE: 148
tttggtctcc tcgagtatgg atccctagca cttttctagc aatattgc    48

<210> SEQ ID NO 149
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ppfor-F2, forward

<400> SEQUENCE: 149
aaacagctat gaccgcggcc gcaaaatagt    30

<210> SEQ ID NO 150
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ppfor-R2, reverse

<400> SEQUENCE: 150
ttactcattg gattcctctc cttt    24

<210> SEQ ID NO 151
<211> LENGTH: 29

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ptb-Buk-F2, forward

<400> SEQUENCE: 151
ggaatccaat gagtaaaaac tttgatgag                                    29

<210> SEQ ID NO 152
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ptb-Buk-F2, reverse

<400> SEQUENCE: 152
caggcctcga gatctcctag taaaccttag cttgttc                           37

<210> SEQ ID NO 153
<211> LENGTH: 7884
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL82256-ptb-buk, plasmid

<400> SEQUENCE: 153
gagatctcga ggcctgcaga catgcaagct tggcactggc cgtcgtttta caacgtcgtg    60
actgggaaaa ccctggcgtt acccaactta atcgccttgc agcacatccc cctttcgcca   120
gctggcgtaa tagcgaagag gcccgcaccg atcgcccttc ccaacagttg cgcagcctga   180
atggcgaatg gcgctagcat aaaaataaga agcctgcatt tgcaggcttc ttatttttat   240
ggcgcgccgt tctgaatcct tagctaatgg ttcaacaggt aactatgacg aagatagcac   300
cctggataag tctgtaatgg attctaaggc atttaatgaa gacgtgtata taaaatgtgc   360
taatgaaaaa gaaaatgcgt taaaagagcc taaaatgagt tcaaatggtt ttgaaattga   420
ttggtagttt aatttaatat atttttttcta ttggctatct cgataccttat agaatcttct   480 gttcactttt gttttttgaaa tataaaaagg ggcttttttag cccctttttt ttaaaactcc   540
ggaggagttt cttcattctt gatactatac gtaactattt tcgatttgac ttcattgtca   600
attaagctag taaatcaat ggttaaaaaa caaaaaactt gcattttttct acctagtaat   660 ttataatttt aagtgtcgag tttaaaagta aatttaccaa ggaaaggagc aagttttttta   720 ataaggaaaa attttttcctt ttaaaattct atttcgttat atgactaatt ataatcaaaa   780
aaatgaaaat aaacaagagg taaaaactgc tttagagaaa tgtactgata aaaaagaaa   840 aaatcctaga tttacgtcat acatagcacc tttaactact aagaaaaata ttgaaaggac   900
ttccacttgt ggagattatt tgtttatgtt gagtgatgca gacttagaac attttaaatt   960
acataaaggt aattttttgcg gtaatagatt ttgtccaatg tgtagttggc gacttgcttg  1020
taaggatagt ttagaaatat ctattcttat ggagcattta agaaagaag aaaataaga   1080 gtttatattt ttaactctta caactccaaa tgtaaaaagt tatgatctta attattctat  1140
taaacaatat aataaatctt ttaaaaaatt aatggagcgt aaggaagtta aggatataac  1200
```

```
taaaggttat ataagaaaat tagaagtaac ttaccaaaag gaaaaataca taacaaagga    1260
tttatggaaa ataaaaaaag attattatca aaaaaaagga cttgaaattg gtgatttaga    1320
acctaatttt gatacttata atcctcattt tcatgtagtt attgcagtta ataaaagtta    1380
ttttacagat aaaaattatt atataaatcg agaaagatgg ttggaattat ggaagtttgc    1440
tactaaggat gattctataa ctcaagttga tgttagaaaa gcaaaaatta atgattataa    1500
agaggtttac gaacttgcga aatattcagc taaagacact gattatttaa tatcgaggcc    1560
agtatttgaa attttttata aagcattaaa aggcaagcag gtattagttt ttagtggatt    1620
ttttaaagat gcacacaaat tgtacaagca aggaaaactt gatgtttata aaagaaaga    1680 tgaaattaaa tatgtctata tagtttatta taattggtgc aaaaaacaat atgaaaaaac    1740
tagaataagg gaacttacgg aagatgaaaa agaagaatta aatcaagatt taatagatga    1800
aatagaaata gattaaagtg taactatact ttatatatat atgattaaaa aaataaaaaa    1860
caacagccta ttaggttgtt gttttttatt ttctttatta attttttttaa tttttagttt    1920 ttagttctttt tttaaaataa gtttcagcct ctttttcaat atttttttaaa gaaggagtat    1980 ttgcatgaat tgccttttttt ctaacagact taggaaatat tttaacagta tcttcttgcg    2040
ccggtgattt tggaacttca taacttacta atttataatt attatttttct tttttaattg    2100 taacagttgc aaaagaagct gaacctgttc cttcaactag tttatcatct tcaatataat    2160
attcttgacc tatatagtat aaatatattt ttattatatt tttacttttt tctgaatcta    2220 ttatttttata atcataaaaa gttttaccac caaaagaagg ttgtactcct tctggtccaa    2280 catattttttt tactatatta tctaaataat ttttgggaac tggtgttgta atttgattaa    2340
tcgaacaacc agttatactt aaaggaatta taactataaa aatatatagg attatctttt    2400
taaatttcat tattggcctc cttttttatta aatttatgtt accataaaaa ggacataacg    2460
ggaatatgta gaatatttttt aatgtagaca aaattttaca taaatataaa gaaggaagt    2520 gtttgtttaa atttttatagc aaactatcaa aaattagggg gataaaaatt tatgaaaaaa    2580
aggttttcga tgttatttttt atgtttaact ttaatagttt gtggtttatt tacaaattcg    2640
gccggccgaa gcaaacttaa gagtgtgttg atagtgcagt atcttaaaat tttgtataat    2700
aggaattgaa gttaaattag atgctaaaaa tttgtaatta agaaggagtg attacatgaa    2760 caaaatata aaatattctc aaaacttttt aacgagtgaa aaagtactca accaaataat    2820
aaaacaattg aatttaaaag aaaccgatac cgtttacgaa attggaacag gtaaagggca    2880
tttaacgacg aaactggcta aaataagtaa acaggtaacg tctattgaat tagacagtca    2940
tctattcaac ttatcgtcag aaaaattaaa actgaatact cgtgtcactt taattcacca    3000
agatattcta cagtttcaat tccctaacaa acagaggtat aaaattgttg ggagtattcc    3060
ttaccattta agcacacaaa ttattaaaaa agtggttttt gaaagccatg cgtctgacat    3120
ctatctgatt gttgaagaag gattctacaa gcgtaccttg gatattcacc gaacactagg    3180
gttgctcttg cacactcaag tctcgattca gcaattgctt aagctgccag cggaatgctt    3240
tcatcctaaa ccaaaagtaa acagtgtctt aataaaactt acccgccata ccacagatgt    3300
tccagataaa tattggaagc tatatacgta ctttgtttca aaatgggtca atcgagaata    3360
tcgtcaactg tttactaaaa atcagtttca tcaagcaatg aaacacgcca agtaaacaa    3420 tttaagtacc gttacttatg agcaagtatt gtctattttt aatagttatc tattatttaa    3480
cgggaggaaa taattctatg agtcgctttt gtaaatttgg aaagttacac gttactaaag    3540
```

```
ggaatgtgtt taaactcctt tttgataatc tcatgaccaa aatcccttaa cgtgagtttt    3600
cgttccactg agcgtcagac cccgtagaaa agatcaaagg atcttcttga gatccttttt    3660
ttctgcgcgt aatctgctgc ttgcaaacaa aaaaccacc gctaccagcg gtggtttgtt    3720
tgccggatca agagctacca actcttttc cgaaggtaac tggcttcagc agagcgcaga    3780
taccaaatac tgttcttcta gtgtagccgt agttaggcca ccacttcaag aactctgtag    3840
caccgcctac atacctcgct ctgctaatcc tgttaccagt ggctgctgcc agtggcgata    3900
agtcgtgtct taccgggttg gactcaagac gatagttacc ggataaggcg cagcggtcgg    3960
gctgaacggg gggttcgtgc acacagccca gcttggagcg aacgacctac accgaactga    4020 gataccctaca gcgtgagcta tgagaaagcg ccacgcttcc cgaagggaga aaggcggaca    4080
ggtatccggt aagcggcagg gtcggaacag gagagcgcac gagggagctt ccaggggggaa    4140 acgcctggta tctttatagt cctgtcgggt ttcgccacct ctgacttgag cgtcgatttt    4200
tgtgatgctc gtcagggggg cggagcctat ggaaaaacgc cagcaacgcg gcctttttac    4260
ggttcctggc cttttgctgg ccttttgctc acatgttctt tcctgcgtta tcccctgatt    4320
ctgtggataa ccgtattacc gcctttgagt gagctgatac cgctcgccgc agccgaacga    4380
ccgagcgcag cgagtcagtg agcgaggaag cggaagagcg cccaatacgc agggcccccct    4440 gcttcggggt cattatagcg attttttcgg tatatccatc ttttttcgca cgatatacag    4500
gattttgcca aagggttcgt gtagactttc cttggtgtat ccaacggcgt cagccgggca    4560
ggataggtga agtaggccca cccgcgagcg ggtgttcctt cttcactgtc ccttattcgc    4620
acctggcggt gctcaacggg aatcctgctc tgcgaggctg gccggctacc gccggcgtaa    4680
cagatgaggg caagcggatg gctgatgaaa ccaagccaac caggaagggc agcccaccta    4740
tcaaggtgta ctgccttcca gacgaacgaa gagcgattga ggaaaaggcg gcggcggccg    4800
gcatgagcct gtcggcctac ctgctggccg tcggccaggg ctacaaaatc acgggcgtcg    4860
tggactatga gcacgtccgc gagctggccc gcatcaatgg cgacctgggc cgcctgggcg    4920
gcctgctgaa actctggctc accgacgacc cgcgcacggc gcggttcggt gatgccacga    4980
tcctcgccct gctggcgaag atcgaagaga agcaggacga gcttggcaag gtcatgatgg    5040
gcgtggtccg cccgagggca gagccatgac tttttagcc gctaaaacgg ccggggggtg    5100
cgcgtgattg ccaagcacgt ccccatgcgc tccatcaaga agagcgactt cgcggagctg    5160
gtgaagtaca tcaccgacga gcaaggcaag accgatcggg cccctgcag gataaaaaaa    5220 ttgtagataa atttttataaa atagttttat ctacaatttt tttatcagga aacagctatg    5280
accgcggccg caaaatagtt gataataatg cagagttata aacaaggtg aaaagcatta    5340 cttgtattct tttttatata ttattataaa ttaaaatgaa gctgtattag aaaaaataca    5400
cacctgtaat ataaaattt aaattaattt ttaattttt caaaatgtat tttacatgtt    5460
tagaattttg atgtatatta aaatagtaga atacataaga tacttaattt aattaaagat    5520
agttaagtac ttttcaatgt gcttttttag atgtttaata caaatcttta attgtaaaag    5580
aaatgctgta ctatttactg tactagtgac gggattaaac tgtattaatt ataaataaaa    5640
aataagtaca gttgtttaaa attatatttt gtattaaatc taatagtacg atgtaagtta    5700
ttttatacta ttgctagttt aataaaaaga tttaattata tgcttgaaaa ggagaggaat    5760
ccaatgagta aaaactttga tgagttatta tcaagattaa aggaagttcc aacaaaaaaa    5820
gtggctgtag ccgtagcaca agatgaacca gtattagagg ctataaaaga agctacagaa    5880
aataacatcg cacaagcaat attggttggt gataaacaac aaatccatga aatcgcaaag    5940
```

```
aaaataaact tggacttatc tgattatgaa ataatggata ttaaagatcc aaagaaagca    6000
acattagaag cagtaaaatt agtttctagt ggtcatgcag atatgttaat gaaaggtcta    6060
gttgatactg caacattcct aagaagcgta ttaaacaaag aggttggtct tagaacagga    6120
aaattaatgt cccatgtagc tgtgtttgat gtggaaggtt gggatagact gttattttta    6180
actgatgcag catttaatac atatccagaa tttaaggata agttggaat gataaataat     6240 gcagttgtag ttgctcatgc atgtggaata gatgttccaa gagtagcacc tatatgccca    6300
gttgaagttg taaatacaag tatgcaatca acagttgatg cagcattgtt agctaaaatg    6360
agtgacaggg ggcaaattaa aggatgcgta attgatggac ttttgccctt agataatgca    6420
atatcagaag aagcagctca tcataaaggt gttacaggat cagtagcagg taaagctgat    6480
atattattat taccaaatat agaagcagca aatgtaatgt ataaaacatt aacatatttc    6540
tctaaatcaa gaaatggtgg actttagta ggtacatcag caccagtaat tttaacttca     6600
agagcagatt cattcgaaac taagttaat tcaattgctc ttgcagcatt agttgcagca     6660
agaaataagt aataaatcaa tccataataa ttaatgcata attaatggag agatttatat    6720
ggaatttgca atgcactatt agattctata ataatttctt ctgaaaatta tgcattatga    6780
ctgtatagaa tgcattaaat ttaaggggga ttcagaatgt catataagct attaataatc    6840
aatccaggtt caacatcaac aaagattggt gtttacgaag gagaaaagga actatttgaa    6900
gaaactttga gacacacaaa tgaagaaata aagagatatg atacaatata tgatcaattt    6960
gaatttagaa aagaagttat attaaatgtt cttaaagaaa agaattttga tataaagact    7020
ctaagtgcta ttgttggtag aggtggaatg cttagaccag ttgaaggtgg aacatatgca    7080
gtaaatgatg caatggttga agatttaaaa gttggagttc aaggacctca tgcttctaac    7140
cttggcggaa taattgccaa gtcaattgga gatgaattaa atattccatc atttatagta    7200
gatccagttg ttacagatga gttagcagat gtagcaagac tatctggagt accagaacta    7260
ccaagaaaaa gtaaattcca tgctttaaat caaaaagcgg tagctaaaag atatggaaaa    7320
gaaagtggac aaggatatga aaacctaaat cttgtagttg tacatatggg tggaggcgtt    7380
tcagttggtg ctcacaatca tgggaaagtt gtcgatgtaa ataatgcatt agatggagat    7440
ggcccattct caccagaaag agctggatca gttccaattg gtgatttagt taaaatgtgt    7500
tttagtggaa aatatagtga agcagaagta tatggcaagg ctgtaggaaa aggtggattt    7560
gttggttatc taaacacaaa tgatgtaaaa ggtgttattg ataagatgga agaaggagat    7620
aaagaatgtg aatcaatata caaagcattt gtttatcaaa tttcaaaagc aatcggagaa    7680
atgtcagttg tattagaagg taaagttgat caaattattt ttaccggagg aattgcatac    7740
tcaccaacac ttgttccaga ccttaaagca aaagttgaat ggatagcccc agttacagtt    7800
tatcctggag aagatgaatt acttgctcta gctcaaggtg ctataagagt acttgatgga    7860
gaagaacaag ctaaggttta ctag                                           7884
```

<210> SEQ ID NO 154
<211> LENGTH: 436
<212> TYPE: PRT
<213> ORGANISM: Clostridium autoethanogenum
<220> FEATURE:
<221> NAME/KEY: MISC_FEATURE
<223> OTHER INFORMATION: thioesterase 1

<400> SEQUENCE: 154

Met Asn Asn Asp Asn Cys Thr Ile Lys Ile Thr Pro Glu Val Ser Arg

-continued

```
1               5                   10                  15
Val Asp Glu Pro Val Asp Ile Lys Ile Asn Gly Leu Pro Lys Asn Glu
                20                  25                  30
Lys Val Ile Ile Arg Ala Val Ser Ser Asp Tyr Tyr Cys Ile Asn Ala
                35                  40                  45
Ser Ile Leu Glu Ile Gly Asp Asn Thr Leu Trp Glu Ser Tyr Ala Val
                50                  55                  60
Phe Glu Thr Asp Glu Cys Gly Asn Ile Asn Phe Glu Asn Ala Val Pro
65                  70                  75                  80
Val Asp Gly Thr Tyr Ser Asn Cys Asp Lys Met Gly Leu Phe Tyr Ser
                85                  90                  95
Met Arg Pro Lys Gln Ile Arg Lys Ser Lys Leu Ile Gln Lys Leu Ser
                100                 105                 110
Ser Ile Asn Glu Asn Arg Lys Tyr Lys Ile Thr Phe Thr Val Glu Lys
                115                 120                 125
Asn Gly Lys Ile Ile Gly Ser Lys Glu His Thr Arg Val Tyr Cys Asp
                130                 135                 140
Asp Thr Ile Lys Ser Ile Asp Val Val Glu Lys Asn Leu Leu Ala Arg
145                 150                 155                 160
Tyr Phe Thr Ser Lys Asp Asn Ile Lys His Pro Ala Ile Ile Val Leu
                165                 170                 175
Ser Gly Ser Asp Gly Arg Ile Glu Lys Ala Gln Ala Ile Ala Glu Leu
                180                 185                 190
Phe Ala Met Arg Gly Tyr Ser Ala Leu Ala Val Cys Tyr Phe Gly Leu
                195                 200                 205
Glu Gly Thr Pro Glu Asp Leu Asn Met Ile Pro Leu Glu Tyr Val Glu
                210                 215                 220
Asn Ala Val Lys Trp Leu Lys Arg Gln Asp Thr Val Asp Glu Asn Lys
225                 230                 235                 240
Ile Ala Ile Tyr Gly Arg Ser Lys Gly Gly Glu Leu Val Leu Leu Ala
                245                 250                 255
Ala Ser Met Phe Lys Asp Ile Ala Cys Val Ile Ala Asn Thr Pro Ser
                260                 265                 270
Cys Tyr Val Tyr Glu Gly Ile Lys Ser Asn Lys Leu Pro Ser His His
                275                 280                 285
Ser Ser Trp Met Tyr Arg Gly Arg Glu Ile Pro Tyr Leu Lys Phe Asn
                290                 295                 300
Phe His Ile Ile Leu Arg Leu Ile Ile Lys Met Met Lys Lys Glu Lys
305                 310                 315                 320
Gly Ala Leu Ala Trp Met Tyr Lys Lys Leu Ile Glu Glu Gly Asp Arg
                325                 330                 335
Asp Lys Ala Thr Ile Ala Leu Asp Lys Ile Asn Gly Ser Val Leu Met
                340                 345                 350
Ile Ser Ser Ala Ala Asp Glu Ile Trp Pro Ser Lys Met His Ser Glu
                355                 360                 365
Thr Val Cys Ser Ile Phe Glu Lys Ser His Phe Lys His Glu Tyr Lys
                370                 375                 380
His Ile Thr Phe Ala Lys Ser Gly His Ile Leu Thr Val Pro Phe Gln
385                 390                 395                 400
Ser Ile Tyr Pro Ser Glu Lys Tyr Pro Tyr Asp Val Glu Ser Trp Ala
                405                 410                 415
Lys Ala Asn Met Asp Ser Trp Asn Glu Thr Ile Lys Phe Leu Glu Lys
                420                 425                 430
```

-continued

Trp Ala Ser Lys
        435

<210> SEQ ID NO 155
<211> LENGTH: 60
<212> TYPE: PRT
<213> ORGANISM: Clostridium ljungdahlii
<220> FEATURE:
<221> NAME/KEY: MISC_FEATURE
<223> OTHER INFORMATION: thioesterase 2

<400> SEQUENCE: 155

Met Tyr Ile Asn Glu Thr Lys Val Val Arg Tyr Ala Glu Thr Asp
1               5                   10                  15

Lys Met Gly Ile Val His His Ser Asn Tyr Tyr Ile Tyr Phe Glu Glu
            20                  25                  30

Ala Arg Thr Gln Phe Ile Lys Lys Thr Gly Ile Ser Tyr Ser Gln Met
        35                  40                  45

Glu Lys Asp Gly Ile Met Phe Pro Leu Val Glu Ser
    50                  55                  60

<210> SEQ ID NO 156
<211> LENGTH: 128
<212> TYPE: PRT
<213> ORGANISM: Clostridium autoethanogenum
<220> FEATURE:
<221> NAME/KEY: MISC_FEATURE
<223> OTHER INFORMATION: thioesterase 3

<400> SEQUENCE: 156

Met Asp Phe Ser Lys Leu Phe Lys Val Gly Ser Thr Tyr Val Ser Glu
1               5                   10                  15

Tyr Ile Val Lys Pro Glu Asp Thr Ala Asn Phe Ile Gly Asn Asn Gly
            20                  25                  30

Val Val Met Leu Ser Thr Pro Ala Met Ile Lys Tyr Met Glu Tyr Thr
        35                  40                  45

Thr Leu His Ile Val Asp Asn Val Ile Pro Lys Asn Tyr Arg Pro Val
    50                  55                  60

Gly Thr Lys Ile Asp Val Glu His Ile Lys Pro Ile Pro Ala Asn Met
65                  70                  75                  80

Lys Val Val Val Lys Val Thr Leu Ile Ser Ile Glu Gly Lys Lys Leu
                85                  90                  95

Arg Tyr Asn Val Glu Ala Phe Asn Glu Lys Asn Cys Lys Val Gly Phe
            100                 105                 110

Gly Ile Tyr Glu Gln Gln Ile Val Asn Leu Glu Gln Phe Leu Asn Arg
        115                 120                 125

<210> SEQ ID NO 157
<211> LENGTH: 436
<212> TYPE: PRT
<213> ORGANISM: Clostridium ljungdahlii
<220> FEATURE:
<221> NAME/KEY: MISC_FEATURE
<223> OTHER INFORMATION: thioesterase 1

<400> SEQUENCE: 157

Met Asn Asn Asp Asn Cys Thr Ile Lys Ile Thr Pro Glu Val Ser Arg
1               5                   10                  15

Val Asp Glu Pro Val Asp Ile Lys Ile Asn Gly Leu Pro Lys Asn Glu
            20                  25                  30

-continued

Lys Val Ile Ile Arg Ala Val Ser Ser Asp Tyr Tyr Cys Ile Asn Ala
            35                  40                  45

Ser Ile Leu Glu Ile Gly Asp Asn Thr Leu Trp Glu Ser Tyr Ala Val
 50                  55                  60

Phe Glu Thr Asp Glu Cys Gly Asn Ile Asn Phe Glu Asn Ala Val Pro
 65                  70                  75                  80

Val Asp Gly Thr Tyr Ser Asn Cys Asp Lys Met Gly Leu Phe Tyr Ser
                 85                  90                  95

Met Arg Pro Lys Gln Ile Arg Lys Ser Lys Leu Ile Gln Lys Leu Ser
            100                 105                 110

Ser Ile Asn Glu Asn Arg Lys Tyr Lys Ile Thr Phe Thr Val Glu Lys
            115                 120                 125

Asn Gly Lys Ile Ile Gly Ser Lys Glu His Thr Arg Val Tyr Cys Asp
130                 135                 140

Asp Thr Ile Lys Ser Ile Asp Val Val Glu Lys Asn Leu Leu Ala Arg
145                 150                 155                 160

Tyr Phe Thr Ser Lys Asp Asn Ile Lys His Pro Ala Ile Ile Val Leu
                165                 170                 175

Ser Gly Ser Asp Gly Arg Ile Glu Lys Ala Gln Ala Ile Ala Glu Leu
            180                 185                 190

Phe Ala Met Arg Gly Tyr Ser Ala Leu Ala Val Cys Tyr Phe Gly Leu
            195                 200                 205

Glu Gly Thr Pro Glu Asp Leu Asn Met Ile Pro Leu Glu Tyr Val Glu
            210                 215                 220

Asn Ala Val Lys Trp Leu Lys Arg Gln Asp Thr Val Asp Glu Asn Lys
225                 230                 235                 240

Ile Ala Ile Tyr Gly Arg Ser Lys Gly Gly Glu Leu Val Leu Leu Ala
                245                 250                 255

Ala Ser Met Phe Lys Asp Ile Ala Cys Val Ile Ala Asn Thr Pro Ser
            260                 265                 270

Cys Tyr Val Tyr Glu Gly Ile Lys Ser Asn Lys Leu Pro Ser His His
            275                 280                 285

Ser Ser Trp Met Tyr Arg Gly Arg Glu Ile Pro Tyr Leu Lys Phe Asn
290                 295                 300

Phe His Ile Ile Leu Arg Leu Ile Ile Lys Met Met Lys Lys Glu Lys
305                 310                 315                 320

Gly Ala Leu Ala Trp Met Tyr Lys Lys Leu Ile Glu Glu Gly Asp Arg
                325                 330                 335

Asp Lys Ala Thr Ile Ala Leu Asp Lys Ile Asn Gly Ser Val Leu Met
            340                 345                 350

Ile Ser Ser Ala Ala Asp Glu Ile Trp Pro Ser Lys Met His Ser Glu
            355                 360                 365

Thr Val Cys Ser Ile Phe Glu Lys Ser His Phe Lys His Glu Tyr Lys
            370                 375                 380

His Ile Thr Phe Ala Lys Ser Gly His Ile Leu Thr Val Pro Phe Gln
385                 390                 395                 400

Ser Ile Tyr Pro Ser Glu Lys Tyr Pro Tyr Asp Val Glu Ser Trp Ala
                405                 410                 415

Lys Ala Asn Met Asp Ser Trp Asn Glu Thr Ile Lys Phe Leu Glu Lys
            420                 425                 430

Trp Ala Ser Lys
            435

```
<210> SEQ ID NO 158
<211> LENGTH: 137
<212> TYPE: PRT
<213> ORGANISM: Clostridium autoethanogenum
<220> FEATURE:
<221> NAME/KEY: MISC_FEATURE
<223> OTHER INFORMATION: thioesterase 2

<400> SEQUENCE: 158
```

Met Tyr Ile Asn Glu Thr Lys Val Val Arg Tyr Ala Glu Thr Asp
1               5                   10                  15

Lys Met Gly Ile Val His His Ser Asn Tyr Ile Tyr Phe Glu Glu
            20                  25                  30

Ala Arg Thr Gln Phe Ile Lys Lys Thr Gly Ile Ser Tyr Ser Gln Met
        35                  40                  45

Glu Lys Asp Gly Ile Met Phe Pro Leu Val Glu Ser Asn Cys Arg Tyr
50                  55                  60

Leu Gln Gly Ala Lys Tyr Glu Asp Glu Leu Leu Ile Lys Thr Trp Ile
65                  70                  75                  80

Lys Glu Leu Thr Pro Val Lys Ala Glu Phe Asn Tyr Ser Val Ile Arg
                85                  90                  95

Glu Asn Asp Gln Lys Glu Ile Ala Lys Gly Ser Thr Leu His Ala Phe
            100                 105                 110

Val Asn Asn Phe Lys Ile Ile Asn Leu Lys Lys Asn His Thr Glu
        115                 120                 125

Leu Phe Lys Lys Leu Gln Ser Leu Ile
    130                 135

```
<210> SEQ ID NO 159
<211> LENGTH: 128
<212> TYPE: PRT
<213> ORGANISM: Clostridium ljungdahlii
<220> FEATURE:
<221> NAME/KEY: MISC_FEATURE
<223> OTHER INFORMATION: thioesterase 3

<400> SEQUENCE: 159
```

Met Asp Phe Ser Lys Leu Phe Lys Val Gly Ser Thr Tyr Val Ser Glu
1               5                   10                  15

Tyr Ile Val Lys Pro Glu Asp Thr Ala Asn Phe Ile Gly Asn Asn Gly
            20                  25                  30

Val Val Met Leu Ser Thr Pro Ala Met Ile Lys Tyr Met Glu Tyr Thr
        35                  40                  45

Thr Leu His Ile Val Asp Asn Val Ile Pro Lys Asn Tyr Arg Pro Val
50                  55                  60

Gly Thr Lys Ile Asp Val Glu His Ile Lys Pro Ile Pro Ala Asn Met
65                  70                  75                  80

Lys Val Val Lys Val Thr Leu Ile Ser Ile Glu Gly Lys Lys Leu
                85                  90                  95

Arg Tyr Asn Val Glu Ala Phe Asn Glu Lys Asn Cys Lys Val Gly Phe
            100                 105                 110

Gly Ile Tyr Glu Gln Gln Ile Val Asn Leu Glu Gln Phe Leu Asn Arg
        115                 120                 125

```
<210> SEQ ID NO 160
<211> LENGTH: 11184
<212> TYPE: DNA
<213> ORGANISM: Artificial sequence
<220> FEATURE:
<223> OTHER INFORMATION: Synthetic polynucleotide
```

<220> FEATURE:
<221> NAME/KEY: misc_feature
<223> OTHER INFORMATION: pMTL8225-pta-ack::ptb-buk, plasmid

<400> SEQUENCE: 160

| | | | | | |
|---|---|---|---|---|---|
| aaactccttt | tgataatct | catgaccaaa | atcccttaac | gtgagttttc | gttccactga | 60 |
| gcgtcagacc | ccgtagaaaa | gatcaaagga | tcttcttgag | atcctttttt | tctgcgcgta | 120 |
| atctgctgct | tgcaaacaaa | aaaccaccg | ctaccagcgg | tggtttgttt | gccggatcaa | 180 |
| gagctaccaa | ctcttttcc | gaaggtaact | ggcttcagca | gagcgcagat | accaaatact | 240 |
| gttcttctag | tgtagccgta | gttaggccac | cacttcaaga | actctgtagc | accgcctaca | 300 |
| tacctcgctc | tgctaatcct | gttaccagtg | gctgctgcca | gtggcgataa | gtcgtgtctt | 360 |
| accgggttgg | actcaagacg | atagttaccg | gataaggcgc | agcggtcggg | ctgaacgggg | 420 |
| ggttcgtgca | cacagcccag | cttggagcga | acgacctaca | ccgaactgag | atacctacag | 480 |
| cgtgagctat | gagaaagcgc | cacgcttccc | gaagggagaa | aggcggacag | gtatccggta | 540 |
| agcggcaggg | tcggaacagg | agagcgcacg | agggagcttc | caggggaaa | cgcctggtat | 600 |
| ctttatagtc | ctgtcgggtt | tcgccacctc | tgacttgagc | gtcgattttt | gtgatgctcg | 660 |
| tcaggggggc | ggagcctatg | gaaaaacgcc | agcaacgcgg | cctttttacg | gttcctggcc | 720 |
| ttttgctggc | cttttgctca | catgttcttt | cctgcgttat | ccctgattc | tgtggataac | 780 |
| cgtattaccg | cctttgagtg | agctgatacc | gctcgccgca | gccgaacgac | cgagcgcagc | 840 |
| gagtcagtga | gcgaggaagc | ggaagagcgc | ccaatacgca | gggccccctg | cttcggggtc | 900 |
| attatagcga | ttttttcggt | atatccatcc | tttttcgcac | gatatacagg | attttgccaa | 960 |
| agggttcgtg | tagactttcc | ttggtgtatc | caacggcgtc | agccgggcag | gataggtgaa | 1020 |
| gtaggcccac | ccgcgagcgg | gtgttccttc | ttcactgtcc | cttattcgca | cctggcggtg | 1080 |
| ctcaacggga | atcctgctct | gcgaggctgg | ccggctaccg | ccggcgtaac | agatgagggc | 1140 |
| aagcggatgg | ctgatgaaac | caagccaacc | aggaagggca | gcccacctat | caaggtgtac | 1200 |
| tgccttccag | acgaacgaag | agcgattgag | gaaaaggcgg | cggcggccgg | catgagcctg | 1260 |
| tcggcctacc | tgctggccgt | cggccagggc | tacaaaatca | cgggcgtcgt | ggactatgag | 1320 |
| cacgtccgcg | agctggcccg | catcaatggc | gacctgggcc | gcctgggcgg | cctgctgaaa | 1380 |
| ctctggctca | ccgacgaccc | gcgcacgcg | cggttcggtg | atgccacgat | cctcgccctg | 1440 |
| ctggcgaaga | tcgaagagaa | gcaggacgag | cttggcaagg | tcatgatggg | cgtggtccgc | 1500 |
| ccgagggcag | agccatgact | tttttagccg | ctaaaacggc | cggggggtgc | gcgtgattgc | 1560 |
| caagcacgtc | cccatgcgct | ccatcaagaa | gagcgacttc | gcggagctgg | tgaagtacat | 1620 |
| caccgacgag | caaggcaaga | ccgatcgggc | cccctgcagg | ataaaaaaat | tgtagataaa | 1680 |
| ttttataaaa | tagttttatc | tacaattttt | ttatcaggaa | acagctatga | ccgcggccgc | 1740 |
| ggcgccaagc | ttagaaaaat | ataaataaga | agtagcttta | agagaattaa | attattaaga | 1800 |
| aaagcaaagg | tgtttaaaaa | ataaatttt | aaacacctt | gcttttctta | aattataaat | 1860 |
| aagataaaaa | agaatcctga | ataaaataaa | aagggtgtc | tcaaaatttt | attttgagac | 1920 |
| gaccccttt | tattctatat | gtcgatgcta | tagctgagat | cgtggaattc | ttgttagcta | 1980 |
| ccagattcac | atttaagttg | tttctctaaa | ccacagatta | tcaattcaag | tccaaaaga | 2040 |
| aatgctggtt | ctgcgccttg | atgatcaaat | aactctattg | cttgtcttaa | caatggaggc | 2100 |
| attgaatctg | ttgttggtgt | ttctctttcc | tcttttgcaa | cttgatgttc | ttgatcctcc | 2160 |
| aatacgcaac | ctaaagtaaa | atgtcctaca | gcacttagtg | cgtataaggc | attttctaaa | 2220 |

```
ctaaaacoct gttgacataa gaatgctaat tgattttcta atgtttcata ttgttttca      2280
gttggtctag ttcctaaatg tactttagcc ccatctctat gtgataatag agcacaacga      2340
aaagatttag cgttattcct aagaaaatct tgccatgatt caccttctaa aggacaaaag      2400
tgagtgtgat gtctatctaa catttcaata gctaaggcgt caagtaaagc tctcttattc      2460
ttcacatgcc aatacaacgt aggttgttct actccaagtt tctgagctaa ctttcttgta      2520
gttagtcctt ctattccaac ttcatttagt aattccaatg cactattgat aactttactt      2580
ttatcaagtc tagacatcat ttaatatcct cctcttcaat atatttaagt cgactgatcg      2640
gatcctgatc ggagctccca tggcggccgg tcgatatcga tgtgtagtag cctgtgaaat      2700
aagtaaggaa aaaaagaag taagtgttat atatgatgat tattttgtag atgtagatag      2760
gataatagaa tccatagaaa ataggtta tacagttata taaaaattac tttaaaatct        2820
atcattgata gggtaaaata taaatcgtat aaagttgtgt aattttttaag gaggtgtgtt     2880
acagacgtcc gcgagagacc ttaaatatat tgaagaggag gaaatacata tggtttcaag     2940
atatgttcca gatatgggag atttaatatg ggttgatttt gatccaacaa aaggatcaga     3000
acaagcagga catagaccag cagttgtttt atcaccattt atgtataata ataaaacagg     3060
aatgtgttta tgtgttccat gtacaacaca atcaaaagga tatccatttg aagttgtttt     3120
atcaggacaa gaaagagatg gagttgcatt agcagatcaa gttaaatcaa tagcatggag     3180
agcaagagga gcaacaaaaa aaggaacagt tgcaccagaa gaattacaat taataaaagc     3240
aaaaataaat gttttaatag gataatgtta ttaagctagc ataaaaataa gaagcctgca     3300
tttgcaggct tcttattttt atggcgcgcc gttctgaatc cttagctaat ggttcaacag     3360
gtaactatga cgaagatagc accctggata agtctgtaat ggattctaag gcatttaatg     3420
aagacgtgta tataaaatgt gctaatgaaa agaaaatgc gttaaaagag cctaaaatga     3480
gttcaaatgg ttttgaaatt gattggtagt ttaatttaat atattttttc tattggctat     3540
ctcgatacct atagaatctt ctgttcactt ttgttttttga atataaaaa ggggctttt     3600
agccccttt ttttaaaact ccggaggagt ttcttcattc ttgatactat acgtaactat      3660
tttcgatttg acttcattgt caattaagct agtaaaatca atggtaaaa aacaaaaaac      3720
ttgcattttt ctaccctagta atttataatt ttaagtgtcg agtttaaaag tataatttac    3780
caggaaagga gcaagttttt taataaggaa aaattttcc ttttaaaatt ctatttcgtt      3840
atatgactaa ttataatcaa aaaatgaaa ataaacaaga ggtaaaaact gctttagaga      3900
aatgtactga taaaaaaga aaaatccta gatttacgtc atacatagca cctttaacta      3960
ctaagaaaaa tattgaaagg acttccactt gtggagatta tttgtttatg ttgagtgatg     4020
cagacttaga acattttaaa ttacataaag gtaattttg cggtaataga tttttgtccaa    4080
tgtgtagttg gcgacttgct tgtaaggata gtttagaaat atctattctt atggagcatt     4140
taagaaaaga agaaaataaa gagtttatat ttttaactct tacaactcca aatgtaaaaa     4200
gttatgatct taattattct attaaacaat ataataaatc ttttaaaaa ttaatggagc      4260
gtaaggaagt taaggatata actaaaggtt atataagaaa attagaagta acttaccaaa     4320
aggaaaaata cataacaaag gatttatgga aaataaaaaa agattattat caaaaaaaag    4380
gacttgaaat tggtgattta gaacctaatt ttgatactta taatcctcat tttcatgtag     4440
ttattgcagt taataaagt tattttacag ataaaaatta ttatataaat cgagaaagat     4500
ggttggaatt atggaagttt gctactaagg atgattctat aactcaagtt gatgttagaa     4560
```

```
aagcaaaaat taatgattat aaagaggttt acgaacttgc gaaatattca gctaaagaca    4620
ctgattattt aatatcgagg ccagtatttg aaattttta taaagcatta aaaggcaagc     4680
aggtattagt ttttagtgga ttttttaaag atgcacacaa attgtacaag caaggaaaac   4740
ttgatgttta taaaagaaa gatgaaatta aatatgtcta tatagtttat tataattggt   4800
gcaaaaaaca atatgaaaaa actagaataa gggaacttac ggaagatgaa aaagaagaat   4860
taaatcaaga tttaatagat gaaatagaaa tagattaaag tgtaactata ctttatatat   4920
atatgattaa aaaaataaaa aacaacagcc tattaggttg ttgttttta ttttctttat    4980 taattttttt aattttagt ttttagttct tttttaaaat aagtttcagc ctcttttca    5040 atatttttta aagaaggagt atttgcatga attgccttt ttctaacaga cttaggaaat   5100
attttaacag tatcttcttg cgccggtgat tttggaactt cataacttac taatttataa   5160
ttattatttt cttttttaat tgtaacagtt gcaaagaag ctgaacctgt tccttcaact    5220 agttatcat cttcaatata atattcttga cctatatagt ataaatatat ttttattata   5280
tttttacttt tttctgaatc tattatttta taatcataaa aagttttacc accaaaagaa   5340
ggttgtactc cttctggtcc aacatatttt tttactatat tatctaaata attttgga    5400 actggtgttg taatttgatt aatcgaacaa ccagttatac ttaaaggaat tataactata   5460
aaaatatata ggattatctt tttaaatttc attattggcc tcctttttat taaatttatg   5520
ttaccataaa aaggacataa cgggaatatg tagaatattt ttaatgtaga caaaatttta   5580
cataaatata aagaaaggaa gtgtttgttt aaatttata gcaaactatc aaaaattagg    5640
gggataaaaa tttatgaaaa aaaggttttc gatgttattt ttatgtttaa ctttaatagt    5700
ttgtggttta tttacaaatt cggccggcca agattgctc tatgtttaag ctattatatg    5760
aacttccaat tctttttatt gatatgggag taatattgct ttttattctt attaggttt    5820 ttaaatattc tatacctaaa atattgtttg gagattgaag tatttcatct atattgtact   5880
ttgtaagaga acttttagta tttaatagaa aattattta agcactattt cgtgcagaag   5940
gataggacat accctgtgac attttttcct ttaaaataa tttaaattgg gtaggctctt    6000
ctgcaagaat ttttgcaata gatttcagca agtttatatt actatattcg cttccaaaac   6060 aaagatttt tactacaccc aagttttcta agagacttac agcaccatag gcaaaaaatt    6120
cagcagaaga tagactgtag ataacaggaa gttcaaatac caggtctact ccatttagaa   6180
gtgccatttt ggtttagtc catttgtcaa ctatagatgg tgaacctctt tgcacgaagt    6240
taccactcat aactgctatt acagcatcac atttttgtagc agaacgagca cttcaatat    6300 gatatttatg tccattgtga aagggatta attcaactat tattccagtt acgttcatag    6360
aaattttcct ttctaaaata ttttattcca tgtcaagaac tctgttatt tcattaaga    6420 actataagta caaagtataa ggcatttgaa aaaataggct agtatattga ttgattattt    6480
attttaaaat gcctaagtga aatatataca tattataaca ataaaataag tattagtgta   6540
ggatttttaa atagagtatc tattttcaga ttaaattttt gattatttga tttacattat   6600
ataatattga gtaaagtatt gactagcaaa atttttgat actttaattt gtgaaatttc    6660
ttatcaaaag ttatattttt gaataatttt tattgaaaaa tacaactaaa aaggattata   6720
gtataagtgt gtgtaatttt gtgttaaatt taaagggagg aaatgaacat gaaattgatg    6780
agtaaaaact ttgatgagtt attatcaaga ttaaaggaag ttccaacaaa aaagtggct    6840 gtagccgtag cacaagatga accagtatta gaggctataa aagaagctac agaaaataac    6900
atcgcacaag caatattggt tggtgataaa caacaaatcc atgaaatcgc aagaaaata    6960
```

```
aacttggact tatctgatta tgaaataatg gatattaaag atccaaagaa agcaacatta    7020
gaagcagtaa aattagtttc tagtggtcat gcagatatgt taatgaaagg tctagttgat    7080
actgcaacat tcctaagaag cgtattaaac aaagaggttg gtcttagaac aggaaaatta    7140
atgtcccatg tagctgtgtt tgatgtggaa ggttgggata gactgttatt tttaactgat    7200
gcagcattta atacatatcc agaatttaag gataaagttg gaatgataaa taatgcagtt    7260
gtagttgctc atgcatgtgg aatagatgtt ccaagagtag cacctatatg cccagttgaa    7320
gttgtaaata caagtatgca atcaacagtt gatgcagcat tgttagctaa aatgagtgac    7380
agggggcaaa ttaaaggatg cgtaattgat ggacctttg ccttagataa tgcaatatca     7440
gaagaagcag ctcatcataa aggtgttaca ggatcagtag caggtaaagc tgatatatta    7500
ttattaccaa atatagaagc agcaaatgta atgtataaaa cattaacata tttctctaaa    7560
tcaagaaatg gtggacttt agtaggtaca tcagcaccag taattttaac ttcaagagca     7620
gattcattcg aaactaaagt taattcaatt gctcttgcag cattagttgc agcaagaaat    7680
aagtaataaa tcaatccata ataattaatg cataattaat ggagagattt atatggaatt    7740
tgcaatgcac tattagattc tataataatt tcttctgaaa attatgcatt atgactgtat    7800
agaatgcatt aaatttaagg gggattcaga atgtcatata agctattaat aatcaatcca    7860
ggttcaacat caacaaagat tggtgtttac gaaggagaaa aggaactatt tgaagaaact    7920
ttgagacaca caaatgaaga aataaagaga tatgatacaa tatatgatca atttgaattt    7980
agaaaagaag ttatattaaa tgttcttaaa gaaaagaatt ttgatataaa gactctaagt    8040
gctattgttg gtagaggtgg aatgcttaga ccagttgaag gtggaacata tgcagtaaat    8100
gatgcaatgg ttgaagattt aaaagttgga gttcaaggac ctcatgcttc taaccttggc    8160
ggaataattg ccaagtcaat tggagatgaa ttaaatattc catcatttat agtagatcca    8220
gttgttacag atgagttagc agatgtgtca agactatctg gagtaccaga actaccaaga    8280
aaaagtaaat tccatgcttt aaatcaaaaa gcggtagcta aaagatatgg aaaagaaagt    8340
ggacaaggat atgaaaacct aaatcttgta gttgtacata tgggtggagg cgtttcagtt    8400
ggtgctcaca atcatgggaa agttgtcgat gtaaataatg cattagatgg agatggccca    8460
ttctcaccag aaagagctgg atcagttcca attggtgatt tagttaaaat gtgttttagt    8520
ggaaaatata gtgaagcaga agtatatggc aaggctgtag aaaaaggtgg atttgttggt    8580
tatctaaaca caaatgatgt aaaaggtgtt attgataaga tggaagaagg agataaagaa    8640
tgtgaatcaa tatacaaagc atttgtttat caaatttcaa aagcaatcgg agaaatgtca    8700
gttgtattag aaggtaaagt tgatcaaatt attttaccg gaggaattgc atactcacca     8760
acacttgttc cagaccttaa agcaaaagtt gaatggatag ccccagttac agtttatcct    8820
ggagaagatg aattacttgc tctagctcaa ggtgctataa gagtacttga tggagaagaa    8880
caagctaagg tttactagta ccgttcgtat aatgtatgct atacgaagtt atccttagaa    8940
gcaaacttaa gagtgtgttg atagtgcagt atcttaaaat tttgtgtata ataggaattg    9000
aagttaaatt agatgctaaa aatttgtaat taagaaggag ggattcgtca tgttggtatt    9060
ccaaatgcgt aatgtagata aacatctac tgttttgaaa cagactaaaa acagtgatta     9120
cgcagataaa taaatacgtt agattaattc ctaccagtga ctaatcttat gacttttaa     9180 acagataact aaaattacaa acaaatcgtt taacttctgt atttatttac agatgtaatc    9240
acttcaggag taattacatg aacaaaaata taaatattc tcaaaacttt ttaacgagtg     9300
```

| | |
|---|---|
| aaaaagtact caaccaaata ataaaacaat tgaatttaaa agaaaccgat accgtttacg | 9360 |
| aaattggaac aggtaaaggg catttaacga cgaaactggc taaaataagt aaacaggtaa | 9420 |
| cgtctattga attagacagt catctattca acttatcgtc agaaaaatta aaactgaaca | 9480 |
| ttcgtgtcac tttaattcac caagatattc tacagtttca attccctaac aaacagaggt | 9540 |
| ataaaattgt tgggagtatt ccttaccatt taagcacaca aattattaaa aaagtggttt | 9600 |
| ttgaaagcca tgcgtctgac atctatctga ttgttgaaga aggattctac aagcgtacct | 9660 |
| tggatattca ccgaacacta gggttgctct tgcacactca agtctcgatt cagcaattgc | 9720 |
| ttaagctgcc agcggaatgc tttcatccta aaccaaaagt aaacagtgtc ttaataaaac | 9780 |
| ttacccgcca taccacagat gttccagata aatattggaa gctatatacg tactttgttt | 9840 |
| caaaatgggt caatcgagaa tatcgtcaac tgtttactaa aaatcagttt catcaagcaa | 9900 |
| tgaaacacgc caaagtaaac aatttaagta ccattactta tgagcaagta ttgtctattt | 9960 |
| ttaatagtta tctattattt aacgggagga ataattcta tgagtcgctt ttttaaattt | 10020 |
| ggaaagttac acgttactaa agggaatgga gataaattat tagatatact actgacagct | 10080 |
| tccaagaagc taagagggtc ataacttcgt ataatgtatg ctatacgaac ggtagacttg | 10140 |
| actttttaatg ctcatctcta tataataggt tgtggctaat atatagaggt gagtgatatg | 10200 |
| aaattaaatg tatcgatttt actaagtgaa gaagttgtta caaaggacat aaatgttaca | 10260 |
| gtagaagaaa agggattcta tgatggaagt gaatacataa agttattaga gcctctaaag | 10320 |
| tttagcggaa ctttaagtaa agaaggagat attcttctgt tggaaggaag aattaatact | 10380 |
| ttactagagc tcacttgttc acgatgtcta ggtaaattct cttatgctgt gaatgttgct | 10440 |
| attactgaaa aatttacaaa taataacaag gaaaataagg atgatgaagc catctttata | 10500 |
| gatagtaata tcattgatat tacggaaata atagaaaata acattatatt aattttacca | 10560 |
| attaagaggc tttgcagcga gaattgtaag gggttatgcc aacagtgcgg cactaactta | 10620 |
| aataattcta aatgtcagtg caaaagcgat gatattgatc cgagattggc aaagctaaaa | 10680 |
| gatatgtttt tcactgatta aggaggtgtt tactgtggga aatccagcca gcagaatatc | 10740 |
| aaaagcaaaa agagactcaa gaagagcaca gacttttaaa ttaggtttac caggtttagt | 10800 |
| tgagtgtcct cagtgccatg aaatgaaact tgcacataga gtttgtaaga attgtggata | 10860 |
| ttataagggt aaggaaatca tttcaactga aaataaataa aagaaagtca tttgactttc | 10920 |
| ttttttttgtt catggggtct ataaaagtta gatcatatta agtaacaaaa ttaggtaaca | 10980 |
| aaggtccaga ttataggata ggatgtgaaa atatgataat tgctgtggat ggtatgggag | 11040 |
| gagattttgc accttgtgct gtagtggaag gtgtggtaga agcagttaaa aagcaaaacg | 11100 |
| taaatataat aataaccggc caaaagagc aaattgaaaa tgaattagct aaatataatt | 11160 |
| atcctaagga caaatagat attt | 11184 |

<210> SEQ ID NO 161
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN22f

<400> SEQUENCE: 161
tttacaaatt cggccggcca agattgctc tatgtttaag ct                42

<210> SEQ ID NO 162
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN23r

<400> SEQUENCE: 162
catcaaagtt tttactcatc aatttcatgt tcatttcctc cct        43

<210> SEQ ID NO 163
<211> LENGTH: 46
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN24f

<400> SEQUENCE: 163
agggaggaaa tgaacatgaa attgatgagt aaaaactttg atgagt        46

<210> SEQ ID NO 164
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN25r

<400> SEQUENCE: 164
gtatagcata cattatacga acggtactag taaaccttag cttgttcttc        50

<210> SEQ ID NO 165
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN26f

<400> SEQUENCE: 165
gaagaacaag ctaaggttta ctagtaccgt tcgtataatg tatgctatac        50

<210> SEQ ID NO 166
<211> LENGTH: 45
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN27r

<400> SEQUENCE: 166
agagatgagc attaaaagtc aagtctaccg ttcgtatagc ataca        45

<210> SEQ ID NO 167
<211> LENGTH: 45
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN28f

<400> SEQUENCE: 167
tgtatgctat acgaacggta gacttgactt ttaatgctca tctct            45

<210> SEQ ID NO 168
<211> LENGTH: 47
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN29r

<400> SEQUENCE: 168
catgagatta tcaaaaagga gtttaaatat ctattttgtc cttagga          47

<210> SEQ ID NO 169
<211> LENGTH: 47
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN30f

<400> SEQUENCE: 169
tcctaaggac aaaatagata tttaaactcc ttttgataa tctcatg           47

<210> SEQ ID NO 170
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SN31r

<400> SEQUENCE: 170
agcttaaaca tagagcaatc tttggccggc cgaatttgta aa               42

<210> SEQ ID NO 171
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Og29f

<400> SEQUENCE: 171
agccacatcc agtagattga acttt                                  25

<210> SEQ ID NO 172
<211> LENGTH: 25
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Og30r

<400> SEQUENCE: 172
aattcgccct acgattaaag tggaa                                      25

<210> SEQ ID NO 173
<211> LENGTH: 35
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Pfdx-F1, forward

<400> SEQUENCE: 173
aaaggtctcc ggccgcgctc actatctgcg gaacc                           35

<210> SEQ ID NO 174
<211> LENGTH: 38
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Pfdx-R1, reverse

<400> SEQUENCE: 174
tttggtctcg aattctgtaa cacctcctta atttttag                        38

<210> SEQ ID NO 175
<211> LENGTH: 52
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: aor1-F1, forward

<400> SEQUENCE: 175
aaaggtctcg aattcaaaga tctatgtatg gttatgatgg taaagtatta ag        52

<210> SEQ ID NO 176
<211> LENGTH: 54
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: aor1-R1, reverse

<400> SEQUENCE: 176
tttggtctcc tcgagtatgg atccctagaa cttacctata tattcatcta atcc      54

<210> SEQ ID NO 177
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-pta-ack - ack-DuetI2-R1

<400> SEQUENCE: 177
```

```
-continued
```
gggtacctta tttattttca actatttctt ttgtatc                         37

<210> SEQ ID NO 178
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-pta-ack - DuetI2-ack-F1

<400> SEQUENCE: 178
ttgaaaataa ataaggtacc ctcgagtctg gtaaag                          36

<210> SEQ ID NO 179
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-pta-ack - DuetI2-pta-R1

<400> SEQUENCE: 179 tttttccat atgtatatct ccttcttata cttaac                           36

<210> SEQ ID NO 180
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-pta-ack - pta-DuetI2-F1

<400> SEQUENCE: 180
aggagatata catatggaaa aaatttggag taaggc                          36

<210> SEQ ID NO 181
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-tesB - DuetI2-tesB-F1

<400> SEQUENCE: 181
gaaatcataa ttaaggtacc ctcgagtctg gtaaag                          36

<210> SEQ ID NO 182
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-tesB - DuetI2-tesB-R1

<400> SEQUENCE: 182
cctgactcat atgtatatct ccttcttata cttaac                          36

<210> SEQ ID NO 183
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-tesB - tesB-DuetI2-F1

<400> SEQUENCE: 183

| | |
|---|---|
| aagaaggaga tatacatatg agtcaggcac ttaaaa | 36 |

<210> SEQ ID NO 184
<211> LENGTH: 35
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pETDuet-tesB - testB-DuetI2-R1

<400> SEQUENCE: 184

| | |
|---|---|
| agggtacctt aattatgatt tctcataaca ccttc | 35 |

<210> SEQ ID NO 185
<211> LENGTH: 7606
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pDUET-pta-ack, plasmid

<400> SEQUENCE: 185

| | |
|---|---|
| ggggaattgt gagcggataa caattcccct ctagaaataa ttttgtttaa ctttaagaag | 60 |
| gagatatacc atgggcagca gccatcacca tcatcaccac agccaggatc cgaattcgag | 120 |
| ctcggcgcgc ctgcaggtcg acaagcttgc ggccgcataa tgcttaagtc aacagaaag | 180 |
| taatcgtatt gtacacggcc gcataatcga aattaatacg actcactata ggggaattgt | 240 |
| gagcggataa caattcccca tcttagtata ttagttaagt ataagaagga gatatacata | 300 |
| tggaaaaaat ttggagtaag gcaaaggaag acaaaaaaaa gattgtctta gctgaaggag | 360 |
| aagaagaaag aactcttcaa gcttgtgaaa aaataattaa agagggtatt gcaaatttaa | 420 |
| tccttgtagg gaatgaaaag gtaataaaag aaaaagcgtc aaaattaggt gtaagtttaa | 480 |
| atggagcaga aatagtagat ccagagattt cagataaact aaaggcatat gcagatgctt | 540 |
| tttatgaatt gagaaagaag aagggaataa cgccagaaaa agcggataaa atagtaagag | 600 |
| atccaatata ctttgctaca atgatggtta aacttggaga tgcagatgga ttggtttcag | 660 |
| gtgcggttca tactacaggc gatcttttga gaccaggact tcaaatagta aagacagctc | 720 |
| caggtacatc agtagtttcc agtacattta atggaagt accaaattgt gagtatggtg | 780 |
| acaatggtgt acttctattt gctgattgtg ctgtaaatcc atgcccagat agtgatcaat | 840 |
| tggcttcaat tgcaataagt acagcagaaa ctgcaaagaa cttatgtgga atggatccaa | 900 |
| aagtagcaat gctttcattt tctactaagg gaagtgcaaa acacgaatta gtagacaaag | 960 |
| ttagaaatgc tgtagagatt gcaaaaaaag ctaaaccaga tttaagttta gacggagaat | 1020 |
| tacaattaga tgcctctatc gtagaaaagg ttgcaagttt aaaggctcct ggaagtgaag | 1080 |
| tagcaggaaa agcaaatgta cttgtatttc cagatctcca agcaggaaat ataggctata | 1140 |

```
aactcgttca aagatttgca aaagcagatg ctataggacc tgtatgccaa ggatttgcaa    1200
aacctataaa tgatttgtca agaggatgta attctgatga tatagtaaat gtagtagctg    1260
taacagcagt tcaagcacaa gctcaaaagt aataacaaaa agcataaatg attcattttt    1320
aggaggaata ttaaacatga aaatattagt agtaaactgt ggaagttcat ctttaaaata    1380
tcaacttatt gatatgcaag atgaaagtgt tgtagcaaag ggtcttgtag aaagaatagg    1440 aatgacggt tcaattttaa cacacaaagt taatggagaa aagtttgtta cagagcaacc    1500
aatggaagac cacaaagttg ctatacaatt agtattaaat gctcttgtag ataaaaaaca    1560
tggtgtaata aaagacatgt cagaaatatc cgctgtagga catagagttt tgcacggtgg    1620
aaagaaatat gcagcatcca ttcttattga cgaaaatgta atgaaagcaa tagaagaatg    1680
tatcccacta ggaccactac ataatccagc taatataatg gaatagatg cttgtaaaaa     1740 attaatgcca aatactccaa tggtagcagt atttgataca gcatttcatc agacaatgcc    1800
agattatgct tatacttatg caatacctta tgatatatct gaaaagtatg atatcagaaa    1860
atatggtttt catggaactt ctcatagatt cgtttcaatt gaagcagcta aattattaaa    1920
gaaagatcca aaagatctta agttaataac ttgtcattta ggaaatggag ctagcatatg    1980
tgcagtaaac caaggaaaag cagtagatac aactatggga cttactcctc ttgcaggact    2040
tgtaatggga actagatgcg gtgatataga tccagctata gtaccatttg taatgaaaag    2100
aacaggcatg tctgtagatg aagtggatac cttaatgaat aaaaagtcag gaatacttgg    2160
agtatcagga gtaagcagtg attttagaga tgtagaagaa gctgcaaatt caggaaatga    2220
tagagcaaaa cttgcattaa atatgtatta tcacaaagtt aaatctttca taggagctta    2280
tgttgcagtt ttaaatggag cagatgctat aatatttacg gcaggacttg agaaaaattc    2340
agcaactagc agatctgcta tatgtaatgg attaagctat tttggaatta aaatagatga    2400 agaaagaat aagaaaaggg gagaggcact agaaataagc acacctgatt caaagataaaа    2460 agtattagta attcctacaa atgaagaact tatgatagct agggatacaa aagaaatagt    2520
tgaaaataaa taaggtaccc tcgagtctgg taaagaaacc gctgctgcga aatttgaacg    2580
ccagcacatg gactcgtcta ctagcgcagc ttaattaacc taggctgctg ccaccgctga    2640
gcaataacta gcataacccc ttggggcctc taaacgggtc ttgaggggtt ttttgctgaa    2700
aggaggaact atatccggat tggcgaatgg acgcgccct gtagcggcgc attaagcgcg    2760
gcgggtgtgg tggttacgcg cagcgtgacc gctacacttg ccagcgccct agcgcccgct    2820
cctttcgctt tcttcccttc ctttctcgcc acgttcgccg gctttccccg tcaagctcta    2880 aatcggggc tccctttagg gttccgattt agtgctttac ggcacctcga ccccaaaaaa    2940
cttgattagg gtgatggttc acgtagtggg ccatcgccct gatagacggt ttttcgccct    3000
ttgacgttgg agtccacgtt ctttaatagt ggactcttgt tccaaactgg aacaacactc    3060
aaccctatct cggtctattc ttttgattta agggattt tgccgatttc ggcctattgg      3120
ttaaaaaatg agctgattta acaaaaattt aacgcgaatt ttaacaaaat attaacgttt    3180
acaatttctg gcggcacgat ggcatgagat tatcaaaaag gatcttcacc tagatccttt    3240
taaattaaaa atgaagtttt aaatcaatct aaagtatata tgagtaaact tggtctgaca    3300
gttaccaatg cttaatcagt gaggcaccta tctcagcgat ctgtctattt cgttcatcca    3360
tagttgcctg actccccgtc gtgtagataa ctacgatacg ggagggctta ccatctggcc    3420
ccagtgctgc aatgataccg cgagacccac gctcaccggc tccagattta tcagcaataa    3480
```

```
accagccagc cggaagggcc gagcgcagaa gtggtcctgc aactttatcc gcctccatcc    3540
agtctattaa ttgttgccgg gaagctagag taagtagttc gccagttaat agtttgcgca    3600
acgttgttgc cattgctaca ggcatcgtgg tgtcacgctc gtcgtttggt atggcttcat    3660
tcagctccgg ttcccaacga tcaaggcgag ttacatgatc ccccatgttg tgcaaaaaag    3720
cggttagctc cttcggtcct ccgatcgttg tcagaagtaa gttggccgca gtgttatcac    3780
tcatggttat ggcagcactg cataattctc ttactgtcat gccatccgta agatgctttt    3840
ctgtgactgg tgagtactca accaagtcat tctgagaata gtgtatgcgg cgaccgagtt    3900
gctcttgccc ggcgtcaata cgggataata ccgcgccaca tagcagaact ttaaaagtgc    3960
tcatcattgg aaaacgttct cggggcgaaa actctcaag gatcttaccg ctgttgagat    4020
ccagttcgat gtaacccact cgtgcaccca actgatcttc agcatctttt actttcacca    4080
gcgtttctgg gtgagcaaaa acaggaaggc aaaatgccgc aaaaaaggga ataagggcga    4140
cacggaaatg ttgaatactc atactcttcc tttttcaatc atgattgaag catttatcag    4200
ggttattgtc tcatgagcgg atacatattt gaatgtattt agaaaaataa acaaataggt    4260
catgaccaaa atcccttaac gtgagttttc gttccactga gcgtcagacc ccgtagaaaa    4320
gatcaaagga tcttcttgag atcctttttt tctgcgcgta atctgctgct tgcaaacaaa    4380
aaaaccaccg ctaccagcgg tggtttgttt gccggatcaa gagctaccaa ctcttttcc    4440 gaaggtaact ggcttcagca gagcgcagat accaaatact gtccttctag tgtagccgta    4500
gttaggccac cacttcaaga actctgtagc accgcctaca tacctcgctc tgctaatcct    4560
gttaccagtg gctgctgcca gtggcgataa gtcgtgtctt accgggttgg actcaagacg    4620
atagttaccg gataaggcgc agcggtcggg ctgaacgggg ggttcgtgca cacagcccag    4680
cttggagcga acgacctaca ccgaactgag atacctacag cgtgagctat gagaaagcgc    4740
cacgcttccc gaagggagaa aggcggacag gtatccggta agcggcaggg tcggaacagg    4800
agagcgcacg agggagcttc caggggggaaa cgcctggtat ctttatagtc ctgtcgggtt    4860
tcgccacctc tgacttgagc gtcgattttt gtgatgctcg tcagggggc ggagcctatg    4920 gaaaaacgcc agcaacgcgg ccttttacg gttcctggcc ttttgctggc cttttgctca    4980
catgttcttt cctgcgttat cccctgattc tgtggataac cgtattaccg cctttgagtg    5040
agctgatacc gctcgccgca gccgaacgac cgagcgcagc gagtcagtga gcgaggaagc    5100
ggaagagcgc ctgatgcggt attttctcct tacgcatctg tgcggtattt cacaccgcat    5160
atatggtgca ctctcagtac aatctgctct gatgccgcat agttaagcca gtatacactc    5220
cgctatcgct acgtgactgg gtcatggctg cgccccgaca cccgccaaca cccgctgacg    5280
cgccctgacg ggcttgtctg ctcccggcat ccgcttacag acaagctgtg accgtctccg    5340
ggagctgcat gtgtcagagg ttttcaccgt catcaccgaa acgcgcgagg cagctgcggt    5400
aaagctcatc agcgtggtcg tgaagcgatt cacagatgtc tgcctgttca tccgcgtcca    5460
gctcgttgag tttctccaga agcgttaatg tctggcttct gataaagcgg ccatgttaa    5520 gggcggtttt ttcctgtttg gtcactgatg cctccgtgta aggggattt ctgttcatgg    5580 gggtaatgat accgatgaaa cgagagagga tgctcacgat acgggttact gatgatgaac    5640
atgcccggtt actggaacgt tgtgagggta aacaactggc ggtatggatg cggcgggacc    5700
agagaaaaat cactcagggt caatgccagc gcttcgttaa tacagatgta ggtgttccac    5760
agggtagcca gcagcatcct gcgatgcaga tccggaacat aatggtgcag gcgctgact    5820 tccgcgtttc cagactttac gaaacacgga aaccgaagac cattcatgtt gttgctcagg    5880
```

-continued

```
tcgcagacgt tttgcagcag cagtcgcttc acgttcgctc gcgtatcggt gattcattct    5940
gctaaccagt aaggcaaccc cgccagccta gccgggtcct caacgacagg agcacgatca    6000
tgctagtcat gccccgcgcc caccggaagg agctgactgg gttgaaggct ctcaagggca    6060
tcggtcgaga tcccggtgcc taatgagtga gctaacttac attaattgcg ttgcgctcac    6120
tgcccgcttt ccagtcggga aacctgtcgt gccagctgca ttaatgaatc ggccaacgcg    6180
cggggagagg cggtttgcgt attgggcgcc agggtggttt ttcttttcac cagtgagacg    6240
ggcaacagct gattgcccct caccgcctgg ccctgagaga gttgcagcaa gcggtccacg    6300
ctggtttgcc ccagcaggcg aaaatcctgt ttgatggtgg ttaacggcgg gatataacat    6360
gagctgtctt cggtatcgtc gtatcccact accgagatgt ccgcaccaac gcgcagcccg    6420
gactcggtaa tggcgcgcat tgcgcccagc gccatctgat cgttggcaac cagcatcgca    6480
gtgggaacga tgccctcatt cagcatttgc atggtttgtt gaaaaccgga catggcactc    6540
cagtcgcctt cccgttccgc tatcggctga atttgattgc gagtgagata tttatgccag    6600
ccagccagac gcagacgcgc cgagacagaa cttaatgggc ccgctaacag cgcgatttgc    6660
tggtgaccca atgcgaccag atgctccacg cccagtcgcg taccgtcttc atgggagaaa    6720
ataatactgt tgatgggtgt ctggtcagag acatcaagaa ataacgccgg aacattagtg    6780
caggcagctt ccacagcaat ggcatcctgg tcatccagcg gatagttaat gatcagccca    6840
ctgacgcgtt gcgcgagaag attgtgcacc gccgctttac aggcttcgac gccgcttcgt    6900
tctaccatcg acaccaccac gctggcaccc agttgatcgg cgcgagattt aatcgccgcg    6960
acaatttgcg acggcgcgtg cagggccaga ctggaggtgg caacgccaat cagcaacgac    7020
tgtttgcccg ccagttgttg tgccacgcgg ttgggaatgt aattcagctc cgccatcgcc    7080
gcttccactt ttttcccgcgt tttcgcagaa acgtggctgg cctggttcac cacgcgggaa    7140
acggtctgat aagagacacc ggcatactct gcgacatcgt ataacgttac tggtttcaca    7200
ttcaccaccc tgaattgact ctcttccggg cgctatcatg ccataccgcg aaaggttttg    7260
cgccattcga tggtgtccgg gatctcgacg ctctccctta tgcgactcct gcattaggaa    7320
gcagcccagt agtaggttga ggccgttgag caccgccgcc gcaaggaatg gtgcatgcaa    7380
ggagatggcg cccaacagtc ccccggccac ggggcctgcc accataccca cgccgaaaca    7440
agcgctcatg agcccgaagt ggcgagcccg atcttcccca tcggtgatgt cggcgatata    7500
ggcgccagca accgcacctg tggcgccggt gatgccggcc acgatgcgtc cggcgtagag    7560
gatcgagatc gatctcgatc ccgcgaaatt aatacgactc actata             7606
```

<210> SEQ ID NO 186
<211> LENGTH: 7492
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pDUET-ptb-buk, plasmid

<400> SEQUENCE: 186

```
ggggaattgt gagcggataa caattcccct ctagaaataa ttttgtttaa ctttaagaag      60
gagatatacc atgggcagca gccatcacca tcatcaccac agccaggatc cgaattcgag     120
ctcggcgcgc ctgcaggtcg acaagcttgc ggccgcataa tgcttaagtc gaacagaaag     180
taatcgtatt gtacacggcc gcataatcga aattaatacg actcactata ggggaattgt     240
```

```
gagcggataa caattcccca tcttagtata ttagttaagt ataagaagga gatatacata    300
tgagtaaaaa ctttgatgag ttattatcaa gattaaagga agttccaaca aaaaaagtgg    360
ctgtagccgt agcacaagat gaaccagtat tagaggctat aaaagaagct acagaaaata    420
acatcgcaca agcaatattg gttggtgata acaacaaat ccatgaaatc gcaaagaaaa    480
taaacttgga cttatctgat tatgaaataa tggatattaa agatccaaag aaagcaacat    540
tagaagcagt aaaattagtt tctagtggtc atgcagatat gttaatgaaa ggtctagttg    600
atactgcaac attcctaaga agcgtattaa acaaagaggt tggtcttaga acaggaaaat    660
taatgtccca tgtagctgtg tttgatgtgg aaggttggga tagactgtta tttttaactg    720
atgcagcatt taatacatat ccagaattta aggataaagt tggaatgata aataatgcag    780
ttgtagttgc tcatgcatgt ggaatagatg ttccaagagt agcacctata tgcccagttg    840
aagttgtaaa tacaagtatg caatcaacag ttgatgcagc attgttagct aaaatgagtg    900 acaggggca aattaaagga tgcgtaattg atggacctt tgccttagat aatgcaatat    960
cagaagaagc agctcatcat aaaggtgtta caggatcagt agcaggtaaa gctgatatat   1020
tattattacc aaatatagaa gcagcaaatg taatgtataa aacattaaca tatttctcta   1080
aatcaagaaa tggtggactt ttagtaggta catcagcacc agtaattta acttcaagag   1140 cagattcatt cgaaactaaa gttaattcaa ttgctcttgc agcattagtt gcagcaagaa   1200
ataagtaata aatcaatcca taataattaa tgcataatta atggagagat ttatatggaa   1260
tttgcaatgc actattagat tctataataa tttcttctga aaattatgca ttatgactgt   1320
atagaatgca ttaaatttaa gggggattca gaatgtcata taagctatta ataatcaatc   1380
caggttcaac atcaacaaag attggtgttt acgaaggaga aaaggaacta tttgaagaaa   1440
ctttgagaca cacaaatgaa gaaataaaga gatatgatac aatatatgat caatttgaat   1500
ttagaaaaga agttatatta aatgttctta agaaaagaa ttttgatata aagactctaa   1560
gtgctattgt tggtagaggt ggaatgctta gaccagttga aggtggaaca tatgcagtaa   1620
atgatgcaat ggttgaagat ttaaaagttg gagttcaagg acctcatgct tctaaccttg   1680
gcggaataat tgccaagtca attggagatg aattaaatat tccatcattt atagtagatc   1740
cagttgttac agatgagtta gcagatgtag caagactatc tggagtacca gaactaccaa   1800
gaaaaagtaa attccatgct ttaaatcaaa aagcggtagc taaaagatat ggaaaagaaa   1860
gtggacaagg atatgaaaac ctaaatcttg tagttgtaca tatgggtgga ggcgtttcag   1920
ttggtgctca caatcatggg aaagttgtcg atgtaaataa tgcattagat ggagatggcc   1980
cattctcacc agaaagagct ggatcagttc caattggtga tttagttaaa atgtgtttta   2040
gtggaaaata tagtgaagca gaagtatatg caaggctgt aggaaaaggt ggatttgttg   2100
gttatctaaa cacaaatgat gtaaaaggtg ttattgataa gatggaagaa ggagataaag   2160
aatgtgaatc aatatacaaa gcatttgttt atcaaatttc aaaagcaatc ggagaaatgt   2220
cagttgtatt agaaggtaaa gttgatcaaa ttattttac cggaggaatt gcatactcac   2280
caacacttgt tccagacctt aaagcaaaag ttgaatggat agccccagtt acagtttatc   2340
ctggagaaga tgaattactt gctctagctc aaggtgctat aagagtactt gatggagaag   2400
aacaagctaa ggtttactag gtaccctcga gtctggtaaa gaaaccgctg ctgcgaaatt   2460
tgaacgccag cacatggact cgtctactag cgcagcttaa ttaacctagg ctgctgccac   2520
cgctgagcaa taactagcat aacccccttgg ggcctctaaa cgggtcttga ggggttttt   2580
```

-continued

```
gctgaaagga ggaactatat ccggattggc gaatgggacg cgccctgtag cggcgcatta    2640
agcgcggcgg gtgtggtggt tacgcgcagc gtgaccgcta cacttgccag cgccctagcg    2700
cccgctcctt tcgctttctt cccttccttt ctcgccacgt tcgccggctt tccccgtcaa    2760
gctctaaatc gggggctccc tttagggttc cgatttagtg ctttacggca cctcgacccc    2820
aaaaaacttg attagggtga tggttcacgt agtgggccat cgccctgata dacggttttt    2880 cgcccttga cgttggagtc cacgttcttt aatagtggac tcttgttcca aactggaaca     2940
acactcaacc ctatctcggt ctattctttt gatttataag ggattttgcc gatttcggcc    3000
tattggttaa aaaatgagct gatttaacaa aaatttaacg cgaattttaa caaaatatta    3060
acgtttacaa tttctggcgg cacgatggca tgagattatc aaaaaggatc ttcacctaga    3120
tccttttaaa ttaaaaatga agttttaaat caatctaaag tatatatgag taaacttggt    3180
ctgacagtta ccaatgctta atcagtgagg cacctatctc agcgatctgt ctatttcgtt    3240
catccatagt tgcctgactc cccgtcgtgt agataactac gatacgggag gcttaccat    3300 ctggccccag tgctgcaatg ataccgcgag acccacgctc accggctcca gatttatcag    3360
caataaacca gccagccgga agggccgagc gcagaagtgg tcctgcaact ttatccgcct    3420
ccatccagtc tattaattgt tgccgggaag ctagagtaag tagttcgcca gttaatagtt    3480
tgcgcaacgt tgttgccatt gctacaggca tcgtggtgtc acgctcgtcg tttggtatgg    3540
cttcattcag ctccggttcc caacgatcaa ggcgagttac atgatccccc atgttgtgca    3600
aaaaagcggt tagctccttc ggtcctccga tcgttgtcag aagtaagttg gccgcagtgt    3660
tatcactcat ggttatggca gcactgcata attctcttac tgtcatgcca tccgtaagat    3720
gcttttctgt gactggtgag tactcaacca agtcattctg agaatagtgt atgcggcgac    3780
cgagttgctc ttgcccggcg tcaatacggg ataataccgc gccacatagc agaactttaa    3840
aagtgctcat cattggaaaa cgttcttcgg ggcgaaaact ctcaaggatc ttaccgctgt    3900
tgagatccag ttcgatgtaa cccactcgtg cacccaactg atcttcagca tcttttactt    3960
tcaccagcgt ttctgggtga gcaaaaacag gaaggcaaaa tgccgcaaaa aagggaataa    4020
gggcgacacg gaaatgttga atactcatac tcttcctttt tcaatcatga ttgaagcatt    4080
tatcagggtt attgtctcat gagcggatac atatttgaat gtatttagaa aaataaacaa    4140
ataggtcatg accaaaatcc cttaacgtga gttttcgttc cactgagcgt cagaccccgt    4200
agaaaagatc aaaggatctt cttgagatcc ttttttttctg cgcgtaatct gctgcttgca    4260
aacaaaaaaa ccaccgctac cagcggtggt ttgtttgccg gatcaagagc taccaactct    4320
ttttccgaag gtaactggct tcagcagagc gcagatacca aatactgtcc ttctagtgta    4380
gccgtagtta ggccaccact tcaagaactc tgtagcaccg cctacatacc tcgctctgct    4440
aatcctgtta ccagtggctg ctgccagtgg cgataagtcg tgtcttaccg ggttggactc    4500
aagacgatag ttaccggata aggcgcagcg gtcgggctga acggggggtt cgtgcacaca    4560
gcccagcttg gagcgaacga cctacaccga actgagatac ctacagcgtg agctatgaga    4620
aagcgccacg cttcccgaag ggagaaaggc ggacaggtat ccggtaagcg cagggtcgg     4680 aacaggagag cgcacgaggg agcttccagg gggaaacgcc tggtatcttt atagtcctgt    4740
cgggtttcgc cacctctgac ttgagcgtcg attttttgtga tgctcgtcag ggggggcggag   4800 cctatggaaa aacgccagca acgcggcctt tttacggttc ctggccttttt gctggccttt   4860 tgctcacatg ttctttcctg cgttatcccc tgattctgtg gataaccgta ttaccgcctt    4920
tgagtgagct gataccgctc gccgcagccg aacgaccgag cgcagcgagt cagtgagcga    4980
```

-continued

```
ggaagcggaa gagcgcctga tgcggtattt tctccttacg catctgtgcg gtatttcaca   5040
ccgcatatat ggtgcactct cagtacaatc tgctctgatg ccgcatagtt aagccagtat   5100
acactccgct atcgctacgt gactgggtca tggctgcgcc ccgacacccg ccaacacccg   5160
ctgacgcgcc ctgacgggct tgtctgctcc cggcatccgc ttacagacaa gctgtgaccg   5220
tctccgggag ctgcatgtgt cagaggtttt caccgtcatc accgaaacgc gcgaggcagc   5280
tgcggtaaag ctcatcagcg tggtcgtgaa gcgattcaca gatgtctgcc tgttcatccg   5340
cgtccagctc gttgagtttc tccagaagcg ttaatgtctg gcttctgata aagcgggcca   5400
tgttaagggc ggttttttcc tgtttggtca ctgatgcctc cgtgtaaggg ggatttctgt   5460 tcatggggt aatgataccg atgaaacgag agaggatgct cacgatacgg ttactgatg    5520 atgaacatgc ccggttactg gaacgttgtg agggtaaaca actggcggta tggatgcggc   5580
gggaccagag aaaaatcact cagggtcaat gccagcgctt cgttaataca gatgtaggtg   5640
ttccacaggg tagccagcag catcctgcga tgcagatccg gaacataatg gtgcagggcg   5700
ctgacttccg cgtttccaga ctttacgaaa cacggaaacc gaagaccatt catgttgttg   5760
ctcaggtcgc agacgttttg cagcagcagt cgcttcacgt tcgctcgcgt atcggtgatt   5820
cattctgcta accagtaagg caaccccgcc agcctagccg ggtcctcaac gacaggagca   5880
cgatcatgct agtcatgccc cgcgcccacc ggaaggagct gactgggttg aaggctctca   5940
agggcatcgg tcgagatccc ggtgcctaat gagtgagcta acttacatta attgcgttgc   6000
gctcactgcc cgctttccag tcgggaaacc tgtcgtgcca gctgcattaa tgaatcggcc   6060
aacgcgcggg gagaggcggt ttgcgtattg ggcgccaggg tggtttttct tttcaccagt   6120
gagacgggca acagctgatt gcccttcacc gcctggccct gagagagttg cagcaagcgg   6180
tccacgctgg tttgccccag caggcgaaaa tcctgtttga tggtggttaa cggcgggata   6240
taacatgagc tgtcttcggt atcgtcgtat cccactaccg agatgtccgc accaacgcgc   6300
agcccggact cggtaatggc gcgcattgcg cccagcgcca tctgatcgtt ggcaaccagc   6360
atcgcagtgg gaacgatgcc ctcattcagc atttgcatgg tttgttgaaa accgacatg    6420 gcactccagt cgccttcccg ttccgctatc ggctgaattt gattgcgagt gagatattta   6480
tgccagccag ccagacgcag acgcgccgag acagaactta atgggcccgc taacagcgcg   6540
atttgctggt gacccaatgc gaccagatgc tccacgccca gtcgcgtacc gtcttcatgg   6600
gagaaaataa tactgttgat gggtgtctgg tcagagacat caagaaataa cgccggaaca   6660
ttagtgcagg cagcttccac agcaatggca tcctggtcat ccagcggata gttaatgatc   6720
agcccactga cgcgttgcgc gagaagattg tgcaccgccg ctttacaggc ttcgacgccg   6780
cttcgttcta ccatcgacac caccacgctg gcacccagtt gatcggcgcg agatttaatc   6840
gccgcgacaa tttgcgacgg cgcgtgcagg gccagactgg aggtggcaac gccaatcagc   6900
aacgactgtt tgcccgccag ttgttgtgcc acgcggttgg gaatgtaatt cagctccgcc   6960
atcgccgctt ccactttttc ccgcgttttc gcagaaacgt ggctggcctg gttcaccacg   7020
cgggaaacgg tctgataaga gacaccggca tactctgcga catcgtataa cgttactggt   7080
ttcacattca ccaccctgaa ttgactctct tccgggcgct atcatgccat accgcgaaag   7140
gttttgcgcc attcgatggt gtccgggatc tcgacgctct cccttatgcg actcctgcat   7200
taggaagcag cccagtagta ggttgaggcc gttgagcacc gccgccgcaa ggaatggtgc   7260
atgcaaggag atggcgccca acagtccccc ggccacgggg cctgccacca tacccacgcc   7320
```

| | |
|---|---|
| gaaacaagcg ctcatgagcc cgaagtggcg agcccgatct tccccatcgg tgatgtcggc | 7380 |
| gatataggcg ccagcaaccg cacctgtggc gccggtgatg ccggccacga tgcgtccggc | 7440 |
| gtagaggatc gagatcgatc tcgatcccgc gaaattaata cgactcacta ta | 7492 |

<210> SEQ ID NO 187
<211> LENGTH: 6233
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pDUET-tesB, plasmid

<400> SEQUENCE: 187

| | |
|---|---|
| ggggaattgt gagcggataa caattcccct ctagaaataa ttttgtttaa ctttaagaag | 60 |
| gagatatacc atgggcagca gccatcacca tcatcaccac agccaggatc cgaattcgag | 120 |
| ctcggcgcgc ctgcaggtcg acaagcttgc ggccgcataa tgcttaagtc gaacagaaag | 180 |
| taatcgtatt gtacacggcc gcataatcga aattaatacg actcactata ggggaattgt | 240 |
| gagcggataa caattcccca tcttagtata ttagttaagt ataagaagga gatatacata | 300 |
| tgagtcaggc acttaaaaat ttacttactt tacttaatct tgaaaaaata gaagaaggtt | 360 |
| tatttagagg acagtcagaa gatttaggat taagacaagt atttggaggt caagtagttg | 420 |
| gtcaggcact ttatgcagct aaagaaactg tacctgaaga aagacttgtt catagttttc | 480 |
| attcttattt tcttagacct ggagattcta aaaaaccaat tatatatgat gtagaaactc | 540 |
| ttagagatgg aaattcattt agtgcaagaa gagttgcagc tattcaaaat ggtaaaccta | 600 |
| tattttacat gacagcttct tttcaagcac cagaagctgg atttgaacat cagaaaacta | 660 |
| tgccttcagc acctgctcca gatggattac catcagaaac acaaatagca cagagtttag | 720 |
| ctcatttact tcctccagta cttaaagata aatttatttg tgatagacct ttagaagtta | 780 |
| gaccagttga atttcataat cctcttaaag gacatgtagc agaaccacat agacaagttt | 840 |
| ggataagagc taatgaagt gtaccagatg atcttagagt tcatcagtat cttcttggtt | 900 |
| atgcatctga tttaaatttt cttcctgtag ctttacaacc acatggaata ggttttcttg | 960 |
| aacctggaat acagatagca actatagatc attcaatgtg gtttcataga ccatttaatc | 1020 |
| ttaatgaatg gcttctttat agtgtagaat ctacatcagc aagttctgct agaggatttg | 1080 |
| ttaggggtga atttatact caagatggag tacttgttgc tagtacagta caggaaggtg | 1140 |
| ttatgagaaa tcataattaa ggtaccctcg agtctggtaa agaaaccgct gctgcgaaat | 1200 |
| ttgaacgcca gcacatggac tcgtctacta gcgcagctta attaacctag gctgctgcca | 1260 |
| ccgctgagca ataactagca taaccccttg gggcctctaa acgggtcttg aggggttttt | 1320 |
| tgctgaaagg aggaactata tccggattgg cgaatgggac gcgccctgta gcggcgcatt | 1380 |
| aagcgcggcg ggtgtggtgg ttacgcgcag cgtgaccgct acacttgcca gcgccctagc | 1440 |
| gcccgctcct ttcgctttct tcccttcctt tctcgccacg ttcgccggct ttccccgtca | 1500 |
| agctctaaat cggggctcc ctttagggtt ccgatttagt gctttacggc acctcgaccc | 1560 |
| caaaaaactt gattagggtg atggttcacg tagtgggcca tcgccctgat agacggtttt | 1620 |
| tcgccctttg acgttggagt ccacgttctt taatagtgga ctcttgttcc aaactggaac | 1680 |
| aacactcaac cctatctcgg tctattcttt tgatttataa gggattttgc cgatttcggc | 1740 |
| ctattggtta aaaaatgagc tgatttaaca aaaatttaac gcgaatttta acaaaatatt | 1800 |

```
aacgtttaca atttctggcg gcacgatggc atgagattat caaaaaggat cttcacctag   1860
atccttttaa attaaaaatg aagttttaaa tcaatctaaa gtatatatga gtaaacttgg   1920
tctgacagtt accaatgctt aatcagtgag gcacctatct cagcgatctg tctatttcgt   1980
tcatccatag ttgcctgact ccccgtcgtg tagataacta cgatacggga gggcttacca   2040
tctggcccca gtgctgcaat gataccgcga gacccacgct caccggctcc agatttatca   2100
gcaataaacc agccagccgg aagggccgag cgcagaagtg gtcctgcaac tttatccgcc   2160
tccatccagt ctattaattg ttgccgggaa gctagagtaa gtagttcgcc agttaatagt   2220
ttgcgcaacg ttgttgccat tgctacaggc atcgtggtgt cacgctcgtc gtttggtatg   2280
gcttcattca gctccggttc ccaacgatca aggcgagtta catgatcccc catgttgtgc   2340
aaaaaagcgg ttagctcctt cggtcctccg atcgttgtca gaagtaagtt ggccgcagtg   2400
ttatcactca tggttatggc agcactgcat aattctctta ctgtcatgcc atccgtaaga   2460
tgcttttctg tgactggtga gtactcaacc aagtcattct gagaatagtg tatgcggcga   2520
ccgagttgct cttgcccggc gtcaatacgg gataataccg cgccacatag cagaacttta   2580
aaagtgctca tcattggaaa acgttcttcg gggcgaaaac tctcaaggat cttaccgctg   2640
ttgagatcca gttcgatgta acccactcgt gcacccaact gatcttcagc atctttttact  2700
ttcaccagcg tttctgggtg agcaaaaaca ggaaggcaaa atgccgcaaa aaagggaata   2760
agggcgacac ggaaatgttg aatactcata ctcttccttt ttcaatcatg attgaagcat   2820
ttatcagggt tattgtctca tgagcggata catatttgaa tgtatttaga aaaataaaca   2880
aataggtcat gaccaaaatc ccttaacgtg agttttcgtt ccactgagcg tcagaccccg   2940
tagaaaagat caaaggatct tcttgagatc ctttttttct gcgcgtaatc tgctgcttgc   3000
aaacaaaaaa accaccgcta ccagcggtgg tttgtttgcc ggatcaagag ctaccaactc   3060
tttttccgaa ggtaactggc ttcagcagag cgcagatacc aaatactgtc cttctagtgt   3120
agccgtagtt aggccaccac ttcaagaact ctgtagcacc gcctacatac ctcgctctgc   3180
taatcctgtt accagtggct gctgccagtg gcgataagtc gtgtcttacc gggttggact   3240
caagacgata gttaccggat aaggcgcagc ggtcgggctg aacggggggt tcgtgcacac   3300
agcccagctt ggagcgaacg acctacaccg aactgagata cctacagcgt gagctatgag   3360
aaagcgccac gcttcccgaa gggagaaagg cggacaggta tccggtaagc ggcagggtcg   3420
gaacaggaga gcgcacgagg gagcttccag ggggaaacgc ctggtatctt tatagtcctg   3480
tcgggtttcg ccacctctga cttgagcgtc gatttttgtg atgctcgtca ggggggcgga   3540
gcctatggaa aaacgccagc aacgcggcct ttttacggtt cctggccttt tgctggcctt   3600
ttgctcacat gttctttcct gcgttatccc ctgattctgt ggataaccgt attaccgcct   3660
ttgagtgagc tgataccgct cgccgcagcc gaacgaccga gcgcagcgag tcagtgagcg   3720
aggaagcgga agagcgcctg atgcggtatt ttctccttac gcatctgtgc ggtatttcac   3780
accgcatata tggtgcactc tcagtacaat ctgctctgat gccgcatagt taagccagta   3840
tacactccgc tatcgctacg tgactgggtc atggctgcgc cccgacaccc gccaacaccc   3900
gctgacgcgc cctgacgggc ttgtctgctc ccggcatccg cttacagaca agctgtgacc   3960
gtctccggga gctgcatgtg tcagaggttt tcaccgtcat caccgaaacg cgcgaggcag   4020
ctgcggtaaa gctcatcagc gtggtcgtga agcgattcac agatgtctgc ctgttcatcc   4080
gcgtccagct cgttgagttt ctccagaagc gttaatgtct ggcttctgat aaagcgggcc   4140
atgttaaggg cggttttttc ctgtttggtc actgatgcct ccgtgtaagg gggatttctg   4200
```

```
ttcatggggg taatgatacc gatgaaacga gagaggatgc tcacgatacg ggttactgat    4260
gatgaacatg cccggttact ggaacgttgt gagggtaaac aactggcggt atggatgcgg    4320
cgggaccaga gaaaaatcac tcagggtcaa tgccagcgct tcgttaatac agatgtaggt    4380
gttccacagg gtagccagca gcatcctgcg atgcagatcc ggaacataat ggtgcagggc    4440
gctgacttcc gcgtttccag actttacgaa acacggaaac cgaagaccat tcatgttgtt    4500
gctcaggtcg cagacgtttt gcagcagcag tcgcttcacg ttcgctcgcg tatcggtgat    4560
tcattctgct aaccagtaag gcaaccccgc cagcctagcc gggtcctcaa cgacaggagc    4620
acgatcatgc tagtcatgcc ccgcgcccac cggaaggagc tgactgggtt gaaggctctc    4680
aagggcatcg gtcgagatcc cggtgcctaa tgagtgagct aacttacatt aattgcgttg    4740
cgctcactgc ccgctttcca gtcgggaaac ctgtcgtgcc agctgcatta atgaatcggc    4800
caacgcgcgg ggagaggcgg tttgcgtatt gggcgccagg gtggtttttc ttttcaccag    4860
tgagacggga acagctgat tgcccttcac cgcctggccc tgagagagtt gcagcaagcg    4920
gtccacgctg gtttgcccca gcaggcgaaa atcctgtttg atggtggtta acggcgggat    4980
ataacatgag ctgtcttcgg tatcgtcgta tcccactacc gagatgtccg caccaacgcg    5040
cagcccggac tcggtaatgg cgcgcattgc gcccagcgcc atctgatcgt tggcaaccag    5100
catcgcagtg ggaacgatgc cctcattcag catttgcatg gtttgttgaa accggacat    5160 ggcactccag tcgccttccc gttccgctat cggctgaatt tgattgcgag tgagatattt    5220
atgccagcca gccagacgca gacgcgccga gacagaactt aatgggcccg ctaacagcgc    5280
gatttgctgg tgacccaatg cgaccagatg ctccacgccc agtcgcgtac cgtcttcatg    5340
ggagaaaata atactgttga tgggtgtctg gtcagagaca tcaagaaata acgccggaac    5400
attagtgcag gcagcttcca cagcaatggc atcctggtca tccagcggat agttaatgat    5460
cagcccactg acgcgttgcg cgagaagatt gtgcaccgcc gctttacagg cttcgacgcc    5520
gcttcgttct accatcgaca ccaccacgct ggcacccagt tgatcggcgc gagatttaat    5580
cgccgcgaca atttgcgacg gcgcgtgcag ggccagactg gaggtggcaa cgccaatcag    5640
caacgactgt ttgcccgcca gttgttgtgc cacgcggttg ggaatgtaat tcagctccgc    5700
catcgccgct tccactttt cccgcgtttt cgcagaaacg tggctggcct ggttcaccac    5760
gcgggaaacg gtctgataag agacaccggc atactctgcg acatcgtata acgttactgg    5820
tttcacattc accaccctga attgactctc ttccgggcgc tatcatgcca taccgcgaaa    5880
ggttttgcgc cattcgatgg tgtccgggat ctcgacgctc tcccttatgc gactcctgca    5940
ttaggaagca gcccagtagt aggttgaggc cgttgagcac cgccgccgca aggaatggtg    6000
catgcaagga gatggcgccc aacagtcccc cggccacggg gcctgccacc atacccacgc    6060
cgaaacaagc gctcatgagc ccgaagtggc gagcccgatc ttccccatcg gtgatgtcgg    6120
cgatataggc gccagcaacc gcacctgtgg cgccggtgat gccggccacg atgcgtccgg    6180
cgtagaggat cgagatcgat ctcgatcccg cgaattaat acgactcact ata            6233
```

<210> SEQ ID NO 188
<211> LENGTH: 3120
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: codon optimized gene cassette containing the -continued Wood-Ljungdahl promoter in front of the genes meaB, hcmA and hcmB

<400> SEQUENCE: 188

```
atgacttatg taccatcatc agcactttta gaacaactta gagcaggaaa tacttgggct      60
ttaggaagac ttatatcaag agcagaagct ggagttgcag aagctagacc tgcacttgct     120
gaagtatata gacatgcagg ttcagctcat gttataggtt aacaggagt accaggatct     180
ggtaaatcaa ctcttgtagc aaaacttaca gcagctctta gaaaaagagg agaaaaagtt     240
ggtatagtag ctattgatcc tagttctcca tatagtggag gagcaatact tggagataga     300
attagaatga ctgaattagc aaatgattca ggagtattta agaagtat ggcaactaga      360
ggtgctactg gaggaatggc tagagcagct cttgatgcag ttgatttact tgatgtagct     420
ggatatcata ctattatttt agaaacagtt ggagtaggtc aagatgaagt tgaagtagca     480
catgcttctg atactacagt agttgtatca gcacctggac ttggtgatga atacaggca      540
attaaagctg gagttttaga aattgctgat attcatgttg taagtaaatg tgatagagat     600
gatgcaaata gaactcttac agatcttaaa caaatgctta ctttaggaac aatggtagga     660
cctaaaagag catgggctat accagttgta ggagtttcaa gttatacagg agaaggtgta     720
gatgatttac ttggtagaat tgcagctcat agacaagcaa ctgctgatac agaacttgga     780
agagaaagaa gaagaagagt agctgaattt agacttcaaa aaactgcaga aacattactt     840
ttagaaagat ttactacagg agcacagcct ttttcaccag cattagctga tagtcttct       900
aatagagcta gtgatcctta tgcagctgca agagaattaa tagctagaac tataagaaaa    960
gaatattcta atgatcttgc atgtgctaaa cttactataa catggttaga accacaaatt    1020
aaaagtcaac ttcagtctga aagaaaagat tgggaagcaa atgaagttgg agcatttctt    1080
aaaaaagcac ctgaaagaaa agaacaattt catacaattg gagattttcc agtcagaga     1140
acttatacag ctgcagatat agcagatact cctcttgaag atattggttt acctggaaga    1200
tatccattta ctagaggacc ttatccaaca atgtatagaa gtagaacttg gacaatgaga    1260
caaatagctg gatttggtac tggagaagat acaaataaaa gatttaaata tcttatagca    1320
cagggtcaga ctggaatatc aacagatttt gatatgccta cattaatggg atatgattca    1380
gatcatccaa tgagtgatgg tgaagttgga agagaaggtg tagctataga tacacttgca    1440
gatatggaag cacttcttgc tgatattgat ttagaaaaaa tttcagttag ttttactata    1500
aatccaagtg catggattct tttagcaatg tatgtagctt taggtgaaaa aagaggttat    1560
gatcttaata aactttctgg aacagtacaa gctgatatac ttaaagaata tatggcacag    1620
aaagaatata tttatcctat agctccaagt gttagaattg taagagatat aattacttat    1680
tctgcaaaaa atcttaaaag atataatcct attaatattt ctggatatca tatatcagaa    1740
gctggttctt caccattaca agaagctgca tttactcttg caaatcttat tacttatgta    1800
aatgaagtaa ctaaaacagg aatgcatgta gatgaatttg cacctagatt agcatttttc    1860
tttgttagtc aaggagattt cttttgaagaa gtagcaaaat ttagagcttt aagaagatgt    1920
tatgctaaaa taatgaaaga aagatttgga gcaagaaatc ctgaatctat gagacttaga    1980
tttcattgtc aaactgctgc agctactctt acaaaaccac agtatatggt taatgttgta    2040
agaacaagtc ttcaagcatt atctgctgta ttgggaggag cacaaagtct tcatactaat    2100
ggatatgatg aagcatttgc tatacctact gaagatgcaa tgaaaatggc tcttagaaca    2160
caacagatta tagctgaaga atctggagtt gcagatgtaa tagatcctct tggaggaagt    2220
tattatgttg aagcattaac tacagaatat gaaaagaaaa tatttgaaat tcttgaagaa    2280
```

-continued

```
gtagaaaaaa gaggtggaac tattaaactt attgaacaag gatggtttca aaaacagata    2340
gcagattttg cttatgaaac tgcacttaga aaacaatcag gacagaaacc tgttataggt    2400
gtaaatagat ttgttgaaaa tgaagaagat gtaaaaattg aaatacatcc ttatgataat    2460
actacagctg aaagacaaat atcaagaact agaagagtta gagcagaaag agatgaagca    2520
aaagtacaag ctatgcttga tcagttagtt gcagtagcta aagatgaaag tcagaatctt    2580
atgcctctta ctattgaatt agtaaaagca ggagctacaa tgggtgatat tgtagaaaaa    2640
cttaaaggta tttggggaac ttatagagaa acaccagtat tttaagcact agttggagag    2700
cttcccacga tggatcagat tcctattaga gtattattag caaaagtagg tttagatgga    2760
catgatagag gtgtaaaagt tgtagcaaga gcattaagag atgctggaat ggatgtaata    2820
tatagtggtc ttcatagaac tcctgaagaa gtagttaata cagcaattca agaagatgta    2880
gatgttttag gagttagttt actttctggt gtacagctta ctgttttttcc taaaattttt    2940 aaattacttg atgaaagagg agctggtgat ttaatagtaa ttgctggagg agtaatgcca    3000
gatgaagatg cagctgcaat aagaaaactt ggagtaagag aagtttttact tcaagataca    3060 ccaccacagg caataataga ttcaataaga agtttagtag cagcaagagg agcaagataa    3120
```

<210> SEQ ID NO 189
<211> LENGTH: 894
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<223> OTHER INFORMATION: hcmA and meaB fusion

<400> SEQUENCE: 189

```
Met Thr Tyr Val Pro Ser Ser Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Asp Ser Gly Val
            100                 105                 110

Phe Ile Arg Ser Met Ala Thr Arg Gly Ala Thr Gly Gly Met Ala Arg
        115                 120                 125

Ala Ala Leu Asp Ala Val Asp Leu Leu Asp Val Ala Gly Tyr His Thr
    130                 135                 140

Ile Ile Leu Glu Thr Val Gly Val Gly Gln Asp Glu Val Glu Val Ala
145                 150                 155                 160

His Ala Ser Asp Thr Thr Val Val Ser Ala Pro Gly Leu Gly Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Asp Ala Asn Arg Thr Leu Thr Asp
```

```
                195                 200                 205
Leu Lys Gln Met Leu Thr Leu Gly Thr Met Val Gly Pro Lys Arg Ala
210                 215                 220

Trp Ala Ile Pro Val Val Gly Val Ser Ser Tyr Thr Gly Glu Gly Val
225                 230                 235                 240

Asp Asp Leu Leu Gly Arg Ile Ala Ala His Arg Gln Ala Thr Ala Asp
                245                 250                 255

Thr Glu Leu Gly Arg Glu Arg Arg Arg Val Ala Glu Phe Arg Leu
            260                 265                 270

Gln Lys Thr Ala Glu Thr Leu Leu Glu Arg Phe Thr Thr Gly Ala
            275                 280                 285

Gln Pro Phe Ser Pro Ala Leu Ala Asp Ser Leu Ser Asn Arg Ala Ser
290                 295                 300

Asp Pro Tyr Ala Ala Arg Glu Leu Ile Ala Arg Thr Ile Arg Lys
305                 310                 315                 320

Glu Tyr Ser Asn Asp Leu Ala Cys Ala Lys Leu Thr Ile Thr Trp Leu
                325                 330                 335

Glu Pro Gln Ile Lys Ser Gln Leu Gln Ser Glu Arg Lys Asp Trp Glu
                340                 345                 350

Ala Asn Glu Val Gly Ala Phe Leu Lys Lys Ala Pro Glu Arg Lys Glu
                355                 360                 365

Gln Phe His Thr Ile Gly Asp Phe Pro Val Gln Arg Thr Tyr Thr Ala
370                 375                 380

Ala Asp Ile Ala Asp Thr Pro Leu Glu Asp Ile Gly Leu Pro Gly Arg
385                 390                 395                 400

Tyr Pro Phe Thr Arg Gly Pro Tyr Pro Thr Met Tyr Arg Ser Arg Thr
                405                 410                 415

Trp Thr Met Arg Gln Ile Ala Gly Phe Gly Thr Gly Asp Thr Asn
                420                 425                 430

Lys Arg Phe Lys Tyr Leu Ile Ala Gln Gly Gln Thr Gly Ile Ser Thr
                435                 440                 445

Asp Phe Asp Met Pro Thr Leu Met Gly Tyr Asp Ser Asp His Pro Met
450                 455                 460

Ser Asp Gly Glu Val Gly Arg Glu Gly Val Ala Ile Asp Thr Leu Ala
465                 470                 475                 480

Asp Met Glu Ala Leu Leu Ala Asp Ile Asp Leu Glu Lys Ile Ser Val
                485                 490                 495

Ser Phe Thr Ile Asn Pro Ser Ala Trp Ile Leu Leu Ala Met Tyr Val
                500                 505                 510

Ala Leu Gly Glu Lys Arg Gly Tyr Asp Leu Asn Lys Leu Ser Gly Thr
                515                 520                 525

Val Gln Ala Asp Ile Leu Lys Glu Tyr Met Ala Gln Lys Glu Tyr Ile
530                 535                 540

Tyr Pro Ile Ala Pro Ser Val Arg Ile Val Arg Asp Ile Ile Thr Tyr
545                 550                 555                 560

Ser Ala Lys Asn Leu Lys Arg Tyr Asn Pro Ile Asn Ile Ser Gly Tyr
                565                 570                 575

His Ile Ser Glu Ala Gly Ser Ser Pro Leu Gln Glu Ala Ala Phe Thr
                580                 585                 590

Leu Ala Asn Leu Ile Thr Tyr Val Asn Glu Val Thr Lys Thr Gly Met
                595                 600                 605

His Val Asp Glu Phe Ala Pro Arg Leu Ala Phe Phe Val Ser Gln
610                 615                 620
```

```
Gly Asp Phe Phe Glu Glu Val Ala Lys Phe Arg Ala Leu Arg Arg Cys
625                 630                 635                 640

Tyr Ala Lys Ile Met Lys Glu Arg Phe Gly Ala Arg Asn Pro Glu Ser
            645                 650                 655

Met Arg Leu Arg Phe His Cys Gln Thr Ala Ala Thr Leu Thr Lys
        660                 665                 670

Pro Gln Tyr Met Val Asn Val Arg Thr Ser Leu Gln Ala Leu Ser
        675                 680                 685

Ala Val Leu Gly Gly Ala Gln Ser Leu His Thr Asn Gly Tyr Asp Glu
690                 695                 700

Ala Phe Ala Ile Pro Thr Glu Asp Ala Met Lys Met Ala Leu Arg Thr
705                 710                 715                 720

Gln Gln Ile Ile Ala Glu Glu Ser Gly Val Ala Asp Val Ile Asp Pro
                725                 730                 735

Leu Gly Gly Ser Tyr Tyr Val Glu Ala Leu Thr Thr Glu Tyr Glu Lys
            740                 745                 750

Lys Ile Phe Glu Ile Leu Glu Glu Val Glu Lys Arg Gly Gly Thr Ile
            755                 760                 765

Lys Leu Ile Glu Gln Gly Trp Phe Gln Lys Ile Ala Asp Phe Ala
770                 775                 780

Tyr Glu Thr Ala Leu Arg Lys Gln Ser Gly Gln Lys Pro Val Ile Gly
785                 790                 795                 800

Val Asn Arg Phe Val Glu Asn Glu Asp Val Lys Ile Glu Ile His
                805                 810                 815

Pro Tyr Asp Asn Thr Thr Ala Glu Arg Gln Ile Ser Arg Thr Arg Arg
            820                 825                 830

Val Arg Ala Glu Arg Asp Glu Ala Lys Val Gln Ala Met Leu Asp Gln
            835                 840                 845

Leu Val Ala Val Ala Lys Asp Glu Ser Gln Asn Leu Met Pro Leu Thr
850                 855                 860

Ile Glu Leu Val Lys Ala Gly Ala Thr Met Gly Asp Ile Val Glu Lys
865                 870                 875                 880

Leu Lys Gly Ile Trp Gly Thr Tyr Arg Glu Thr Pro Val Phe
            885                 890
```

<210> SEQ ID NO 190
<211> LENGTH: 849
<212> TYPE: DNA
<213> ORGANISM: Clostridium acetobutylicum
<220> FEATURE:
<221> NAME/KEY: misc_feature
<223> OTHER INFORMATION: hbd

<400> SEQUENCE: 190

```
atgagtatta aaagtgtagc ggttttaggt agtggaacta tgtctcgtgg aattgtgcag    60
gcttttgcag aagcaggtat agatgtaatt atccgtggaa gaactgaagg tagtattgga   120
aaaggtctag cagcagtaaa gaaagcttat gataaaaaag tatcaaaggg gaaaatttcc   180
caggaagatg ctgataaaat agttggaaga gtaagtacaa caactgaact tgaaaaattg   240
gctgattgtg atcttataat agaagcagca tcagaggata tgaatataaa gaaagactat   300
tttgaaaaat tagaagaaat atgcaagcct gaaacaattt ttgctactaa tacttcttca   360
ttatctataa ctgaagtagc aacagctaca aagagaccag ataaattcat aggaatgcat   420
ttctttaatc cagcaaatgt tatgaaatta gttgaaatca taagaggtat gaatacttca   480
```

-continued

| | |
|---|---|
| caagaaactt tgatattat aaaagaagct tccattaaaa taggaaaaac tcctgtagaa | 540 |
| gttgcagaag ctccaggatt tgttgtaaac aagatattag taccaatgat caatgaagca | 600 |
| gtaggaattt tggcagaagg aatagcttca gcagaagata tcgatacagc tatgaaatta | 660 |
| ggcgctaatc acccaatggg tcctttagca ttaggagatc ttattggact tgatgtagtt | 720 |
| cttgcagtta tggatgtact ttatagtgaa actggagatt caaaatatag agctcataca | 780 |
| ttacttagaa aatatgtaag agcaggatgg cttggaagaa aatcaggaaa aggattcttc | 840 |
| gcttattaa | 849 |

<210> SEQ ID NO 191
<211> LENGTH: 10647
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL83155-thlA-hbd-Pwl-meaBhcmA-hcmB

<400> SEQUENCE: 191

| | |
|---|---|
| cctgcaggat aaaaaattg tagataaatt ttataaaata gttttatcta caattttttt | 60 |
| atcaggaaac agctatgacc gcggccgcaa tatgatattt atgtccattg tgaaagggat | 120 |
| tatattcaac tattattcca gttacgttca tagaaatttt cctttctaaa atattttatt | 180 |
| ccatgtcaag aactctgttt atttcattaa agaactataa gtacaaagta taaggcattt | 240 |
| gaaaaaatag gctagtatat tgattgatta tttattttaa aatgcctaag tgaaatatat | 300 |
| acatattata acaataaaat aagtattagt gtaggatttt taaatagagt atctattttc | 360 |
| agattaaatt tttgattatt tgatttacat tatataatat tgagtaaagt attgactagc | 420 |
| aaaattttt gatactttaa tttgtgaaat ttcttatcaa aagttatatt tttgaataat | 480 |
| ttttattgaa aaatacaact aaaaaggatt atagtataag tgtgtgtaat tttgtgttaa | 540 |
| atttaaaggg aggaaatgaa catgaaacat atgaaagaag ttgtaatagc tagtgcagta | 600 |
| agaacagcga ttggatctta tggaaagtct cttaaggatg taccagcagt agatttagga | 660 |
| gctacagcta taaggaagc agttaaaaaa gcaggaataa aaccagagga tgttaatgaa | 720 |
| gtcattttag gaaatgttct tcaagcaggt ttaggacaga atccagcaag acaggcatct | 780 |
| tttaaagcag gattaccagt tgaaattcca gctatgacta ttaataaggt ttgtggttca | 840 |
| ggacttagaa cagttagctt agcagcacaa attataaaag caggagatgc tgacgtaata | 900 |
| atagcaggtg gtatggaaaa tatgtctaga gctccttact tagcgaataa cgctagatgg | 960 |
| ggatatagaa tgggaaacgc taaatttgtt gatgaaatga tcactgacgg attgtgggat | 1020 |
| gcatttaatg attaccacat gggaataaca gcagaaaaca tagctgagag atggaacatt | 1080 |
| tcaagagaag aacaagatga gtttgctctt gcatcacaaa aaaaagctga agaagctata | 1140 |
| aaatcaggtc aatttaaaga tgaaatagtt cctgtagtaa ttaaaggcag aaagggagaa | 1200 |
| actgtagttg atacagatga gcaccctaga tttggatcaa ctatagaagg acttgcaaaa | 1260 |
| ttaaaacctg ccttcaaaaa agatggaaca gttacagctg gtaatgcatc aggattaaat | 1320 |
| gactgtgcag cagtacttgt aatcatgagt gcagaaaaag ctaaagagct tggagtaaaa | 1380 |
| ccacttgcta agatagtttc ttatggttca gcaggagttg acccagcaat aatgggatat | 1440 |
| ggacctttct atgcaacaaa agcagctatt gaaaaagcag gttggacagt tgatgaatta | 1500 |
| gatttaatag aatcaaatga agcttttgca gctcaaagtt tagcagtagc aaaagattta | 1560 |

```
aaatttgata tgaataaagt aaatgtaaat ggaggagcta ttgcccttgg tcatccaatt   1620
ggagcatcag gtgcaagaat actcgttact cttgtacacg caatgcaaaa aagagatgca   1680
aaaaaaggct tagcaacttt atgtataggt ggcggacaag gaacagcaat attgctagaa   1740
aagtgctagg aattctcaaa aattcggtta aataaaataa ttaggaggtt caatcatgtc   1800
tattaaatca gttgcagttt taggttcagg tacaatgtca agaggtattg ttcaagcatt   1860
tgctgaagca ggtatagatg taataattag aggtagaaca gaaggatcaa taggaaaagg   1920
acttgctgct gttaagaaag catacgataa aaaggtaagt aaaggaaaga tatcacaaga   1980
agatgctgat aaaatagttg gtagagtatc tactactaca gaattagaaa attagcaga    2040 ttgcgacctt ataattgagg ctgcatcaga agatatgaac ataaagaaag attattttgg   2100
aaaacttgaa gaaatatgta aaccagaaac tattttttgct actaatacat caagtttaag   2160
tattacagaa gtagcaacag caactaaaag accagataag ttcataggaa tgcacttctt   2220
taatcctgct aatgtaatga agcttgtaga gattataaga ggtatgaata cttctcagga   2280
aacatttgat ataattaagg aagcaagtat taaaatagga aaaactcctg tagaagtagc   2340
agaagcacca ggatttgttg ttaataagat acttgttcct atgataaatg aggctgtagg   2400
tatacttgct gaaggtattg ctagtgctga agacatagac actgctatga agttaggtgc   2460
aaaccatcct atgggaccat tagcattagg tgatcttatt ggattagatg ttgttttagc   2520
agtaatggat gtactttatt ctgagacagg tgattctaaa tatagagctc atacacttct   2580
tagaaagtat gtaagagctg gttggttagg tagaaagtct ggtaaaggat ttttcgcata   2640
ttaaggtacc gcagatagtc ataatagttc cagaatagtt caatttagaa attagactaa   2700
acttcaaaat gtttgttaaa tatataccaa actagtatag atattttta aatactggac    2760 ttaaacagta gtaatttgcc taaaaaattt tttcaatttt ttttaaaaaa tccttttcaa   2820
gttgtacatt gttatggtaa tatgtaattg aagaagttat gtagtaatat tgtaaacgtt   2880
tcttgatttt tttacatcca tgtagtgctt aaaaaaccaa aatatgtcac atgcaattgt   2940
atatttcaaa taacaatatt tattttctcg ttaaattcac aaataattta ttaataatat   3000
caataaccaa gattatactt aaatggatgt ttattttta acactttat agtaaatata    3060 tttattttat gtagtaaaaa ggttataatt ataattgtat ttattacaat taattaaaat   3120
aaaaaatagg gttttaggta aaattaagtt attttaagaa gtaattacaa taaaaattga   3180
agttatttct ttaaggaggg aattattcat atgacttatg taccatcatc agcacttta    3240 gaacaactta gagcaggaaa tacttgggct ttaggaagac ttatatcaag agcagaagct   3300
ggagttgcag aagctagacc tgcacttgct gaagtatata gacatgcagg ttcagctcat   3360
gttataggtt taacaggagt accaggatct ggtaaatcaa ctcttgtagc aaaacttaca   3420
gcagctctta gaaaagagg agaaaaagtt ggtatagtag ctattgatcc tagttctcca   3480
tatagtggag gagcaatact tggagataga attagaatga ctgaattagc aaatgattca   3540 ggagtatta taagaagtat ggcaactaga ggtgctactg gaggaatggc tagagcagct   3600
cttgatgcag ttgatttact tgatgtagct ggatatcata ctattatttt agaaacagtt   3660
ggagtaggtc aagatgaagt tgaagtagca catgcttctg atactacagt agttgtatca   3720
gcacctggac ttggtgatga atacaggca attaaagctg gagttttaga aattgctgat   3780
attcatgttg taagtaaatg tgatagagat gatgcaaata gaactcttac agatcttaaa   3840
caaatgctta ctttaggaac aatggtagga cctaaaagag catgggctat accagttgta   3900 ggagttttcaa gttatacagg agaaggtgta gatgatttac ttggtagaat tgcagctcat   3960
```

```
agacaagcaa ctgctgatac agaacttgga agagaaagaa gaagaagagt agctgaattt    4020
agacttcaaa aaactgcaga aacattactt ttagaaagat ttactacagg agcacagcct    4080
ttttcaccag cattagctga tagtctttct aatagagcta gtgatcctta tgcagctgca    4140
agagaattaa tagctagaac tataagaaaa gaatattcta atgatcttgc atgtgctaaa    4200
cttactataa catggttaga accacaaatt aaaagtcaac ttcagtctga agaaaagat     4260 tgggaagcaa atgaagttgg agcatttctt aaaaaagcac ctgaaagaaa agaacaattt    4320
catacaattg gagattttcc agtacagaga acttatacag ctgcagatat agcagatact    4380
cctcttgaag atattggttt acctggaaga tatccattta ctagaggacc ttatccaaca    4440
atgtatagaa gtagaacttg gacaatgaga caaatagctg gatttggtac tggagaagat    4500
acaaataaaa gatttaaata tcttatagca cagggtcaga ctggaatatc aacgattttt    4560
gatatgccta cattaatggg atatgattca gatcatccaa tgagtgatgg tgaagttgga    4620
agagaaggtg tagctataga tacacttgca gatatggaag cacttcttgc tgatattgat    4680
ttagaaaaaa tttcagttag ttttactata aatccaagtg catggattct tttagcaatg    4740
tatgtagctt taggtgaaaa aagaggttat gatcttaata aactttctgg aacagtacaa    4800
gctgatatac ttaaagaata tatggcacag aaagaatata tttatcctat agctccaagt    4860
gttagaattg taagagatat aattacttat tctgcaaaaa atcttaaaag atataatcct    4920
attaatattt ctggatatca tatatcagaa gctggttctt caccattaca agaagctgca    4980
tttactcttg caaatcttat tacttatgta aatgaagtaa ctaaaacagg aatgcatgta    5040
gatgaatttg cacctagatt agcatttttc tttgttagtc aaggagattt ctttgaagaa    5100
gtagcaaaat ttagagcttt aagaagatgt tatgctaaaa taatgaaaga aagatttgga    5160
gcaagaaatc ctgaatctat gagacttaga tttcattgtc aaactgctgc agctactctt    5220
acaaaaccac agtatatggt taatgttgta agaacaagtc ttcaagcatt atctgctgta    5280
ttgggaggag cacaaagtct tcatactaat ggatatgatg aagcatttgc tatacctact    5340
gaagatgcaa tgaaaatggc tcttagaaca caacagatta tagctgaaga atctggagtt    5400
gcagatgtaa tagatcctct tggaggaagt tattatgttg aagcattaac tacagaatat    5460
gaaaagaaaa tatttgaaat tcttgaagaa gtagaaaaaa gaggtggaac tattaaactt    5520
attgaacaag gatggtttca aaaacagata gcagattttg cttatgaaac tgcacttaga    5580
aaacaatcag gacagaaacc tgttataggt gtaaatagat tgttgaaaaa tgaagaagat    5640
gtaaaaattg aaatacatcc ttatgataat actacagctg aaagacaaat atcaagaact    5700
agaagagtta gagcagaaag agatgaagca aaagtacaag ctatgcttga tcagttagtt    5760
gcagtagcta aagatgaaag tcagaatctt atgcctctta ctattgaatt agtaaaagca    5820
ggagctacaa tgggtgatat tgtagaaaaa cttaaggta tttggggaac ttatagagaa     5880
acaccagtat tttaagcact agttggagag cttcccacga tggatcagat tcctattaga    5940
gtattattag caaaagtagg tttagatgga catgatagag gtgtaaaagt tgtagcaaga    6000
gcattaagag atgctggaat ggatgtaata tatagtggtc ttcatagaac tcctgaagaa    6060
gtagttaata cagcaattca agaagatgta gatgttttag gagttagttt actttctggt    6120
gtacagctta ctgttttttcc taaaattttt aaattacttg atgaaagagg agctggtgat    6180
ttaatagtaa ttgctggagg agtaatgcca gatgaagatg cagctgcaat aagaaaactt    6240
ggagtaagag aagtttttact tcaagataca ccaccacagg caataataga ttcaataaga    6300
```

```
agtttagtag cagcaagagg agcaagataa ccatggagat ctcgaggcct gcagacatgc   6360
aagcttggca ctggccgtcg ttttacaacg tcgtgactgg gaaaaccctg gcgttaccca   6420
acttaatcgc cttgcagcac atccccettt cgccagctgg cgtaatagcg aagaggcccg   6480
caccgatcgc ccttcccaac agttgcgcag cctgaatggc gaatggcgct agcataaaaa   6540
taagaagcct gcatttgcag gcttcttatt tttatggcgc gccgccatta ttttttttgaa   6600 caattgacaa ttcatttctt attttttatt aagtgatagt caaaaggcat aacagtgctg   6660
aatagaaaga aatttacaga aagaaaatt atagaattta gtatgattaa ttatactcat   6720
ttatgaatgt ttaattgaat acaaaaaaaa atacttgtta tgtattcaat tacgggttaa   6780
aatatagaca agttgaaaaa tttaataaaa aaataagtcc tcagctctta tatattaagc   6840
taccaactta gtatataagc caaaacttaa atgtgctacc aacacatcaa gccgttagag   6900
aactctatct atagcaatat ttcaaatgta ccgacataca agagaaacat taactatata   6960
tattcaattt atgagattat cttaacagat ataaatgtaa attgcaataa gtaagatttta   7020 gaagtttata gcctttgtgt attggaagca gtacgcaaag gcttttttat ttgataaaaa   7080
ttagaagtat atttattttt tcataattaa tttatgaaaa tgaaaggggg tgagcaaagt   7140
gacagaggaa agcagtatct tatcaaataa caaggtatta gcaatatcat tattgactttt   7200 agcagtaaac attatgactt ttatagtgct tgtagctaag tagtacgaaa gggggagctt   7260
taaaaagctc cttggaatac atagaattca taaattaatt tatgaaaaga agggcgtata   7320
tgaaaacttg taaaaattgc aaagagttta ttaaagatac tgaaatatgc aaaatacatt   7380
cgttgatgat tcatgataaa acagtagcaa cctattgcag taaatacaat gagtcaagat   7440
gtttacataa agggaaagtc caatgtatta attgttcaaa gatgaaccga tatggatggt   7500
gtgccataaa aatgagatgt tttcagagg aagaacagaa aaaagaacgt acatgcatta   7560
aatattatgc aaggagcttt aaaaaagctc atgtaaagaa gagtaaaaag aaaaaataat   7620
ttatttatta atttaatatt gagagtgccg acacagtatg cactaaaaaa tatatctgtg   7680
gtgtagtgag ccgatacaaa aggatagtca ctcgcatttt cataatacat cttatgttat   7740
gattatgtgt cggtgggact tcacgacgaa aaccccacaat aaaaaaagag ttcggggtag   7800
ggttaagcat agttgaggca actaaacaat caagctagga tatgcagtag cagaccgtaa   7860
ggtcgttgtt taggtgtgtt gtaatacata cgctattaag atgtaaaaat acggatacca   7920
atgaagggaa aagtataatt tttggatgta gtttgtttgt tcatctatgg gcaaactacg   7980
tccaaagccg tttccaaatc tgctaaaaag tatatccttt ctaaaatcaa agtcaagtat   8040
gaaatcataa ataaagttta atttttgaagt tattatgata ttatgttttt ctattaaaat   8100
aaattaagta tatagaatag tttaataata gtatatactt aatgtgataa gtgtctgaca   8160
gtgtcacaga aaggatgatt gttatggatt ataagcggcc ggccagtggg caagttgaaa   8220
aattcacaaa aatgtggtat aatatctttg ttcattagag cgataaactt gaatttgaga   8280
gggaacttag atggtatttg aaaaaattga taaaaatagt tggaacagaa aagagtattt   8340
tgaccactac tttgcaagtg taccttgtac ctacagcatg accgttaaag tggatatcac   8400
acaaataaag gaaagggaa tgaaactata tcctgcaatg ctttattata ttgcaatgat   8460
tgtaaaccgc cattcagagt ttaggacggc aatcaatcaa gatggtgaat tggggatata   8520
tgatgagatg ataccaagct atacaatatt tcacaatgat actgaaacat tttccagcct   8580
ttggactgag tgtaagtctg actttaaatc attttttagca gattatgaaa gtgatacgca   8640
acggtatgga aacaatcata gaatggaagg aaagccaaat gctccggaaa acattttaa   8700
```

| | | |
|---|---|---|
| tgtatctatg ataccgtggt caaccttcga tggctttaat ctgaatttgc agaaaggata | 8760 | |
| tgattatttg attcctattt ttactatggg gaaatattat aaagaagata acaaaattat | 8820 | |
| acttcctttg gcaattcaag ttcatcacgc agtatgtgac ggatttcaca tttgccgttt | 8880 | |
| tgtaaacgaa ttgcaggaat tgataaatag ttaacttcag gtttgtctgt aactaaaaac | 8940 | |
| aagtatttaa gcaaaaacat cgtagaaata cggtgttttt tgttacccta agtttaaact | 9000 | |
| ccttttgat aatctcatga ccaaaatccc ttaacgtgag ttttcgttcc actgagcgtc | 9060 | |
| agacccgta gaaagatca aaggatcttc ttgagatcct ttttttctgc gcgtaatctg | 9120 | |
| ctgcttgcaa acaaaaaaac caccgctacc agcggtggtt tgtttgccgg atcaagagct | 9180 | |
| accaactctt tttccgaagg taactggctt cagcagagcg cagataccaa atactgttct | 9240 | |
| tctagtgtag ccgtagttag gccaccactt caagaactct gtagcaccgc ctacatacct | 9300 | |
| cgctctgcta atcctgttac cagtggctgc tgccagtggc gataagtcgt gtcttaccgg | 9360 | |
| gttggactca agacgatagt taccggataa ggcgcagcgg tcgggctgaa cggggggttc | 9420 | |
| gtgcacacag cccagcttgg agcgaacgac ctacaccgaa ctgagatacc tacagcgtga | 9480 | |
| gctatgagaa agcgccacgc ttcccgaagg gagaaaggcg gacaggtatc cggtaagcgg | 9540 | |
| cagggtcgga acaggagagc gcacgaggga gcttccaggg ggaaacgcct ggtatcttta | 9600 | |
| tagtcctgtc gggtttcgcc acctctgact tgagcgtcga ttttttgtgat gctcgtcagg | 9660 | |
| ggggcggagc ctatggaaaa acgccagcaa cgcggccttt ttacggttcc tggccttttg | 9720 | |
| ctggccttt gctcacatgt tctttcctgc gttatcccct gattctgtgg ataaccgtat | 9780 | |
| taccgccttt gagtgagctg ataccgctcg ccgcagccga acgaccgagc gcagcgagtc | 9840 | |
| agtgagcgag gaagcggaag agcgcccaat acgcagggcc cctgcttcg gggtcattat | 9900 | |
| agcgattttt tcggtatatc catccttttt cgcacgatat acaggatttt gccaaagggt | 9960 | |
| tcgtgtagac tttccttggt gtatccaacg gcgtcagccg gcaggatag gtgaagtagg | 10020 | |
| cccacccgcg agcgggtgtt ccttcttcac tgtcccttat tcgcacctgg cggtgctcaa | 10080 | |
| cgggaatcct gctctgcgag gctggccggc taccgccggc gtaacagatg agggcaagcg | 10140 | |
| gatggctgat gaaaccaagc caaccaggaa gggcagccca cctatcaagg tgtactgcct | 10200 | |
| tccagacgaa cgaagagcga ttgaggaaaa ggcggcggcg gccggcatga gcctgtcggc | 10260 | |
| ctacctgctg gccgtcggcc agggctacaa aatcacgggc gtcgtggact atgagcacgt | 10320 | |
| ccgcgagctg gcccgcatca atggcgacct gggccgcctg gcggcctgc tgaaactctg | 10380 | |
| gctcaccgac gacccgcgca cggcgcggtt cggtgatgcc acgatcctcg ccctgctggc | 10440 | |
| gaagatcgaa gagaagcagg acgagcttgg caaggtcatg atgggcgtgg tccgcccgag | 10500 | |
| ggcagagcca tgacttttttt agccgctaaa acggccgggg ggtgcgcgtg attgccaagc | 10560 | |
| acgtccccat gcgctccatc aagaagagcg acttcgcgga gctggtgaag tacatcaccg | 10620 | |
| acgagcaagg caagaccgat cgggccc | 10647 | |

<210> SEQ ID NO 192
<211> LENGTH: 10539
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL83155-thlA-phaB-Pwl-meaBhcmA-hcmB

<400> SEQUENCE: 192

-continued

```
cctgcaggat aaaaaaattg tagataaatt ttataaaata gttttatcta caatttttt        60
atcaggaaac agctatgacc gcggccgcaa tatgatattt atgtccattg tgaaagggat      120
tatattcaac tattattcca gttacgttca tagaaatttt cctttctaaa atattttatt      180
ccatgtcaag aactctgttt atttcattaa agaactataa gtacaaagta taaggcattt      240
gaaaaaatag gctagtatat tgattgatta tttatttaa aatgcctaag tgaaatatat       300
acatattata acaataaaat aagtattagt gtaggatttt taaatagagt atctattttc      360
agattaaatt tttgattatt tgatttacat tatataatat tgagtaaagt attgactagc      420
aaaattttt gatactttaa tttgtgaaat ttcttatcaa agttatatt tttgaataat        480
ttttattgaa aaatacaact aaaaaggatt atagtataag tgtgtgtaat tttgtgttaa      540
atttaaaggg aggaaatgaa catgaaacat atgaaagaag ttgtaatagc tagtgcagta      600
agaacagcga ttggatctta tggaaagtct cttaaggatg taccagcagt agatttagga     660
gctacagcta taaggaagc agttaaaaaa gcaggaataa aaccagagga tgttaatgaa       720
gtcattttag gaaatgttct tcaagcaggt ttaggacaga atccagcaag acaggcatct     780
tttaaagcag gattaccagt tgaaattcca gctatgacta ttaataaggt ttgtggttca     840
ggacttagaa cagttagctt agcagcacaa attataaaag caggagatgc tgacgtaata     900
atagcaggtg gtatggaaaa tatgtctaga gctccttact tagcgaataa cgctagatgg     960
ggatatagaa tgggaaacgc taaatttgtt gatgaaatga tcactgacgg attgtgggat    1020
gcatttaatg attaccacat gggaataaca gcagaaaaca tagctgagag atggaacatt    1080
tcaagagaag aacaagatga gtttgctctt gcatcacaaa aaaagctga agaagctata     1140
aaatcaggtc aatttaaaga tgaaatagtt cctgtagtaa ttaaaggcag aaagggagaa    1200
actgtagttg atacagatga gcaccctaga tttggatcaa ctatagaagg acttgcaaaa    1260
ttaaaacctg ccttcaaaaa agatggaaca gttacagctg gtaatgcatc aggattaaat    1320
gactgtgcag cagtacttgt aatcatgagt gcagaaaag ctaaagagct tggagtaaaa    1380
ccacttgcta agatagtttc ttatggttca gcaggagttg acccagcaat aatgggatat   1440
ggacctttct atgcaacaaa agcagctatt gaaaaagcag gttggacagt tgatgaatta    1500
gatttaatag aatcaaatga agcttttgca gctcaaagtt tagcagtagc aaaagattta   1560
aaatttgata tgaataaagt aaatgtaaat ggaggagcta ttgcccttgg tcatccaatt   1620
ggagcatcag gtgcaagaat actcgttact cttgtacacg caatgcaaaa aagagatgca   1680
aaaaaaggct tagcaacttt atgtataggt ggcggacaag gaacagcaat attgctagaa   1740
aagtgctagg aattctcaaa aattcggtta ataaaataa ttaggaggtt caatcatgac    1800
tcagcgcatt gcgtatgtga ccggcggcat gggtggtatc ggaaccgcca tttgccagcg   1860
gctggccaag gatggctttc gtgtggtggc cggttgcggc cccaactcgc cgcgccgcga   1920
aaagtggctg gagcagcaga aggccctggg cttcgatttc attgcctcgg aaggcaatgt   1980
ggctgactgg gactcgacca agaccgcatt cgacaaggtc aagtccgagg tcggcgaggt   2040
tgatgtgctg atcaacaacg ccggtatcac ccgcgacgtg gtgttccgca agatgacccg   2100
cgccgactgg gatgcggtga tcgacaccaa cctgacctcg ctgttcaacg tcaccaagca   2160
ggtgatcgac ggcatggccg accgtggctg gggccgcatc gtcaacatct cgtcggtgaa   2220
cgggcagaag ggccagttcg gccagaccaa ctactccacc gccaaggccg gcctgcatgg   2280
cttcaccatg gcactggcgc aggaagtggc gaccaagggc gtgaccgtca acacggtctc   2340
```

| | |
|---|---|
| tccgggctat atcgccaccg acatggtcaa ggcgatccgc caggacgtgc tcgacaagat | 2400 |
| cgtcgcgacg atcccggtca agcgcctggg cctgccggaa gagatcgcct cgatctgcgc | 2460 |
| ctggttgtcg tcggaggagt ccggtttctc gaccggcgcc gacttctcgc tcaacggcgg | 2520 |
| cctgcatatg ggctgaggta ccgcagatag tcataatagt tccagaatag ttcaatttag | 2580 |
| aaattagact aaacttcaaa atgtttgtta aatatatacc aaactagtat agatattttt | 2640 |
| taaatactgg acttaaacag tagtaatttg cctaaaaaat ttttttcaatt tttttttaaaa | 2700 |
| aatccttttc aagttgtaca ttgttatggt aatatgtaat tgaagaagtt atgtagtaat | 2760 |
| attgtaaacg tttcttgatt tttttacatc catgtagtgc ttaaaaaacc aaaatatgtc | 2820 |
| acatgcaatt gtatatttca ataacaata tttattttct cgttaaattc acaaataatt | 2880 |
| tattaataat atcaataacc aagattatac ttaaatggat gtttatttt taacactttt | 2940 |
| atagtaaata tatttatttt atgtagtaaa aaggttataa ttataattgt atttattaca | 3000 |
| attaattaaa ataaaaaata gggttttagg taaaattaag ttatttttaag aagtaattac | 3060 |
| aataaaaatt gaagttattt ctttaaggag ggaattattc atatgactta tgtaccatca | 3120 |
| tcagcacttt tagaacaact tagagcagga aatacttggg ctttaggaag acttatatca | 3180 |
| agagcagaag ctggagttgc agaagctaga cctgcacttg ctgaagtata tagacatgca | 3240 |
| ggttcagctc atgttatagg tttaacagga gtaccaggat ctggtaaatc aactcttgta | 3300 |
| gcaaaactta cagcagctct tagaaaaaga ggagaaaaag ttggtatagt agctattgat | 3360 |
| cctagttctc catatagtgg aggagcaata cttggagata gaattagaat gactgaatta | 3420 |
| gcaaatgatt caggagtatt tataagaagt atggcaacta gaggtgctac tggaggaatg | 3480 |
| gctagagcag ctcttgatgc agttgattta cttgatgtag ctggatatca tactattatt | 3540 |
| ttagaaacag ttggagtagg tcaagatgaa gttgaagtag cacatgcttc tgatactaca | 3600 |
| gtagttgtat cagcacctgg acttggtgat gaaatacagg caattaaagc tggagtttta | 3660 |
| gaaattgctg atattcatgt tgtaagtaaa tgtgatagag atgatgcaaa tagaactctt | 3720 |
| acagatctta aacaaatgct tactttagga acaatggtag gacctaaaag agcatgggct | 3780 |
| ataccagttg taggagtttc aagttataca ggagaaggtg tagatgattt acttggtaga | 3840 |
| attgcagctc atagacaagc aactgctgat acagaacttg gaagagaaag aagaagaaga | 3900 |
| gtagctgaat ttagacttca aaaaactgca gaaacattac ttttagaaag atttactaca | 3960 |
| ggagcacagc cttttccacc agcattagct gatagtcttt ctaatagagc tagtgatcct | 4020 |
| tatgcagctg caagagaatt aatagctaga actataagaa aagaatattc taatgatctt | 4080 |
| gcatgtgcta aacttactat aacatggtta gaaccacaaa ttaaaagtca acttcagtct | 4140 |
| gaaagaaaag attgggaagc aaatgaagtt ggagcatttc ttaaaaaagc acctgaaaga | 4200 |
| aaagaacaat ttcatacaat tggagatttt ccagtacaga aacttatac agctgcagat | 4260 |
| atagcagata ctcctcttga agatattggt ttacctggaa gatatccatt tactagagga | 4320 |
| ccttatccaa caatgtatag aagtagaact tggacaatga caaaatagc tggatttggt | 4380 |
| actggagaag atacaaataa agatttaaa tatcttatag cacagggtca gactggaata | 4440 |
| tcaacagatt ttgatatgcc tacattaatg ggatatgatt cagatcatcc aatgagtgat | 4500 |
| ggtgaagttg aagagaagg tgtagctata gatacacttg cagatatgga agcacttctt | 4560 |
| gctgatattg atttagaaaa aatttcagtt agttttacta taaatccaag tgcatggatt | 4620 |
| cttttagcaa tgtatgtagc tttaggtgaa aaaagaggtt atgatcttaa taaactttct | 4680 |
| ggaacagtac aagctgatat acttaaagaa tatatggcac agaaagaata tatttatcct | 4740 |

```
atagctccaa gtgttagaat tgtaagagat ataattactt attctgcaaa aaatcttaaa    4800
agatataatc ctattaatat ttctggatat catatatcag aagctggttc ttcaccatta    4860
caagaagctg catttactct tgcaaatctt attacttatg taaatgaagt aactaaaaca    4920
ggaatgcatg tagatgaatt tgcacctaga ttagcatttt tctttgttag tcaaggagat    4980
ttctttgaag aagtagcaaa atttagagct ttaagaagat gttatgctaa aataatgaaa    5040
gaaagatttg gagcaagaaa tcctgaatct atgagactta gatttcattg tcaaactgct    5100
gcagctactc ttacaaaacc acagtatatg gttaatgttg taagaacaag tcttcaagca    5160
ttatctgctg tattgggagg agcacaaagt cttcatacta atggatatga tgaagcattt    5220 gctatacccta ctgaagatgc aatgaaaatg gctcttagaa cacaacagat tatagctgaa    5280
gaatctggag ttgcagatgt aatagatcct cttggaggaa gttattatgt tgaagcatta    5340
actacagaat atgaaaagaa aatatttgaa attcttgaag aagtagaaaa aagaggtgga    5400
actattaaac ttattgaaca aggatggttt caaaaacaga tagcagattt tgcttatgaa    5460
actgcactta gaaaacaatc aggacagaaa cctgttatag gtgtaaatag atttgttgaa    5520
aatgaagaag atgtaaaaat tgaaatacat ccttatgata atactacagc tgaaagacaa    5580
atatcaagaa ctagaagagt tagagcagaa agagatgaag caaaagtaca agctatgctt    5640
gatcagttag ttgcagtagc taaagatgaa agtcagaatc ttatgcctct tactattgaa    5700
ttagtaaaag caggagctac aatgggtgat attgtagaaa aacttaaagg tatttgggga    5760
acttatagag aaaaccagt attttaagca ctagttggag agcttccac gatggatcag    5820 attcctatta gagtattatt agcaaaagta ggtttagatg gacatgatag aggtgtaaaa    5880
gttgtagcaa gagcattaag agatgctgga atggatgtaa tatatagtgg tcttcataga    5940
actcctgaag aagtagttaa tacagcaatt caagaagatg tagatgtttt aggagttagt    6000
ttactttctg gtgtacagct tactgttttt cctaaaattt ttaaattact tgatgaaaga    6060
ggagctggtg atttaatagt aattgctgga ggagtaatgc cagatgaaga tgcagctgca    6120
ataagaaaac ttggagtaag agaagtttta cttcaagata caccaccaca ggcaataata    6180
gattcaataa gaagtttagt agcagcaaga ggagcaagat aaccatggag atctcgaggc    6240
ctgcagacat gcaagcttgg cactggccgt cgttttacaa cgtcgtgact gggaaaaccc    6300
tggcgttacc caacttaatc gccttgcagc acatccccct ttcgccagct ggcgtaatag    6360
cgaagaggcc cgcaccgatc gcccttccca acagttgcgc agcctgaatg gcgaatggcg    6420
ctagcataaa aataagaagc ctgcatttgc aggcttctta tttttatggc gcgccgccat    6480
tatttttttg aacaattgac aattcatttc ttattttta ttaagtgata gtcaaaaggc    6540
ataacagtgc tgaatagaaa gaaatttaca gaaaagaaaa ttatagaatt tagtatgatt    6600
aattatactc atttatgaat gtttaattga atacaaaaaa aaatacttgt tatgtattca    6660
attacgggtt aaaatataga caagttgaaa aatttaataa aaaataagt cctcagctct    6720 tatatattaa gctaccaact tagtatataa gccaaaactt aaatgtgcta ccaacacatc    6780
aagccgttag agaactctat ctatagcaat atttcaaatg taccgacata caagagaaac    6840
attaactata tatattcaat ttatgagatt atcttaacag atataaatgt aaattgcaat    6900
aagtaagatt tagaagttta tagcctttgt gtattggaag cagtacgcaa aggcttttt    6960 atttgataaa aattagaagt atatttattt tttcataatt aatttatgaa aatgaaaggg    7020
ggtgagcaaa gtgacagagg aaagcagtat cttatcaaat aacaaggtat tagcaatatc    7080
```

```
attattgact ttagcagtaa acattatgac ttttatagtg cttgtagcta agtagtacga    7140
aaggggagc tttaaaaagc tccttggaat acatagaatt cataaattaa tttatgaaaa     7200
gaagggcgta tatgaaaact tgtaaaaatt gcaaagagtt tattaaagat actgaaatat    7260
gcaaaataca ttcgttgatg attcatgata aaacagtagc aacctattgc agtaaataca    7320
atgagtcaag atgtttacat aaagggaaag tccaatgtat taattgttca agatgaacc    7380
gatatggatg gtgtgccata aaatgagat gttttacaga ggaagaacag aaaaagaac     7440
gtacatgcat taaatattat gcaaggagct ttaaaaagc tcatgtaaag aagagtaaaa    7500
agaaaaaata atttatttat taatttaata ttgagagtgc cgacacagta tgcactaaaa   7560
aatatatctg tggtgtagtg agccgataca aaaggatagt cactcgcatt ttcataatac    7620
atcttatgtt atgattatgt gtcggtggga cttcacgacg aaaacccaca ataaaaaaag    7680
agttcggggt agggttaagc atagttgagg caactaaaca atcaagctag datagcagt    7740
agcagaccgt aaggtcgttg tttaggtgtg ttgtaataca tacgctatta agatgtaaaa    7800
atacggatac caatgaaggg aaaagtataa ttttggatg tagtttgttt gttcatctat    7860
gggcaaacta cgtccaaagc cgtttccaaa tctgctaaaa agtatatcct ttctaaaatc    7920
aaagtcaagt atgaaatcat aaataaagtt taattttgaa gttattatga tattatgttt    7980
ttctattaaa ataaattaag tatatagaat agtttaataa tagtatatac ttaatgtgat    8040
aagtgtctga cagtgtcaca gaaaggatga ttgttatgga ttataagcgg ccggccagtg    8100
ggcaagttga aaaattcaca aaaatgtggt ataatatctt tgttcattag agcgataaac    8160
ttgaatttga gagggaactt agatggtatt tgaaaaaatt gataaaaata gttggaacag    8220
aaaagagtat tttgaccact actttgcaag tgtaccttgt acctacagca tgaccgttaa    8280
agtggatatc acacaaataa aggaaaaggg aatgaaacta tatcctgcaa tgctttatta    8340
tattgcaatg attgtaaacc gccattcaga gtttaggacg gcaatcaatc aagatggtga    8400
attggggata tatgatgaga tgataccaag ctatacaata tttcacaatg atactgaaac    8460
attttccagc ctttggactg agtgtaagtc tgactttaaa tcattttag cagattatga    8520
aagtgatacg caacggtatg gaaacaatca tagaatggaa ggaaagccaa atgctccgga    8580
aaacattttt aatgtatcta tgataccgtg gtcaaccttc gatggcttta atctgaattt    8640
gcagaaagga tatgattatt tgattcctat ttttactatg gggaaatatt ataaagaaga    8700
taacaaaatt atacttcctt tggcaattca agttcatcac gcagtatgtg acggatttca    8760
catttgccgt tttgtaaacg aattgcagga attgataaat agttaacttc aggtttgtct    8820
gtaactaaaa acaagtattt aagcaaaaac atcgtagaaa tacggtgttt tttgttaccc    8880
taagtttaaa ctccttttg ataatctcat gaccaaaatc ccttaacgtg agttttcgtt    8940
ccactgagcg tcagaccccg tagaaaagat caaaggatct tcttgagatc cttttttct    9000
gcgcgtaatc tgctgcttgc aaacaaaaaa accaccgcta ccagcggtgg tttgtttgcc    9060
ggatcaagag ctaccaactc tttttccgaa ggtaactggc ttcagcagag cgcagatacc    9120
aaatactgtt cttctagtgt agccgtagtt aggccaccac ttcaagaact ctgtagcacc    9180
gcctacatac ctcgctctgc taatcctgtt accagtggct gctgccagtg cgataagtc    9240
gtgtcttacc gggttggact caagacgata gttaccggat aaggcgcagc ggtcgggctg    9300
aacggggggt tcgtgcacac agcccagctt ggagcgaacg acctacaccg aactgagata    9360
cctacagcgt gagctatgag aaagcgccac gcttcccgaa gggagaaagg cggacaggta    9420
tccggtaagc ggcagggtcg gaacaggaga gcgcacgagg gagcttccag ggggaaacgc    9480
```

```
ctggtatctt tatagtcctg tcgggtttcg ccacctctga cttgagcgtc gattttgtg      9540 atgctcgtca gggggcgga gcctatggaa aaacgccagc aacgcggcct ttttacggtt      9600
cctggccttt tgctggcctt ttgctcacat gttctttcct gcgttatccc ctgattctgt      9660
ggataaccgt attaccgcct ttgagtgagc tgataccgct cgccgcagcc gaacgaccga      9720
gcgcagcgag tcagtgagcg aggaagcgga agagcgccca atacgcaggg ccccctgctt      9780
cggggtcatt atagcgattt tttcggtata tccatccttt ttcgcacgat atacaggatt      9840
ttgccaaagg gttcgtgtag actttccttg gtgtatccaa cggcgtcagc cgggcaggat      9900
aggtgaagta ggcccacccg cgagcgggtg ttccttcttc actgtccctt attcgcacct      9960
ggcggtgctc aacgggaatc ctgctctgcg aggctggccg gctaccgccg gcgtaacaga      10020
tgagggcaag cggatggctg atgaaaccaa gccaaccagg aagggcagcc cacctatcaa      10080
ggtgtactgc cttccagacg aacgaagagc gattgaggaa aaggcggcgg cggccggcat      10140
gagcctgtcg gcctacctgc tggccgtcgg ccagggctac aaaatcacgg gcgtcgtgga      10200
ctatgagcac gtccgcgagc tggcccgcat caatggcgac ctgggccgcc tgggcggcct      10260
gctgaaactc tggctcaccg acgacccgcg cacggcgcgg ttcggtgatg ccacgatcct      10320
cgccctgctg gcgaagatcg aagagaagca ggacgagctt ggcaaggtca tgatgggcgt      10380
ggtccgcccg agggcagagc catgactttt ttagccgcta aaacggccgg ggggtgcgcg      10440
tgattgccaa gcacgtcccc atgcgctcca tcaagaagag cgacttcgcg gagctggtga      10500
agtacatcac cgacgagcaa ggcaagaccg atcgggccc                              10539
```

<210> SEQ ID NO 193
<211> LENGTH: 487
<212> TYPE: DNA
<213> ORGANISM: Clostridium autoethanogenum
<220> FEATURE:
<221> NAME/KEY: misc_feature
<223> OTHER INFORMATION: promoter region of phosphate acetyltransferase

<400> SEQUENCE: 193

```
ggccgcaata tgatatttat gtccattgtg aaagggatta tattcaacta ttattccagt        60
tacgttcata gaaattttcc tttctaaaat attttattcc atgtcaagaa ctctgtttat      120
ttcattaaag aactataagt acaaagtata aggcatttga aaaataggc tagtatattg      180 attgattatt tattttaaaa tgcctaagtg aaatatatac atattataac aataaaataa      240
gtattagtgt aggattttta aatagagtat ctattttcag attaaatttt tgattatttg      300
atttacatta tataatattg agtaaagtat tgactagcaa aatttttga tactttaatt      360 tgtgaaattt cttatcaaaa gttatatttt tgaataattt ttattgaaaa atacaactaa      420
aaaggattat agtataagtg tgtgtaattt tgtgttaaat ttaaagggag gaaatgaaca      480
tgaaaca                                                                  487
```

<210> SEQ ID NO 194
<211> LENGTH: 7884
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL82256-ptb-buk

<400> SEQUENCE: 194

-continued

```
gagatctcga ggcctgcaga catgcaagct tggcactggc cgtcgtttta caacgtcgtg      60
actgggaaaa ccctggcgtt acccaactta atcgccttgc agcacatccc cctttcgcca     120
gctggcgtaa tagcgaagag gcccgcaccg atcgccctcc caacagttg cgcagcctga      180 atggcgaatg cgctagcat aaaaataaga agcctgcatt tgcaggcttc ttatttttat      240
ggcgcgccgt tctgaatcct tagctaatgg ttcaacaggt aactatgacg aagatagcac     300
cctggataag tctgtaatgg attctaaggc atttaatgaa gacgtgtata taaaatgtgc     360
taatgaaaaa gaaatgcgt taaagagcc taaaatgagt tcaaatggtt ttgaaattga      420
ttggtagttt aatttaatat attttttcta ttggctatct cgatacctat agaatcttct     480
gttcactttt gttttgaaa tataaaaagg ggcttttag cccctttttt ttaaaactcc      540
ggaggagttt cttcattctt gatactatac gtaactattt tcgatttgac ttcattgtca     600
attaagctag taaaatcaat ggttaaaaaa caaaaaactt gcattttct acctagtaat      660 ttataatttt aagtgtcgag tttaaaagta taatttacca ggaaaggagc aagtttttta     720
ataaggaaaa attttttcctt ttaaaattct atttcgttat atgactaatt ataatcaaaa    780
aaatgaaaat aaacaagagg taaaaactgc tttagagaaa tgtactgata aaaaagaaa     840 aaatcctaga tttacgtcat acatagcacc tttaactact aagaaaaata ttgaaaggac    900
ttccacttgt ggagattatt tgtttatgtt gagtgatgca gacttagaac attttaaatt    960
acataaaggt aattttttgcg gtaatagatt ttgtccaatg tgtagttggc gacttgcttg  1020
taaggatagt ttagaaatat ctattcttat ggagcattta agaaaagaag aaaataaaga  1080
gtttatattt ttaactctta caactccaaa tgtaaaagt tatgatctta attattctat    1140
taaacaatat aataaatctt ttaaaaaatt aatggagcgt aaggaagtta aggatataac    1200 taaggttat ataagaaaat tagaagtaac ttaccaaaag gaaaaataca taacaaagga    1260
tttatggaaa ataaaaaaag attattatca aaaaaaagga cttgaaattg gtgatttaga   1320 acctaattt gatacttata atcctcattt tcatgtagtt attgcagtta ataaagttta    1380
ttttacagat aaaaattatt atataaatcg agaaagatgg ttggaattat ggaagtttgc   1440
tactaaggat gattctataa ctcaagttga tgttagaaaa gcaaaaatta atgattataa   1500
agaggtttac gaacttgcga atattcagc taaagacact gattatttaa tatcgaggcc   1560
agtatttgaa atttttttata aagcattaaa aggcaagcag gtattagttt ttagtggatt  1620
ttttaaagat gcacacaaat tgtacaagca aggaaaactt gatgtttata aaagaaaga   1680 tgaaattaaa tatgtctata tagtttatta taattggtgc aaaaaacaat atgaaaaaac   1740
tagaataagg gaacttacgg aagatgaaaa agaagaatta aatcaagatt taatagatga   1800
aatagaaata gattaaagtg taactatact ttatatatat atgattaaaa aaataaaaaa    1860
caacagccta ttaggttgtt gtttttttatt ttctttatta attttttttaa tttttagttt  1920 ttagttcttt tttaaaataa gtttcagcct cttttttcaat atttttttaaa gaaggagtat  1980 ttgcatgaat tgcctttttt ctaacagact taggaaatat tttaacagta tcttcttgcg    2040
ccggtgattt tggaacttca taacttacta atttataatt attattttct ttttttaattg  2100 taacagttgc aaaagaagct gaacctgttc cttcaactag tttatcatct tcaatataat    2160
attcttgacc tatatagtat aaatatattt ttattatatt tttactttttt tctgaatcta   2220 ttatttttata atcataaaaa gttttaccac caaaagaagg ttgtactcct tctggtccaa   2280
catatttttt tactatatta tctaaataat ttttgggaac tggtgttgta atttgattaa   2340
tcgaacaacc agttatactt aaaggaatta taactataaa aatatatagg attatctttt   2400
```

```
taaatttcat tattggcctc cttttttatta aatttatgtt accataaaaa ggacataacg    2460
ggaatatgta gaatatttt aatgtagaca aaattttaca taaatataaa gaaggaagt     2520 gtttgtttaa attttatagc aaactatcaa aaattagggg gataaaaatt tatgaaaaaa   2580
aggttttcga tgttattttt atgtttaact ttaatagttt gtggtttatt tacaaattcg   2640
gccggccgaa gcaaacttaa gagtgtgttg atagtgcagt atcttaaaat tttgtataat   2700
aggaattgaa gttaaattag atgctaaaaa tttgtaatta agaaggagtg attacatgaa   2760
caaaaatata aaatattctc aaaactttt aacgagtgaa aaagtactca accaaataat   2820
aaaacaattg aatttaaaag aaaccgatac cgtttacgaa attggaacag gtaaagggca   2880
tttaacgacg aaactggcta aaataagtaa acaggtaacg tctattgaat tagacagtca   2940
tctattcaac ttatcgtcag aaaaattaaa actgaatact cgtgtcactt taattcacca   3000
agatattcta cagtttcaat tccctaacaa acagaggtat aaaattgttg ggagtattcc   3060
ttaccattta agcacacaaa ttattaaaaa agtggttttt gaaagccatg cgtctgacat   3120
ctatctgatt gttgaagaag gattctacaa gcgtaccttg gatattcacc gaacactagg   3180
gttgctcttg cacactcaag tctcgattca gcaattgctt aagctgccag cggaatgctt   3240
tcatcctaaa ccaaaagtaa acagtgtctt aataaaactt acccgccata ccacagatgt   3300
tccagataaa tattggaagc tatatacgta ctttgtttca aaatgggtca atcgagaata   3360
tcgtcaactg tttactaaaa atcagtttca tcaagcaatg aaacacgcca agtaaacaa    3420 tttaagtacc gttacttatg agcaagtatt gtctattttt aatagttatc tattatttaa   3480
cgggaggaaa taattctatg agtcgctttt gtaaatttgg aaagttacac gttactaaag   3540
ggaatgtgtt taaactcctt tttgataatc tcatgaccaa aatcccttaa cgtgagtttt   3600
cgttccactg agcgtcagac cccgtagaaa agatcaaagg atcttcttga gatcctttt    3660 ttctgcgcgt aatctgctgc ttgcaaacaa aaaaaccacc gctaccgcg gtggtttgtt   3720 tgccggatca agagctacca actctttttc cgaaggtaac tggcttcagc agagcgcaga   3780
taccaaatac tgttcttcta gtgtagccgt agttaggcca ccacttcaag aactctgtag   3840
caccgcctac atacctcgct ctgctaatcc tgttaccagt ggctgctgcc agtggcgata   3900
agtcgtgtct taccgggttg gactcaagac gatagttacc ggataaggcg cagcggtcgg   3960
gctgaacggg gggttcgtgc acacagccca gcttggagcg aacgacctac accgaactga   4020 gataccaca gcgtgagcta tgagaaagcg ccacgcttcc cgaagggaga aggcggaca    4080 ggtatccggt aagcggcagg gtcggaacag gagagcgcac gagggagctt ccaggggaa    4140 acgcctggta tctttatagt cctgtcgggt ttcgccacct ctgacttgag cgtcgatttt   4200
tgtgatgctc gtcagggggg cggagcctat ggaaaaacgc cagcaacgcg ccttttttac   4260
ggttcctggc cttttgctgg ccttttgctc acatgttctt tcctgcgtta tcccctgatt   4320
ctgtggataa ccgtattacc gcctttgagt gagctgatac cgctcgccgc agccgaacga   4380
ccgagcgcag cgagtcagtg agcgaggaag cggaagagcg cccaatacgc agggcccct    4440 gcttcgggt cattatagcg atttttttcgg tatatccatc cttttttcgca cgatatacag   4500 gattttgcca aagggttcgt gtagactttc cttggtgtat ccaacggcgt cagccgggca   4560
ggataggtga agtaggccca cccgcgagcg ggtgttcctt cttcactgtc ccttattcgc   4620
acctggcggt gctcaacggg aatcctgctc tgcgaggctg gccggctacc gccgcgtaa    4680 cagatgaggg caagcggatg gctgatgaaa ccaagccaac caggaagggc agcccaccta   4740
```

```
tcaaggtgta ctgccttcca gacgaacgaa gagcgattga ggaaaaggcg gcggcggccg      4800
gcatgagcct gtcggcctac ctgctggccg tcggccaggg ctacaaaatc acgggcgtcg      4860
tggactatga gcacgtccgc gagctggccc gcatcaatgg cgacctgggc cgcctgggcg      4920
gcctgctgaa actctggctc accgacgacc cgcgcacggc gcggttcggt gatgccacga      4980
tcctcgccct gctggcgaag atcgaagaga agcaggacga gcttggcaag gtcatgatgg      5040
gcgtggtccg cccgagggca gagccatgac ttttttagcc gctaaaacgg ccggggggtg      5100
cgcgtgattg ccaagcacgt ccccatgcgc tccatcaaga agagcgactt cgcggagctg      5160
gtgaagtaca tcaccgacga gcaaggcaag accgatcggg cccccctgcag gataaaaaaa      5220 ttgtagataa attttataaa atagttttat ctacaatttt tttatcagga aacagctatg      5280
accgcggccg caaaatagtt gataataatg cagagttata acaaaggtg aaaagcatta      5340 cttgtattct tttttatata ttattataaa ttaaaatgaa gctgtattag aaaaaataca      5400
cacctgtaat ataaaatttt aaattaattt ttaattttt caaatgtat tttacatgtt      5460 tagaattttg atgtatatta aaatagtaga atacataaga tacttaattt aattaaagat      5520
agttaagtac ttttcaatgt gcttttttag atgtttaata caaatcttta attgtaaaag      5580
aaatgctgta ctatttactg tactagtgac gggattaaac tgtattaatt ataaataaaa      5640
aataagtaca gttgtttaaa attatatttt gtattaaatc taatagtacg atgtaagtta      5700
ttttatacta ttgctagttt aataaaaaga tttaattata tgcttgaaaa ggagaggaat      5760
ccaatgagta aaaactttga tgagttatta tcaagattaa aggaagttcc aacaaaaaaa      5820
gtggctgtag ccgtagcaca agatgaacca gtattagagg ctataaaaga agctacagaa      5880
aataacatcg cacaagcaat attggttggt gataaacaac aaatccatga aatcgcaaag      5940
aaaataaact tggacttatc tgattatgaa ataatggata ttaaagatcc aaagaaagca      6000
acattagaag cagtaaaatt agtttctagt ggtcatgcag atatgttaat gaaaggtcta      6060
gttgatactg caacattcct aagaagcgta ttaaacaaag aggttggtct tagaacagga      6120
aaattaatgt cccatgtagc tgtgtttgat gtggaaggtt gggatagact gttattttta      6180
actgatgcag catttaatac atatccagaa tttaaggata agttggaat gataaataat      6240 gcagttgtag ttgctcatgc atgtggaata gatgttccaa gagtagcacc tatatgccca      6300
gttgaagttg taaatacaag tatgcaatca acagttgatg cagcattgtt agctaaaatg      6360
agtgacaggg ggcaaattaa aggatgcgta attgatggac cttttgcctt agataatgca      6420
atatcagaag aagcagctca tcataaaggt gttacaggat cagtagcagg taaagctgat      6480
atattattat taccaaatat agaagcagca aatgtaatgt ataaaacatt aacatatttc      6540
tctaaatcaa gaaatggtgg acttttagta ggtacatcag caccagtaat tttaacttca      6600
agagcagatt cattcgaaac taagttaat tcaattgctc ttgcagcatt agttgcagca      6660
agaaataagt aataaatcaa tccataataa ttaatgcata attaatggag agatttatat      6720
ggaatttgca atgcactatt agattctata ataatttctt ctgaaaatta tgcattatga      6780
ctgtatagaa tgcattaaat ttaagggggga ttcagaatgt catataagct attaataatc      6840
aatccaggtt caacatcaac aaagattggt gtttacgaag gagaaaagga actatttgaa      6900
gaaactttga gacacacaaa tgaagaaata aagagatatg atacaatata tgatcaattt      6960
gaatttagaa aagaagttat attaaatgtt cttaaagaaa agaatttga tataaagact      7020 ctaagtgcta ttgttggtag aggtggaatg cttagaccag ttgaaggtgg aacatatgca      7080
gtaaatgatg caatggttga agatttaaaa gttggagttc aaggacctca tgcttctaac      7140
```

```
cttggcggaa taattgccaa gtcaattgga gatgaattaa atattccatc atttatagta     7200
gatccagttg ttacagatga gttagcagat gtagcaagac tatctggagt accagaacta     7260
ccaagaaaaa gtaaattcca tgctttaaat caaaaagcgg tagctaaaag atatggaaaa     7320
gaaagtggac aaggatatga aaacctaaat cttgtagttg tacatatggg tggaggcgtt     7380
tcagttggtg ctcacaatca tgggaaagtt gtcgatgtaa ataatgcatt agatggagat     7440
ggcccattct caccagaaag agctggatca gttccaattg gtgatttagt taaaatgtgt     7500
tttagtggaa aatatagtga agcagaagta tatggcaagg ctgtaggaaa aggtggattt     7560
gttggttatc taaacacaaa tgatgtaaaa ggtgttattg ataagatgga agaaggagat     7620
aaagaatgtg aatcaatata caaagcattt gtttatcaaa tttcaaaagc aatcggagaa     7680
atgtcagttg tattagaagg taaagttgat caaattattt ttaccggagg aattgcatac     7740
tcaccaacac ttgttccaga ccttaaagca aaagttgaat ggatagcccc agttacagtt     7800
tatcctggag aagatgaatt acttgctcta gctcaaggtg ctataagagt acttgatgga     7860
gaagaacaag ctaaggttta ctag                                            7884

<210> SEQ ID NO 195
<211> LENGTH: 6624
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pMTL82256-tesB

<400> SEQUENCE: 195
gagatctcga ggcctgcaga catgcaagct tggcactggc cgtcgtttta caacgtcgtg       60
actgggaaaa ccctggcgtt acccaactta atcgccttgc agcacatccc cctttcgcca      120
gctggcgtaa tagcgaagag gcccgcaccg atcgcccttc ccaacagttg cgcagcctga      180
atggcgaatg cgctagcat aaaaataaga agcctgcatt tgcaggcttc ttattttat        240 ggcgcgccgt tctgaatcct tagctaatgg ttcaacaggt aactatgacg aagatagcac      300
cctggataag tctgtaatgg attctaaggc atttaatgaa gacgtgtata taaaatgtgc      360
taatgaaaaa gaaaatgcgt taaaagagcc taaaatgagt tcaaatggtt ttgaaattga      420
ttggtagttt aatttaatat attttttcta ttggctatct cgatacctat agaatcttct      480
gttcactttt gttttttgaaa tataaaaagg ggcttttag ccccttttt ttaaaactcc       540 ggaggagttt cttcattctt gatactatac gtaactattt tcgatttgac ttcattgtca      600
attaagctag taaaatcaat ggttaaaaaa caaaaaactt gcattttct acctagtaat       660 ttataatttt aagtgtcgag tttaaaagta aatttaccca ggaaaggagc aagttttta      720 ataaggaaaa attttccttt taaaattct atttcgttat atgactaatt ataatcaaaa      780
aaatgaaaat aaacaagagg taaaaactgc tttagagaaa tgtactgata aaaaagaaa      840 aaatcctaga tttacgtcat acatagcacc tttaactact aagaaaaata ttgaaaggac      900
ttccacttgt ggagattatt tgtttatgtt gagtgatgca gacttagaac atttaaatt       960 acataaaggt aattttgcg gtaatagatt ttgtccaatg tgtagttggc gacttgcttg     1020
taaggatagt ttagaaatat ctattcttat ggagcattta agaaagaag aaataaaga     1080 gtttatattt ttaactctta caactccaaa tgtaaaaagt tatgatctta ttattctat    1140 taaacaatat aataaatctt ttaaaaaatt aatggagcgt aaggaagtta aggatataac     1200
```

-continued

```
taaaggttat ataagaaaat tagaagtaac ttaccaaaag gaaaaataca taacaaagga   1260
tttatggaaa ataaaaaaag attattatca aaaaaaagga cttgaaattg gtgatttaga   1320
acctaatttt gatacttata atcctcattt tcatgtagtt attgcagtta ataaaagtta   1380
ttttacagat aaaaattatt atataaatcg agaaagatgg ttggaattat ggaagtttgc   1440
tactaaggat gattctataa ctcaagttga tgttagaaaa gcaaaaatta atgattataa   1500
agaggtttac gaacttgcga atattcagc taaagacact gattatttaa tatcgaggcc    1560
agtatttgaa attttttata aagcattaaa aggcaagcag gtattagttt ttagtggatt   1620
ttttaaagat gcacacaaat tgtacaagca aggaaaactt gatgtttata aaagaaaga    1680 tgaaattaaa tatgtctata tagtttatta taattggtgc aaaaaacaat atgaaaaaac   1740
tagaataagg gaacttacgg aagatgaaaa agaagaatta aatcaagatt taatagatga   1800
aatagaaata gattaaagtg taactatact ttatatatat atgattaaaa aataaaaaa    1860 caacagccta ttaggttgtt gtttttttatt ttctttatta attttttttaa ttttttagttt 1920 ttagttcttt tttaaaataa gtttcagcct cttttttcaat atttttttaaa gaaggagtat  1980 ttgcatgaat tgccttttttt ctaacagact taggaaatat tttaacagta tcttcttgcg   2040
ccggtgattt tggaacttca taacttacta atttataatt attattttct tttttaattg    2100
taacagttgc aaaagaagct gaacctgttc cttcaactag tttatcatct tcaatataat   2160
attcttgacc tatatagtat aaatatattt ttattatatt tttacttttt tctgaatcta   2220
ttattttata atcataaaaa gttttaccac caaaagaagg ttgtactcct tctggtccaa   2280
catatttttt tactatatta tctaaataat tttttgggaac tggtgttgta atttgattaa   2340
tcgaacaacc agttatactt aaaggaatta taactataaa aatatatagg attatctttt   2400
taaatttcat tattggcctc cttttttatta aatttatgtt accataaaaa ggacataacg   2460
ggaatatgta gaatattttt aatgtagaca aaatttttaca taaatataaa gaaggaagt    2520 gtttgtttaa attttatagc aaactatcaa aaattagggg gataaaaatt tatgaaaaaa   2580
aggttttcga tgttatttttt atgtttaact ttaatagttt gtggtttatt tacaaattcg   2640
gccggccgaa gcaaacttaa gagtgtgttg atagtgcagt atcttaaaat tttgtataat   2700
aggaattgaa gttaaattag atgctaaaaa tttgtaatta agaaggagtg attacatgaa   2760
caaaaatata aaatattctc aaaacttttt aacgagtgaa aaagtactca accaaataat    2820
aaaacaattg aatttaaaag aaaccgatac cgtttacgaa attggaacag gtaaagggca   2880
tttaacgacg aaactggcta aaataagtaa acaggtaacg tctattgaat tagacagtca   2940
tctattcaac ttatcgtcag aaaaattaaa actgaatact cgtgtcactt taattcacca   3000
agatattcta cagtttcaat tccctaacaa acagaggtat aaaattgttg ggagtattcc   3060
ttaccattta agcacacaaa ttattaaaaa agtggttttt gaaagccatg cgtctgacat   3120
ctatctgatt gttgaagaag gattctacaa gcgtaccttg gatattcacc gaacactagg   3180
gttgctcttg cacactcaag tctcgattca gcaattgctt aagctgccag cggaatgctt   3240
tcatcctaaa ccaaaagtaa acagtgtctt aataaaactt acccgccata ccacagatgt   3300
tccagataaa tattggaagc tatatacgta ctttgtttca aaatgggtca atcgagaata   3360
tcgtcaactg tttactaaaa atcagtttca tcaagcaatg aaacacgcca agtaaacaa    3420 tttaagtacc gttacttatg agcaagtatt gtctattttt aatagttatc tattatttaa   3480
cgggaggaaa taattctatg agtcgctttt gtaaatttgg aaagttacac gttactaaag   3540
```

```
ggaatgtgtt taaactccdt tttgataatc tcatgaccaa aatcccttaa cgtgagtttt    3600
cgttccactg agcgtcagac cccgtagaaa agatcaaagg atcttcttga gatccttttt    3660
ttctgcgcgt aatctgctgc ttgcaaacaa aaaaccacc gctaccagcg gtggtttgtt     3720
tgccggatca agagctacca actcttttc cgaaggtaac tggcttcagc agagcgcaga     3780
taccaaatac tgttcttcta gtgtagccgt agttaggcca ccacttcaag aactctgtag    3840
caccgcctac atacctcgct ctgctaatcc tgttaccagt ggctgctgcc agtggcgata    3900
agtcgtgtct taccgggttg gactcaagac gatagttacc ggataaggcg cagcggtcgg    3960
gctgaacggg gggttcgtgc acacagccca gcttggagcg aacgacctac accgaactga    4020
gatacctaca gcgtgagcta tgagaaagcg ccacgcttcc cgaagggaga aggcggaca    4080
ggtatccggt aagcggcagg gtcggaacag gagagcgcac gagggagctt ccaggggga    4140
acgcctggta tctttatagt cctgtcgggt ttcgccacct ctgacttgag cgtcgatttt    4200
tgtgatgctc gtcaggggg cggagcctat ggaaaaacgc cagcaacgcg gcctttttac     4260
ggttcctggc cttttgctgg ccttttgctc acatgttctt tcctgcgtta tcccctgatt    4320
ctgtggataa ccgtattacc gcctttgagt gagctgatac cgctcgccgc agccgaacga    4380
ccgagcgcag cgagtcagtg agcgaggaag cggaagagcg cccaatacgc agggcccct    4440
gcttcggggt cattatagcg attttttcgg tatatccatc ttttttcgca cgatatacag    4500
gattttgcca aagggttcgt gtagactttc cttggtgtat ccaacggcgt cagccgggca    4560
ggataggtga agtaggccca cccgcgagcg ggtgttcctt cttcactgtc ccttattcgc    4620
acctggcggt gctcaacggg aatcctgctc tgcgaggctg gccggctacc gccggcgtaa    4680
cagatgaggg caagcggatg gctgatgaaa ccaagccaac caggaagggc agcccaccta    4740
tcaaggtgta ctgccttcca gacgaacgaa gagcgattga ggaaaaggcg gcggcggccg    4800
gcatgagcct gtcggcctac ctgctggccg tcggccaggg ctacaaaatc acgggcgtcg    4860
tggactatga gcacgtccgc gagctggccc gcatcaatgg cgacctgggc cgcctgggcg    4920
gcctgctgaa actctggctc accgacgacc cgcgcacggc gcggttcggt gatgccacga    4980
tcctcgccct gctggcgaag atcgaagaga agcaggacga gcttggcaag gtcatgatgg    5040
gcgtggtccg cccgagggca gagccatgac ttttttagcc gctaaaacgg ccggggggtg    5100
cgcgtgattg ccaagcacgt ccccatgcgc tccatcaaga agagcgactt cgcggagctg    5160
gtgaagtaca tcaccgacga gcaaggcaag accgatcggg ccccctgcag gataaaaaaa    5220
ttgtagataa attttataaa atagtttat ctacaatttt tttatcagga aacagctatg     5280
accgcggccg caaaatagtt gataataatg cagagttata acaaaggtg aaaagcatta     5340
cttgtattct ttttatata ttattataaa ttaaaatgaa gctgtattag aaaaaataca     5400
cacctgtaat ataaaatttt aaattaattt ttaattttt caaaatgtat tttacatgtt    5460
tagaattttg atgtatatta aaatagtaga atacataaga tacttaattt aattaaagat    5520
agttaagtac tttcaatgt gctttttag atgtttaata caaatcttta attgtaaaag     5580
aaatgctgta ctatttactg tactagtgac gggattaaac tgtattaatt ataaataaaa    5640
aataagtaca gttgtttaaa attatatttt gtattaaatc taatagtacg atgtaagtta    5700
ttttatacta ttgctagttt aataaaaaga tttaattata tgcttgaaaa ggagaggaat    5760
ccaatgagtc aggcacttaa aaatttactt actttactta atcttgaaaa aatagaagaa    5820
ggtttatta gaggacagtc agaagattta ggattaagac aagtatttgg aggtcaagta    5880
gttggtcagg cactttatgc agctaaagaa actgtacctg aagaaagact tgttcatagt    5940
```

-continued

```
tttcattctt attttcttag acctggagat tctaaaaaac caattatata tgatgtagaa    6000
actcttagag atggaaattc atttagtgca agaagagttg cagctattca aaatggtaaa    6060
cctatatttt acatgacagc ttcttttcaa gcaccagaag ctggatttga acatcagaaa    6120
actatgcctt cagcacctgc tccagatgga ttaccatcag aaacacaaat agcacagagt    6180
ttagctcatt tacttcctcc agtacttaaa gataaattta tttgtgatag acctttagaa    6240
gttagaccag ttgaatttca taatcctctt aaaggacatg tagcagaacc acatagacaa    6300
gtttggataa gagctaatgg aagtgtacca gatgatctta gagttcatca gtatcttctt    6360
ggttatgcat ctgatttaaa ttttcttcct gtagctttac aaccacatgg aataggtttt    6420
cttgaacctg gaatacagat agcaactata gatcattcaa tgtggtttca tagaccattt    6480
aatcttaatg aatggcttct ttatagtgta gaatctacat cagcaagttc tgctagagga    6540
tttgttaggg gtgaatttta tactcaagat ggagtacttg ttgctagtac agtacaggaa    6600
ggtgttatga gaaatcataa ttaa                                           6624
```